US012697322B2

(12) United States Patent
Chaffer et al.

(10) Patent No.: US 12,697,322 B2
(45) Date of Patent: Aug. 4, 2026

(54) METHODS OF TREATING CANCER USING ANDROGEN RECEPTOR ANTAGONISTS

(71) Applicant: Garvan Institute of Medical Research, New South Wales (AU)

(72) Inventors: Christine Chaffer, New South Wales (AU); Beatriz Pérez San Juan, New South Wales (AU)

(73) Assignee: Garvan Institute of Medical Research, New South Wales (AU)

( * ) Notice: Subject to any disclaimer, the term of this patent is extended or adjusted under 35 U.S.C. 154(b) by 786 days.

(21) Appl. No.: 17/771,180

(22) PCT Filed: Oct. 23, 2020

(86) PCT No.: PCT/AU2020/051146
§ 371 (c)(1),
(2) Date: Apr. 22, 2022

(87) PCT Pub. No.: WO2021/077174
PCT Pub. Date: Apr. 29, 2021

(65) Prior Publication Data

US 2022/0387394 A1 Dec. 8, 2022

(30) Foreign Application Priority Data

Oct. 25, 2019 (AU) ................................ 2019904027

(51) Int. Cl.

| | |
|---|---|
| ***A61K 31/4192*** | (2006.01) |
| ***A61K 31/277*** | (2006.01) |
| ***A61K 31/4166*** | (2006.01) |
| ***A61K 31/58*** | (2006.01) |
| ***A61K 45/06*** | (2006.01) |
| ***A61P 35/00*** | (2006.01) |

(52) U.S. Cl.
CPC ........ *A61K 31/4192* (2013.01); *A61K 31/277* (2013.01); *A61K 31/4166* (2013.01); *A61K 31/58* (2013.01); *A61K 45/06* (2013.01); *A61P 35/00* (2018.01)

(58) Field of Classification Search
CPC . A61P 35/00; A61K 31/4166; A61K 31/4192; A61K 31/277; A61K 31/58; A61K 45/06
See application file for complete search history.

(56) References Cited

U.S. PATENT DOCUMENTS

| | | | | |
|---|---|---|---|---|
| 10,391,173 | B2 * | 8/2019 | Abazeed | A61K 31/167 |
| 2008/0051380 | A1 | 2/2008 | Auerbach | |
| 2015/0209359 | A1 | 7/2015 | Yaffe | |
| 2017/0319692 | A1 | 11/2017 | Abazeed | |

FOREIGN PATENT DOCUMENTS

| | | | | |
|---|---|---|---|---|
| WO | 2011064663 A1 | 6/2011 | | |
| WO | WO-2016179002 A1 * | 11/2016 | | A61P 35/00 |
| WO | 2019113301 | 6/2019 | | |

OTHER PUBLICATIONS

Lokeshwar, B. L., V. B. Lokeshwar, and N. L. Block. "Expression of CD44 in prostate cancer cells: association with cell proliferation and invasive potential." Anticancer research 15, No. 4 (1995): 1191-1198 (Year: 1995).*

Chen, M. E., Lin, S. H., Chung, L. W., & Sikes, R. A. (1998). Isolation and Characterization of p. 1 andGage-7: New Genes Expressed in The LNCaP Prostate Cancer Progression Model That Share Homology With Melanoma-Associated Antigens. Journal of Biological Chemistry, 273(28), 17618-17625 (Year: 1998).*

Kawada, Manabu, Hiroyuki Inoue, Ihomi Usami, Kozo Takamoto, Tohru Masuda, Yoko Yamazaki, and Daishiro Ikeda. "Establishment of a highly tumorigenic LNCaP cell line having inflammatory cytokine resistance." Cancer letters 242, No. 1 (2006): 46-52 (Year: 2006).*

Baskar, Rajamanickam, Kuo Ann Lee, Richard Yeo, and Kheng-Wei Yeoh. "Cancer and radiation therapy: current advances and future directions." International journal of medical sciences 9, No. 3 (2012): 193. (Year: 2012).*

Al Ssadh et al. "Measurements of heterotypic associations between cluster of differentiation CD74 and CD44 in human breast cancer-derived cells." Oncotarget 8, No. 54 (2017): 92143 (Year: 2017).*

Gordon, Michael A., Nicholas C. D'Amato, Haihua Gu, Beatrice Babbs, Julia Wulfkuhle, Emanuel F. Petricoin, Isela Gallagher et al. "Synergy between androgen receptor antagonism and inhibition of mTOR and HER2 in breast cancer." Molecular cancer therapeutics 16, No. 7 (2017): 1389-1400 (Year: 2017).*

Gupta et al "Phase I study of seviteronel, a selective CYP17 lyase and androgen receptor inhibitor, in men with castration-resistant prostate cancer." Clinical Cancer Research 24, No. 21 (2018): 5225-5232. (Year: 2018).*

Shiota, Masaki, Takashi Dejima, Yoshiaki Yamamoto, Ario Takeuchi, Kenjiro Imada, Eiji Kashiwagi, Junichi Inokuchi et al. "Collateral resistance to taxanes in enzalutamide-resistant prostate cancer through aberrant androgen receptor and its variants." Cancer Science 109, No. 10 (2018): 3224-3234. (Year: 2018).*

Vikram, Rajeev, Wen Cheng Chou, Shih-Chieh Hung, and Chen-Yang Shen. "Tumorigenic and metastatic role of CD44-/low/CD24-/low cells in luminal breast cancer." Cancers 12, No. 5 (2020): 1239 (Year: 2020).*

Su, Chen-Ying, Gwo-Che Huang, I-Cheng Chen, Pei-Yu Chen, Yu-Jen Chen, and Hsu-Wei Fang. "Distinct expression of surface and genetic biomarkers in prostate cancer cell lines." in vivo 37, No. 1 (2023): 242-246 (Year: 2023).*

National Cancer Institute Dictionary of Cancer Terms, "anticancer therapy," https://www.cancer.gov/publications/dictionaries/cancer-terms/def/anticancer-therapy, Accessed: Jul. 23, 2025) (Year: 2025).*

(Continued)

*Primary Examiner* — James H Alstrum-Acevedo
*Assistant Examiner* — Carolyn L. Ladd
(74) *Attorney, Agent, or Firm* — Riverside Law LLP

(57) ABSTRACT

The present disclosure generally relates to cancer and methods of treating and diagnosing cancer.

11 Claims, 18 Drawing Sheets

Specification includes a Sequence Listing.

(56) References Cited

OTHER PUBLICATIONS

Altogen Labs, "BT474 Xenograft Model," Accessed: Jul. 29, 2025, https://altogenlabs.com/xenograft-models/breast-cancer-xenograft/bt474-xenograft-model/#:~:text=BT474%20is%20a%20well%2Destablished,therapies%2C%20and%20novel%20combination%20treatments (Year: 2025).*

Altogen Labs, "MDA-MB-453 Xenograft Model," Accessed: Jul. 29, 2025, https://altogenlabs.com/xenograft-models/breast-cancer-xenograft/mda-mb-453-xenograft-model/#:~:text=Metastatic%20MDA%2DMB%2D453%20Xenograft%20Model&text=While%20MDA%2DMB%2D453%20tumors,receptor%20antagonists%20and%20MEK%20inhibitors (Year: 2025).*

National Center for Biotechnology Information. PubChem Compound Summary for CID 132971, Abiraterone. https://pubchem.ncbi.nlm.nih.gov/compound/Abiraterone. Accessed Jul. 29, 2025 (Year: 2025).*

National Center for Biotechnology Information. PubChem Compound Summary for CID 78357816, Seviteronel. https://pubchem.ncbi.nlm.nih.gov/compound/Seviteronel. Accessed Jul. 30, 2025 (Year: 2025).*

Barton, V. N., et al., "Androgen Receptor Supports an Anchorage-Independent, Cancer Stem Cell-like Population in Triple-Negative Breast Cancer," Cancer Research, vol. 77, No. 13 (2017), pp. 3455-3466.

Fushimi, C., et al., "A prospective phase II study of combined androgen blockade in patients with androgen receptor-positive metastatic or locally advanced unresectable salivary gland carcinoma," Annals of Oncology, vol. 29, No. 4 (2018), pp. 979-984.

Gerratana, L., et al., "Androgen receptor in triple negative breast cancer: A potential target for the targetless subtype," Cancer Treatment Reviews, vol. 68 (2018), pp. 102-110.

Gordon, M. A., et al., "Synergy between Androgen Receptor Antagonism and Inhibition of mTOR and HER2 in Breast Cancer," Molecular Cancer Therapeutics, vol. 16, No. 7 (2017), pp. 1389-1400.

Goscinski, M. A., et al., "Nuclear, cytoplasmic, and stromal expression of ZEB1 in squamous and small cell carcinoma of the esophagus," APMIS, vol. 123, No. 12 (2015), pp. 1040-1047.

Kuasne, H., et al., "Nuclear loss and cytoplasmic expression of androgen receptor in penile carcinomas: role as a driver event and as a prognostic factor," Virchows Archiv, vol. 473 (2018), pp. 607-614.

Morris, M. J., et al., "Phase Ib Study of Enzalutamide in Combination with Docetaxel in Men with Metastatic Castration-Resistant Prostate Cancer," Clinical Cancer Research, vol. 22, No. 15 (2016), pp. 3774-3781.

Naderi, A., et al., "Synergy between inhibitors of androgen receptor and MEK has therapeutic implications in estrogen receptor-negative breast cancer," Breast Cancer Research, vol. 13, No. 2(2011), R36.

Speers, C., et al., "Androgen receptor as a mediator and biomarker of radioresistance in triple-negative breast cancer," NPJ Breast Cancer, vol. 3 (2017), Article 29.

Wardell, S. E., et al. "Abstract 1588: Effects of the selective CYP17-lyase and androgen receptor (AR) inhibitor, seviteronel, and the cyclin-dependent kinase (CDK) 4/6 inhibitor, G1T38, on tumor growth in an AR-V7+ castration-resistant prostate cancer (CRPC) xenograft model," Endocrinology, vol. 77, No. 13 Supplement (2017), Abstract 1588.

Rahim, B., et al., "AR Signaling in Breast Cancer," Cancers, vol. 9, No. 3 (2017), Article 21, 26 pages.

* cited by examiner

A

A

B

A

B

C

B

| | Estimate | Std. Error | z value | Pr(>\|z\|) |
|---|---|---|---|---|
| (Intercept) | -5.8857 | 2.7152 | -2.17 | 0.0302 |
| age | 0.1093 | 0.0525 | 2.08 | 0.0374 |
| baselineTreatmentTAX | 0.1332 | 1.6452 | 0.08 | 0.9355 |
| Cytoplasmic | 3.4217 | 1.8634 | 1.84 | 0.0663 |
| treatmentM | 1.3938 | 1.0739 | 1.30 | 0.1943 |
| treatmentP | 19.7244 | 2648.1119 | 0.01 | 0.9941 |
| baselineTreatmentTAX:Cytoplasmic | -4.8944 | 2.6918 | -1.82 | 0.0690 |

METHODS OF TREATING CANCER USING ANDROGEN RECEPTOR ANTAGONISTS

CROSS-REFERENCE TO RELATED APPLICATIONS

This application is the U.S. National Phase application filed under 35 U.S.C. § 371 claiming benefit to International Patent Application No. PCT/AU2020/051146, filed on Oct. 23, 2020, which is entitled to priority of Australian Patent Application No. 2019904027, filed on Oct. 25, 2019, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206142-0012-00US_Sequence_Listing.txt" in ASCII format. The text file containing the Sequence Listing of the present application was created on Apr. 22, 2022.

TECHNICAL FIELD

The present disclosure generally relates to cancer and methods of treating and diagnosing cancer.

BACKGROUND

Cancer cells can undergo bi-directional conversions between a poorly tumourigenic state and a highly tumourigenic state. This cellular plasticity is often observed when cancer cells initiate tumours, metastasise and evade conventional chemotherapies. However, the regulation of this process has yet to be fully elucidated.

Numerous studies have shown that histological grading provides useful prognostic information in breast cancer. For example, in the clinic, estrogen, progesterone and androgen receptors are scored on nuclear expression (Elston and Ellis, 2002) in an effort to provide such prognostic information. However, cytoplasmic expression has not been explored in this context.

SUMMARY

The present disclosure is based at least in part on the inventors' finding that activation of the androgen receptor is associated with the transition of poorly aggressive cancer cells to a highly aggressive state. The inventors have demonstrated that inhibiting the androgen receptor with an androgen receptor antagonist inhibits the transition of cancer cells from the poorly aggressive state to the highly aggressive state. For cancer cells that already exist in a highly aggressive state, inhibiting the androgen receptor decreases their aggressiveness. The present disclosure also demonstrates that standard-of-care chemotherapy promotes poorly aggressive cancer cells to transition into a highly aggressive state, and that the addition of an androgen receptor antagonist inhibits this process. The inventors have further demonstrated that the presence of the androgen receptor and/or zinc finger E-box-homeobox 1 (ZEB1) in the cytoplasm of a cancer cell is an indicator of that cancer cell's likely response to treatment, such as treatment with a chemotherapeutic agent.

Accordingly, disclosed herein are new methods of sensitizing cancer cells to an anti-cancer agent, methods of inhibiting the development of resistance of a cancer cell to an anti-cancer agent, and methods of inhibiting cancer cell proliferation, each comprising administering an androgen receptor antagonist. Also disclosed herein are methods of determining the prognosis of a subject suffering from cancer, methods of selecting a subject for therapy with an anti-cancer agent and methods of predicting a subject's response to an anti-cancer agent, each comprising determining the level of expression and/or activity of the androgen receptor and/or ZEB1 in the cytoplasm.

In one aspect, the present disclosure provides a method of sensitizing a cancer cell in a subject to an anti-cancer agent, comprising administering to the subject an androgen receptor antagonist.

The methods disclosed herein may further comprise determining whether a cancer cell is a poorly tumourigenic cell or a highly tumourigenic cell.

The cancer cell may be a poorly tumourigenic cell or a highly tumourigenic cell. The cancer cell may be a $CD44^{Lo}$ cell or a $CD44^{Hi}$ cell. The cancer cell may be resistant to an anti-cancer therapy.

The methods disclosed herein may comprise impeding or preventing the development of resistance to the anti-cancer agent.

The methods disclosed herein may comprise inhibiting proliferation of a $CD44^{Hi}$ cell or reducing resistance of a $CD44^{Hi}$ cell to an anti-cancer agent.

The anti-cancer agent may be a chemotherapeutic agent. For example, the anti-cancer agent may be selected from the group consisting of: docetaxel, paclitaxel and doxorubicin.

The androgen receptor antagonist may be selected, for example, from the group consisting of: Seviteronel, Enzalutamide, Abiraterone and Bicalutamide. It will be appreciated that the androgen receptor antagonist may be administered separately, simultaneously or sequentially with the anti-cancer agent. Preferably, the androgen receptor antagonist is administered before the anti-cancer agent.

The androgen receptor antagonist may be an inhibitor of CYP17A1. The CYP17A1 inhibitor may be a selective inhibitor of 17,20-lyase. In one example, the androgen receptor antagonist is Seviteronel. In one example, the androgen receptor antagonist may be incapable of being metabolised to form an androgen receptor agonist.

Any of the methods disclosed herein may comprise determining the level of expression and/or activity of the androgen receptor in the cell. Alternatively or in addition, any methods disclosed herein may comprise determining the level of expression and/or activity of ZEB1 in the cell.

The methods disclosed herein may comprise determining the level of expression and/or activity of the androgen receptor in the cytoplasm of the cell. Alternatively or in addition, the methods disclosed herein may comprise determining the level of expression and/or activity of ZEB1 in the cytoplasm of the cell. The methods disclosed herein may comprise determining the level of expression and/or activity of the androgen receptor and/or ZEB1 in the cytoplasm of the cell, or in the nucleus of the cell, or both, so as to provide a measure of the relative amount of expression and/or activity of the androgen receptor in the cytoplasm compared to the nucleus.

The determination of the level of expression and/or activity of the androgen receptor and/or ZEB1 in the cell may be performed actively by experimentation, for example, by performing a measurement of the level of expression and/or activity of the androgen receptor and/or ZEB1 in the cell.

Alternatively, the determination may be made based on an analysis of a measurement that has previously been made. Thus, any of the methods disclosed herein may not require actively determining the level of expression and/or activity of the androgen receptor in the cell (for example, in the cytoplasm). Similarly, any of the methods disclosed may not require actively determining the level of expression and/or activity of ZEB1 in the cell (for example, in the cytoplasm). Instead, any of the methods disclosed herein may comprise a determination that is made based on an analysis of a measurement that has previously been made.

For example, the present disclosure provides a method of sensitizing a cancer cell in a subject to an anti-cancer agent, in which the level of expression and/or activity of the androgen receptor and/or ZEB1 in the cell (for example, in the cytoplasm) has been determined, the method comprising administering to the subject an androgen receptor antagonist. The method may comprise administering to the subject an androgen receptor antagonist if the level of expression and/or activity of the androgen receptor and/or ZEB1 in the cell (for example, in the cytoplasm) is low.

Similarly, the methods disclosed herein may comprise determining whether a cancer cell is poorly tumourigenic or highly tumourigenic, and/or whether a cancer cell is a $CD44^{Lo}$ cell or a $CD44^{Hi}$ cell, by performing a measurement of tumourigenicity and/or CD44 expression. Alternatively, the determination may be made based on an analysis of a measurement that has previously been made.

Thus, the methods disclosed herein may comprise providing, or having provided, a measurement of the level of expression and/or activity of androgen receptor and/or ZEB1 in a cell (for example, in the cytoplasm). Alternatively or in addition, the methods disclosed herein may comprise assessing, or having assessed, a test sample obtained from a subject, wherein the assessment is or has been performed to allow determination of level of expression and/or activity of androgen receptor and/or ZEB1 in a cell (for example, in the cytoplasm) in the test sample. The methods may comprise administering to the subject an androgen receptor antagonist if the level of expression and/or activity of the androgen receptor and/or ZEB1 is low. The subject may be a subject suffering from, or suspected of suffering from cancer. The subject may be a subject who has been identified as being resistant to chemotherapy.

In another aspect, the present disclosure provides a method of inhibiting the development of resistance to an anti-cancer agent in a cancer cell in a subject, the method comprising:

determining the level of expression and/or activity of the androgen receptor in the cancer cell; and administering to the subject an androgen receptor antagonist if the level of expression and/or activity of the androgen receptor is low.

Further, the present disclosure provides a method of inhibiting the development of resistance to an anti-cancer agent in a cancer cell in a subject, the method comprising:

administering to the subject an androgen receptor antagonist if the level of expression and/or activity of the androgen receptor in the cancer cell has been determined to be low.

In another aspect, the present disclosure provides a method of inhibiting the development of resistance to an anti-cancer agent in a breast cancer cell in a subject, the method comprising:

determining the level of expression and/or activity of the androgen receptor in the cancer cell; and administering to the subject an androgen receptor antagonist if the level of expression and/or activity of the androgen receptor is low.

Further, the present disclosure provides a method of inhibiting the development of resistance to an anti-cancer agent in a breast cancer cell in a subject, the method comprising:

administering to the subject an androgen receptor antagonist if the level of expression and/or activity of the androgen receptor in the cancer cell has been determined to be low.

Alternatively or in addition, the present disclosure provides a method of inhibiting the development of resistance to an anti-cancer agent in a cancer cell in a subject, the method comprising:

determining the level of expression and/or activity of ZEB1 in the cancer cell; and administering to the subject an androgen receptor antagonist if the level of expression and/or activity of ZEB1 is low.

Further, the present disclosure provides a method of inhibiting the development of resistance to an anti-cancer agent in a cancer cell in a subject, the method comprising:

administering to the subject an androgen receptor antagonist if the level of expression and/or activity of ZEB1 in the cancer cell has been determined to be low.

Alternatively or in addition, the present disclosure provides a method of inhibiting the development of resistance to an anti-cancer agent in a breast cancer cell in a subject, the method comprising:

determining the level of expression and/or activity of ZEB1 in the cancer cell; and administering to the subject an androgen receptor antagonist if the level of expression and/or activity of ZEB1 is low.

Further, the present disclosure provides a method of inhibiting the development of resistance to an anti-cancer agent in a breast cancer cell in a subject, the method comprising:

administering to the subject an androgen receptor antagonist if the level of expression and/or activity of ZEB1 in the breast cancer cell has been determined to be low.

In another aspect, the present disclosure provides a method of inhibiting the proliferation of a cancer cell in a subject, the method comprising:

determining the level of expression and/or activity of the androgen receptor in the cancer cell; and administering to the subject an androgen receptor antagonist if the level of expression and/or activity of the androgen receptor is high.

Further, the present disclosure provides a method of inhibiting the proliferation of a cancer cell in a subject, the method comprising:

administering to the subject an androgen receptor antagonist if the level of expression and/or activity of the androgen receptor in the cancer cell has been determined to be high.

In another aspect, the present disclosure provides a method of inhibiting the proliferation of a breast cancer cell in a subject, the method comprising:

determining the level of expression and/or activity of the androgen receptor in the cancer cell; and administering to the subject an androgen receptor antagonist if the level of expression and/or activity of the androgen receptor is high.

Further, the present disclosure provides a method of inhibiting the proliferation of a breast cancer cell in a subject, the method comprising:

administering to the subject an androgen receptor antagonist if the level of expression and/or activity of the androgen receptor in the breast cancer cell has been determined to be high.

Alternatively or in addition, the present disclosure provides a method of inhibiting the proliferation of a cancer cell in a subject, the method comprising:

determining the level of expression and/or activity of ZEB1 in the cancer cell; and administering to the subject an androgen receptor antagonist if the level of expression and/or activity of ZEB1 is high.

Further, the present disclosure provides a method of inhibiting the proliferation of a cancer cell in a subject, the method comprising:

administering to the subject an androgen receptor antagonist if the level of expression and/or activity of ZEB1 in the cancer cell has been determined to be high.

Alternatively or in addition, the present disclosure provides a method of inhibiting the proliferation of a breast cancer cell in a subject, the method comprising:

determining the level of expression and/or activity of ZEB1 in the cancer cell; and administering to the subject an androgen receptor antagonist if the level of expression and/or activity of ZEB1 is high.

Further, the present disclosure provides a method of inhibiting the proliferation of a breast cancer cell in a subject, the method comprising:

administering to the subject an androgen receptor antagonist if the level of expression and/or activity of ZEB1 in the breast cancer cell has been determined to be high.

The level of expression and/or activity of the androgen receptor and/or ZEB1 is determined in the cytoplasm of the cell. The cell may be a breast cancer cell. The breast cancer may be triple negative breast cancer.

In another aspect, the present disclosure provides a method of determining the prognosis of a subject suffering from cancer, the method comprising determining the presence of the androgen receptor in the cytoplasm of a cell, wherein the presence of the androgen receptor in the cytoplasm indicates a poor prognosis. Alternatively or in addition, the present disclosure provides a method of determining the prognosis of a subject suffering from cancer, the method comprising determining the presence of ZEB1 in the cytoplasm of a cell, wherein the presence of ZEB1 in the cytoplasm indicates a poor prognosis.

Thus, a lower amount of the androgen receptor in the cytoplasm of the cell may indicate a better prognosis. Alternatively or in addition, a lower of amount ZEB1 in the cytoplasm of the cell may indicate a better prognosis.

In another aspect, the present disclosure provides a method of selecting a subject for therapy with an anti-cancer agent, the method comprising determining the level of expression and/or activity of the androgen receptor in the cytoplasm of a cell of the subject, wherein if the level of expression and/or activity of the androgen receptor is low, the subject is selected for treatment with the anti-cancer agent. Alternatively or in addition, the present disclosure provides a method of selecting a subject for therapy with an anti-cancer agent, the method comprising determining the level of expression and/or activity of ZEB1 in the cytoplasm of a cell of the subject, wherein if the level of expression and/or activity of ZEB1 is low, the subject is selected for treatment with the anti-cancer agent.

In another example, the present disclosure provides a method of selecting a subject for therapy with an anti-cancer agent, the method comprising determining the level of expression and/or activity of the androgen receptor in the cytoplasm of a cell of the subject, wherein if the level of expression and/or activity of the androgen receptor is high, the subject is selected for treatment with the anti-cancer agent.

Alternatively or in addition, the present disclosure provides a method of selecting a subject for therapy with an anti-cancer agent, the method comprising determining the level of expression and/or activity of ZEB1 in the cytoplasm of a cell of the subject, wherein if the level of expression and/or activity of ZEB1 is high, the subject is selected for treatment with the anti-cancer agent.

In one embodiment, if the subject is selected for treatment with the anti-cancer agent, the subject may also be selected for treatment with an androgen receptor antagonist.

The methods disclosed herein may further comprise administering the anti-cancer agent. Alternatively or in addition, the methods disclosed herein may further comprise administering the androgen receptor antagonist.

In another aspect, the present disclosure provides a method of predicting the response of a subject to an anti-cancer agent, the method comprising determining the level of expression and/or activity of the androgen receptor in the subject, wherein a low level of expression and/or activity of the androgen receptor in the subject is indicative that the subject's response to the anti-cancer agent alone is decreased relative to the subject's response to the anti-cancer agent when administered with an androgen receptor antagonist. Alternatively or in addition, the present disclosure provides a method of predicting the response of a subject to an anti-cancer agent, the method comprising determining the level of expression and/or activity of ZEB1 in the subject, wherein a low level of expression and/or activity of ZEB1 in the subject is indicative that the subject's response to the anti-cancer agent alone is decreased relative to the subject's response to the anti-cancer agent when administered with an androgen receptor antagonist.

In another aspect, the present disclosure provides a method of enhancing the efficacy of an anti-cancer therapy, comprising administering or co-administering an androgen receptor antagonist.

In another aspect, the present disclosure provides a pharmaceutical composition comprising an androgen receptor antagonist and an anti-cancer agent. The pharmaceutical composition may be for use in treating cancer.

In another aspect, the present disclosure provides a method of preparing the pharmaceutical composition, comprising combining an androgen receptor antagonist and an anti-cancer agent.

In another aspect, the present disclosure provides the use of an androgen receptor antagonist and an anti-cancer agent in the manufacture of a medicament for the treatment of cancer.

The androgen receptor antagonist may be selected from the group consisting of: Seviteronel, Enzalutamide, Abiraterone and Bicalutamide. The androgen receptor antagonist may be an inhibitor of CYP17A1. The CYP17A1 inhibitor may be a selective inhibitor of 17,20-lyase. In one example, the androgen receptor antagonist is Seviteronel.

In any of the methods and uses disclosed herein, the cancer may be breast cancer. For example, the breast cancer may be triple negative breast cancer.

In another aspect, the present disclosure provides a pharmaceutical composition comprising Seviteronel and an anti-cancer agent for use in treating triple negative breast cancer.

In another aspect, the present disclosure provides a method of preparing the pharmaceutical composition, comprising combining Seviteronel and an anti-cancer agent.

In another aspect, the present disclosure provides the use of Seviteronel and an anti-cancer agent in the manufacture of a medicament for the treatment of triple negative breast cancer.

The anti-cancer agent may be a chemotherapeutic agent. The anti-cancer agent may be selected from the group consisting of: docetaxel, paclitaxel and doxorubicin. In one example, the anti-cancer agent is docetaxel. In another example, the anti-cancer agent is paclitaxel. In another example, the anti-cancer agent is doxorubicin.

BRIEF DESCRIPTION OF THE DRAWINGS

The following figures form part of the present specification and are included to further demonstrate certain aspects of the present disclosure. The disclosure may be better understood by reference to one or more of these figures in combination with the detailed description of specific embodiments presented herein.

A. Triple-negative breast cancer can be classified into four molecular subtypes with distinct prognoses based on overall survival and distant metastasis-free survival (DMFS): Basal-like 1 (BL1), Basal-Like 2 (BL2), Luminal Androgen Receptor (LAR), and Mesenchymal (M)(Lehmann et al., 2016). B. Subpopulations of breast cancer cells from multiple breast cancer cell lines based on CD44 and CD104 expression profiles were isolated and RNAseq was performed to identify a signalling network driving cell plasticity. C. $CD44^{Hi}$ cells indeed classify differently to their matched $CD44^{Lo}$ counterparts. According to the Lehmann et al., 2016 molecular subtypes, $CD44^{Lo}$ cells are called 'BL1 or BL2', while the $CD44^{Hi}$ cells are called 'M' (UMAP analysis, FIG. 3C). Hence, bulk signatures do not define molecular programs operating in minority subpopulations.

Figure 2:
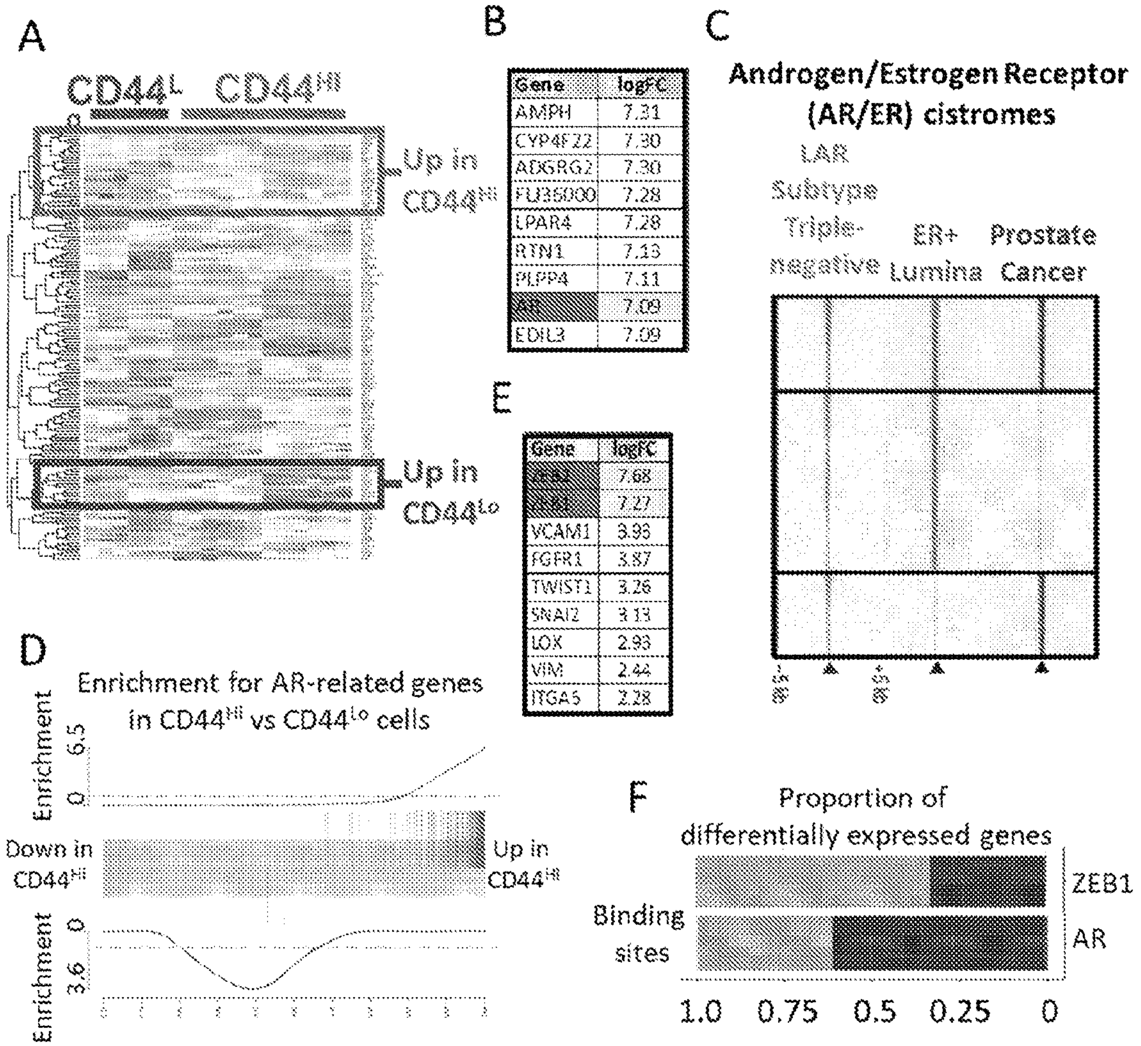

FIG. 2. Androgen receptor signalling regulated cancer cell plasticity

A. Heat map showing differentially expressed genes between HMLER and HCC38 CD44Lo and CD44Hi cells. B. Table listing highly ranked differentially expressed genes that include Androgen Recpetor (AR). C. ChIPseq analysis comparing binding patterns of AR or ER in triple-negative breast cancer, ER+luminal breast cancer and prostate cancer (Hickey et al., 2012). D. Barcode plots showing that AR-regulated genes are enriched in the cohort of differentially expressed genes in $CD44^{Hi}$ cells. F. Bar graph showing a high proportion of genes with AR and ZEB1 binding sites in their promoters are differentially expressed between $CD44^{Hi}$ and $CD44^{Lo}$ cells.

Figure 3:
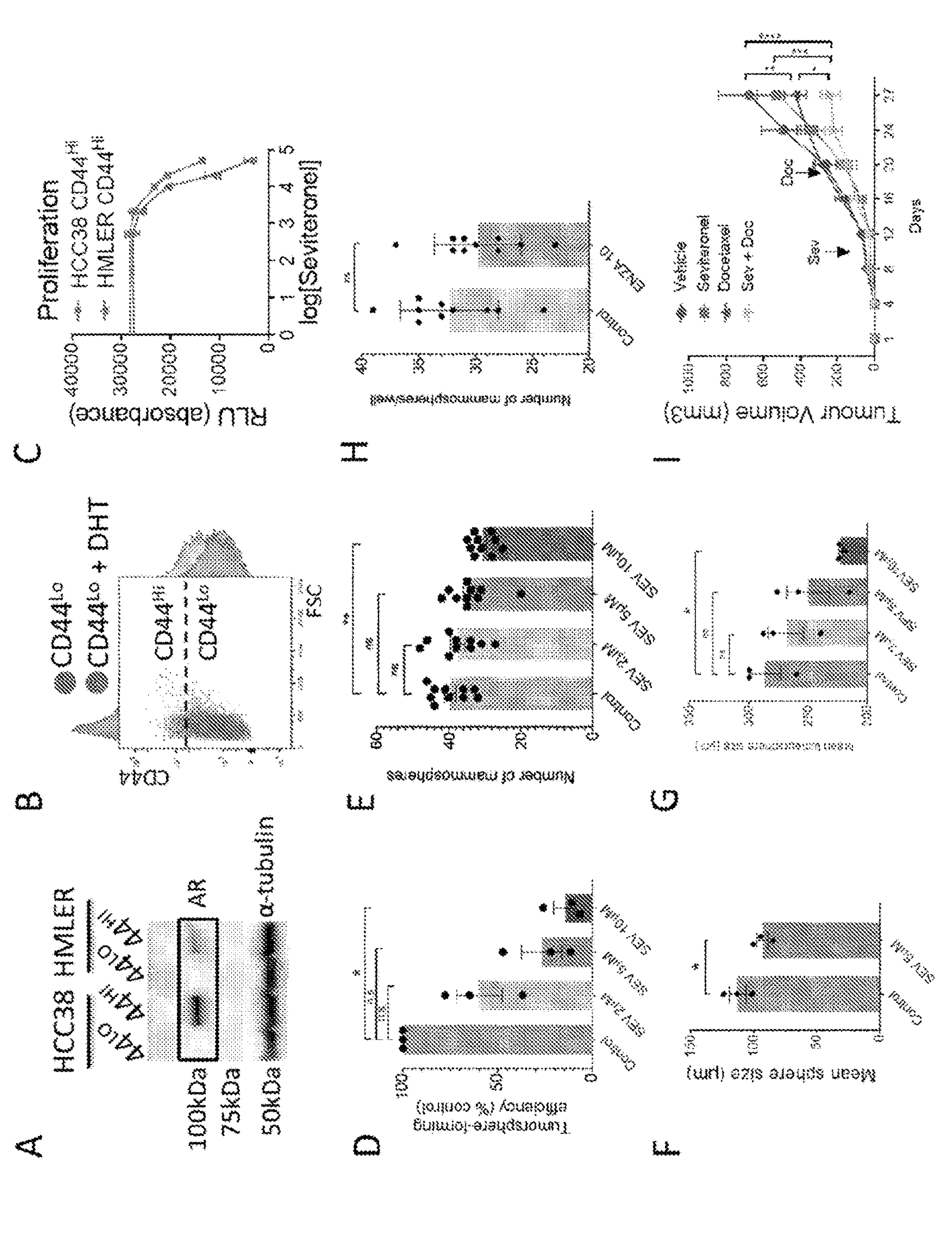

FIG. 3. AR activation increases CD44Lo-to-CD44Hi transitions. AR antagonism inhibits CD44Hi proliferation and tumoursphere forming ability.

A. Western blot showing that AR protein levels are up-regulated in CD44Hi cells compared to $CD44^{Lo}$ cells in HMLER and HCC38 cell lines. B. Flow cytometry analysis demonstrating the dihydrotestosterone (DHT) induces HMLER $CD44^{Lo}$ cells to switch to the $CD44^{Hi}$ state. C. Proliferation analysis demonstrating that Seviteronel inhibits the growth of $CD44^{Hi}$ cells isolated from HMLER and HCC38 cell lines. D. Tumoursphere analysis showing that Seviteronel dose-dependently inhibits tumoursphere-forming ability of $CD44^{Hi}$ cells. E. HCC38 CD44Hi cells, F. HMLER-CD44Hi cells). F-G. Seviteronel reduces the size of tumorspheres (F:HCC38 CD44Hi cells, G. HMLER-CD44Hi cells) H. Enzalutamide does not reduce tumorsphere-forming efficiency. I. Seviteronel+Docetaxel inhibits tumour growth significantly more than either Seviteronel or Docetaxel alone in a xenograft model of triple-negative breast cancer.

Figure 4:
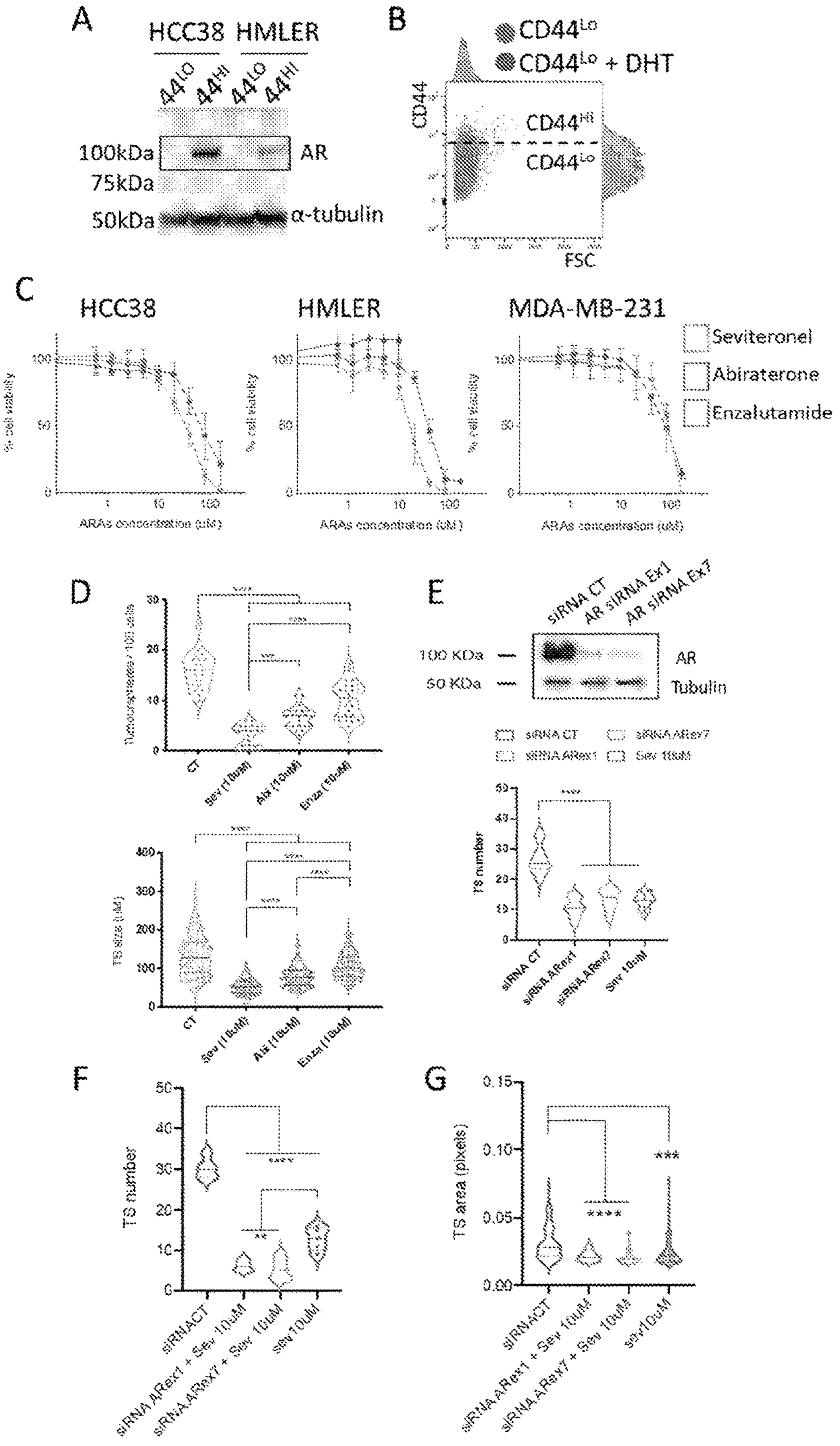

FIG. 4. Modifying AR signalling modulates CSC behaviour and plasticity

A. Western Blot analysis of the androgen receptor protein shows that it is differentially expressed between $CD44^{Lo}$ and $CD44^{Hi}$ cells. B. Flow cytometric analysis shows purified $CD44^{Lo}$ cells treated with the androgen receptor agonist dihydrotestosterone (DHT) transition into the $CD44^{Hi}$ state. Thus, androgen receptor activation drives cellular plasticity. C and D. Seviteronel, Abiraterone and Enzalutamide decrease $CD44^{Hi}$ proliferation and tumoursphere formation. E. Transient knockdown of the Androgen Receptor (siRNA) reduces tumorsphere formation. F and G. The combination of Seviteronel+siRNA against AR further reduces tumorsphere formation and size.

Figure 5:
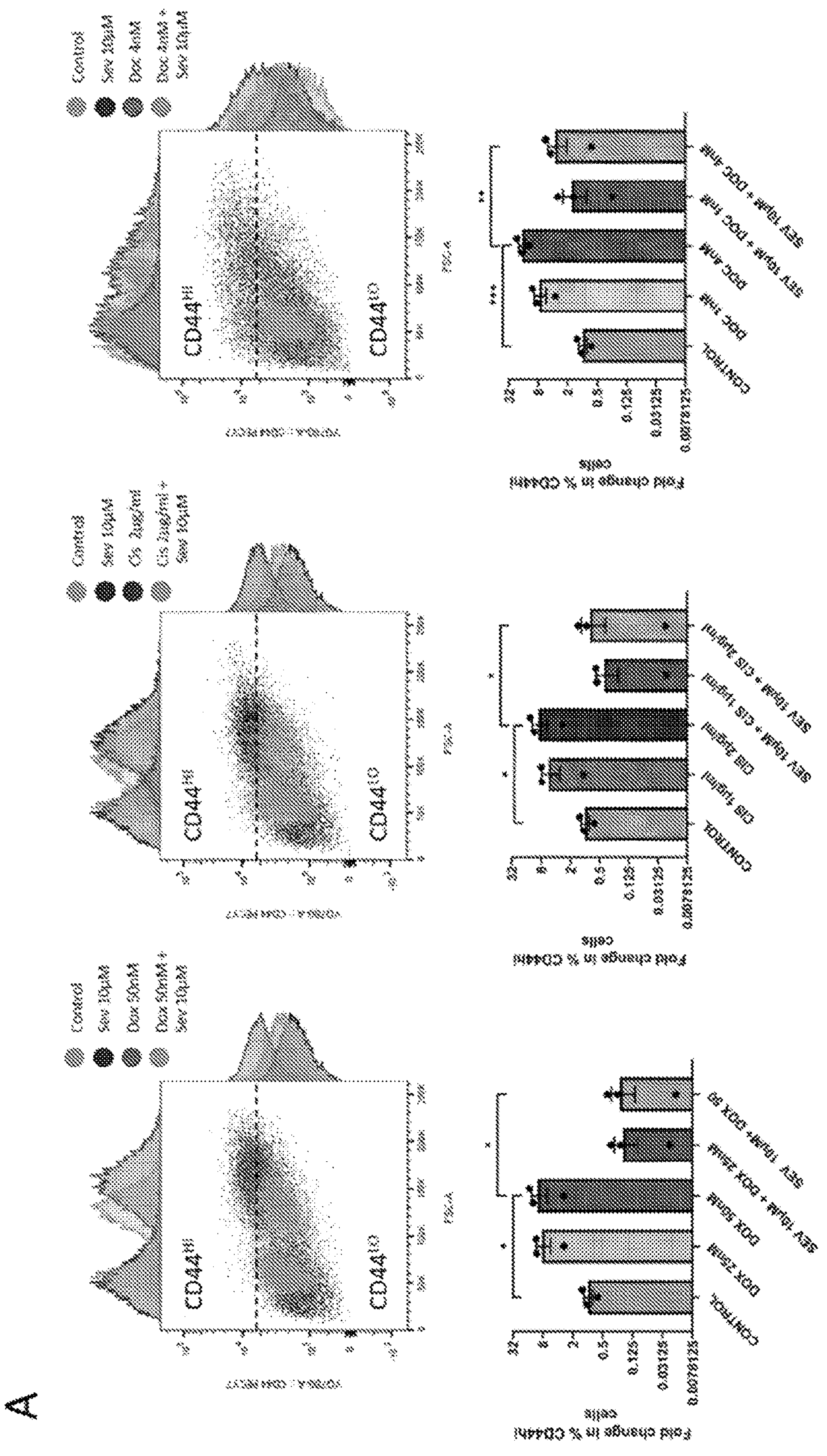
Figure 5:
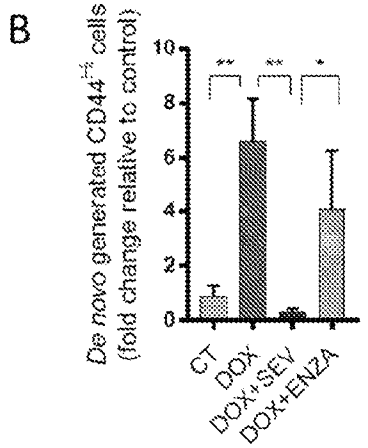

FIG. 5. Seviteronel inhibits chemotherapy-induced CD44Lo-to-CD44-Hi plasticity.

A. Flow cytometry analysis and quantification (bar graph) of CD44 status in HMLER cells. Doxycycline induces $CD44^{Lo}$ cells to switch to the $CD44^{Hi}$ state. Those transitions can be blocked by Seviteronel. B. Enzalutamide is not as effective as Seviteronel at blocking Doxorubicin-induced $CD44^{Lo}$-to-$CD44^{Hi}$ switching.

Figure 6:
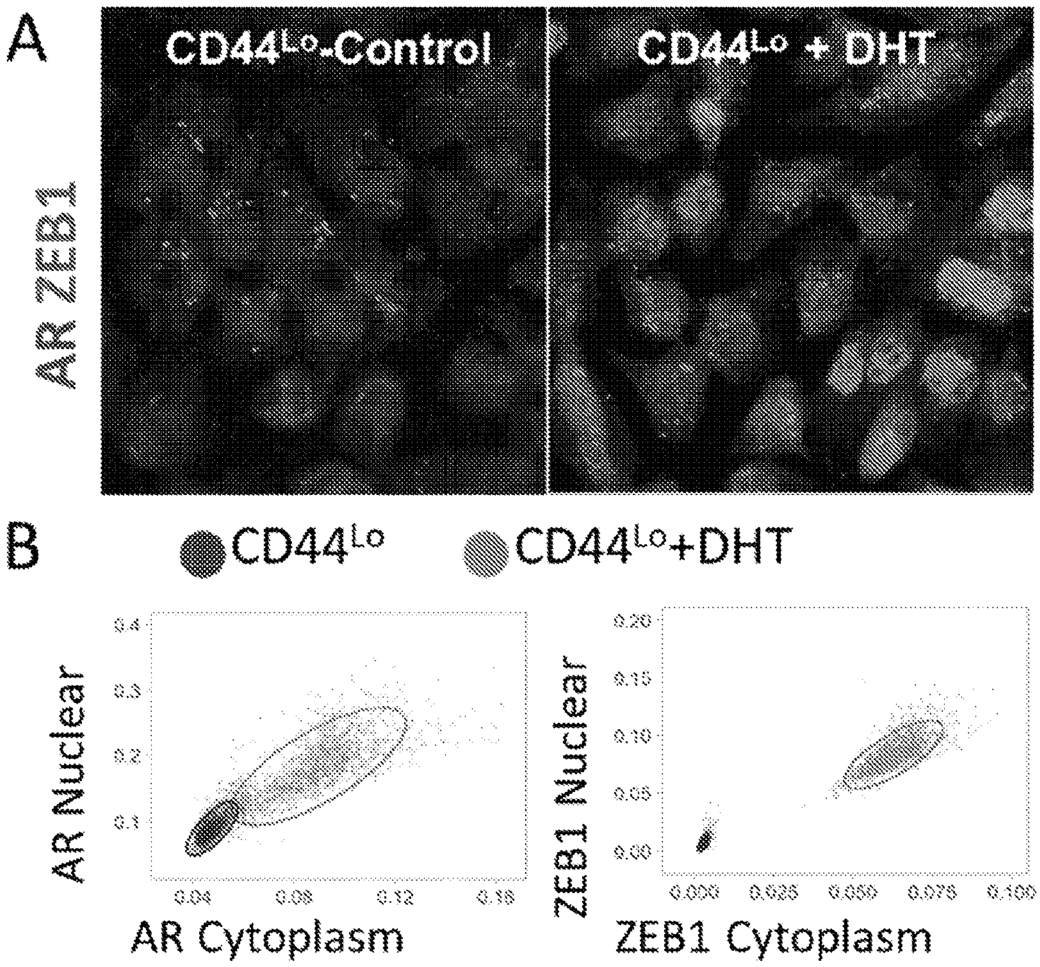

FIG. 6. DHT-induced changes in AR and ZEB1 localization and expression.

A. Immunofluorescence staining and quantification (B) for AR and ZEB1 in HMLER $CD44^{Lo}$ cells. Dihydrotestosterone (DHT) increases AR and ZEB1 protein levels in both the cytoplasm and nucleus.

Figure 7:
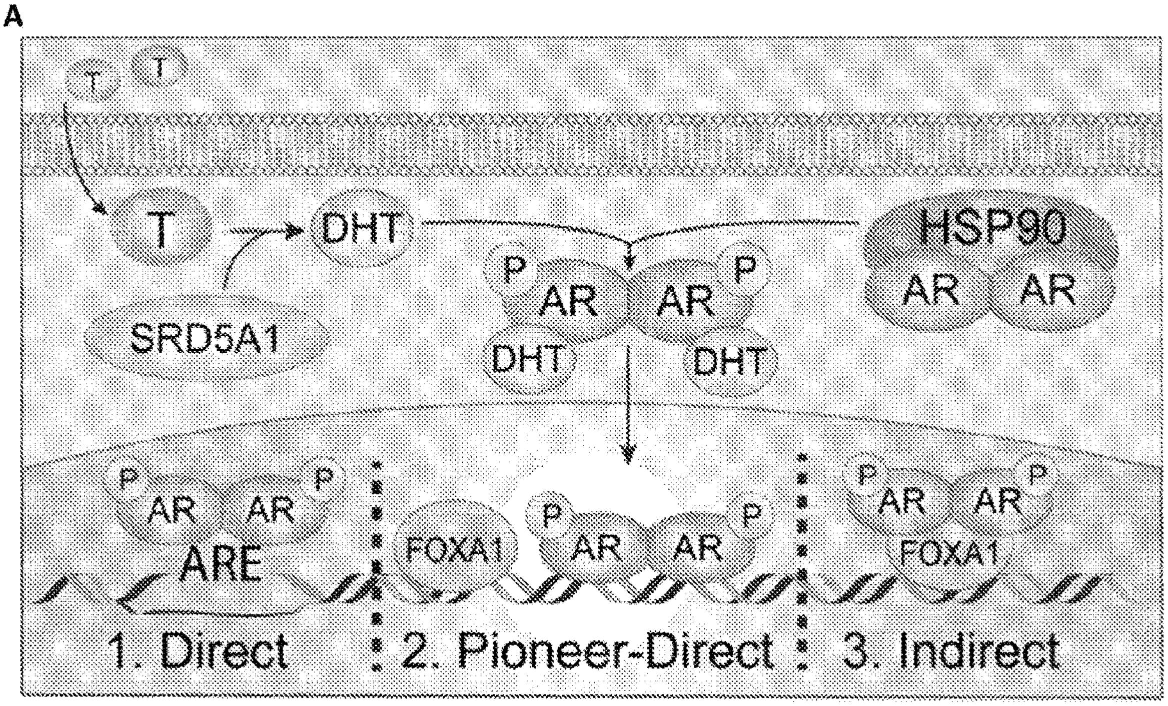
Figure 7:
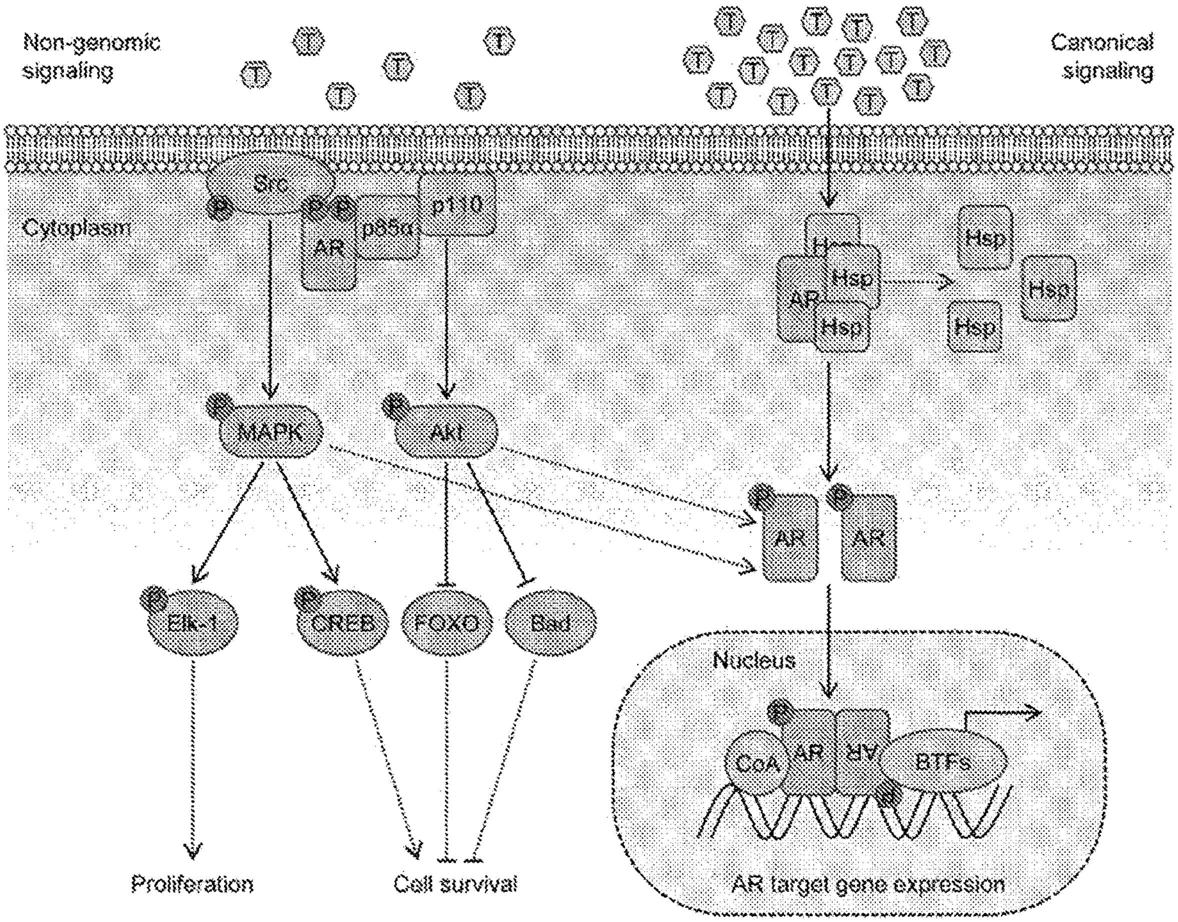

FIG. 7. Schematic of DHT regulating AR localization and signalling.

A. In the presence of testosterone (T) gets converted to dihydrotestosterone (DHT) within a cell. DHT can bind to AR causing a conformational change that enables AR to dissociate from heatshock proteins (e.g. HSP90) enabling it to translocate from the cytoplasm into the nucleus, where it can then activate gene transcription by 1) directly binding to androgen response elements (AREs), 2) bind to AREs made accessible by pioneering factors (e.g. FOXA1), or 3) indirectly bind to DNA by acting as a cofactor for other proteins. B. AR can interact with Src kinase and p85α regulatory subunit of phosphoinositide 3-kinase in the cytoplasm and activate mitogen-activated protein kinase (MAPK) and Akt pathways to enhance cell proliferation and survival in a non-genomic fashion (Leung and Sadar, 2017).

Figure 8:
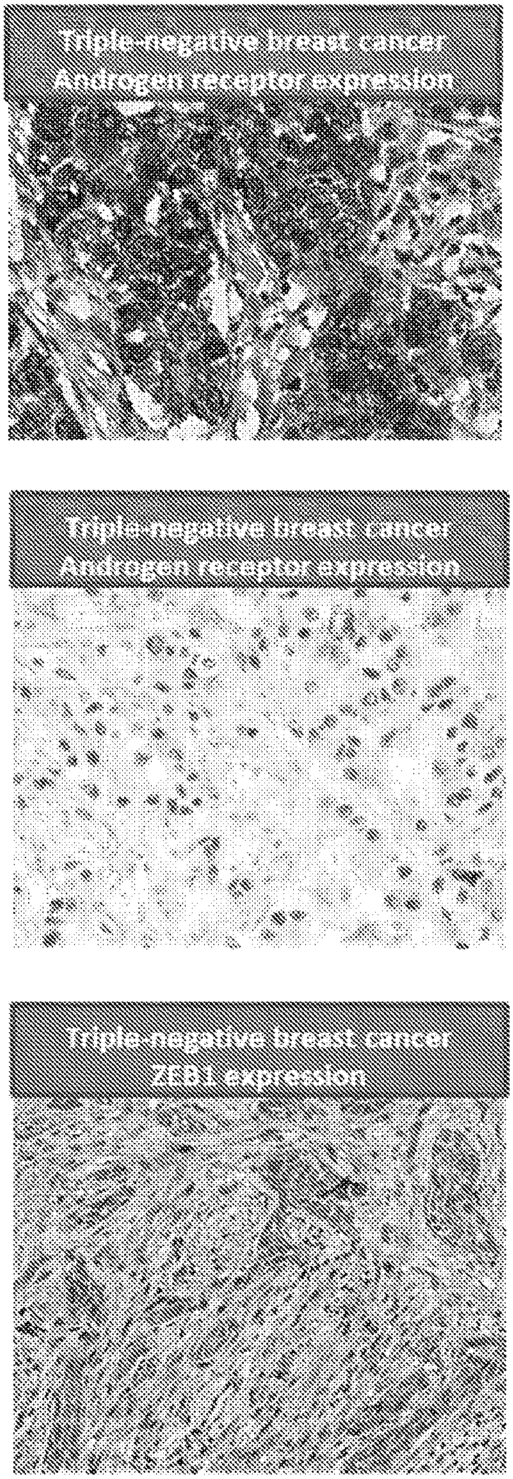
Figure 8:
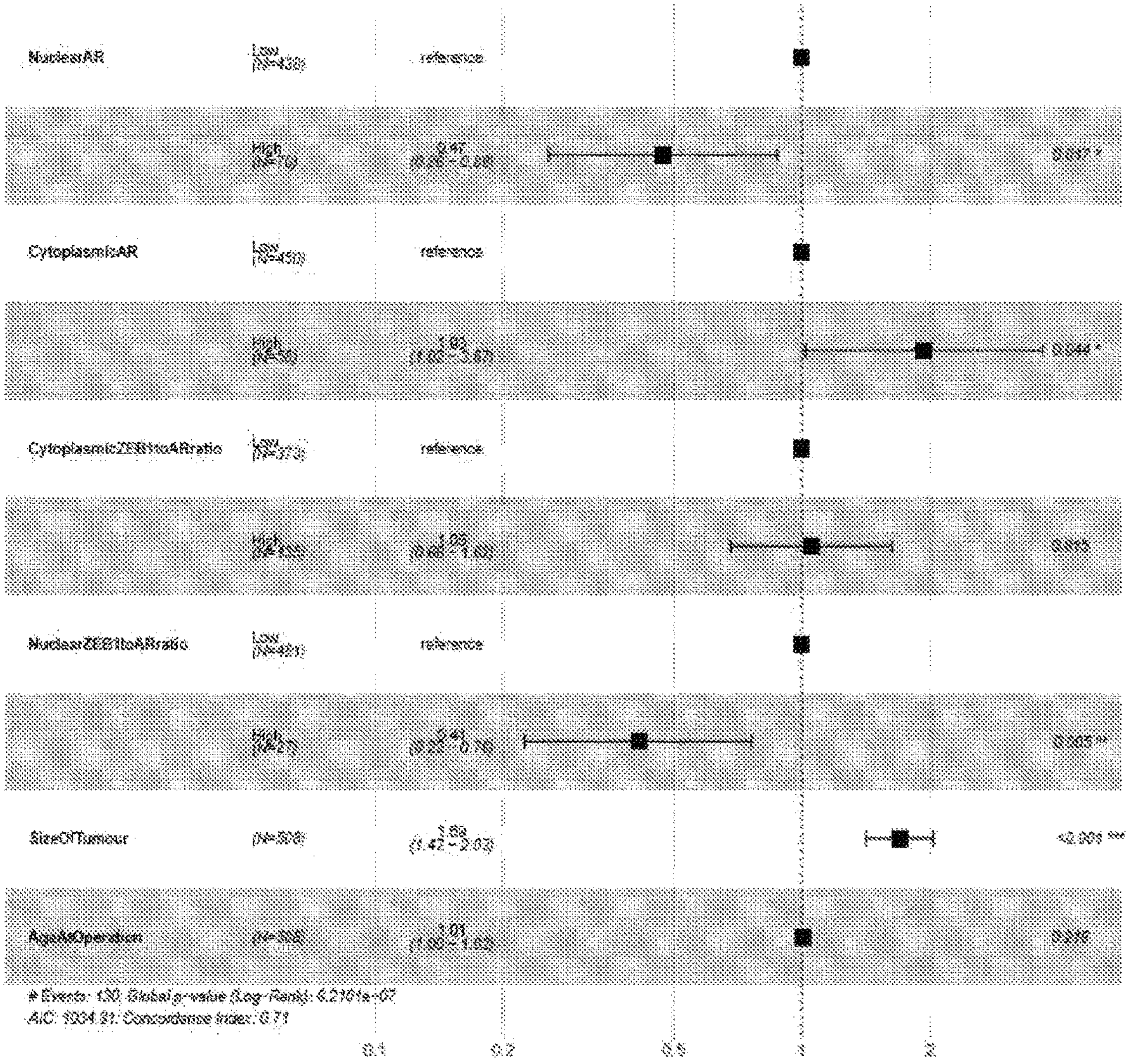
Figure 8:
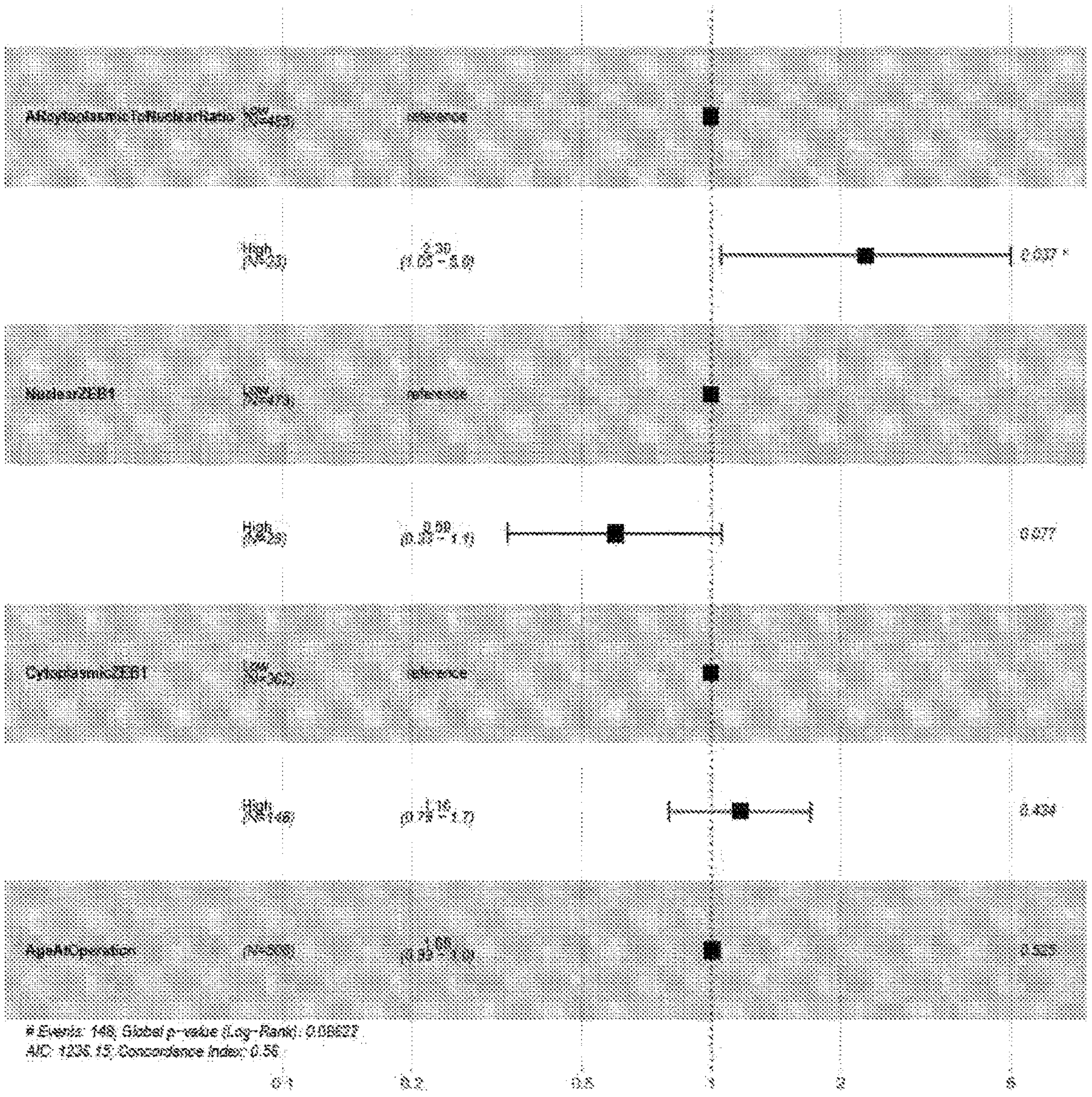

FIG. 8. Cytoplasmic androgen receptor expression or ZEB1 expression predicts poor prognosis.

A. Tissue microarrays of triple-negative breast cancer specimens were stained for androgen receptor (AR) or ZEB 1 expression. B. Cytoplasmic AR or ZEB1 expression was found to correlate with poor prognosis, whereas nuclear AR expression correlates with good prognosis. C. The ratio of cytoplasmic AR to nuclear AR is also a good indicator of prognosis, where a high cytoplasmic to nuclear ratio is associated with poor prognosis.

Figure 9:
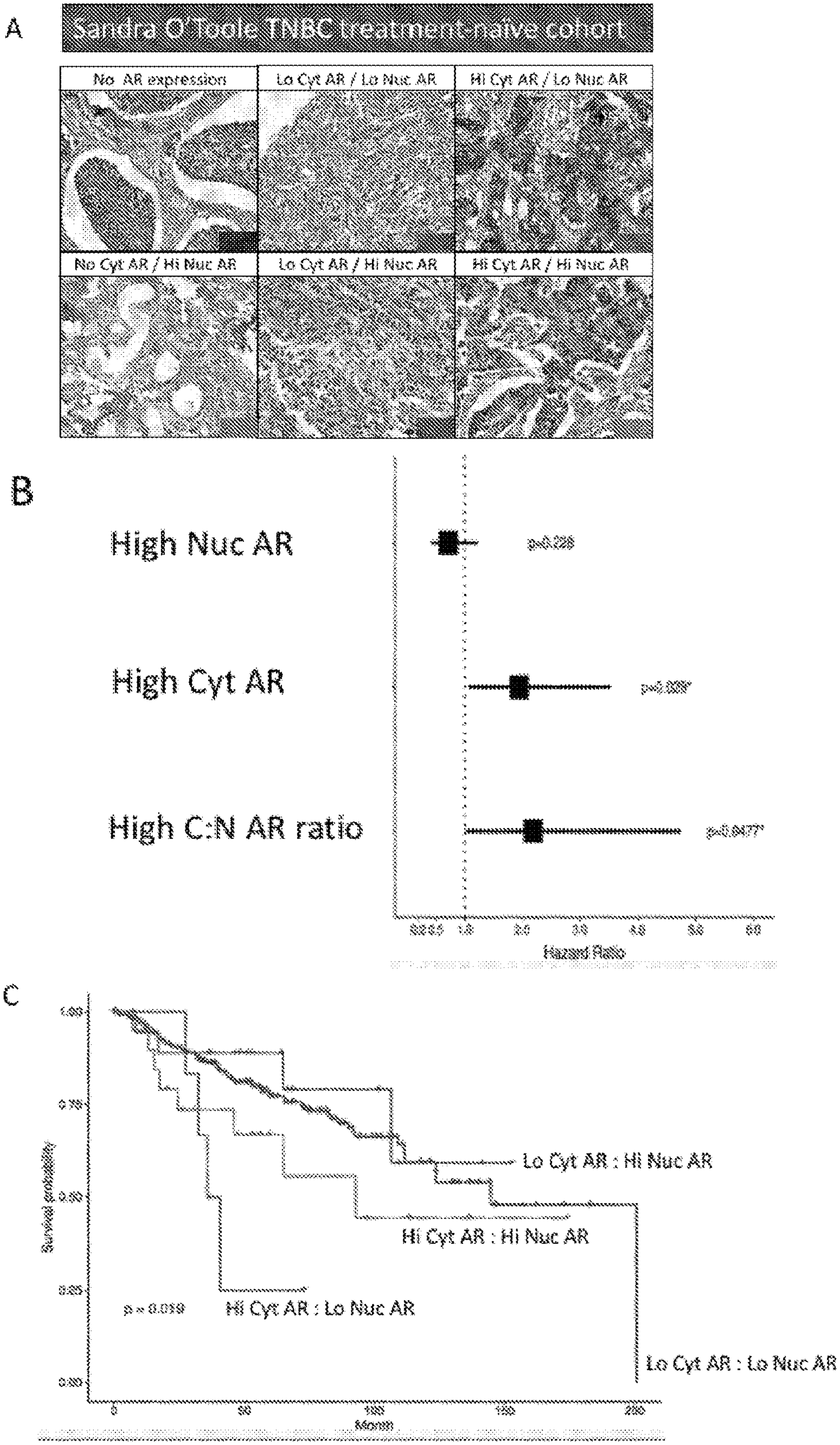

FIG. 9. High cytoplasmic AR and/or cyt:nuc AR ratio predicts poor prognosis in treatment-naïve triple-negative patients.

A. Representative immunohistochemistry images showing different categories of tumours based on cytoplasmic and nuclear AR expression. Top-left no AR expression, Top-center low cyt:low nuc AR, Top-right high cyt:low nuc AR, Bottom-left high nuc AR expression, Bottom-center low cyt:high nuc AR, Bottom-right high cyt:high nuc AR. B. Graph representing patient hazard ratio based on relative nuclear and cytoplasmic AR levels showing that high cytoplasmic AR expression, or a high AR cytoplasmic to nuclear ratio, predict poor outcome. C. Kaplan Meier curves showing significant poor patient survival for high cyt:nuc AR expression pattern. Cox Proportional Hazard models was used to determine the impact of Cyt AR and Cyt:Nuc AR ratio on survival probability.

Figure 10:
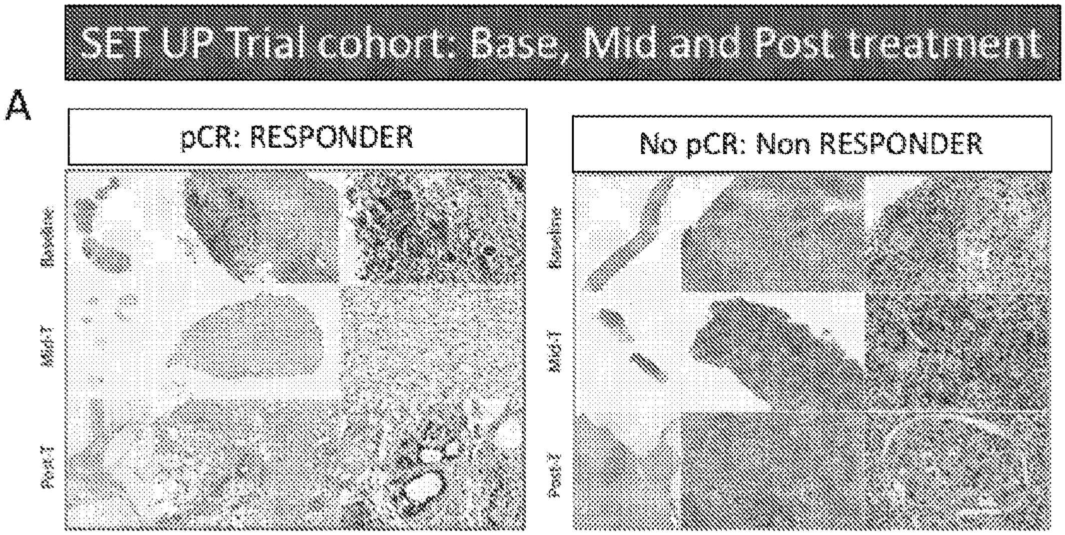

FIG. 10. High cytoplasmic AR at baseline is strongly associated with lack of therapeutic response to chemotherapy.

A. Representative immunohistochemistry images showing AR expression in patient biopsies at baseline (top row), mid-treatment (middle row) and post-treatment (bottom row). Left panel: pCR (responder). Right panel no pCR (no responder). Patients with high cytoplasmic AR expression pre-treatment do not respond well to chemotherapy evidenced by a poor pathological complete response. B. Summary table showing prognostic value for patient age, treatment type and cytoplasmic AR at baseline, mid and post-chemotherapy treatment. Cytoplasmic AR at baseline predicts lack of pCR at 10% type I error. Logistic Regression (generalized binomial model) was used to define the prognostic potential for AR cytoplasmic levels at Base, Mid and Post-treatment to predict PCR or no PCR.

Figure 11:
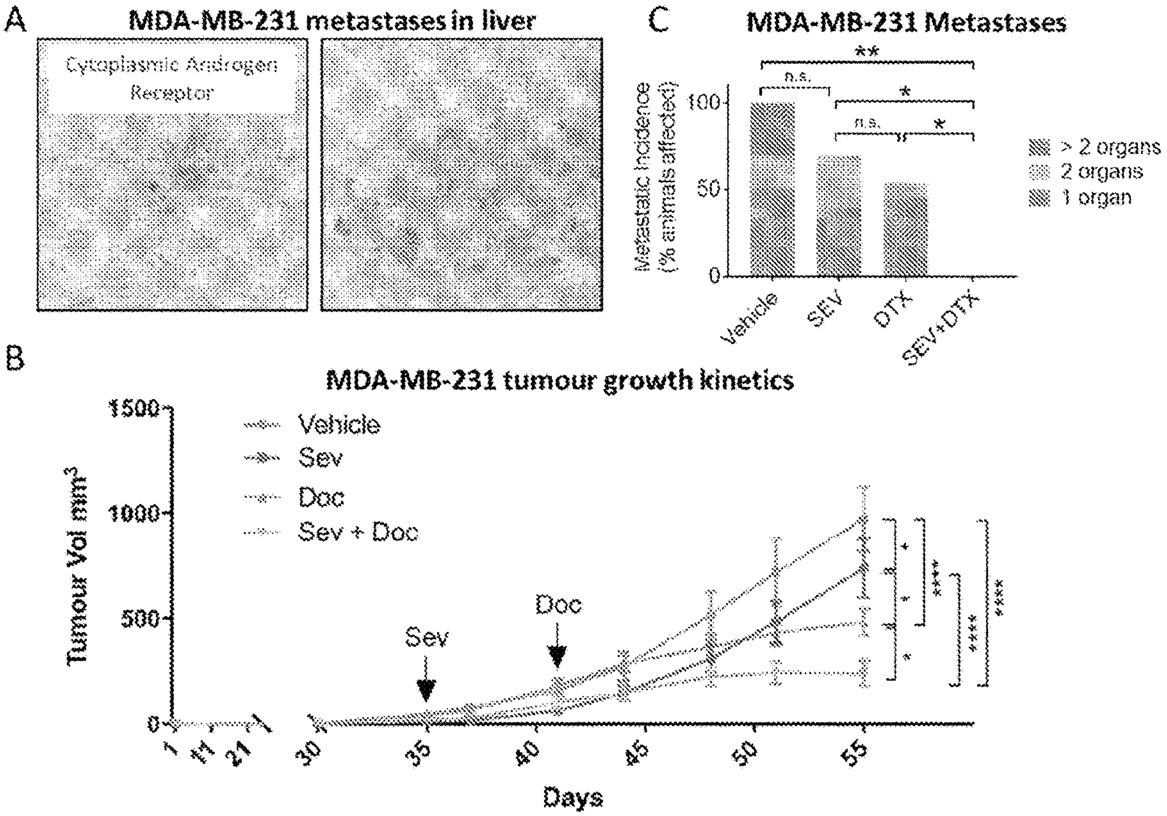

FIG. 11. Seviteronel sensitises a triple-negative breast cancer model expressing cytoplasmic androgen receptor to docetaxel.

A breast cancer xenograft model, MDA-MB-231 that expresses high levels of cytoplasmic androgen receptor in its primary tumour and metastases (liver metastasis shown in FIG. 11A) was subjected to no treatment, seviteronel alone, docetaxel chemotherapy alone, or seviteronel+docetaxel. Seviteronel alone significantly reduces tumour growth kinetics compared to control, docetaxel alone significantly reduces tumour growth compared to Seviteronel alone, and, notably, the combination of seviteronel+docetaxel significantly reduces tumour growth more than docetaxel alone (FIG. 11B). Moreover, the combination of seviteronel+docetaxel significantly reduced metastases more than any other single treatment (FIG. 11C).

Figure 12:
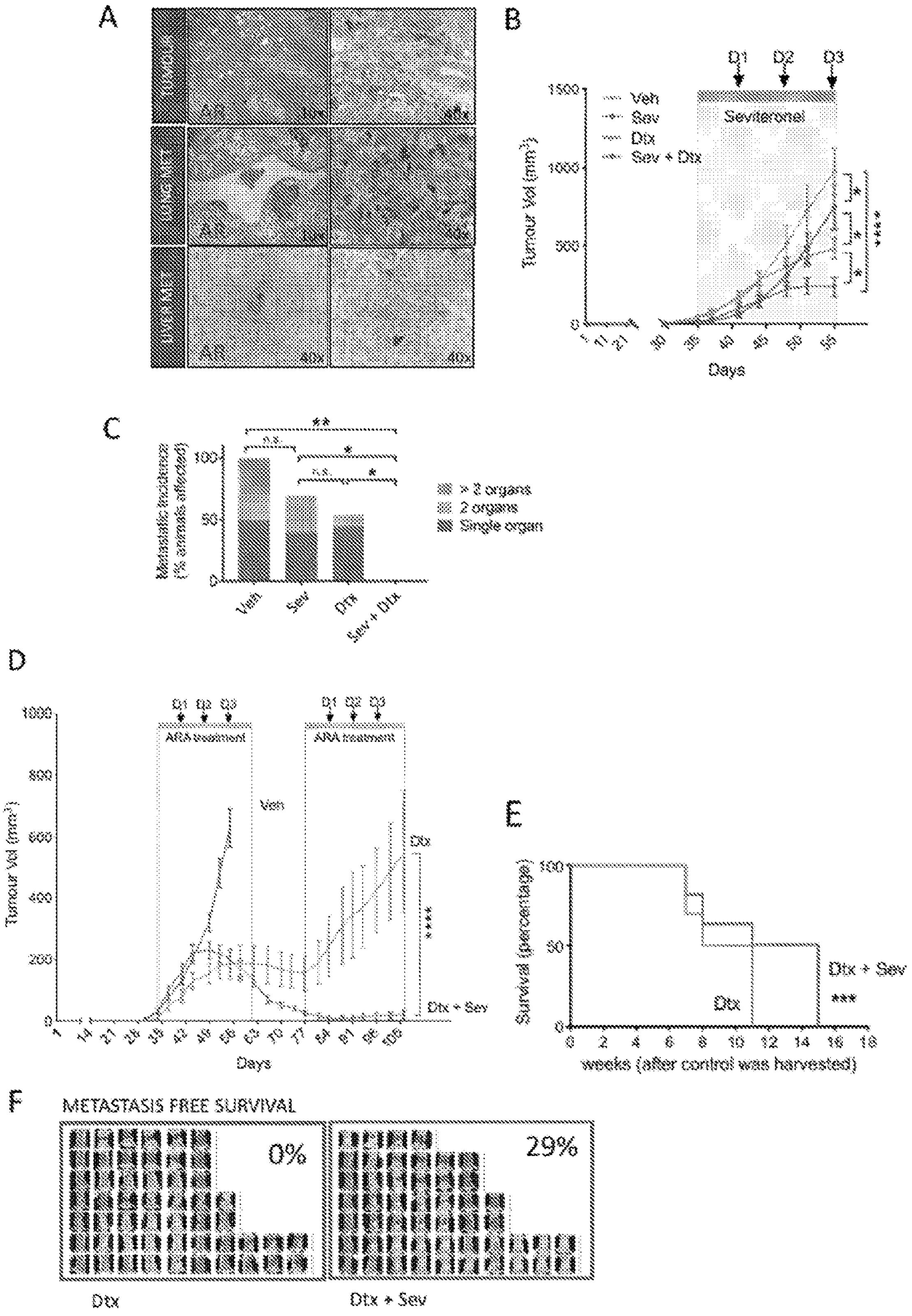

FIG. 12. Combination therapy (Seviteronel+Docetaxel) reduces/blocks tumour growth and metastasis development.

A. Immunohistochemistry images of MDA-MB-231 xenografts showing high cytoplasmic AR expression in matching primary tumour (top), lung metastasis (middle) and liver metastasis (bottom). B. Graphical representation of tumour growth evolution for Vehicle arm (Veh), Seviteronel (Sev), Docetaxel (Dtx) and docetaxel+Seviteronel. Seviteronel treatment was administrated daily (6 days a week) for 4 weeks. Seviteronel dose regime: 150 mg/kg/day for the 1st week, followed by 100 mg/kg/day for 3 weeks. Individual cycles are highlighted by grey boxes. 3 chemotherapy (Dtx 20 mg/kg) i.p injections (indicated as D1, D2, D3) were administrated starting one week after Seviteronel treatment commenced. Seviteronel treatment alone (*p-value<0.05) or in combination with Dtx (****p-value<0.0001) significantly reduces tumour growth compared with Veh treatmet arm. Dtx+Sev also shows significant benefit (*p-value<0.05) when compared with Dtx treatment alone. C. Graph representing metastatic incidence across treatment arms (defined by IVIS imaging) showing that the combination of Dtx+Sev significantly reduces metastatic burden compared to Sev or Dtx alone. D. Graphical representation of tumour growth evolution for Veh arm, Dtx, Dtx+Sev. Dtx+Sev treatment shows significant benefit compared with Dtx alone (*p-value<0.05). Kaplan-Meier curves representing significant survival benefit (***p-value<0.001) for Dtx+Sev compared with all other treatment arms. F. IVIS images showing metastatic burden within treatment arms for 10 weeks following commencement of second round of treatment (Day 77). Dtx+Sev combination therapy was the only group with animals clear of metastasis (29%) compared to 0% for Dtx. Percentage of animals showing metastasis free survival for the different groups are specified for each treatment inside each box.

Figure 13:
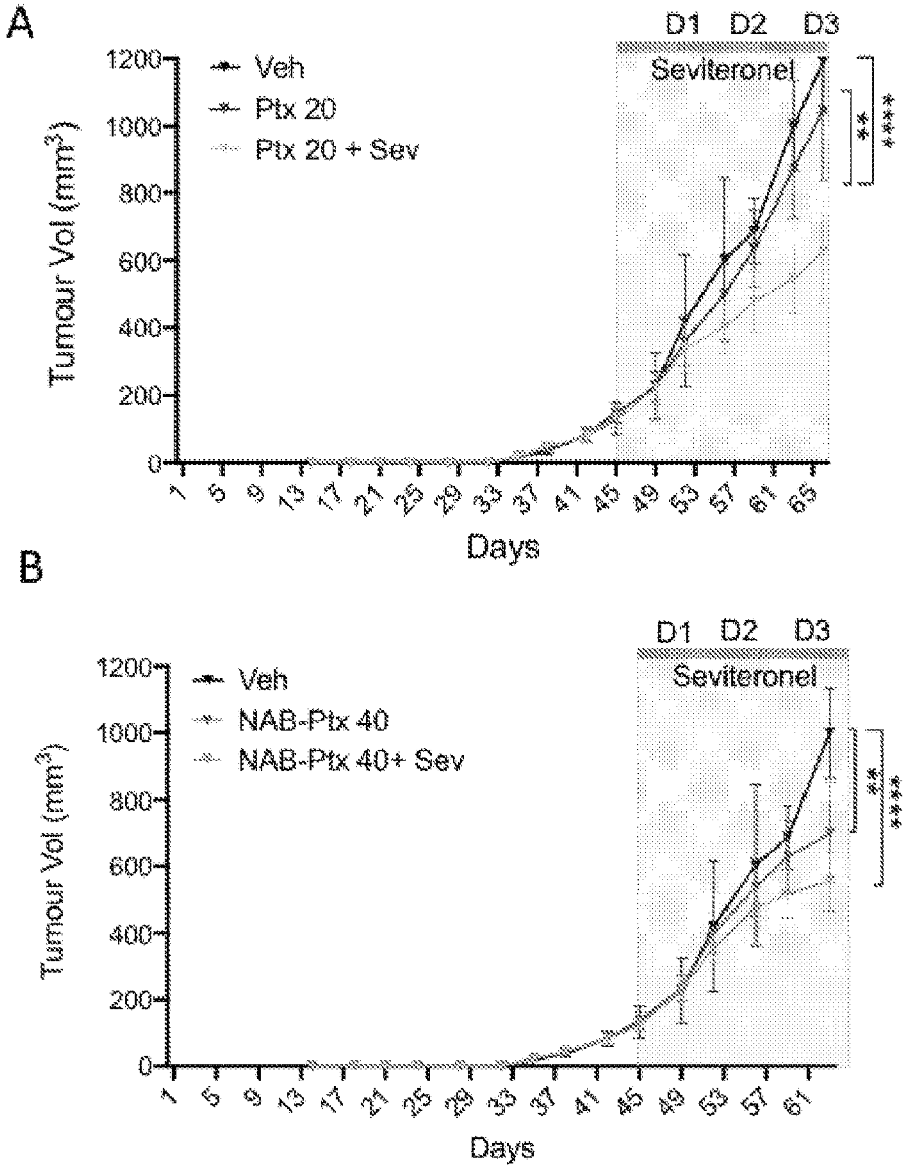

FIG. 13. Seviteronel treatment in combination with Paclitaxel (Ptx) or NAB-Ptx inhibits tumour growth greater than chemotherapy alone.

Graphical representation of tumour growth kinetics. A. Veh arm, Paclitaxel (Ptx,) and Ptx+Sev. B. Veh arm, NAB-Ptx and NAB-Ptx+Sev. Treatments were administrated as previously described. Ptx was administrated at 20 mg/kg and Nab-Ptx at 40 mg/kg. Two-way anova multiple comparison analysis shows stronger tumour growth reduction for both combination treatments, Ptx+Sev and NAB-Ptx+Sev (****p-value<0.0001) compared with vehicle.

Figure 14:
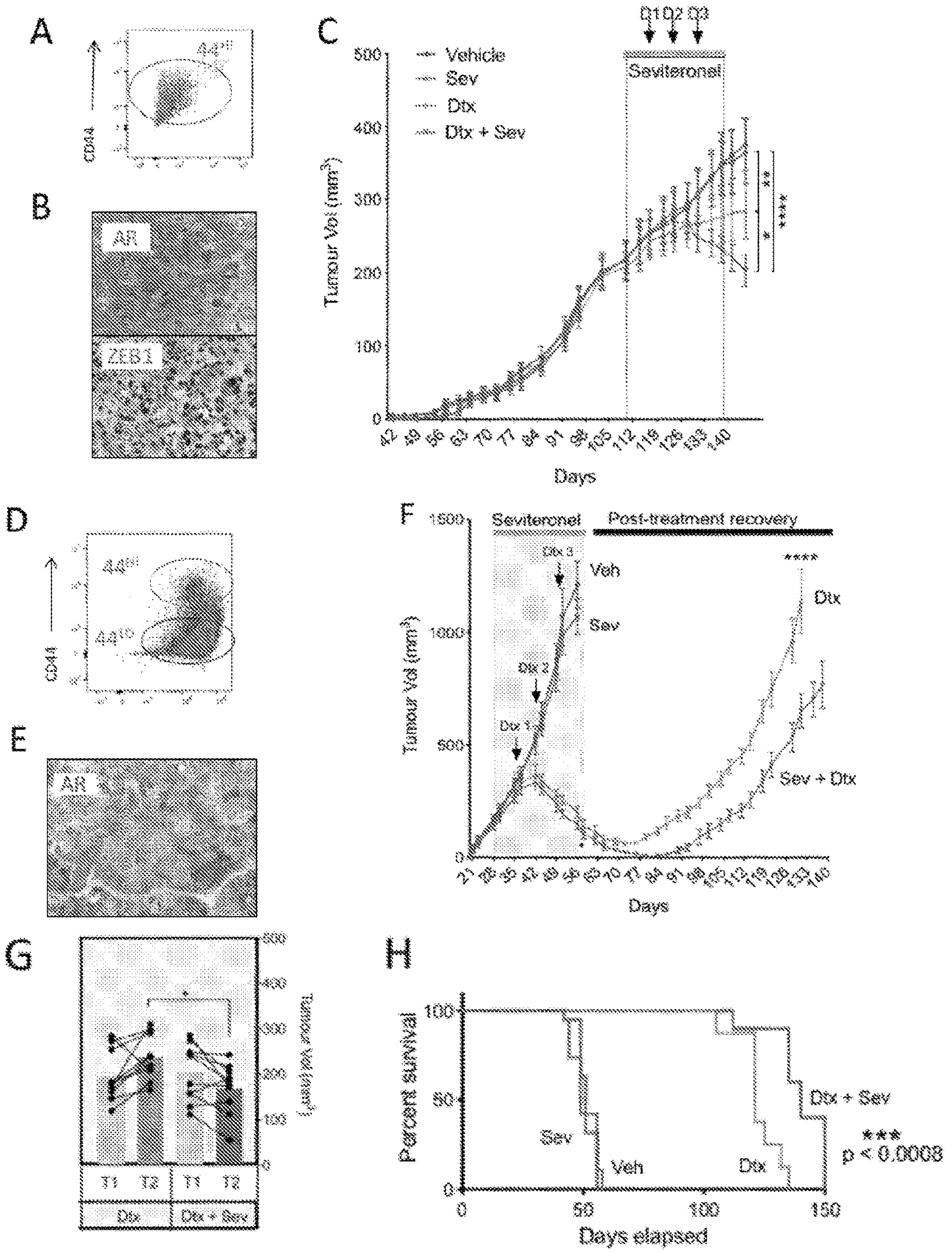

FIG. 14. Combination therapy (Seviteronel+Docetaxel) inhibits tumour growth greater than chemotherapy alone in PDX models that express cytoplasmic AR.

A. FACS plot profile of representative dissociated tumour from PDX model HCI-010. B. Immunohistochemistry images showing cytoplasmic AR and ZEB1 expression in representative HCI-010 tumour sections. C. Graphical representation of tumour growth kinetics for Veh, Sev, Dtx and Dtx+Sev treatment arms in HCI-010 PDX model. Dtx+Sev combination therapy significantly reduces tumour growth, compared to Dtx alone (*p-value<0.05). D) FACS plot profile of representative dissociated tumour from the ELX-12-58 PDX model. E. Immunohistochemistry image showing cytoplasmic AR expression (brown) in a representative ELX-12-58 tumour section. F. Tumour growth kinetics for Veh, Sev, Dtx and Dtx+Sev treatment arms in ELX-12-58 PDX model. Dtx+Sev significantly reduces tumour burden (*p-value<0.5) compared with Dtx alone and also delays tumour relapse (****p-value<0.0001). G. Graph representing the evolution of tumour volume from treatment start to treatment end. Dtx+Sev, but not Dtx alone shows a reduction in tumour volume during treatment (*p-value<0.5). H. Kaplan Meir curve analysis showing a significant survival increase for Dtx+Sev treatment arm compared to Dtx alone (***p-value<0.001).

Figure 15:
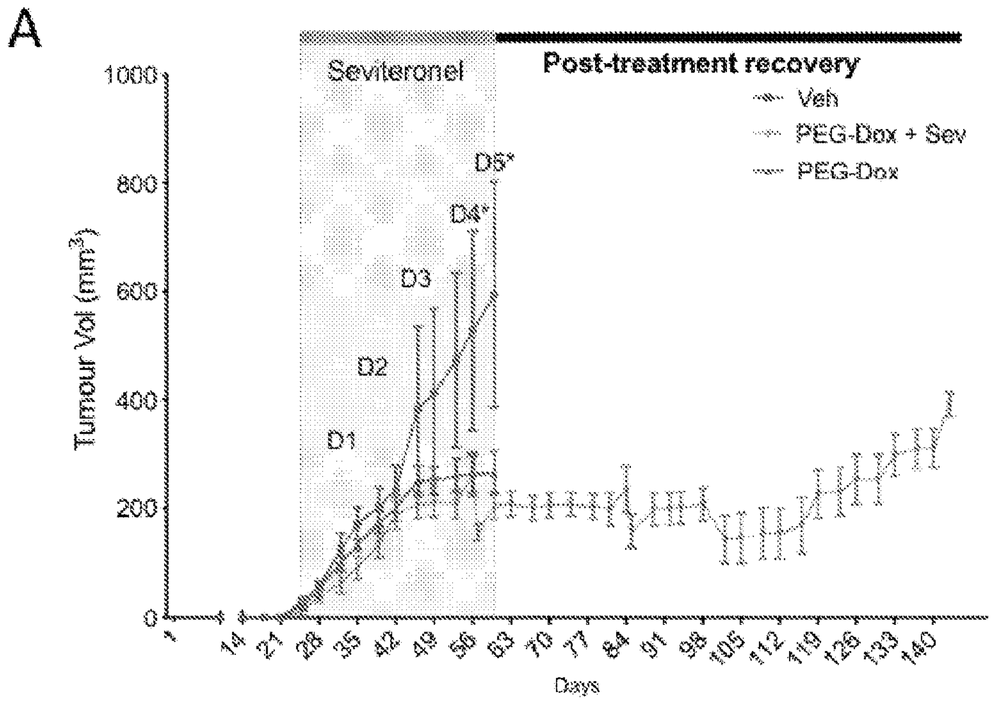
Figure 15:
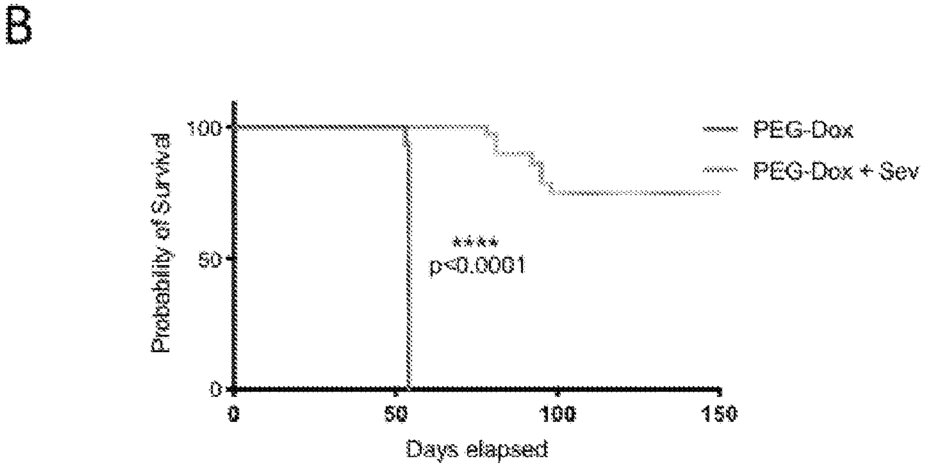

FIG. 15. Seviteronel in combination with PEG-Doxorubicin significantly improves survival.

A. Graphical representation of tumour growth kinetics for Veh, PEG-Doxorubicin (PEG-Dox) and PEG-Dox+Sev, Cisplatin (Cis) and Cisplatin+Sev (Cis+Sev) treatment arms in ELX-12-58 PDX model. Animals receiving PEG-Dox treatment had to be culled due to ethical end-point right after receiving the 3rd dose of chemotherapy. Animals treated with PEG-Dox+Sev, were able to receive up to 5 doses of chemotherapy, showing static tumour growth for more than 2 months. Cisplatin alone and Cis+Sev treatment arms did not reduce ELX-12-58 tumour burden. B. Kaplan Meir survival curve showing a significant survival benefit for PEG-Dox+Sev treatment arm compared with PEG-Dox treatment alone (****p-value<0.0001).

Statistical analysis: Two-way Anova multiple comparison. Statistical significance represented as: *p-value<0.5, p-value<0.0, *p-value<0.001 and ****p-value<0.0001.

KEY TO THE SEQUENCE LISTING

SEQ ID NO: 1 Amino acid sequence for a reference human androgen receptor (Uniprot accession no. P10275).

SEQ ID NO: 2 Amino acid sequence for a reference human ZEB1 protein (Uniprot accession no. P37275).

SEQ ID NO: 3 Nucleotide sequence for a reference human androgen receptor (NCBI accession no. NG_009014.2).

SEQ ID NO: 4 Nucleotide sequence for a reference human ZEB1 protein (NCBI accession no. NG_017048.1).

SEQ ID NO: 5 Amino acid sequence for a reference human CYP17A1 (Uniprot accession no. P05093).

SEQ ID NO: 6 Nucleotide sequence of siRNA targeting AR exon 2.

SEQ ID NO: 7 Nucleotide sequence of siRNA targeting AR exon 7.

DETAILED DESCRIPTION

General Techniques and Definitions

Unless specifically defined otherwise, all technical and scientific terms used herein shall be taken to have the same meaning as commonly understood by one of ordinary skill in the art (e.g. in genomics, immunology, molecular biology, immunohistochemistry, biochemistry, oncology, and pharmacology).

The present disclosure is performed using, unless otherwise indicated, conventional techniques of molecular biology, microbiology, recombinant DNA technology and immunology. Such procedures are described, for example in Sambrook, Fritsch & Maniatis, Molecular Cloning: A Laboratory Manual, Cold Spring Harbor Laboratories, New York, Fourth Edition (2012), whole of Vols I, II, and III; DNA Cloning: A Practical Approach, Vols. I and II (D. N. Glover, Second Edition., 1995), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984) and Methods In Enzymology (S. Colowick and N. Kaplan, eds., Academic Press, Inc.), whole of series.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features. Thus, each feature of any particular aspect or embodiment of the present disclosure may be applied mutatis mutandis to any other aspect or embodiment of the present disclosure.

The present disclosure is not to be limited in scope by the specific embodiments described herein, which are intended for the purpose of exemplification only. Functionally equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

As used herein, the singular forms of "a", "and" and "the" include plural forms of these words, unless the context clearly dictates otherwise.

The term "and/or", e.g., "X and/or Y" shall be understood to mean either "X and Y" or "X or Y" and shall be taken to provide explicit support for both meanings or for either meaning.

Throughout this specification, the word "comprise" or variations such as "comprises" or "comprising" will be understood to imply the inclusion of a stated element, integer or step, or group of elements, integers or steps, but not the exclusion of any other element, integer or step, or group of elements, integers or steps.

Androgen Receptor

The androgen receptor (AR), also known as NR3C4 is a nuclear receptor, which is activated by binding of the androgenic hormones. It is a DNA-binding transcription factor. The sequence of the androgen receptor is publicly available. An exemplary amino acid sequence is set forth in SEQ ID NO: 1. An exemplary nucleotide sequence is set forth in SEQ ID NO: 3.

Androgen Receptor Antagonist

An antagonist may be anything that reduces the expression and/or activity of the androgen receptor. Androgen receptor antagonists are known in the art. As used herein, "androgen receptor antagonists" shall be understood to include, without limitation: antagonists that bind directly to the androgen receptor; androgen synthesis inhibitors; and antigonadotropins. In addition, the term "androgen receptor antagonists" as used herein, shall be understood to include androgen receptor degraders. Any known androgen receptor antagonist may be used in the methods disclosed herein.

Examples of suitable androgen receptor antagonists include, but are not limited to, steroidal antiandrogens (e.g., cyproterone acetate, chlormadinone acetate, spironolactone, oxendolone); androgen degraders (e.g. ARV-110); nonsteroidal antiandrogens (e.g., seviteronel (CAS no. 1610537-15-9), flutamide (CAS no. 13311-84-7), nilutamide (CAS no. 63612-50-0), bicalutamide (CAS no. 90357-06-5), enzalutamide (CAS no. 915087-33-1), apalutamide (956104-40-8), abiraterone (CAS no. 154229-19-3) and N-Terminal domain antiandrogens (e.g., bisphenol A, EPI-001, ralaniten, JN compounds).

One example of a suitable androgen receptor antagonist is seviteronel ((1S)-1-[6,7-bis(difluoromethoxy)naphthalen-2-yl]-2-methyl-1-(2H-triazol-4-yl)propan-1-ol; CAS no. 1610537-15-9). Seviteronel is a nonsteroidal CYP17A1 inhibitor. Seviteronel has been shown to inhibit the production of androgens and estrogens in the body. Alternative androgen receptor antagonists having structural and functional similarities to seviteronel can also be used. For example, any of the androgen receptor antagonists disclosed in any one or more of WO2011/082245, WO2012/082746 and WO2012/064943 can be used in the methods disclosed herein. Such antagonists include, for example, an androgen receptor antagonist of formula (I).

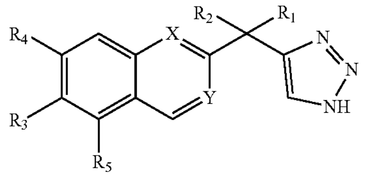

wherein X is CH or N; Y is CH or N;

$R_1$ is optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl;

$R_2$ is H, OH, alkoxy, amino, alkylamino, or dialkylamino; and $R_3$, $R_4$ and $R_5$ are independently H, halogen, alkoxy, thioalkoxy, cycloalkoxy, fluoroalkoxy containing 1-5 fluorines, cyano, carboxamido, optionally substituted aryl, or optionally substituted heteroaryl.

In one example, the compound of formula I is that wherein X is CH or N; Y is CH or N; and $R_3$, $R_4$ and $R_5$ are independently H, halogen, alkoxy, thioalkoxy, cycloalkoxy, fluoroalkoxy containing 1-5 fluorines, cyano, carboxamido, optionally substituted aryl, or optionally substituted heteroaryl.

In one example, the compound of formula I is that wherein X is CH. In one example, the compound of formula I is that wherein X is N. In one example, the compound of formula I is that wherein Y is CH. In one example, the compound of formula I is that wherein Y is N. In one example, the compound of formula I is that wherein X is CH and Y is N. In one example, the compound of formula I is that wherein X is N and Y is CH. In one example, the compound of formula I is that wherein X and Y are CH. In one example, the compound of formula I is that wherein X and Y are N. In one example, the compound of formula I is that wherein $R_6$ is H. In one example, the compound of formula I is that wherein $R_3$ is OH.

In one example, the compound of formula I is that wherein $R_1$ is optionally substituted alkyl, and $R_2$ is OH.

In one example, the compound of formula I is that wherein X and Y are CH, $R_1$ is an optionally substituted alkyl, $R_2$ is OH, $R_3$ and $R_4$ are fluoroalkoxy containing 1-5 fluorines, $R_5$ is H.

In one example, the compound of formula I is that wherein the compound has the formula:

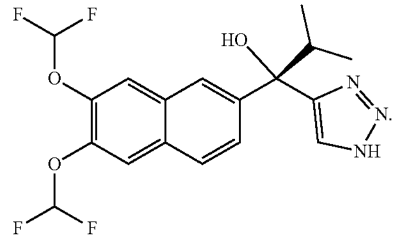 [SMILES: CC(C)[C@](O)(c1ccc2cc(OC(F)F)c(OC(F)F)cc2c1)c1c[nH]nn1]

In one example, the androgen receptor antagonist is seviteronel.

Seviteronel and alternative androgen receptor antagonists having structural and functional similarities to seviteronel may be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. Design And Optimization in Organic Synthesis, 2nd Edition, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

An exemplary method of preparing seviteronel may be by preparing A by Friedel-Crafts acylation of 2,3-dimethoxynaphthalene with isobutyryl chloride/aluminum trichloride.

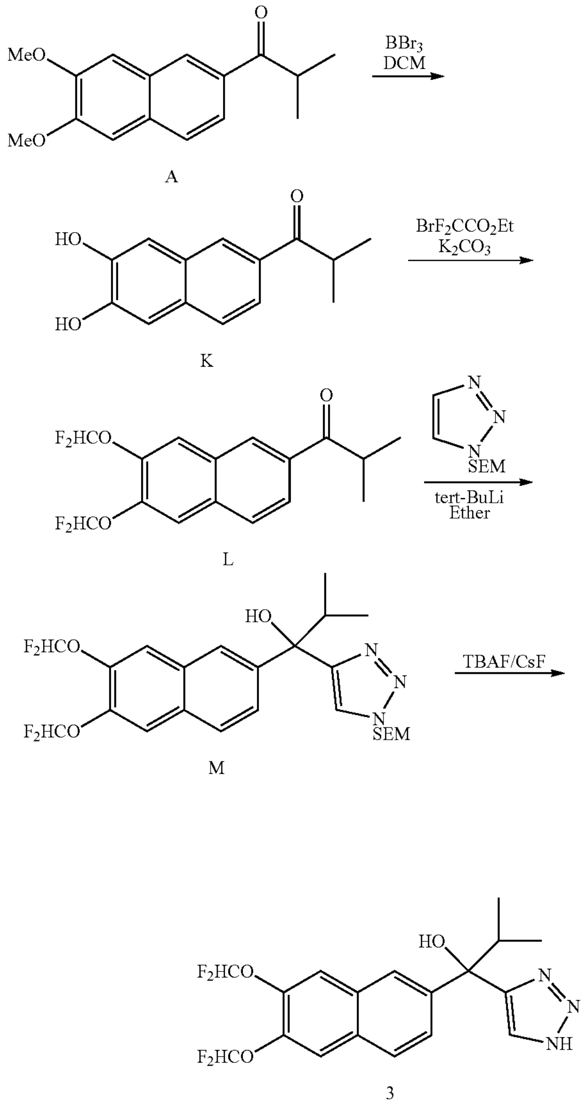

To a stirred solution of A in DCM (180 mL), $BBr_3$ (87.2 g, 348 mmol) may be added dropwise at −40° C. After completion of addition, stirring may be continued for 1 h at −40° C. and 1 h at RT. The reaction mixture may then be poured into cold water and the aqueous layer then extracted with DCM (2×200 mL). The combined organic extracts may then be washed with water (100 mL), brine (100 mL) and dried over anhydrous $Na_2SO_4$. After filtration and evaporation of solvent under reduced pressure, the crude material may be purified by column chromatography ($SiO_2$, 100-200 mesh) to afford K as a brown solid.

To a stirred solution of K in DMF (50 mL), ethyl bromo difluoroacetate (17.6 g, 86.6 mmol) and $K_2CO_3$ (18 g, 130 mmol) may be added, with subsequent stirring of the mixture at 110° C. for 48 h. The reaction mixture may then be poured into cold water and aqueous layer be then extracted with DCM (2×100 mL). Combined organic extracts may be washed with water (50 mL), brine (50 mL), and dried over anhydrous $Na_2SO_4$. After filtration and evaporation of solvent under reduced pressure, the crude material may then be purified by column chromatography ($SiO_2$, 100-200 mesh) to afford L as a solid.

To a stirred solution of N-SEM-1,2,3-triazole (2.25 g, 11.8 mmol) in dry ether (25 mL), t-BuLi (0.69 g, 10.7 mmol) may be added dropwise at −78° C. under inert atmosphere. After stirring for 1 h at −78 'C, compound-L (1.5 g, 2.83 mmol) in dry ether (25 mL) may then be added to reaction mixture, with stirring being continued for additional 1 h at −78° C. The reaction mixture may then be quenched with saturated $NH_4Cl$ solution and extracted with ethyl acetate (2×50 mL). Combined organic phases can then be washed with brine, dried over anhydrous $Na_2SO_4$ and concentrated under reduced pressure to afford M as thick syrup. Crude material may be taken up for next step without further purification.

To a stirred solution of M (3.0 g, 5.6 mmol) in THF (30 mL), TBAF (1.48 g, 5.67 mmol, 1 M in THF) and CsF (2.58 g, 16.8 mmol) may be added at RT under inert atmosphere. The reaction mixture may then be stirred at 80° C. for 4 h. The mixture may then be concentrated in vacuo; the obtained residue then partitioned between water and DCM. The organic phase may be separated and the aqueous layer extracted with DCM (2x25 mL); the combined organic phases then washed with brine, dried over anhydrous Na2SO4, and concentrated under reduced pressure to give crude material. The crude material may then be purified by column chromatography ($SiO_2$, 100-200 mesh) to afford 3 (2.2 g, 5.5 mmol, 61%) as a white solid.

One example of a suitable androgen receptor is enzalutamide (4-{3-[4-cyano-3-(trifluoromethyl)phenyl]-5,5-dimethyl-4-oxo-2-sulfanylideneimidazolidin-1-yl}-2-fluoro-iV-methylbenzamide; CAS no. 915087-33-1). Thus, the androgen receptor antagonist may be the molecule defined in the following Formula II:

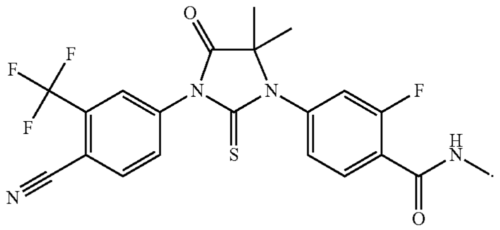

In one example, the androgen receptor antagonist is enzalutamide.

Methods of the preparation of enzalutamide are known in the art. An exemplary method is described in WO2014/043208. Briefly, amorphous enzalutamide may be prepared by spray-drying a 3 wt % solution of enzalutamide dissolved in acetone using a lab-scale spray drier. The lab-scale drier may consist of a 27.6-cm diameter spray drier having a diameter-to-height ratio of greater than 3. The lab-scale drier may be equipped with a Schlick 2.0 pressure nozzle. Heated drying gas (nitrogen) may be delivered to the drying chamber through a perforated plate to provide a uniform flow of drying gas through the drying chamber. To form amorphous enzalutamide, the spray solution may be delivered to the nozzle at a flow rate of 20 g/min and a pressure of 110 psig. In the drying chamber, the atomized droplets were combined with the nitrogen drying gas, which entered the system at a flow rate of 470 g/min and a temperature of 100° C. The spray-dried particles, evaporated solvent, and drying gas were removed from the spray-drying chamber at a temperature of 45° C. through an outlet port and sent to a high-efficiency cyclone separator where the spray-dried particles were collected. The evaporated solvent and drying gas were then sent to a filter for removal of any remaining particles before discharge.

Alternatively, enzalutamide dispersions may be prepared with concentration enhancing polymers.

A solid amorphous dispersion of 25 wt % enzalutamide and 75 wt % HPMCAS may be prepared using a spray drying process as follows. A spray solution may be prepared by dissolving 1 wt % enzalutamide and 3 wt % HPMCAS-M in acetone. This solution may be spray-dried using the lab-scale spray drier as described above. The solution may be delivered to a Schlick 2.0 pressure nozzle atomizer at a pressure of 114 psig. The spray solution may be delivered to the spray drier at a flow rate of 20 gm/min. The nitrogen drying gas may be delivered to the nozzle at 102° C. and at a flow rate of 470 g/min. The outlet temperature of the spray dryer may be 46° C. The resulting spray dried particles were removed using a cyclone separator. The spray drying parameters are summarized in Table 1. Additional dispersions were made using various polymers and formulations, as summarized in Table 1.

TABLE 1

Preparation conditions for spray-dried dispersions (SDDs) of enzalutamide with polymers.

| SDD Composition and (Dispersion Number) | Spray Dryer | Solids in Spray Soln. (%) | Run Size (gA) | Drying Gas T in (° C.) | Drying Gas T out (° C.) | Drying Gas Flow Rate (g/min) | Spray Solution Feed Rate (g/min) | Spray Nozzle | Nozzle Pressure (psi) |
|---|---|---|---|---|---|---|---|---|---|
| 25% A HPMCAS-MSDD (D1) | lab-scale drier | 4.0 | 6.4 | 102 | 46 | 470 | 20 | Schlick 2.0 | 114 |

TABLE 1-continued

Preparation conditions for spray-dried dispersions (SDDs) of enzalutamide with polymers.

| SDD Composition and (Dispersion Number) | Spray Dryer | Solids in Spray Soln. (%) | Run Size (gA) | Drying Gas T in (° C.) | Drying Gas T out (° C.) | Drying Gas Flow Rate (g/min) | Spray Solution Feed Rate (g/min) | Spray Nozzle | Nozzle Pressure (psi) |
|---|---|---|---|---|---|---|---|---|---|
| 25% A PVP-VA64 SDD (D2) | lab-scale drier | 4.0 | 9.0 | 109 | 46 | 470 | 20 | Schlick 2.0 | 111 |
| 60% A HPMCAS-M SDD (D3) | lab-scale drier | 8.0 | 50 mg | 100 | 47 | 470 | 25 | Schlick 2.0 | 109 |
| 25% A HPMCAS-M SDD (D4) | mini | 2.0 | 50 mg | 100 | 23 | 20 | 0.65 | 2-fluid* | |
| 40% A HPMCAS-M SDD (D5) | mini | 1.5 | 50 mg | 100 | 23 | 20 | 0.65 | 2-fluid | |
| 60% A HPMCAS-M SDD (D6) | mini | 1.0 | 50 mg | 100 | 23 | 20 | 0.65 | 2-fluid | |
| 80% A HPMCAS-M SDD (D7) | mini | 1.0 | 50 mg | 100 | 23 | 20 | 0.65 | 2-fluid | |
| 25% A HPMCAS-H SDD (D8) | mini | 2.0 | 50 mg | 100 | 23 | 20 | 0.65 | 2-fluid | |
| 40% A HPMCAS-H SDD (D9) | mini | 1.5 | 50 mg | 100 | 23 | 20 | 0.65 | 2-fluid | |
| 40% A PVP VA64-SDD (D10) | mini | 1.0 | 50 mg | 100 | 23 | 20 | 0.65 | 2-fluid | |
| 25% A HPMCAS-MG SDD (D11) | lab-scale drier | 8.0 | 10 | 107 | 44 | 510 | 22 | Schlick 2.0 | 106 |
| 60% A HPMCAS-MG SDD (D12) | lab-scale drier | 8.0 | 20 | 109 | 55 | 490 | 22 | Schlick 2.0 | 104 |
| 60% A HPMCAS-MG SDD (D13) | PSD-1 | 18.0 | 900 | 99 | 30 | 1750 | 230 | Spray Systems SK79-16 | 330-370 |
| 60% A HPMC-E3Prem SDD (D14) | mini | 1.5 | 100 mg | 105 | 23 | 20 | 0.65 | 2-fluid | |
| 60% A HPMCP-55 SDD (D15) | mini | 1.5 | 100 mg | 105 | 23 | 20 | 0.65 | 2-fluid | |
| 60% A Eudagrit-L100 SDD (D16) | mini | 1.5 | 100 mg | 105 | 23 | 20 | 0.65 | 2-fluid | |

*2-fluid nozzle is a Spraying Systems 1650 liquid, 64 air cap, available from Spray Systems Co. ®, Wheaton, IL. The "mini" sprayer-dryer consisted of an atomizer in the top cap of a vertically oriented 11-cm diameter stainless steel pipe. The PSD-1 spray dryer is a Niro type XP Portable Spray-Dryer with a Liquid-Feed Process Vessel.

One example of a suitable androgen receptor is bicalutamide ((R,S)—N-(4-cyano-3-(4-fluorophenylsulfonyl)-2-hydroxy-2-methyl-3-(trifluoro-methyl)propionanilide); CAS no. 90357-06-5. Alternative androgen receptor antagonists having structural and functional similarities to bicalutamide may also be used. For example, any of the androgen receptor antagonists disclosed in any one or more of EP1622604, US20080045600, WO2008068770, EP 100172 and U.S. Pat. No. 4,636,505 can be used in the methods disclosed herein. Thus, the androgen receptor antagonist may be the molecule defined in the following Formula III:

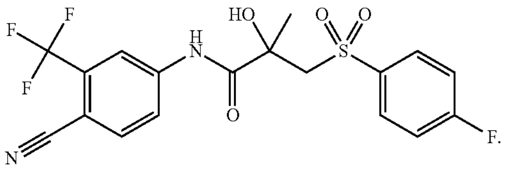 [SMILES: CC(O)(CS(=O)(=O)c1ccc(F)cc1)C(=O)Nc1ccc(C#N)c(C(F)(F)F)c1]

In one example, the androgen receptor antagonist is bicalutamide.

One example of a suitable androgen receptor antagonist is abiraterone (((3p)-17-(pyridin-3-yl) androsta-5, 16-dien-3-ol; CAS no. 154229-19-3). In another example, a suitable androgen receptor antagonist may be abiraterone acetate (CAS no. 154229-18-2). Abiteraterone is a CYP17A1 inhibitor. Abiraterone has been shown to inhibit the production of testosterone and dihydrotesterone in the body. Alternative androgen receptor antagonists having structural and functional similarities to abiraterone can also be used. For example, any of the androgen receptor antagonists disclosed in any one or more of U.S. Pat. Nos. 8,822,438, 10,292,990 and 9,889,144 can be used in the methods disclosed herein. Such antagonists include, for example, an androgen receptor antagonist of formula (IV):

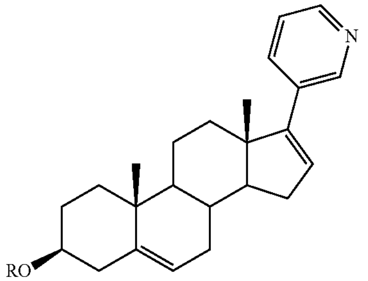

wherein R represents hydrogen or a lower acyl group having 1 to 4 carbons. Suitable inhibitors also include derivatives, analogs, or pharmaceutically acceptable salts of formula (IV).

In one example, the compound of formula IV is that wherein the compound has the formula:

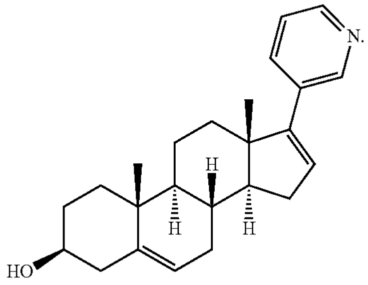

In one example, the compound of formula IV is that wherein the compound has the formula:

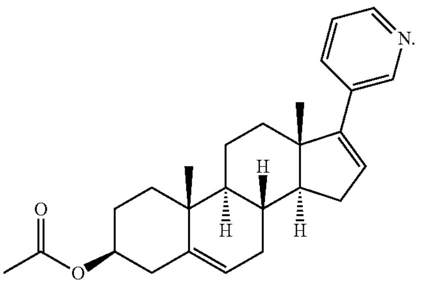

In one example, the androgen receptor antagonist is abiraterone. In another example, the androgen receptor antagonist is abiraterone acetate.

Methods of the preparation of abiraterone and abiraterone related compounds are known in the art. Exemplary methods are described in U.S. Pat. Nos. 5,604,213, 10,292,990 and 9,889,144. In one exemplary method, an aqueous solution of sodium hydroxide (10% w/v, 10 ml) may be added to a solution of 3β-acetoxy-17-(3-pyridyl)androsta-5,16-diene (4.90 g, 12.5 mmol) in methanol (50 ml). The mixture may be heated, with stirring, on an oil bath at 80° C. for 5 min., then allowed to cool. The mixture may then be poured into water, neutralised with hydrochloric acid (1 M), rebasified with saturated sodium bicarbonate solution, and extracted with hot toluene (3×100 ml). The toluene extracts may be combined, dried ($Na_2CO_3$), and concentrated. Chromatography, on elution with toluene-diethyl ether (2:1) afforded the title compound (3.45 g, 79%) which may be crystallised from toluene, mp 228°-229° C.

ZEB1

The Zinc finger E-box-binding homeobox 1 (ZEB1) is a zinc finger and a homeodomain transcription factor. The sequence of ZEB1 is publicly available. An exemplary sequence is set forth in SEQ ID NO: 2.

The present disclosure demonstrates that the presence of ZEB1 in the cytoplasm indicates a poor prognosis for the subject. Accordingly, disclosed herein are methods of determining the prognosis of a subject suffering from cancer, methods of selecting a subject for therapy with an anti-cancer agent and methods of predicting a subject's response to an anti-cancer agent comprising determining the level of expression and/or activity of ZEB1.

The methods disclosed herein may further comprise administering a ZEB1 inhibitor. The inhibitor may be a genetic inhibitor ZEB1. Methods of designing suitable genetic inhibitors are known in the art. Suitable examples of genetic inhibitors include, but are not limited to, DNA (gDNA, cDNA), RNA (sense RNAs, antisense RNAs, mRNAs, tRNAs, rRNAs, small interfering RNAs (siRNAs), short hairpin RNAs (ShRNAs), micro RNAs (miRNAs), small nucleolar RNAs (SnoRNAs), small nuclear RNAs (snRNAs), ribozymes, aptamers, DNAzymes, antisense oligonucleotides, vectors, plasmids, other ribonuclease-type complexes, and mixtures thereof. The gene sequence of ZEB1 is publicly available and can be used to design suitable genetic inhibitors by methods known in the art. A reference nucleotide sequence of ZEB1 is provided in SEQ ID NO: 4.

CYP17A1 Inhibitors

The androgen receptor antagonist may be a CYP17A1 inhibitor. A CYP17A1 inhibitor may be any compound which inhibits the enzyme CYP17A1. CYP17A1, also called steroid 17α-monooxygenase, 17α-hydroxylase, 17,20-lyase, or 17,20-desmolase, is an enzyme of the hydroxylase type that in humans is encoded by the CYP17A1 gene on chromosome 10. The sequence of CYP17A1 is publicly available. An exemplary sequence is set forth in SEQ ID NO: 5. A CYP17A1 inhibitor may inhibit both of the functions of the enzyme, 17α-hydroxylase and 17,20-lyase. Alternatively or in addition, a CYP17A1 inhibitor may be partially or completely selective for inhibition of one of these two functions. Thus, the CYP17A1 inhibitor may be a selective inhibitor of 17,20-lyase function. Alternatively, the CYP17A1 inhibitor may be a selective inhibitor of 17α-hydroxylase function. A "selective" inhibitor may inhibit the 17,20-lyase function of CYP17A1 to a greater extent than it inhibits the 17α-hydroxylase function; or may inhibit the 17α-hydroxylase function of CYP17A1 to a greater extent than it inhibits the 17,20-lyase function. For example, the extent of the selective inhibition may be at least 2-fold, at least 3-fold, at least 4-fold, at least 5-fold, at least 6-fold, at least 7-fold, at least 8-fold, at least 9-fold, at least 10-fold or greater than 10-fold.

Methods of Sensitizing

As used herein, the term "sensitizing" shall be taken to include that a cancer cell in a subject is made more susceptible to the effects of an anti-cancer agent relative to a cancer cell in a subject to whom an androgen receptor antagonist has not been administered. The term "sensitizing" also encompasses maintaining an initially sensitive cancer cell in a state that is sensitive to an anti-cancer agent and inhibiting the development of resistance to the anti-cancer agent. Thus, the methods of sensitizing disclosed herein may comprise maintaining a cancer cell's sensitivity to an anti-cancer agent or enhancing a cancer cell's response to an anti-cancer agent relative to a cancer cell in a subject to whom an androgen receptor antagonist has not been administered.

The cell may be sensitized in any measurable amount. Sensitization may be complete or may be partial. Thus, the methods disclosed herein may comprise at least partial sensitization of cancer cells. For example, cell sensitization may increase the cell's response to the anti-cancer agent by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% following administration of an androgen receptor antagonist. It will be appreciated that the cell's response may be any measurable response that is indicative of a positive therapeutic outcome. For example, the cell's response may be reduced proliferation or cell death. Thus, for example, sensitization may increase the proportion of cells killed by the anti-cancer agent and/or may decrease the rate of proliferation of the cells. Methods of determining cell death and proliferation are known in the art and any such method can be employed in the methods disclosed herein.

The methods disclosed herein may be performed in vivo or in vitro. It will be appreciated that the methods disclosed herein may be performed in the context of treating a subject. Thus, the methods disclosed herein may comprise administering an androgen receptor antagonist to a subject, such as a subject suffering from cancer. Alternatively or in addition, the methods disclosed herein may comprise administering an anti-cancer agent to a subject.

Cancer

As used herein, the term "cancer" refers to a disease characterized by the rapid and uncontrolled growth of cells. Cancer cells can spread locally or through the bloodstream and lymphatic system to other parts of the body. Examples of various cancers include, but are not limited to, thoracic cancer, including non-small cell lung cancer and small cell lung cancer, thymoma, thymic carcinoma, thyroid cancer and mesothelioma; head and neck cancer including of the oropharynx, nasopharynx and hypopharynx; melanoma including cutaneous and uveal; skin cancer including basal cell carcinoma, merkel cell carcinoma and squamous cell carcinoma; neurological cancer including glioma, astrocytoma, oligodendroglioma, glioblastoma multiforme and rare brain tumours; germ cell cancers of any primary site; sarcoma including all sub-types of soft tissue and bone; hepatobiliary cancer including liver, cholangiocarcinoma and gall bladder cancer; upper gastrointestinal cancers including oesophageal, gastric, pancreas and small bowel; lower gastrointestinal cancers including colon, rectal and anal; breast cancer; CNS cancer; gynaecological cancer including ovarian, primary peritoneal, endometrial and vulval; genitourinary cancer including testicular, penile, prostate, bladder and kidney; neuroendocrine and adrenal cancers including carcinoid; cancer of unknown primary; lymphoma including Hodgkin and non-Hodgkin lymphomas, T-cell and B-cell lymphomas of all sub-types; leukaemia including lymphoid and myeloid leukaemia of all subtypes and plasma cell neoplasms including multiple myeloma. In one example, the cancer is breast cancer. In another example, the cancer is triple negative breast cancer. Sub-types of breast cancer include but are not limited to, Basal-like 1 (BL1), Basal-Like 2 (BL2), Luminal Androgen Receptor (LAR), and Mesenchymal (M). In another example, the cancer is brain cancer. Examples of brain cancer include, but are not limited to glioblastoma, astrocytoma, pituitary adenoma, acoustic neuroma, meningioma, oligodendroglioma, haemangioblastoma, CNS lymphoma and unspecified glioma.

The methods disclosed herein may be applied to any cancer cells. The cancer cells may be highly tumourigenic or poorly tumourigenic. The tumourigenicity of the cancer cells may be determined by any suitable method known in the art. For example, one or more biomarkers may be indicative of the level of tumourigenicity and the methods disclosed herein may comprise identifying and/or measuring the presence of one or more of such biomarkers. Examples of suitable biomarkers include, but are not limited to CD24, ALDH1, CD133, OCT4, CD49f, CD104, EPCAM, and STAT3 signalling (Friedrichs et al., 1996, Lipscomb et al., 2005, Ginestier et al., 2007, Liu et al., 2013, Neumeister et al., 2010, Wei et al., 2014, Nadal et al., 2013, Bierie, et al., 2017; Al-Hajj et al., 2003. One example of such a biomarker is CD44.

CD44 is a non-kinase transmembrane glycoprotein which is over expressed in cancer stem cells. It frequently shows alternative splice variants that are thought to play a role in cancer development and progression. CD44 expression is also unregulated in subpopulations of cancer cells and is recognized as a molecular marker for cancer stem cells (CSC) (Yin et al., 2016). In the methods disclosed herein, the cancer cell may be a $CD44^{Lo}$ cell or a $CD44^{Hi}$ cell. Methods to determine whether a cancer cell is a $CD44^{Lo}$ cell or a $CD44^{Hi}$ cell are known in the art. For example, flow cytometry, RNA-sequencing or Western Blot may be used to determine whether a cancer cell is a $CD44^{Hi}$ cell or a $CD44^{Lo}$ cell. In one example, the cancer cell may be a $CD44^{Lo}$ cell. In another example, the cancer cell may be a $CD44^{Hi}$ cell.

In one embodiment, a cell may be defined as $CD44^{Lo}$ if the level of CD44 expression in the cell is low relative to the level of CD44 expression in a population of cells. Thus, the level of CD44 expression in a population of cells may be ranked in increasing order and a "low" level of CD44 expression may be defined as being in the lowest 1%, 5%, 10%, 15%, 20%, 25%, 30%, 35% or 40% of the ranked order of CD44 expression exhibited by that population of cells. For example, the "low" level of CD44 expression may be defined as being in the lowest 1%, 5%, 10%, 15%, 20% or 25% of the ranked order of CD44 expression exhibited by that population of cells. A cell may be defined as $CD44^{Hi}$ if the level of CD44 expression in the cell is high relative to the level of CD44 expression in a population of cells. Thus, a "high" level of CD44 expression may be defined as being in the top 99%, 95%, 90%, 85%, 80%, 75%, 70%, 65% or 60% of the ranked order of CD44 expression exhibited by that population of cells. For example, the "high" level of CD44 expression may be defined as being in the top 99%, 95%, 90%, 85%, 80% or 75% of the ranked order of CD44 expression exhibited by that population of cells. Again, it will be appreciated that the population of cells may be taken from any tissue in a subject. For example, the population of cells may be taken from a biological sample as described herein. The population of cells may comprise cells taken from a single subject or from multiple subjects. Thus, the population of cells may be derived from a population of individuals. Any suitable number of cells and/or individuals may be sampled in order to provide a statistically meaningful average level of CD44 expression. The population of cells may be derived from healthy subjects. The population of cells may be a tissue matched control population of cells derived from healthy subjects. Alternatively, the population of cells may be a population of cancer cells that are known to be resistant to anti-cancer therapy. Methods of determining whether a cell is resistant to anti-cancer therapy are known in the art. The level of CD44 expression in a population of cells may be actively determined by experimentation, or may have been performed previously. For example, the level of CD44 expression in a population of cells may determined by accessing a database storing such information.

Methods of Impeding or Preventing the Development of Resistance

As used herein, the term "impeding" shall be taken to include hindering, delaying or preventing a cancer cell from acquiring resistance to an anti-cancer agent relative to a cancer cell in a subject to whom an androgen receptor antagonist has not been administered. Thus, the methods disclosed herein may comprise maintaining a cancer cell's resistance to an anti-cancer agent relative to a cancer cell in a subject to whom an androgen receptor antagonist has not been administered.

The development of resistance to an anti-cancer agent may prevented in any measurable amount. Thus, the prevention of resistance to an anti-cancer agent may be complete or may be partial. Accordingly, the methods disclosed herein may comprise at least partial resistance to an anti-cancer agent. For example, resistance to an anti-cancer agent may be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% following administration of an androgen receptor antagonist. It will be appreciated that the cell's response may be any measurable response that is indicative of a positive therapeutic outcome. For example, the cell's response may be reduced proliferation or cell death. Thus, for example, the prevention of resistance to an anti-cancer agent may increase the proportion of cells killed by the anti-cancer agent and/or may decrease the rate of proliferation of the cells. Methods of determining cell death and proliferation are known in the art and any such method can be employed in the methods disclosed herein.

Methods of Inhibiting Proliferation

The methods disclosed herein may achieve inhibition of cancer cell proliferation. As used herein, the term "inhibit" shall be taken to include hinder, reduce, restrain or prevent cancer cell proliferation relative to a cancer cell in a subject to whom an androgen receptor antagonist has not been administered.

Cell proliferation may be inhibited in any measurable amount. Inhibition of cell proliferation may be complete or may be partial. Thus, the methods disclosed herein may comprise at least partial inhibition of cancer cell proliferation. For example, cell proliferation may be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% following administration of an androgen receptor antagonist. It will be appreciated that the cell's response may be any measurable response that is indicative of a positive therapeutic outcome. For example, the cell's response may be reduced proliferation or cell death. Thus, for example, inhibition of cancer cell proliferation may increase the proportion of cells killed by the anti-cancer agent and/or may decrease the rate of proliferation of the cells. Methods of determining cell death and proliferation are known in the art and any such method can be employed in the methods disclosed herein.

Methods of Subject Selection

The inventors have surprisingly shown for the first time that (i) administration of an androgen receptor antagonist inhibits cancer cells from transitioning from a poorly aggressive state to a highly aggressive state; (ii) for cancer cells that already exist in a highly aggressive state, inhibiting the androgen receptor decreases their aggressiveness; (iii) administration of an androgen receptor antagonist improves the efficacy of anti-cancer agents and (iv) the presence of the androgen receptor and/or ZEB1 is prognostic of a subject's response to an anti-cancer agent. Based on this finding, the inventors have developed and provide herein (i) methods of selecting a subject for treatment or identifying whether a subject suffering from cancer is suitable for treatment with an androgen receptor antagonist and/or an anti-cancer agent;

(iii) methods of determining the prognosis of a subject suffering from cancer and (iv) methods of predicting a response of a subject to an anti-cancer agent.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, reducing size of the cancer, inhibiting tumour growth, inhibiting cancer progression or metastasis, ameliorating or palliating the disease state, and remission or improved prognosis. Any one or more of these effects may be measured to provide an indication of a cell's response to an anti-cancer agent in the methods disclosed herein.

As used herein, the term "subject" refers to any animal for example, a mammalian animal, including, but not limited to humans, non-human primates, livestock (e.g. sheep, horses, cattle, pigs, donkeys), companion animals (e.g. pets such as dogs and cats), laboratory test animals (e.g. mice, rabbits, rats, guinea pigs), performance animals (e.g. racehorses, camels, greyhounds) or captive wild animals. In one embodiment, the "subject" is a human. Typically, the terms "subject" and "patient" are used interchangeably, particularly in reference to a human subject. The subject may be a subject suffering from, suspected of suffering from, or predisposed to, cancer. The cancer may be any cancer disclosed herein.

In one example, the present disclosure provides a method of selecting a subject for therapy with an anti-cancer agent, the method comprising determining the level of expression and/or activity of the androgen receptor in the cytoplasm of a cell of the subject, wherein if the level of expression and/or activity of the androgen receptor is low, the subject is selected for treatment with the anti-cancer agent.

In another example, the present disclosure provides a method of selecting a subject for therapy with an anti-cancer agent, the method comprising determining the level of expression and/or activity of the androgen receptor in the cytoplasm of a cell of the subject, wherein if the level of expression and/or activity of the androgen receptor is high, the subject is selected for treatment with the anti-cancer agent.

Alternatively or in addition, the present disclosure provides a method of selecting a subject for therapy with an anti-cancer agent, the method comprising determining the level of expression and/or activity of ZEB1 in the cytoplasm of a cell of the subject, wherein if the level of expression and/or activity of ZEB1 is low, the subject is selected for treatment with the anti-cancer agent.

Alternatively or in addition, the present disclosure provides a method of selecting a subject for therapy with an anti-cancer agent, the method comprising determining the level of expression and/or activity of ZEB1 in the cytoplasm of a cell of the subject, wherein if the level of expression and/or activity of ZEB1 is high, the subject is selected for treatment with the anti-cancer agent.

As disclosed elsewhere herein, the methods disclosed herein may not comprise determining the level of expression and/or activity of the androgen receptor in the cytoplasm of a cell of the subject by actively performing an experimental measurement. Alternatively or in addition, the methods disclosed herein may not comprise determining the level of expression and/or activity of ZEB1 in the cytoplasm of a cell of the subject by actively performing an experimental measurement. Instead, the methods may comprise determining such levels based on an analysis of an experimental measurement that has previously been made.

In one example, if the subject is selected for treatment with the anti-cancer agent, the subject is also selected for treatment with an androgen receptor antagonist. In addition, the methods disclosed herein may further comprise administering the anti-cancer agent and/or the androgen receptor antagonist.

Any anti-cancer agent approved for the treatment of cancer is suitable for use in combination with the methods as disclosed herein. The anti-cancer agent may be an alkylating agent, a topoisomerase inhibitor, a mitotic inhibitor, an antimetabolite, a corticosteroid, an anti-tumour antibiotic, a PARP inhibitor or any other chemotherapeutic agent.

The alkylating agent may be any one or more of Altretamine, Busulfan, Carboplatin, Carmustine, Chlorambucil, Cisplatin, Cyclophosphamide, Dacarbazine, Lomustine, Melphalan, Oxaliplatin, Temozolomide, Thiotepa, or any other alkylating agent.

The topoisomerase inhibitor may be any one or more of Topotecan, Irinotecan (CPT-11), Etoposide (VP-16), Teniposide, Mitoxantrone or any other topoisomerase inhibitor.

The mitotic inhibitor may be any one or more of Docetaxel, Estramustine, Eribulin Ixabepilone, Paclitaxel, protein-bound Paclitaxel, Vinblastine, Vincristine, Vinorelbine or any other mitotic inhibitor. In one particular embodiment, the anti-cancer agent is Docetaxel ($C_{43}H_{53}NO_{14}$; CAS number 114977-28-5). In another embodiment, the anti-cancer agent is Paclitaxel ($C_{47}H_{51}NO_{14}$; CAS number 33069-62-4).

The antimetabolite may be any one or more of 5-fluorouracil (5-FU), 6-mercaptopurine (6-MP), Capecitabine (Xeloda®), Cytarabine (Ara-C®), Gemcitabine (Gemzar®), Floxuridine, Fludarabine, Methotrexate, Pemetrexed (Alimta®), Hydroxyurea or any other antimetabolite.

The corticosteroid may be any one or more of Dexamethasone (Decadron®), Prednisone, Methylprednisolone (Solumedrol®), or any other corticosteroid.

The anti-tumour antibiotic may be any one or more of Actinomycin-D, Bleomycin, Daunorubicin, Doxorubicin (Adriamycin®), pegylated liposomal Doxorubicin (Doxil), Doxurubicin, Epirubicin, Mitomycin-C, Idarubicin Mitoxantrone or any other anti-tumour antibiotic. In one embodiment, the anti-cancer agent is Doxorubicin (CAS number 23214-92-8).

The PARP inhibitor may be any one or more of niraparib, olaparib, rucaparib, or any other PARP inhibitor.

Thus, the anti-cancer agent may be a DNA-damaging agent. The DNA-damaging agent may be irradiation (or ionizing radiation).

In one example, the anti-cancer agent is selected from the group consisting of cisplatin, doxorubicin and docetaxel.

In one example, the present disclosure provides a method of determining the prognosis of a subject suffering from cancer, the method comprising determining the presence of the androgen receptor in the cytoplasm of a cell, wherein the presence of the androgen receptor in the cytoplasm indicates a poor prognosis. Thus, a lower amount of the androgen receptor in the cytoplasm indicates a better prognosis.

Alternatively or in addition, the present disclosure provides a method of determining the prognosis of a subject suffering from cancer, the method comprising determining the presence of ZEB1 in the cytoplasm of a cell, wherein the presence of ZEB1 in the cytoplasm indicates a poor prognosis. Thus, a lower amount of ZEB1 in the cytoplasm indicates a better prognosis.

In one example, the present disclosure provides a method of predicting the response of a subject to an anti-cancer agent, the method comprising determining the level of expression and/or activity of the androgen receptor in the subject, wherein a low level of expression and/or activity of the androgen receptor in the subject is indicative that the subject's response to the anti-cancer agent alone is decreased relative to the subject's response to the anti-cancer agent when administered with an androgen receptor antagonist.

It will be understood by the person skilled in the art that one or more mutations in a subject's androgen receptor nucleotide sequence may affect its expression and/or activity. Thus, the methods disclosed herein may comprise determining the sequence of a subject's androgen receptor nucleotide sequence and comparing it to a reference androgen receptor sequence. The presence of one or more genetic alterations relative to a reference androgen receptor sequence may indicate that the subject has, or is likely to have a reduced level of expression and/or activity. The one or more genetic alterations may include one or more mutations, deletions, insertions, inversions, translocations, epigenetic modifications (for example, but not limited to methylation). Thus, the step of determining the level of expression and/or activity of the androgen receptor in a subject in the methods disclosed herein may comprise determining the nucleotide sequence encoding the androgen receptor in the subject. Alternatively or in addition, the methods disclosed herein may comprise determining the sequence of a subject's androgen receptor amino acid sequence and comparing it to a reference androgen receptor sequence.

The expression and/or activity of the androgen receptor may be measured through any means known in the art, for example through immunohistochemistry. Alternative methods including Western blotting, qRT-PCR, mass spectrometry, immunoprecipitation, immunostaining and others, may also be used. The expression and/or activity of the androgen receptor may be measured in a biological sample taken from the subject. The biological sample may comprise one or more cells derived from the subject. Any of the methods disclosed herein may comprise a step of taking a biological sample from a subject and determining the level of expression and/or activity of the androgen receptor in the sample. The level of expression and/or activity of the androgen receptor may be determined in the cytoplasm of the cell. Alternatively, any of the methods disclosed herein may not comprise a step of taking a biological sample from a subject and determining the level of expression and/or activity of the androgen receptor in the sample. Instead, the level of expression and/or activity of the androgen receptor in the sample may have been determined previously. In any of the methods disclosed herein, the level of expression and/or activity of the androgen receptor in the cytoplasm of the cell may be determined by its presence in the cytoplasm.

Any of the methods disclosed herein may comprise a step of establishing a reference level of androgen receptor expression and/or activity. Alternatively, any of the methods disclosed herein may comprise a step of comparing a measurement of androgen receptor expression and/or activity to a predetermined reference level. For example, the predetermined reference level may be stored in a database including such information. Suitable threshold levels can then be determined according to the particular methodology used to identify and/or measure androgen expression and/or activity. It will be appreciated that the precise thresholds will vary depending on the samples used to establish those threshold levels and according to the particular analytical methodology used in each instance. Thus, a "low" level of androgen receptor expression and/or activity is a level of androgen receptor expression and/or activity that is decreased relative to a reference level of androgen receptor expression and/or activity. Conversely, a "high" level of androgen receptor expression and/or activity is a level of androgen receptor expression and/or activity that is greater than a reference level of androgen receptor expression and/or activity. A "reference" level of androgen receptor expression and/or activity can be determined by selecting any suitable population of cells from which to derive the level of androgen receptor expression and/or activity. That population of cells may be taken from any tissue in a subject. For example, the population of cells may be taken from a biological sample as described herein.

In one embodiment, a "low" level of androgen receptor expression and/or activity may be defined relative to the level of androgen receptor expression and/or activity in a population of cells. Thus, the level of androgen receptor expression and/or activity in a population of cells may be ranked in increasing order and a "low" level of androgen receptor expression and/or activity may be defined as being in the lowest 1%, 5%, 10%, 15%, 20%, 25%, 30%, 35% or 40% of the ranked order of androgen receptor expression and/or activity exhibited by that population of cells. For example, the "low" level of androgen receptor expression and/or activity may be defined as being in the lowest 1%, 5%, 10%, 15%, 20% or 25% of the ranked order of androgen receptor expression and/or activity exhibited by that population of cells. Thus, a "high" level of androgen receptor expression and/or activity may be defined as being in the top 99%, 95%, 90%, 85%, 80%, 75%, 70%, 65% or 60% of the ranked order of androgen receptor expression and/or activity exhibited by that population of cells. For example, the "high" level of androgen receptor expression and/or activity may be defined as being in the top 99%, 95%, 90%, 85%, 80% or 75% of the ranked order of androgen receptor expression and/or activity exhibited by that population of cells. Again, it will be appreciated that the population of cells may be taken from any tissue in a subject. For example, the population of cells may be taken from a biological sample as described herein. The population of cells may comprise cells taken from a single subject or from multiple subjects. Thus, the population of cells may be derived from a population of individuals. Any suitable number of cells and/or individuals may be sampled in order to provide a statistically meaningful average level of androgen receptor expression and/or activity. In one example, the level of expression of androgen receptor is determined by one or more immunohistochemical methods. For example, the level of expression may be determined by contacting a sample with an antibody capable of binding specifically to the androgen receptor, which antibody is conjugated to a detectable label (e.g., a fluorescent label). The level of expression of the androgen receptor may be determined by one or more protein quantitation methods. For example, the level of expression of the androgen receptor may be determined by mass spectrometry, Western blotting or immunohistochemistry.

Alternatively or in addition, the present disclosure provides a method of predicting the response of a subject to an anti-cancer agent, the method comprising determining the level of expression and/or activity of ZEB1 in the subject, wherein a low level of expression and/or activity of ZEB1 in the subject is indicative that the subject's response to the anti-cancer agent alone is decreased relative to the subject's response to the anti-cancer agent when administered with an androgen receptor antagonist.

It will be also be understood by the person skilled in the art that one or more mutations in a subject's ZEB1 nucleotide sequence may affect its expression and/or activity. Alternative isoforms of ZEB1 have been described. Thus, the methods disclosed herein may comprise determining the sequence of a subject's ZEB1 nucleotide sequence and comparing it to a reference androgen receptor sequence. The presence of one or more genetic alterations relative to a reference ZEB1 sequence may indicate that the subject has, or is likely to have a reduced level of expression and/or activity. The one or more genetic alterations may include one or more mutations, deletions, insertions, inversions, translocations, epigenetic modifications (for example, but not limited to methylation). Thus, the step of determining the level of expression and/or activity of ZEB1 in a subject in the methods disclosed herein may comprise determining the nucleotide sequence encoding ZEB1 in the subject. Alternatively or in addition, the methods disclosed herein may comprise determining the sequence of a subject's ZEB1 amino acid sequence and comparing it to a reference ZEB1 sequence.

The expression and/or activity of ZEB1 may be measured through any means known in the art, for example through immunohistochemistry. Alternative methods including Western blotting, qRT-PCR, mass spectrometry, immunoprecipitation and others, may also be used. The expression and/or activity of ZEB1 may be measured in a biological sample taken from the subject. The biological sample may comprise one or more cells derived from the subject. Any of the methods disclosed herein may comprise a step of taking a biological sample from a subject and determining the level of expression and/or activity of ZEB1 in the sample. The level of expression and/or activity of ZEB1 may be determined in the cytoplasm of the cell.

Any of the methods disclosed herein may comprise a step of establishing a reference level of ZEB1 expression and/or activity. Alternatively, any of the methods disclosed herein may comprise a step of comparing a measurement of ZEB1 expression and/or activity to a predetermined reference level. The reference level may be determined from a population of cells taken from any tissue in a subject. The tissue may be a tissue matched control from a subject who does not have cancer. Alternatively, the tissue may be a cancer matched control from a subject who is not resistant to anti-cancer therapy. Suitable threshold levels can then be determined according to the particular methodology used to identify and/or measure ZEB1 expression and/or activity. It will be appreciated that the precise thresholds will vary depending on the samples used to establish those threshold levels and according to the particular analytical methodology used in each instance. Thus, a "low" level of ZEB1 expression and/or activity is a level of ZEB1 expression and/or activity that is decreased relative to the reference level of ZEB1 expression and/or activity.

Conversely, a "normal" level of ZEB1 expression and/or activity is a level of ZEB1 expression and/or activity that is similar to, equal to, or greater than the reference level of ZEB1 expression and/or activity. The "normal" level of ZEBlexpression and/or activity or the reference level of ZEBlexpression and/or activity can be determined by selecting any suitable population of cells from which to derive the level of ZEB1 expression and/or activity. That population of cells may be taken from any tissue in a subject. For example, the population of cells may be taken from a biological sample as described herein.

In one embodiment, a "low" level of ZEB1 expression and/or activity may be defined relative to the level of ZEB1 expression and/or activity in a population of cells. Thus, the level of ZEB1 expression and/or activity in a population of cells may be ranked in increasing order and a "low" level of androgen receptor expression and/or activity may be defined as being in the lowest 1%, 5%, 10%, 15%, 20%, 25%, 30%, 35% or 40% of the ranked order of ZEB1 expression and/or activity exhibited by that population of cells. For example, the "low" level of ZEB1 expression and/or activity may be defined as being in the lowest 1%, 5%, 10%, 15%, 20% or 25% of the ranked order of ZEB1 expression and/or activity exhibited by that population of cells. Thus, a "normal" level of ZEB1 expression and/or activity may be defined as being in the top 99%, 95%, 90%, 85%, 80%, 75%, 70%, 65% or 60% of the ranked order of ZEB1 expression and/or activity exhibited by that population of cells. For example, the "normal" level of ZEB1 expression and/or activity may be defined as being in the top 99%, 95%, 90%, 85%, 80% or 75% of the ranked order of ZEB1 expression and/or activity exhibited by that population of cells. Again, it will be appreciated that the population of cells may be taken from any tissue in a subject. For example, the population of cells may be taken from a biological sample as described herein. The population of cells may comprise cells taken from a single subject or from multiple subjects. Thus, the population of cells may be derived from a population of individuals. Any suitable number of cells and/or individuals may be sampled in order to provide a statistically meaningful average level of ZEB1 expression and/or activity. In one example, the level of expression of ZEB1 is determined by one or more mRNA quantitation methods. For example, the level of expression may be determined by RT-PCR. The level of expression of ZEB1 may be determined by one or more protein quantitation methods. For example, the level of expression of ZEB1 may be determined by mass spectrometry, Western blotting or immunohistochemistry.

Determining Prognosis

The inventors have identified the presence of the androgen receptor and/or ZEB1 in the cytoplasm of a cell of a subject suffering from cancer indicates a poor prognosis for the subject. Thus the present disclosure also provides method of determining the prognosis of a subject suffering from cancer, the method comprising determining the presence of the androgen receptor in the cytoplasm of a cell, wherein the presence of the androgen receptor in the cytoplasm indicates a poor prognosis. Thus, it will be understood by a person skilled in the art that a lower amount of the androgen receptor in the cytoplasm of the cell indicates a better prognosis.

Alternatively or in addition, method of determining the prognosis of a subject suffering from cancer, the method comprising determining the presence of ZEB1 in the cytoplasm of a cell, wherein the presence of ZEB1 in the cytoplasm indicates a poor prognosis. Thus, it will be understood by a person skilled in the art that a lower amount of ZEB1 in the cytoplasm of the cell indicates a better prognosis.

The presence of the androgen receptor in the cytoplasm of a cell from the subject may be determined by any means known in the art. For example, the presence of androgen receptor may be determined through immunohistochemistry, using antibodies against the androgen receptor. The antibody may be labelled with any suitable detectable label. For example, the antibody may be labelled with a fluorescent label.

It will be appreciated by a person skilled in the art that the presence of ZEB1 in the cytoplasm of a cell from the subject may be determined by any means known in the art. For example, the presence of ZEB1 may be determined through immunohistochemistry, using antibodies against ZEB1. The antibody may be labelled with any suitable detectable label. For example, the antibody may be labelled with a fluorescent label.

Pharmaceutical Compositions and Kits

The present disclosure also provides a pharmaceutical composition comprising an androgen receptor antagonist and an anti-cancer agent. The pharmaceutical composition may be provided for use in treating cancer. In one example, the pharmaceutical composition may be provided for use in treating triple negative breast cancer.

The present disclosure also provides the use of an androgen receptor antagonist and an anti-cancer agent in the manufacture of a medicament for the treatment of cancer. In one example, the cancer is triple negative breast cancer.

The medicament or the composition may also include excipients or agents such as solvents, diluents, dispersion media, coatings, antibacterial and antifungal agents, isotonic and absorption delaying agents and the like that are physiologically compatible and are not deleterious to the inhibitor as described herein or use thereof. The use of such carriers and agents to prepare compositions of pharmaceutically active substances is well known in the art (see, for example Remington: The Science and Practice of Pharmacy, 21st Edition; Lippincott Williams & Wilkins: Philadelphia, PA, 2005).

The pharmaceutical composition may be diluted prior to use. Suitable diluents may be selected from, for example: Ringer's solution, Hartmann's solution, dextrose solution, saline solution and sterile water for injection.

The term "composition" as used herein is intended to encompass a product comprising the specified ingredients in the specified amounts, as well as any product which results, directly or indirectly, from combination of the specified ingredients in the specified amounts.

The pharmaceutical compositions include those for oral, rectal, nasal, topical (including buccal and sub-lingual), parenteral administration (including intramuscular, intraperitoneal, subcutaneous and intravenous), or in a form suitable for administration by inhalation or insufflation. The androgen receptor antagonist and the anti-cancer agent, together with a conventional adjuvant, carrier or diluent, may be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, or in the form of sterile injectable solutions for parenteral (including subcutaneous) use.

The pharmaceutical compositions for the administration of the inhibitors of this disclosure may conveniently be presented in unit dosage form and may be prepared by any of the methods well known in the art of pharmacy.

The pharmaceutical compositions and methods disclosed herein may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

When other therapeutic agents are employed in combination with those disclosed herein, they may be used for example in amounts as noted in the Physician Desk Reference (PDR) or as otherwise determined by one of ordinary skill in the art.

It will be understood, however, that the specific dose level and frequency of dosage for any particular subject may be varied and will depend upon a variety of factors including the activity of the specific compound employed, the metabolic stability and length of action of that compound, the age, body weight, general health, gender, diet, mode and time of administration, rate of excretion, drug combination, the severity of the particular condition, and the subject undergoing therapy.

The pharmaceutical compositions disclosed herein may be delivered to a subject by any suitable means. The pharmaceutical compositions may be targeted specifically to the cancer cells. For example, the pharmaceutical compositions disclosed herein may be provided with one or more delivery vehicles capable of specifically targeting the cancer cells. The present disclosure also provides a kit comprising an androgen receptor antagonist and an anti-cancer agent for treating cancer. The kit may contain instructions for use.

EXAMPLES

Example 1. CD44$^{Lo}$-to-CD44$^{Hi}$ Plasticity

Figure 1:
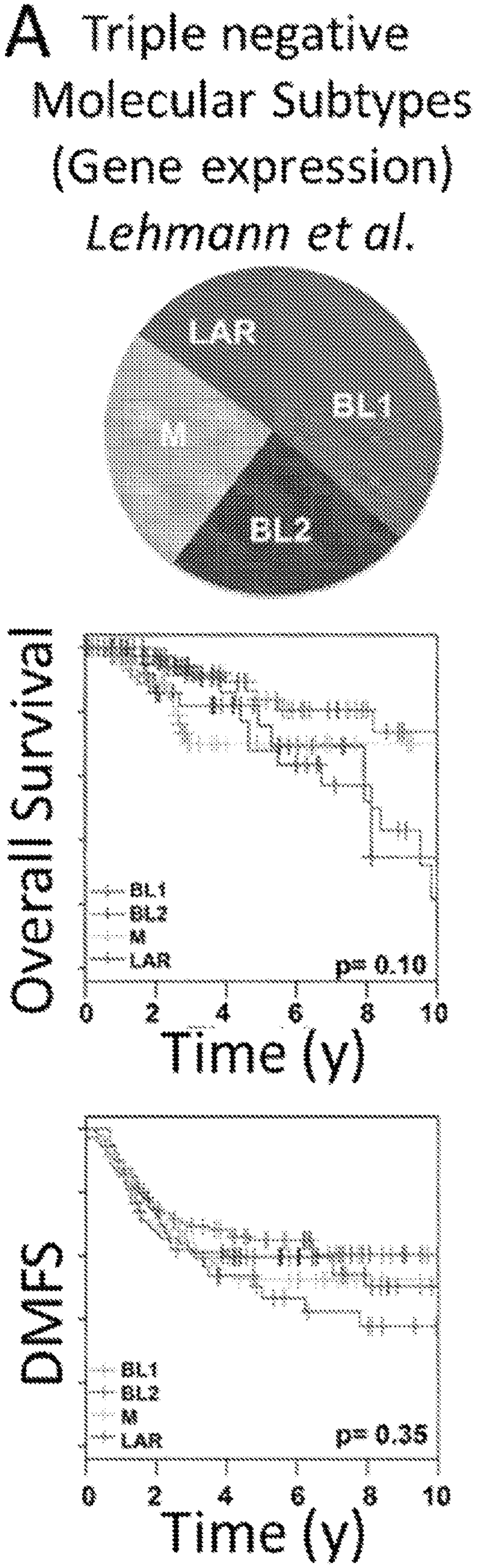
FIG. 1. Molecular classification of triple-negative subtypes
Figure 1:
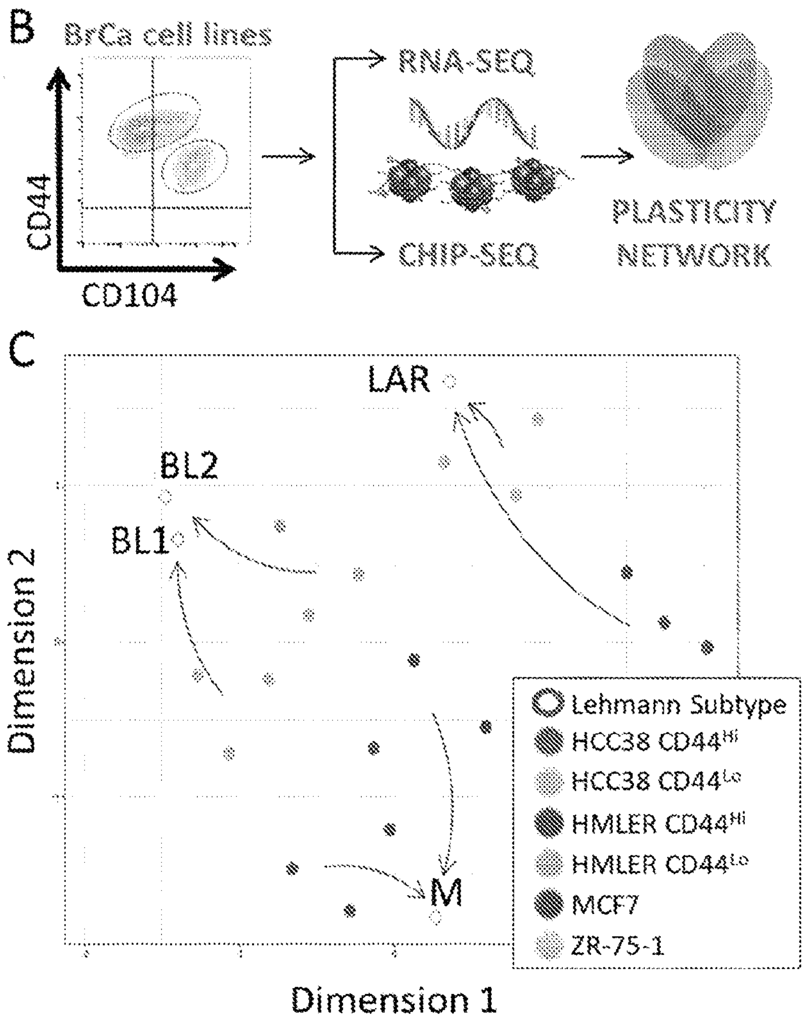

Transcriptomics on whole tumours currently classify triple-negative breast cancer into four molecular subtypes with distinct prognoses: Basal-like 1 (BL1), Basal-Like 2 (BL2), Luminal Androgen Receptor (LAR), and Mesenchymal (M)20 (FIG. 1A). To add to that complexity, it is known that each individual tumour also comprises a variety of cancer cell types, exemplified by CD44$^{Lo}$ and CD44$^{Hi}$ populations. A major limitation of whole tumour transcriptomic studies thus lies in the fact that the molecular signature of minority CD44$^{Hi}$ populations is masked.

To address that gap in knowledge and define the molecular drivers of CD44$^{Lo}$-to-CD44$^{Hi}$ plasticity and maintenance of the CD44$^{Hi}$ state, transcriptomic (RNAseq) and epigenomic (Mint-ChIP, Van Galen et al., 2016) analyses on sorted populations of CD44$^{Lo}$ and CD44$^{Hi}$ cells (FIG. 1B) was performed.

CD44$^{Hi}$ cells were found to indeed classify differently to their matched CD44$^{Lo}$ counterparts. According to the Lehmann et al., 2016 molecular subtypes, CD44$^{Lo}$ cells are called 'BL1 or BL2', while the CD44$^{Hi}$ cells are called 'M' (UMAP analysis, Becht et al., 2018, FIG. 1C). Hence, bulk signatures do not define molecular programs operating in minority subpopulations.

Differential gene expression analysis revealed that the androgen receptor is significantly up-regulated in CD44$^{Hi}$ cells compared to CD44$^{Lo}$ cells (FIGS. 2A and B). A series of computational tests to identify genes differentially expressed between CD44$^{Lo}$ and CD44$^{Hi}$ cells was performed, including differentially gene expression analysis, shrunken nearest centroid test and canonical correlation analysis. All analyses identified the AR as significantly up-regulated in CD44$^{Hi}$ cells compared to CD44$^{Lo}$ cells. This was unexpected as the androgen receptor is a known marker of the 'LAR' triple-negative subtype, not the 'M' subtype that classifies CD44$^{Hi}$ cells. The androgen receptor can drive context-specific transcriptional programs. Indeed, androgen receptor signalling in the LAR subtype is very similar to luminal breast cancer (mimicking estrogen signalling), but very different to prostate cancer (an estrogen receptor-negative context) (Hickey et al., 2012, FIG. 2C).

Example 2. The Prostate Cancer Androgen Receptor Signalling Network is Enriched in $CD44^{Hi}$ Cancer Cells The inventors tested whether AR-regulated genes regulated in prostate cancer were enriched in $CD44^{Hi}$ cells compared to $CD44^{Lo}$ cells. It was found that the prostate cancer androgen receptor signalling network is enriched in triple-negative $CD44^{Hi}$ cancer cells (FIG. 2D). ZEB1 and ZEB2—key drivers of cellular plasticity—were the highest differential expressed members of that network (FIG. 2E). Motif enrichment tools were used to further demonstrate that promoters of differentially expressed genes are also highly enriched for androgen receptor and ZEB1 binding sites (FIG. 2F). These analyses support a key role of the androgen receptor in regulating cellular plasticity in triple-negative breast cancer.

Example 3. The Androgen Receptor Protein is Differentially Expressed (I)

Cell Culture

HMEC cells were purchased from ATCC and transformed into HMLER cells by the sequential addition of hTERT, SV40-ER and RAS as previously described in Chaffer et al., 2011. Cells were cultured in serum-free mammary epithelial growth medium (MEGM) and MEGM Single Quots (Lonza, cat no. CC-4136: 1 ml bovine pituitary extract (BPE), 0.5 ml GA-1000 (30 mg/ml Gentamicin and 15 μg/ml Amphotericin), 0.5 ml insulin, 0.5 ml hydrocortisone and 0.5 ml hEGF). Cells were maintained at 37° C. with 5% $CO_2$. HCC38 cells were purchased from ATCC and cultured in RPMI containing 10% FBS containing penicillin/streptomycin (PS; 5.000 units penicillin and 5 mg streptomycin/ml in $H_2O$, Sigma Aldrich, cat no. P4333). All cell lines were routinely tested to confirm the absence of mycoplasma contamination.

Reagents

Reagents were obtained from the following sources: Dihydrotesterone—DHT (Innovative Research of America), Seviteronel (Innocrin Pharmaceuticals, North Carolina, USA), Enzalutamide (Selleck Chemicals, Houston, USA), Doxorubicin (Sigma-Aldrich, Missouri, USA), Docetaxel (Selleck Chemicals, Houston, USA), Cisplatin Cisplatin (Pharmacy grade) 1 mg/ml Sterile Concentrate, #3788, Hospira UK Ltd), Enobosarm (Jomar Life Science).

Western Blot Analysis

Protein was extracted from cell lysates using RIPA lysis buffer (sc-24948) or specific lysis buffer for phospho-proteins detection (20 mM Tris-HC1 pH 7.6, 137 mM NaCl, 1% NP40, 0.5% Na-deoxycholate, 10 mM NaF, 20 mM β-glycerophosphate, 1 mM Na-orthovanadate and 1:200 complete protease inhibitors). 25-30 μg of proteins were run in a 4-12% Bis-tris gel (Invitrogen). Proteins were transferred to a PVDF membrane (BioRad). After blocking with 5% BSA (w/v) and 0.05% (v/v) Tween-20 in PBS, the membranes were incubated overnight with the indicated antibodies, washed with PBS 0.05% (v/v) Tween-20 and incubated with the corresponding horseradish peroxidase-conjugated secondary antibodies (Cell Signaling; Dil 1/5000, Table 3) for 30 min. Blots were developed using Western Lightning Plus ECL (PerkinElmer) and FusionFx7 Digital Imager, Band intensities were quantified using Fiji (Schindelin et al., 2012) and results were represented relative to controls.

Flow Cytometry

HMLER and HCC38 CD44Lo cells were seeded at a density of 200,000 cells per 10 cm plate and 600,000 cells per 6 cm plate respectively and treated with 10 nM DHT for 24 hours. Cell suspension was then stained with Anti-Human CD44-PeCy7 (1:800) and anti-human CD104-efluor660 (1:400) (eBioscience) for 25 minutes at 4° C., before fixing with 4% PFA at RT for 15 minutes. The process was repeated with cells exposed to daily DHT treatment for 48, 72 and 96 hours. Cells were also seeded at a density of 450,000 cells per 10 cm plate (HMLER 44Lo) and 200,000 cells per 6 cm plate (HCC38 44LO) and treated with one dose of chemotherapy for 72 hours (Table 2). Alternatively, the cells were seeded in the same manner as with chemotherapy and treated with the AR antagonist Seviteronel, or a combination of Dox+Sev, Cis+Sev or Doc+Sev simultaneously for 72 hours (doses in table below). Cells were stained and fixed as with DHT treatment. Flow cytometry (LSRII Fortessa) was used to collect data on 10,000 cells using FACSDiva software (BD Biosciences) and analysis was performed using FlowJo.

TABLE 2

Doses or reagents used to analyse effects on $CD44^{Lo}$ to $CD44^{Hi}$ plasticity by flow cytometry.

| | | HMLER $CD44^{Lo}$ | HCC38 $CD44^{Lo}$ |
|---|---|---|---|
| Doxorubicin | | 25 nM, 50 nM | 50 nM, 100 nM |
| Cisplatin | | 1 μg/ml, 2 μg/ml | 0.5 μg/ml, 1 μg/ml, 2 μg/ml |
| Docetaxel | | 1 nM, 4 nM | 1 nM, 2 nM, 4 nM |
| Seviteronel | | 10 uM | 10 uM |
| Seviteronel 10 μM + | Doxorubicin | 25 nM, 50 nM | 50 nm |
| | Cisplatin | 1 μg/ml, 2 μg/ml | 0.5 μg/ml |
| | Docetaxel | 1 nM, 4 nM | 4 nM |

Results

Through Western Blot analysis, it was found that androgen receptor protein is differentially expressed between $CD44^{Lo}$ and $CD44^{Hi}$ cells (FIG. 3A).

Flow cytometric analysis shows purified $CD44^{Lo}$ cells treated with the androgen receptor agonist dihydrotestosterone (DHT) transition into the $CD44^{Hi}$ state (FIG. 3B). Hence, androgen receptor activation drives cellular plasticity.

Example 4. The Androgen Receptor Protein is Differentially Expressed (II)

Western blot analysis and flow cytometry was performed as described in Example 3.

AR siRNA Knockdown siRNAs targeting exon 1 and 7 of AR full length were designed in-house (SEQ ID NOs: 6 and 7). HCC38 $CD44^{Hi}$ cells ($10^5$/well) were seeded in M6 plate wells 24 hours prior to siRNA transfection. 20 nM of siRNA CT, siRNA AR Ex1 or AR Ex7 were delivered using lipofectamine 3000 (Thermofisher) as per manufacturer instructions. Protein lysates were extracted 72 h post transfection and subjected to western blot analysis, confirming strong reduction in expression of AR full length (100 kDa).

Tumorsphere Assay (AR siRNA)

$1\times10^5$ HCC38 CD44Hi cells were seeded in M6 plate wells 24 hours prior to siRNA transfection. siRNA CT, siRNA AR Ex1 or siRNA AR Ex7 (20 nM) were transfected following the standard protocol for lipofectamine 3000. 24 h post-transfection cells were trypsinized into single cell suspensions, washed twice with cold PBS, counted and seeded into a tumour-sphere assay. Cells from each treatment were seeded in different quadrants of a 96 well plate (400 cells/well): siRNA CT, siRNA AR Ex1, siRNA AR Ex7 and siRNA CT+Sev (10 μM). Seviteronel was added at seeding time. One raw (10 wells) per condition: siRNA CT, siRNA AR Ex1, siRNA AR Ex7 was treated with Sev (10 μM) to define if AR knockdown enhanced the reduction in tumour-initiation observed for AR antagonism. 7 days post-seeding, single images for each well were taken with a Leica microscope at 4× magnification. Images were analyzed using an ImageJ macro developed in-house. Analyses reported number of spheres per well and area. Data were plotted using prism software, applying one-way Anova multiple comparison statistical analysis.

Results

The androgen receptor protein is differentially expressed between $CD44^{Lo}$ and $CD44^{Hi}$ cells (FIG. 4A). Flow cytometric analysis shows purified CD44Lo cells treated with the androgen receptor agonist dihydrotestosterone (DHT) transition into the CD44Hi state (FIG. 4B). Hence, androgen receptor activation drives cellular plasticity.

Seviteronel, Abiraterone and Enzalutamide decreased CD44Hi proliferation (FIG. 4C) and tumoursphere formation (FIG. 4D). Transient knockdown of the Androgen Receptor (siRNA) reduces tumorsphere formation (FIG. 4E). The combination of Seviteronel+siRNA against AR further reduces tumorsphere formation and size (FIG. 4F-G).

Example 5. Treatment of $CD44^{Hi}$ with Androgen Receptor Antagonists Inhibits $CD44^{Hi}$ Proliferation In one experiment, $CD44^{Hi}$ cells were treated with two androgen receptor antagonists: Seviteronel—an androgen receptor antagonist and inhibitor of endogenous androgen production, or Enzalutamide—an androgen receptor antagonist only.

Cell Proliferation Assay

HMLER, HCC38 and MDA-MB-231 cells were plated in triplicate in 96-well plates at the densities outlined in Table 3. After 24 hours, cells were treated with various chemotherapeutic agents at the following doses: Doxorubicin (0 nM, 25 nM, 50 nM, 75 nM, 100 nM, 200 nM), Cisplatin (0 μg/ml, 0.1 μg/ml, 0.5 μg/ml, 1 μg/ml, 2 μg/ml, 5 μg/ml) or Docetaxel (0 nM, 1 nM, 5 nM, 10 nM, 25 nM, 50 nM); Androgen receptor agonists: Enobosarm (0 nM, 25 nM, 50 nM, 100 nM, 200 nM, 400 nM) or DHT (0 nM, 1 nM, 5 nM, 10 nM, 20 nM, 40 nM); or AR antagonist: Seviteronel (0 nM, 0.5 nM, 2 nM, 10 nM, 20 nM, 50 nM). Assays were harvested daily for five days by removing culture media and storing at −80'C. Cell proliferation was determined using CyQuant Cell Proliferation assay kit according to manufacturer's protocol (ThermoFisher Scientific) and fluorescence was measured at ~480 nm excitation and ~520 nm emission using a microplate reader.

TABLE 3

Cell densities plated for proliferation assays

| | HMLER | | HCC38 | | MDA-MB- |
|---|---|---|---|---|---|
| | $44^{LO}$ | $44^{HI}$ | $44^{LO}$ | $44^{HI}$ | 231 |
| Chemotherapy | $3 \times 10^3$ | $1.8 \times 10^3$ | $4 \times 10^3$ | $2.4 \times 10^3$ | $2.4 \times 10^3$ |
| AR agonist or antagonist | $1 \times 10^3$ | $1.8 \times 10^3$ | $2 \times 10^3$ | $2.4 \times 10^3$ | $2 \times 10^3$ |

Tumourspheres

Single cell suspensions were plated in ultra-low attachment 96-well plates (Corning #CLS3474, New York, USA). HMLE-$CD44^{Hi}$ cells were plated at a density of 50 cells/well in 100 μl of BPA-free MEGM media (Lonza # CC-3150, Basal, Switzerland). HCC38-$CD44^{Hi}$ cells were plated at a density of 100 cells/well in serum-free RPMI with 1% penicillin/streptomycin, 20 ng/ml EGF, 20 ng/ml FGFb, 4 μg/mL heparin, 1×B27 and 1% methyl cellulose (Sigma). Media was replenished every five days by adding 50 μL of the appropriate tumoursphere media to each well. Tumourspheres were counted at Day 14. Results are presented as tumoursphere formation efficiency (number of spheres per well divided by the number of cells seeded per well). At Day 14, mammospheres were collected using a 40 μm cell strainer, washed with PBS and dissociated using trypsin-EDTA solution, and stained with anti-CD44PECy7 and anti-CD104PE as per standard FACS staining protocol.

Results

Seviteronel decreased $CD44^{Hi}$ proliferation (FIG. 3C), and tumoursphere formation (FIG. 3D). Tumourspheres are an in vitro surrogate for in vivo tumour-initiating ability. Similar results were observed with Enzalutamide. However, daily treatment of Enzalutamide was required to equal one dose of Seviteronel. Hence, androgen receptor antagonism inhibits proliferation and tumour-initiating ability of $CD44^{Hi}$ cells.

In another experiment, $CD44^{Hi}$ cells in vivo were treated with Seviteronel, Docetaxel, or a combination of both.

Methods

Forty-eight mice were enrolled in the experiment and randomized into 4 treatment arms: Vehicle (Veh), Seviteronel (Sev), Docetaxel (DTX) or combination therapy (Sev+Dtx). Animals were 6-8 weeks of age at the time of injection. MDA-MB-231 EGFP-Luciferase cells were cultured in DMEM 10% FBS 1% P/S. On the surgery date, $1\times10^6$ cells resuspended in 20% Matrigel/DMEM were injected unilaterally into the mammary fat pad. Tumour growth was monitored twice per week to establish growth kinetics. Five weeks post-injection, when tumour size ranged between 50-100 $mm^3$, animals were randomized to receive daily oral gavage with either vehicle (1% Carboxymethylcellulose, 0.1% Tween-80 and 5% DMSO) or Seviteronel (100 mg/kg). Animals were dosed from Monday to Saturday, leaving 1 day recovery per week. After one week, animals were again randomized within the Vehicle or Seviteronel groups to Control or Chemotherapy (DTX). DTX was administrated at 40 mg/kg by itraperitoneal (i.p.) injection. After completing 3 doses of chemotherapy the experiment was terminated and animals were harvested (a total of 8 weeks post-surgery). Metastatic burden and tumour size was determined using the IVIS-spectrum imaging system. On the day of harvest, animals were weighed and subsequently injected with 10 μl/gram animal weight of D-luciferin Potassium Salt stock (15 mg/ml, Sigma, LUCK-2G) subcutaneously. Ten minutes after D-luciferin administration, animals were scarified, and the chest opened to expose internal organs for signal detection. Images (auto-exposure and 1 sec. C and B magnification) were taken in the presence and absence of primary tumour to record metastatic burden. Primary tumours, lung, liver, femurs and tibias were collected from each individual animal. When present, peritoneum and lymph node metastases were also collected. The presence of metastatic cells in each organ was additionally determined by FACS analysis (fluorescence activate cell sorting) using a panel of antibodies previously established in the lab (CD298-PE, CD44-PEcy7 and CD104EF660). Results were analyzed and graphed using Flowjo3 and prism 8. Two-way ANOVA Tukey's multiple comparison was used to determine statistical significance for tumour volume/weights. Metastatic incidence was analyzed applying two-way ANOVA uncorrected Fisher's LSD test.

Results

As shown in FIG. 11, Seviteronel alone significantly reduces tumour growth kinetics compared to control; docetaxel alone significantly reduces tumour growth compared to Seviteronel alone; and, notably, the combination of seviteronel+docetaxel significantly reduces tumour growth more than docetaxel alone (FIG. 11B). Moreover, the combination of seviteronel+docetaxel significantly reduced metastases more than any other single treatment (FIG. 11C). Thus, a representative androgen receptor antagonist has been shown to sensitize cancer cells to an anti-cancer agent, resulting in significantly improved treatment outcomes (including reduced tumour volume and reduced metastasis). Accordingly, the present disclosure demonstrates that an androgen receptor antagonist sensitizes cancer cells (such as breast cancer cells, including triple negative breast cancer cells) to an anti-cancer agent (such as docetaxel).

Example 6. Chemotherapy Drives the Development of Chemo-Resistance

Using purified populations of $CD44^{Lo}$ cells (with no $CD44^{Hi}$ fraction) the effects of chemotherapy on cellular plasticity was investigated using flow cytometry. HMLER and HCC38 $CD44^{Lo}$ cells were seeded at a density of 450,000 cells per 10 cm plate (HMLER $44^{Lo}$) and 600,000 cells per 6 cm plate (HCC38 $44^{Lo}$) and treated with one dose of chemotherapy alone, AR antagonist Seviteronel alone, or a combination of Dox+Sev, Cis+Sev or Doc+Sev simultaneously for 72 hours (Table 4). Cells were then stained with Anti-Human CD44-PeCy7 (1:800) and anti-human CD104-efluor660 (1:400) (eBioscience) for 25 minutes at 4° C., before fixing with 4% PFA at RT for 15 minutes, then analysed by flow cytometry.

TABLE 4

Doses or reagents used to analyse effects on CD44Lo to CD44Hi plasticity by cytometry.

| | | HMLER $CD44^{Lo}$ | HCC38 $CD44^{Lo}$ |
|---|---|---|---|
| Doxorubicin | | 25 nM, 50 nM | 50 nM, 100 nM |
| Cisplatin | | 1 μg/ml, 2 μg/ml | 0.5 μg/ml, 1 μg/ml, 2 μg/ml |
| Docetaxel | | 1 nM, 4 nM | 1 nM, 2 nM, 4 nM |
| Seviteronel | | 10 M | 10 μM |
| Seviteronel 10 μM + | Doxorubicin | 25 nM, 50 nM | 50 nM |
| | Cisplatin | 1 μg/ml, 2 μg/ml | 0.5 μg/ml |
| | Docetaxel | 1 nM, 4 nM | 4 nM |

Results

Doxorubicin (anthracycline), Docetaxel (Taxane) and Cisplatin (platinum-therapy) induce $CD44^{Lo}$ cells to transition to the $CD44^{Hi}$ state (FIG. 5). Thus, chemotherapy itself drives the development of chemo-resistance. Excitingly, the inventors show that Seviteronel blocks chemotherapy-induced $CD44^{Lo}$-to-$CD44^{Hi}$ transitions (FIG. 5).

Example 7. ZEB1 is Upregulated in Response to Treatment with an Androgen Agonist Microscopy Image data was acquired using a Nikon MR confocal and Plan Apo 20× air objective (N.A. 0.75). Images were acquired in resonance scanning mode at 512×512 pixels, 1× zoom, giving a pixel dimension of 3.25 μm per pixel. Montage (large) images were acquired as stitched 4×4 images with 10% overlap, resulting in 1895×1895 pixel final images. DAPI, AR and ZEB1 images were acquired as channel series. Between 8-15 montages were acquired per experimental condition, depending on cell density.

Image Analysis

Image analysis was performed using CellProfiler software (v3.1.8). After importing, AR and ZEB1 channel data was summed to create a $4^{th}$ channel enabling improved detection of complete cell bodies.

Nuclei detection was performed using global minimum cross entropy thresholding, and nuclei were de-clumped (separated) based on shape. Nuclei smaller than 500 $pixels^2$ were removed, as were nuclei touching the montage image borders. Cell bodies were detected via seeding from filtered nuclei and propagation to the edges of summed AR+ZEB1 cell body segmentation images, using global cross entropy thresholding. Cytoplasm per cell was defined as the residual of cell body pixels minus nuclei pixels.

Object (cell body, nucleus, cytoplasm) shape and intensity features were measured per object. Cell body proximity features were also measured per cell. Segmentation boundaries (cell body and nucleus) were overlaid onto combined DAPI—AR—ZEB1 RGB images and saved as tiff files. For each object (cell body, nucleus, cytoplasm), per object shape, intensity and proximity features were exported to .csv files combining all image and condition data.

Quantitative Analysis and Data Visualization

Quantitative analyses and data visualization were performed using KNIME software (v4.0) integrated with Microsoft R Open (v3.5.1). Csv. Files containing cell body, nucleus and cytoplasm feature data were independently imported and joined in KNIME, with experimental metadata incorporated via the HCS Tools 'Load Layout' function. Nuclear: Cytoplasmic intensity ratios were calculated per image channel (DAPI, AR, ZEB1). All quantitative feature distributions were then normalized via Z-score normalization. Principle components analysis (PCA), t-distributed stochastic neighbor embedding (t-SNE) (R package 'rtsne') and uniform manifold approximation and projection (UMAP) (R package 'umap') dimension-reduction techniques were used to explore phenotypic variation amongst cells and conditions. Automated unsupervised cluster (i.e. phenotype) detection was performed in t-SNE- and UMAP-project data using the OPTICS cluster detection algorithm (R package 'dbscan'). Exploratory data visualization was performed in KNIME, including sequential gating using the Erlwood '2D/3D Scatterplot' function and in-built hilite functionality. Publication plots were generated using the R package 'ggplot2'.

Immunofluorescence

Cells were fixed with 4% paraformaldehyde (Electron Microscopy Sciences) for 15 min and permeabilized with 0.3% Triton X-100 for 20 min at RT. Then, they were blocked with PBS 3% BSA, 10% Horse Serum, stained with the indicated antibodies, followed by the appropriate secondary antibodies conjugated with Cyanine Cy3 (excitation at 533 nm and emission at 568 nm), Alexa Fluor 647 (excitation at 633 nm and emission from 650 nm) or with phalloidin-iFluor 488 (excitation at 488 nm and emission collected at 505-530 nm), and processed as described. Coverslips were mounted on glass slides with ProLong Diamond Antifade Mountant (Thermo Fisher Scientific). Fluorescence was examined using a confocal laser-scanning microscope Leica DMI 6000 SP8 with 40× or 63× oil objectives. Brightness and contrast were optimized with Fiji software (National Institutes of Health). Lift images were converted to TIFF format.

Treatment of $CD44^{Lo}$ cells with the androgen receptor antagonist DHT linearly increases cytoplasmic and nuclear androgen receptor protein expression (FIG. 6). This could be due to protein stabilization as DHT generally represses androgen receptor transcription (Cai et al., 2011). ZEB1 expression is also upregulated in response to DHT treatment (FIG. 6B).

Example 8. Cytoplasmic Expression of Androgen Receptor and ZEB1 in Breast Cancer (I)

In the absence of ligand, the androgen receptor is sequestered in the cytoplasm by heat shock protein 90. Upon ligand binding, conformational changes cause it to detach, dimerize, stabilize and translocate to the nucleus to activate transcription of target genes (FIG. 7). In the clinic, steroid receptors (estrogen, progesterone, androgen) are clinically scored on nuclear expression alone (Elston and Ellis., 2002).

Tissue Microarrays representing 167 treatment-naiive triple-negative breast cancer specimens collected from the Royal Prince Alfred Hospital and Concord Repatriation General Hospital in New South Wales, Australia, were stained for androgen receptor (AR) or ZEB1 expression. Each tumour core was scored by a pathologist for percentage of positive tumour cells, for staining intensity (1+, 2+ 3+) and for localization (nuclear, cytoplasmic). Details and antibodies are provided in Table 5. Antigen retrieval was performed in a pressure cooker for 10 seconds at pH 9. Anti-androgen receptor antibody (Table 5) was detected using the Novolink detection system. Nuclei were counterstained with haematoxylin.

TABLE 5

Antibodies used in this study

| Target | Source | Assay ID | Dilution |
|---|---|---|---|
| ZEB1 | SantaCruz #sc-25388 | IF/IHC<br>Western | 1:100<br>1:1000 |
| AR | Dako #M3562 | IF/IHC | 1:250 |
| AR | Cell Signaling #5153 | Western | 1:1000 |
| GAPDH | Cell Signaling #97166 | Western | 1:5000 |
| E-Cadherin | Cell Signaling #24610 | Western | 1:1000 |
| CD104 | SantaCruz # SC-9090 | Western | 1:1000 |
| CD44-PeCy7 | ThermoFisher Scientific #25-0441-81 | Flow | 1:800 |
| CD104-eFluor 660 | ThermoFisher Scientific #50-1049-82 | Flow | 1:400 |

TABLE 5-continued

Antibodies used in this study

| Target | Source | Assay ID | Dilution |
|---|---|---|---|
| Secondary Antibodies | | | |
| Mouse IgG HRP-linked | Cell signaling #7076 | Western | 1:5000 |
| Rabbit IgG HRP-linked | Cell signaling #7074 | Western | 1:5000 |
| Rabbit IgG Alexa Fluor Cy3-linked | Jackson ImmunoResearch #711-545-152 | IF | 1:500 |
| Mouse IgG Alexa Fluor 647-linked | Jackson ImmunoResearch #715-605-150 | IF | 1:500 |
| Others | | | |
| Phalloidin-iFluor 488 | Abcam # ab176753 | IF | 1:500 |
| DAPI | MERK # 268298 | IF | 1:5000 |

A multivariate analysis was done considering all prognostic indicators. The clinical data contains 508 observations recording the fraction of cells observed at three intensity levels for AR and ZEB1 genes in the nucleus and/or cytoplasm from a triple negative breast cancer cohort, along with survival data (dead/alive status, date of diagnostic, date of last follow-up), and other clinical records from 167 patients. Multiple observations were recorded for each patient. In order to assess any potential association between the presence of markers of interest in the nucleus or cytoplasm with good prognosis, the observed fraction of cells at different intensity levels was summarised into a single continuous number to obtain one measurement per spot on the array. A Cox Proportional Hazard model was fitted to survival (in months), death/alive events and the single continuous number to test for associations. The single metrics obtained from immunohistochemical stainings include HSCORE and normalised scores (normalised across all categories). The normalisation applied not only facilitates the comparison between different categories, but also maps the HSCORES to probabilities, resulting in more reliable estimates of ratios.

Results

ZEB1 nuclear staining was not prognostic, however, ZEB1 cytoplasmic staining was strongly prognostic (coefficient=3.77, p=7e−5), where very high cytoplasmic staining associated with a worse outcome. For AR expression, it was found that nuclear staining was weakly prognostic (coefficient=−0.046, p=0.0041), with higher stain amounting to a better outcome. Conversely, cytoplasmic AR staining was also prognostic (coef=0.045, p=0.0073), with a higher intensity associated with a worse outcome. Hence, both AR and ZEB1 cytoplasmic staining both independently associated with a worse outcome in triple-negative breast cancer (FIGS. 8A-C).

FIG. 8B confirms that cytoplasmic AR is associated with poor prognosis and nuclear AR is associated with good prognosis.

FIG. 8C shows that the ratio of cytoplasmic AR to nuclear AR is also a good indicator of prognosis, where a high cytoplasmic to nuclear ratio is associated with poor prognosis. There is a trend towards good prognosis for nuclear ZEB1 and a trend for poor prognosis for cytoplasmic ZEB1.

Example 9. Cytoplasmic Expression of Androgen Receptor in Breast Cancer (II)

AR Immunohistochemistry Analysis

Tumour microarrays from the Garvan cohort of treatment-naïve triple negative breast cancer (gift from A/P Sandra O'toole) were cut and stained for AR (DAKO antibody. H2(30'). 1:250 dilution). 150 tumours were scored by an independent pathologist (Cristina Vargas), reflecting percentage of cells expressing cytoplasmic and/or nuclear AR at 3 different intensities (+1,+2,+3). Results from the pathologist scoring plus follow up data were analyzed by a statistician to define the prognostic value of cytoplasmic and/or nuclear AR.

Results

FIG. 9A shows representative immunohistochemistry images showing different categories of tumours based on cytoplasmic and nuclear AR expression. The top-left shows no AR expression, the top-center shows low cyt:low nuc AR, the top-right shows high cyt:low nuc AR, the bottom-left shows high nuc AR expression, the bottom-center shows low cyt:high nuc AR and the bottom-right shows high cyt:high nuc AR. FIG. 9B shows that high cytoplasmic AR expression, or a high AR cytoplasmic to nuclear ratio, predicts poor outcome. FIG. 9C is a Kaplan Meier curve showing significant poor patient survival for high cyt:nuc AR expression pattern. Cox Proportional Hazard models was used to determine the impact of Cyt AR and Cyt:Nuc AR ratio on survival probability.

Example 10. High Cytoplasmic AR at Baseline is Strongly Associated with Lack of Therapeutic Response to Chemotherapy AR Immunohistochemistry Analysis Matching tumour biopsies from the SET-UP trial collected prior, during and post-chemotherapy treatment were cut and stained for AR. The percentage of cells expressing cytoplasmic or nuclear AR with intensities ranging from +1, +2 or +3 was summarized as an H-score. The H-score was calculated by combining the relative frequency of cells observed for each cytoplasmic or nuclear intensity (Ex: 25% 1+, 75% 3+=0.25*1+0.75*3=0.25+2.25=2.5). Data on patient response to chemotherapy (complete response (pCR) vs no response (No pCR)) was integrated to define if AR expression predicts patient response to chemotherapy.

Results

FIG. 10A shows representative immunohistochemistry images of AR expression in patient biopsies at baseline (top row), mid-treatment (middle row) and post-treatment (bottom row). Left panel: pCR (responder). Right panel no pCR (no responder). Patients with high cytoplasmic AR expression pre-treatment do not respond well to chemotherapy evidenced by a poor pathological complete response. FIG. 10B is a summary table showing prognostic value for patient age, treatment type and cytoplasmic AR at baseline, mid and post-chemotherapy treatment. Cytoplasmic AR at baseline predicts lack of pCR at 10% type I error. Logistic Regression (generalized binomial model) was used to define the prognostic potential for AR cytoplasmic levels at Base, Mid and Post-treatment to predict PCR or no PCR.

Example 11. Cytoplasmic Expression of Androgen Receptor in Brain Cancer

A cohort of glioma patient samples that had been previously stained for Androgen receptor expression was rescored. Each tumour core was scored by a pathologist for percentage of positive tumour cells, for staining intensity (1+, 2+ 3+) and for localization (nuclear, cytoplasmic).

TABLE 6

Androgen receptor expression in a clinical cohort of glioma patients

| Glioma | Nuclear expression (% positive cells) | | | Cytoplasmic expression (% positive cells) | | |
|---|---|---|---|---|---|---|
| Patient sample | N1+ | N2+ | N3+ | C1+ | C2+ | C3+ |
| 1 | 0 | 30 | 0 | 80 | 0 | 0 |
| 2 | 0 | 0 | 0 | 80 | 0 | 0 |
| 3 | 0 | 0 | 0 | 100 | 0 | 0 |
| 4 | 0 | 0 | 0 | 100 | 0 | 0 |
| 5 | 0 | 0 | 0 | 80 | 0 | 0 |
| 6 | 10 | 0 | 0 | 100 | 0 | 0 |
| 7 | 0 | 0 | 0 | 100 | 0 | 0 |
| 9 | 10 | 0 | 0 | 0 | 0 | 0 |
| 10 | 0 | 0 | 0 | 80 | 0 | 0 |
| 11 | 0 | 0 | 0 | 100 | 0 | 0 |
| 12 | 0 | 0 | 0 | 100 | | |
| 13 | 0 | 0 | 0 | 50 | 0 | 0 |
| 14 | 0 | 30 | 0 | 80 | 10 | 0 |
| 16 | 0 | 0 | 0 | 0 | 0 | 0 |
| 17 | 5 | 0 | 0 | 0 | 0 | 0 |
| 18 | 5 | 0 | 0 | 10 | 0 | 0 |
| 19 | 0 | 0 | 0 | 0 | 0 | 0 |
| 20 | 0 | 0 | 0 | 80 | 0 | 0 |
| 21 | 0 | 0 | 0 | 0 | 0 | 0 |
| 22 | 0 | 0 | 0 | 5 | 0 | 0 |
| 23 | 0 | 0 | 0 | 20 | 0 | 0 |
| 24 | 0 | 0 | 0 | 0 | 0 | 0 |
| 25 | 0 | 0 | 0 | 0 | 0 | 0 |
| 26 | 10 | 0 | 0 | 0 | 0 | 0 |
| 27 | 0 | 0 | 0 | 10 | 0 | 0 |
| 28 | 5 | 0 | 0 | 0 | 0 | 0 |
| 29 | 10 | 0 | 0 | | | |
| 30 | 0 | 0 | 0 | 10 | 0 | 0 |
| 31 | 0 | 0 | 0 | 50 | 0 | 0 |
| 32 | 0 | 0 | 0 | 80 | 0 | 0 |

It was found that 17% of patient samples had positive nuclear staining only, 13% had positive nuclear and cytoplasmic staining, 55% had positive cytoplasmic staining only, and 16% were negative for cytoplasmic and nuclear Androgen Receptor expression (Table 6). Glioblastoma (GBM) is among the most deadly neoplasms associated with one of the worst 5-year overall survival (OS) rates among all human cancers. The median Overall Survival (OS), despite aggressive treatment, remains about 15 months. 3-5% of patients survive for more than 3 years and are referred to as long-term survivors. The 10-year survival rate in the population with GBM is 0.71% (Tykocki and Eltayeb, 2018).

68% of the patients showed cytoplasmic AR expression. Thus, cytoplasmic AR expression is a good prognostic indicator.

Example 12. Combination Therapy Reduces/Blocks Tumour Growth and Metastasis Development and Increases Survival Materials and Methods $1\times10^6$ MDA_MB-231-EGFP-Luc cells were injected orthotopically into the mammary fat pad of NSG female mice. 14 animals were enrolled per treatment arm to reach 80% statistical power. Tumour size was monitored by caliper measurement twice per week. At the time tumour size reached 50-150 $mm^3$ animals were randomized into treatment arms: Vehicle (Veh), Seviteronel (Sev), Docetaxel, Docetaxel+Seviteronel. Seviteronel (100 mg/kg) was administrated via oral gavage daily (6 days on+1 day off) for cycles of 4. Seviteronel was resuspended into a 5% DMSO, 0.1% Tween 80, Hydro-methylcellulose solution at a 5 mg/ml concentration. Animals enrolled in the Vehicle and Docetaxel treatment arms received 7.5 μl/gr of diluent and those enrolled in the Seviteronel or Docetaxel+Seviteronel arms received 7.5 μl/gr of Seviteronel solution. Docetaxel (Docetaxel Accord: 5 mg/ml) was administrated via intraperitoneal injections at 20 mg/kg once per week for 3 consecutive weeks, commencing 1 week after starting Seviteronel treatment. Seviteronel and Vehicle treatment arms were injected with a saline solution to reproduce treatment variables. Growth kinetics were monitored through the course of treatment and plotted using graph-pad prism (V9). Two-way Anova multiple comparison was applied to define statistical significance. At treatment endpoint, animals were injected with luciferin (10 μl/gr of 15 mg/ml stock) and metastatic burden analyzed using an IVIS spectrum imager 10 min post injection. Following IVIS imaging, primary tumour, lymph node metastasis (when present), lung and liver were collected to generate formalin embedded blocks (FFPE) for histopathology analysis (Standard procedure). Metastatic burden (early stage) was defined by luciferin signal observed in peritoneum, lymph nodes and organs exposed upon chest cavity opening.

$1\times10^6$ MDA_MB-231-EGFP-Luc cells were injected orthotopically into the mammary fat pad of NSG female mice. 1 5 animals were enrolled per treatment arm. Tumour size was monitored by caliper measurement twice per week. At the time tumour size reached 50-150 $mm^3$ animals were randomized into 5 different treatment arms: Vehicle (Veh), Docetaxel (Dtx) and Dtx+Sev. Seviteronel was administrated at (100 mg/kg) via oral gavage daily (6 days on+1 day off) for cycles of 4 weeks, with 2 weeks gaps between treatment rounds. All drugs were resuspended into a 5% DMSO, 0.1% Tween80, Hydro-methylcellulose solution at a 5 mg/ml concentration. Treatment administration was performed as described above, administrating Docetaxel at 20 mg/kg. Growth kinetics were monitored through the course of treatment by caliper measurement. Animals were harvested after concluding treatment rounds, collecting primary tumour, lymph node metastasis (when present), lung and liver for histopathology analysis. Once finalized the first round of treatment, 7 animals were subjected to primary tumour resection, to monitor therapeutic efficacy restricting metastasis development. Metastasis development was monitored until animals reached ethical end-point by weekly IVIS imaging. Luciferin signal intensity was used as a measure of metastasis development. Survival was plotted using graph-prism and statistical analysis define using one-way Anova multiple comparison.

Results

FIG. 12A shows the immunohistochemistry images of MDA-MB-231 xenografts showing high cytoplasmic AR expression in matching primary tumour (top), lung metastasis (middle) and liver metastasis (bottom). FIG. 12B is a graphical representation of tumour growth evolution for Vehicle arm (Veh, grey), Seviteronel (Sev), Docetaxel (Dtx) and docetaxel+Seviteronel. Seviteronel treatment was administrated daily (6 days a week) for 4 weeks. Seviteronel dose regime: 150 mg/kg/day for the 1st week, followed by 100 mg/kg/day for 3 weeks. Individual cycles are highlighted by grey boxes. 3 chemotherapy (Dtx 20 mg/kg) i.p injections (indicated as D1, D2, D3) were administrated starting one week after Seviteronel treatment commenced. Seviteronel treatment alone (*p-value<0.05) or in combination with Dtx (****p-value<0.0001) significantly reduces tumour growth compared with Veh treatmet arm. Dtx+Sev also shows significant benefit (*p-value<0.05) when compared with Dtx treatment alone. FIG. 12C is a graph representing metastatic incidence across treatment arms (defined by IVIS imaging) showing that the combination of Dtx+Sev significantly reduces metastatic burden compared to Sev or Dtx alone. FIG. 12D is a graphical representation of tumour growth evolution for Veh arm, Dtx, Dtx+Sev. Dtx+Sev treatment shows significant benefit compared with Dtx alone (*p-value<0.05). FIG. 12E shows Kaplan-Meier curves representing significant survival benefit (***p-value<0.001) for Dtx+Sev compared with all other treatment arms. F) IVIS images showing metastatic burden within treatment arms for 10 weeks following commencement of second round of treatment (Day 77). Dtx+Sev combination therapy was the only group with animals clear of metastasis (29%) compared to 0% for Dtx. Percentage of animals showing metastasis free survival for the different groups are specified for each treatment inside each box.

$1\times10^6$ MDA_MB-231-EGFP-Luc cells were injected orthotopically into the mammary fat pad of NSG female mice. 8 animals were enrolled per treatment arm. Tumour size was monitored by caliper measurement twice per week. At the time tumour size reached 50-150 $mm^3$ animals were randomized into 5 different treatment arms: Vehicle (Veh), Paclitaxel (Ptx), Ptx+Sev, NAB-Paclitaxel (NAB-Ptx) and NAB-Ptx+Sev. Treatment administration was performed as described above, administrating Paclitaxel (Selleckchem Paclitaxel) at 20 mg/kg and NAB-Ptx (Abraxane. Abraxis bioscience) at 40 mg/Kg following previously established tolerated concentrations. Growth kinetics were monitored through the course of treatment by caliper measurement. Animals were harvested after concluding treatment rounds, collecting primary tumour, lymph node metastasis (when present), lung and liver for histopathology analysis.

Results

FIG. 13 shows that Seviteronel treatment in combination with Paclitaxel (Ptx) or NAB-Ptx inhibits tumour growth greater than chemotherapy alone.

ELX12-58 Model with Docetaxel and Seviteronel

Freshly cut tumour chunks derived from a previously expanded tumour (ELX12-58 PDX model) were transferred unilaterally into the mammary fat pad of NSG female mice. 15 animals were enrolled per treatment arm. Tumour size was monitored by caliper measurement as previously described. At the time tumour size reached 50-150 $mm^3$ animals were randomized into treatment arms: Vehicle (Veh), Seviteronel (Sev), Docetaxel, Docetaxel+Seviteronel. Drug preparation and treatment administration was followed as previously described. At treatment end-point animals were harvested and primary tumour, lymph node metastasis (if present), lung and liver were collected to generate FFPEs for histopathology analysis. Seven mice from the Docetaxel and Docetaxel+Seviteronel treatment arms were followed up beyond endpoint treatment to define time to relapse. When tumours reached 1000 $mm^3$, tumours were resected and organs collected (FFPE) to define metastatic burden. Survival curves were generated for animals tracked beyond treatment end-point.

HCI-010 PDX Model with Docetaxel and Seviteronel

Freshly cut tumour chunks derived from a previously expanded tumour (HCI-010 PDX model) were transferred into the mammary fat pad of NSG female mice bilaterally. 15 animals were enrolled per treatment arm. Tumour size was monitored by caliper measurement as previously described. At the time tumour size reached 50-150 $mm^3$ animals were randomized into treatment arms: Vehicle (Veh), Seviteronel (Sev), Docetaxel, Docetaxel+Seviteronel. Drug preparation and treatment administration was followed as previously described. At treatment end-point animals were harvested and primary tumour, lymph node metastasis (if present), lung and liver were collected to generate FFPEs for histopathology analysis.

ELX12-58 PDX Model with Doxorubicin and Seviteronel

Freshly cut tumour chunks derived from a previously expanded tumour (ELX12-58 PDX model) were transferred into the mammary fat pad of NSG female mice. 15 animals were enrolled per treatment arm. Tumour size was monitored by caliper measurement as previously described. At the time tumour size reached 50-150 $mm^3$ animals were randomized into treatment arms: Vehicle (Veh), PEG-Doxorubicin (PEG-Dox) and PEG-Dox+Sev. Drug preparation and treatment administration was followed as previously described for the first round of treatment. PEG-Dox (Liposomal Doxorubicin Sun. R:202827) was administrated by weekly injections to a final concentration of 4 mg/kg. At treatment end-point animals were harvested and primary tumour, lymph node metastasis (if present), lung and liver were collected to generate FFPEs for histopathology analysis. For the PEG-Dox animals, as a relevant protective effect was observed for the combination therapy (PEG-Dox+Sev), 7 mice were kept alive to monitored tumour evolution and survival. Treatment was extended for 2 additional weeks, following the 3rd dose of chemotherapy, administrating a total of 5 EPG-Dox injections for these animals. Animals were followed up for 2.5 months, culling mice before if reached ethical end-point. Primary tumour and organs to determine metastatic burden were collected.

Results

FIG. 14 shows that combination therapy (Seviteronel+Docetaxel) inhibits tumour growth greater than chemotherapy alone in PDX models that express cytoplasmic AR and that Seviteronel in combination with PEG-Doxorubicin significantly improves survival (FIG. 15).

Accordingly, the present disclosure demonstrates that combination therapy of an androgen receptor antagonist with an anti-cancer agent (such as paclitaxel, docetaxel and doxorubicin) reduces tumour growth better than therapy with an anti-cancer agent alone.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

REFERENCES

Al-Hajj et al., *Proc Natl Acad Sci USA.* 100(7):3983-8 (2003). Erratum in: *Proc Natl Acad Sci USA.* 100(11):6890 (2003).

Bierie et al., *Proc Natl Acad Sci USA.* 114(12):E2337-E2346 (2017).

Cai et al., *Cancer cell.* 20:457-471 (2011).

Elston and Ellis, *Histopathology.* 19:403-410 (2002).

Friedrichs et al., *Cancer Res.* 55(4):901-6 (1995).

Ginestier et al., *Cell Stem Cell.* 2007 November; 1(5):555-67 (2007).

Hickey et al., *Mol Endocrinol.* 26:1252-1267 (2012).

Jahnisch, et al., *Angew. Chem. Int. Ed. Engl.* 43: 406-446 (2004).

Lehmann, et al., *PloS one* 11, e0157368 (2016).

Leung and Sadar., Front Endocrinol (Lausanne). 17; 8:2 (2017).

Lipscomb et al., *Cancer Res.* 65 (23): 10970-6 (2005).

Liu et al., *Stem Cell Reports.* 2(1):78-91 (2013)

Nadal et al., *Int Cancer.* 133(10):2398–407 (2013).

Neumeister et al., *Am J Pathol.* 176(5):2131-8 (2010).

Tykocki & Eltayeb., *J Clin Neurosci.* 54, 2-13 (2018).

van Galen, et al., *Molecular cell* 61, 170-180 (2016).

Wei et al., *Stem Cells.* 32(10): 2571-82. (2014).

Yin et al., *Cell Immunol.* 300:41-45 (2016).

The invention claimed is:

1. A method of sensitizing a cancer cell in a subject to an anti-cancer agent, comprising administering to the subject an androgen receptor antagonist, wherein the cell is a breast cancer cell, wherein the anti-cancer agent is docetaxel, paclitaxel, or doxorubicin, and wherein the androgen receptor antagonist is seviteronel.

2. The method according to claim 1 wherein the cancer cell is a poorly tumourigenic cell or a highly tumourigenic cell.

3. The method according to claim 1, wherein the cancer cell is a $CD44^{Lo}$ cell.

4. The method according to claim 2, wherein the method comprises impeding or preventing the development of resistance to the anti-cancer agent.

5. The method according to claim 1, wherein the cancer cell is a $CD44^{Hi}$ cell.

6. The method according to claim 5, wherein the method comprises inhibiting proliferation of the $CD44^{Hi}$ cell or increasing sensitivity of the $CD44^{Hi}$ cell to an anti-cancer agent.

7. The method according to claim 1, wherein the method comprises determining the level of expression and/or activity of the androgen receptor and/or ZEB1 in the cell.

8. The method according to claim 1, wherein the method comprises determining the level of expression and/or activity of the androgen receptor and/or ZEB1 in the cytoplasm of the cell.

9. A method of inhibiting the development of resistance to an anti-cancer agent in a cancer cell in a subject, the method comprising: determining the level of expression and/or activity of the androgen receptor and/or ZEB1 in the cancer cell; and administering to the subject an androgen receptor antagonist if the level of expression and/or activity of the androgen receptor and/or ZEB1 is low, wherein the cell is a breast cancer cell, wherein the anti-cancer agent is docetaxel, paclitaxel, or doxorubicin, and wherein the androgen receptor antagonist is seviteronel.

10. A method of inhibiting the proliferation of a cancer cell in a subject, the method comprising: determining the level of expression and/or activity of the androgen receptor and/or ZEB1 in the cancer cell; and administering to the subject an androgen receptor antagonist if the level of expression and/or activity of the androgen receptor and/or ZEB1 is high, wherein the cell is a breast cancer cell, wherein the anti-cancer agent is docetaxel, paclitaxel, or doxorubicin, and wherein the androgen receptor antagonist is seviteronel.

11. The method according to claim 9, wherein the level of expression and/or activity of the androgen receptor and/or ZEB1 is determined in the cytoplasm of the cell.

* * * * *

SEQUENCE LISTING

```
<160> NUMBER OF SEQ ID NOS: 7

<210> SEQ ID NO 1
<211> LENGTH: 920
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln
    50                  55                  60

Gln Gln Gln Gln Gln Gln Gln Gln Gln Gln Gln Gln Gln Gln Gln
65                  70                  75                  80

Glu Thr Ser Pro Arg Gln Gln Gln Gln Gln Gln Gly Glu Asp Gly Ser
                85                  90                  95
```

-continued

```
Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly Gly Gly
    450                 455                 460

Gly Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510
```

-continued

```
Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920
```

-continued

<210> SEQ ID NO 2
<211> LENGTH: 1124
<212> TYPE: PRT
<213> ORGANISM: Homo sapiens

<400> SEQUENCE: 2

```
Met Ala Asp Gly Pro Arg Cys Lys Arg Arg Lys Gln Ala Asn Pro Arg
1               5                   10                  15

Arg Asn Asn Val Thr Asn Tyr Asn Thr Val Val Glu Thr Asn Ser Asp
            20                  25                  30

Ser Asp Asp Glu Asp Lys Leu His Ile Val Glu Glu Glu Ser Val Thr
        35                  40                  45

Asp Ala Ala Asp Cys Glu Gly Val Pro Glu Asp Asp Leu Pro Thr Asp
    50                  55                  60

Gln Thr Val Leu Pro Gly Arg Ser Ser Glu Arg Glu Gly Asn Ala Lys
65                  70                  75                  80

Asn Cys Trp Glu Asp Asp Arg Lys Glu Gly Gln Glu Ile Leu Gly Pro
                85                  90                  95

Glu Ala Gln Ala Asp Glu Ala Gly Cys Thr Val Lys Asp Asp Glu Cys
            100                 105                 110

Glu Ser Asp Ala Glu Asn Glu Gln Asn His Asp Pro Asn Val Glu Glu
        115                 120                 125

Phe Leu Gln Gln Gln Asp Thr Ala Val Ile Phe Pro Glu Ala Pro Glu
    130                 135                 140

Glu Asp Gln Arg Gln Gly Thr Pro Glu Ala Ser Gly His Asp Glu Asn
145                 150                 155                 160

Gly Thr Pro Asp Ala Phe Ser Gln Leu Leu Thr Cys Pro Tyr Cys Asp
                165                 170                 175

Arg Gly Tyr Lys Arg Phe Thr Ser Leu Lys Glu His Ile Lys Tyr Arg
            180                 185                 190

His Glu Lys Asn Glu Asp Asn Phe Ser Cys Ser Leu Cys Ser Tyr Thr
        195                 200                 205

Phe Ala Tyr Arg Thr Gln Leu Glu Arg His Met Thr Ser His Lys Ser
    210                 215                 220

Gly Arg Asp Gln Arg His Val Thr Gln Ser Gly Cys Asn Arg Lys Phe
225                 230                 235                 240

Lys Cys Thr Glu Cys Gly Lys Ala Phe Lys Tyr Lys His His Leu Lys
                245                 250                 255

Glu His Leu Arg Ile His Ser Gly Glu Lys Pro Tyr Glu Cys Pro Asn
            260                 265                 270

Cys Lys Lys Arg Phe Ser His Ser Gly Ser Tyr Ser Ser His Ile Ser
        275                 280                 285

Ser Lys Lys Cys Ile Ser Leu Ile Pro Val Asn Gly Arg Pro Arg Thr
    290                 295                 300

Gly Leu Lys Thr Ser Gln Cys Ser Ser Pro Ser Leu Ser Ala Ser Pro
305                 310                 315                 320

Gly Ser Pro Thr Arg Pro Gln Ile Arg Gln Lys Ile Glu Asn Lys Pro
                325                 330                 335

Leu Gln Glu Gln Leu Ser Val Asn Gln Ile Lys Thr Glu Pro Val Asp
            340                 345                 350

Tyr Glu Phe Lys Pro Ile Val Val Ala Ser Gly Ile Asn Cys Ser Thr
        355                 360                 365

Pro Leu Gln Asn Gly Val Phe Thr Gly Gly Gly Pro Leu Gln Ala Thr
    370                 375                 380
```

-continued

```
Ser Ser Pro Gln Gly Met Val Gln Ala Val Val Leu Pro Thr Val Gly
385                 390                 395                 400

Leu Val Ser Pro Ile Ser Ile Asn Leu Ser Asp Ile Gln Asn Val Leu
                405                 410                 415

Lys Val Ala Val Asp Gly Asn Val Ile Arg Gln Val Leu Glu Asn Asn
            420                 425                 430

Gln Ala Asn Leu Ala Ser Lys Glu Gln Glu Thr Ile Asn Ala Ser Pro
        435                 440                 445

Ile Gln Gln Gly Gly His Ser Val Ile Ser Ala Ile Ser Leu Pro Leu
    450                 455                 460

Val Asp Gln Asp Gly Thr Thr Lys Ile Ile Ile Asn Tyr Ser Leu Glu
465                 470                 475                 480

Gln Pro Ser Gln Leu Gln Val Val Pro Gln Asn Leu Lys Lys Glu Asn
                485                 490                 495

Pro Val Ala Thr Asn Ser Cys Lys Ser Glu Lys Leu Pro Glu Asp Leu
            500                 505                 510

Thr Val Lys Ser Glu Lys Asp Lys Ser Phe Glu Gly Gly Val Asn Asp
        515                 520                 525

Ser Thr Cys Leu Leu Cys Asp Asp Cys Pro Gly Asp Ile Asn Ala Leu
    530                 535                 540

Pro Glu Leu Lys His Tyr Asp Leu Lys Gln Pro Thr Gln Pro Pro Pro
545                 550                 555                 560

Leu Pro Ala Ala Glu Ala Glu Lys Pro Glu Ser Ser Val Ser Ser Ala
                565                 570                 575

Thr Gly Asp Gly Asn Leu Ser Pro Ser Gln Pro Pro Leu Lys Asn Leu
            580                 585                 590

Leu Ser Leu Leu Lys Ala Tyr Tyr Ala Leu Asn Ala Gln Pro Ser Ala
        595                 600                 605

Glu Glu Leu Ser Lys Ile Ala Asp Ser Val Asn Leu Pro Leu Asp Val
    610                 615                 620

Val Lys Lys Trp Phe Glu Lys Met Gln Ala Gly Gln Ile Ser Val Gln
625                 630                 635                 640

Ser Ser Glu Pro Ser Ser Pro Glu Pro Gly Lys Val Asn Ile Pro Ala
                645                 650                 655

Lys Asn Asn Asp Gln Pro Gln Ser Ala Asn Ala Asn Glu Pro Gln Asp
            660                 665                 670

Ser Thr Val Asn Leu Gln Ser Pro Leu Lys Met Thr Asn Ser Pro Val
        675                 680                 685

Leu Pro Val Gly Ser Thr Thr Asn Gly Ser Arg Ser Ser Thr Pro Ser
    690                 695                 700

Pro Ser Pro Leu Asn Leu Ser Ser Ser Arg Asn Thr Gln Gly Tyr Leu
705                 710                 715                 720

Tyr Thr Ala Glu Gly Ala Gln Glu Glu Pro Gln Val Glu Pro Leu Asp
                725                 730                 735

Leu Ser Leu Pro Lys Gln Gln Gly Glu Leu Leu Glu Arg Ser Thr Ile
            740                 745                 750

Thr Ser Val Tyr Gln Asn Ser Val Tyr Ser Val Gln Glu Glu Pro Leu
        755                 760                 765

Asn Leu Ser Cys Ala Lys Lys Glu Pro Gln Lys Asp Ser Cys Val Thr
    770                 775                 780

Asp Ser Glu Pro Val Val Asn Val Ile Pro Pro Ser Ala Asn Pro Ile
785                 790                 795                 800

Asn Ile Ala Ile Pro Thr Val Thr Ala Gln Leu Pro Thr Ile Val Ala
```

-continued

```
                805                 810                 815

Ile Ala Asp Gln Asn Ser Val Pro Cys Leu Arg Ala Leu Ala Ala Asn
            820                 825                 830

Lys Gln Thr Ile Leu Ile Pro Gln Val Ala Tyr Thr Tyr Ser Thr Thr
        835                 840                 845

Val Ser Pro Ala Val Gln Glu Pro Pro Leu Lys Val Ile Gln Pro Asn
    850                 855                 860

Gly Asn Gln Asp Glu Arg Gln Asp Thr Ser Ser Glu Gly Val Ser Asn
865                 870                 875                 880

Val Glu Asp Gln Asn Asp Ser Asp Ser Thr Pro Pro Lys Lys Lys Met
                885                 890                 895

Arg Lys Thr Glu Asn Gly Met Tyr Ala Cys Asp Leu Cys Asp Lys Ile
            900                 905                 910

Phe Gln Lys Ser Ser Ser Leu Leu Arg His Lys Tyr Glu His Thr Gly
        915                 920                 925

Lys Arg Pro His Glu Cys Gly Ile Cys Lys Lys Ala Phe Lys His Lys
    930                 935                 940

His His Leu Ile Glu His Met Arg Leu His Ser Gly Glu Lys Pro Tyr
945                 950                 955                 960

Gln Cys Asp Lys Cys Gly Lys Arg Phe Ser His Ser Gly Ser Tyr Ser
                965                 970                 975

Gln His Met Asn His Arg Tyr Ser Tyr Cys Lys Arg Glu Ala Glu Glu
            980                 985                 990

Arg Asp Ser Thr Glu Gln Glu Glu  Ala Gly Pro Glu Ile  Leu Ser Asn
        995                 1000                1005

Glu His  Val Gly Ala Arg Ala  Ser Pro Ser Gln Gly  Asp Ser Asp
    1010                1015                1020

Glu Arg  Glu Ser Leu Thr Arg  Glu Glu Asp Glu Asp  Ser Glu Lys
    1025                1030                1035

Glu Glu  Glu Glu Glu Asp Lys  Glu Met Glu Glu Leu  Gln Glu Glu
    1040                1045                1050

Lys Glu  Cys Glu Lys Pro Gln  Gly Asp Glu Glu Glu  Glu Glu Glu
    1055                1060                1065

Glu Glu  Glu Val Glu Glu Glu  Glu Val Glu Glu Ala  Glu Asn Glu
    1070                1075                1080

Gly Glu  Glu Ala Lys Thr Glu  Gly Leu Met Lys Asp  Asp Arg Ala
    1085                1090                1095

Glu Ser  Gln Ala Ser Ser Leu  Gly Gln Lys Val Gly  Glu Ser Ser
    1100                1105                1110

Glu Gln  Val Ser Glu Glu Lys  Thr Asn Glu Ala
    1115                1120
```

<210> SEQ ID NO 3
<211> LENGTH: 186599
<212> TYPE: DNA
<213> ORGANISM: Homo sapiens

<400> SEQUENCE: 3

```
agcgccccct ccgagatccc ggggagccag cttgctggga gagcgggacg gtccggagca      60

agcccagagg cagaggaggc gacagaggga aaaagggccg agctagccgc tccagtgctg     120

tacaggagcc gaagggacgc accacgccag ccccagcccg gctccagcga cagccaacgc     180

ctcttgcagc gcggcggctt cgaagccgcc gcccggagct gccctttcct cttcggtgaa     240

gtttttaaaa gctgctaaag actcggagga agcaaggaaa gtgcctggta ggactgacgg     300
```

-continued

```
ctgcctttgt cctcctcctc tccaccccgc ctccccccac cctgccttcc ccccctcccc    360
cgtcttctct cccgcagctg cctcagtcgg ctactctcag ccaaccccc tcaccaccct    420
tctccccacc cgcccccccg cccccgtcgg cccagcgctg ccagcccgag tttgcagaga    480
ggtaactccc tttggctgcg agcgggcgag ctagctgcac attgcaaaga aggctcttag    540
gagccaggcg actggggagc ggcttcagca ctgcagccac gacccgcctg gttaggctgc    600
acgcggagag aaccctctgt tttcccccac tctctctcca cctcctcctg ccttccccac    660
cccgagtgcg gagccagaga tcaaaagatg aaaaggcagt caggtcttca gtagccaaaa    720
aacaaaacaa acaaaaacaa aaaagccgaa ataaaagaaa aagataataa ctcagttctt    780
atttgcacct acttcagtgg acactgaatt tggaaggtgg aggattttgt ttttttcttt    840
taagatctgg gcatcttttg aatctaccct tcaagtatta agagacagac tgtgagccta    900
gcagggcaga tcttgtccac cgtgtgtctt cttctgcacg agactttgag gctgtcagag    960
cgctttttgc gtggttgctc ccgcaagttt ccttctctgg agcttcccgc aggtgggcag   1020
ctagctgcag cgactaccgc atcatcacag cctgttgaac tcttctgagc aagagaaggg   1080
gaggcggggt aagggaagta ggtggaagat tcagccaagc tcaaggatgg aagtgcagtt   1140
agggctggga agggtctacc ctcggccgcc gtccaagacc taccgaggag ctttccagaa   1200
tctgttccag agcgtgcgcg aagtgatcca gaacccgggc cccaggcacc cagaggccgc   1260
gagcgcagca cctcccggcg ccagtttgct gctgctgcag cagcagcagc agcagcagca   1320
gcagcagcag cagcagcagc agcagcagca gcagcagcag cagcaagaga ctagccccag   1380
gcagcagcag cagcagcagg gtgaggatgg ttctccccaa gcccatcgta gaggccccac   1440
aggctacctg gtcctggatg aggaacagca accttcacag ccgcagtcgg ccctggagtg   1500
ccaccccgag agaggttgcg tcccagagcc tggagccgcc gtggccgcca gcaaggggct   1560
gccgcagcag ctgccagcac ctccggacga ggatgactca gctgccccat ccacgttgtc   1620
cctgctgggc cccactttcc ccggcttaag cagctgctcc gctgacctta aagacatcct   1680
gagcgaggcc agcaccatgc aactccttca gcaacagcag caggaagcag tatccgaagg   1740
cagcagcagc gggagagcga gggaggcctc gggggctccc acttcctcca aggacaatta   1800
cttagggggc acttcgacca tttctgacaa cgccaaggag ttgtgtaagg cagtgtcggt   1860
gtccatgggc ctgggtgtgg aggcgttgga gcatctgagt ccaggggaac agcttcgggg   1920
ggattgcatg tacgccccac ttttgggagt tccacccgct gtgcgtccca ctccttgtgc   1980
cccattggcc gaatgcaaag gttctctgct agacgacagc gcaggcaaga gcactgaaga   2040
tactgctgag tattcccctt tcaagggagg ttacaccaaa gggctagaag gcgagagcct   2100
aggctgctct ggcagcgctg cagcagggag ctccgggaca cttgaactgc cgtctaccct   2160
gtctctctac aagtccggag cactggacga ggcagctgcg taccagagtc gcgactacta   2220
caactttcca ctggctctgg ccggaccgcc gcccccctccg ccgcctcccc atccccacgc  2280
tcgcatcaag ctggagaacc cgctggacta cggcagcgcc tgggcggctg cggcggcgca   2340
gtgccgctat ggggacctgg cgagcctgca tggcgcgggt gcagcgggac ccggttctgg   2400
gtcaccctca gccgccgctt cctcatcctg gcacactctc ttcacagccg aagaaggcca   2460
gttgtatgga ccgtgtggtg gtggtggggg tggtggcggc ggcggcggcg gcggcggcgg   2520
cggcggcggc ggcggcggcg gcggcgaggc gggagctgta gccccctacg gctacactcg   2580
gccccctcag ggctggcgg gccaggaaag cgacttcacc gcacctgatg tgtggtaccc   2640
```

-continued

```
tggcggcatg gtgagcagag tgccctatcc cagtcccact tgtgtcaaaa gcgaaatggg   2700
cccctggatg gatagctact ccggacctta cggggacatg cggtaagttt ttccttccag   2760
aaatgtcgcc tttcggccca gggcagagtc actctgtgtt ctggggtatc tagcggctcc   2820
tacctgcgcg aacactcaga ttgcccctgg gagagctcag cagggtaaac ctagagctct   2880
cccgtggact cccggcctgc cagaggttta acctgagctc tcctaatttc tgctgcgtgc   2940
cctgggtgct gattcctgcc ctcccagatt cttcaactcc cccaaccgcc ccaaattctc   3000
actacctcct ggtactcgag gtcccaaaca gaaatcctat tgcacgggcc accttcagag   3060
ataaagctcc caagccctcc actcttcctt tcctcctgtc ctcaaagtct gagaacctca   3120
acaggaattt gggcaatttc tcctcttcag gtctgttagg atttcacttt cagcctgcgc   3180
agattagagt caaaaagacc ggcccaatag cttctcagcg ggtatcctcc agagaggtaa   3240
agtgaaattc tcggttaggg aaagaaagtg gtctctgggt gctgaggtct gctgtgtgaa   3300
agggtgaact tctttctcct gaagcaactg gggacttgct ccagggctgg aggtcagtag   3360
agataatcca aaccgtcatg tttagagtag gcagaggggc aactttcttg gtaaagactt   3420
cacaggattt gcactcacag tttctcaacg ttggttgact atgttgaaag tagttgcttg   3480
ggtcggtttt ctcttgtaaa gtgtttattt tctctgtgga ttataacaga tccacagccc   3540
cctacttcag gtttgcatca gatctataaa gaggagaata ttcttttaat gtacaattta   3600
attaggcttg actctgactt acaaaactgt tggaaaacat ttttttgtaa agcatttcct   3660
gctatttcag tgtgctccaa aatctccact ggggagggtg gagtgaggtt ttttattata   3720
ttcctttatt tttaggacat gtttgcattt tagaatatgt gcagttagct ctaacaaatt   3780
gagtaagaac tcttaatgac ctatgagccg taatcttacc ccaaagtttt aattagcata   3840
tgagaaaagt ggcaggcaat tgcatcgtgc ttattaaaaa ttattcctca ccgcagttgt   3900
tgagcttctt ggagaccatg ctgaagattt tctcccccag caaattaaga tattagttta   3960
tctgctgagg gaggacagac tgaattgggg aattaactcc tcaggtaggc caggtgctga   4020
tgtccctgtg gacttttgtc ttattctttg tttctatggc tgttttcttt tacctgtgac   4080
ttctccgaaa tttctttgtt agccttaaca tctttgtttg gggacttaaa tccagcaatt   4140
tgccttcttt cactgatgct ttccttctta caaggtagat agcacagtgt tagtaaagaa   4200
agaaagagga gggtaggatt tcatattatt tcgtgggctg ttgaagaaac agcttcttac   4260
caggctttac attccattag gtttttaatg tttgacttac aagattttca gagggttcat   4320
ttgatattgt caaagtcttt tccagttaat ttagactctt catttttgta atgggtttat   4380
gctatgggac aaaaaaagta ttcttcattt tataagaaca aatttacttg gtagggttaa   4440
ttttttttct agggctgtca ctagacggtg gagcccctct tctactgtaa actttttcttg   4500
ggggaaaatg tctaaggtgc attttgacct gccatgatac taaacccaga cactggaacc   4560
ttccatcttc tgcatgcctc ccccacaact tacttactta acagggaaaa aactgatggt   4620
tccacatatt tgctaaaaaa tgtgtgcctt caaagacaaa accaaaattt ttagggaata   4680
actatagaga gcaaaagtta ctcccatcaa gtagacaacg agcttggtga ttttatttca   4740
ggtcttaatg aaaaaagctt ctttatgagg aaggttatca tatcttggtg cctccttgac   4800
agtccgctta aattaatgac ataaactaat gagaatttag cagttcctgc agaaagtaca   4860
agtttatttt ttttttctgg tttgtgattg ctgcactgaa tatgaggagt ctagttaaag   4920
ggacaactgg tgttcctgtc ttgtgagttg acgaagactt tccatttcta ggatatagaa   4980
aatccttaag ccggtttatt gaaaattaat caatttaatc agaatgcaat caattccaat   5040
```

acaaaagtta gtattttctt tctttttatt gaaaattaat ttaatcagaa tacaatcaat 5100
tccaatccaa aagttgatat tttcttactt tctctttttt tccctcattt tgtagggata 5160
caatttggtg aaaggcaaga gatttcttaa gccaaagcaa gagtgtcttc cctctctgtg 5220
ttgcatgcat tatgtgccat gtttgagcta aaaatctcaa aattgggcag gcttccaatg 5280
acctgttggg tccctccctt taccattcat gtgtgtgttt atgtacataa ttttgtggag 5340
gggttttttt aaaccttagt aacatctgca ctcactctgt gttcttatac atttacagtg 5400
tttctgctga gaggagggaa gatgcaaagg tggtctcttt tacttaattt agcatgtggt 5460
ttgaacagaa ggaaaaataa aaagtgatgg ggcttgtgtg caaccctgat gatattttat 5520
ggagctgtct gtcttctctc tgagatcaaa caggactaca actttgttaa ttgaccactg 5580
gctcccttgg caaaagtagg gcttcttata ttccagcaag cagcacaata atatgacaaa 5640
aatttattct tgggagttgg gttctaagag agtgcatgcc agaattagag tttggggttt 5700
agagaaatta tccagatgcc aaaagaacat tttaattttt ctcttggtaa tttgttctgg 5760
tctccatagt aggtagtatt ttagtagtgc tttgatattg acaagtcttg ctccctttct 5820
ctattagatt tttcaaaata aggcatttta ttaattcctc tttccttctc ctctctcctc 5880
tcagttatca agcattttta tgactatctt acaagcaaca gtttgtcttg taaagcagaa 5940
ttttcctttg aaaccaagac agattatttc tgcccatagg cttcaggaac caatattttg 6000
gcaagaagca tcttttcttt gtggtcagca aataggtggt gagttctgtc tggatcccaa 6060
caatcaacac ctgaggacca aatagccaca ctgggtggca ccccattcgg aagtatacac 6120
aggaagtagc cctcttgctt gttcacagct caagtcagcc aaagattaac actggtgaga 6180
gatattttca aagaagtttg caggcttcca attgcagggt cattttgggg tgctttcttg 6240
cctgtactaa ttttatctca tcaagcttcc attctttgag ctgtaaactt tgaaataata 6300
tactggattt gctggtacgt ttaattttct ttgttaagtg ttttcattcc catagtaatt 6360
tttcatctag tgtacatata tgcatttaaa acaaaaaattc tttggtctcc ttatgcgtat 6420
atgcactgcg gcttgtacac gtacaagcta cttggtggga ttatgtgaac tggagttaga 6480
aatgtggaca attttattat gattattttt aatggtgata tcaagatcac cagtttcatt 6540
cggaaccttg cataagcagg gagcagaatg cggactgggt gtggcaaagc aagggcttat 6600
tttatagcca aacctgaaat cacaactctg aaaaataaaa aaaaaaaaaa ccaaacaaaa 6660
aaatcaagtt ttgtgagctt ggtcagagaa ggaaaaggaa atctctccct accccccacc 6720
tccaccattt tctctttgtc tgcagcttcc tcaagtgctg cctgtccccg attttctttt 6780
attccactcc tttcatgttt ttgacattga aatacagact cttctttcca cttctcaggg 6840
tatttttctt attacacctg tggcatgctc ctaaagaatt tcttttttaa aaaaaatctg 6900
tagagtagta gattagatta accccagtat ctctccctta agactagatg acatgagggg 6960
attgcaaaat gaatagctgg gttttttttt tttttttttt ttttaccttg aggttaaagc 7020
ctggttcaac agttgctgag agagttaact agattgcttg aggacttggc aatttcataa 7080
agtattttgt cttatgctgt ctctgtctct gtcttgatct ctgtctctct ctgtctactg 7140
taatgttggc tactttctct cagagcctga gagacagctc tgagacactt cccaggtctg 7200
ttcggttcag acctcagtag ctggatcaca agcagtaccc aatatgcata tgagggtgcg 7260
tgctgcaagt gtccggctgg gctaatctgc ttaagcttca taaaaattaa tcatttgaaa 7320
acaaagaaag atattaaaga aattattcta tctccgactt cccctatcag cattccatca 7380

-continued

```
agttctggga tgttaaattc agagaaagtt aaccttatct taaacacaaa gttgactttt   7440
aaacaaaatt gcttataaag ttctgtacag ttaccagcat tggttgccct ttgtcgtacg   7500
gaagagaatt atgaaatctc atatttacat agcattcttc caaaaaaaga gacggtgttt   7560
tccagtttat tcactgcatt cgtgtaagtg tgagtaggcc aggaggggtg cttagtgatt   7620
accctttttgc taggtaacaa agtagaaagt tagattttct atgatatttg tttaccacgt  7680
aggggaacct ctctagagca atactcccaa gctttttctt cttgaaattt cccacctgac   7740
agataatact ttagattgtt gctcttaagg acttctctca gtagctgcta catagagatg   7800
attgtccgtg aattattgct tgcacactca tgggtgatgc tactccctct ctctcatggc   7860
aattcttgct gccaacctgc aggccacacc aggattgagg gcagctcatc tcgataaatt   7920
tatagcatta aagtgctggg tcatttgaga atgttgtcaa tttaggttac ttagtaccta   7980
agttttattc tttaaataac agctttattg agacgtaatt tacaatccat acaattcact   8040
catctaaagt gtacagtttc atgcttttta gaatattcag agttgtgcaa ccattattgc   8100
aatcaatttt agaacatttt aatcaccccc aaaggaaacc ctatgcacct ttgtgttcat   8160
ccccctatat tccctcagtc cttagcaacc aataatctac ttctatctat ggatgtgctt   8220
attctaacat tttgtatgaa tgaaatcatg taatatgtgg tcttttgtga ctagcttctt   8280
tcacataaaa tatgttttca aggtcatcca tgttgaagca catatcagta cttcactatt   8340
ttttatagcc taataatgtt ccactatatg gatataccac attctatcta tccatttatc   8400
aggtgatgag cattacggtt gtttccacct tttggctatt atgaataata ctgctgtgaa   8460
cattcacgtg caagtttatt gtggacatat tcagtccaca tattttggac attttcagtt   8520
cttttggata catacatagg attgaaatct ctgagtcata tgatacctct gtgtttatcc   8580
ttttgaagaa ctgtcaaact gttttctaaa gtgtctgcac tgttttacaa tcccatcagc   8640
aacctatggg ggtccatttc ttccacatcc ttgccaacac ttgttattct ctgtcttttt   8700
cattatagct atattagtgg gtgtgaagtg gtacctcatt gtggctttta tttccatttc   8760
cctaataaca aataatgttc agtatccatg ttcttattgg ccatttgtat atcttctttt   8820
ttgagaaata tctatttgga tcctttgctc agtttttagt tgggtttttt attattgagt   8880
tttaagattt ttaaaaaata tattctggat acatgtcctt taatagattg tgatttgtag   8940
atatttttttc acattctgtg agttgtcttt tttactttcc ttttttttct ttttacgttc  9000
ttaatggtat ctagattgaa gcacaaaaat gtttttaagt ttgatgaagt ccaattcatc   9060
tatttatttt ctgttttggc ttatgatttt ggcgtcgtat ctaagaagtc tttgcctaat   9120
ccaagatcac aaagatttac atatgtttcc ttctaagagt tttatagttt tcgctattta   9180
catttaggtc tttcatcagt tttgatgtaa tgtttatata tgactgaggt aggggtccaa   9240
cttcattctt ttgcatgtag atattcagtt ctcacaatat tgttgttgaa tctttcctca   9300
cttaactgtc ttggcaccct ttgtgtaaaa tcagttgacc gtaaatgtga gggtttaatt   9360
gtggactctc aactatattc agttgatcta tatgtttatt cctatgccgg taccacgtta   9420
tcttgattat tgtaggtttt tagtgagttt tgaaattagg aattttgaac tcttcaactt   9480
tggtcttctt tttcaagatt gctttggctc ttgtgggtcc cttgaatttt caaatgaatt   9540
gggataagct tgtcaatttc tacgaagaag tcagctagga ttctcacagg aactatatta   9600
aatctgtaaa ccaatttggg gagcattgtc atctcaacaa cgttaagtta ttttcatcca   9660
taaatatgcg atgtcttccc atttatttag gtcttccttt tgtcaacaat ttttattgtt   9720
ttcagattat aagttttgca gttcttttta aaatttattc ctaagtgatt tattttttga   9780
```

-continued

```
tactataaat tgaactgtct tattgatttt attttcagat tattcgctgc caatgtatgg   9840
aaatataatt gttttgtata ttgatcttgt atcctgcaac cttgctgaaa atacctgagt   9900
tttgaatgct tctgggactt atggggaaga gggcttctgc tgctgcactg aaagttaaag   9960
cttacttcat ttcatcctgt atgaaggctg catggggaca ttcttctcag ttttactcag  10020
ctataaattc gaactggtaa tcccatcccc tttcgggatg aataggagag tgtttttaaa  10080
tgttcatctc tttagagaac agcaggaaag aagcctagta aggtttgggt agtttataat  10140
cccttttta gaatttggat ttgggaacta ttagcaaggc agtgagtaat aataataatt  10200
tctatataga aaactaacat gtagaggtga caaatgaaat cactagctat attaggctta  10260
tgtttaggtt atcgtaagca gctaaaatca taattttatg tttttatatg ttgtcctttg  10320
gacaaagtaa attccagtac tccttctgat gtgcatttct agatggggaa aggattcatt  10380
tactctcata taatttaagc ttctttttag ggatgtactc catagccatg aagcaaagat  10440
aaaattcatc tatacacaga ctgaactttg tcttcattaa cactctaggc taagggtcat  10500
agctaatcag ctacaactgt aatgtcctga taattgtgaa ttaactgcag ggcacccagc  10560
aaaaggttta gttataatct aatagctgtc tgtagagatt agcctaataa agggattttt  10620
taaaaaagaa tctggccggg catggtggct caatcctgta atcccagcac tttgggaggc  10680
cgaggtgggt ggatcacctg agatcgggag tccaagacca gcctggccaa catggtgaaa  10740
ccccatgtct actaaaaata caaaaattat ccaggcgttt tggtgagcac ccacaatccc  10800
agctacttgt gaggctgagg caggaggatc acttaagcct aagaggcaga ggttgcagtg  10860
agccgagatc atgccactgc actccaggct ccgtcaaaaa aaaaaaaaaa aaagaatcta  10920
tcaatcaacc acttttcatt aagcacctgc tatgtgccca gcatgtgcta ggaagagata  10980
aggtgaaagg ggacacaatt cagacagaat cttcttgagg taactgctta cgaggagctt  11040
atagccacta aaaacaaaaa caaacaaaaa ccaaacaacc aaaaaccaaa cagaaatgca  11100
gtatcatcat gccatgatgc ctgtatgaga tcctggattg tacggtatgg atttcttaaa  11160
atgtagatat tttaaaaaaa aagaggaatg aatcaataga ggctgaagtg gtcagcaatg  11220
ttacctgtgg ctgcttttaa tccttcgtgg aagtaagtag gagcatgtct aaactcaagc  11280
aatagattaa agatcttgat gtatatttta aataacagaa gttagtacca ctggaaagaa  11340
tgaactggag gaatgggttg aaatctattt ctgcttattc aatagtgcac cccagtcaag  11400
ttagttgcca atttcttctt cagtttcttt ggctatatca ttgcacttgg tgggtacatg  11460
tttatgatgt ctttatctga acaagtcagc aataatatga gtaataaatt aaaattgaag  11520
gtgattaatg gctctgaatt tgacataaga gttgttttcc tgccttctaa gtttccattg  11580
atcctgatga attgcacaaa ccaaacaatt cggggagtaa gggggcacat gatgatctta  11640
taagagcttt gctgtattag acaacgtaac attctgaaat ggcctaccac ctaacatggg  11700
ctctgttctc tgcaggttga gtaggttcct tgcttgtgga actgtagtcc cgctatttgg  11760
ccgctagggg gactgcaagt gccccgtggc aggatttccc tgggaatggt gagcctccat  11820
tgatggtttc aacacacagc caaggcccta tcgcaggata acttgaacca gaactgccta  11880
gcaccagaca ataaataagc tactatggta cttactgttt catttgggat gttgtttctc  11940
gaagtggcaa gcattttta gtaatatttt gactttttaa tacctttctt tgcatatgga  12000
gcagaaaaca gtgacactgg atatattcaa gtagcactgt ccagtttata gagaagtttc  12060
atattccatt attgcatttc attcttgttt ctacctttta caagtaacta gagtttggag  12120
```

-continued

```
tattataata gtattcatac tattacagta ctattattcc cattataaaa attgtgcaaa  12180
gagtggttaa gttacatgtt tacaatcaaa cagcttcaaa gtgactgatc tggaatttca  12240
gtcccattct ttcttctcca gatcatgtgt tccctgcttt tatctcacag ctctttttac  12300
cttatagatg ggaaacatga gagtcagaga ggcaaaagaa ccacaagtgg tatcaatact  12360
agaaatttat gaatttctta aggcttctag gtttgttacc catccaccag actgatggat  12420
ttggttgtgt gagagttctg ggtgccaata accttgccat tctactttac agactgcata  12480
tattcaataa atgcttatta agcatctact atatgccaaa ttctgtacta ggcaccaatg  12540
atgtagtggt gaacagaaca gacaaaaatc tcttcgtgga gcagacagtt taatgagagg  12600
agacatgtag tgtacatctg agcatgaaaa gtgccatgca gaataacttc acagagtgta  12660
gggtatagag attgatggtg agagggaata ttttatattt gctggccagg gaaaacctta  12720
ctggaaaagt aaattttgag tagtgacctg aaggaaatta ggaaatgagc tgctatttgg  12780
acatctggag ttagaatatt ccaggcccag ggaaccacag gcgcaaaggg cctgaggcag  12840
gagcacactt gctgtgatgg aggacaaaga ggcccatatg gctggtttaa ataagtgaag  12900
gatggtagac aatgagatca gagttaatga ggttgcatgg taggtcttcc ttaggacttt  12960
gaattttact cctaagcagg ttgtattgga cggttttgag cagggtaaca tgacctgact  13020
tacattttaa caggctccct cctcttcata acatctgtca ctctgatata ttatacgttt  13080
gtttgtttac ttactgtatg tggggggaag agactgtggg agcaaggggg gaagcaggga  13140
aacaagtaca ctgcagtgat ctgggtgaga ggtgaccgtg tctcagacta aggtggtatt  13200
ggtggagaag gtaggaagtg gctgaattct ggatgagttt tgatggtata gccaacagca  13260
tttactgaca gattggatat tcactgtgaa aaaaatagag atgaggatga ttgccaagtt  13320
tttggtctga gtaactggaa aaatgagatt gccatttact gaaatggtga agactgtatg  13380
tagagcaggt gcatgggcag ggtagaaatc aagagtttga tttttgactt ataaagtttg  13440
aattatctga tgaacatcct gatggcttct tctcagttag ttctcatgca gtgccttcag  13500
ctttgctgtt cttcaagaaa attaaaaagg aacttagaga tcgcctaggc tgtaggtacc  13560
ctctcccctc tttcctttta ctttatagag gtctatagaa gggtagggac ttatccaagg  13620
tgaaacagtg agctggcgac agaactaggg cacaaaccca gttctcttga attctgaatc  13680
agtagatttt cttttttag tgtgattctg aggactcatt tgggcaagag tgagtttttt  13740
gttattgttt tttgtttgtt tctttgccca aacctaaaac caggtaatta aactaaatag  13800
tgaataaaac tgggaaacta tacaaattgg ttgctctccc caatcacact gaaatattat  13860
tatttttact gaaccacata ccaaaatatt tttcctgtaa aaacacagta agtgaacttt  13920
taaaggcaat tgagctttta acaaagctag aatctacaga ggacctggac agaaatggcc  13980
ttaaatccta ggaaattaga gttcatggaa cctgggagac catcttgtcc agctagctca  14040
ttttatgggt gaggtgcctg aggcaccaag atggaaaggg acctggctaa gctcatacag  14100
caagctagtg cctgagccta gtcagagcct gttttaaggg ttagtcgtat gttgttttct  14160
tgaaaaaagt tacattggaa aagtgaaaat tctttggtcc atactgagaa caaagaatta  14220
tacataatca tatataataa taatgatagc acttcctgaa tgtttgctgt gtaaactttg  14280
gcaccttgca tgaattgatt catttaattc tcatgtcaac tttaggaagc aggcctagag  14340
aggttaagga acatgtccaa gggtcacaca gctaggaagt agcagaactt gtgtgcactc  14400
ccaggaagtc tggcttctaa ccacaaggtt ctaactactg tgcaatacca ggagcttctc  14460
agattaccct tcacctttac caacccaaat gactggtgac gtaggtgact tcattatgct  14520
```

ctgcccctat tatagtccac tgatcctcac caaataggtg ggtggcctag aggttaaagt 14580
agaggcagag tgatggaaag gggtggttag aagaagttga tgactcatga tagggattgg 14640
aaaacaggac tacaggaatt attgaaaagg gcctagagat cccaaggagg ttgatctccg 14700
actgctacaa acctgggcaa ttcaatgcct gcttaaatag gagagttaag ataagaaaaa 14760
taaaattgcc aatttttaca gtcagacatt gttttattta ttttacatgt attaattcat 14820
ttaatcctca aaatactcca tgaggtagct acaattatca tttctatgtt gtagatgaag 14880
aaacaggcac agagcaatta aataacatgc acaagattag agaacaagta agtggaagtg 14940
ccaatattag aatctaggta gttcagctcc acaacttatg ttattttcca ctatatttat 15000
ggaatgaggt aattttctta taacagaaag tttttaaaat gcaaaaacat tgtgcctgaa 15060
cttcaaacac tgaacaactc atatccttaa tatgcaccag tttcttttaa gcactcttag 15120
aaggaaggat acttaaccta atgtcacatg gtgagtaagt agcagaaccg gaacttgaat 15180
ttgagactcc ggactgccag acctctttcc actctatcac ttgggctccc ttctaacatt 15240
gacttgtctc cctccattcc tcctccgtat tgttctgccc ttcacctttt aattacctgt 15300
ctccatcaac aagattggac agagaattgg gagagtgagc agagtccatt tccttccaga 15360
gactggacaa aaggaacaaa atgttaggaa aaaatgtcag catgtgggat ttgtgggatt 15420
tacactaaat aagaagggac acttcccagg actgacaaga tgctacctcc gtccctctag 15480
gccccaatgt gttgtgcagg atcccatagg aagtcatgaa tgtggttgtc agataacctt 15540
tttgttactg tggaaatgga agcaggctac tgcaaaaatc tgtctctcca ggttttcttt 15600
taaagaaggt agtcttgcta aatgataact atttcagcat ttatttgaaa atgggcagtg 15660
caggagagaa agaatttttc caagcttgtc acattgggcc acctctctga agcattgtcc 15720
aacttctaat tagatgagga gactgcataa accaagagtt gagagtaaag atggaaacac 15780
ttgatgtttg gtgtttgggt gcagaaagga ttccagaaca tgttttgggt ctctttactc 15840
tgtccatccc tccttccctt tcatctttgt ttaaaaacca cagttagcaa atgtgtagtc 15900
tgtttgcaat tgttcatctg aaaaatttgt ttgatcagcc ttttgaataa aaaagaccaa 15960
attagactga gatatttcag tcaccaacta tctaataata gaccaaaaat tttaaccatg 16020
ctcatacttt catatggtat gtagtttgct ttagacattt tctgggcttc agtgaggtgc 16080
tagattgact caaaatatgg caggtcagat gtgggattga gcagggtgga ctcttctcta 16140
cccttcccaa ttcagagttc cccatcaaag atgatctcat agtgtttgaa aaaccaagct 16200
gaaggctttg ggaattaggg tgctgaaggg atatgctgtt tcccaaagcc ttctcagtca 16260
ttccttctcc ccccagttca gattcttaac acctctttcc aggattagtg cagtgatccc 16320
acgtcctttc tctctagctc tctctgctac tctctaattc ctattgtatt tgtgccacca 16380
gatctttcca aagtttagct ccaatcttgt ctgtatactg ctttaaatgt ctattagtct 16440
ttaagctcct taagggtggg agtcctgtct tattttttcc ctattcttcg tgcttaatgc 16500
aaaggaagcc ttgctgtata gttgtgtaat gcatgattac aatttcagct tctccccatt 16560
ggcttatggg ttaaagtcca aattatttaa atctggtgtt caagtccttt tatgatctgc 16620
ttatttttcc agcctgaatt cctggagttc ccttacaaaa ctcttaaaac ccagccaaaa 16680
ggatctagtc actgtcactt taaaccatcc tcactctctt gttttttgaa catgttattt 16740
ttcttataat ccctttgacc ttgaaggcta tcccaatttc aatactatcc attcttctat 16800
gacagccccc tacaaaatga atattctcaa cctcccaacc caaggagaag tgatctatat 16860

-continued

```
gacacaatat ggttgaaaga atgttggctt cacttcttta tctgtaaacc aggggctaga  16920
aatctctagt ttataagatt ttgtggagag gggatcatat gtgattatgg atgttaggca  16980
caagtcaaga gtgcataaga ccttttggat ttatcccttt tttctttctc catcaatatg  17040
gtacttagtc ccttaaatca gaagtacttg tgttaatgtc tgataacgtc cttctaaata  17100
tacctctaaa catctgtctc tctttagggc aaaggttgga tatatctgca aagattctct  17160
ttggatataa gatatccaca gcacataact taacagtggt gtacacagta ggtattccat  17220
aagtatttct ttatgaaatg attcagagtc aatagtagta agtaactgcc aaaaacaact  17280
gatggattgt aagttccatt aacataaata cagtcagccc tccatatcca tggattccat  17340
atccacagat ttaagcaact gcagatggaa aatatatttt agagacacag taaaaataac  17400
aattcgacag taaaaaaata caaataaaat tatgtaaaac aactatttac ataacattgt  17460
attagctatt acaagtaatc tagatataaa tgaaatatat gggggatgta tataggttaa  17520
atacaaatat gacaccattt tatatgtttt agttaaggaa catgaatatt tttggatttt  17580
ggtattcatg ggagtggggg aatggaacca tgccccttca aataccaagg gactattata  17640
tgggacacag aataaaggag ttgattgtct tgctctgtta aattctggtc agacacattt  17700
gcaatgtatt gttcagcccc agtattcatg gagcatctcc ttttgtaaag catggaggag  17760
ctgtgagaga gacatggagc agtgaacata actattgttt caacgtacct gaaggattat  17820
catggaataa agaagttaga tgtttttctg tagtacccca aagggcaaaa gcaatgagga  17880
cagattacag ttcagtaaac gaaagaggtt tttttttttt tttttttttt tttttgagat  17940
gggagtcttc actcttgtcg cccaggctgg agtgcaatgg cgcaatcttg gctcactgca  18000
acctcgcctc ccgggttcaa gtgattctcc tgccttagcc tctggagtag ctgggattac  18060
aggtgtatac caccactcct gggtaatttt atttattatt tatttatttc tttatttatt  18120
ttagtagaga cggagatttc atcatgttgg ccaagctggt ctcaaactcc tgactgcagg  18180
tgatccgcct gcctcggcct cccaaattgt tgagattaca ggcgtgaatc aatgtgccca  18240
gcctgaaaga tattttctta gaatagcttc tttcaccctt catcagaagt tgtcaacatg  18300
gaccatatga gttttgtttg gtctatatgg tgtatatgtg tgtgtgtgtg tgtgtgtgtg  18360
tgtgtgtgtg tgtgtatgtg tgtgtgttta ttgaattact tgctaacatt ttacttcaaa  18420
attcagattt ccaccatagg gaatgaagat ctggcaatac aggactttca ttcctacatg  18480
gtaatgacca gctgtaggtg aaaagcagct gatcctctgg atgggccatg cactttgcag  18540
tttgcccagg cagcactgat ccgctttatt catttaagtt acctgcttga ctcttctagt  18600
cattcgagta tgtcatcccc atcagatcag agacctaagc aaatcttggg tcccttgctt  18660
actccaaggg ctttcactcc tcgtatagga ggagctaaag aaatgtacaa gcagcaccac  18720
aataggatca gacctggctt tcaattctag cacggccaca taacatagtt ggatgacctc  18780
aggacagtaa cataacccct ctgagcctct agatcttcat tatctgtaga gcactcttct  18840
tatagagtta ttataagaat gaaataaaac aactaggata aagggcatgg cacttagtag  18900
gtgctgaaat attagttccc ttcttctaat tcaccacacc atatctgtct atctattggc  18960
tgaatcacat aaatagtaaa ttcacattca ctgaagacat tcaagaagag tctggaccct  19020
ttgggaacca tgtatagggc aaaggtttga actcatagta gatgattttt acagtcactt  19080
tttaacaatt taaaagccta tagatgactc caaaatgccc atttggatga tatgaggcat  19140
actttgtgta gttaaggatt ttaaatacat aacagagagg ctgaagggcc ttcgggaaag  19200
aagctggggt aagagtcaaa gtgtagtatg ttgaccgatg ttcaggaata ggctttggca  19260
```

tctgacagat tttgttttaa atactggctc tgggtcttac tagcttccag ttctgggctg 19320
cttcacctct cttgagtttc agtttcttca tttctaaaat gaagatacta atgcttcctt 19380
tgttgggttt ttgtgaatat aagtgagata ataaatgtaa atatctagcc cagggcctgg 19440
tgcatagtac aagcttcata aattgtacct attattatta gtagtagtag tagtccagac 19500
aaacagagct tgggaaaacg ctagactctg gctgacatac atgggctttt ccccaggcca 19560
ctgctgcctg gcttcccctt ccacaaagct ttgagtctcc aaaatgcttt ggctggaatg 19620
taagcgtgag gtcattgcag ataacagggg agcatgattt gcttcggtaa tgcaagttat 19680
taagttactt ccctcagccc agctgaaatc tcttattggt tgatgtgtgc ttcaaagtgt 19740
gagacagagc tagtctgagg agagagggag agtgagaaga ttcctcttct tggccagagg 19800
tcatggtctt ccacaaggaa cagaatgact caatgcaaat tatgggacct ctttgagttt 19860
ggggccccta catttaaact agtaactccg ttgcacatat tggcaccctt cccccaacaa 19920
aattactggg caggaatttt cttgaatcct tccgtggcct ggaatgatct cccttctcat 19980
ccttgtgatc cacacagctg gcaaatggca ggcagcagaa caaaaacaag cctcttagca 20040
tatagggaga gaaagagtca cagcagtact gaatttgctt gggaacctaa tgttaacaaa 20100
ggaccttcct ctcaacaccc caaacagatt aaaacatttt tttaacagca agttgtgtct 20160
cggagcagct ctttgcttgg gtatatttaa agatctgctg agtcatttaa gagcaggctg 20220
gcatatccta agaggcaagg actatacccc agtctatggg ggagtaagtt gagaggtgaa 20280
atctgtttgg ctttctccca tggaaacaaa caaggtgatc cacttccatc tcccacgact 20340
ctggagagca tctactaagc cttcttattc tatcaacttt gaactcctca gtgtataata 20400
gagtaagggt gagagggaag gagcagtcgt accagtgtca ttattggtat gttcaggagt 20460
tcaatttctt cctgattcag tcttggcggg atgtatttgt ttgggaattt atccattttt 20520
tctagatttt tctagtttgt gtgcatagag gtgttcataa taccttctga tagttatttt 20580
tatttctgtg gtgtcagtgg taataacccc tgctgtctga aattgtaatg gccctgctat 20640
tggtagctga gagtagcatg gaagtgtcag gttgatgggt tcatttaatt cttttctttt 20700
cagtttcagt cacatgcatt gttaccatgg catatgacag ttgctagaaa gtgaaataat 20760
tttttttcta ctttattctc cactgcactt ctaaatttat tagtggagaa attagcagtt 20820
accaactgtt cattataggt acacattggg gtttccttag agccaatttt ccccctggtt 20880
ttcatcttgt aaatctgtaa tcctaaaaat tagcaaaacc tagagcttct ctttggtcct 20940
ggcctgtttg aaccctgttc cacagacccc aatcttcttt cttgtttgag gcaactatcc 21000
ttctctttgc ccaccgccat tttccttcat ctacttttcc cttctctagc acctcagact 21060
gtcttcccac agtggcacag cctcccactc cactttcact gtgccatctc cttgccatca 21120
aaaccatcct cacagaccct tctgaaacca cttctaggaa gggaaatcac aatggatcca 21180
tgaaggatgc tttctggatg actttaaaag attggtatta agatatttta tcagtggtag 21240
caacactgac ttattcaggc agccatgccc cggatctata agaaatcagg taagctaaaa 21300
gttgcttgag ctggcaggag acctagttct ctttttttcct ttccctcttg cattttgttt 21360
atcgatggtt ttcaaaggac ttagaggctg gctttgttat agttagttgg taagagaaat 21420
ggtggaggac cggaaaatgg gagtggaacg aatgagcatg tttgagacta agttattaca 21480
attcctagga tgtataaatt gcttgaaatc taccaagtac tttcagacac attatctttt 21540
ttactcttca aaatcaactt ggaggtaggc acaacaggga tcaaatcctt agttcacaga 21600

-continued

```
tgagtaaact gagactggag gaaattaaag gagattccaa ggtaactcag acaataagca  21660
acagaaccag gatttggtga attttttggg gggtgggagg tacagagtct cactcaggct  21720
ggagtgcagt ggcaaggtct cgtctcactg caacctctgc ctcctgagtt caagtgattc  21780
tcgtgcctca acctcctgag tagctgggat tacagacatg tgctacaatg cctggctaat  21840
ttttgtattt ttagtagaga tgaggttttg tcatgttgcc caggccggtc ctgaattctt  21900
ggtctcaagt gatccacctc cattggcctt ccaaagtgca gggattataa gcatgagcca  21960
ctgctcccag ccccagacca ttaatttttg acagtaagtc caactttttt caagttcaca  22020
gctcagattt gctattgaat gaatgagtat atatgtcatt tgggaacatt ctttccaact  22080
tttggttgaa gatttgtttt atcacttgtg aaaatttttt ttcattctta gcaatgtcag  22140
tttagttaaa tgagcatttc atttgcgaat tcactaatta attattttat tcatcaatac  22200
atttcctgag taccaacttt ctatcaaacc ctgtgctgga ttctgaggct acaaagagaa  22260
ataagatacc atctcaggcc tctaaaatct cacagactgg ggactgacat ctcagtagta  22320
aacatatgaa cagcaacttg tgaaacgcca ttagcaaaat ctcaagttat attcttcagt  22380
gactatggcc atcctaaaaa tggggtgtct tttatttggg gtaaatgaag atgaagcctt  22440
atgagaaatt gcattttaat ctaatcttgt cttgctaaga acagaagtgg aatgtttcag  22500
cctctgtgtg tgtatttgtg tgtgtgaagg ttgagtgtgt gatgatggat ggggctgcga  22560
gattgttaag taggatctat ggggggcctt aaatggtcct ggtgagtccc aactttctgg  22620
ttatgtattt gagtagagta tgggggtgac aaagattgtt gtttaagagt tgattttaga  22680
tttttccaa gtaaatggtc agctgacttg gagcatcatc attccacttg ctttgaaaac  22740
ctgccactta aggctccttc cagtcatagg ttaactcttt ctggtcaagt attactcttt  22800
ttgagcattt acctgtcagt gacaggtaca atgttagatg ttgtctctct gttttcttgt  22860
ttaatcttta ctttgatcct aggtagctct tattagttcc actttatagg taagaaactg  22920
aatttcagag acttgaatga cttgttcaag atcacatagt atagtaactt ggtagtttgg  22980
gacttgaatt ttgattgttc agtttttttgt ttgtttgttt cctggcctcc ctgctgtttt  23040
cactattcca caccacttca gctttatttt tcatagaggc cattaaatgt accctccatc  23100
agccaaagcc tcttgcctcc cttcaacgta actcttctct agcgtcctct taataatctt  23160
ctgaaaaggt tttacagcct ttctgggtac tgggacccag agtcttaatc caggctctta  23220
agtgccttat ttaactgtaa tatggaaaat caaagtcaca gctaattcag gaaaaatgag  23280
tttgggatgt gaatttccta ggcaacttgt catctctttt ttacttcctt agcttcataa  23340
acttacccac aatgttccct gaggactaag agtaatggag ggtgatgagg aaaggctttc  23400
ctcccttcct ttccgagagt cctttagcca aatgccacac ctcctcctgt ttccctagtc  23460
tccgtgcaga gatggaagtg ggagatagac atgggttcct ttcagccctg agttcatgcc  23520
agggttttct ttccctctag ctggactgag gtaggaggag aggttgaagt ccaccaataa  23580
gaccatgagt gaagaagact aaagtacttg aaagagcagc agacctacgc ttaaaatact  23640
agggtttgtg tccagacttt gtgggttact atctgtataa ttttgggcaa gtcaacagtt  23700
ctgagtcaga gttcccttat cagcagattg gaagataaat tctaattata tagatgaaac  23760
attaagtcta gaagtaattt gtaaattcag aaaagggctta tagatttaaa gtgtagccgt  23820
tttgattacc acaaactaaa tcctatactt cagggataaa atcttctcct gtttttttcta  23880
aaagcctgtg catgtgtggt gtaaggggtg ggttttccct tgtaccagca acttagcaat  23940
tgtagtaacg gggctgaggg cagtggcatg cttcttcatt gagcaagtgt gaaaagaggg  24000
```

-continued

```
ttatgcattc aggggtcagc agatggcagg cagagtagcc cctccaaatc tccctcccat  24060
accacaaagc cctcttattt attcaaactt aacattagaa gctcatttca agtaggcacg  24120
tctgtgtctg ggcgtctatt ttccttcttt gtatatagca ggcatttgtc aacttggtga  24180
aaagcattac tcttctttcc atttctgagg actaattgtg cttcttcgct agacacgagt  24240
tcaaaacagt gggttgaaag agggcaagtt tatgccaaag aatcagaaat agtcataatt  24300
tagagagaat tctagaggtc agttcccttt cgtatggact gggcaactga aacccagaca  24360
gggaagggaa ttagaccaag ttcacaagca caaacacttt actggcacat tcagattgga  24420
aatcgagggc ttctgctccc aggtcagaac taaatgccct ttctagctag ggtgttcttt  24480
gatctcagtg attttgactc tttctactgc actctgggga cagtgggttc tgcggtacca  24540
actccaatta aagtgggaat atgtaccagc ccctcccctt ggtttttatt tttcagaggc  24600
ctggcagtca gagggattct gatctctata tgcaatattt tcacactact gtacttattg  24660
aaatcacatt tgaatcttgg caattaacaa ggcagtaatt ggcatcagga gggtatgtta  24720
gtttgcttat ctgcgccgtc cctcctcttc ccaacccact gtgtattgca gaatgtttta  24780
tcagctctga tttgccaagt tgctctcttc tccagtaggt gctgcgagca gagagggatt  24840
cctcggaggt catctgttcc atcttcttgc ctatgcaaat gcctgcctga agctgctgga  24900
ggctggcttt gtaccggact ttgtacaggg aaccagggaa acgaatgcag agtgctcctg  24960
acattgcctg tcactttttc ccatgatact ctggcttcac aggtgggagg ttcttcaatt  25020
gaaaacttag aactcagttt ctagggtagt gagtgttgta aggtttggac tgtgacctaa  25080
tattacgcag ccatgacatt atctattagg catctagact agcttgcttg aatatcttag  25140
catgttgact aatttggggc agaatatagt gtgggtgggg gattttgtgt gtgggggggg  25200
gttgggggtt gagcaattca ttattattaa aatgcaaaaa gcacttaatt cgctatgata  25260
agattgcctt tttcatgcat actggcctac ctgcaagacc cctagagaca gtaagcagca  25320
tacatggtgt cttccagttt tcagcctttg tgcaaggaac aactgtgggt ttctgcacat  25380
gtgttgtggt ttgatgtttg tatgtgattg tgtaccaggg tatgtgtgtc tgttattgtg  25440
agttcatttc tgagcagttg tgacacacag agatccagaa acagtgtctt accctgtgtg  25500
ctttgctagt gggaacgtgt cttttctttt gtgctcgtat ctctgtgtaa tcgagtgtct  25560
tgctaagtca atgtgcctct gtctcttttt accagttctg tctttgtgtc tctgtgcctt  25620
catgtatttt ttcccctgag tttgcacgtc tctgtctatg tggatatctc tcactccagg  25680
ccactgtatc actgtgtctg tattacagct gtttatttct gtcggtgtgt ggatttctat  25740
gtctgttttc atcttaattt gtgtgtctaa gcaagactgt tttggggtga ctatttcagt  25800
ttatgtcata gccattcttt gtgtgactgc ttctaggtat gtctttttct atgcccctat  25860
tgtccccatc tccatgtgtc tctgtgtgta tatgttctaa tgtatctgcc tacttatctt  25920
agtttgtatt tctctgggtg tatatccctc tcttgcagtt ctgggccttt gcagtttttg  25980
gcttatgttt ttgtatatat ccactagaat tggcttctta tcttttttgt gcatgtttta  26040
gtttgtatga gtgagcatat ccaactctgt ctttgagaag cagaactgtc tgtgtttgca  26100
gtcagttgtg ttggctgtcc ctgtgtttgt ccctgtgtgt gcatttcatt gtatgtgtac  26160
gcatccatgt atctttctgc ttctctgtga ccagatattt ctgtgtagct gtctatgtat  26220
attggcttct gtctgtgtct gtgttgttgg ctctacgtct gtgcatatgc acccaccggg  26280
ttcataaaaa gctcacctgc tctccaagga atctaccaga ttattttgtg aaataactca  26340
```

-continued

```
cgtttcgttt ttttacttgc cagctgctat ggtacttaaa agtgtgttgg tacgtaggtg  26400
tgcataattt attcatgtag gatgtcaaaa gagtcagtta aaaattatgc acagtgtgtc  26460
tttattaaca ggacacttgt gtgtagagaa tccttgagaa atgagtggtt agatgataaa  26520
tcttttcata ttaatttcat gatgtcagtg aagtaaattt gcaagatatg ggctgcataa  26580
gaactatgtt ctttttaaaa ctcagcatat tgatggtgga gaaagcattt atttgtactg  26640
caaagtctta tttctgataa gacatcacaa ataagaatta ttgtgatgag acttatcaca  26700
aataagaatt attgtgataa ttcttatttg tgataagaat tactgggtta gaaggtgtta  26760
cttttctggt tttgtttggg tttttgtttt gaagtgttac tacagatggt gtcttaggga  26820
caaagagctc tgaggttgac ttagaacaca tggagtacag ataaaaagga gaatgaaaag  26880
taacagagag atgggcatat tccttgtttg aatggagtca tccaggggct caggatggag  26940
tgcacaggaa atggagaggt gaaggtcata gagagaagtt tagcaggacc agatctttcc  27000
ttgtcctggg ctgctgtgac catataagga aggcagtaag gggaggggta gggatgagga  27060
agagaccagc tctcctcttt ctttctgatg gaaggttacc acctctattt aaaacttctg  27120
ttcttttggt ttctctttct ttctttgatt atattatttt ctggacttgt tctgccaaag  27180
caagaaggaa attccacatg tggctcactc atttattata cttgtttctt tgcacgatat  27240
taaagacagc ttgttaagtg tcactgcaaa catcatacac actgatccac tgatatgggc  27300
agggggttct ttatgccagt tctgctctct tcccagtgta tctgtggtgc ttaatgggcg  27360
caaccatgat ttttctgatg tcagtctgtg atgtcagttg tccagtgtgt atgcaggctg  27420
cttaagagta catacagttc cttcacaatt atggtagtcc ctgagaagga agtggtcatt  27480
aataaaagac taggttcagt agaaacatgt aagttgtcta ggtgttggaa attaatacag  27540
tactgtgcta agggaacata tatctagaag ttaactgaat tatgctcaat aaaaagagta  27600
caaatgtttc ataaatattt tgacctaatc ctcctgtaag attaggagag ggatatttcc  27660
gatattcaaa taattttttt aattggcaaa caccttagac atactattta cataaaattg  27720
acatgacaaa attaagtcat tgtgtctgtt ttatgataaa acaggctctt ttgatttagt  27780
tagaattatt gaatgtaaaa taatgaaaat taaaaaaaaa acaaggagga ggaatctatc  27840
ctattttata attcagaccg ttgaattgag tttttctttt gttgtattga tttaaatgca  27900
gagaagtcta tgatgctgga ttccagtcag aagataaaca tttgtatgtg ggctctacat  27960
tgcagccaac cttgataatt tcaaacctcg attttctcat ctgtataatg gtaataataa  28020
agcctgtctc agtagctacc aaatgattgc atatgacaaa cttctcactt atttaaggga  28080
aaaaataaga aaaagaagga caatagggtg gatttttcat atagtaaaat ttattcagtt  28140
agggtaatat tctgagattg tcttctgaag caaaccctgc aaaccctggc cattctgttt  28200
tgtttaggaa agaattcatc agttctgatt ctgccttttc tggggaggga ggctgagtat  28260
tggattgaag aggagtcact acttttctga gatgatatat ccgtggtaaa aattattaat  28320
gctttgcaca tgcaacatag agtgttcaat tttgttagtc aacaaatatt taagtggcag  28380
ctgttatgac ctcaggggtg tagtgacttc cttattgtcc tttaattatt aaaaaagaaa  28440
tctatatcag aatatcaggt aaactcttat tacatcaaat attataataa agatactttt  28500
tatattctct aaacaaagta gagatctcag atgttggttc atttatcaat ataatattag  28560
atttgaaaat tccagtatac aaaaggaaaa ggacagcttc ttaaagttta tagtgatttt  28620
ctatgaacta tcaattccgt ttttttctgt tttactggta tgatggaaac taaatttcga  28680
gttgtaagta gtagataatt agactgcagg gtaagccttg agattacttc ttttcaggta  28740
```

ggaaactcta ctgtgtattt ggctagttca acctatcatg ggtagtcaaa aatagttaca 28800
tatacaagtc agcatttttt aaattgttca gttgtgctta agattggtcc tttccaggaa 28860
caatccagct ttatcaaaaa attattgcgt acatgtaaag tgttctgaca ttttaatgct 28920
cacaatagcc gaatgacgtg ggtaagaatc ttcgtcttca ttttatagat gaagaaatga 28980
agacacagag acataaatta actgggccag ggtcctacca ctagaatgtg atagatgata 29040
atttgagctc agcacatagt tatttcccta taatatttgt tttatgattg tatagatgtc 29100
tgctgaccaa ccttaatctc tgctccctaa gattaaccat tctacaaagc agaaactgga 29160
ggtcattcaa atgaaagctc tacactttta gagggccatt aacaatgctc aagttaaaga 29220
aaagcaatca aagacaacta aaatactggt accttcaaac agtacttatg aattatttaa 29280
ccttagataa tttggctttg agttagaaag atagagtaag atggaggaac caattcttcc 29340
ctgggttgat atttatttat cttgctcttt tgaagtctag gccaatcatc ctatttattc 29400
tgaatggccc gttaacgttt atccatttag ggacagcagg tttggcacaa atggattggt 29460
tttctgaggt cttatgtaga gggctgcact gactgacttc tgaaagtccc ccctaaccct 29520
tcaaatctca gggtcatctg gtctcaagcc ttcaattatg aatacatttc tattgccttt 29580
ttgagtaaca gcacaacact gcaagctgac ccactgggtg gatggaatgg ggctcttgcc 29640
ctaccaccct ttggcaaaca atttgagggt ggcattgtca ctacctcatt gtatataggg 29700
tctcttgagg cccagaatgg caaaataatt ttcccagtgt cacacagcga gttattgtca 29760
gagtaaatat caattttgaa tttgtagacc acgtggtttt acctcatcat ttctgtttgt 29820
tatgaaagtt ttacaaataa ttagaagtag aaataatgat taaaataaag cataactact 29880
aaaaaatagt ttattgcagc accacctaaa ttcatctcac cactctacca gtagcataca 29940
tttcacaatt gggttaacat tgctctggat cttatagctg ttgaagaaga caaaattctt 30000
tccattctcc agcttatatt ttccccattt gtaaaacata atggaagtgt acggaaaata 30060
ggagttgata atttttaagg cccttgccag cacattagta cataggattc ttgcaagtgg 30120
tggtttactt cacttcaact atagaaggcc tatgcgacac cacccataga gggtagtttg 30180
aaagaaaatg ctagtgacta cgtgtgtttc cttcctgaca tattttatag aaggtgatga 30240
gttccagcat tttttcagac ttggatctgg ctttcattcc ccttctcctc ccaccctcta 30300
aaacaacaga ggcagcaacc atttacacac tttccagaag taagtaagta agactgtatt 30360
ccagaaacac cctatatcaa aatggaaata tactcaagtg ccccaatgac ccattgggct 30420
agtttgaacg tgtgcagtct ctgtgctccc cgttttagct taagcctact ccctaacctg 30480
tcatatgtca cccagccatg gagcctaggg caatgactgc catcatatct gactttatgg 30540
cctctcagct ttcaatgact agctttgtag cagaagttta gcctctcatc cccataactt 30600
tggaagtagt gttgagataa agaaacgttg aattgaaggt tgtgttttct agatttcttt 30660
caattgctcc ttaggcttta gaagataaat tctcctaaaa gagaggtgct acaattaatc 30720
caagcaaagg gaaagatgtc agtaaaactg ccccttttca tagaggtgtg gcaactgctg 30780
ggaaggaaga aattagcctg aggccatgtg attactaata aactcaaagc ggcatttttt 30840
tacttctcaa tatgaggttg aaactataag cttaaattgc tgactttctg gcagcaccaa 30900
acagtaagga aaccacaaag ataaacccaa ataatagagc caattttctt tttttccggg 30960
ggggatgact tctaactagt gatatgagga aggataagaa aatgtttctt tgtaggacat 31020
atgatctttg ctaagtgcac tgaatgtatg tagaggagac aagtctgctg agggtatgag 31080

```
aattgggcca agatttaaca cattttcaaa gctccatgaa gaagcctact gagcagtggg  31140
agtggagcag gttggggata gtgaagtatt tgtaattcat ttttaaaaag gagagggaga  31200
gagaaaagga aaaactgggc cacccatcct ttgaaaagaa accttgaaag aggtccaaat  31260
atccttagaa atccttgact tcttaaaagt gatgtttgtt ttttccccct gacaattata  31320
gaggtcagag agtttttctt ttctattaca aaacattgag agtgtgtaga aataattgta  31380
ggtagcttag ccttggctgt agtcagaact tttgtactgt gactttagga tctgtatgga  31440
atcgtatgat atgcggatac accaaaaact ctatgggtta tcaaaatggg atagcattaa  31500
aagaaatagt gcttttgttt agaagaagaa atgaaatgct tgtgtccaga tgcttaaagg  31560
aaggcagtgc agactttcag aaactagact ttaagagctg tactcagata ctgagaaggg  31620
ctgatggctg aaggaggaac aatttaaaag aataaccgtc tctcctctcc ctgtatattg  31680
gacataaaag aatatcccat tcttttcaga aatgtaatac aacagtttag cttgctagta  31740
acttcacatg ctatttcctt tacctcttat atttgaggtg tctatttgga gtgggctgtg  31800
tttctagcta ttctgtttat ctggtttgtt tttgttggtg taggaaactg gtataaattt  31860
tatttgggta aatatcacct caattttcaa ctaaagcttt atttaagttt cacatgaaaa  31920
agacaaatga ggcaaaggaa gagaaaaatg cattgtcaga atcagaatta tgagaaaaaa  31980
agtcaaacaa acatatttga aatgtccaga aaacctgtga gtttttatgt atactataca  32040
ggaaagatat tctgtcatct ggttgccaaa ctatggaggg tgggagactt cgaatttttg  32100
tcaaaaagta ttctttcatt agaaagatac atgggtgtgc ttccatgtca gcaacatgac  32160
tgcagaccag gaagtcctca cggagagctg gaatatgggt attttggact ctctggttag  32220
atgcagcttt tacttcacat cctcagtggt actactgtaa attttcattt tcctgtggaa  32280
taccctattt ggttccattg tatatagttg acaactagaa ttcgttcgct gttgcttgag  32340
cccaactata acttcttggc actataccta tcttctgatg tgcctgtgga agagctacca  32400
taatgaatgt gtacatggac aaaaaaaaag agagagagag agagaattaa atcatgagtt  32460
tgtgccttgg gagctacagt ttaaacattt gctgtttttc tcacttaatg aaaaatttat  32520
ttgaaaataa cagcacagaa aggaagaaag acaggctggc aagcatcctc ctcctaatac  32580
acttatccac gtttggatac cttggtctca gcctcagagg tcatattttt agtaaaatgg  32640
ccaccagaaa taaaggattt tattttccag actttggtgt ttggagctgg tgtgctgaga  32700
gctagcagag aaagccctac tcaggtagat gtaccagagc aggatggttg ctggtggata  32760
tggtggaata cctttttatgt ggttatctcc tccttgtaac tcttggctgc ataaccctta  32820
ttttcttttc tatttttatt ctctctcttg gaaaaaaaat tggtggtaaa ttttcatgtg  32880
agccatattg tctttttaaa tagttttatt aatataaaat gtacgtacca taaagcatac  32940
ccatttaaac tgtaaatgtc aatgggtttc tctctctctc tctctttttt tttttttttt  33000
tggatgctca gagttgtgca acaattatca aaatcaattt tggaacaatt tcattgcccc  33060
aaaaggaaac cctctgccca ttagcagtta ctccccattt cccccacccc ctgacccttc  33120
aaccctaggc aagcacaaat gtactttctg tctctataga tttagccatt ctggacattt  33180
catgtaaaca gaatcatgca atatgtcacc ctttgtatct ggcttctttc acttagcatg  33240
atgtttccaa ggttcatctg cattgtagca tctgccaata cttcattcct tatttatggc  33300
tgaataatat tccattgtat taatgtatca tatttgtttt ttccaatcat cagttgatgg  33360
acatttgggt tgttttcatc cttttttttag ctattttaaa taatgctgct atgaacgttc  33420
gtgtacaagt ttttgtatga acatctgttt ttatttctcc ttggtataca cctaggagtg  33480
```

gaattgctgg gtaatatggt agcttaacat ttaatctttt gaggaactgc cagatttttc 33540
caaagcagca gaatcatttt acattttgac cagaagtata tgagagtttt agtttctcca 33600
catcctcaac aacactcatt attgtcattg tccttttcag ctttttttgat aatagtaatc 33660
tcaatgggtg tgaattggga ccccatcatg cttttgattt gcatttcctt gaagagtaag 33720
gatattgatc atcttttcat gtgcttattg gccgtttgta tattttttga tcctttgctc 33780
atttccaaat tgggttattt gtctttgcat tattgagttg taagatctta caatatattt 33840
tggatgtttg tcattttagg gatgatactt cacagttata tgatgttttc tagcaagcat 33900
ttgcgttgtt ctactggtgt tacatatctt agctgcatta gccactttgc tgggtatgaa 33960
tgccagcaga atctaagtga ccttggcttc actactgaga atgcaaccca agaacagaaa 34020
tttgtcagaa atttagcact gaagcccccc acttcccaaa cttatctggg acaaggagaa 34080
tctacattta aagctctata ctttgtgttg tgtttttttt actttagctt ggttggattt 34140
aggatctttt ctttttgttt tgccttatgc atacctaagc agaggcaagg gaggaaaggg 34200
atatgaacct ggtagaaaag taagtaagct ttattcagat tggcatatcc atcttaatat 34260
ggttcaattg gctgaagaag tatctcaact aaaactctgg aatactttga agtaccagca 34320
atatgtacca aatgtacttt ttatttatgt ttggtctcta tgtacttgtg tgtgaaacaa 34380
tgagcacaaa taataccctc cttgttttta agcaatttat attggtgatt taaaaataaa 34440
ataaactcaa gtgggaaatc atgaaacccc atgtaaaaac aataagagca tgttttaaaa 34500
tcccacagac tttagtttca aatagtggtt ttgctatttc ttagctgtgt gtcactgtgc 34560
aagttacttt gtttctctga gtctttattg gtgatatatg taaaaaccca ccttctcaaa 34620
ttattgtgag gacaaaatga agtaattaac ataaagttcc tggtgtataa taagtgttca 34680
tattttgtat ttgagcacag ggcaactggg tttttgaaac tgcacattac tgttgcagtc 34740
aaatctggca tgaaattagt gcatagacag aatgggctgg gaaaatgaaa ggactttgaa 34800
catttatatt ctgctttatt taggcataag tgcttaataa ttattgatag tttcttctgg 34860
ttatctgaca ttttgaagat actattacct agcagaaatt tcttgtaata ataatctctt 34920
acacttatat actgttttgt gcctttagaa gtacttaatg ctctttattt cactatctgt 34980
tcataaacat tctctgaagc aagcatacag tcagtatgaa ttccattttt cagatgagac 35040
agctgaggct gaaagacata gagttacttg tctcaattca caaagtaaag tgccagagtt 35100
tgaaccagag cccaggtctt ctctctcaac gtagctcttt ttctccttca ttatatcagg 35160
catagtagca acgtattctt ttactagctt tttatcttga atatcctttt agcgacttgc 35220
ctttggtgtt agtgtgccta taacattgtc gttgaatatc ttaatacatt tagtggtctt 35280
ggcaagcagt tttgtcttca gaaggacact gaaatctgtg gaaaggactg cagaagattg 35340
ggtgggcaga cacctatcac tttcggggct ggtagacttt ctattgaagc aatttgcaag 35400
gctactttgt attgtctaaa agcactactt cagaaaaggg ttgtgatgtc aaaataggca 35460
ctttgagtga agaaagggct gtaagcatgg gtggaaaatg tggtagatga ttgtcttgag 35520
ttattttctt taatgtcaaa caggcagtcc ttggaatgct acttcaaaaa gtgttgtata 35580
atgttgaaga tacagttaca gatttccaac acgaaactca taaatatgca attccctgtc 35640
ctcctaggca catgaaggaa aatttatgag cttcaggttt ctatgcagct attaaagcat 35700
atttaatctg ctttgagctc aagctcactc tcgttggctc tcttcgtttc ttcctcttac 35760
atgagcaaac tgcctttctt tttgtttaaa aatagtaagt aggtttgttt tcctccaggt 35820

-continued gtcatgaatg caaacattgt aatttctcat ctgttcagcc tttttgcaca acaaaatggc 35880
agcacccagg aggttgaaag ggttaaattg ttccttctct gagtagtacc ataagttgtt 35940
agtctgctac tctttctccc agttggcaca tgaccctaac atccaatcgc tagtggtgtg 36000
gccatttttt ggtcttattt tggcctttcc tcagccacca ctcatcagtt ctcatgcgta 36060
tttgtcagat cctgctcccc aactccacag ttcttagttc atcttaagca tatggctgtc 36120
tgtcttttct ctaaagatcc tcaagggaaa aaaaaaaaag catctccagg gggaatttac 36180
tgcctcatag ccctgacaga gatttctgac caaaccctaa cgaaaaaatt tcttccctcc 36240
atttgtcttt tattgttttt acaggggaga tatgtaacat aataacaatt atattgcaca 36300
taataattac ttctacaaat aataatctgt tgtcaaaaat atacacagct ttggatttcc 36360
ttattatggc ccttcattaa gttgtggttt aagaatagct atgattatta cttttgtgat 36420
aattataatc cataaatatgg aaacttataa aattaccttt aaagtgttac tattattctg 36480
gccacaggat ggaaagttgt tcgctagtta ctcatttata acctgaatgt actttttact 36540
gaatctaaag gtatcatctt tgcttggcaa ttcccatgac ttgtctttct gactcttcag 36600
atctcagctt aaaagctctc ccttcaaaga agccttccct gaccactctg gttttttctt 36660 cttttttac ctctactcct tttcccatta cttgctgtca tagcattctg tttgtttcct 36720
ttgaagtgcc tattccaatt tgtcattatg aatgagtttt tttgttctgt tgcttattat 36780
ccattttccc cactagattg tcaactctgt gagggcagag accatgatac tctgttcact 36840
cctatataca ttcccagcac tatcagactt tttggcacat agaagatact cagtaaatat 36900
ttgttgaatg aataagtcat aaagaagagt ttatatttta actcttagtt gaataatcta 36960
agccaagaat tatcaacctg ggttggacgt gagaatcatt aatgaatctt taaaacaatg 37020
acaaggcaat ctatttatta attatctcca ggtctaaact ttagcacgta tatacatttt 37080
aaaagcccat aagtgattct tacgtatagc cagtgctatc tgtctcttct cctgtccttt 37140
cccctcctct ccttactcct ctctcatagt tttaggatta gcatggcccc acaacaaatc 37200
tttaattcac atggcaattt ctaggattta tcatggaaaa tgagccaaat tgccttcaag 37260
aagtttttac gtacctctta tatagaatgt gatgttttat atgtacctct tatagaatgt 37320
gagcttttaa gaggcatatc ttattgcaag aaatttcaat gttgaaaaaa atattgaata 37380
tttataaagt caaaaatgca aactttttata tgattttcaa acctatgaag ttatatcatg 37440
ttcaggcctt ctttccagca tgtggctctc agccctggta ctgtccttaa ccataaacct 37500
catctttgcc ctctataggg agaggtttat ggttataatt actcatttta aatagtgtat 37560
attagtaatg tacactattt gtatatttgt tgactgcctc ctatatgcca accactatgc 37620
tagaaatttt gtaatattct tcacgatatt caagatatta acatatccgc attttataaa 37680
tgaggaaact gctctcaaag aggttagttt acacagccag taagccgcta agcctagatt 37740
ggatggaagg tatgtgagaa aaaagcagca tccataaggt tttcattctc ctaccctgta 37800
cgacagaggt aatagaaatt attagttaaa gaaataatag aattttacaa gactctagga 37860
agggagaatg tgaaggatac agttctcagt tactggaatg agtgccagag taccagtaca 37920
tggcttgcct tggggtttgg actacctatc ttaactcctt tgctcctccc aatcttgatc 37980
tcatttgttt gaaagatcat ctgcccaaca taaaaatgca tttctaattc tgtaatttaa 38040
gtcagtggca agatcagatt cagttaaagt ttactttcct gacagctttt tagtatcata 38100
tctattttgc aaaactctag tgataaatgt atgcacattt acacatacag catctcttct 38160
gattctgact aagatattac tgggttgtgt agaagtgatg ggctctttag aagaaaggtt 38220

```
tgatatacta ctaatctaag gactgaattt tctcatcttt gtctttgccc cttttgactg  38280
atgaccagag caggagcaca taacattctt ttgtgctaac agtatctctg catcacattg  38340
atcaggagaa ttggcatctc cagagccctg ggatggtaac ttctctgttg attttcagga  38400
aagattaggt gatattttct ccatgggaag aggatgtttg atgtgtgttg gctttagcaa  38460
aaggaagctt gtggagtcaa ctgtaagtag acagaattgc ctttgactta atctgtttca  38520
gtcgttgttc atactcaggt cctccagagg acctttaagc atttttattg actttgtggt  38580
ctattacacg aaactaaaga tactgattct cagtcatgag tctgctccaa aattgcctag  38640
ggaatcaaaa ataattgtac cagttcctat tcctggacat tatgattcat ttggtctggt  38700
atgaaggcca ggaatctgta tttttaaaat tcactcaagc aattttcata tatagctata  38760
attgaaaatc tgtggctgaa cttctccact cccgtatcca tcgcaatact tccccaaggt  38820
ggcatttaag atgggcctag agggttatat aagatttcaa tattaaaaca tggattaaaa  38880
gtgaagactt ttcacatgga gataatttgg aagaaaaact tgcaaaaatg tgagagcatt  38940
gagaactttt ctttcccaag gaaagaagtg gcagcttcat tttggtcat tgcaaacagc  39000
agtgccatac atgaaaggaa agtggtggtg ctcatcaact ttgaataact ttgtacagaa  39060
cccttgagac tcctctctgc ttataaagaa aaagtgtcaa ctgtaaagtt gatttattta  39120
tgaaccatag gctactatga aatctctgtt cccagctaga ggcctgggag agtaagataa  39180
ctacttgttt attccacgga gccacttatt agctttttct atagcacata cctcaaatga  39240
agcatttcaa taaaagaacc acattctatt cacatgcttc attttattct gatttatgta  39300
aaaattccca aactcctcaa gcagtgtttc tttgtaaggc aataatcttc agttctgttg  39360
caaaggtcag gagtgataga atgaaaatgg tactagatac aacagctctt tggtatttgc  39420
atggccatta cattgccatg gggctgcaag acttgtgagt gcttgatatt ttgcttgttg  39480
atgaatgagt ctgtgtttgt gctaatggag tgatttgaga ggtagttctc cactgtcagt  39540
caagaggttg gttttgaaag ctgattgcca atggtcattc tgctaaccac tctggttctc  39600
ctttagatag agacttattc agattcaagt cttcatgtac tttgtggcat aaacattgta  39660
cacaccagat gtattcaaca accataaaaa aaaacaatta ggactcaagt agtatgtcag  39720
agtgtagtca ctgatgatat ataattctcc actaccaaga agatggaagc acactgttga  39780
gtagctacat cctacatatg ttggccagaa tttaggaata cacatgtgat ctatacattt  39840
tgaggtattg tctgacccct agaaaatcct ggtgaagttt ttctggtgtc agtttggtct  39900
taatgtttag gaaatgccca cagactactc ctgctttctg cttattcaca tagtaaacgc  39960
aaagcacagg actagtttgt catctggatc aaggagaaat gagttagcag atataaaata  40020
aatcagaaag gaggtagttc tcaaatattt actccatgaa tagttgctgg atgttcatta  40080
actctatagc atttgttact acttattggg gatcctggaa agaaaatata ttgtctatat  40140
ccactgttca ctgaggccct ctccctaccc agaaactccc tgtctccatc actcactctc  40200
cacattcatt gacccagggg aacagttcat ggatgagtga acttgagctc tatcttaaag  40260
gatggagttc gatttcaagg caagaggtat aagagaaagt tcagagacaa cactggctat  40320
ggtctttgtg aagaaaagtg aattgaatag gctcctgtgg agatcttaag taagtacttc  40380
tggagataag gttgaggaaa agtaggtttg aatcttcatc cagaggtagc ccctaaatgt  40440
gttgagttta ttgaaagagt acttgacttg gattcagaca gatctgcatt tgactcctgt  40500
tttgccattt ataagaattt gagtaattat tgtttctaaa taagagttta ttgagccaag  40560
```

-continued

```
cactcagtaa atgtttgaat gggaaaatta actgccctgt ttttctattg tcagatggtc  40620
ctcttcgttg gataacttgg taactgttga taacettttc tcaggaatca gaaggtagaa  40680
aggttgggaa aatataagaa acaaaaaggc atattcctat ttttattttc atattgtctt  40740
ccaactctcc caggcttctt tgtttgcaag gctgactttt ataatacttt ttgggtagag  40800
caggtccttc tttggtttgg ggttaaaccg tgagtaacct tattttctag gtctcagcca  40860
actttgaagg gcatgaactc acagtagcct cactaggatc acttcagcag tgagaattta  40920
tctttcttgt ataaaagtgt aagagttgat ggcggccagg cgcagtggct cacgactgta  40980
atcccagcac tttaggaggt tgagatgggt ggatcacctg aggtcaggag ttcaagacca  41040
gcctgaccaa catggtgaaa ccccatgtct actaaaaata caaaaattag ttgggtgtgg  41100
tggcacatgc ctgtaatccc agctactcag gaggctgaga cagaagaatt gcttgaacct  41160
ggaaagcaga ggttggagat tgcagtgagc cgagattgca ccactgcact ccagcctggg  41220
tgacagagtg agactgtcaa aaaaaaaaaa aaaaaagagt tgatagcaaa ataactatct  41280
gtagcataaa cctcagtatt ctttatcatt cagtatcaac attattactg aaaacaataa  41340
gcaatatgga ctgagtttct gtggggtgga aatgtgaagt ggatcatagc atgatataac  41400
ttgtcatttg gcttccttta taaacattat caactacctc agctctatca atcacttggc  41460
agtccgtagt gaacattata actcaaatga ctagtcaggt ctgttcattg cccatgtaaa  41520
ggcatatacc tgaagtgaga agtctgaggt aacttagcaa taagcttgca gtacagtgtt  41580
tagtgaagcc gaggaattca aggatttgag tcatgccaga ttgctccata accatagcct  41640
atctttgtca caagtaagaa ggtttaaaaa tcaccatacc attattggtc acaacgtttg  41700
gagataggga agagtttgtg gatggatcat ggcagtgcat ggacagtgat tagcccataa  41760
cacaaccagt gaacactgtt gtacccaaag cacataaatc accacatata ctattaatat  41820
atttatggat gacaacagac actataattt tatgtcagtg ctttctgctg tgaaaaacaa  41880
agaaagttaa gggtaccttt tttatatttg catcatatct ccagaccttt tcctttatct  41940
ccttcttgca agttcttctt tctttcagct gactatctgc tgttcctgct atggctccca  42000
gtggcttttc aagagggtac ttgtttttta agagaagacc cttgaaggac agagagagcc  42060
tgaatcattc aaaataatga attactcagg atgaaatttc aataatttgc aagtgtgtgg  42120
agatagatat tttgaggaag cataattttc tatgtacccc tcaaatcgtg gctggagatg  42180
acagcctctt ccacctccat ataagaccat ttcatttcct tctacttttt tctccctcct  42240
tcccccaaac acacaaacat acacatatcc tgtgcttcag tcacacagaa cttcttacta  42300
tttcatttca attctctatg gctttgcatg ttctgctcct tctgcctaga atgctccttt  42360
cctttttca cctggaaaca tcccaattca aatgtcacct cccttattta taccaacttt  42420
gtctgtaact cctttatcac acttcttcct gtgattagtc aattcacttg tctgctgtta  42480
cacctctatg agagatgaaa attccttctc catctctgga actcatgccc ttcgcatata  42540
gtaggcaatc tgtaaatgtt tgaaggttga gtgaattaat gaatgacctt caacctttca  42600
ggcttccaat tttctctctg aaaaggacag ccaaatgaaa actcataatt ttagaagatg  42660
aggttagacg gttggtaggt gcatgcagag accagttatt atttaggtat tatggaagtt  42720
tatagttctt gtatgttgag ttcagtgtaa gagtggcccc aaacatagtt aatgaccact  42780
ccagacccag ttgttataga gttggcccca gctgtattgc ttctatttaa gactaggata  42840
agaaatgaca ctttcctact ttttacctta ttgaaagggt agaggctcac tgttatcaat  42900
ctcagttcac ttgttgattg cactggcttg ccaagtgaga atattagcac ctctgcacat  42960
```

```
ttctatagct ctgccactta tgagatcttt ccttcccatt gtcatattta ataatcagga  43020
tagccctata aaatatgcat tctcatttcc cagatgagga tactaaggct caagtaggag  43080
aacttacttg tttagtaaga tcatacagct aggaagtggg agaggcaaga gttgaaccca  43140
gatcttccta gctcctagtc cattgttctg tctactgggt cacactggac cagccaggag  43200
gcaggaaaat cagctgggga atgtggtgcc aacgtgtgat gtttgcctaa atgtgtgcat  43260
ccttgctgga agccagccat gattcatgct gcataagtat tcattaatgt tcatttcatt  43320
tatttggcta tccatatgct ttccagggcg aaggcaagct aggacaaggg cagacaagca  43380
gccttaaagt ttgggtgctt tccttcgaag ttgagctgcc tgtttgaaaa tcacactttt  43440
tggtgataga agatggttcc agtacagatt ttatttatta ctgcatctac atggatagac  43500
attttccaaa gcatagctga aaatatgtgt aagtcccaga atattttctg atttagacac  43560
agactttgag catgataacc acatttagca tgttaggaaa ttctgtcaga atgcttctgg  43620
aaaggctacc tttccagaat gaaatgaaaa aagaaaagga tggactttga aactggctag  43680
atttgggtta tacttactca tagtgtgacc ctggcaaatg atttaacttc tccgaatttc  43740
acttttctta ttctttgaag tgaaatttta aaatgccatc ttgcctgatt tttgtgagaa  43800
tgaaaatgag atcccacacc aggaatttag aagctactca gtaaatattg cttctctcct  43860
ttccccttcc ccagtcctgt cccccgagac attcagtagt tattcacagg catgcattct  43920
gaagtctgcc tactgctcca tgttgaaatg cactgctctt gcaaggactg attatctatt  43980
tttctgtctt ccaaggcccc ctgtgttcca ctccaccctc ccaattctgg gggcttccaa  44040
agtgggcagg tacagaatgt tctgtggagc atcggaggct gttactcaat atcttggcca  44100
gcactctcaa ctgctctttg cacacactcc atatgaaggc aaactccaga tcttggagcc  44160
catgtgtgtg tcatgcattg tactgcttct tgtacccaaa tccatctcaa gggtgagtag  44220
accaggctca gacttgtcct gggagcagat ttctcaagct gcccatgtcc ccacactgtt  44280
tgattaaaag gaggtgcttc aaactctttg gctttatata gactagaatc agaatgattg  44340
gtggtgcctc tgttctcaag gtatcccaaa gcactttgta aggaaatatg acaagcgctg  44400
aggccatgca ggccagtaca acagccgcca cccagcactt cacaattagt catgcccagc  44460
ctgggatcat caagcctgtt tttattggaa gagcaagaga gagagggaat gctagctggc  44520
aatttcccca ggtacccttt atgaaagtgc ccttggctct tccaatttca tctgaataac  44580
cagctcaggc aaattttcct ctatcaaaaa gcagaatgtg atagtgacaa gctgatgccc  44640
ggctgatgcc ccaggacatt gactaaatag acttggcctc acaattggtt tttattctct  44700
atctcctttc ttccctttg ttctttttct gtgtttcttt ccccattgcc atctgcagag  44760
tgttctcagt cagaagtcag ctgtggggtg gacagtttgt cattttaaga tcatccctat  44820
tctgtctacc tttcttatcc ctcatatcat tgcttttaga gcaaggacaa ttctggaagt  44880
gaaactacaa taacactctg ggctcctttc cctctagtag tactcaacac acttgtaatt  44940
acatgttcaa atttgtcttt cttatttcta cttaggttca tgaaggcaag ggacatgcct  45000
gtgttgctta ctttctcttg gcaggcacat acagcaagtc ttcaaaaaat gcttgttaac  45060
tacaaattaa gtgtttaaga agtccactgt taattagccg ggcgcggtgg cgggcgcctg  45120
tagtcccagc tactcgggag gctgaggcag gagaatggcg tgaacccggg aagcggagct  45180
tgcagtgagc cgagattgcg ccactgcagt ccgcagtccg gcctgggcga cagagcgaga  45240
ctccgtctca aaaaaaaaaa aaaaaaagaa gtccactgtt agtatctttt cccctgccta  45300
```

gtttgtaagc aactggcctc ttctatttgt aagttacctg ttttcatttc catatgcccc 45360
aaagcaaact ttagctcacg gccttacaga gtgtgtatgt tagtatgtta aaatgaaatc 45420
aactttcctc tcccaggcct tctaattgac atgaatttgg gagtagactt gcattggcct 45480
ttgtcctgac agccaacaga gtcctcttct gttgtattca ctgttgcctt ccatgaggat 45540
cccatggaga aagtttgtca ttgatataca ttttgagggc agactcaact tgagtaaacc 45600
tgattgagct ttccccatct gcctcccaga gatcactgcc tgtgctttgt taaaaagaga 45660
attataggag tcctctcaag gcagagaggc ctaaaattag acatggcagc catgcctttg 45720
gtgtgcatgg aggttggata caggcagcca gtttcccctc tgttttctcc cttgcttaca 45780
cagccaagga gtggagccaa gcctcaaggg gaggagctgt atactcgagc atgccctgtg 45840
gttcctggcc ctgactgagg gactatttta tatatcccaa tagagaagcg tggaagacat 45900
ctaggttgcc actgtcattt gaaattggaa tttttaaaag agaaacctga agacttgaag 45960 aaagcttct tttgcctccc cttacagttg atttttgagc ttcttaaagc tacctagtcc 46020
aaagtaccca cactcttatt cttttgtctt tcctactggt tttatttttt tttcatcttc 46080
ccaggtgttt gatgatcact aagagcttca acattgctca ccctgaccag gtatgaagcc 46140
aagagtttgg tttagggcat aaaagaatgt cggaactcaa ggactaggtt gaggtgggga 46200
agggggatga aggcttcttt ttttcttggg ttaagcagaa ataacttaga tctcagagtg 46260
aaagccttga attatcacat atatcactgg aaaagactag ttctttgcta tgataacaat 46320
tgttcatcat ctctcccctg aggatttggg gtcaaggcct ggctacacct tttaatgatt 46380
tcagtcatgt gacttaacct ctttaaactt ggattttctt catctttaca atggaaatga 46440
tgacaataat cactacctca cagatattga taataatgat atctcactag gaagagaatt 46500
aagtaatatg agggataaaa aggcatttgt aaatggtaaa atgagattat gattttgaaa 46560
gctattatta ttttcctttc actgtctatt atctcaactc ttctattttc ttgccttttg 46620
tacagcatgg ataatttaga tgtgactctg gacagaggga tggatcagat gacttcttaa 46680
gttatcttcc agtttaggag ttcgtaaact atactttctc ctttccagac tatcctagta 46740
agaaaattct cttttaagac agagtagaac tctggaattc atcagttttg atgtttctta 46800
aagtgtaatc taagatagtg ctcctgtatt aagttctgat gtctgaccat tgttcaaata 46860
aagagtaaaa tgcaaatgac aggaaattgg ctgcgttctg aatcctattt ttatttggga 46920
taacaataag cctgtatggt cactgtgacc tttgatttgc tgtttctgca acctcacact 46980
tgtctcagga ttcttcttcc acttctgcac tttatattgg gtttcttcca ggcatcatat 47040
taaactttaa gccaggtatg tgtatatgca tgggctgtgg gcctgaaaaa aattagcccg 47100
agagagaaaa aaatttaagt agtgggctag aagtaagcat gctactagaa acagaatttg 47160
ggaacacagc tctgggccta gaaaagcgac ctgtcaactt gttacagtta acatcaataa 47220
ctataggatg ggtttggtgg aaaattatgc tgaccaacag ggtgggagag aatagggtca 47280
gaatatatat cgctgtaagg ttgagaaaaa aagaagtgaa aaaaaaagaa atgcatagag 47340
agaaaaagga gtttagaggt aacatgttaa agtgtgagaa ataaactgga gagcttgact 47400
tctcttgaat atatttttaa ataaagtact cctttcaact ccaaatgcag caggcttggt 47460
tcccttctcc tacctccatt gcggatgaaa gcttaatctt taagatgggc ttgggtgggt 47520
agagtacgcc ccttggtgag cactgtgctc tctgcaaccc caataaggcc caacagggct 47580
ctccaaggag gcaaaattct gatgatacat ttctgtttag tggaaaatgg gtagggaaaa 47640
ttatgtctta gaatcaatta accaaacata aaatcctcca aggggcttgg taggatgcct 47700

```
agggaagagc cacgagataa aaactccagg ctggaagggc attgttgcag cactgtcatt  47760
ctccagtttc tcttggagtt gtcaccaccc tctcctttgt tctcactgct gacatcattt  47820
gtaaaataat ttcttccctt aaataaacaa gacatacaat cctctaaatg actaaagaac  47880
agttacctag aagaaacctt agtggaaagt attttcttca tctaacggat gattgtcttt  47940
acagaggtgg agtaaaggat gtgcgaggga gcataatcaa gctaagagat gcatgctgac  48000
ttaaaaggca tgatatatgt gaaactaaga taatgtgttc aagagtgatg ctttgttgat  48060
gcagaaccac tgaattcctt actattatgt ttgcctgact atcggcctct taataaagaa  48120
cttgtggttt gagtgttcat tgaaattagc catattaggt ttatgtgggg atgtgaggat  48180
ctatgtctac caattgcagc ctctgctgca aattggaggc agaaatctgg gctgaacaat  48240
aggtaagagt gtcaactcta cagatctctc acatgctaag caagcacaat atagggcaat  48300
ccaggtttac acaaaggatt aatttgggaa caattatcct cattttcact tcctaaaaag  48360
attttgaata agatgtcttt taagtaagaa gctccctgaa tgcatttaaa atatgatttg  48420
attatgtaca tttcagattt ttctaccttt ctaggagtat ctctgttgta taaaaacaca  48480
aaattctgga acttttgaaa ggaagatgtg cctctcttca tacatttgtc attcttgaac  48540
gattgtaaaa tgaagtgact gcatatcacg tcatgtgccc tattgatttc ttttcttgtt  48600
ttaggaatat tcccagaaaa aaaaaaaact tttttttttt taaaatctac taagcatgct  48660
aggtaagact gaagatgaat ctatttaagt tatgtcaata tctatttata aagatttttg  48720
tgatattctt ttcactgtag aacttcaagc atatcctaaa aggaacggtt agatacctct  48780
acaaactgtg gcaatgactt actgagtaat tgctggcaac tgatttttgg tgcttcttgt  48840
tttgatagta tagcagtgcg agtaggtttc agaagagcaa aactaagaca atccagggaa  48900
atgccatttg agaatttcta actttaaaaa aacaagtaaa atagtgccaa gaatattatc  48960
taactaaccc caaagtctac aatgtaactc ttttattttg ataatgctgt tctaacccta  49020
tctacttcag tcctttccca cccagctggt ttaggaatca aattcccaat gtttcatcac  49080
tgttaacatt actgttttac tcttcacttt agttcttaaa tggcatagtg tcttaaattc  49140
cctcagcctc tttcacattt gatttctttg gaaacttttt accttttcat tgaagcccat  49200
atgatctttt ccgaaacaga cccttatctt tacctccttc tttggagtct ttctcctact  49260
tgaatttctg aacttcttaa aatggccgct ttgggttggt gtcagtaatt cagtaataag  49320
ttttcttttc tttttttttt tttcttttt tttgagacag agtcttgctc tgtcaccagg  49380
ctgcaggctg tagtgcagtg gagtgatctt ggctcactgc aacctccacc tcccgggttc  49440
aagcgattcc cttgcctcag actcccaagt agcaagtagc agcaccatgc ccagctaatg  49500
tttgtatttt tagtagagtc ggggtttcgc catgttggcc aggatggtct cgatctcttg  49560
acctcatgat ctgcccgcct tgccctccca aagtgctggg attacaggcg tgtgccagta  49620
tgcccagcca gtaataagtt ttcttaagtg ctttcttaat attctgatat ttttaaaaaa  49680
gatctggact attttgtcat acaggcaaca gaatgttaaa ccatttcata aaacaatgac  49740
aaatatacat gaatttttca tcagttataa atgcatttcc tttataacat tgaacatgtt  49800
tttgcaactg aaataagtac ggttttcatt tttagaaggc acatgataaa gttaaggcag  49860
tggttaatta attttttcag attaattttt cagaaaagtg actgtttctg tctattgtct  49920
taaccccagg catcaaagga ttttaatcag aaagaaccga ggaataattt ggttatttta  49980
gtgccttttt ttgagacaaa gtcttattct gtctcccagg ctggagtaca gtagtgcgct  50040
```

```
catggcttac tacagcctcg atctcctggt tcaagtgatc ctccaacttc actttcccag  50100
ctaactggga ccacaagtgg gcaccacact ctctgcaatt tattttaatt tttcatagaa  50160
atggggtctc actatgttgc cctggctggt ctcagaatcc taggttcaag caatccttcc  50220
acctcagcct cctaaagtgc tgtgatttca ggcataagcc actacactca ccctatttta  50280
gagctttgtc aagctttgga aagaaaacca tttataatat aatagataaa ttatggatat  50340
ttgaggcagt ttttatcata gtatacatgg taaaccacag cccccctta taatatttgt  50400
atttaataaa aatgaaaata ttacttttat cttaaacatg ttttaacaaa gcaagcatat  50460
gtagattagc actaattaaa acaaaaacct ttgtaatgat agctgttttt tatatgatta  50520
caaaaaattt actatacaaa tttttatcct aatcagtgtg aaaaactgca aatattagct  50580
tatagggcta gtcttcagag tcctcttcct acctactact gctaataagc caatgaaaaa  50640
ctctctgatg tgtgtggtgg ctcaggcctg taatcccagc actttgggag gccaaggtgg  50700
gtggatcact tgcactcagg agtttaagac cagcctgggc aacatggtga aaccctgtct  50760
ctactaaaaa tacaaaaaat tagctaggcg ttgtggtacg cacctgtagt cccagctact  50820
caggaggctg aggtgggagg atcacttgag cccaggaggt tgaggttgca gtgagccaag  50880
atcacaggac tgcactccag cctgagctac aaagtgaaac cttgtcaaaa agaaagaaag  50940
aagagagaga gagagagaca ggctcctccg ctttttcagt tcctaaataa ttttccaatc  51000
tagaatgcaa aagattctga aggaagacag ttaccatttc agatcggcag aagttgtggc  51060
tttaatctag actcgaatat gttttacatc aaagggttgc ctcaacagtg ctcaaacctg  51120
cctctctgaa aacatgctga gcacgaaggt tacttgaagt cttagcttga gtacttaaga  51180
gagtgctatg gagggattgt tgatgagagc tgtgtcacag ctaatttttc tttagtaatt  51240
aaaggtttat aaaaatctta cactgtatat tgacaaattt agcaacaaaa tgagcttgag  51300
aaaaaaatca aggcctgcca tggcatcttt gctttttttt cttaaaaaaa aaactttta  51360
gaaagattat gcgactgtat tatctgtaac tactgcaatg gtgtaaatcc tgatggtata  51420
atttgctttt taaagctatc tttacttcag tataacttag attaaattta ttttaaattt  51480
aaatgatatt tttctctttg tttattattt tataatgttt cccatagaat tcacaaaatt  51540
cattagaaag attttttttt acttccttag gtcattaaga ttctgatttg tcaatggatt  51600
tcacataaac cctgtctttc caaaaatata caaaaaaaaa aaaaatagcc aggcgtgatg  51660
gtgcgtgcct atagtcccag ctactcagaa ggccgagttg ggaggattgc ttgaacccag  51720
gaagttatgg ctgcagtgag ctatggtcac accactgcac tccagcctgg gcaacaaagt  51780
gagaccccat ctccaataaa taaataaaca aataagtaaa taattttcac cttgaaaagc  51840
ttataaatgt atgaaatcac aatgagggtc gctgatatag tttggatgtg tgtccctgcc  51900
caaatttggt tttgaattgt aatccccagt gttggagatg gggcctggag ggaggtgatt  51960
ggatcatgag ggcagttttt tcatgaatgg ctcagcacca tccccttggt gctgttgtgg  52020
tgatagtaag ttctcatgag atctggttgt atagcacctc ccccttgct ctcttgttcc  52080
tgctttcacc atgtgacatg cctgctcccc cttcaccttc tgccataatt ttaagttgcc  52140
tgaggcctca ccagaagccg aacagatgcc ggcaccatgc tttctgcaca gcttgcaaag  52200
ccatgagcca attaaacctc tttttttttt ttttataaat tacccagtct caagtattct  52260
ttatagcaag gcaagaatgg acttacacag tctcttttgt atcagggaga gggtcttctt  52320
ggtgactcca cttcttttct ttgtttatgt atccttccag atgatgtatt tatttccttt  52380
gtttttcaat tgatatttac tcttaaatta aactaattat ttaaaaaagc attttaaagt  52440
```

ctcattttag attattttga ctatctgatt tttaaaatgg tttaaaaaat ctatcttggc 52500
ctccatatgc aatcaaataa gaaacacatt ttaagcatat tatttacctt gtggattctg 52560
ccttcctcag tgtgttcagt ctgtgtatat tcatttctcc cacactgtaa gaagctagtc 52620
agatgtataa ttggattatc atgctacata atcttagcac actcatttta agcatacata 52680
gactagtgag caccactcat tacatgtcat ttctctagag aaactagttg ggccatggct 52740
gcaggactct cacttgaaaa gacatgtgtg gtgatgtttt ctcaggcagt taagcaataa 52800
agtgtaccct gatttgcact gaaaataaag attcctttaa agggagcagt tctagttatc 52860
tctctcttta ggtaccatat gctgaacgtt tttctatgca ctaaaacagc aactaggttt 52920
tatactctgc cttacagcct acttcacacc catttcacag ggagaggaac agagaggtaa 52980
gtgatttgcc ccaaattaca taactaggaa gttatttgct cagtgtggaa acttgttcag 53040
aaggtcattt cattgaaatg taggaagagt ttctggcact tctcttgagc aggagtcaaa 53100
aacctttttt tgcactagcc cagatagtaa acattttagg ctttgtgggc catatgatct 53160
ctgtcaaaac tcctctactt cgttgttgta gtgcaaaagc agctatacac aatcctgaaa 53220
tgaatgggtg tggccgtgtt ccagtacaac cttacagaaa aggcaatagg ctggatttgg 53280
ctctgagact gtagtttgct gacctcagct cttgaactga gctctttaac tgacctcagc 53340
tcttgaacta tggtacaaga tcccatggtc ctgtttggta cctccatttg ccctcctttt 53400
cactctctgg gagcatagct aagttcaaaa ttgaattagg tacttgtagt aagagcatac 53460
ttataatcct gggatcttca tgttgccaga tattaacctc ttgaagtttt tcaccacaac 53520
ctgggcactt ttctgatttg ctcacttcta gccccacctt tgggcccctt cataagcaaa 53580
catgcaggtt ttccagagag ctgtatgcta ctgaatgcag aaaatttggc tcatactggc 53640
ctatggacta tctgctcact gccctgataa ctattttcca agggagtggg tgccctacct 53700
ttcctacatg aagtttttttg ctagtcttgc cctaaaaatt ctaggtatcc cttgctttta 53760
ggataaatat gtttcactgg gaccagctgg aaaacgaaaa atagaattat ccaactacca 53820
ctttaaaatt ggacaaagac ttttgttgtt gttgttggag ggggtggtaa acatcatttt 53880
agcagaccaa atatactttt ggtgaaaggc agcctgttgc aaagacacaa cacttggaca 53940
agattttgaa gccctggttg cctttactac tgacttaact acagtatttg cggacttgag 54000
caagttgctt cccttctgtg agcctcaggt tattcatctt tgaaatgagt ataatacctg 54060
tgattataat tacttatctg gattctgcag agaattgaag gagataatgg gtgtaaaagt 54120
actttagcgc ccagcactgc tccttatgaa aatgaggaaa taattgagat gagtgagcca 54180
ttgaggcaac agtacaaaaa gtgctgaaaa ctcactgctt aaataagcac ctcttactgc 54240
ttttgtggca ctttgtagca atgttttttt tttttttttt gagacggagt cttgctgtct 54300
tgcccaggct ggagttcagt ggcacgatct cggctcactg caacctccgc ctcacaggtt 54360
caagcattct ctgacttcag cctcctgaat agctggatta gaggtgcgtg ccaccacgcc 54420
cagctaattt ttgtattttt agtagagacg gggtttcacc atgttgatca ggttggtctc 54480
gaactcctga cctcatgatc tgcccgcctt ggcctcccaa aatgctagga ttacagatgt 54540
gagccaccgc accccacctc agcaatgtgt ttttattctg actagaaaag taatgtttgg 54600
ttttgtttgg ctctttgctt aatataccca taataagggt acctatttgc ctttggacca 54660
ttagttcaaa tattatttta ttaatatgga attactgggc tccagaagcc atagtcttct 54720
tagctgctcc ctatccccac tctcacctca attttttttt ttcacttttg tttttcttct 54780

-continued

```
cagggaaagg tttgaggcaa agaatgtctt cttatgatcc aaaaccaagc atggtggtga  54840
tttattcacc aagagattcc taagtacctg tgtgatggac atggtagaat ctttgtcctg  54900
agggagctat ctagatccat tccttctgat atgcagccag tagccacttg tggtaatgga  54960
gcaatagaaa caacactagt tcaagtggaa acgtgagatg agaagtagga ggtggagaga  55020
actaaccaga agagggtacc caaataaacc agaaatatgt atgtgttaga gaaggggcct  55080
attgagcggg tggcagtggc atgtgtggca ttacttgctc ctgtattctc tgctttttac  55140
ttagttgtgg ctttggtggt atagtctcaa atctaagtta cgtaggtaat attgttatgt  55200
atcatgtttt ggcaatgtag actaaatact tgctcataag agtacaggac aatgaggata  55260
gtttggtttt gtttactgca tggaaaatgc aggatgttta gtaaatagat tcatggcgta  55320
gtgagttcac tactaaaatc agactctgag aatgggtttg atttaaatgg ctagtttaga  55380
agactgaatt taggccactt gattgagaaa ggccattttg ggtaattata aaccaccaac  55440
attgtgtttt gaatgttaaa gcttatattt gtcttccagt taccagaatg taagcttctt  55500
gaggagggag agaggagttt tcttaatctc tgaacctgca cctttcttct gtgcctagcc  55560
cagtgcctgg caccaaacag gtgctcaatc aatgttgatt ctatgctacc aacaaaaatg  55620
agtccatgat gtttactatt caacaaatga atacaatttt agagtaaatt tttactgctt  55680
acactacatg tagattttct ttttagagat ttcgcaatgc tgatttattt caaaataagc  55740
ttgaagctaa gcgacaaagc tgaatgatga tttgtttttt atttattttt aaatccaaac  55800
ttacaatttt acatgtcatt gccagaaaaa tcattaaata aattatgata tgcgcatatg  55860
gaatactttg caaccattaa atcaaccatt aaatactatg caaccattaa atcaaccatt  55920
aaatatgttg gtatatgcaa atgtgcatat accaacatat tatatagttg agtaagaaaa  55980
gctagtttca aatgagtatg ttaatatcat ctgactcttg caaaaggaaa accatacatt  56040
tgaatgtaca tatatgcata tgtttatatg tgcatagaaa aagctatgag gggatatacc  56100
tcaagttgct aaaagtggct ccacctggag agggacatgg aaaggagttg gctaaaaact  56160
gaggtttgtt atggtataca cccctgcaca gtttgatttt ttaaaaacaa tgattataaa  56220
ttacttttat tatttataaa aatattattt aaaattttgg tactaaaaac agagctccat  56280
caacaggtca atggataaag aaaatgtggt acatatatac aaccgagtac tattcgtcat  56340
aaaaaaatga gaccctgtca tttttgcaac aaaatggatg gaactggaaa ttattatatt  56400
aagtgaaata aggcaggcac agaaaggcaa acattgcatg ttctcattta atctgtggaa  56460
tctaaaaatc aaaacaattg aactaatgga tatagaaagt agaaggatgg taaccaaagg  56520
ctagaaagga tagttggtgg ggcaggggag ggtgaggtga gcatgtttaa tgggcacaaa  56580
aaaatagaaa caatgaataa gacctattat gtgatagcac aataaggtga ctatagttaa  56640
taataattta attgtacatt ttaaaataac taaagaggta taataggatt gattgtaaca  56700
caaagaataa atgcttgagg gatgtatacc tcattctcta taatgtgatt agtacacatt  56760
gcatgcttct atcaaaaatt ttcatatacc ccataaatat atacatccat tgtgtactca  56820
caaaattaaa aaaaactgtg cattaaagaa aaacaaaaat aaaaaccata gttcaagtta  56880
taaacaaaat aaaggtaatt tggaggaaaa ctgtcttcag ttatattgga tatttggggg  56940
acatttttgt atgttagtta gcaaagatca cttgaaaaag aagattcttc cttctatgat  57000
tcaagggagc ctagcaaaaa ataaatgaaa tgaaataaaa taatacaaag agaaaagatt  57060
attccataaa ttctgcttac ttatttctgg caaacttgtt gacagcacat gtgacctttt  57120
ggtaaaaaga catttttata tttttagtta agtttcaaat ataaattgtt tgtgttttta  57180
```

-continued

```
aaataaatta aatggatgat ttcagccaga tcattatgaa aacacatgag atattgggtt  57240
atgcaatgac taacagtgtg taccttttct tgatatttat tcataaactg gggaataaaa  57300
gtacattttg gcccatttac tccttaaata attttatgtc tcccaaggag agttgtaagt  57360
tgcttgatag taaatgctat gtattttgta ccttagtgta tatattatgg gatttcagcg  57420
ttagaagagc tcttaaatgc cgtgttcata gtccaacctg tcttctgatg cttgaaatcc  57480
ccttgcagta ggaaatgcaa agtagagagc agacactcaa taatgtagtt agtgaattat  57540
ttagaaagag gcattttgag cccataatgt atgataggta cttctacatt tattatttta  57600
ttctttgcag acctgcagaa aactgtaaga aaaaagttta tttcagattc atgtgtttat  57660
ttgattaatc tcttcatagg tttcattttt cagctcctgt cagaaaatac agattcttat  57720
aaggttcacc ttttacccat aagaataata gtataaaggg gataatgtga aatacaatca  57780
cttcacagac tgtttcaatt aaataagagc tcgtagataa ttcagtccac cacaccccat  57840
tttacagatg ttgaaattga agcccccacc aaaaggaaaa gacttgttca aagtcacaca  57900
gcaagtcagt ggtgaaccta attaggcccc ctgccttcca ttttagtgag attcctgtgc  57960
tgatagtcat acccatatca aatcctcttt ggcagttata gcttgcccac agtaatgtgt  58020
cctgaaaaat atgacaatta attaagttgg agacagaacc ataacctctt tataaaaatt  58080
ttctggaaag tttacatgac agtaagtaat atataattag aaaggataat tcttatttca  58140
tatttatctt tttgtttcag aataataaac taagctatct ctactcagtc cattttaata  58200
caaaaatatt tttacccgga ctgagttttt atgcttttta ggaactttgt atctgcctca  58260
cttagttaaa atcctagctg cactaatcac ttactgtggt gggcagaatt ctagaatgac  58320
cctgaatacc ttgtccttgt atgattcctt cctctttaag taaggataaa aactgtgaat  58380
atgatatcac tcccttgatt aggctttgtt atatggcaca gttaacttta agaaaggacc  58440
aatcacacaa gccatttgaa agcagagggt ttgggtattt tttaactggt ggcagaaagc  58500
cacgcagaga tttgaacatt gaggggaatt tgaatttgat gtgccagtac taacttgaag  58560
atagaggagg ctgcatggaa agtggccttt aggagtgatc cctggctgac agccagtaag  58620
aaaatgaggg cctcagacct acagccataa agaattctgt cagtgaactt gaacttggaa  58680
gtggattctt cctctagaac ttccatataa gagtccagcc tgattgacac cttgattttg  58740
gacttgtgag accctgagca gagaatccag ttgacttctg acctaaaaaa aaagtcagat  58800
aataaatgag tattgtttta aactgctaat tttgtgataa tttgttatgc agcaataaaa  58860
aactaatata tttaccatgc aaggcaaggc atttatcctc tcatgattca gtttcttttt  58920
acctgacata atggaattaa tttatactgc tgtgaagttg tagttgagaa acatgacttc  58980
taaagtaata gaggacatgt attattaatt ttagtagtat taatagtaat gatactgatt  59040
ctcccaggcc tatacaaatc ctttgataca caaatgaata gtaaaggaac ataaattgtc  59100
tctaggtaga ctttcccaca atgcaatttt aggatacaga ggtcatatgc ctgttattct  59160
actgtggcag agaaaatatg gagcctggaa aactgttcat ttgcatcaca tacatcttgg  59220
gagctcactc tgaacctggt accataataa gctctgtaga cagtataaag aggaaaggaa  59280
tcagacatgg tgtctgacct caagtgtctc ataacgtagt agaagaggta aaatatgggt  59340
cacactaact ctactgcaaa gtaggaagtg cttgtcgcct tgagattgac aaaatttggt  59400
aagagttcag aggagattgt ctgtgaactg ggccttgaag aatagttagg atttgaatag  59460
gagaaggtga agaaggaagg cattccagct agggagaaga gcacaaacaa aagcatagat  59520
```

-continued

```
aaccttgaac atcatcatat gggataattc aatagttcag tataatggaa gtataagatg  59580
cataaaaata agtgtagtag gaaacaagtt taaaagtata gattggggtt agtcatacaa  59640
ggccttgaat ttcaggctaa ggagtttaga cattaacatt tgtttttgaa caaaggggtg  59700
aactgatcac atctgtgatt tagaaagaaa attctagcaa tagtgtagat aagggttgat  59760
ggtaaagttt ggaaggtggt gaggcagagg ctggagacag ggagcacatt taggatagaa  59820
agatgataaa gagatgattt agaagagttg ttttggaaaa ggagaagaca gaaaatgttt  59880
tagaggtgtc atagagataa aattggcatg gcatggtgca aggaggtaaa gcccaatagc  59940
tttgtaaggt gctgagatag attgaaatca cagagttagg aagttttaga gtcaggatta  60000
gtaccaagac agcttggctc tagatctcat acttaacact tacagtataa ttctgagagg  60060
gtgggtaaca gcaatagtca gaggaaagaa cccttttata catgatggta caggaacaac  60120
actggcttcc aaccccacag ctgctcttta acagaaggtc agaagctggg gagaaatatg  60180
tgtgtgtgtg tgtgtgtgtg tgtgtgtgtg tgtgtgtgtg tgtgtatgtg ccatttctgg  60240
gactaaggat gggaagtaga ttagttgagg ccactgcagt ggggtctgca agttgctagc  60300
actcacccgt tccaagaggc cttaaaggtg ttgatctgtt ccctgggcat caccacattc  60360
cacaaattaa tgttcctctg agagaatagg gtgattcaat ttcactgtgc ccgaaggtta  60420
cttttggggt tcatgtttgt tctaagtcta tgctaatgat ctgccaactg tctgtttgtc  60480
actttctcta acccttagca tgtataaact gatctgttgg gaaatgtgta gcatttatag  60540
gatggtagga tttgtaacat gcgatcacag gactgtttat atagagtccc tgggaagggg  60600
agagaagagt atttctgtta caaatgtgga ttctttggcc cctcctcaaa cttactgagg  60660
ttcaagaatt gacatttata ataagcacat atccattttc aataaacatg aaagtttcat  60720
accctctttt aatgtttgaa atcctcaaat aaattagtca ttggtgccag agtatcaaat  60780
aattatggta cagaatgtat ttctctgaat gacaccttct cccagagatt ctgatatata  60840
ttcctctgca ctcaccctgt ttgataatta ccagtatatg gaccatttac ctgaagaata  60900
agagtagggt ttcctactgt tgttgaaaat ttgcttgact cttaacaact tgtgtgtgac  60960
tgtaacaaga tcacacaggg taaacaatat tagcttattc aaccactggc tgaagaaatt  61020
taggaaagtg aacacatttt tctttacatt tctctttgtt ctgtgagcct tttatgctgg  61080
aatagtttcc actgcaggct gttattgtct gcctccagag gagggagttg acctagcagt  61140
ggtaactgga gagtgttttt tgaaacctct ttccaaggtt agttgccaat ggcatctttg  61200
gaacagtgtc cttcactttt gtccctcagg gaccagtgtg agaatgggaa ctttatgatc  61260
tggagctggt taagtgaagt ccaaaaataa ttaagaaagt gtttccttcc ctgggaatga  61320
gttcagtagg aatctcaatg tattgtagag cactaaggac tcagcctcag gcatttgcaa  61380
aggattcttc cagttgcctg tgttacagag gacacagttg gcatttcctt ttggtgttga  61440
ggggagatgt gtacatggtt gtgagatgac tcaccctttt tgcttagata gttccacttt  61500
cattgtggac agactctttg gagggccagt ttggcatgca cgtgtgtgtt cattccatcc  61560
tggagcattc tttatgagaa agccatttgt tgagtggttt gccattttgt tttacagcca  61620
ctctgtgggc tatgaaatgg tcatccggcc gctttatttg tccctaaaaa aagcagtttt  61680
tccctttctt atcttcatgg ctgccaagca gcagaaagag taactcaggg aagccatgtg  61740
atagcctttt atctgtctgt tcagaaactg atgatgtatt ggatttgata attcatcaaa  61800
tctgaggttt actggtttgt atttgcctca aaatgggcat ataatatttt gtcaggtaac  61860
ataatagaca gatcattggc attgctttat tgaagtgaat taattcaata agcctgtaag  61920
```

tgcctgacat gtgccaggca ctgtgctagg cattctgtta acagatgaga caaatctctg 61980
tcttttaggt gttttcagtc gaacagggga gacaaatata tgagcaaatt gctatttttt 62040
ttaaatttca tagtgtacat gagtataagg tgctgaatat gtgattgatt ctgagggaaa 62100
agagagataa gggaaagttc tcagagaaag tcaagctgag ggaagaaaag caccccagac 62160
agagggacta gcatagagct atgctagtac attgagttta agggaatggc acatacttca 62220
ctgttgcttc agcagacagc aggcctgtta ggttacaaag ggccttggat gacatgctga 62280
ggggttttaa aattttattt aaattttaat tgacaaaata taattgtata tttctgtgag 62340
gtacaatgtg acgttatgat atatgtatgc aatgtagaat gattaaatca agctaatttg 62400
tatatctacc acctcacata cttatttttt ggttagaaca tttaaaattt attctcttaa 62460
caactttgaa atagacaaca cattattatc aactgtagtc accatgttgt gcagatctca 62520
aaaacttcta acaaaaactt tttacccttt gaagatattg aactgtttta tgaacacaat 62580
cttagaagga tttaaaaaat aatttgctat tcaccaagta cttcttacgt acactgtgca 62640
tgaaatgatt attacttttt ctaatattag ttttcttgat tgaggcttgg caattattag 62700
tttgtatgcc tttagaagga tcataagcag aggtttatcc cagtaggatt tgcattttag 62760
aatgatgact ttgggagtaa aatacagaga agtgaaacca gagatagtgg gatcattctg 62820
gagtctgttg cctacactga acagtagttg agcgaaaaag gatgggcaga atgtgttggt 62880
tctgggtatt gcaaattcat ggcacttgag tgaaaaagtt taagccttct attggctctt 62940
tgtgaatatc ttcaacatgc atgactacaa atagaacaca tggttttgtt gttattgttg 63000
ttgtgttttt gttttttttt ttatttgaga tggagttttg ctcttcttgc ccagactgga 63060
gtgcaatggc acgaatttgg ctcaccacaa cctccgcctc ccaggttcaa gcgattctcc 63120
tgcctcagcc tcctgagtag ctgggattag aatcatgcgc caccacaccc ggctaatttt 63180
gtatttttag tagaaacagg gtttctccat gttggtcagg ctgtcttgaa ctcccgacct 63240
cagatgatcc tcccacctcg gcctcccaaa gtactgagat tacgggcatg agccaccgcg 63300
cccggcccac acggtatttt tgaaagaaca gtgagcttgg attagaacac tagtgtccag 63360
gccctgctgc tactacataa gtaattatga atccatagcc atcttgttgc tcttcttctc 63420
tgagccttgg tttctttagc tataaaatgg gaagttgaaa ctttctagct acttctttga 63480
gttatgagta acaagttagg taatacactt aaaagagaat gtgctataca aatactggtt 63540
cttaagacag ctgttgttaa tgtactgagt attatgctta cctcacaggg ttattgtgag 63600
catcaaatgg gataatggat ttgtaagcat tttgtttaaa gtgtgattca aatgttaaga 63660
attagtaaaa atagtaaaag aacaattcat tctccatcca gatgttctgt ccccactgtg 63720
acttatgtgc tcattcagag ttgtacagaa aaacctccac ttaattttca caagctggag 63780
ttccacatgt aacagaatca tatgggacca aaaaattctc tgtattggct tcttccctgc 63840
cgtattttgg ctctgggacc aacaagacac ccattttgca tgagctgcct gccaccaact 63900
ttgcgctcac atctagttct gttgcccatg tgcaagctga atttgggccc gggcccccag 63960
atctaacatg aaactcaagt ttccttctgt tcaaactgtc caggcataat agtcttaaag 64020
tccgatgccc agcagagccg tagatttttc actggccaaa aatcaacatg aaaccagatg 64080
tatctgtaaa tctagtttca taacactttg tagtcaatgg aaatacagta gcaggcagac 64140
cagaccagag tttactattt gcagtggaat taataaccac atggaaactt tgcctttggt 64200
atctgcgaga tggaagataa aggtgcgaat tcaaagcagt tcccacctta ccctctaaat 64260

-continued

```
tccaacataa agaggccttg aatgtccttc tatcttattg tatatttcat taacagaagt  64320
atgttcctag ctacttagtc attctatctc tattctcctt tgttttaact tcagtggtgc  64380
cagcttaaga tgctctggct ttcagctttc atggagcacg tcatgttttt aaacttatct  64440
ttagggacag aaatgttagg aagatcctag ttcctcatct ctttgctcct gacaaggaaa  64500
tttagaattg cctaaagaaa ggatgtattg gccaacctaa taataaatca gtattagtga  64560
atctaaagca tatttgaaaa atttgtaaca tgagttgaaa ttcagacctg caatgaagtg  64620
tttttaaaag atttaaaatc gaaataatat aaaagaatgt taaaaacaag taaaacatat  64680
cactagttaa tcactctacc aaaattcatt tttatgtttg catatttaac catttttatt  64740
ttctatattt gtccatgaac atgtgttttt atatattgtt tatattaaac atggttttaa  64800
tcatggctta tttcttttat gttttacttc ttttcctttg acataaaata ttgtattttt  64860
taaattttaa ttgcttcttg gcataccctt ccaatattgg tggctatata gattgaagtt  64920
aaaactaatt acaatcagag aaaattaaca attcatccct tcaatctcat tagtcacaag  64980
ttaaatactc aatagccaca tctatctagt tgctactgtt ttgaatagta cagatataag  65040
acattttcat caacacagaa aattcacttg gaaagcattg ccctggagta aatgtgccag  65100
actgtactat atcatttttc tcttgttgga catctaagtt atttcttatt ttttaaatat  65160
tttatataac ttgacggtga atatacctat gtacatagct atttgctttg gctgaattat  65220
ttcttagaat caatttcaaa agtggagtta ttaggtcaaa gagcatgaga agatttttttg  65280
gaacctgcag tgtattgcca tagtcctctc aaaaaagttt atgtcaactt aaagtacttc  65340
tagcagcata tgattgtact aatttcgctg caatctcaac aacactggac attataagtt  65400
tttattctac cctattttcc attaaaagat agcttatgct tgattgactt tgcattttat  65460
tttattatta ataatgatgt ggtttccttt tttctagatt ttattttttat ttaaggcatc  65520
ctttgatttt aacctgattt tttttctcta aaaattattc taagaaaaga caaaggtgat  65580
acgaaatata tcctgagttt ttattttttt cttgcatggg atttgtatat ttgcaccttt  65640
gcccatttat actatgattt cttagtgtct tccctggcaa ttttaatgaa gacttcatgt  65700
atatcaattt ttccacaaat ataatctttc taaaaatatg tttttttccac aatataattc  65760
agacgtattc tccgaaatgt tggaaaaact taagtaggca tcaaagcatt tgaagatttg  65820
tttaaaggtt gtttttatac cagttttaaa ttgtaattta agggtcataa aataggtgaa  65880
aattaaatca tttttcagta agggggcaag accacttaac tcttggaaaa tacaggaaac  65940
gtagatttct agaggccaag aaggaggtag ggattatttt gtaactgccc ccaaccttct  66000
aacctgtaat gaaacaaaca ctgaaggccc ttaaacattt ttaggcttaa ttggctgtcc  66060
ttgtacttag ggcacatcta aaaatcctga ggcaaccact caagagaaca tgcttttgtt  66120
aattcaaagg gagctgtcct acgagtgtcc agaatcctct gtagtcttgg gcctggtgct  66180
tgagagaccc aaaggaaagg tcaatggaat tacagcttag tgttagagct ttcatgcatc  66240
acactaatta attaatgtca taaaggtctc tctcctgtta tgggaaaaag cagcaaatag  66300
gaacttctgg tagggtgctt aaagttggtt tgatattttt tattagcatt tttaactaat  66360
acaagtaata catgcttatg gtagaatgat aaaactgaaa aaaaaggtat gaaaatttag  66420
aagttctcct actcatgacc tcaccccttc tttcactccc agtttcactc ctcagagggt  66480
aaccacagtg actagcttct tgtgtttggt tcctgagatt ttctatgtat atatattgtt  66540
agatatatgc atggtatgtt ttcaaaattc ctgttacact ataattactg ttctacaact  66600
taattttttc acttaattaa tagaccttat atatgctttt ccatatcggt atatatagat  66660
```

ctatataagt tttcttaaag gttgcacaac tttcaattgt atggctgtct tgtaatttac 66720
tttttgtttc ccttactaat ggatatttca tgtttcccta actcttttga tattaagagt 66780
agtgctgcaa ttaacatcct tgagaggcag tatatatggt gtttaagatg aatggttctg 66840
gagccagact actttggatt gaatattggt gccaccaatt ccttgctgta tgaccttagg 66900
caagttgctt aatttctttg cctcagtgtc cttgtgtgaa aaaatggagg caataatggt 66960
cactatccag tagggctttt atgaggattt agtaagttaa taatgcactt taagaactta 67020
gttattttta gattaagtag tgaaggacta tataattgtt agtataattg tataccttta 67080
ttatcatact tttgcatgta tagcaataag acaaattctt agatgtttaa ccattggaca 67140
taaggaatgt acgcatttta agtactggta gatattacct tttccctgcc aaaaattgca 67200
aatattggat attaactttt taaatcttag taaatctgat aagtataaat aacagtttat 67260
catcatttta agttgcctat cttaattttg tgtgaaaatg attatctttt cacatgtttt 67320
tttggccatt tatgtttctt tccatgtgaa ctaactgttc ctggccattg cctatttgtt 67380
gttgctgtta ctatatggct tttcatctgt ttcttattgg tttatggagc tctttgtata 67440
tacaggaatt tagcctctat ttatatgtgt gacaaatact ttttccaatt tatctttaaa 67500
atttgtttat gttttcctat tcatcagtct aaaattatgt agttaaattc atcattgttt 67560
tttcttatga ctttagagtt tggagatcat gcttcaaagg tctttctagg tggggatgat 67620
ttaaatcatg tactggaagt atttttgcca aaaagactca cgaattatgg atgttagagc 67680
taaaagggac cttagagatt tcctagttca accacctttt cttcatacct ttttaatttt 67740
tctctgcaga tgaaaagaag tttagtccta aagaaagaaa agagtctaaa ggttctccag 67800
taagctaatg gcaaaaatgt agactggaac ttctagctcc tgatgtgtat ttcagtgatc 67860
attcaattta accagatggt ttcacaaaaa gagctttcta ctaaaaaata aaatacatac 67920
ttaagcaact cagagaattt tttttttatt tttcagatta attttcactt agagattcat 67980
cagcatatgt actatacatg tacaaatcac ctgtgtgttt tggatattta gttaaacaaa 68040
tgtgcaaata ttttaaccaa aggagcatat tcatttgtgt tttattttct taatggtttt 68100
cgttatgaat gtgaaatgtg tatttacctt aacagaaatt aagtatattt ttggtctgac 68160
atatatgaga actgaaaagc attggcttgg ctgctaactg cattctcatc tttctttctc 68220
tgctttggca aagtctggga ttaaatctaa taccttttaa actgtttggg acttcagcca 68280
gagtgacctg tcttgaattc agaactgcgc agatcattcc ccattctaag gccctctcat 68340
gcctcctcat tgcctgtagg atgagatcca agtaccttag catagcttat gcactgtagt 68400
cacttgacct ctagcaccta tgcagtcttc cagtcttatt tacacattcc tttgcacatg 68460
ctgtttcccc gtgtggggca acttttttct tgcctgtctg cctgcctaag ccaacttaaa 68520
taaacatcat ttctgtaact tctgtgaagc cttttccaat ctctccactc caagacgaag 68580
gtgtttctat aggcatgact tctggaatgg cagatcaagg atctggtgga ccctctactc 68640
agtgaaacaa ccgtttaact agtaaaaatg atcaatcaac catttaaaat cttcagaaaa 68700
tatcctaagg gcacatagca aaaagagaaa catttattca agaaaagcta ttaagcctca 68760
gtaaaaacag caagagtcta tggcatttga gtcatgacct gttcctaatc cttcccttat 68820
ctccattctt caggcaagtg caaccaagaa gatggaggct tcctctctct caaaatctta 68880
ctccatagtt ataatttcac ccacaatggg gcagaccaca agcatctctt ttttttcccc 68940
cagccctata ttacagaatc actgttctag gaaggcatag cttagaggat tggagattcc 69000

-continued

```
ttccacaccc actttctacg tatgagggct ttgccccagg gatggtaagt caagaataca  69060
gggatcctgc ttgtgcctgc ctcagctcat atataaggta aagcttccac actaggaaag  69120
gcaaattaag aggactaggg aatataccgt tatccccagg gtccacttgt agaacagggg  69180
tgtcattctg ggagaagcag gtcactgccc cacttgtgga acaggggagt cactcgtcac  69240
tgtccctggt tcaaattcta ttgcagtgac agaggttctg tcccagggaa aggcaggttg  69300
ttaggatgga gaactccaca gttctccctg aggtgactga ctttatttgg aacagagcat  69360
gaagaagttc atgcctaagg gcactgtcaa aaataatgga gatcttggtg gtgagcaatt  69420
aagagtggat tggtagctcc atgatactag taacaacaag caaaacagca gaccagcatg  69480
gaggatacca gagaaccaga caaaggaatc actaagaaga gcccttgtgg aattgcactc  69540
actgctgggt gtgtggaaag ttatgcatgt gtgctttact gtaccctctc aaaagcaacc  69600
taaacaggat gtggggtagg ctctaaagca ttcctcaagc cacacatgga tccatcagta  69660
aaatgtggag ggcttaagga taaaaaggct taagtacaat ctctggccct acattttcta  69720
aatgttatgc caccctgacc aaggggcaac tcctacaaag ccaggcaaaa taataaaatc  69780
atatttgtct ctagtggaat ggataactat gcctaaaact gtgccctttg aaaagcaact  69840
agagagataa tttctgaagt gtttgtccct acctgaatgt gtggcaaaat tctaaactcc  69900
ctgaagtgtg aaagtggttt ccaagccaca tgcacatcca gtagtggtaa agggtgaaaa  69960
tctaactggc taagagggct tcatagcaac attaaccaaa aagtggttta tgtagtcttt  70020
gcctgcttca taattcccta ggcattctat gctattctgt actcagaagg cttaaagtca  70080
ggttagggaa aggaggccta tgaggttact gtgcagaggc agtgctggga aataaatgaa  70140
gttaaataaa tttaggccat cgtggtttaa agaatggatt gtggagataa gaaggataaa  70200
ggaaacccag agtcaagaaa aataaaactt ttcattggtg ccatgccaac ccatatccga  70260
gcctgaggca aaaggaaaaa tgtgctccct gatatacact tatacaaaat atcaactaat  70320
tttatttgtt ggactgaata gaaaaagtca acaaaaatta aaaataaaaa aatcatgact  70380
atatttttaa taagtggttt atgtaaaccc agagttgacc aatgggatgc cagtctcaac  70440
cataaaaaca aacaaaacat tgtgagtaac aacaccagaa gtctcaaagt gtcagggaaa  70500
ccaatttcac agaagcagtt cagccaagtc actaaacaaa caaacgacta agcaaaaaac  70560
aagaatgagt ctcagaaagg gtcaagtcag tatccagagt tgttacaata tagtatctaa  70620
aatattgttt tgaactaaaa attttgaggc atgcaaagaa tgaggaaagt atgactcata  70680
catggtatta tatgaaaaaa tcaacaaaaa actatccatg aggaaacaaa gatgttgaaa  70740
ttcactaggg aaagacttta aaaaccagct atttaaatat attcaaagaa ctgaaggaac  70800
tatgtctaaa atactaaaat aaagtataat aacaatttct tgtcaagtag agaatgccaa  70860
taaagagata gaagttataa aaaaagaaaa aaatggaaaa tctggagttg aaaattataa  70920
taactgaaat gaaaaattca ctagaaaagg tcacaagaag atataacttg gcagaagaaa  70980
caatcagcaa attagaacat agatcaatat agattattca ttttgaaggg tagaaagaaa  71040
aaaagaatga agaaaactga agattcccaa agaaatgtag gacatcttaa agacacatca  71100
ttaggagaag aaaagaaggg aaagaaaaga gcagaaagaa tattttttaa aaaatggata  71160
aaatcttcca aaatttaatg aaaaacatca acctacacat caaagaaaat ttttttaaaa  71220
cttcaagcag gaaaatgtaa cgatattgat acttagatac atcatagtca aaatattgga  71280
gtcaaatata aagagaaaat tttgaaatta gcaagagaaa aatgaaatgg aaccacaata  71340
agattaacag ctgattctca tcagaaataa cagagagcag aaggcagtgc aatcccatat  71400
```

```
tctaaacgtt gaaagaataa aaaaactgtc agtcaagaat catatattca acaaaactat  71460
ctttaaaggt aaaaatgaaa tgaagacatt cctaggtaaa caaaggctga gagaattttt  71520
cattagctga catgccttgc aagaaatact aaaagcttcc tagacagtag ctttaatctg  71580
catgaaaaaa aattccaata aagggaaatt tgtaaataat aaaaatacat cattatatat  71640
tcttttccac ttaacttatt taaaatcaat ttcttaaagc actatctgta aaattgtatt  71700
gttatttgac aataaaatgt aaaagagggg agtgggaatt aagctaaatt ggagtaagga  71760
aatggtatca catggtaaat tgaatttaca gaaagaaatg aaaaaattaa gtggcaaata  71820
tgaagagtaa cattaaaaac ttctataaat taattgtggc ctcctttctt cccttagctt  71880
ctgtaaaaga cataagacta ttaaaaatga caataattat aaacacattg ttttattagt  71940
aataaacata gacaaattat ctacaacaat tattattata caaggagagg gaatggagct  72000
gtagaggagt aaagttttta taacctactg gaactaagtc agtataaata tgatgtcgat  72060
tctgttaatt tgagatatat gttagaagcc ccaaagtaat cactgagaaa atgatgcaaa  72120
aatacagttt taaaaagtta aaaacatagt ttagcttatg tgtgcctagt actccattat  72180
tatttttta ttatatttta agttctgggg tacatgtgca gaatgtgcag gtttgttaca  72240
taggcataca tgtgccatgg tggtttgctg cacccatcaa tccgtcatat acattaggta  72300
tttctcctaa tactatccct ccccctgtcc cctaaccccc tcaacaggcc ctggtgtgtg  72360
atgttcccct ccctgtgtcc atgtgttctc attgttcaac tcccacttat gagtgagaac  72420
atgcggtgtt tcgttttctg ttcttgtgtt agtttgctga gaatgatggt ttccagcttc  72480
atccatgtcc ttgcagagga catgaactca tcctttttat ggctgcatag tagtccatcg  72540
tgtatatgtg ccacattttc tttctgcttg ttcccaggag aaagtggctg aagattccag  72600
agagaagctg aatgcagttt aattcttttt gccataaaca cgacaaccca ttttcctgca  72660
agctgtgtta gtttgctctc ttcttggttc attcattcat ttattcatag cttccataaa  72720
tatttaacaa acactaatta ggggccaagc catgtgctag gcacagggga taaaactgtg  72780
aacaaaacaa gccccagcta ctcttaagga actgatagac aaatggacca gcaaacacgc  72840
tggtcctgtt ttgaaggcaa agcgcctggt gctcctgatc tcatgagcac agagcattta  72900
gcctaagtct catcctccta aggcctcaga aataaggcct tattttaata agtgcaagtc  72960
agtcatttga agactaaatc atagaatcct agaaaactag taccgggagc aaggcaaaag  73020
aatgggatga gcatgaaaca tatattcaga agttgtggtg tgtaggtata taagccaagc  73080
tcttttcttc acttgcttgc taagtcactt agcttttctg ccttttttgtt tgctctgtct  73140
ggaaatggag ttaatgaaat atatctacat gatagggata ttgagacgat taaataagat  73200
gctgctgtca cccagtatgc ccttaccctg ctgtacttag aagtatatga aattcatttt  73260
ctaaattttt gtatgagtgt ttcatgcatg cccaccacca tggaagctac cttaagacag  73320
tgagggactt tgtttaactt gtttgtacta catcctcagt ctaatggtgt ctggcttatg  73380
gtaggcacca aatataattt tattgacaga aaggatgata atgaatgtga aggcattttt  73440
aagtttatga agtgttgtgc atattgttgt taattttaag ctgttacgtt aaagaacccc  73500
taatccaact ctcttgagtt ttatagatat catagaagat atatcttccc ttgacataga  73560
agcttccctt gaaggttccc ttgactcatg tatttgcctc acagtgattg tgcagatccc  73620
acaagataaa tttatgtgaa tgtgctttat gtgcttgaag tgctccacaa atatgggttt  73680
tataagatga gaaaatagag tcagggagaa aggtgactga tccaaggtca tgcaaagagt  73740
```

tagtgtcaga atttataatg gaatttcagg ctcccaactc ccactccagt atactaaggc 73800
agattccaga gaagaaacag tggagagcag gcactgatga gggacaaaga aaagcaggct 73860
ccgtctggct gcaacttgtc tcttcatggc aaaaagaaac taggaaagtg ctatgccaga 73920
gacgacatga taactttgca gaatggaaag agcttgttta ccacattgaa tactttatct 73980
gtgtttatct aacgacagtt ccaccagctc tttaccactt gacttttgcc taattcaaaa 74040
atataccaac tatgaaacat tttccttctc agtttttatt ctagattaca ttttgttcaa 74100
ctttatctta atgtgtagtg tagaaagagt aaggtaagag tatagcaagt ggttattttc 74160
catttctact gaggacagag aaataatcta agggatttgt attagagatg aagaagtgca 74220
tggccaggac atgagagata ctgtgataga atggatattg tgaagtcttt ggtagttttt 74280
gaggggaaaa aagagaaggt tttctttgtc tgatatagtt tagcaacgtc ttaatttagg 74340
attcaaaagt tgttcagggt ccatcttggc cttcaaatta agatgccctt tgagagataa 74400
cattgttgtt ttcaaactct gttctgtgac ttaagaatga gaggagaagg aagaaaagag 74460
gagaaaattt gagggaaaag tgcccaagca gcgtcaaggc tagacactgg aaatttatca 74520
atgaaagcca catggtggat gggaatcaga tatgtgcatc aattatttgt gttccaatcc 74580
atatagaagt accgtataat gcaccaagct aataggtgct ttgaaagaag accatacaag 74640
tggagatgtg ttcctattct atctagggat agagtcagga agggcttcat tgaataagtg 74700
gtagcctctt gggctgagac ctgagttatg agatgatgtg gcaaaggaga cagatggctg 74760
ggggcaaggt ggggtcattg aaattggagg cagtagcaat ataagcaaag ctacaggggc 74820
atgaaaaagc aaggttagat tagtgaattg caacagggtg gtactgctgg aaggtcacat 74880
ggaaaagatt gtgaaggtat tgagataaga agctagaaat aagctttgaa tgccatccta 74940
gtactttgaa tttgcatgct gtaagccaag tggttttcac ttggtcattt aataaaatta 75000
cagattctca ggtctcacct gtaacttcag attcagaaga gtctgctaac tgaaggtgga 75060
atcagtgttc catattgcta attagctcct cagaggattc taatatatca gtgagttatg 75120
accactgctg taagccatag gtagttattg aaagctgcta tggagaggag ccacagaagc 75180
agatgtttta gataggattc ctctggggtc ctgtgtaatt tatggactgg agaggatcag 75240
acaggaagca gaaagacttg aataagacag ttgcagttat tttggaggca aagattctct 75300
ctctctctct ctgtgtgtgt gtgtgtgtgt gtaattgtag gaactattta ggcagtaaaa 75360
ttaacagata ttagtcactg attgactgag tggatggcag tgataggtgg ggtgcgttga 75420
gggaagtgta ttacattaag tccaggatga ctcatggttt tctaagttga gtcattgggg 75480
attgccatcc aatgtgagaa actatatagt cttatcatag ttgatcttgg aggtagactt 75540
gaattaaaat cttgaagcca tcaattgctg tatgtgggtc ttgggcagaa cacttaaggt 75600
ttctggacct cagttatttc ttctgtaaaa tgaggaaaat aatgcatacc tcatgcattt 75660
gttgtaaaga ctaaatgagg ttaaagtatg tagagtgtag tttagtaact gggacgtata 75720
gtggtccagt aaacatcagc tgttattatt gtgctatatg ttgtgatgtg tactggagtg 75780
agatggggta ggggattttt tagtctctgc caatgactcc tctccccatg atcaaaatca 75840
gaaaatcagt ctcttatgtg ttgaggagtg agacacttct cccaagtgtt taaggctaat 75900
accttgcctt gttttgcctt gggccagacc tcactacaca tctgtttaag agatcagggt 75960
aagctctgtt cttggtgagt atctcaatgg ggctgttttt ctagttcttg tagtttcttt 76020
gggccaacat gaaatgtcta accttggctt cttggttgtg gattctcgtc aacatttcac 76080
tgctacccaa gttgtgtctg cttacatgat gctatcttcc ttcttttggg tttctgaagc 76140

-continued

```
cctcagacac ttggctgaac atttttcaca tttcttaagc tatatcatct gtgttttccc  76200
tgccacagac aaagtcacaa aaggacttta agataggttt tggttttttt tttccccagg  76260
gtttttatac attttgggta agggcaagtg gtaaatgctg cttttctgcc ttaaccagta  76320
gtgtctgaca gaggaggtag catgatgatt gcagagctca ctggactgaa agtcagatgc  76380
tttacccgcc tagactctag taccaagggg aagatggagt gagatggggt aaatggggag  76440
aaattaccat ttattttgag tgtgccaggc cttttctcat gtattgtcta atgcatttgt  76500
cacaattctc tttgggtttg aaatgtgatt ttcttcattt tatagataag gaaacttatg  76560
ggaagggagg ttaggttcat cttgtgccca actttacatg gctagtgatc aataatagtg  76620
agattcaaac tcagatttct ctgccccaaa gcctttgctt tttcctcttt tgacactgta  76680
actaatgaga agatgtattt aactctgagt ctcatttgcc tcaactgtaa aatggagctc  76740
tgtaactctt gctctgtatg acagtaaatc tcctcagacc agacttatga taggggataa  76800
ggatatttgt atctttgggc cctaatgta ttgaaagtgc ttctaagtgc ctggcacata  76860
gaagggcact caataaatat ttaccacatt ttccagaaag agggtagctc cataatgggt  76920
gagatacatt ttggtggcta ctgtagtgtt taatgctttt accatctgtt aaaatgattt  76980
tggagtatag ctagataact gatgatggtt gttatataga ttttttcata ggttgcctgt  77040
tccaaattct atgccgtgga agaagttaaa tatccagaat ttgacaggaa atattattct  77100
acaacagatc cctggcgtaa gaatgataac acctgtgttc tagtctcaga cttgcctctg  77160
aataactgtt tctcctggtc aattctctgt ctctatctag gcttgaaatt tcccccaaat  77220
gatgaaggag ttggactagt ttagtggggt tcagcctcga gtggccatta aaattatttg  77280
gggatctttg aaaaaaatta gatgcccaga tttttgtcgt tgttgttgtt gtttttgttt  77340
gtttgttttt taattatact ttaagttctg ggatacatgt gcagaacatg caggtttgtt  77400
acataggtat acacgtgcca tggtggtttg ctgcacccat caacccgtca tctacattag  77460
gtatttctcc taatgctatc cctccctagt cccctaaccc cagacaggcc ctggtgtgtg  77520
atgttcccct ccctgtgtct atgtgctctc attgttcagc tccccctat gagtgagaac  77580
gtgcagtgtt tggttttctg ttcctgtgtt agtttgctga gaatgatggt ttccagtttc  77640
atccatgttc tttcaaagga catgaaccca tcctttttta tggtggcctg atattccatg  77700
gtgtattgaa ctgctcactc cagttcaatt aaatcagaat acagaatgtt gagaggagca  77760
tcagtatttt aagaaggccc cctagtgaag ttcaatgtgc agccaagggt gagaaacact  77820
ggactagatg attgataagg gccatccaac tttgatagtc aacaagagac aatgctatag  77880
agtatggtgg acagagcatg ggctttagag ttagccaggt atgcattcag accctggctc  77940
tgttacttac tagttgtgtg atcttgaaga aatcaaaatg gagatacact atgtacctgg  78000
cagtaatagt tgtggggatt aagcaccttc accagagctt aggacataat aagcccccag  78060
taaatagctt ctttaatatc agaagttcag atggaagatg tgagaaaaat attggttcag  78120
taagatttaa caggtaaatt aaaatcaagt atttgaaaac attttcctgt ttctttagca  78180
atggattcca gaaacataat gtggaaatag ctctcagtcc ttagatttga tgacattgca  78240
gaaagaaatc tggctagtcg tcccatggct gattggctat gatggctaga aagccattgg  78300
aaaaaaaaaa ttggctcaca gaagacagca gatgtggctt gggaaatgca aggacatgac  78360
tgtaataagg atttgtctat ccagccccat ttatgagagt gattccagga gaaaaggaca  78420
gatttgtatt gtcagtggga tacgctgtta aaaaacactt ttgctactac cactccagct  78480
```

```
gtcttggcat gtttgttggt gatgtaagct acagaaaatg gaaatcacca atagggctat  78540
agcaacctga tgcatagtga caagtaattg ttctattcat ggttatgtgt tgtacagagc  78600
acttgctgca tgtcaggttt gagacttgag tatgcattag ggccatggac acccccatct  78660
tatctttaag tagatttcaa agtaaatatt tgatgaatat gtaaaatatt tagtttggtc  78720
agtcataggg ctgagaacat ggtggcagtt acctcctagt atctgcaagc aaaaaaagtt  78780
ttttcttcct atagcaattg ccatctcagc cacttttgca gcatttcttt ttgctacact  78840
ttgcattaac catttgtgca cttgtcttag cctcaaacag gccatgaaag ctccttgagg  78900
ataggggcta tgtctttttc atctttatat atgcatcatt tagcagagct gtccctttat  78960
aatgtactaa ttactgaatg aagggatgca tagatgaata aatgaatgaa aagtaggagt  79020
gacctgtctt ctctctttct tcacgatggg gactagtgtg tgtatataag ggataatttt  79080
ttgtgtcaca taaaatataa ccttacttag aaggcaagac ttccagaatg gtggaatgag  79140
aaccaccccc ccgcccccat aaatccgccc tttcatgaaa gcagtgaaaa cgctagcaaa  79200
cgttgtgaaa attaactttt ccagaactct ggaaaggaaa cagaggcttc caacaatctg  79260
agaagaatgt attcaagaaa aacttcggta agctctctga tcacagtgga aataataaac  79320
aattagtaat agaaggatag ttgggaaatt caccatttgt gggatataaa cagtggatca  79380
aagaagaaat cataagggaa atgagaaaat actttgagat taatgaaaat gaaaatacat  79440
tgttccaaaa cttacaggat acagccaagc taaagcagta cttaaaggga aatttgtaac  79500
tgcgaaggcc tatatcaaca aagacaaatg atctcaaatc aagaacctaa ccttccacct  79560
tagactagga aaggaacagc aaactacaaa gaaagcagga agaaagacta ataaagacta  79620
aaagggaaat aaatgaaata atagagtaga aaaacactag aatcaatgaa attaaacatt  79680
gattctttga agagatcaac aaaactgaaa aaaactttag tcagattgaa taagaaaaaa  79740
agagagaaaa ttcaaattat caaaatgagc aatgaaaatg gggccatcac tacctacctt  79800
aaaaagaatt ttcaaaggat taaaagaaaa tgccattgca ttagttcatt ctcacacaac  79860
tataaaaaag ctacctgaga tggggtagtt tatgaagaaa agcgctttaa ttgactcaca  79920
gttccacagt ctgtacagca ggcatggatc atgaggcctt aggaaattta catcaggtga  79980
aaggctaagg ggcatggaag acatgtcttc acacggcagc aggagagaga gcaaagaggg  80040
aagtgccaca cacttttaaa ccatcagctc tcatgacaac tcactcacta tcatgagaac  80100
agcaagggga aaatctgccc tcatgatcca attacttcct accaggtccc ttccccaaca  80160
ctggaaatta caattcaacg tgcgatttgg atggtgtgac acagagcaaa accatatcaa  80220
ccatactgta tgccaaaaaa ttagatgacc tagatgaaat ggacaaatac tcagaaaaac  80280
acaaactatc taaagtgacc agtgaagaaa cagaaaatct gagtagtcct gtaacaagtc  80340
ctgtaacaaa actggattag taattaagaa acttcccaca aagaaaagcc caggttcagt  80400
cttcactggt gaatactatc aaatatttaa ggaagattta atccttcaca aattatttca  80460
aaacttggaa gaggctggaa ccctttccaa ctaattctgc aaagtcagca ttaccctgat  80520
gccaaaacca aagatatgac acaaaaataa aactgcaggc taatatcaca tttgaatata  80580
gataactttc taaaaatctc aacaaaatgc tagcaaacag aattcagcaa caaataaaaa  80640
gggttataaa gggtgaccaa gtaggattta tctctggaat gtaaattaac attcaaaaac  80700
ctaagaatag gaggaaactt tcttaacttt gtaatggaca tctctgaaaa acacacagct  80760
aacatcatac taaataggga aagattgaaa tttttccttg taagatcagg aacaagacaa  80820
ggatgactgt tctcaccatt tcaatttacc attgtattgt agattcaagt caaggcaatt  80880
```

aggcaaaaaa aaaaaaaaaa aaaaaaaaaa aaaagaaaga ggtaaaaggc acccatattg 80940
gaaaggaaga ggtgaaaata tctatattca cagatgacat gatcttatac aaagaaaacc 81000
ttaaggaatc catgataaac tattaaaacg agtaaacgag ttcagcaagg tttcagaata 81060
caagattaat gtgcaaaaat caattgtatt tctgtacact agcaatgagc aatctgaaaa 81120
tgagattaag aaaacagttc actcacaata taatcaaaat accagaatac ttaaaaataa 81180
atttaacaaa agaagcgtaa gacttgtatg ctgcaaacca caaaacactg tggaaagtaa 81240
ttaaaaatct aaataaatag aaaaacatcc cttgttcatg tactagagga ctcaatattg 81300
tcaagatgga aatactcccc aaagattgaa ggaaatccct atcaaaatac tggctgtttt 81360
cttagcagaa aatgaaaatc tgaccctaaa attaatattt aaatacatgg aacctaggat 81420
aaccaaaata atattgagaa agaaaaacaa agtcggcgta cccatgcttc ctgattccaa 81480
accttattac aaagcagtgg taatcaagag tgtatggtat tggcataagg acaaacagat 81540
caataaatgg aatactattg agaatccaaa agttaactct tacatttaag accaattgac 81600
tttcaaaagt gttgctaaga catttcaatg aggaaagaat agtcttttca ataaattgta 81660
ctggaaaaat tggatatcca catgaaaata aaagattttg gaccacttca aacctgcaaa 81720
aaaaataaaa tgatctcatg gtgtatcatg gatctaaatg ctatagagct aagatgataa 81780
atctcagaag aaaatatcaa agtaaatctt tatgaccttg aagtaggcaa tggtttttttg 81840
gctataacac caaaagcaca agcaataaga gaaaaaaaat ttttttaaaa aaacccttga 81900
ttattttatt aaaattttgt tgtgggtaca aagtaggtgt gtatatttat ggggtatatg 81960
agatattttg atacaggcat acaatgttca atgatcatat taggataaat gaagtatcca 82020
gtacctcaag catttatcat ttgtgttaca aacaatccaa ttatactctt ttagttattt 82080
ttaaatgtac agtacattat tattgtagtc attcccttgt gctatcaaat actatatgtt 82140
attcattcta tctaactata ttattgtacc cattaaccat ccccactccc ctgcctccca 82200
gctacacttc gtagcatctg gtaaccatga tttcctctta tctccatgag ttcagtagtt 82260
tcagctcatg gagatagaca gaactaattt tattagctcc cacaaattag ctcccatgtc 82320
agaacatgta aagtttgtct ttctgtgcca ggtttatttc acataacata acgaactcta 82380
gttccaacca tgttggtgca aatgacaggc tctctctttt tttttttttt tttttttttt 82440
gagatggagt ctggctgtct cccaggctgg actgcagtgg tgcaatctca gctcactgca 82500
agctccgcct cccaggttca tgccattctc ctgcctcagc ctcctgagta gctgggacta 82560
caggcacccg ccaccatgcc cgactaattt tatatatata tatatatata tatatttatt 82620
attattatac tttaagtttt agggtacatg tgcacaatgt gcaggttagt tacatatgta 82680
tacatgtgcc atgcaggtgc gctgcaccca ctaactcatc atctagcatt aggtatatct 82740
cccaatgcta tccctccccc ctcccccacc ccacaacatt ccccagagtg tgatgttccc 82800
cttcctctgt ccatgtgttc tcattgttca attcccacct atgagtgaga acatgcggtg 82860
tttggttttt tgttcttgcg atagtttact gagaatgatg atttccaatt tcatccatgt 82920
ccctacaaag gacatgaact catccttttt tatggctgca tagtattcca tggtgtatat 82980
gtgccacatt ttcttaatcc agtctatcat tgttggacat ttgggttggt tccaagtctt 83040
tgctattgtg aataatgccg caatgaacat acgtgtgcat gtgtctttat agcagcatga 83100
tttatagtcc tttgggtata tacccagtaa tgggatggct ggttcaaatg gtatttctag 83160
ttctagatcc ctgaggaatc accacactga cttccacaag ggttgaacta gtttacagtc 83220

```
ccaccaacag tgtcaaagtg ttcctatttc tccacatcct ctccagcacc tgttgtttcc  83280
tgacttttta atgattgcca ttctaactgg cgtgagatga tatctcattg tggttttgat  83340
ttgcatttct ctgatggcca gtgatggtga gcattttttc atgtgttttt tgggtgcata  83400
aatgtcttct ttttagaagt gtctgttcat atccttcgcc cactttttga tggggtcgtt  83460
tgtttttttc ttgtaaattt gtttgagttc attgtagatt ctggatatta gccctttgtc  83520
agatgagtac gttgcgaaaa ttttctctca ttttgtaggt tgcctgttca atctgatggt  83580
agtttctttt gctgtgcaga agctctttag ttgaattaga tcccatttgt caattttgac  83640
ttttggtgtt ttagacatgc ttttggtgtt ttagacatga agtccttgcc catgcctatg  83700
tcctgaatgg taatgcctag gttttcttct agggttttta tggttttagg tctaacgttt  83760
aagtctttaa tccatctcga attgattttt gtataaggtg taaggaaggg atccagtttc  83820
agctttctac atatggctag ccagtttttc cagcaccatt tattaaatag ggaatccttg  83880
ccccattgct tatttttgtc aggtttgtca aagatcagat agttgtagat atgcggcatt  83940
atttctgagg gctctgttct gtttcattga tctatatctc tcttttggta ccagtaccat  84000
gctgttttga ttactgtagc cttgtagtat agttagaagt cagggagtgt gatgcctcca  84060
gctttgttct tttggcttag gattgacttg ggatgtgggg ctcttttttg gttccatatg  84120
aactttaaag tagtttttc caattctgtg aagaaagtca tcagtagctt gatggggatg  84180
gcattgaatc tataaattac cttgggcagt atggccattt tcacgatatt gattcttcct  84240
acccatgagc atggaatgtt cttccatttg tttgtatcct cttttatttc cttgagcagt  84300
ggtttgtagt tctccttgaa gaggtccttc acatcccttg aaagttggat tcctaggtat  84360
tttattctct ttgaagcaat tgtgaatggg agttcactca tgatttggct ctctgtttgt  84420
ctgttattgg tgtataagaa tgctgtgatt tttgtacatt gattttgtat cctgagactt  84480
tgctgaagtt gcttatcagc ttaaggagat tttgggctga gacaacgggg ttttctagat  84540
atacaatcat gtcatctgca aacagggaca atttgacttc ctcttttcct aattgaatac  84600
cctttatttc cttcttctgc ctaattgccc tggccagaac ttccaacact atgttgaata  84660
ggagtggtga gagagggcat ccctgtcttg tgccagtttt caaagagaat gcttccagtt  84720
tttgaccatt cagtatgtta ttggctgtgg gtttgtcata gatagctctt attattttaa  84780
aatacggccc atcaatacct aatttattga gagtttttag catgaagcgt tattgaattt  84840
tgtcaaaggc cttttctgca tctattgaga taatcatgtg gtttttgtct ttggttctgt  84900
ttatatgctg gattacattt attgatttgc gtatattgaa ccagccttgc atcccaagga  84960
tgaagcccac ttgatcatgg tggataagct tttgatgtg ctgctggatt ccgtttgcca  85020
gtattttatt gaggattttt gcatcaatgt tcatcaagca tattggtcta aaattctctt  85080
ttttggttgt gtctctgccc gtctttggta tcaggatgat gctggcctca taaaatgagt  85140
tagggaggat tccctctttt tctattgatt ggaatagttt cagaaggaat ggtaccagtt  85200
cctccttgta cctctgatag aattcggctg tgaatccatc tggtcctgga ctctttttgg  85260
ttggtaagct attgattatt gccacaattt cagatcctgt tattggtcta ttcagagatt  85320
caacttcttc ctggtttagt cttgggaggg tgtatgtgtc aaggaattta tccatttctt  85380
ctagatttc tagtttattt gcgtagaggt gtttgtagta ttctctgatg gtagtttgta  85440
tttctgtggg atcggtggtg atatccccctt tatcattttt tattgtgtct atttgattct  85500
tctctctttt tttctttatt agtcttgcta gcagtctatc aattttgttg atcctttcaa  85560
aaaaccacct cctggattca ttaatttttt gaagggtttt ttgtgtctct atttccttta  85620
```

gttctgctct gattttagtt atttcttgcc ttctgctagc ttttgaatgt gtttgctctt 85680
gcttttctag ttcttttaat tgtgatgtta gggtgtcaat tttggatctt tcctgctttc 85740
tcttgcgggc atttagtgct ataaatttcc ctctacacac tgctttgaat gtgtcccaga 85800
gattctggta tgttgtgtct ttgttctctt tggtttcaaa gaacatcttt atttctgcct 85860
tcatttcgtt atgtacccag tagtcattca ggagcaggtt gttcagtttc catgtagttg 85920
agcggttttg agtgagattc ttaatactga gttctagttt gattgcacgg tggtctgaga 85980
gatagtttgt tataatttct gttcttttac atttgctgag gagagcttta cttccaacta 86040
tgtggtcaat tttggaatag gtgtggtgtg gtgctgaaaa aaatgtatat tctgttgatt 86100
tggggtagag agttctgtag atgtctatta ggtctgcttg gtgcagagct gagttcaatt 86160
cctgggtatc cttgttaact ttctgtctcg ttgatctgtc taatgttgac agtggggtgt 86220
taaagtctcc cattattaat gtgtgagagt ctaagtctct ttgtaggtca ctaaggactt 86280
gctttatgaa tctgggtgct cctgtattgg gtgcatatat atttaggata cttagctctt 86340
cttgttgaat tgatcccttt accattatgt aatggccttc tttgtctctt ttgatctttg 86400
ttggtttaaa gtctgtttta tcagagacta gaattgtaac cctgcctttt tttttgtttt 86460
ccatttgctt ggtagatctt cctccatcct tttattttga gcctatgtgt gtctctgcat 86520
atgagatggg tttcctgaat acagcacact gatgggtctt gactctttat ccaatttgcc 86580
agtctgtgtc ttttaattgg agcatttagt ccatttacat ttaaagttaa tattgttatg 86640
tgtgaatttt atcctgtcat tatgatttta gctggttatt ttgctcgtta gttgatgcag 86700
tttcttccta gtctcgatgg tctttacatt ttggcatgat tttgcagcgg ctggtaccgg 86760
tcgttccttt ccatgtttag tgcttccttc aggacctctt ttagggcagg cctggtggtg 86820
acaaaatctc tcggcatttg cttgtctgta aaggatttta tttctccttc acttatgaag 86880
cttagtttgg ctggatatga aattctgggt tgaaaattct tttctttatg aatgttgaat 86940
attggcccct actctcttct ggcttgtaaa gtttctgccg agagatctgc tgttagtctg 87000
atgggcttcc ctttgagggt aacctgacct ttctctctgg ctgcccttaa catttttttcc 87060 ttcatttcaa cttttttgaa tctgacaatt atgtgtcttg gagttgctct tctcaaggag 87120
tatctttgtg gcattctctg tatttcctga atctgaatgt tggcctgcct tgctagactg 87180
gggaggttct cctggataat atcctgcaga gtgttttcca acttggttcc attctccccg 87240
tcactttcag gtacaccaat cagacataga tttggtcttt tcccatagtc ccatatttct 87300
tggaggcttt gctcgttttct ttttattctt ttttctctaa agttcccttc tcacttcatt 87360
tcattcattt catcttccat cgctgatacc ctttcttcca gttgatcgca ttggctcctg 87420
aggtttctgc attcttcacg tagttctcga gccttagttt tcagctccat cagctccttt 87480
aagcacttct ctgtattggt tattctagtt atacattctt ctaaattttt ttcaaagttt 87540
tcaacttctt tgcctttggt ttgaatgtcc tcccatagct tggagtaatt tgattgtctg 87600
aagccttctt ctctcatctc atcaaagtca ttctctgtcc agctttgttc cgttgctggt 87660
gaggaactgc gttcctttgg aggaggagag gcgctctgct ttttagtgtt tccagttttt 87720
ctgctctgtt tttccccatc tttgtggttt tatctacttt tggtgtttga tgatggtgat 87780
gtacagatgg gtttttggtg tggatgtcct ttctgttttt tagttttcct tctaagagac 87840
aggaccctca gctgcaggtc tgttggagta cccggccgtg tgaggtgtca gtctgcccct 87900
gctggggggt gcctcccagt taggctgctc aggggtcagg ggtcagggac ccacttgagg 87960

-continued

```
aggcagtctg cccattctca gatctccagc tgcgtgctgg gagaaccact gctctcttca  88020
aagctgtcca acagggacat ttaagtctgc agaggttact gctgtctttt tgtttgtcta  88080
tgccctgccc ccagaggtga agcctataga ggcaggcagg cctccttgag ctgtggtggg  88140
ctccacccag ttcgagcttc ccagctgctt tgtttaccta agcaagcctg ggcaatggca  88200
ggtgcccctc ccccagcctc gctgccacct tgcagtttga tctcagactg ctgtgctagc  88260
aataagcaag actccatggg cgtaggaccc tctgagccat gtgcgggata taatctcctg  88320
gtgcgccgtt ttttaagccc gtcagaaaaa cgcagtattt gggtgggagt gacccaattt  88380
tccaggtgcc gtctgtcacc cctttctttg actaggaatg ggaactccct gacccccttgc  88440
gcttcccgag tgaggcaatg cctcgccctg cttcggctca cacacggtgc gctgcaccca  88500
ctgacctgcg cccactgtct ggcactccct agtgagatga gcccgctacc tcagatggaa  88560
atgcagaaat cacccgtctt ctgcttcgct catgctggga gctgtagacc tgagctgttc  88620
ctattcggcc atcttggctc cagaaaaaaa aattgttaaa ttggacttca tcaaatttga  88680
aatttttgtg ctgcaaatga taccatcaag aaagtgaaaa tctcacccac agaatgagag  88740
aaagtatttg caaatcatat atctgataag ggtattgaat ttagaatata taaagaactc  88800
ttgcaactca atataaaaag acaacccaat tttaaaatgg gcaaagtatt tgaatagaaa  88860
tttcttgata gaagatatac aaatttaaaa atgctcaaca tcattagtca ttagggaaat  88920
gcagatcaaa accaaattga gataccggtt tacacctatt aagatggcta tagaataaaa  88980
gaacaaataa caagtattgg ctttaatgtg gaggagccag aacccttata tattgctggt  89040
aaaatgtaaa gtcatgcagc cctttgaaat acagtctgca agtctttaaa aaattactat  89100
ttgttatttg gtttttcttc acttttaatt taggttcaga ggtacatatg caggtttgct  89160
atatagctaa attgtgtgtc acaggagttt agtgtacaca ttatttcatc acccaggtaa  89220
taagcatggt acccaatagg tagtttttct atcctcaccc tcctcctacc ctccaccatc  89280
aagtaggccc tggtgcctct tgttcttttc tttgtgttca tatgtactca atatttagct  89340
tccacttatc agtgagaaca tgtggtattt ggttttctgt tcctgcttta gtttgcttag  89400
gatactggcc tccagattca tccacgttgc tgcaaaggac atgatctcat tctttttgca  89460
tagtatacta tggtgtacat gtatcaaaaa tgttactgtt tgacctagta attctattcc  89520
aaggtaaata ctcaagagaa atgaaaacat gtccacacaa atacttgtac acaaatgttc  89580
attgcagcat tatttataat agccaaagag tggacgacaa atgtcttcca aatgtgggct  89640
ccaaatgtcc accaactgat aaatggaaaa acaaaatgtg gtatatccat gccatggttt  89700
atctgtcaat aataagaaat gaagtactca tacatgctcc aacatggatg aaccttgaaa  89760
acattatgct aggtgaaaaa agcaactcac aaaagactac actgtatgat tttatttgta  89820
ttaaatgtcc ataaaagaaa aatatttaga gatagaaagg aaattagttt ttccagggtc  89880
tgggaggaga cagtatgagg agtggctgct aatgggtaca ggatttcttt ttggagtgat  89940
ataattgctc taaaattagt ttgcagtaat agatgtgagt atgctaaaat gggtgaattt  90000
tatagtatgt gaaatataac tcagtaagcc cattaaaaac aacctaatta aattaaaacc  90060
aagctataac agaaatatta tatggctttg gcagtttaga atagtgggaa aatatggagt  90120
aagggtgggg aaatagtccc aagtataatt ctggttttgt cactactagt gtatggactt  90180
ggacaagtca tttgctttct ctaagtatca gtttgcatat atgcaaaata gaggtaatga  90240
tacctacctc agtggtacct tttcaaaacc ttgttcttcc tcatctctcc tctaccactt  90300
tctcataata ttattacagt aataaccatt tattaagcac tgtgtccgca gtggtgtggg  90360
```

gctgctttac ctccacaact tcactgaatc ctcactgcag tcttgtggga tctttatttc 90420
tttgcccatt ttacatgtaa ataaattgaa gtcaaatgag ttgttcaagg tccttctgtt 90480
agcaagtggc agagatggac atgaaaacta gatcttctac ctatgtgtct ttccacttca 90540
actaaagaat ttattaaaga gaattgaaaa gctatgaact aaatttcggt aatactttta 90600
atagtaaaca ttgctgccct cgtgaatgaa cacacactaa atttcaaatc tcacggtggc 90660
agggaataaa gatgctacct atcttaagcc attacttcac caacttctcc accaaaatat 90720
tccttgtaac cacaaataag taagcacaat agatctataa ggagagaata attgtgaact 90780
ctgattttat cttaaaaagt catgtaggga tgtcatgttc cacaatgtga ttaataaaat 90840
atattttgtt actaaacaca aggaaaaata ttatgttcca taaagatgtt tggtggttgc 90900
ctcgacctct tttagtttga aaagtaggta tgtatgagaa agatatgtgt ttacatgttt 90960
acccttgcct tctctctgtc tcttcccctc tctctccctc cctccccaac ccctatgccc 91020
tacacccccg caaccccccac atgtatttac ctttctctaa aagctctgca tagccaagaa 91080
aagtgctctt ttttattttt aggatattag atatttcatt ttcttatggt aagacaaaag 91140
attaaggcaa ccaagactta caatgtgcct accatgtggc aggcacagag gcaagggctt 91200
ttacatgtta tttaatgtaa ttgtaattct cacaaaagcc gtctagagtt gaaaatattt 91260
ccaactctaa atgaggcaaa tggagcacag agagccttaa ttatttcacc caaagttcag 91320
tggtagaggc aggattccaa cccaggtctg gtgggctcca aatccttgtt gggttgccat 91380
tcctcttgct aacaaataaa actggtctgt gacttttgca tttcaccccg cttccacagt 91440
cactggtggg acttacttaa gttaatcaga ttcttcaaag tatccccaag tcctcctttg 91500
aaaagaaagt tgggggacag gaggaggagc agaggagagg agataaaaag gaaaggagtc 91560
agggagagag agagagagag agaaacctgg tgatctcagc tgggtgccaa ggtttcctaa 91620
gcccaagttc cccatggttg agcctgtatt gtcaggccaa cagcttctag taatccactt 91680
ttatttaatt aatagtgaaa ctgttgaaga attgcaagtg gtgttctggt tcagaaacct 91740
tccgttctat ggggcactgc ttttgcttca gattcataaa accaaatgct ctgcctcaag 91800
ataataagtg aacgtgtaac cctcgggagg taagaaaaaa cacaatgtca cgtgcaaatt 91860
ctgcacttgt tctcaaagca aacctctcct gtgtttgcaa ttaggatgtt atctaggagc 91920
atattcaaaa cttttgaggt ttttatttta gtttttcttt cattatgtgc tgttttagta 91980
atatcaaaga atacatgtaa tatataattt atatgtcata acaataaaat taatgttgat 92040
gagcccagat taaagaatca acaacattaa catcatgatt gcatcaaccc tattagaatg 92100
gaagctctgt gaaggcatgg atttttgtcc attttgttca ctgctatatc cccaggacct 92160
agaggagtgt cagccacata ataggagctt agtcaatatt ttaaaaataa gagcataaat 92220
ctacttatat cctctttcct cttaccatca ctcccagcct cccctcagag gtaaccacta 92280
tcctatattt gggctttatt attcccttgc attttgataa gttttcacat gtatattccc 92340
aaataatata ttgcttgctt ttgcttcttt ttaaacttta tataatggaa tcatattgta 92400
tgtatcctat tgtgaattat gtcttttaca caacattagt atttgagatt caactatgtg 92460
tagctcgatt ccattccttt tcattgctga ttgtagttta ttggatatgt gtgccataaa 92520
ttatttttct cctgtcagtt aatgtttatc atttatgctt taataaacaa aactgctatg 92580
actgttcctg catgtgcctc ctagtacata tgtgaccaac tttctctagg atataagcct 92640
gagagaggga ctgcagttgg aatttacatt tccaaagccc aaagtttagc tcatgagtca 92700

-continued

```
gagctgcaat gtgccctttg tccacactag gtcaggatca gtgggagtgc tacccaaaat  92760
attttgctag ctggggagtc agggagaagc agagactgac ctagtgaggc caggaggcac  92820
tatctcaggt ctctagtcaa aatgggttgc aattagtaaa agtccagatt ctgaatcccc  92880
ttcactattt atcttcctct tcctccttta cagttatttt tgttcaaggt gcactttatt  92940
aaactcatgc ctaacaaaca aaactctaat gaatattttg tctttcattg attgtaaatt  93000
caattaatta gattgcttga aaaaatttta actgtatttt cactttagta tggatgaaaa  93060
tttcgatttc tttaaaaaac attttttaat aataacacaa cataaagtct accctcataa  93120
caaaatttaa gggcacaaca ccatattgtt tttttttat tttattatta ttatacttta  93180
agttttaggg tacatgtgca caacgtgcag gtttgttgca tatgtataca tgtgccatgt  93240
tggtgtgctg cacccattaa ctcgtcattt agcattaggt atatctccta atgctatccc  93300
tccccctcc ccccacccca caacagtccc cagtgtgtga tgttcccctt cctgtgtcca  93360
tgtgttctca atgttcagtt cccacctatg agtgagaaca tgtggtgttt ggttttttgt  93420
ccttgccata gtttgctgag gatgatggtt tccagcttca tccatgtccc tacaaaggac  93480
atgaactcat cctttttat ggctgcatag tattccacgg tgtatatgtg ccacattttc  93540
ttaatccagt ctatcattgt tggacatttg ggttggttcc aagtctttgc tattgtgaat  93600
agtgccgcaa taaacatacg tgtgcatgac aacaccatat tgttaactgt aggcacaatg  93660
ttgtacagca gacgtctaga actttttctt caggcttaac tgaaacttta tagccattga  93720
acagcaacac tccatttccg tttcttaaag gtcctttaca aaatgagctt tctgcgtgtt  93780
tccattttgt ttatctgata actttttttt cttttttat tatactttaa gttctggggt  93840
acatgtgcag aatgtacagg tttgttacat aggtacacac atgccagggt gtttggctgc  93900
acctatcaac ctgtcatcta cattagatat ttctcctaat gctattccct cccttgcccc  93960
tcacccctca ctggccccag tgtgtgatgt tccctagcct gtgtccaagt gttctcattg  94020
ttcaactccc acttttgagt gagaacatgc agtgtttgat ttcttttct tgtgttagtt  94080
tgctgagaat gatggtttcc agcttcatcc atgtccctgc aaaggacatg aactcttcct  94140
tttatatggc tgcacaatat tccatggtgt atatgtgcca caatttcttt atccaatcta  94200
tcattgatgg gcatttcagt tgttccaagt ctttgctatt gtgaatagtg ccacagtaga  94260
cataagtgtg catgtgtctt tatggtagaa tgatttataa tcctttgttt atatacccag  94320
taatagaaat gcttggtcaa atggtatttc tagttctaga tccttgagga attgccacac  94380
tgtcttccac aatggttgaa ctaatttaca ctcccaccaa caatgtaaaa gcgttcctat  94440
ttcttcacat cctctccagc acctgttgtt tcctgacttt ttaatgatca cgattctaac  94500
tggcgtgaga tggtatttca ttgtggtttt gatttgcatt tctctaatga ccagtgatga  94560
tgagcttttt ttcatgtttg ttgaccgcat aaatgtcttc ttttgagaag tgcctgttca  94620
tttccttcac ccacttttg atggggttgt ttgtcttttt cttgtaaatt tgtttaagtt  94680
cattgcacat tctggatatt aattaacctt tcgtcagatg gatagactgc agaaattttc  94740
tcccattctg taggttgctt gttcactctg atgatcgttt cttttgctgt gcagaagctc  94800
ttgagtttaa ttagatcaca tttgtcaatc ttggctcttg ttgccattgc ttttggtgtt  94860
ttagtcatgt agtctttgcc catgcctatg tcctgaatgg tattgcctag gttttcttct  94920
agggttttca tggttttagg tcttacgtga ctcatcttga tttaattttt gtgtaaggtg  94980
taaggaaggg gtccagtttc agttttctgc atatggctag ctagttttcc caacaccatt  95040
tattaaatag ggaatccttt ccccattgct tgtctttgtc aggtttgtca aagattagat  95100
```

-continued

```
ggttgtagat gtgtggtatt atttctgaga cctctgttct gttccattgg tctatatatc  95160
tgttttggta ccagtaccgt gctattttgg ttactgtagc cttgtagtat agtttgaagt  95220
caggtagcat gatgcctcca gctttgtgct tttggcttag aattgccttg gctatgcagg  95280
ctctttattg gttccatatg aaatttaaag tagttttttt ataattctgc gaagaaagtc  95340
attggcagct tgatggggtt agtattgaat ctgtaaaaca ctttgggcag tttggccatt  95400
ttcatgataa tgattcttcc tatccatgag catggaatgg ttttccattt atttttgtct  95460
tctcttattt ccttgagcag tggtttgtaa ttctccttga agaggtcctt cacatccctt  95520
gtaagttgga ttcctacata ttttattctg tttgtagcaa ttgtgaatgg gagttcactc  95580
atgatttggc tctctgtttg tctgttattg gtgtatagga atgcttgtga ttttcgcaca  95640
ctgattttgt atcctgagac tttgctgaag ttgcttgtca gcttaaggtg attttgggct  95700
gagagaatgg ggttttctga atatacattc atgtcatctg caaacagaga caatttgact  95760
tcctgttttc ctatttgaat atcctttatt gctttctctt tcctgattgc cctggccaga  95820
acttccaata ctatgttgaa taggggtggt gagagacggc atccttgtct tgttctggtt  95880
ttcaaaggga gtgcttccag tttttgacca ttcagtatga tattgggtgt gggtttgtca  95940
taaatagctc ttattatttt gagatatatt ccatcaatac ctagtttatt gagagtttga  96000
gcatgaagca gtgttgtatt ttgtcgaagg ccttttctgc atctattgag ataatcatat  96060
ggttttgtca ttggttctgt tgatgtgatg gattatgttt attgatttgt gtatgttgaa  96120
ccagccttgc atcccagggg tgaagcggac ttgatcgtgg tggataagct ttttgatgtg  96180
ctgctggatt gggtttgcca gtattttttt attgaggatt tttgcactga tgttcatcag  96240
ggttattggc ctgacgtttt cttttttttgt tgtgtctctg ccaggttttg gtatcaggat  96300
gatgctggcc cataaaatga gttagggagg attccttctt tttctgttgt ttggaatagt  96360
ttcggaagga atggtaccag ctcctctttg tacatctggt agaattcatc tgtgaatcct  96420
tctggttctg gacttttttt ggttggtagg ctattaatta cttcctcaat ttcagaactt  96480
gttatagttc tattcaggta tttgacttcc tgctttaggc ttgggagggt atatgcgttc  96540
aggaatttat ctatttcttc tagattttct attttatttg ccccagaggt gtttatagta  96600
ttctctgatg gtaatttgta tttctgtggg atccgtggtg atatcccctt tatcattttt  96660
tattgcatct gtgattcttc tctcttttct tctttagtag tctggctagt ggtctatcta  96720
caaaatagac tgtttatctg atatttattt tgtaattatc taataataac catcattatc  96780
atcatcagca ttatcattat catctccttt acccatacat acatttgtgt ctttcaaata  96840
ataatcccat ctttgaagtg catcctcatc tttagcagtc tgcactctgc tttcttatat  96900
catttattat cttattttat aattatttat ttccagtcct tcttctctaa cagatagtag  96960
tttcttaggg ccaaggaaat atctcgatca ccactatatc cccagcacct aaccctgtgc  97020
ctggtccata gggccagatg ctaagagttg agttgaacca ttgtacctaa tcttaacctt  97080
cattagcaca acatggtttg tcagtggtta agaatctaca ctttggagtc agactcaccc  97140
aggatggaat cctggcattg ccacttatta ttaatagatg cgtgatcttg aacaagttta  97200
cttaattgtt ctgagcatca gtttcctctt ctgcaatata gggatgatac acagctacct  97260
ggtaggttgt tgggaaaatt aaatgggatg atatgtatga aatggcctgg catatagagt  97320
gcctaaatac atgttcttct gattctattt ggacagtttg tgttagtaac agaagtcaaa  97380
aaggtggaga aaggagaaag gtacttgtga aaattttcta tttcttctcc atgtttcatt  97440
```

-continued

```
caggactgag gaagggggca cagtttttac ccaaggaaat gacattttta gccaaaagaa  97500
atgatcttag catttagctg aattatatat tggaagtaag ctccttccat gtggaactta  97560
tggccttgct agccttggtt tgttggaagt gctcttgctg gctttctagt tagggtaggg  97620
aaaggaaggc ttgtggggaa tgaagatagg ccatgatatc aagccactgg gtttgcaaat  97680
cagtagaatt ttttattgct ttctgttgta cttgggactt gaataaaggc tgatatttgt  97740
gtcttgctgg taaagtgctt gtaaagtgag tgaaagtttt ctttgctctt gtcctgacat  97800
agctgttcac ttggggttga ggggaggata acctttcatg tttttttttt ttcttcattc  97860
tgatgactgt gctgaacatt caaaccaaaa ggccattggt ggaaagtaaa ggtgagtggt  97920
gagaagacaa tagggtaatg gaaactgtgt tggacttgta atcaaattgt cctgcacttc  97980
ccctctccaa gtcttaacgt ttttcatctg tacagtggat attaaaatga gaaaataagc  98040
ttgtcttcac agagttttcg ttaggtgttg acacaacaaa caggctccca ttagggctca  98100
ttttccttca ttccttagta aggaagaagt gcttataaaa tatagcagtt gtgctcttgt  98160
gaatgatagc atgggcagtt gtcatctccc tgaagcagat gtaacccaga atgtcacttg  98220
agttttgttt aatgcttagg cataagacat aggaatgaca aaagctgacc tttgggtagt  98280
gagaacaatg ttccattttg ttcaaacttg aattttttac tataggagac tgagaattaa  98340
ccttccatga aggttttagg attggctttc tggcccttct ccttcatatc cacctgaaag  98400
agcttgggcg cagaagttct tgcagaaagg cagttagaca aggtgacttc tgaagctcca  98460
gtggccaagt attttgatgg tagcctaaaa gatgtccaga atcattgtac atcatttttt  98520
caacagaagc ttcaggcata gggattatgc ttggtacttt atgttgtgga atggaatctg  98580
gcggatgtcc atgtgatcta tagaaacacc taaggaaagt gaagaaatga gggaaaaaaa  98640
agaacaagac ttttatgata atactaatca cgatccttgt gtatttattc caatggcatt  98700
ttatccatta tctgatttat attaccactc acagcagcag ctcaatagga tgggagatat  98760
tatctctatt ttatagatga gatttgaggc tcacgaagct aaagcaagga acatcaaatc  98820
actttgatat ttggtctggt tttgttatag gtctcccttt ggatgaggta aagttacaaa  98880
cctgggttca tatcatttaa ttagtctgaa aatgttgcct ggacaccacc ttcagttaga  98940
tatcttaacc tcaggcttcc tgccttcatt gctcccgcat atagacatag actatgagat  99000
tggctaatcc cagagaactt ccctaatccc ttggcaagat ccaaaaaggc tcagtcacac  99060
cctacaacca tcatctttag gagaagtctc agaaaattca gcttcacact aactaacttg  99120
agcaatgaat aatagtcatt tatgcctgca ggttaatgct gaagacctga gacttcactt  99180
gcctatttct gccattcagt gacatgtgtt gcattggttt tttgtgtctt tccagtttgg  99240
agactgccag ggaccatgtt ttgcccattg actattactt tccaccccag aagacctgcc  99300
tgatctgtgg agatgaagct tctgggtgtc actatggagc tctcacatgt ggaagctgca  99360
aggtcttctt caaaagagcc gctgaaggta aagggtcttg cacatgcact tctctttccc  99420
tttctccttt accttccaga gagagacact aacctttcag ggcccaggat tttatcatct  99480
cagaaataga gtcattggca aggccctatc aaataactta ggagcctaag gaagcaaatt  99540
tttgtacttg ctagttccct ggtttcagca gccttgtttg tacaggcaat ttaggcagtg  99600
aaggtggtcc cagctggggc ttggggctca gtgggtccta gaaatgaaag aaaaattaat  99660
gatttgaaaa gatttaattt cctcccttct tgttttctac tctgctggct agtaaaggaa  99720
aaatttgtcc ttattagaga ggttagaagt ggagaaaccc caactgagtc cccagcctgt  99780
tccttgggat gaatatgaga ctgttcctta gcaaaggctt cctggcctcg gccccagaaa  99840
```

gggagtgttc tcactcttca gcagactatc agtctctgca cctgctccct cctgttgtgg 99900
cctccttggg acctgtcttt gcattaatag ttcctaggta ggtaagaact cagagtgaag 99960
aaacacattt attctcctct ccagagacct gatctcaaag cctgtccatt agtccctaac 100020
cttaatctaa ggtagcatct tatatctggc taaattggct caagccctag ctccttagtt 100080
ttatttagct tagaacaact catgtctgct caacctctag aggcgctcag cccacattct 100140
gcagtagaaa ctcccatttt caggcctctt atatacggta atgtctcctt cctctaacca 100200
cccagggctt aagcttcctg cttatccact tcaccctgta ttgagggctt tcttctcaaa 100260
gagacattga tgaggagccc ctagagagag atgctgtgct ctgggaccag accccttgtt 100320
aaacaccagt attcacctct gccccaactt tccccaaaga ggtacttcct gccaaggcct 100380
ttctctttcc tctcactggc tggaagtgtt gagttccact tcagaaccag aacagagaac 100440
ctttccttct ataagagcta taaaccttga gaacagtctt aaaacatagg tatgtaggcc 100500
acaccattca ccacgaatgt actgatactc atcagaatat ggaagaagca ccagagagtt 100560
tgaagcatct agagaaaagg tagaaagaga atgcccttta actgacctcc tcagtgatag 100620
ccaatcacaa tgatgagtgt tgattcatca ttttggctag gtggcagaaa tatctataaa 100680
acagaagctg ccatgttgtt ttcttccagt cctcagggcc tacaagaagg cagctatcat 100740
ttggtattac tgaaaacatg ccccatgttc agctcatacc cccaaattac ccattgctac 100800
tgtttatgct gggctaatat gaagcccagg gccctaatgt ctaggtctag gcagtaaggc 100860
ctagagcagt gcctaaagag cctgagagca gtgccttcct ttcttcagag tactcatgaa 100920
aggatggctg tcagaaaagg aaatgaggat gggttccaga gacttcagac caccccaact 100980
tccccagtga gaccctggca cctccccata ccctctcacc tagcgggccc tgtctataga 101040
gcagagaatg aaacagagca ctcatctaga ggtagtgtgt cagcaagccc aggcactgca 101100
ccacagtaat agcagccata tcagatggga aaggagttca agtgaacaaa caagcaaatt 101160
caatagtcag atagattaga ttatacttga tgcttcctct gagttttaca aatatgggtc 101220
actaaattgt tattttcaga aaacagggga aatgctcaat cacattgtga aagggaagat 101280
tttgctgtca tatcatacat cccacatggg agctttctgc agaagttaga gctgaaggag 101340
ggaggcaggc agaagggcaa ctggcagggc tgcctgggag gagctctgca atgaggtgga 101400
tcctgtgcca tttgagaaca gggaagaaaa gaaatgaggt tttggggagg gaatcaccca 101460
actcacagaa cacacagaaa tccagcaagg tttcaaaacg ctctacacct tagagtctgt 101520
taagttaggg aaactctgtg agctcatagg gccaaatgca cttgcctgct tgaaatatga 101580
aaaatcagca atggattcct tgaaaaacaa tgaaaaggga accttctgag ccccttggtt 101640
attttgacat atggaccata gatttcagtc ctgagccctt tgaaggtagg agaaggtggt 101700
ttagaaaaca cacacacaca cgcacacaaa cacacaccag aatgaagcaa aaaaaaaatt 101760
actggtgttt tctttctcct cccatctgtg aagctgttgg attgatttta ctgccatcat 101820
tatccctgtt tgaaggcagg gggctgtctt attacccaaa gaggacattt attgatttgg 101880
ttttcttttt ccatttttac aatgcatctt tatcgcccat atggcctttc tggaggtggt 101940
tttcagtctg gcttgttgaa acatcaaatt atacctgtct tagagaaaat agaaacaaaa 102000
atctttctct tccttacttg cttgttgtag tcagttaact cggactgagt attcagagtc 102060
ttgattatca cttaattcat agtttcataa atctctggaa tgggcatagg tacaggactt 102120
aaaagcctgg catctcagac agaaatatgt ttttagcttt ggtggtttat aacagatggg 102180

-continued

```
acttttaggc tgtcattggt gcagggctca gcacagagtc agttgtaatc tggacaggtt 102240
ttgttgttga ggaagagtgg gaagagggag tcctacattt tctccttgtc agtaatgttg 102300
gagaattggg gtgagggtga ggctgggcag ggagggtctg catagaaaaa agggtgcggt 102360
gagaaaaaat aatgctacta agccatgagg gtaaaatgac caaattctgg ttgagagaaa 102420
cttggtcaaa gtgtgtatgg ggagagaaag ttggtcaaag tctgtgtctg agtgcttggt 102480
gggatgaact ctgggttaga aacaggcatg gagggaaata gttggtttat ggagtgggta 102540
ggatgagtgg ggtggtgaaa gggaaggcat tttggatgct aagagaccag gaagtcaaag 102600
caaggcaata cacataaaca gaggtaaggg ctcagagagg ttttagttgt gtagacttgg 102660
ataagaaatt ttccctttg gacctcagtt ttccttgttt gtaaaacaac ggacttgaac 102720
tagatatttt aaaatgtgct tccagcttag acattttgtg accgttctac aaattacaaa 102780
cataatcatc atcatttcag caaactcaca tgtatttata cctgcataag tttttggtct 102840
tgctttccta gaaggtgact aatcccagat cctaatcaat taaagaagca atcttcagat 102900
ggggatagag ccagctgaga gagtgtacta tggatggagt gagttaaaac tcaggactca 102960
gattttctcc ttgtgatcat tgctgggtaa cttcctttct tttctatttt ctcatctgga 103020
aaatcaggat atgaatcccc atctctacct cattatgttt caaagagggt taattaatcc 103080
atcatgtgca ttatgtgctc aagaatttac tatttttcag acattttcta gtaaaacatt 103140
gaagattata tgtccatttg ttttgtacac atggagtgct gtttggtaca catcataaaa 103200
ttgaaactgt agtttacatt ctgaactcaa agaattacac catcctcact gatgtttaca 103260
ataggtccca atttagtttc tttagcaaat tttatgtaag tatggctttg attctctctc 103320
tcactccagg tttttgttag ggaagaaatg caagtgaacc ctcattgaac tctttctgtc 103380
ctttaaatcc attctttccc acctcaactc atgtggaatt gaatgttgcc tctagtttgg 103440
agtctagcag agagtttttg gtgcatatca gtgtcccctt cactccctga cttttcaagt 103500
aacatttccc agaggcaaat taactctgct aagaggatct gcttgcagct tcaacagagc 103560
cttcatcagg tatctttggc caaggagttg actgatcctg actttgcgag tcctagagat 103620
cttttcacaa agctcctctc atgtttctgc ctctgatttt cttaaatgtc acagacagac 103680
tttagattta ggggttggtt aacttttttt gtaaagggcc atgtagtaaa tattttaggc 103740
tttgtagatc atatggtctc tgtgtcaact actcaactct gcctttgtag gatgaaagca 103800
gccatagaca atactggaac taatgggagt agctgtgttc caataaaact ttatgggcac 103860
tgaaatttga atttcactta attttcacat gtcgtttaat attatttttc tttttttacca 103920
tttaaaaatt tagaaatcat tcttagctct ttgggcctca caaaaacaga tggtagagtg 103980
gatttggttt atgggctgca gtttgttgac ctgtgcttta gctaatcact tctgtactta 104040
taaatctgca taggttttat gtttttccat ctcttggtat cttagtaggc cagtcaaagt 104100
ttgaacaact tgttagcaca gaatacctgg cctagtggct tcttggtcct gagcttattt 104160
actaaacaag agaaaaaata aataagtcta gaaatgctag aagaggatac tttttttgttt 104220
taatgatcta gtagatcact cctccttgca atacccagag gagaaactga aaatatttca 104280
aacattttct agacttctgt gttgtaaatt tgtggataac tatgaactat atatgaatga 104340
acttttctgg atgacacata tattccagat ggtaaaaagg aagggctttg gggactctct 104400
ggtaccaagt gtcatggaaa aactgtgtgt ctcatagaaa gtagatccca ggaggccagc 104460
agagttgtgg atctgccata tattacctca tgattctgtc ttcgcacact caccggctta 104520
attctgggcc tccccataac acgactagac cacaggcttg cagaagaaat aatttagctc 104580
```

```
tgtaactcat tgaagttggt gcccacccaa gtctctgtca gtgcccaatt cgggagccat 104640
gccaagaatt tgccattgct gcttcatggt ggccttgtgc ctgcttattt atagcctgtg 104700
cattttatga aacagggatt aataagaagt tgccatagca cttgcaccat tatgtaaata 104760
tctgtaatgc ttacataact tttgtcactt gcaagacctt ttgagtccat tgccttctgc 104820
taccatgcct taccaatttc ctagtccctt attattattt ttcaattcat tatatttaac 104880
ttctgtgata cacgttcaga atatgcaggt ttcttatata ggtatacacg tgccgtggtg 104940
gtgtgctgca accaacaacc cgtcatctac attaggtatt tctcctaatg ctatccctcc 105000
actagcccac cacccctaa taagccccag tgtgtgatgt tcccctccct gtgtccatgt 105060
gttctcattg ttcaactccc acttatgagt gagaacatgc agtgtttggt tttctgttcc 105120
tgtgtttgtt ttctgagaat gatggtttcc agcttcatcc gtgtccctgc aaaggacatg 105180
aactcatcct tttttatgac tgcatagtat tccatggtgt atatgtgcca cattttcttt 105240
atccagtata tcattgatgg gcatttcggt tggttccaag tctgtgctat tgtgaatagt 105300
gctgcaataa acatacgtat gcatgcgtct ttatagaaga atgacttata atcctttggg 105360
tatataccca gtaatgggat ggctgggtca aatggcattt caggttctag atccttgagg 105420
aatctccaca ctgtcttcca caatggttga actgatttac acccccacca acaatgtaaa 105480
agtgttccta tttctccata ttctctccag catctgttgt ttcctgactt tttaatgatc 105540
gccattctaa ctggcattga catggtatct cactgtggtt ttgatttgca tttccctaat 105600
gaccagtgat gataagcttt ttttcatatg tttgttggcc gcataaatgt cttcttttga 105660
gaagtgtctg ttcatatcct tcacccactt tctggtgtgg ttggttattt ttttcttgta 105720
aatttgttta agttccttgt agattctgga tattagccct ttgtcagatg gatagattgc 105780
gaaaattttc tctcattctg taggttggtt gttcactctg atgatagttt cttttgctgt 105840
gcagaagctc tttagtttaa ttagatttca tttgtcaatt ttggcttttg ttgccattgc 105900
ttttggtgtt ttagccatga agactttgcc cattcacaat tgctacaaag agaataaaat 105960
acctaggaat acaactcaca agggatgtga aggacctctt caaggagaac tacaaaccac 106020
tgctcaaggc aataagagag gacacaaaca aaaggagaaa cattccatgc tcatggatag 106080
gaacaatcaa tatcgtgaaa attgccatac tgcccaaagt aaattataga ttcaatgcta 106140
tccccattaa gctaccattg actttcttca cagaattaga aaatactact ttaaatttca 106200
tatggaacca aaaagagccc atatacccaa gacaattcta agcaaaaaga ataaagctgg 106260
aggtatcaag ctacctgact tcaaactata ctacaaggct acagtaaccc ttatcaattt 106320
tttatgtgcc tctccatatt ctgcagtcag aagcttcttc agtcctttca gggaattgct 106380
gggtgactat caaactctgg tagttcattt ttgcagttgg ctgctgttgt gaggataaga 106440
gttagactca ctttctcttc agagatagaa attatgtatt aattctctgg gttctagacc 106500
cacagcaagg agcatactgc tcctcaaaat aactgaattc tgcgagaagc catcattgta 106560
aaacaacaat atcttcagtt atagtagcca tgtgtgcaac ttctggaaac tgttattcag 106620
attttcatgt tccttccctg tctcttcata gctaggcagc tgctttcagc cttgtacaga 106680
tgctagtgag ctttctacct acaaacctgc agaaaattga actgagattt ggaggtgaaa 106740
gactcttgat aaagggaaca aggtttagaa ttctcagtcc ctttgctccc aggctgtgtt 106800
gtgactactg aggcactcca gtgaaatcac tattcctcct atctagacta atgcctgtct 106860
ctgcagagca cctcataaga acaggcctgg tagtaatatc ctcatgcatt cagtcagtaa 106920
```

-continued

```
atatttacag agtgcttact acatataggg tattgggctg acatatgcaa gatacagggc 106980
ctgcttccag gaggttatag cttattgatc ataaatgtgg catttttttt ttttgagacg 107040
gagtcttgct ctgtctgtca cccaggctgg agtgcagtgg cacgatctcg gctcactgca 107100
acctccacct cccaggttca tgtgattttc ctgcctcacc ctcctgagca gctgagacta 107160
caggggctca tcaccacacc cagctttttt ttttttttct gtatttttag tagagacagg 107220
gtttcaccat attggccagg ctggtctcga actcctgacc tcgtgatcca cccacctcag 107280
cctcccaaag tgctgggatt acaggcgtga aaatgtggca atctttaaag ctcttcagtg 107340
gatgaaaggc caccctatct gctgtccttt tgaacttcgc aactttcttg gtacagagtg 107400
agaggttatt ctcttggttt tccatataag taaactgagg ctttgccagt tcatcaacag 107460
gtagtaaata atatatttgg aatttgaacc caagtcttct ggggtcaaag gcagcattca 107520
ctctgctctg tcacagcagc tcctcaaata agccaacata gaaaccaagt actatgccta 107580
ggcaacaaga aaggcagcaa tgaagagcaa cagcagagtc aaatatgaga gaaggaagtt 107640
aagaaagatg ttaagtactg tggggagtaa ctgagaaacc accaagtatc gctaacatca 107700
cagggaactt gtcttcctaa gaaaattcca agcacttaaa accgctggta gttcatcagc 107760
aactctcttc attagatgtg cgagggacat gtgggccata gtccttctac taacttatat 107820
tcttcagggg aaagttctga ttctgatgag acccagcatg gtagctctta attcactgtt 107880
gtcacacgac tatagaacag gaagcacaac ttaacacctg tgctcatgag aattttgctc 107940
cttatgacca agctaaagaa agagcttaga caggatgtgt ggctataaat gtagattaat 108000
ggttccttgg ctctttggtt tgagccttct cagcagagca tcccacggag tgttttccat 108060
ggggccacga gcaagagaaa tccacttccc tcctcctcaa tgtcagaaaa tagagaatat 108120
tgtctttcag gatagaatta aaaagtcata gaggcagcaa cttgttttcc tatattaggg 108180
ttttaaaatt ctgtttttcc ttcctctcct gggtcagatc attgtgtgga tggaccttga 108240
tttcattgtg gtatctgtat gtggaccctg aagaccatgg acttctaaca attccttaag 108300
ttacataagc acattcctac aggtcacaag ctcatttact tacaggatgg ttgatttggt 108360
cacaggttat ttcatgaaaa tacttaaaag atttgcagtg ttcaaaactg cagtatcttt 108420
aaacactaaa acttgaagga agggaattta gaaatcaaaa aatctggtca aaccatttca 108480
tggaaaagga aagtgaggct cagagagagg aaattacttt cctgggtttg tatagcctat 108540
aaatggcaga aatgagagcc tccctgccat ttctagtttt ctgtctgaga gactctcctg 108600
cctaatagct aattagcaga gtcacagagg tcattacctt gcaattctca agaattatgt 108660
gaggcagcat agtaagcatt tatggccctt ggttcctaga aggagcttag tccctgatag 108720
tcatctctgc ctttgccatt gtgtgagact gtcttctgta actgtatgtc ttcctcccta 108780
gtaagttaat gagtaataaa ggtattctat agtgagagga ctctgtaaga catttcttgg 108840
tgtgaggatt gttccaaggt tgttttgtgt gtatgtgcat gtataaactt ttttagggag 108900
catattcata gcttttacat ggatctcaga ggctctataa cccagagaag attacagaat 108960
accagtcttg tctttggtaa ggattttata gacccatcct gactacagtg atatccaaca 109020
tggctatgta atgactggca ctttccccac ataacatata tttattccac actcagtgcc 109080
tactgtgtac atgagaccta taccgggcac tgggataaga gacatgaaat aacagctaaa 109140
attgtttatt gagcagtcag tatgcattag atgctttgta gtcattttct tattcaatct 109200
gtataccctc aatttacaaa tgaggaaact gaggcacaga agagttgagt gatttgccca 109260
aagtcataca aatagtcagt ggctatgtga tgaatagtta ccaacataaa agagtgagat 109320
```

tactgctgta ctaaaagtag gtacataatc ccctgagcag acagtatgag agaatgattt 109380
attttacctg gaaagtttag gaaggcttca cagaggagtt aagggttgat ctgggtcttg 109440
agggatggat aagagtttgc cagatacaaa aaggtaggaa gagaacttca ggaggaggga 109500
acaggctgag caaagacacg gcgatgtgaa agtgggaggc ttgtttgggg aacattatgg 109560
aatctggagg ttattgtggg gaatctcatc agatgcagca agctgtttga caggccttca 109620
gttggctctt tgtaccttgc tccctccgca tgctgagctg tccatagctg ccctaggctg 109680
gtgtctggga ttttcggaag aaggttacta tccaggtagt gtaacaagat gcagtgcaaa 109740
agcaccagat tggggctctg gctctgctgc tgacttacca cctggcctta agcatgtcta 109800
gttccctctt tgtacattaa aatctccatt ggaacagtaa catggttgta ttaaatgatc 109860
ttgaagattt tacctgcacg ttttgcacat gtaccctaaa acttaaagta taataaaaaa 109920
attaaaataa aaaataaaaa tataacaata taaatcttta acaataattt tagtagtaaa 109980
tctctacaat tttacagata atccagatgc atccattggc caatggttca ctttgtatgc 110040
ataatatttg ggaaacaggc agacccaatt tcaatcctta gttgtaagac ttaatacata 110100
tgtgatctcg agcaaatcac ttttgtatgc ctctataagg ataataatag ctcacagaat 110160
tattttaaga actaaatgat gtgtaataaa gctactggta ctcagtaagt tttgtatcct 110220
tttcctagag tgagtcttgg tcataggcat gcgtatactt gcagcgtccc tgggtaggcc 110280
gaaagagcaa ataagagatg gtatctatgg tattccccag gtaaaggagg ccttgggttg 110340
gcataagatt tcacttctct ttagagttac ttaattaggg accagaaagg ccatcagcat 110400
ttgtatgaga atataacaaa ggtcaatctc ttcctcttta ctttttacct cccagtacac 110460
tgtgagtaac attccccagc cagcccagcc agcacgtgtt cattgcctct cttgacttcc 110520
agactttgga cttgaaggtg tcagagctct ctgtgtatct ttgtccccaa caagataagt 110580
ctgacctccc cagcaaattc aagtcctaag ccactgtcca ggagaaaagc tagcaaggtc 110640
ataaattatt ctccatattt tccagccatt ggtttccctt gtccagccag aggtgtgtct 110700
caaagtatgc tgaggccaga ttcaatagaa acctgagcca gcacctgtgt aaataatttt 110760
taaagctcct tttcctgaag ctggatgaat atttttaaaa actaagctgg attgtctttt 110820
atctagcatg ccgtctccta cattcctagt gctatggacc tcttggagga atgtggtttg 110880
gttatagtgg tattgtcttg tctgttgtgg gggagggaga catttctttc agaagcaagg 110940
taatactttg gtctggtcta tgactctatt ttgtttaaaa tgaaactatg gcagtatagt 111000
ggtattcatt ctgcttccca taggttaact ttacatccct ctgtcttcac ccactcttca 111060
gttctgattc ttttaaaagc agccaaccaa aaccagcaag tacatactgc ttatctctga 111120
cttccaccag aatcaacttc agatcttgtc caaagctcca tctgaagaga ggggaataac 111180
acccagccaa gagccctcag ggcccatcag taagtagaca tcctgtcctt gaggttcctt 111240
aactctgctc agcttcagaa tacagaaggg gttggttctt catttgtgtt gtttataact 111300
aaaagcctcc tactccccac ttttttgcat agcttcttct gccatcccac ctgtgtagcc 111360
tcttcaactc ccccaaaact cctctgtagc ccatgtcact tggaaagagt tttctttgtc 111420
tcttttgcaa cttgacaatg actagccagc aagtttaagt tcaaattatt gttccatggg 111480
agcagagata gatataggaa acaaaaaaaa gggatatgga ggtatagagt gatttcccac 111540
ctacctagtg agcactactg agatattcaa gtactctcta cccaagaatt ctattgatat 111600
aaaggtaaaa aacttgatct taggtctaat atccgttagt agtgtgacct tgggaaaatg 111660

-continued

```
ataccacccc caaaggctta gttttcttaa ctgtaaaata ggcatacaga tgaccacccc 111720
cagaggattc ataaggataa catgagataa ggcaacttga aatttcctag catagtgata 111780
gactttcgaa aataaaatga atcaaacact gataacagta cttcctagta cacaaatgag 111840
aaatcagtcc ctcatcaaat tacagcacat tttcaatgct ccaattatgt cactgtagaa 111900
atgctaatgt ggattaaata atttgtctgt tgctatttat acggataatt tgatagtagt 111960
tatttttgga catggatagc tttgaagcct tacagatgag tccatcccca agtacccaaa 112020
actaaagaaa gttggctaga gtgatgacaa ggtggcagca cagagctccc tgcgttctgg 112080
gccctgtccc ctagctagag agaactccag gctataagca tttgtattct catagtccaa 112140
tggcagggaa gaagggctgg aggtgagtag ttttcactca tttatttttt caacaagcat 112200
gtatggtatc aggccttgta tgcatccaga gacaaatgtg aactagccgt gtcctcaagg 112260
agattccagt ctggtgggcc tgccttccaa ggtcagttgc agctttagca ctataaagag 112320
cacctacctg cggcagatac aatgtgatgg gacatgacag agaaaaaatc tataagcaga 112380
gcctccccat tcccaggcat tgaaacaatc ctaaccaaga ctggcatagt acaatgagcc 112440
tgtccctatc agcaggtttg gaagccttaa caacaacaac aaaaacaata ataatggtga 112500
tgataatcat agagcctaat gttaccaaac attttccatg tgttaagtac tatactaagt 112560
gcatacttaa tcctcacaac aatgctataa gatagtagat actcttacta ctaccctgat 112620
tttacaaatg tggaaactga ggcacagaag actaagagaa caggaataca cctaattcac 112680
ctcagttcaa caaacatcaa gcatctgttt tatgtcaggc ctcgtgctgg atggcaggga 112740
gagagagatg agtaaagcat agtttcagtc cagtgggagc aaatgacagc acacagtggg 112800
gcaggtatat tgcagccctt ctgcttgatg ctaagaactc agtgtcagtg atgaatgaaa 112860
cacagtcatt ctctcaaaga tcttaaagct tagtaggaga tatctgtgtg gaaacaaaaa 112920
ttaaatactg ctgtgataag tgtcataaga gataagtgga aaatgagaga gagagatcac 112980
tgtagcaatt gattggttta aatcaaagcc cccaaaaaaa tgttattgag aattataaaa 113040
caactaattg atttaaatca aagcccaaac agaagtgttt gctaatttta tttcaatttg 113100
gttgataatt tggttgaaat gaatttattt catttttttat tccatcctta caatggaaga 113160
ttagtgcttg tttcccaccc aaggatacca ggatatttca ggggctgtat tacaatatag 113220
ttaaattatt cctttatctc aaagcacatc cacactttcc cctatcctta cctttactca 113280
gggtatctct tctgcctcag gtgctttttc tccacatttc catattctta agtcctacct 113340
tccttcaggg cctcactcaa atgcctcctc ctccatgaag cattcacccg actgaaaggt 113400
accccgccct ctcctgtact ccacatcact tcatgggtgt ctccacttcc tgctttatct 113460
ttcagtaata cacttacagt tctctttcct ccactagact gagctcttca gaggaagact 113520
cacttggctg aaaccatgat tttactttaa acacattgaa aacctctact ggagtgcatt 113580
gtgtctggtg ggcttcaacc ttaattctta agtatgtgaa aacacatcac ctatctggag 113640
gtttacactt tctgctaatg actttatttt taagcccacc accctaacac aacaaatact 113700
taaaacttgt cttcatttcc tttaggtctg gccctcatgc atgcatataa tttatagagt 113760
cactgttttg ctcggttgtc ctcatgcctc tatattattg gaggtttaga ttgtttccat 113820
atactcaggt tgtattcatg tcctttttttt ctttttaaat ttccttagca tccatttcca 113880
ccattggaaa ttcagggtca aaacaggggt ttgggattgg agcatgtcta tcacagataa 113940
ccaatcatgt gttatgactt aagaatttat gaaagggccc tctacctgaa gatatcttgc 114000
tactgatgct gtctcacagt gtctgaaact cccatcatat gtggaattgt tttggaaggc 114060
```

tttgcctcct gggacacatt cagccataat caagaaatag tattgagcat tagactgtca 114120
gtatgtccat tagcaagact gtggaggaat ggaatcacca atattatatt ttatagggga 114180
tacagaatac aagagaagtt ctgaagagaa aattcttatg tagaatagga aggcttagat 114240
acagcatgaa agctgcaggc tttgaggagc cagaggtcaa atgaaagcat tgagtatttg 114300
tttagatgaa agaacagaaa gggaaaaaga agcagaggaa gggatagtag agagaaatgt 114360
ataagtttta tccatttaac ttgtaattgt gtttggctat gggcacaata gaagcagtga 114420
gatcacttta ttttatttta ttctttatag acagggtctt gctatgttgc ccaggctgca 114480
gtgtgcagct cttcacaagt gtgatcatag cgtactacac cctcaaactc ctggactcaa 114540
gcaatcctcc catctcagcc tcctgagtag ctgggactac aagtgcacac caccacgccc 114600
agtgagatca cttgaaacta gggagagatg tgtgagttct gggcaaccag tagttggctt 114660
tacatagaac tgtaggggtc aaggccaaag gggacgtcct gttccaagtc accttctttg 114720
gacattagaa aaccacgagg ggtttggaaa tcagaaaacc agcagaggca ggaaaactca 114780
gggcagcatg ggagattcag tatatacaaa aaggttcaca ccagtaatca aacagaattt 114840
taactgctga tgtggagtag aggcagcttt gtctgctgtg tgataaccaa acctttacga 114900
atagtaggtg tatatgggga attggaggga gataggtggc tgtgtttagt aattggttga 114960
cttcactgag atggtttggg gattgtggct tccagatgat cagattttct tttttaggta 115020
gagactccaa catcattaca gaactataaa ttacatgtgg aaaagaaagg cctcctatgt 115080
tagaatagaa aataaaatgc tgtggggttg agggacagag gtgctgtcta ggaagtcaga 115140
tagcgttttc cagttctgtc cctcagagtt ccttgtcctc attgagactc aatttctctt 115200
actttttttt ttatacttta agttttaggg tacatgtgca caacatgcag gtttgttaca 115260
tatgtataca tgtgccatgt tggtgtgctg cacccattaa ctcatcattt aacattaggt 115320
atatctccta atgctatcct tcccctctcc cctctcccca ccacaggccc tagtgtgtga 115380
tgttcccctt cctgtgtcca tgtgttctca ttgttcaatt ctcacctgtg agtgagaaca 115440
tgcggtgttt ggttttttgt ccttgtgata gtttgctgag aatgatggtt tccagcttca 115500
tccatgtccc tacaaaggac atgaactctt catttttttat ggctgcgtag tattccatgg 115560
tatatatgtg ccacattttc ttaatccagt ttatcattga tggacatttg ggttggttcc 115620
aaggctttgc tattgtgaat agtgccatga taaacatacg tgtgcatgtg tctttatagc 115680
agcatgattt ataatcctta gggtatatac ccagtaatgg gatggctggg tcaaatggta 115740
tttctagttc tagatccctg aggaatcgcc acactgactt ccacaatggt tcaactagtt 115800
tacagtccca ccaacagtgt aaaagggttc ctatttctcc acgtcctctc cagcacctgt 115860
tgtttcctga ctttttaatg atcaccattc taattggtgt gagatggtat ctcgtggttt 115920
tgatttgcat ttctctgatg gccagtgatg atgagcattt tttcatgtgt ctgttggctg 115980
tgtaaatgtc ttctttgaga cgtgtctgtt catatccttt gcccactttt tgatagggtt 116040
gtttgttttt ttcttgtaaa tttgtttgag ttctttgtag attctggata ttaccctttg 116100
tcagatgagt agattgcaaa agttttctcc cattctgtag gttgcctgtt cactctgatg 116160
gtagtttctt ttgctatgca gaagttcttt agttgaatta gatcccattt gtcaattttg 116220
gcttttgttg ccattgcttt tggtgtttta gacatgaagt ccttgcccat gcctatgtcc 116280
tgaatggtat tgcgtaggtt ttcttctagg gtttttatgg ttttaggtct aacatgtaag 116340
tctttaatcc atcttgaatt aattttagta taaggtgtaa ggaagggatc cagtttcagc 116400
tgtctacata tggctagcca gttttcccaa caccatttat taaataggga atcctttccc 116460
catttcttgt ttttgtcagg tttgtcaaag atcagatggt tgtatatatg cggcattatt 116520
tctcagggct ctgttctgtt ccattggtct atatctctgt tttggtacca gtaccatgct 116580
gttttggcta ctgtagcctt gtagtatagt ttgaagtcag atagcgtgat gcctccagct 116640
ctgttctttt ggcttagggt tgacttggcg attcaggctc ttttttggtt ccatatgaac 116700
tttaaagtag ttttttccat ttctgtgaag aaagtcatgg gtagcttgat gaggatggca 116760
ttgaatctat aaattacctt gggcagtatg gccattttca caatattgat tcttcctacc 116820
catgagcatg gaatgttctt ccatttgttt gtatcttctt ttatttcatt gagcagtggt 116880
ttgtagttct ccttgaagag gtccttcaag tcccttgtaa gttggattcc taggtatttt 116940
attctcttag aagcaattgc aaatgggagt tcactcatga tttggctctc tgttttctgt 117000
tattggtgca taagaatgct tgtgattttt gcacattgat tttgtatcct gagactttgc 117060
tgaagttgct tatcagctta aggagatttt gggttgagac gatggggttt tctaggtata 117120
caatcatgtc atctgcaaac agagacaatt tgacttcctc ttttcctaat tgaatgccct 117180
ttatttcctt ctcctgcctg attgccctgg ccagaacttc caacagtatg ttgaatagga 117240
gtggtgagag agggcatccc tgtcttgtgc cagttttcaa agggaatgct tccagttttt 117300
gcccattcag tatgatattg gctgtgggtt tgtcatagat agctcttatt attttgagat 117360
acgtcccatc aataactaat ttattgagag tttttagcat gaagcgctgt tgaattttgt 117420
taaaggcctt ttctgcatct attgagataa tcatgtggtt tttgtcgttg gttctgttta 117480
tatgctggat tatgtttatt gatttgcgta tattgaacca gccttgcatc ccagggatga 117540
agcccacttg atcatagtgg atacgctttt tgctggtatt ttattgagga tttttgcatc 117600
aatgtttatc agggatatcg gtctaaaatt ctcttttttg ttgtgtctct gcctggcttt 117660
ggtatcagga tgatgttggc ctcctaaaat gagttaggga ggattccctc tttttctatt 117720
tattggaata gtttcagaag gaagggtacc agctcctcct tgtacctctg gtaggattca 117780
gctgtgaatc catctggttc tggacttttt ttgattggta agctattagt tatatcctca 117840
atttcagagc ctgttattgg tctattcaga gattcaactt cttcctggtt tagtcttggg 117900
atggtgtatg tgtcgaggaa tttatccatt tcttctagat tttctagttt atttgcatac 117960
aggtgtttat agtatgctct gatggtagtt tgtacttctg tgggatcggt gattatatcc 118020
cctttatcat tttttattgc gtctatttga ttcttctccc ttttcttctt tattagtctt 118080
gctagtggtc tatcaatttt gttgatcttt tcaaaaaacc agttcctgga ttcattgatt 118140
ttttgaaggg ttttttacat ctctatttcc ttcagttctg ctctgatctt agttatttct 118200
tgccttctgc tagcttttga atgtgtttgc ccttgcttct ctagttcttt taattgtgat 118260
gttagggttt caattttgga tctttcctgc tttctcttgt gggcatttag tgctataaat 118320
ttccctctcc acactgcttt gaatgtgtcc cagagattct ggtatgttgt gtctttgttc 118380
tcattggttt caaagaacat ctttatttct gccttcattt cattatgtac ctagtagtca 118440
ttaaggagta ggttgttcag tttccatgta gttgagcggt tttgagtgag tttcttaatc 118500
ctgagttcta gtttgattgc actgtagtct gagagacagt ttgttataat ttctgttctt 118560
ttacatttgc tgaggagtgc tttacttcca actatgtggt caattttgga ataggtgtgg 118620
tgtggtgctg aaaagaatgt atattctgtt gatttggggt ggagagttct gtagatgtct 118680
gttaggtctg cttgacagtg gagtgttaaa gtctcccatt attattgtgt gggagtctaa 118740
gtctctttgt aggtctctaa ggacttgctt tatgaatctg ggtgctcctg tattggttgc 118800
atatatattt aggatagtta gctcttcttg ttgaattgat ccctttacca ttatgtaatg 118860
gccttctttg tctcttttga tctttgttgg tttaaagtct gttttatctg agactaggat 118920
tgcaatccct gcctttttgt gttttccgtt tgcttgataa atcttcttcc atccctttat 118980
tttgagccta tgtgtgtctc tgcatgttag acgggtttcc tgaatacagc acactgatgg 119040
gtcttgtctc tttatccaat ttgccagtct gtgtctttta attggagcat ttagcccatt 119100
tacatttaag gttaatattg ttatgtgtga atttgatcct gtcattatga tgttagctgg 119160
ttattttgct cgttagttga tgcagtttct tcctagcctc gacggtcttt acaatttggt 119220
atgtttttgc agtggctggt accggttgtt cctttccatg tttagtgctt ccttcaggag 119280
ctcctgcagt gcaggcctgg tggtgacaaa atttctcagc atttgcttgt ctgtaaagga 119340
ttttatttct ccttcaccta tgaaggttag tttggctgga tatgaaattc tggttttaaa 119400
attcttttct ttaagaatgt tgaatattgg cccccactct cttctggctt gtagagtttc 119460
tgctgagaga tcagctctta atctgatggg cttccctttg tggggaacct gacctgtttc 119520
tctggctgcc tttaacattt tttccttcat ttcaactttg gtgaatctga caattatgtg 119580
tcttggagtt gctcttctca aggagtatct ttgtggtgtt ctctgtattt cctgaatttg 119640
aatattggcc tgccttgcta gattggggaa gttgtcctgg ataatatcct acagagtgtt 119700
ttccaacttg gttccattct ccccatcact ttcaggtaca ccaatcagac atagatttgg 119760
tcttttcaca tagtcccata tttcttggag gctttgttca tttcttttta ttctttttcc 119820
tctgaacttc tcgcttcatt tcattcattt gatcttcaat cactgatacc ctttcttcca 119880
gttgatctaa tcggctactg aggcttgtgc atttgtcacg tagttctcgt gctgtgtttt 119940
tcagctccat caggtccttt aaggacttct ctgcattggt tattctagtt agccatttgt 120000
ctaatttttt ttcaaggttt ttaacttctt tgccatgcgt tcgaacttcc tcctttagct 120060
cagagtagtt tgattgtctg aagccttctt ctctcaactc gtcaaagtca ttctccatcc 120120
agctttgttc cattgctggt gaggagctgc attcctttgg aggaagaaag gcactctgat 120180
ttttagagtt tccggttttt ctgctctgtt ttttccccat ctttgtggtt ttatctccct 120240
ttggtctttg aagatggtga tgtacagatg agcgtttggt gtggatgtcc tttctgtttg 120300
ttagttttcc ttctgtcagg accctcagct gcaggtctgt tggagtttgc tgcaggtcca 120360
ctccagaccc tgtttgcctg gttatcagca gcagaggctg cagaacagtg gatattggtg 120420
aacagaaaat gttgctggtt gatcattcct ctggaagttt tgtctcagag gaatacccgg 120480
atgtgtgagg tgtcagtctg cccctacttg ggggtgcctc ccagttaggc tactcggggt 120540
tcagggaacc acttgaggag gcagtctgtc cgttctcaga tctccagctg catactggga 120600
gaaccactac tctcttcaaa gctgtcagac agggacattt aagtctgcag aggtttctgc 120660
tgccttttgt tcggctatgc cctgccccca gaggtggagt ctacagaggc aggcaggcct 120720
ccttgagctg tggtgggctc cacccagttc gagcttccca gctgctttgt ttacctactc 120780
aagcttcagc aatggcgggc acccctcccc cagcctcgct gctgccttgc agtttggtct 120840
cagactgcta tactagcaat gagcgaggct ctgtgggcgt aggaccctct gagccaggca 120900
caggatataa tctcctggtg tgccgtttgt gaagaccatt gaaaaagtgc agtattatgg 120960
tgggagtgac ccgattttcc aggtgccatc tgtcacccct ttctttgact aggaaaggga 121020
attctctgat cccttgtgct tcctgggtga ggcgatgtct cgccctgctt tggctcatgc 121080
tcggtgcgct gcacccactg tcctgcaccc accatttgac actcccctgt gagatgaacc 121140

-continued cggtacctca gttggaaatg cagaaatcac ccatcttctg tgttgctcac gctgggagct 121200
gtagactgga gctgttccta ttcggccatc ttcacaaaaa tcttactttg gtttctagtg 121260
ttaccaccca ctgttctttc tcatctcaac cctgagtata agtacagatc acattccttg 121320
ggttcttaga aaataataga aatgaactct cattcatcaa aatgcccatt agtaaatact 121380
gagggagaac aaactagaaa tccagtatag aaaataaaaa taggattata ttccttggaa 121440
tctcagaaaa aaacaatgaa gagctttctt tgggcattag acactttccc ataaggtggc 121500
tgactctctt ttagtcatgt cagcttggcc caatcttcac ttggtagccc ttctttcttc 121560
ttcattaatc catctcctat gctcctatgg ggtcctagag aaatgcccat catgtacaca 121620
cacatctaat aacacaaaga tcactctcga ctagcaagcc cttttatgat ggtgtgagca 121680
tttgacaccc ttgttgctag taacatcagt gagtgacctg acccattttt ggaacagaat 121740
atgatcagta tgttgcctca aggaggccct cactgttcta ggaaatataa ttccagagtt 121800
tgctgactca caccatggaa tatatgcata aaatggatcc tgcagataag cctttctctg 121860
actagtttca gacatttttt tctgggtaat tttaaagtta ttttttattt ttgtgggtac 121920
aaagtaggtg tatatatgta tgaggtacct gaggcatttt gatacaagca tacagtgtat 121980
aataatcacc agagttaatg gggtatccct caccacaagc atttatcctt tctttgtgat 122040
acaaacaatc caattatatt cttttagtta ttttaagatg tataataaat tattgttgac 122100
tgcagtcacc ctgttgagct atcaaatact agatcttatt cattctaact atacttttgt 122160
acccagtagc catcccactt cctcccctcc cactaccctt cccagcctct gataaccatc 122220
attccactct ctatctctat gagctcaatt gttttaagtt ttagctccca caaatatgtg 122280
agaaaatgcc aagtttgtct ttctgtgcct ggcttatttc acataatata atgtcctcta 122340
gttccatcca tgttattgca aatgacagga tctctttctt ttttatggct taatagtact 122400
ttattgtatg tatgtaccac attttcttca tccatttgtc tgttgataga caagagttgc 122460
ttccaaatat tgactattgt gaatagtgct gcaataaacg tgggaatgca gatctctttg 122520
atatactgat tttctttctt tagggtgtat acccagcagt gggattgctg ggtcatatga 122580
tagctctatt tttagtattt tgtggaacct caaatctatt ctacataatg gttttactga 122640
cttacatatc caccaacagt gtatgaggat actcttttct ccacatcctc accagcattc 122700
attactgcct gttctttgga tgaaagccat tttaactgtg gtgaaatgag atctcattgt 122760
tgttttgatg tgcacttctc tgatgatcag tgaggttgag gaccttgtca tatatctgtt 122820
tgtcatttgt atgttttatt ttgagagatg tctacccaga tcttttgccc attttttaat 122880
cagattgtta gatttttttt ttcctacaga gtgcttgagc tctttatatg ccctagttac 122940
tagtccctgg tcagatgggt agtttgcaaa tagttgctct cattctgtgg gttgtctctt 123000
cactttgttg atcgaatcac ttgctgtgca gaaggttttt aacttgatgt gacctcattt 123060
gtccattttt agttgcctgt gctggtgcgg tattactcaa gaaatttttg cccagattaa 123120
tgttctggag agtttcccca atgttttctt gaagtagttt catggattga tgtcttagat 123180
ttaagtcttt aatatgtttt gattttattt ttgtatttgc tgagagatag ggctctagtt 123240
tccttctgca tatggatatc cagtttttct agcacctttt gttaaagaga ctattcattc 123300
tctaatatac gttcttggca cctttgttga aaataagttc actgtagatg tatggacttg 123360
tttctgggtt ctctgttctg ttccattggt ctatgtgtct gcttttatgt gaataccatg 123420
ttgttttggt tgcaaaagct ctgtagtata atttgaaatc aggtaatgtg attcttccag 123480
ttttgctctg ttctttttcc tcaagatagc tttgcctatc ctgggtctct tgtggttcta 123540
tataaatttt aggattattt tttctattta tgtcaagaat gtcattgata ttttgatata 123600
aattgcgttg aatctgtaga tagcttcagg tagtgtggac attttaacaa tatcaattct 123660
tgaaatccac gaacatggaa tatccttcta ttatttggat gtcttcttca atttcttata 123720
ttaatttttt tttagttttc attgtagaga tatttcattt atttgactaa gtttattgct 123780
aggtatttta ttttattttt acctattgac aatgggattg ctttcttgat ttcttttttta 123840
gattgttcac tgttggcata cagaaatgct actgattttt atgtgatgat tttgtatccc 123900
gcaactttac tgaatttgtt tatcagttct aataggcttt tggtgcagac tttaggcttt 123960
tccaaatata agatcatatt atctgcaaac aagaataatt tgacttcttt cttttcaatt 124020
tggatgcctt tcatttcttt ctcttgtctg attgctctaa ctaggacttc cagtactctg 124080
ttgaataaca gtggggaaag ttaacatcct tgttttgttt cagatcttat agccaaggcc 124140
ttcagttttt ctgaatttag tatgatacta gctatgggtc tgtcatatat ggcttttatt 124200
atgttgaagt atgttcccta gtttttgaa ggtttttata ttttaaggaa gataaaaatt 124260
gaactttatc aaatgctttt catgcaacaa ttgaaatgat caagtgcttt ttgtctttca 124320
ttctgttgat acgatgtatc acactgattg acttgtgtat ttagaaccat ccttgcatcc 124380
cgtggtaaat cccacttagt catggtgaat gaacttttta atgtgttgtt gaattcagtt 124440
tgctagtatt ttgttgggga tttttgcatc agtgtttatc agggatattg gcctatagtt 124500
ttcctttttt ttatgtgtct tttgggtttt gttatcaggg taatactggc cttgtagaat 124560
gagtttggaa tgattctctc ctctattttt tgaaatactt tgaataggat tgatgttact 124620
tctttaaatg tttggtaaaa ttctgcactg aagccattgg gtcctgggct ttttactgct 124680
ggggagactt ttcattacag cttcaatctt attacttgtt attggtctgt tcaggcttta 124740
gattttttttc atgaatcaat cttcacaagt tgtctgtttc tcaaaattta tcaatttctt 124800
ctaggttttc caatgtattg tcatccagtt gctcataatg ccctctaatg atgccttgaa 124860
tttttgcagt aaccactgta atgtttcctt ttttaatctc tgattttatt tgagctttct 124920
ctttttttct tagtctagct aaatatttgt caatgttgtt tgttcatcca caaaaccaac 124980
ttttcatttc actgatcttt tgtattattt tttcctttta attttattta tttctattct 125040
gatatttatc atttcatttc ttccagttat ttgagtttgg tttgctcttg cttttccagt 125100
tctttaagat gcattgttag gttatttatt tgaacttttt tgatataggt gcatattgct 125160
ataaactttc accataatat tgcttttgct gtatcccata ggttttagta tgttgtttag 125220
tatgtttcca atttggtaca tttcaataaa tttttaaatt ttcttcttta tttattgaca 125280
tagtcattcc agagtatact gtttaatttc catgtggttt gtatagtttc caaaattcct 125340
cttgttattg atttctagtt ttattccatt gtggtcagag aagaagcttg atatgaatgc 125400
aattgttaat aattttttta aaacttgttt tgtgacctaa gatatgatct gtcattgaga 125460
atgatccata tgctgaggaa agaatgtata ttctgcagcc attggataaa attgtcttta 125520
aatatctatt aggtccattt aagacataat gcagattaaa gccgatgttt cattgttcat 125580
ttttctgtct ggatgatctc ttcagtgctg aaagtggtgt gttaaaatct ctaaatatta 125640
ttgttttggg atctttctct tctttcaact ctgataatat ttgctttaga tacctgggtg 125700
ctccagtgtt gggtgcatat atacttaaaa ttgttgtatc ctcctgatga attgacccct 125760
ttatcattat ataatgacct tctttttctc tttgtgtagt gtttgtcttg aaatctattt 125820
tgtcggatat tagtattgct gctaattttt ttggtttcca tttgcatgaa atatcttttt 125880
cattccttta ttttcaggca gcgtgtttct ttatatttaa taggtgaaat atgtttcttg 125940
taaataaaaa ttattatttt aaaatatttt taaaataata ctatttttta ataagaacaa 126000
ttattatttt ttaaaaaatt tcattagttt tgggggcaca agtggatttt ggttaaatgg 126060
gtgagttctt tagtagtgga ttttgagatt ttagtgcagc agccacctga gaagtgtaca 126120
ttacccatat attatatata tactatatat gctttatata tatagtgtgt atatataata 126180
tatatacaac tacatattgg gtaatgtaca cttctcaggt gactgctgca ctaaaatctc 126240
aaaatccact actaaagaac tcacccattt aaccaaaatc cacttgtgcc cccaaaacta 126300
atgaaatttt ttaaaaaata ataattgttc ttattaaaaa atagtattat tttaaaaata 126360
ttttaaaata ataattttta tttacaagaa acataattca cctattaaat ataaagaaac 126420
acgctgcctg aaagtaaagg aatgaaaaag atatttcatg caaatggaaa ccaaaaaaat 126480
tagcagctat actaatatat tatatatata ctacataaag catatatata gtatagtata 126540
tatataatac atttataaag catatatata gtatgtagat aatatatgtt tatatacttt 126600
aagttctggg atacatgtgc agaacgtgca ggtttcttac ataggtatac tcgtgccatg 126660
gtggtttgct gcacccatca acctgccata tacattaagt atttctccta atgctatctt 126720
tcccctagcc ctaccccact ccctgacagg ccctggtgta tgatgttccc ctccctgtgt 126780
ccatgtgttc tcattgttca actgccactt atgagtgaga acatgtggtg tttggttttc 126840
tgttcttgtg ttttagtttg ctgaggatga tggtttccag cttcatccat gtccctgcaa 126900
aggacatgaa ctcatccttt ttgatggctg catagtattc catggtgtat atgtgccacg 126960
ttttctttat ccagtatatc attgatgggc attttggttg gttccaagtc tttgctattg 127020
tgaatagtgc tgcaataaac atacgtgtgc atttgtcttt atagaagaat gatttataat 127080
cttttgggta tatacccagt aatgggattg ctgagtcaaa tgatatttct ggttctagat 127140
ccttaatgaa ttgccacact gtcttccaca atggttgaac taatttatgc tcccaccaac 127200
agtgtaaaag cgttcctatt tcttcaaatc ctcaccagca tctgttgttt cctgactttt 127260
taatcgccat tctaactggc atgagatggt atctcattgt ggttttgatt tgcatttctc 127320
taatgaccag tgatgatgag cttttttttca tgtttgttgg cagcataaat gtcttctttt 127380
gagaagtgtc tgttcatatt cttcacccac tttttgatgg agttatttgt tttcttcttg 127440
taaatttgtt taagttcctt gtcgattctg gatattagct ctttgtcaga tgaatagatt 127500
gcaaaaattt tctcccattc tgtaagttgc ctgttccctc tgctgatagt ttcttctgct 127560
gtgcagaagc tctttagttt aattagatcc catttgtcaa ttttggcttt tgttgccatt 127620
gcttctggtg ttttagtcat gaagtctcta cccatgccta tgtcctggat ggtattgcct 127680
tggttttctt ctacagtttt tatggtttta ggtcttgcat ttaagtcttt aatccatctt 127740
gagttaattt tgtataacgt gtaaggaaga ggtccacttt cagttttctg catgaggcta 127800
acgagttttc ccaacaccat ttattaaata gggaatcctt tccccattgt ttgtttttgt 127860
caagtttgtc aaagatcagg tggttgtaga tgtgtggtgt tatttctgag gcctctgctc 127920
tgttccacgt gtctatatct ctgttttggt accagtacca tgctgttttg ggtactgtac 127980
cacttgattg gtgagagagg gaatccttgt cttgcactgg ttttcaaagg gaatgcttca 128040
gcttttgcct attcagtatg accaatatgt agtcttttat tcctcaccct ctctcaacac 128100
cccaccccca cggagtcctc aaagtccatt atatcactct gtatgttttt gcgttctcat 128160
agcttagctc ccacttataa atgagaaaat acagtatttg gttttccatt ctttggttac 128220
ttaattagta taatggcctc cagctccatc caggtgtctt gtttttcatc cattcagcca 128280

```
gtctataact tttgcttgga gagtttcgtc catttagatt cagcgttatg attgataact 128340
aagggcttac tcctgccatt tggttgtttt ctggttattc tgtggtcttc tcttcctttt 128400
ttccttcttt cctgtctccc ttttagtgaa agtggttttc tctggtggtg tattttattt 128460
tcttcctttt tatttttttt tgtgtgtatt tgttgcatgt tattgatttg aggttaccat 128520
gaggcttgta cataatattt tctaactcat tatttcaaac tgatgacaac actctatcgc 128580
ataaaaaaac atggaaagag aaaactaata aaaactctac attttaactt catctctctg 128640
cttgttgtca ctttgtcgtt tctatttaca tcttattgta ctgtttatgt cttgaaaagt 128700
agtttcagtt attacttttg attggttcat ctcatagtct ttctactcaa gatatgagta 128760
gttcacacac cacaattaca gtgttacaat attctgtgtt tttctgtgta ctttcaatta 128820
cccatgagtt ttgtattttc agataatttg ttattgctca ctaacatcct attctttcag 128880
attaaagagc tccctttagc atttcttgta ggaaaagtct ggtgttaatg aattccttca 128940
gctcttgttg atctgtgaaa gtctttattt ttccttcatg tttcaaggat attttcactg 129000
gatagtctat tctagggtaa aagttttttt tttttttttc ttcagccctt caggtaagtc 129060
atgccactct ctcctggcct ataaggctac cactgaaaag tctgctgcca gacatatatg 129120
agttccattc tatgttactt gtttattttc tcttgttact tttaggatcc tttctttatc 129180
tttgaccttt gggagtttga ttattaaatg ccttgaggtg gtcttttttg gattaaatct 129240
tcttcgtgtt cttgtacttg gatattaata tctttctcta ggtttgggaa gttctctgtt 129300
attatccctt tgaataaact ttctaccaag atctctcttt ctctctctgt ctctctctct 129360
ctctctctct ccttcttaag gccaataact tttagatttg ccctttgag gctgttttct 129420
agatctcgta ggtgtgcttc attgtttgct attttttttt ttttttgtc tcttctgact 129480
acattttcaa atagcctgtt ttaaaactca ctaattcttt cttttgcctg gtcaattatg 129540
ctgttaagag actctgaggc attcttcagt gtgtcagttg catttttcag caccagaatg 129600
tctgcttatt tttttttaga ttatttccat ctctttgtta aatatatctg atagaattct 129660
gaattctttc ttagtgttat ctttaatttc cttgaatttc ctcaacacaa ctattttgaa 129720
ttatctgtct gaaaggtcac atatctctat ttttccagga ttgctatctg gtgctttatt 129780
tagttcattt tgtgaggtca tgttttcctg gatggtgtta atgctagtag atgtttttca 129840
gtgtctgagc attgaaaagt tagatgttta ttgtagtctt cacagtctgg gcttgttcat 129900
acctgccctc cttgggagac tttccaagta ttcgaaggga tttggatgct gtgatcttag 129960
tctttggtca ctgcagccat atctgcttta tggagcatcc catgctcagt aatgctgtgg 130020
ctctttcaga ctcatagagt tactgcctgc atgctcttgg gtaagagcca ggaaaattcc 130080
ctggattacc aagcagagac tcttgttctc ttctctcact ttcccccaaa caaatagagt 130140
ctctctctct ctctctcttt ctctctctct ctctccctct cattctctgc cgacctgcct 130200
gaatctgggg tagggatgac acaatcacat ttgtagtcaa caccattggg actgtgctag 130260
gtcagaccca aagctggcac agcactgagt ctcgcccaac gcccacagag accactccct 130320
gggtaatgtc tgtgtttgct caaagcctaa gggctataca atcagtcagt ggtgaagcca 130380
gcctgtctta tgtccttccc ttcagggtga tgagttcctc aagcaggtcc agggatggtg 130440
tccaggagcc aaggcctcga gctgtgactg agctggcacc caatccataa gacaaagatt 130500
ttttccacac tttccttcct tgtcctcaag caaaggagtc tctccctgtg gccaccacca 130560
cccccatgtt catggcaagt attgtctggc taccaccaat cttcactcaa ggcccagggg 130620
```

ttctttagtt agcttatggt gaatgctacc aaggctgagt ctctcccttc aaggaagtgg 130680
gctcctctct ggcccagggc aggtccggaa atactatcca agagccaagg cctggaatca 130740
gtttccccaa gagtccattt ggtgctctac acccactgtg gcagaaccag tacccaagct 130800
gcaagacaaa gtcctcttta ctcttccttc tcctttacag agactctccc tatagccacc 130860
acagctggga atatgctggg tcactcttga agcaagaaca gctctgagtc tcactcaaaa 130920
ctcctggcaa gtactgcctg gctatcacac tgattattca gggcccaagg gctctttagt 130980
cagcaggaga tgaatcctgc cagtactgat tccttccctt caaggcagcc ggtttctttc 131040
tggcccagtg tgtatctaga aatatcattt gggagctagg gcctggcatg gtgacctcag 131100
gactctgcct ggtgccctgt tctactgtgg ctgatgtagt atccaaattg caagaccaag 131160
tcctctttac tctcccctct cctgtcttca agcagaagga atgagtccgc cctggagttg 131220
ggagctgcat tgcctgggat tggaggaggg gtggcacaag cactctcttg gtcaccccag 131280
ctggtgtctt actaggtcgc atgttcccca agtccactgg ctctgaggct agcacaccag 131340
gatttgacca agaattgcaa ttcttgtggc ttacactgcc tttcaagttt atttgagatc 131400
ccagagcact ttagcccaca gtgacagggc ttgccagaat ttagtttctg actgctgaga 131460
tggacaattt gcgtctgatt agggctggtc taagtgctcc ttctgtgggc actggctgag 131520
ttctgctcca tgttgctttc tgctgtgaca gggcaacatt gagtttcaat gcaagtccca 131580
cagtcactgc aatcttcctc tcccaagcct gctctgaaca ccatgtggtt gctgctgggg 131640
gctgggggag ggatgttgta ggcaattcaa gaatgtcttt cctacccttt tcggtgcttc 131700
tttccttggt atgatattaa aaccagttac tgtgattgct cacctgattt ttggttctta 131760
tgaaggtgct tttttgtgtg gatcactgtt caatttgtgc ctgcaagcgg ggatggggga 131820
caattgctgg aggcttctct ttggccatct tgctccacct ctaccctagt attagcaatt 131880
tcaaagcagt tgggatggag gtagaaggaa agggcgcttg gaatcagaaa atccatgtct 131940
tagctttgag ccttagaaaa ttcatttgac ccttgtaagc ctcagttgct tcatctgtaa 132000
aagagaaata atataatggc tgaaaagatc aaaggtgata atgcttttga aaacactata 132060
gaaaatgaca aaatatcaca tgagtattat tttctagttt ctaggagtct ccttaccatt 132120
gtacaggaca accatgtcta tttttaaata aattattatt tgcctctgag caaccctgca 132180
aagagttgcc tgtaggagaa acagctttac ttgcaaatca ctccactgtt ttctttgtgc 132240
acagcttatt aatacataag gcacatgtcc tccagcctgc agtaacattg gaatcattac 132300
ctctttggag tacctaccag agcttctcaa agtgaatttt gtttatcacc acaaaaaaata 132360 gtctgttgca gagataacct ccaaattcaa tgacaatatt tccaatcact tttgcatgat 132420
gcagaaatag acaaatatat aattttgctt atagagacaa ttattgtctc ccaacaagtg 132480
atcagtagtc agaaaatggc caagaaatac catggggtgt gccttcccat aacagcttat 132540
ctttgtgttt tagttgcaag gttactaaaa gcctgtgcag ggtttatggc aaaagtaaaa 132600
cttgctccag gagcaagccc ttgtttcatt gtctaatgtt cttaatcccc agcagacagg 132660
atttggatct ggcatttggt aacagggcag tttccaaagt tgctgtacgc aacttgagga 132720
agagaggtga tattatcgga atgaatttct ttgttgtaag ttataaatgt atgggctttt 132780
ccaatcccat cacccttaaa actttatttg ttttctgcag tgagggtgtc tccgttgtct 132840
ttaatatgct tgctttgagt tcatggatga acattcctgc ctggctgaca tgtggactct 132900
ctgaaattgt tataaggtct ttttctttgt ttttttcttg atgcccaagc tgccaagggt 132960
agtactggca gtggtgggca gacaaggagg tgatagcaaa ctttgtcctc tggcctccct 133020
tgacccattc cattcattat ctaagggact ccaagccagc attccacaga gtgccctcac 133080
caaactcact aagactgaag gcgaaccagg attccaaaca gccattatga aaggaaagag 133140
agagagactt agggtttgca aaataagata ccctgttgat tctttttatt ccatacagat 133200
actactattc tttaggaaaa cgttaaaatc acatgatctt ccaggacctg ggctgcttct 133260
ttaagaagca tgttacagaa agctttattg gccaacaaca tattgaaaga tagattaatc 133320
aatcattcat tcaaataagg tatattcaga attgaggtat attgtagcca gacagtgaga 133380
ctacaaaaaa agaatgcacc gtacccttat ctcttgcaca atctaacgag ggagataacc 133440
actctttcaa tttatagtga cctataacat ttcgtacact gctgaatatc tttacatggt 133500
aataacacaa tggaaagctt gcaaaataga cagaggctag gggaagaagg attgagtgtg 133560
aatatagcct cttataaatc gagaggaatg gtctgtgtct tctgatcata cagagataat 133620
aaatatggaa atgatttcaa actaacaaag caaatgtgca gaaaatactg agaatatagt 133680
gggcaggata cctgagtttt ggttccatct ctgttattga ctcattgtgt aatctgagtc 133740
aggtctgttc tgctctctgg atctcaccct ttcctatctg taaaatgaga ttgttggatt 133800
agatgatctc catagaggtt ctcacctatt ctgacattca aaaggactcc taatttttct 133860
tatataataa taatatatat gatctgtaga gtgctttaca ctttatatga tatttttgca 133920
tctgttatct catgtgagaa aagcactgga ctgctggact ggcaatgagg acacctggat 133980
tcttgtctct gttttgacac tgattcatgg tgtgatcttc aagcaaattc tctgagtttc 134040
agtttctcaa tctgtaaaat agggggggtat gaagattgga ctaaatcagt aggtctctaa 134100
aatgttccac aaagccctgg ggtggggggc tcctacagag tttcgctaag gcaaaccaca 134160
acgctaagcc tgcatggaag aggagaaaaa gagtggcctg acaagagaag ttcccagttt 134220
cctatgccaa ccccaggcag attacattta attttatctg atttatatag agagtttcta 134280
tgtaatgttt tattcttaaa aatagtttac tataaaaaac tcaactggtt tgatttttaa 134340
agattgcaca tataagtgag atcatgcagt cagtatttgt ctttctatgc ctggcttatt 134400
tcacttagca taatgtcttc cagcatcatc tatgttgctg caaatgacag acttttcttt 134460
tcattaaagg ctatatagta ttccatcgtg tatgtacacc acattttctc ttttgtaact 134520
ttcattttag gttcaggggt tcatgtgcat gtttgatata taggtaaact gcatgtcaga 134580
gaggtttctt gtacagatta tttcatcacc caggtaataa gcatagtatc taatcaattt 134640
ttttctgatc ctctcccttc tcccacccta caacctcaag taggccctgg tgtctattgt 134700
tcccctcttt gtgtccatta caccacattt tctttatcca cttatccatc catggacact 134760
tagtttgctt ccatatgttg gctattgtga ataatgctga aaaaagtcaa actcatagaa 134820
gcagagagta gaatggtggt taccagggac tgggaggcag ttgactgagc taggaaaaga 134880
gagataataa aagggtacaa tgtgtcagtt atatagaagg aataagttat attgaactat 134940
tgcacagcat ggtgaccata gttaataata atgtattata tgtctcagta ttgctaaaag 135000
agtaaattta aatattctaa ccacaaaaaa ttattagtag gcaaggtgat ggatatgtta 135060
atttgcttga tttaatcttt ctagaatgca tacatatatc aaaacatccc actgtacccc 135120
ataaatatat acaattatta tttgtcaatt tagaaattta aaaacttgat ttagatgagc 135180
tctaaggcct taagtattaa agtattaagt attaaagtga tatgtaacca agtatattgt 135240
ttggtaactt catttttgtt attattttaa caaaccaata tattgtgaat atacttccaa 135300
gtgaaaagaa aaaagacatt gcagtcatca ctaataactg caaaacattc ctttgcaaga 135360

-continued

```
atatggaata attcatttaa tcattcccct aatgttagac attcaaatgt ttccaacttt 135420
ttctatttaa ataatgctac aataaacttc tattttgtgc ttattgtatt attttcttac 135480
aacacatccc tagaagtgga attcctagaa gtttatacac atttccaatt tttttccaaa 135540
tatatggcaa aatttctctc taaagtattt ttattcctac cagaaatacc tcttcaccaa 135600
cacgtagtat ttaatctgta ccaatctggc ttaagacaat gatatttaat ttgtatttct 135660
gtgatttcta gctaaattaa ataatcttca tatgcttatt ggtcatttgt acttctaact 135720
gctttctcct gtctgttgcc catttttcta ttgtgctgtt tatttttata tatcgaatat 135780
attgaccatt ggttttacat acttgatgct aataattatt cttagtttat ggtttgtctt 135840
tgagttttat aatggtgttt atttcacata agaaattata aatgttttct aatgaaattt 135900
atcaagtctg tcttcactta tgttttcttc attgtcaata acttaaaatg accttttcta 135960
cctttaaaaa ttttgaaatt ttcctctgta ttgtctaata gtacttacat gatttcctct 136020
tttaaattga catatttaat ccatttggaa tttattttga ttttaactag taatttaact 136080
ttattttctt ctccaaatga ttcactagtt gttctgacat tatttagtga ataattcatc 136140
ctttcttcac tgaattggaa tggcatattc catatactgt gtctggtttt ggcttttctg 136200
atctcttcca ctgatcaacc taagctggag ccagtatcaa actgttgtaa tcattatgcc 136260
tttagatact ttaaatgtac agcagggaat gtcttattac tcttattttt cacaaatatc 136320
ttggcattgt ctcatgtttt attccttcag ataaattttg ggattatttt gtcaagattt 136380
tgtttgagtt gttttaaatt tttagatttc attgggaaag aactgaaatc cttgaaatat 136440
tgcttcttct tagccaggaa tatggtacaa ctttgcattt aattcagttc tttccttaaa 136500
taccaccatg aagtttttttg ttttgttcat ataggtcctg cattaacacc atatatataa 136560
agtgtgagaa atactacatt cttcaggatt ctctgtaggt taacaatgaa gatgatgact 136620
caaccctttc tttgtttgca taatgtgatg ccactaatag tgggtaactt ctctgcctta 136680
cctcctctgt tccaaacagg atttttcaga atgaacaaat taaaagaatc ataatcagac 136740
actaacccca agccatactg catggcagca ccaatgggac tgacagaaaa caacagaaat 136800
aggaagaaat cctacagaga aacaaacttg aaagctgtct catggccttt gaatcatact 136860
taagttttat gatggaagga tacgactatg aagaaagaca cagagcaaca tcagacagtc 136920
aagaatttca gagccagctg gcatgcagtg gacctcatgc cagcccattt tatgactatt 136980
taggtagtca agggtttaag atttttctaa taagacagtt attatgcatt tcaatgagtg 137040
atttctttgc agctctagag tgtggcctta cctacttcaa catgagaaga tttttgtatt 137100
ttgtcagtca tttcacaatg acttttagtg agcccttcat tatagactgt ggatacaact 137160
ttgctgttgg aaattaacag tgtcaaacaa ctgggtataa tgtttgtaat atctgaggag 137220
ggggagctgc ctaggaagtt gtattccctg tgttaatttt tcagtctctt aggttataga 137280
ggaccttcta gaaccacctt acagcaggat tacatcccat ttacacagtt ctctgtcact 137340
tgaatacaga gaagggatcc acaaggccat atgcttccta gacaaagaga aaagatttct 137400
gccacactca gaacgctttg tcttcagact ataatcaccc acaccatatt tcctttggat 137460
ccactttcca gatttttgtg ctggcactaa caccaacttg ctgtggcttg gggcatgtaa 137520
tttcaatact ttgtgcccat tttcataagt gaagtgtcag gcatcacatt ggacatttta 137580
agattcttta cagcccaatg attctgtgtt tctaattagg cccaatgggt tagagctaaa 137640
aggaaacagt gagtttcctg gaaggaaagg acatataaca cagtccagag gtaaaatggg 137700
ctgtattcaa gaaaagatag gacaatactt tgcagggatg ctgcagagag gattcaagcc 137760
```

-continued

```
ttgtatggag gaatggatgt gatacaacca aaaagtcttt aaaaattctt tccaactaat 137820
ctgagatttg taaccttatg gactgtgatt tgcagcaaac caaggatgtg ataaagacta 137880
gtattgtttc tagaatgcaa ggatggttca acatatgcaa atcaatagta ttaacagaat 137940
gaaggacaaa aactatatga tcatctcaat agatgcagaa aaataatttg acaaaattca 138000
acatcatttt atgataaaat ctttcaagaa attgggtatt agaaggaatg tttctcaaca 138060
caataaaggc catatcagac aagcccacag ctaacattat attcaatgac caggaatgag 138120
ataaggatgc tcactctcac cacttctgtt taacatagta ctggaagtcc tagccaattt 138180
catattaatg agcctcattt tcttcatcat agaatgaagt atataataat ccctgttata 138240
cttactttgc acagattatt attattattt aattattatt ttgagacagg gtctcactct 138300
gtcacccagg ctggagtgca gtaccacaat cacagcttac ttcagccacg acctcccagg 138360
cataaaggat cctagcccct cagcctcctg agtagctggg agtacaggtg cacaccacca 138420
cacctagcta attttttttt ttcatttttt tatagagacg gagtctcact atgctgccca 138480
ggctggtctc aaactcctgt gctcaagcaa tctttccacc ttggccttcc aaagtgctgg 138540
gattacagga gtgagccact gcacctggcc ttgcagatta ttattaaact ttgtaaacta 138600
atcaaatgag agtgattatt gttactgtta agaactctga tagcctcatc catatatttg 138660
gagaaattga ataaataata ggaaagaaat aatagcatcc caatgatttt accttggctc 138720
taccatcatt tggggaagtg ataattcaga taggagaagt gacttggaag cagtcttgag 138780
agattgcctg ttccatcccc tatctttgtc cttaaaccaa attgtacaga taaataaggt 138840
cttattttta ggacttacag aaaaaagatt cctttcatat ccatctttgc aatcctcaac 138900
cacttctgtc actattatgt gtcatttcaa acattaaatt cctcattctg ctttgaagga 138960
acacatgtgt catgtgtacc catttgtatg ttttggtgtg ttttatgctt tatgtgatca 139020
cccacatatg cacagataat tccaaaatcc agtgtgtggg tgttgtattc cctgtgttaa 139080
ttattcagtc acactcaaac acctatgcac tcacacatac atgaatacac acatgtacat 139140
tagcatgttt atgcttatgt tgcatgtgac tggcaacatc agtgcctttc taaggcaatg 139200
ttaactacct tgagttttgg gagagcttta gagaacaaag acaagagact aaatgattct 139260
agatgtaaga gacaatgttg caataagtta ctatcctaaa aagacagaat acagggacaa 139320
gagactatta ttttggatag tttcttgctt accagtaata cttaagtcct ttacattaaa 139380
aaaaaaaaac tctgtaaata tattgcagaa gaaatccaga catccttcaa gattcttaga 139440
gctggaaaag attttaatga ctttccagtc caatctatct catgtaatca atggggccca 139500
gagaggcaaa aggtcttgtc caaggtcata tagtgagtta gtgataaggc tgaacaagga 139560
ttcagatgtt ggggcttcca gcccactgct ctttctctca tctgggattt gtgtattttt 139620
gttcattaga gattttcctc tgtaacctca atatccaatg cagggccttg cacataatag 139680
attatcagta aatgttaaat taatatgtca tggctttggt tgtactgggc ttttgcactt 139740
actcctgagt aaattgtaaa gaatatctac gttttaggtt gccttgtttt agaccaagag 139800
gtacccagag aaaaggtgtg aactatgcta aggaaattat ccgagttcca aattgaaaaa 139860
aaaaaaaaat catgcttttc cgctataacc tctctcattc acagagtgat tctctttcag 139920
aagggcaatc tagaactatt atgggagcca tattccattg gtggtgcaac catttcttga 139980
caaactaggg tccaagaaag tattttcctg gggaagatga gatttctcaa agaaggcacg 140040
cactttctaa cctaagctta tttcagtaat caatgtaaca agctggtctt gatgattgca 140100
```

-continued gcagtaccaa tactgtggga gtgtaccagt tctagaacag ctacaacatt ggaattgaac 140160
gcactagaat tggatacagg acctgttttt gaggagctaa cacccaaagg ctgaacagca 140220
ctcgtagcac cgtcctttct gtgcacatat ggtagtcctc agtttgcaac agaaataaag 140280
ctgttagcaa attatgtgtt ctatttatgc aaataaaatc ttgtggtatg ctagaaagag 140340
cactggcctg gagaccttag ttttctcata tgttaaaaac ccctaacaca ggcctggttc 140400
atagtaggca cccaataaat agtagttttc ttcctttggg ggcctccgat tcagtgtgct 140460
tcttcaggta agtcacttcc ctggaactcc tccttggaat gagagttgta ctgttgtgat 140520
ttttaacagt tccttcaagc caagcatttt ggaatccttt cataaaggga gaaaggaagg 140580
aaagaagaaa ggaaaattaa aggaaaaaga acaaataaaa cgttaaaaag gaggaaagga 140640
aaaaggatcc tttactacaa taaaactaat cttatgttct tgcaagtagc actttaagta 140700
aaagaagttc tttgctgacc tggttactac tgaacctact acataaaata gcctactata 140760
atagatgcat ttatgtgcct aatcttcact ttttaggctt agtaaaggga gaggaaagct 140820
gatgtatagt taaatttatg tttttagttg ttttttttc tactctcaaa tatcaatcac 140880
tctttagttt ctctttcttt ttccgaccac aagcattctt cctctgctta aagaagcttc 140940
cctaaaatcc cagtctatcc agtaagccaa agcacagcaa taaatttgag gaaaaaatac 141000
cagggactta gagacagaaa ggagtgaggg gatgcagaag ctgaagctgg agcacggttg 141060
caagcatgag aagttctgcg tgtttcagag cagccaagga tgtatttttg cctattcctg 141120
ctggtgactc tgtgtgtcta tgcatccatc tgctatattt acatgtttag tcagtcaatc 141180
cacgtttgct gagagcctgc tgtgtgccag gattgtgcta gcgtaaagga gcaaagtatt 141240
gagcaaaata tgtttgagca gctgtaattc tgaggatctc taggtctgag catgtgtatg 141300
tgtgtgcgct tctatgtatc tgtgacaact ccaggtgttc atgacagtga tctttgttac 141360
tctgttggct tcatcgaact tccttttact tgctgtgatt cactacatag agtgggcttt 141420
atctctgatt tttataacct gcaagactgg gggtatgatc accagcaatc taaaaacagt 141480
tagaaatccc atggagttat cttttgtaga aattttcctc tactaatatt atgaaaaata 141540
agcatcttat tagctcgagt gtaattctat gcatgattac aggtatcaat aggaagaaac 141600
attgactgag ttcaaatctc ttctacgcca tgctaaaggg gtgacaagtt ccacaatgga 141660
tcattttctc atgggcattt ctgacttttg gtaaaagtag agcaccttat tttaaaaacc 141720
attgagtagt cctaatagtg gagatatcat caggatctga attgttcatc cctaaaaaaa 141780
acaccaatgg aaatcaaaca atatagtgcc aaattaaact gtttgaatat ttaggttctg 141840
tatgatcaaa ttgtttggtg ccatactctg tccacttttt tcatgtggta ggatataatt 141900
tcatatcttt tctgttctag aaatacccga agaaagagac tctggaaact cattatcagg 141960
tctatcaact cttgtatttg ttctcccagg gaaacagaag tacctgtgcg ccagcagaaa 142020
tgattgcact attgataaat tccgaaggaa aaattgtcca tcttgtcgtc ttcggaaatg 142080
ttatgaagca gggatgactc tgggaggtaa gatacttttc tttctcttcc tcctccttcc 142140
tctctccccc ttctccctca ttttctagtc tctctttaga ccagattttc ttctttgatg 142200
cttccaaggg gaccagccat gctctagaca caggctgacc ctttcatagg caacgtggcc 142260
atcagccagc tggtgccttt tttttaatcc ttatctatac caatccccat tccggggctc 142320
agcattagag caggcggtgt gaagcaggga tcaggagcca acagaaggtg agtgaggatg 142380
catctgactg ggcagggccc ccaggggact taatgatact ggcctgatgt tgttcagtgg 142440
tagctaggat gagagaacta agaaatccag aacagtcaga ggtgcaggat gacccaggca 142500
taggcgcagg atgacccagg cacaggctga tcctgaacac ctgggaatat cccttagcta 142560
actgctgcct atgttgtagg gccagccacc tcgaatgaga agctacttct ctttggagcc 142620
tgtgactagg ctgccacaca gagccaattt cctatcctat ctctcccaaa gatgagcagg 142680
tgttttaata atttcctttt ctttgcaaag ctattgacca tttccaaaag catttttttt 142740
cagtagcaca gtaacgtgat agatggaaga tacagctctt tcaagggcgt tcctctatca 142800
taaggctctc tgtcccacaa acctgtctac catgagtgtt gtcaccattc cagaaaggct 142860
tgacatcagt tgattgagac ttatattttc cctctccaaa ctcccccatc tcttcatgtt 142920
tacatctgcc caatgccagg gtcctcgctg ctgcctgcta cttccaaaaa gatgtgtctt 142980
tcatgagaaa aacaagatca ttaatccact tcgatttgga aatggaattt gaagaaaggc 143040
aagcctattt ctgagtgcct gcaactgtag cctcataccc aattattcat tattagcctg 143100
gaaaacccaa gtgcctagaa tccaaccctc tcccctctcc tcttaagtct aatttagacc 143160
agttgtctat ctctggcttt ctgtgaggtg ttcaatacct tgtctgccta tgtgcacatt 143220
tatagacaac aactagttct cttatcctgg agcagggcca tgtgtggatc ttcatataga 143280
taactatatc ctccccatcc tcacagggca gtagtattat ttaaacagaa caaagtacct 143340
cacatgaatt gacccaggct ggatgagaga caatttcaaa agaatcatct caagtagcgt 143400
ccagtactcc caaacatcac aggtagatgt tctgtgagtg gctttccaag catccacatc 143460
aaatgagact cagatatctg agaaaactca accttgtttt ggtttgcttg gtgcacccca 143520
aagaaatcca acaattgagg tctacagtgg agaagaagta ggactggggt cagggagtac 143580
agaggcaaag gcaggaaggg tgacaaagtg attgacaaga aaaaatgttc tccatatgaa 143640
tgttgcagcc ccatgttgag ggttcttata cactcaactg tcaattattt agccttctgt 143700
gaattatgta tagtataaaa gatagggact ctcaagtagg gaacctcttg gcttgccatc 143760
tggcaatatg aattgcaagt ccactttgat gcaggtaaag tttaatggta acaaaagtcc 143820
tcataacatt tggatgcaaa tcttaacatt aattccatgt ctcagccaac attctccatt 143880
attaagcagc ctgtgatgtg attacagtga accacttttg aaaaggagcc tgtgtataac 143940
agatagtttc actatactat ataaccgtca gatgcaggct tgtaaattaa tttgttggtg 144000
acaatgtttc agtacatttt caaattgatt cattggtata gtactcaaat ttgagtgggc 144060
ttggtgaaca caatgaagac aagctgagaa gtgctgtgac tggccttcat ttcagttgca 144120
ggcccatgat attttgagtg tcttccatgt acaaggcacc atgctaggca ttagagcttg 144180
aggctggcaa acttcaggaa gtgttcacaa gataccagga ttcttgatgt tgtgtaaatg 144240
gccttgcctt tagagtcagg cagatctagt ttaaaggctc agctccttta tttactgtgt 144300
gcccctctga gcctcaattt cctcatctct gatttagaaa taccatcctc atagagttat 144360
aatgagtatc agatgacatg atgaatgtga acatccttga taaatagcaa aatgctagac 144420
aaatatgggg gcttaatatg acattgaggt cactagtaat ttagctggaa agtctgtaac 144480
acagcacttc ccgatggctt ttaccctaag taacttggta tgccatataa tatgtaacag 144540
caccaacagg cagagaatcg ccagaaaaca ctcttgatta cctcaaacga aaaagtacca 144600
ccaggatcct gttcagaagc taattttagt aattaaggga atcatatgct atgttcaaat 144660
accatgccag taaaaaccca attgtttacc ttcttaaatc actgcttgaa gagcaaatct 144720
ttccattttg ctgaatgaac ttatctccac gttccctgcc ctactgacac aaccccctcc 144780
caagtttatt gttaacttac acattcaatg cacagcacac ctttactcaa acaatggaaa 144840

-continued agaaagaaag tgtcaattca aagtggccct tgtctattcc ttaaggagta gacttccatt 144900
ttcatcagat ttggatttag catagacata ttgattacct tgaagaagaa ttcatataat 144960
tttatcttct gattcccatc actcaaatca aaattacata atatattcca aaatggcaac 145020
taggaatgtg gccttgggca agtcccttct ctcctctgat gcttggtttt cccatcatag 145080
aactggaatt gtggcttcac cgaggacctt tctggtgcta acattttgtg attctatgta 145140
aaaagccaca cagaaaggat tgtttttcag ccctttctta gattgtctgt tccctgctcc 145200
cagaagtata gatagtgaga cttgagtgct ttgatacatc gtaattgtat ctacctccat 145260
tcacacctac ttaagatatc tgtctaaaag tagactagac agattattca gagagtggag 145320
ggcagaaggg ctgtctctgt atcttaaaga agctggcact cttcagctga tggctgcttg 145380
gtcttgaggc ctcaagatct ttaatctggc tttctctata gtgtttcatt cactgtttgg 145440
tgatggaatc tcttcagttc agagatactt aatagatata gctttttctt tcctgcttcc 145500
aggcctacct acctgtttct tgcttttttt tctagcagct gttgttgttt ctgaaagaat 145560
cttgagggtg tttggagtct cagaatggct tccttaaaga ctaccttcag actctcagct 145620
gctcatccac aacagagatc agcctttctt tgtagatgat tcattcctgg ctgcatttga 145680
aaaccacata ttgttaattg cttgacgaat ttaaatccct tgactacttt tcatttcaga 145740
aaacacttac aaaaaaagtc caaatgagga ccttccctcc agtgaattag ctgtggcttt 145800
ctcacagtcc atagttagga taaatgtaaa gccatttctc atttttctcc gcactttcca 145860
agggtacact ccttgtttcc aagatggaat gagaaataaa gaagtgccct tcctgccatc 145920
ttctcccctg accctttcct ccttcccact ttcctcctat tcctccccaa acatgattta 145980
tttctgcgtt ttgcaactct tgagttctca gcatttagta aatggtgttg gtccctgttg 146040
attccttcct ctcctggacc atggaaggta gtaggccttt cagaaatttc aggtagcagc 146100
caaaccccag aagaagagaa ggaacacaga gacctagacc atgtgagaac ctgaggtgtg 146160
cagcatttac ttcacagatt cgtctagcat atttgagagg tgtctttcct actaggagac 146220
tgaactctgc atctgagaat aaaaacttaa catatctaca ggttttgaca acctctgtga 146280
attatctagt tgagaggatg gctcaaggag cctattgcca tggtctgatg tcgttatgga 146340
cgctatgaac atccttgcag tttccattgt tgaagacagc cctgatgcca gctgtctcat 146400
cattccccat gttcaagagc atcccagcat tgctacctca ggatcccatg tcctgaatgc 146460
aacagagtga tttcgctgct gaattactat tcatggcatg gctcttcaca gcatttattc 146520
atccatgtat ctatccattc atccttccag ccagccaaga agttcacgct ttcatctttt 146580
catccattta ctcacctatt tattcattta gcaaatattt attgagtacc aactatgtgc 146640
cagacactct gctaggcatt ttggggaagc agaactgaat aagatactat tcctttcctc 146700
aaaaatttga gcaagaggag aaaggaagta atgaggaata ttccttagcc ataaaggaaa 146760
aataagaaat cacttggaag aagttaggtg agatggaagg aaaaggacat ctaaggtaaa 146820
gcgtacagtt tgaataaagg cacagagaca tgaacaaaat gcattgaggg tttgaggaac 146880
agcaattggt ttaacatggc cagagctggg gaaatggtaa gggcaagctg aaaccacatt 146940
gaaagcaaac ttggttatta tactaggtag tttagacttc aagcagttga aaatctttga 147000
gcatgggata ggcatgatga cattgtgttt atttgcatgt ttctttaaag aaaactggca 147060
gcagcacaaa tgttttgttg atgagggttt aaattgtaga aagtgagaca attttaggaa 147120
ggccagctag agagaaattt ctagcatcaa attttgctaa acacctagga tttgtagtta 147180
cctccatttg ggttgttacc tgcaagtact gaccacgtat atgaagaagt actggtttag 147240
accaaggcaa ttggcttgta taagaggcct accctcatac caaaagccag tttccttggt 147300
ctaggccagt gtttactggt atgtgtcctg agaaaactag ttccatgaca tgttccatga 147360
aaaatatgat ttctattgtc aaataagtga gggaaacttg catatcatgg tcctgctcag 147420
gaagatttac aatccttatt agcatatcac aggtcctggt gaatactgcg gtaaagtaac 147480
cgaggagctt tgtaactcag gattcccgaa gttgattcaa ccacaggacc tcatttattc 147540
acataacacc tgttatccta caaaaccact gttctctgga atacactttc gaaaacatgg 147600
gtatagacaa aaactctatc ctataggcag agaataccta tacctctagc tcaggtcatc 147660
attttgcaga tgtgtgtgtc attaagaatc agtcaataat gcattaatga tcaaaagcag 147720
accatcctta ccacatggtg cataagatta tgctattatg ctattagcta ctaatgccac 147780
taaagttaat tatgttgggt ctgcaacgtt gtcatacaca aaggatagga tgcaaaactg 147840
tcctaggcca aagcatggtt attgcccaag ttatctaatg tctgcaggta catattcctg 147900
gcctaaggat tgtgctaaag aagttatttc taagaaatat agtgacttcc agcatcatgc 147960
agaatgacca tttaatattt tgaatatcta gacattctgc tgtagaattt aatagtcctt 148020
ttatacactg tctgaccaac attttgacat ttactcagaa ccccatcaca gtgctaccac 148080
ataacctcat tgctaaagtg ggaggcctag aaatcacaga tttgtagaaa ccatccaatg 148140
attgaatccc ctctacttcc tgttcagcag gcagcagagt gtcataaaga attaacaacg 148200
tggaactcag ttactgggat ttcttccatt ctcctttgat tctctagact agaattccaa 148260
agaccctcag gctggtgatg caagtgggaa gtctcatttc tgagaagtgc tgcttcctac 148320
ccacaattct ttgatagctg agtgctttag ctgatctgca taactgaggt gtgcaccaag 148380
gagcagaatt actctataaa ttttggcatc aacatgtgca acttgtgact cagcactttg 148440
aaactctggg gatttttttg tttggttggt ttttgtttta agatgtcctg tggtatagtg 148500
gaaatagtac aatagactca gatacagaga ggccttgttt ctagtcttgg ttctgtcact 148560
tactatcttg atgtccttgc acaaatcacc agacctctct gagcctcagt ttctccaacc 148620
acactgtggg aataataaaa tctttttttac ggcattgttg taagtatgta gagaaactgg 148680
tacacagtag gcacacaatc aatgtcaccg tacccttcag cccttctttt gtggatgaaa 148740
aatggtcttt gtgctcccag tcaccactgg ggtctgttct ctctctctct gctgttacag 148800
tgtggctttt ggttcttgtt tctttgttct ttggtctgta aattaccctt gaaacaaccc 148860
ttgaaatttc cactccatga cctaaatcgt catccctaaa ttggttacat acatatttgg 148920
tgacactttg gaggggaaaa gctttatgtc tctctaactg tagttcttaa gggaatttgc 148980
atatggaaaa aacagagact gcgtctctta attcctccaa accaaattat ctgggatagc 149040
acatatatgt tgtactctgt ctctgagcat ttgctcttag agaactatgg ttagagcgaa 149100
gtaaattttt ctaatcataa aaattaatga taccgcatat ctgatacttg aatgagtacc 149160
tccttgtaaa atttatactt aaatccttga gtttttaaag tgtaatagca atagaaagat 149220
tttattgttg tttactttta ctgtgagtgc tccaaaatcc ctcagttgct cttgaaagag 149280
caagatgatg ccataggcaa tattttccaa aggtagtagg cagaaaactg agtacacagc 149340
acacaatagg ccatatatac aaaagcaagt attttgcaaa taataataat tcaggaaaaa 149400
agcttcactt tcgttggtaa cctgtttgtt taaaaccatt ttattattta ttatttaaaa 149460
agagtgtcac ttgttacaga ttgtgggatg tgttccttaa gatcacaaaa atgtaaaata 149520
ttttcttttt atactgaaca catgcataga caacttacct gagcaagctg ctttttggag 149580
acatttgcac atcttttggg atcacgttgt taagaagtag aactaaggga aaaacacgca 149640
gccacccaga aatcggtaga gccttcagct catctgttat taatatttct gtgacaacag 149700
atatctagga agtaaacagg aaattgcatc gctatcctgc atcacctttt ttggaatcag 149760
gttccattct tctcagtcca gttcaacctt gtgatacttt ttagatctca accaaggcat 149820
agaaatatat tttcccttgc ttaatacccc atggaaccaa tgcccctgtg gttgaagtaa 149880
aaattgattg ttgagggaca tttcagccct ctagcagtca acaattaaaa acatgtaagc 149940
accgagcacc tgcagaaaac ttggactggc atttggatct aagaagaaaa tctgcatctt 150000
gaccaagatg aaaagtcacc agcccaagct tgtgcagtga agtgtcatgt tggccacaat 150060
gaaactgaaa gagactgatg actctcctca gggtggaaaa tgaggcatgg aagctttgat 150120
tagtgagctg ttaggcacac agacattaat ttcaaagcat tctcatctcc agtctgagta 150180
ataatgctta tagtattatg caattgtttg gctgctgcaa gaaattcagc agactccaac 150240
aagtagtctt tcttggtctc tgagtgactg taacttaaat tctacctccc ttctcttctc 150300
ctacatcttc tcactcccca ccccaccccc acatacacac aattcttgtc cactatgttc 150360
agagagatgc acgcacacat atatatgtat atatatagta tatttgtcaa taaagcagaa 150420
aagaagaaaa aactccaagt aaacaatttt ccatttcccc atctcacttc tgtcttacaa 150480
gtggatagga aaagaaaaac ccccagtaaa aaatggcaac cgcccacctc cccaacttta 150540
catgctgctt cctatgttag aggatctgtc ttaggcatct gattatggag cctgctagat 150600
acaagcccgt atttagactg ctacagtcaa caatgtctct ctttcatact agaaaaattc 150660
cgggttggca attgcaagca tctcaaaatg accagaccct gaagaaaggc tgacttgcct 150720
cattcaaaat gagggctcta gagggctcta gtggatagtc tggagaaacc tggcgtctga 150780
ggcttaggag cttaggtttt tgctcctcaa cacagacttt gacgttgggg ttgggggcta 150840
ctctcttgat tgctgactcc ctccagcggg accaatagtg ttttcctacc tcacagggat 150900
gttgtgagga cgggctgtag aagtaatagt ggttaccatt catgtagttg tgagtatcat 150960
gattattgtt tcctgtaatg tggcttggca ttggcaaagt gctttttgat tgttcttgat 151020
cacatatgat gggggccagg cactgactca ggcggatgca gtgaagctct ggctcagtcg 151080
cttgcttttc gtggtgtgct gccaggaaga aactttgctg atgggactca aggtgtcacc 151140
ttggacaaga agcaactgtg tctgtctgag gttcctgtgg ccatctttat ttgtgtatta 151200
ggcaattcgt atttcccccct taggttctag ccttctggat cccagccagt gacctagatc 151260
ttagcctcag gccctgtcac tgagctgaag gtagtagctg atccacagaa gttcagtaaa 151320
caaggaccag atttctgctt ctccaggaga agaagccagc caacccctct cttcaaacac 151380
actgagagac tacagtccga ctttccctct tacatctagc cttactgtag ccacactcct 151440
tgattgctct ctcacatcac atgcttctct tcatcagttg taagcctctc attcttctcc 151500
caagccagac tcaaatattg tattgatgtc aaagaagaat cacttagagt ttggaatatc 151560
ttgttctctc tctgctccat agcttccata ttgacaccag tttctttcta gtggagaagt 151620
ggagtctgtg aagccaggga aacacacatg tgagagtcag aaggactctc cctgacttgc 151680
ctggggcctg tctttcccac cttctccagt ctgtctaaac acacacacac acacacacac 151740
acacacacac acgctctctc tctctctccc cccccaacac acacacactc tctctctctc 151800
tcacacacac acacatacac acacacttct ttctctttcc cctgactcag caacattctg 151860
gagaaaagcc aaggaaggac ttcaggaggg gagtttcccc cttctcaggg cagaatttta 151920
atctccagac caacaagaag ttccctaatg tggattgaaa ggctaatgag gtttattttt 151980
aactactttc tatttgtttg aatgttgcat atttctacta gtgaaatttt cccttaataa 152040
agccattaat acaccaatcg tattttctta tttacaacag actgagagaa ttaatgctgt 152100
taacattgga tcttttttct tttttttttt tcctttttttt tctctctcgt ttgctttcca 152160
ggtcatgctg acctgttcag cttggactgt ttcacatttg tttttaatgt cagtttaaat 152220
gtaattgtaa aagcatgtat gctctaaaat catgtagtta cttttttcag tggaaaagcc 152280
tggtattcga aagcatttcc aggctctgca atttcatatg agcaggtttt tggtaaaatc 152340
ttttgtccct cactcagggt ggtatctgga cagtgagccc ctttcttctg gctcagtagt 152400
cagagagagg agacttggag acagtttctg ctggatcctg tgctttggca aggatgtgca 152460
gcattgcata tcattctatc attaattatg tttactcctc catgaactaa aaaccattag 152520
actaaatagt ccaacataaa ccttgaaaga taaaatttga tattcttttg cctggccatt 152580
tctctgaccc agaattgggg ctgggagggg attggagact tgggggaaag aatcaaggag 152640
ccttcttgcc tgggggaatt tggcatgcac ttattaatcc catttggttg cactccctac 152700
taatccctca ctccatacct gccaaggatt ggctctgctc cctgcttctc atccctgtcc 152760
tagttcttcc tcacctatct ccatttccca ctactgatcc ttctctccag taagatgcta 152820
ttcaacccga tgaaatataa agagtagcac caccctggaa gtcaggatac cttagtttta 152880
gctcctgctc taccattatc tagctgtgtg acctggggca tgacttaacc tttgctcttc 152940
agtctgaaca gtctttaaga attggtttgg aggaggaagg aagggataga caagatccaa 153000
ggcctttgaa ctctttttttg gaaatgggtc cttttcttca aacaaaattt gatgcagagt 153060
cccaaattta cctacagaat aaaatactgc tgttcttgtt tgaaaggaag tggggtgctt 153120
ggagccacat gctcaggccc actttgcccc ctctcaggaa ccctcgaaaa aacttatagg 153180
acttatagga ctgttgggga tctgccaagt ctctcttatg ttacatttca gtccttgtga 153240
aactctatat gtttcatcag ttcacttttt cagaaagttc acctgcttgg ggtaaaggtc 153300
atgaagtgga gaatgtgggg ctcagtaact agcaatagta aaaaacatca ttgattggct 153360
tgcagaattt actctgttct aagcatctta cacacatact catccgaaaa ctcacaacaa 153420
ccttgtgagg tagatctgtt attatcttaa gattctgaaa cctgccagca tgactctcaa 153480
tctttgactt gagaccagtt gcccaacatg gaaggttata cttttcacag tttaccacca 153540
taagcagtct ttcagagtga tttctagcta gagatccatt cttagaaaaa gtcagaacct 153600
gcccattagc atacactgtc acatggtgca gagtaccttc actgggttca tctcatttcc 153660
tcctaaaaat agtcctatgc agtagtccag tcatatcatc accattatat agatgagaaa 153720
aactgaggtg taggagaaat caagagatct gttcaaggtc acacattcca taagactctg 153780
aataccacca tcaagaataa taaacctttt atgtgaaaag cattttagaa cttcagtgtc 153840
attattgcat tctgcctcct ggagttcagt gcactttttc accatgcttt aatcttggag 153900
tcctggtggt acagaatctg ccttctactc tcagacaaca ccacagtgtc tttatccctc 153960
ataacaaact tatgaattaa gtaatgatat tatccccatt ttacaaatta gttaactgag 154020
ataccaagag gctaagtctt gcccaaagtc acacagctag tcagtgatag agccggagtt 154080
acaaatgagg catcctgact ccagaatatt tgctcttaac tactactctt tatacatatg 154140
taaggaaact aaaagcaaaa gagggaaaga tgtccctgag gccccacagt gagctcccct 154200
gactcacaat ccagtattcc tctgaccttc taatcctaaa gttatacagt aaggtccctt 154260
gactctaatc ctagtagatg gaaagatggc tggcatgatt taagccagag gccacaaact 154320

```
ggcttcccca gagccagaat tcacctgcag aattctgttt gtccagcaca gtgtttgttt 154380
agaaaattga cgtagactgc ccctaggcag ggcatcaatc actgtcattg tccccagccc 154440
tccttattta tgtttgccag gctttttac tcatttatgt gtctgcctga cttgtgaagg 154500
tatttgagtt tatgactttt agatttaagc attgcaatat ataagcactg cacacatgca 154560
ttcacaaaag tatagcctag tctagcttca caaagaattt gtagccctac accaaacaca 154620
cctttatgtt tacttagtgt ttagaattag atttaagatc agaatttagt ttcacaggca 154680
ttcatgtgtg gaagaacctc agttattgtt ttttgtttca tactgtctca cccttgcttt 154740
ccctgctgtg tctggacccc tgtcaatcct gctttctgcc attcttcatg cctgagttag 154800
ggcccctgca agccattcac tggttaatct ttaggaatga atggagagtg aaaaccagtt 154860
tggagggttc actgtgtccc aagcatcctc tcatttagtt ctcataagtg tcctaagaga 154920
caggtagcag cacattcgtt ttataaatga ggaaactaaa tctcagagaa gctgaacaaa 154980
gacctcaaag tcattaaggt agtaattaac ggagccggga tttgaacgca agactgttgg 155040
actccagagc ctattctttt gccctacacc acagttcctt acaaggaaga tgtattcatt 155100
ttctattact gcataacaca ttgccacaaa tttagcagct tcaaacattt atcagctcac 155160
tgttttgtaa gtcagaagtc tggcacagca tggctagatt ctcagttcag ggtctctgaa 155220
ggatgaaact gatgtgttta ccaggatgca ttctaatctg aagctcaggg ttctcttcca 155280
agctcatgta attattgcag gattcagtta tttgtggttg taggactaag gctccctctt 155340
cctttctggc taccagccaa gggccattct cagctcttgg aggctgccct ctttccttat 155400
catgtggacc ccaacgcctt caaagccaac aacagagact cttccttgtg ttgaatgttt 155460
ctcactctac ggatgtcttt cctggaggat cccagtcccg taagggctca cctgatgagg 155520
tcaggtacat caagaatagc cacccttcaa attcaactga attagcacct tcattacatc 155580
tacctagcct ttttacaaca gcatctaggt tagtgcttga ctgaatgact ggaaactaag 155640
gtctcagaat ctcggggacc gtcttagaag tcagcctact acagatgttg attcttttca 155700
tgtgtcaaat ttcatagtga gatagggaga acagaaacat cacatccttg accttaggta 155760
aagggattca aacttcctaa gactttggaa acttcacgcc actttcacct tttccttaat 155820
catggttgag aaggcctata tcttggagtg gccaggagtg agactggaac agtacctaaa 155880
ggttaaggac gctaaagaag ttacagattg gttacatctg ctcctcccta ggaatgatcc 155940
atggaacctg atttgaaatt tttttctctg gtgctataga tagctcccac aggggtctaa 156000
tgccccaggg ctgaaaagtt agttccccat aggatccatc caggcatgat atcaggccag 156060
gtgttacaat ctcctaaaga ggaggtatgg actggaaagc cccttgccaa tggccctttc 156120
ttgtcactgc tctgacccaa gactaacagg gcagagatag tgaactcaca tactattaaa 156180
actatccact tatacttccc cctttctctt tgctttatca ctccatttaa gtaaaccaat 156240
gagtctctgc cttgacacag tggcaagctg acctgtatct tatatgaaag aattagattt 156300
gactctgggg ctcaggtgca gagggcagga ggggcataag gatggccttc atggaagaaa 156360
agaagtcctt ggatactgag taacagctga gactagcaag cctcattgtc caggattcca 156420
agtcgtctag caacatcctg gtctctgctg cagacagaac agaggatccc ccggcagaat 156480
gaatggagtc tgatttcaat tacgttcagt atagtcactc tctttaggca gagaagccag 156540
aacacctggt gcagctaggg ccactgtggt cacagggaca agcacactac ctgggtcctg 156600
gaggcaagtg ggaatgcagt tttcttcct taagcagatg ccatataggc ctggggagga 156660
ggatgtgaga ataccagcca agttctcatt ggcactatac agagaaaggg gaattatttc 156720
```

-continued atcttgatgg attctcccca cagtctctgc acatattgat cttacttgta atgagtttgc 156780
ttaggttcac gagtcatcat cccagggaga tctgagtcat tggtgggaaa gtcgaggcga 156840
cagattatat ctcactgatc tcactgtcac caattgctct gtgtgtccct ccacctttg 156900 aaaaagtcca tggattcatt tgtgtgtaat tcatttggat ttatttcttc tttatcaata 156960
gctttagtgg ggtattgcaa atgggaaagt tgccccagag aacagtgtac attcacagca 157020
ttattcagta gaactttctg agatgatgaa aatcttctat atcttatgtt gtacaatata 157080
atacagccac taactacatg tagcttttga acactggaaa tgtggcaggt gagactgagg 157140
gattatattt ttaattttt aatgttgtaa ttaatttaat tttttaaaat ttttgctttc 157200
tattttatag tttaataatt aaactaaact tacgtagccc acatgtggct agttggctac 157260
tatactggac agtacaagtc tagaaggatc tcagagagac acatgctgag atacagcagg 157320
aataagtcaa aaagagagcc aatgtaacat agggaattct ggattgggaa ttagagccct 157380
ggctctaatc tcagctctgc cactaggtga ccttgccctc tctggcttca gcctccccat 157440
ctttgacttg aaaggttaaa ctaactaacg tcgaaagtcc caaaatggtg gctatggact 157500
gaattcaatt ttgggataca caagtttcag gaattttta aaaatctatt aatgccttct 157560
aggtgtgtgt atgcacgctt gcagacatgt gcccatgcac aagcatggga aggcagtaag 157620
gcattcattt caattcacca gtgtactaac cattcacaca cacacacaca cacacacaca 157680
cacacacaca tgcacacaca ccctactgta ttgcctatgt agagcctgaa gatcttttaa 157740
tctgtcacca ttggataaga taatttctaa ggacccttcc tgttttgtca tgctgaaaat 157800
ctttaagcca ctatagtgtc ccaaatctat tccagtttgg gcagatgact ggagtattct 157860
catagcctcc tgtctattcc cttctggatt tgatactagt tatgaagttt ggagtcaagg 157920
gtgaagaagg gaggcaggga tgatataacc ccagccccac tcctcaactc tgcttttgag 157980
ttagaagtag ggttcagggc ttcagattcc ttggggaggc agtagagaga atatgggctt 158040
tataatcaga agatgaggtt cagatgattg ggttctcacc ttttttatag ctgtgttacc 158100
tcagtttatt catttgtaaa atagggataa gaaatatctt taacctccta agatcatgtg 158160
gaattaagtg atgtaatgtg atgaagcgag gcacgcagaa ggccctgaaa aaattagtag 158220
ttacccttaa ggggactaaa tggtctggca actcccgagc tcaaagctag aaaggtccag 158280
taatggggaa gatggggtct ttctgtagga actgtagcag gggagcagat cctgtaggcc 158340
accagtctgt ggagctgtgt ccaagaactc atgtttgcaa taagcccacc aaatgacaag 158400
ttattgtggg gttcaggcct ctaactcaag aagatggtct tggcccagat catacccttgc 158460 agcctgtgcc tttggtggga tgtgggtgtt ggcagtggct atgcatatct ccttattact 158520
ggctgtgcca aagccccgca gaaatgattg ttggacaaag tcatcttgca ctcagggctg 158580
gttttccagg cttccttgtt attttcccct gagttcttct gtgttcctct tgcaacacca 158640
accccactat tttcctcttc cctaccctag ttgttggtcc aaacatgtaa tccattcttg 158700
cagtgattta ttgggtgaca ccatgactgg agtttgcatt gaaggacttc tttttctaat 158760
tagaactaaa agtcagttcc aggctgggtg tggtggctca cgcctataat cccagcactt 158820
tgggaggccg agatgggagg attgcttaag gccaggagtt tgagtccagc ctggacaaca 158880
tagtgagatc ccatctctac aaaaaatgtt aaccaggagt ggtagtgtac aactctggtc 158940
ccagctactt gggagactga ggagggagaa ttgcttgagc ccaggaagtt gaggctacag 159000
tgagctttga tcgtgccact gctctccagc tgggtgacag aggaagatcc tccttcaaaa 159060
aataaataaa aactaaaaaa aaagtcagtt ccaggttgta tctttttca caggggccag 159120
acacagatga gagcaggttt tgttgtattt atccatttaa attgagcaat aaaattctct 159180
ctttggtttc tacctttctt atttattatt attatgttaa agggattaaa gtggttcatg 159240
gtctttctca gtgcaactgc ttatgctaga cctcagaatt atgacctttt caattattta 159300
tatttctgtc tatataaata ctggaaaaaa tagtacaaag taagcatcgg aatgcctaag 159360
gacctctaaa ttgtgtgtgt gagcacatgg ggaagatggt tcttaaggtt tgagttttgg 159420
attattgtgg ttgtcttaaa taatgttatt tctatcattc tttccaatga ctgtctccta 159480
gcatagttcc cattttacag actgatggca gaggcagaaa gattctctca cttctttgat 159540
actattgagg acttcagcct ttcaccgctc ttctcccctt tgctaaaaaa gaaaaaaatc 159600
aatatgtatg ttacagtgca tttttttaaa tattttttat tatactttaa gttctagggt 159660
acgtgtgcac aacttgcagg tttgttacat atgtatacat gtgccaagtt ggtgtgctgc 159720
acccattaac tccttattta cattaagtat atctcctaat gctatccctc cacccttccc 159780
caaccccaca acaggcccca gtgtgtgatg ttccccttcc tgtgtccagg tgttctcatt 159840
gttcaattcc cacctgtgag tgagaacatg cagtgtttgg ctttttgtcc ttgagatagt 159900
ttgctgagaa tgatggtttc cagcttcatc catgtcccta caaaggacat gaactcatca 159960
tttttatgg ctgcatagta ttccatggtg tatatatgcc acattttctt aatccagtct 160020
atcattgatg gacatttggg ttggttccaa ggctttgcta ttgtgaatag tgccacaata 160080
aacatatgtg tgcatgtacc tttagagcag catgacatat aatcctttgg gtatataccc 160140
aataatggga tggctgggtg caatggtatt tctagttcta gatccctgag gaatcaccac 160200
actgacttcc acaatggttg aactagttta cagtcccacc aacagtgtaa aagtgttcct 160260
atttctccac atcctttcca gcacctgttg tttcctgact ttttaatgat cgccattcta 160320
actggtgtga gatggtatct cattgtggtt ttgatttgca tttctctgat ggccagtgat 160380
gatgagcatt ttttcatgtg tctgttggct gcataaatgt cttttttga gaagtatctg 160440
ttaatatcct ctgcccactt tttgatgggg ttgtttgttt ttttcttgta aatttgtttg 160500
agttctttgt agattctggg tatttgccct ttgtcagatg agtagatgga aaaaattttc 160560
tcccattctg taggttgcct gttcactctg atggtagttt cttttgctgt gtagaagctc 160620
tttagtttaa ttagatccca tttgtcaatt ttggcttttg ttgccattgc ttttggtgtt 160680
ttagacatga agtccttgcc ggtgcctatg tcatgaatgg tattgcctag gttttcttct 160740
agggttttat ggttttaggt ctaacattta agtcttgaat ccatcttgaa ttaatttttc 160800
tataaggtgt aaggaaggga tccagtttca gctttctaca tatggctaac cagttttcac 160860
agcaccattt gttaaatagg gaatcttttc ccaatttctt gtttttgtca ggtttgtcaa 160920
agatcagatg gttgtagata cgcagcatta tttctgaggg ctctgttctg ttccattgat 160980
ctatatctct gttttggtac cagtatcatg ctgttttggt tactgtagcc ttgtagtata 161040
gtttgaagtc aggtagcgtg atacctccag ctttgttctt ttggcttagg attgtcttgg 161100
caatgcaggc tctttttgg ttccatatga actttaaagt agttttctcc aattctgtgg 161160
agaaagtcat tgatagcttg atggggatgg cattgaatct atgaattacc ttgggcagta 161220
tggccatttt cacgatattg attcttccta cccatgagca tggaatgttc ttccatttct 161280
ttgtatcctc ttttatttca ttgagcagtg gtttgtagtt ctccttgaag aggtccttca 161340
cgtcccttgt aagttggatt cctaggtatt ttattctctt agaagcagtt gtgaatggga 161400
gttcactcat gatttggctt ctgtttgtgt gttattggtg tataagaatg cttgtgattt 161460
ttgcacattg attttgtatc ctgagacttt gctgaagttg cttatcagct taaggagatt 161520
ttgggctgag acaatggggt tttctagata tacaatcatg tcatcggcaa acagggacaa 161580
tttgacttcc tcttttccta attgaatacc ctttatttct ttctgctgcc tgattgtcct 161640
agccagaact tccaacacta tgttgaatag gaatggtgag agagggcatc cctgtcttgt 161700
gccagttttc aaagggagtg cttccagttt ttgcctattc agtatgatat tggctgtggg 161760
tttgtcataa atagctctta ttattttgag atacgtccca tcaataccta atttattgag 161820
agtttttagc atgaagggct gttgaatttt gtcaaaggcc ttttctgcat ctattgagat 161880
aatcatgtgg tttttgtctt tggttctgtt tgtatgctca attacattta ttgatttgca 161940
tatgtggaac cagtcttgca tcccagggat gaagcccact tgatcatggt ggataagctt 162000
tttgatgtgc tgctggattc agtttgccag tattgtattg aggtttttg catcgatatt 162060
catcagggat attggtgtaa aattctcttt ttttgttgtg tctctgccag gctttggtat 162120
caggatgatg ctggcctcat aaaatgagtt agggaggatt ccctcttttt ctagtgattg 162180
gaatggtttc agaaggaatg gtaccagctc ctccttgtac ctctggtaga attcagctgt 162240
gaaatccatc tagtcctgga ctttttttgg ctggtaagct attaattatt gcctcaattt 162300
cagaacctgt tattggtcta ttaagagatt caacttcctc ctagtttagt cttgggaggg 162360
tgtatgtgtc gaggaattta tccatttctt ctagattttc tagtttattt gcatagaggt 162420
atttatagta ttctctgatg gtagtttgta tttctgtggg atcggtggtg atctcccctt 162480
tatcattttt tattgcatct atttgatttt tctctctttt cttctttatt agtcttgcca 162540
gcagtctatc aattttgttg atcttttcaa aaaaccagct cctggattca ttgatttttt 162600
gaagggtttc ccatgtctct atctccttca gttcttctct gatcttggtt atttcttgcc 162660
ttctgctagc ttttgaatgt gtttgctctt ccttctctag ttcttttaat tgtgatgtta 162720
gggtgtcaat tttagatctt tcctgctttc tcttgtggga atttggtgct ataaatttcc 162780
ctctacacac tactttaaat gtgtcccaga gattctggta tgttgtgtct ttgttctcat 162840
tggtttcaag gaacatcttt atttctgcct tcatttcatt atgtacccag tagtcattca 162900
ggagcaggtt gttcagtttc catgtagtag agtggttttg agtgagtttc ttaatcctga 162960
gttccagttt gattgcactg tggtctgaga gacagtttgt tataatttct gttcttttac 163020
atttgctgag gagtgtttta cttccaactc agtggtcaat tttggaatag gtgtggtgtg 163080
gtgctgagaa gaatgtatat tctgttgatt tggggtggag agttctgtat aagtctatta 163140
ggtccacttg gtacagagct gagttcaatt cctggatatc ctttgtgtct tgttgatctg 163200
tctaatgttg acagtggggt gttaaagtct ccccttgatta ttgtgtggga gtctaagtct 163260
ctttgtaggt ctctaagtaa tcactttatg aatctggttg ttcctgtatt ggtgcatata 163320
tatttaggat agttagttct tcttgttgaa ctgatccctt taccattatg taatggcctt 163380
ctttgtctct tttgatcttt gttggtttaa agtctgtttt atcagagact agcattgcaa 163440
tccctgcctc ttttggtttt ccatttgctt ggtagatctt cctccatccc tttgttttga 163500
gcctatatgt gtctctgcac atgagatggg tttcctgaat acagcacact gatgggtctt 163560
gactctttat ccaatttgcc agtctgtgtc ttttaattgg agcatttagg ttaatattta 163620
cgtttaaggt taatattgtt atatgtgaat ttgatcctgt cattgtgatg ttagctggtt 163680
cttttgctcg ttggttgatg cagtttcttc ctagcctcga tggtctttac aatttggcat 163740
gtttttgcag tggctggtac cggttgttcc tttccatgtt tagtgcttcc ttcaggagct 163800

-continued cctgtagtgc aggcctggtg gtgacaaaat ctctcagcat ttgcttgttt ttaaagtatt 163860
ttatttctcc ttcacttatg aagcttagtt tggctggata tgaaattctg ggttgaaaat 163920
tcttttcttt aagaatgatg aatattggcc cccactctct tctggcttgt agagtttctg 163980
ccaagaaatc cactgttagt ctgatggctt ccctttgtgg gtaacccgac ctttctctct 164040
ggctgccctt aacattgtat ccttcatttc aactttggcg aatctgataa ttatgtgtct 164100
tggagttgct cttctcgagg agtatctttg tggcgttctc tgtatttcct gaatgtgaat 164160
gttggcctgt cttgctaggt tgggtaagtt ctcctgggga atatcctgca gagtgttttc 164220
caacttggtt ccattctccc tgtcactttc aggtacacca atcagatgta gatttggtct 164280
tttcacatag tcccatattt cttggaggct ttgttcgttt ctttttactc tttttttctc 164340
taaacttctc ttctcgcttc atttcattca tttgatcttc aatcactgat acccttttt 164400
ccagttgatc gaatcagcta ctgaagcttg tgcattcgtc atatagttct cgtgccatgg 164460
ttttcagctc catcaggtca tttaaggccg tctctacatt gattattcta gttagccatt 164520
cgtctaatct tttttcaagg tttttaactt ctttgcgatg ggttcaaact tcctccttta 164580
gcttggagaa atttggtcat ctgaagcctt ctctcaactc atcaaagtca ttctccgtcc 164640
aggtttgttc tgttgctggt gaggagctgt gttcctttgg aggagaagag gggctctgat 164700
ttttagaatg tttcagtttt tctgctctgt tttttcccca tctttgtggt tttatctacc 164760
tttggtcttt gatgatggtg acatacagat gggattttgg tgtggatgtc ctttctgttt 164820
gttagttttc cttctaacag tcaggaccct cagctgcagg tctgttggag tttgctggag 164880
gtccactcta gaccctgttt gcctgggtgt cggcagcaga ggctcagaac agcgaatatt 164940
gctgaacagc aaatgttgct gcctactcat tcttctggaa gtttcgtctc agaggggtac 165000
ctagccatgt gaggtatcag tctgccccta ctggtgggtg tctcccagtt aggctactcg 165060
ggggtcaggg agccacttga ggaggcagtc tgtccgttct cagatctcca gctgtgtgct 165120
gggagaacca ctactctctt caaagctgtc agacagggac atttaagtct gcagaggttt 165180
ctgctgcctt ttgttcggct atgccctgcc cccagaggtg gagtctacag aggcatgcag 165240
gcctccttga gttgcggtag gctccaccca gttcgagctt cccagctgct ttgtttacct 165300
actcaagcct cagcaatggc gggtgcccct cccccagcct cactgctgcc ttgcagttcg 165360
atttcagact gctctgctag cagtgagcga tgctccatgg gcgtgggacc ctccgagcca 165420
ggtgtgggat ataatctcct ggtgtgccgt ttgctaagac cattggaaaa gtgcagtatt 165480
agggtgggag tgacccaatt ttccaggtgc catctgtcac agctttgctt ggctaggaaa 165540
gggaatttcc tgaccctttg cacttcccgg gtgaggcgat gcctctccct gctttggctc 165600
acacttggtg cactgcaccc actgtcctgt acccactgtc caacaagccc cagtgagatg 165660
aacccggtac ctcagtcgga aatgcagaaa tcactcatct tctgcgtcac tcacgctggg 165720
agctgtagac tggagctgtt cctattcggc catcttatga atcatgcatg ttcaactatg 165780
agcaactatg tgtattcaat gggaaatgga ataccataaa attgtcatat gttgagccca 165840
aaatgatagg atagaatttg atagtctgag gatggaaagg accttcaagg ccacttttaa 165900
aaaccccatt cccatatgat gcttgaattc ttaaccactg tgtgtctagt attttctcat 165960
ttccagtgat atgtgtgcct gccaaccttt ccgtctccaa gagctttaac tatcaaaatg 166020
tatgtgtgtg tgtttttgtg tgtgcatgtg tgtgtgagtg tgcgtgtgtg tgtgtgtgtg 166080
tttagagaga gagagagaga cagaaagaga aggagagact aaaatccaat tcactgttct 166140
ttctgggacc caaagaacaa gtctagtcat tctccatttc tagtctcttt ccctagcaat 166200
cggctagaca tgctagacat agacacatgt acatcactcc tttgaattac aacattcagt 166260
atttgtctat cacttatatg ataaaataca aacttagctt ttattttat tttttagag 166320
acagtgtttt actatgtcac ccaggctaga gcatcagtgg cacaatcata gcccactgca 166380
gcctggaacc cctgggctca aggaatcctt ccacctctgc ctcctgagta gcagagacta 166440
cagatgtgca ccaccagacc cagctaattt ggtttttac tatttttgt ggagatggtg 166500
tattgtcttg tggtgttgct caggctgatc ttgagctcct ggcctcaagc actcctccca 166560
tctcagcctc ccaaaatgct gggattacag gcatgaacca ccttacccag ccaaatttct 166620
taatatgata tacatgctcc tttaaaatca agcaccatct ttgctttcaa cctcattatt 166680
aaccactttc ccatatatgc aacatatgtt tcagccatac tagtgtctag tttttccctg 166740
aacactcctt ggtgcttttg tttatgccct ttctgcccac ctttgcctgg tgaaatcctc 166800
atcaatcttc aaattctatc aaatactatc ttccatataa agcattttct aaacccacct 166860
atgtaaaaag attagtgttt tcctattttg ttgatgcctc cattgcagca ttttccagtc 166920
caacgttttc tagaattgat tgtggccagg ctaccagact gggccagggc ctgtgtcttt 166980
tctgtcaccc agaagcaaag gtctaacaat ggatatctgc tgaatgaatg aacgaaaatg 167040
aatcattaat atattagtaa atacgttaat taaagttcca ggtatgaata ctgaaggctg 167100
cattcaggca gagctggatc caaggatatg ctaggttggt ctagcacaag aatcagagtt 167160
ttcctctgca agctatgaaa aatttgggtt tagcaggtat ttgggatgat gaattataca 167220
tttaaccagt gttgaatgag cacttgtcct taaggagttt agagtctgtg accagggaga 167280
atggtgattt tcttagctag ggcagttttt ctaaaaaggt agttgcattg tgtgtttttg 167340
accactgatg ataaattcaa gtctctcttc cttcccaata gcccggaagc tgaagaaact 167400
tggtaatctg aaactacagg aggaaggaga ggcttccagc accaccagcc ccactgagga 167460
gacaacccag aagctgacag tgtcacacat tgaaggctat gaatgtcagc ccatctttct 167520
gaatgtcctg gaagccattg agccaggtgt agtgtgtgct ggacacgaca acaaccagcc 167580
cgactccttt gcagccttgc tctctagcct caatgaactg ggagagagac agcttgtaca 167640
cgtggtcaag tgggccaagg ccttgcctgg taaggaaaag ggaagtggga gcatgagata 167700
agggggatca tatttagtga acgctcctat ggaccagcca ccatgtctgg tgcttttctg 167760
cccattaact caggcagtct tcatcataac cctgtgggag agggattgtt acaagtctca 167820
atttaaacat acagggatcg aaactcagaa agcaaagaga aagatagtat tatcgggtgt 167880
cttatgtggc ccacattgat gcacagcagt catgctttca tattcaactc acaaaaatgg 167940
tcagcaaatt ttccattaat cacaaatcac atagacatac ccatatatgc cttaggatgc 168000
tcttctatat ttgcacacac aggctcaccc caaagataat ctctagtttg actgacattc 168060
tgtcttcaat gtcatcttta ggagctatat catgggaact ctcataatat ggtatggtgg 168120
aaagaacatg aggttgggaa tcagaacact tcgggtctgc tcttagctct gctagtaact 168180
tattgtgtga tcccttcccc ttctgggtct caatttctct atctgtataa tgtataaagc 168240
gtggtttgta tcaaattgat ggtttccagt ttttgaaaaa aggaacgctt tttgcacctt 168300
aaactaccta aggaatcata atgagaggaa agattaggta atagtgaaag aattaccaag 168360
tgttggtcta acagaagttg gataacagaa gttcctcagt gatggggaac tcacttcttt 168420
cttatgtcat ctgttgttta aacaagtctg gttattaaaa tattacagct taaggaattc 168480
ttagagatcc tctatccaat gattcacaaa ctttccttta gcagccaagt gctttatttc 168540

-continued

```
tcaaaagaat tgtacacaga tacaagtgga gctagtttat ttaaagccag agcctgtagc 168600
ttgggcctca ccagttcagc ctctttctct ctatcccagg gaagccctag gtcactcttg 168660
caaaatctta gggctccaag gaacacagtt tgaaaaccag tgaagtatat gccctttaaa 168720
ggttctccta atcctgcaat tatgattcaa agattctttt gaaataacaa caaccaaacc 168780
ttctcttgtg gagtcaaaga ttaacctgcc tttcaataat aactgccatt caggtagaaa 168840
tttatagtga acagagcaat tttgtatgta ttacctgaat tgattcttat aggaatccta 168900
taacatgaga ttctttctct tattttacag accaaatagg gaagctgtga gaatgatgtg 168960
attggcctat agttacatag tcagaaaata gcaggaccag aacttgagcc caggttctct 169020
cctgattcca aattctctct attccactcc acctgtaggc tgtagcacca ctgcagttct 169080
gtagctctgg gctttacagt gaggggccaa ggcttcattg aaggccactt gggtcatagt 169140
atgggcttgt tgcatttgaa gacatttcat gttggctgtc aagtcttaga tttgtatttc 169200
caactcacag ggcctggtca cagccctaac catctcttat accttctcag cttgggaagc 169260
tgaggtcgac tagccaataa gaacactggg aaggaaaccc aaggactctg actggatatg 169320
ctctgtgcca aaacagaggg ttcactcaga gaggaaaaat ataaaaaaga aaaaggagaa 169380
ggttgcttta attcttatca ctttttcatc tggatatttt gatatcatgt gtttgacaga 169440
gattcaaagt ttaatcttcc caagcagttt ccaaacactt atctcatttt ataggctaca 169500
gagcttttc atatatatga tcccacttaa tctttacaac aattctatga atcatagaga 169560
ctattatttc catttcacat gccaaggctc aaagaggtta actaacttgc tccatttggt 169620
cacttaacac atggaaccag aacttgacct agaccttcgg gtttctaaat tggttatctt 169680
gacaataacc tagtgcaaaa cactatagca gaatttgtat gacttgggat cactggggct 169740
ttccttggcc caaccaccaa gatggaaagc cccctcccct tacattaaca aatctgcaag 169800
ccaatatcag ttcaccatct agcttgccag actaaatgat ttctgacccc aagtctttta 169860
aaagaatagc ttcaaaagaa agccaattac cacattcaca agaactgttc ttcatattat 169920
ctataattac ctacaagtac aagtaatttg ctaattcaat agattgagtt cttgacctgt 169980
aagatgaact gtgctaggcc cctaataaga taaattttgt tttaagtttt ctgtgacagt 170040
aaagatgtat gaaaattgcc tagtagagta cctggcacat taataaatga taactgttaa 170100
tttggagtgg gtgagtagac tgggtgtgca cagtatattt agaatcaaat ttatctggtt 170160
tggaatccta gctatggact agttctgtga ccttgagcaa atcacatgtc ttctctgtgc 170220
ttctgtgtcc tcatttgtaa gatgatagaa taatcactac ctttcaaatt gttgtcaaca 170280
aaaagattat gtataaagag cacctagtaa cgtagcctga aacatagtca atgctctgta 170340
aatggtggtt tattattatg agacttgaat gctaagccac tgctttcacg aaactcaatt 170400
ttagctacca cttgccttgc ctagaagctc atgcatggac cccaaggtga aattgtgttc 170460
tctgaagacc tcggctggca gatgtactac agcagcaaag atttccaaac tggcctttct 170520
ttgagcccat tctcccagac tagacaggag actacaagtt tctgctgcac atgaaaaaaa 170580
tatgatgtca atcggattct agtgagaaaa cagagtctca aagaaactgc ttctgctccc 170640
tagcgtgttt aatgtgtttc agaacctgag aatgactcct ctctgtttct ccagaacagc 170700
ctaacacagt ggcaaatggg tgttgagtga atgcatactt aaggaaatct gtagggttgc 170760
agctactctt tcctcaagta atcccttgat agtcatgtag gctacttcag agattgggca 170820
ttagagaaca gagtcaggta ttataatcag attagactct agggaggtta gccagccata 170880
ttgctgatat gtgcacagtt actgggtttg agtgctaagc agctctcatt aaggacggtt 170940
```

-continued

```
aattaatatt atggccaaat taagctttcc cttttctctc ctctttgtta gttcggtggc 171000
attttaggga gaaaaaaata agcatcagta tggacaattt gcttgatacc tgtacaattt 171060
aattctcatc cttccatgtg ccttcacatt cacacattcc accagaagac caaggttcac 171120
cagccaaaag cttttcttgc tccccactgc ctcctaccca agatattcag ggtcaacctc 171180
ccaggcctct tctctaagag atccttggtt gctacatgct tagaccctgc ttcttatttc 171240
ctgctgagaa gggtcagtcc aaggcattct gtgctacaga agggttccaa gcaggaacta 171300
ctctgggatc tgaggctcca gccggtctgt cagcgtgtca ttacagtgaa ggtgggaagc 171360
acaggcctgg gagctaagac tgctaagatg agggactcta gaatccctga tacctggaag 171420
gcctaggatc taaaagaaaa gaacagggaa atggggctat atgagtggac agggaccaac 171480
caagcagaac aatgtgtctg gataatgtag acttcagacc tgatcctatg gctgacaaaa 171540
gctggtgacc ttggtagttc ctgagctgta accttcatta gtggagtaga aaaaacactg 171600
gagaagagaa tcagaacacc tgggttctag tattagttca gccacatata aaccatatga 171660
ccttgggtaa gtcagtttat ttctctggcc ctcatgttcc ttgttggtaa aataagtgcc 171720
acatcaccta acctctggga ttattgtgag agttaaatta ggtcatcaac aggaaagtga 171780
gaagtttgat ctaaatttgg ggaagcattc ctaatgaggt atgatgacaa aatttcagat 171840
aattctggat ttgttggtga gaagagagag tgttggtagg gacgagctct gaggtgatgc 171900
ctttataact ttaagcatcc aactgtttca aaaactccag gagaacatgg ccatgtctgt 171960
tctacctgtg tattattgta gacgtagctt ctgggagcct ctgctctctg agcttaaggg 172020
aggtaatttg gagatcattt aattctcatt ttacaaaagg aaaaaaaatt gagggtcttt 172080
aggccatttg tttaggtaat atttcttaag tgcccactca aatacgtgga ctgtactaag 172140
tactagggag gtaaagataa ataagaagat atggtccctg tcttcaagaa gctccaagtc 172200
ttgtggggga gacagacatg tatatacata gacttcaatg ctgtgtaatg actgctataa 172260
ttgggtgagg ctacacaagg tgcaatgaga atgtaaaaga agaatcttta agccttcttc 172320
ttggatgagt tgggaaagcc ttcacagaag aggtagcctt tgagtgaaga cttgaaagat 172380
gagtagtgtt taccggatga aaggcctgag aaggaggaat gcattctagg caaaagtaac 172440
tgcctgtgca gagataacag agatatagag gcatgtgaga gcgcaagtgg caagagatca 172500
gtctaggtag gcaggtcata aagggcctat tcatgtataa tgatggcagt aagatgagga 172560
tggcagtagg gtgggaaatt agtagggcca gggtacctat tgagtagaaa agaatggaga 172620
ggaaatgcca ggcagaaaga ggatggacgc aagagaggga acatgaaagt ggtgaacagg 172680
tggcagtggc tgtcaagaca tctctccata ccctgtacac tgtatgtaat atccatctcc 172740
cagggttgtt agaagggtca aaccagatcg tagctggaaa acagctttgt gaagtgaaaa 172800
ctgctgttta tgtgggggaa atgattgtta aactgcatct ttggaaaggt gaagtgatca 172860
agagcacaga ccttggaatc tgactgcttt gctttgtaac ttggtctgcc aattactagc 172920
tgtatgatct tggacaagtt ccttaacctc tctctgactc acttgtactg gttcacagaa 172980
tggagataat aatagtactt accttactca ttgttgtgaa tgttaaatga gataatataa 173040
gtaaagtgct tagaaaagag ttaaatgtac cccataaata catacaacta tcatgtaccc 173100
aaaattattt ttaatttttt taaaaaagag caatccaata gcaaaagaaa aaaagagttc 173160
actcatataa gcagtcaata agtgttagat tatttttctc ttacaactga caatgccctt 173220
tttgtctcca tcatcatctc atttgagcag ctcagggaag tagggaggat aaggaatatt 173280
```

-continued atcctcacca tatagtttgt gcttttcccc accacccctt aatggccagc ctggatggtc 173340
cctggggatc cttaggggat gcccgaatac cagagcatct ctgcccaaca gggactcaga 173400
cttagctcaa cccgtcagta cccagactga ccactgcctc tgcctcttct tctccaggct 173460
tccgcaactt acacgtggac gaccagatgg ctgtcattca gtactcctgg atggggctca 173520
tggtgtttgc catgggctgg cgatccttca ccaatgtcaa ctccaggatg ctctacttcg 173580
cccctgatct ggttttcaat gagtaagtgc tcctggggcc cagacctcac taaaatacag 173640
cagcttggcc agacctggtt ggtggtgatg gtgatggggt gacagtgaag cttagctcat 173700
ttgatctgca gttgtcgcag cggatgcccc agccagccaa tccagtatga ggcggctttg 173760
ccctggcttt cagccaactg gcaggagccc aggaggatgg tgctgagacc accccttca 173820 cacccaagaa ccaatcctag tcatatttct ggtctgcttt gcagcttatc tcaaaaccac 173880
atggaaagat tcctcccctt cacatataaa agaggcagaa agactctggc tttaagggct 173940
ggagtttctt gggttctttt gctaccacca aaggctactt ctagtcacca tttgctgagc 174000
aactagtttg tgccaagact atgctagata ctttctaaat cctagctcat tgagtcctca 174060
tggtgacctg acctcacctt tttatagata acactatttt tttatggatg gggaaaatca 174120
ggctcagcaa aataaagtga ctcacccaaa gtcacagagc tagtgcctgt tggagacaag 174180
attcaaacgt atgtccctgt cgatctcagc tcttctgcgt catggtggta actgatggga 174240
aggagtacct ctaccgctct ctggctgtgt gaccttggta ctgccatttt ccttccctta 174300
aacagcttta attaatacct gccctgccac cagctccata taacatcatg aatttggcca 174360
gtggctcaga ttttggaatt acatttttct ccactaaaat ctcagttcta ctattttctt 174420
agtcagcatc tttgggaaag acctttaact tttccgaccc tcaatttctt catccattaa 174480
tgataacaga accttcataa gtaatttctt atgataacta aatgggaatt gacagatgtg 174540
gaatgtctgg cccatagtag gcaagaagga aaaaaaaagt ccctttctga ttcacccttt 174600
ccctaatagt gatacatttt ttttccccga gatggggttt tgctctgcca cccaggctgg 174660
agggcagtgg cgcaatgatc tcagcccagt gcaacctcca cctccctggt tcaagcaatt 174720
ctcctgcctc agcttcccga gtagctggga ttatagatgc ccgccaccgt gtccatctaa 174780
tttttgtatt tttggtagag acgggatttc accatgttag ccaggctggt ctcaaactcc 174840
tgacctcatg atctgcccgc ctcagccggg catgataatc ttttctatgt ctgctgtatg 174900
aggtccctcg atggcattgt gaatggagct ggccagagaa atcttcccaa ggaccttgag 174960
ctagtctcac cacagagaat ccttccagtc aggacaggaa ttgaccttcc cccctcttca 175020
gccctctaac ccagaagagt cttaaaataa aatctacagg ccaatggttc cttccagtac 175080
agcactgcaa tgcgagggag agtgagcgtc cccagctgcc ctctcccaac cctgccagcc 175140
tggtagccaa aagctaagaa taaccactag gcttttggca caaactgctt tgtggttttc 175200
agatctccgc aaagttgcct atgatgccat cttctggggc aggccttgaa aagcccccta 175260
actgttcatc tcccatcctt aaacccctgc tgcccttaag cagttgaatc aactccatga 175320
gcacctgctc taccttcccc agagccctga gacctttgga gctttgaaaa gtgataattg 175380
gttgttctct aaatcctcat ttccttctct gcctctaagt aagcatgtgg catcccacct 175440
cggcttcctg gtccagtctt gttcatctta taaaaaggcc tccctacggg gtcagaggcc 175500
tagacccatc aaacccaggg ctcctgaaac aataggaccc ctattcctcc tgtaggaagc 175560
cactgtgtta gagctctcag ggtgtctaca aacatctaga taagtgtttc tcaacatgga 175620
ttctgttgac atattgggaa aaataatttt gtcattatgt agaatatggt taacatacct 175680

-continued ggcaccagcc tactctatac caaataggat tccagtcatt ctgacagccc aaactgctcc 175740
cacacatttc tgacacccac tgaagaggca gtactctcca gttgagtgca actaatccct 175800
gccagccttc ctaaggtgct aatggggagc ctcagaccca aagagagaga gaagaacttg 175860
tccaatgtag gtcaacccat ttgctgatct cttcaacacc aagctctatt atcagccctg 175920
tttttttctt tctttctctc tttgtagaga tcacatgttg tgaggataat gagcttgaac 175980
cttagctgtg tgaccttggg caaattactg aacttctatg tgccgcaaat tttatctgga 176040
gactgctgaa gagtattata atagcacctt tctatatgtc atttattgaa cacctgctat 176100
gtgtcaggca ctgtgctcag tgttttccaa tcttcatttc tcctcttatt ttctctcttg 176160
cactcccacc aaccttgttc tcttcctaaa ttccattcct gcctcatttt tctaccctcc 176220
attctcctct ctcttccttc ctttaactgt ctccctagta tttttcccct tttccccctt 176280
tcttttcccc ttcccccatg aatttcttct ctttcctttc cccttctctt tcctccattc 176340
cccacttttt ctgcccctga ggcctgcagc aatgttaaag gaatcctcat tccagcattg 176400
tgatttcaat ggtaaaaaga ttgcagcatt gtcatcaaca gaggtgggaa agtacattgg 176460
agactggagc agagccagac ctcagggtca gccaatctta ctaaaaaatt ctctacagtg 176520
aaagagcttg gagcaacact gttctgctca attgatttgt gataccatct aaacacttcc 176580
tctttctagt tgggcttcag cctgagttga ataattctac accatctgcc ctcttctctc 176640
tttctccagg acagccaaga tctctctgag ataggatgct gagcttccac ccagacaata 176700
ccaggcctgc tcatcctatg gagtaggcta gtggcttgga aaccaaaatg tcaaaccata 176760
gcctttaggc tccatctggg aggtctttgt cctcaccact taagtgggtg tcaaatttcc 176820
ttccctttct gcacacgctg cacaatcaat ttctgtctta cacacacaca cacacacaca 176880
cacacacacg atttttgaag tgctgaaaac tggaaggcct actagcatga ggatgctgtg 176940
tcttctctta gaggtatgcc atggtcagcc atggaaccga gaggttgctc ttccttgaaa 177000
agctggccaa gcattggcca cttccccata taatttatag gtgataatgt ggtgatctgt 177060
tcagaagtga ctataataaa tgcaactcac atatgtctac agtttccaaa ctgtggtaag 177120
gagcagccag catatgaggg aatgggctcc ccttcagcag gggacattta aactagacat 177180
tcaaaaacac tccctggcag atttaacatt ggaactcgtt ttgaaagaac aatgtggaat 177240
ctccttcact gggagttttt gaataagtat gaaatttcta gtattccagg ccagaggcaa 177300
aggggtcaac aggatgacca aacacttcgg gtcatttgca aatcttgatg tcctgatgtt 177360
aagagctgac tactggggct tctcctaaaa atccttcatg ttgagctgcc tggaaggcag 177420
gttctcattc tggctgtagc tgagatgtta gaactgtagt cagggagacc atgtgcctcc 177480
cccattgtgt tcatttggtt aggctttcct gtccctgact cagaaaacag aaggggcaca 177540
gagacctgga aattccatgt gctaacccat atcctggcca gagaagatga gtagttatca 177600
gggtgtcagg attttggaaa acagagagag aaaaaaaaca aacaaacaga caaacaaaca 177660
aaaaaacctt ttcctggtcc ctggagcacc agcaggagaa acagcaagct cttcttggaa 177720
aacctggcga gggatggcaa tcagagacat tccctctggg cttattgtaa acttcccctc 177780
attccttttt cctctgtgta tctccttccc aggtaccgca tgcacaagtc ccggatgtac 177840
agccagtgtg tccgaatgag gcacctctct caagagtttg gatggctcca aatcaccccc 177900
caggaattcc tgtgcatgaa agcactgcta ctcttcagca ttagtaagtg cctagaagtg 177960
cagggaatgc cccctgaggg cacagagatt cagagaggac cacttttgcc attaaaacat 178020
tattagggaa aagccagctc ctggacattt cccttcttca ttccccctcc ccatccccac 178080
tctactctct ctcagcatca ttttcctaac aagaaacaat ttcatgacta gaagccaatt 178140
tatttgctag aagtcaacct ccatcagatt ccccacctat ccccagtctg tctttgggac 178200
aaggcctttt tgactggtta cagcaggtct ctgaattttt ccatagcttc tgctatagaa 178260
acagacatgg gccaccttgt attctttgca gggcagtaga gcaggaggca tttcctcctg 178320
gaaagatttc ctcttctgcc aacaggagga gatctatgta agcaactcag ataggatttg 178380
tatggcagcc aaggaacttt tctttaatat cttttctaag agccctctct tagcccctac 178440
ggagggagaa gggcaaaatt tgatattcaa agctatgtgt tttggttatc taaatcaggg 178500
ttttactgtg aatgacataa aagcttaggt cctaaaaaat gagtatctga gaagagtaga 178560
aaaagaaaag gttcaggaaa tttgatttac ttgactcctt tcagatcgga tccagctatc 178620
ctttcccctg agatctccct gacagactga aggccccaag cacacagact tcaactaaca 178680
ggaagccaag tagatggttc cctgtggggg tgggggtcaa gtctgtggtc agaaaacttg 178740
gtgctttgtc taatgctcct tcgtgggcat gcttcccctc cccattctgt cttcatccca 178800
catcagttcc agtggatggg ctgaaaaatc aaaaattctt tgatgaactt cgaatgaact 178860
acatcaagga actcgatcgt atcattgcat gcaaaagaaa aaatcccaca tcctgctcaa 178920
gacgcttcta ccagctcacc aagctcctgg actccgtgca gcctgtaagc aaacgatgga 178980
gggtgcttta tcagggagaa cagcctgata gagccaatga taatatgctt ctctagagtc 179040
tggcaccacc tgttgggagg tgcttccatt cccctctggc tttgagtgtg gtccaggaag 179100
aaaatgtggt gaagaaaaga acacgggtca cagtgtccca gctggatatt gtgaaagggg 179160
tggaggagtt gagaacagag cagttgggac tcagggaagg gacttgcagc agatgaattc 179220
tctaggcaga caaaacagac ctggatgttt ttcccctctt ctttgagtca tgttcatgtg 179280
agtttgtctg tctgtgtgtg tgtgtgtgtg tgtgtgtgtg tgtgtgtgtg tgtcagagag 179340
agagagagag agagagagat ggagtgcgga ggcttgggtg agagcacaag ctggagaagt 179400
cttgagtcag agagcttaca atggtataag acatctcttg ggagccctca gtgactccat 179460
ggagaccatt tctttctctc tctctcgctg tctctctcta acacacacac acacacacac 179520
gacctcatgg gggaggacca aggaagtacg gggaaggggg aggaaacaaa aggctgaaag 179580
accaaaaatc agaggttggg gaagaggcta gcagaggcca cctccttgtc aaccctgttt 179640
ttctccctct tattgttccc tacagattgc gagagagctg catcagttca cttttgacct 179700
gctaatcaag tcacacatgg tgagcgtgga ctttccggaa atgatggcag agatcatctc 179760
tgtgcaagtg cccaagatcc tttctgggaa agtcaagccc atctatttcc acacccagtg 179820
aagcattgga aaccctattt ccccacccca gctcatgccc cctttcagat gtcttctgcc 179880
tgttataact ctgcactact cctctgcagt gccttgggga atttcctcta ttgatgtaca 179940
gtctgtcatg aacatgttcc tgaattctat ttgctgggct tttttttttct ctttctctcc 180000 tttctttttc ttcttccctc cctatctaac cctcccatgg caccttcaga ctttgcttcc 180060
cattgtggct cctatctgtg ttttgaatgg tgttgtatgc ctttaaatct gtgatgatcc 180120
tcatatggcc cagtgtcaag ttgtgcttgt ttacagcact actctgtgcc agccacacaa 180180
acgtttactt atcttatgcc acgggaagtt tagagagcta agattatctg gggaaatcaa 180240
aacaaaaaca agcaaacaaa aaaaaaaagc aaaaacaaaa caaaaaataa gccaaaaaac 180300
cttgctagtg tttttcctc aaaaataaat aaataaataa ataaatacgt acatacatac 180360
acacatacat acaaacatat agaaatcccc aaagaggcca atagtgacga gaaggtgaaa 180420
attgcaggcc catggggagt tactgatttt ttcatctcct ccctccacgg gagactttat 180480
tttctgccaa tggctattgc cattagaggg cagagtgacc ccagagctga gttgggcagg 180540
ggggtggaca gagaggagag gacaaggagg gcaatggagc atcagtacct gcccacagcc 180600
ttggtccctg gggctagac tgctcaactg tggagcaatt cattatactg aaaatgtgct 180660
tgttgttgaa aatttgtctg catgttaatg cctcaccccc aaaccctttt ctctctcact 180720
ctctgcctcc aacttcagat tgactttcaa tagtttttct aagacctttg aactgaatgt 180780
tctcttcagc caaaacttgg cgacttccac agaaaagtct gaccactgag aagaaggaga 180840
gcagagattt aacccttgt aaggccccat ttggatccag gtctgctttc tcatgtgtga 180900
gtcagggagg agctggagcc agaggagaag aaaatgatag cttggctgtt ctcctgctta 180960
ggacactgac tgaatagtta aactctcact gccactacct tttccccacc tttaaaagac 181020
ctgaatgaag ttttctgcca aactccgtga agccacaagc accttatgtc ctcccttcag 181080
tgttttgtgg gcctgaattt catcacactg catttcagcc atggtcatca agcctgtttg 181140
cttcttttgg gcatgttcac agattctctg ttaagagccc ccaccaccaa gaaggttagc 181200
aggccaacag ctctgacatc tatctgtaga tgccagtagt cacaaagatt tcttaccaac 181260
tctcagatcg ctggagccct tagacaaact ggaaagaagg catcaaaggg atcaggcaag 181320
ctgggcgtct tgcccttgtc cccagagat gataccctcc cagcaagtgg agaagttctc 181380
acttccttct ttagagcagc taaaggggct acccagatca gggttgaaga gaaaactcaa 181440
ttaccagggt gggaagaatg aaggcactag aaccagaaac cctgcaaatg ctcttcttgt 181500
cacccagcat atccacctgc agaagtcatg agaagagaga aggaacaaag aggagactct 181560
gactactgaa ttaaaatctt cagcggcaaa gcctaaagcc agatggacac catctggtga 181620
gtttactcat catcctcctc tgctgctgat tctgggctct gacattgccc atactcactc 181680
agattcccca cctttgttgc tgcctcttag tcagagggag gccaaaccat tgagactttc 181740
tacagaacca tggcttcttt cggaaaggtc tggttggtgt ggctccaata ctttgccacc 181800
catgaactca gggtgtgccc tgggacactg gttttatata gtcttttggc acacctgtgt 181860
tctgttgact tcgttcttca agcccaagtg caagggaaaa tgtccaccta ctttctcatc 181920
ttggcctctg cctccttact tagctcttaa tctcatctgt tgaactcaag aaatcaaggg 181980
ccagtcatca agctgcccat tttaattgat tcactctgtt tgttgagagg atagtttctg 182040
agtgacatga tatgatccac aagggtttcc ttccctgatt tctgcattga tattaatagc 182100
caaacgaact tcaaaacagc tttaaataac aagggagagg ggaacctaag atgagtaata 182160
tgccaatcca agactgctgg agaaaactaa agctgacagg ttcccttttt ggggtgggat 182220
agacatgttc tggttttctt tattattaca caatctggct catgtacagg atcactttta 182280
gctgttttaa acagaaaaaa atatccacca ctcttttcag ttacactagg ttacatttta 182340
ataggtcctt tacatctgtt ttggaatgat tttcatcttt tgtgatacac agattgaatt 182400
atatcatttt catatctctc cttgtaaata ctagaagctc tcctttacat ttctctatca 182460
aatttttcat ctttatgggt ttcccaattg tgactcttgt cttcatgaat atatgttttt 182520
catttgcaaa agccaaaaat cagtgaaaca gcagtgtaat taaaagcaac aactggatta 182580
ctccaaattt ccaaatgaca aaactaggga aaaatagcct acacaagcct ttaggcctac 182640
tctttctgtg cttgggtttg agtgaacaaa ggagatttta gcttggctct gttctcccat 182700
ggatgaaagg aggaggattt tttttttctt ttggccattg atgttctagc caatgtaatt 182760
gacagaagtc tcattttgca tgcgctctgc tctacaaaca gagttggtat ggttggtata 182820
ctgtactcac ctgtgaggga ctggccactc agacccactt agctggtgag ctagaagatg 182880
aggatcactc actggaaaag tcacaaggac catctccaaa caagttggca gtgctcgatg 182940
tggacgaaga gtgaggaaga gaaaaagaag gagcaccagg gagaaggctc cgtctgtgct 183000
gggcagcaga cagctgccag gatcacgaac tctgtagtca aagaaaagag tcgtgtggca 183060
gtttcagctc tcgttcattg ggcagctcgc ctaggcccag cctctgagct gacatgggag 183120
ttgttggatt ctttgtttca tagctttttc tatgccatag gcaatattgt tgttcttgga 183180
aagtttatta tttttttaac tcccttactc tgagaaaggg atattttgaa ggactgtcat 183240
atatctttga aaaaagaaaa tctgtaatac atatattttt atgtatgttc actggcacta 183300
aaaaatatag agagcttcat tctgtccttt gggtagttgc tgaggtaatt gtccaggttg 183360
aaaaataatg tgctgatgct agagtccctc tctgtccata ctctacttct aaatacatat 183420
aggcatacat agcaagtttt atttgacttg tactttaaga gaaaatatgt ccaccatcca 183480
catgatgcac aaatgagcta acattgagct tcaagtagct tctaagtgtt tgtttcatta 183540
ggcacagcac agatgtggcc tttccccccct tctctccctt gatatctggc agggcataaa 183600
ggcccaggcc acttcctctg ccccttccca gccctgcacc aaagctgcat ttcaggagac 183660
tctctccaga cagcccagta actacccgag catggcccct gcatagccct ggaaaaataa 183720
gaggctgact gtctacgaat tatcttgtgc cagttgccca ggtgagaggg cactgggcca 183780
agggagtggt tttcatgttt gacccactac aaggggtcat gggaatcagg aatgccaaag 183840
caccagatca aatccaaaac ttaaagtcaa aataagccat tcagcatgtt cagtttcttg 183900
gaaaaggaag tttctacccc tgatgccttt gtaggcagat ctgttctcac cattaatctt 183960
tttgaaaatc ttttaaagca gtttttaaaa agagagatga aagcatcaca ttatataacc 184020
aaagattaca ttgtacctgc taagatacca aaattcataa gggcaggggg ggagcaagca 184080
ttagtgcctc tttgataagc tgtccaaaga cagactaaag gactctgctg gtgactgact 184140
tataagagct ttgtgggttt ttttttccct aataatatac atgtttagaa gaattgaaaa 184200
taatttcggg aaaatgggat tatgggtcct tcactaagtg attttataag cagaactggc 184260
tttccttttc tctagtagtt gctgagcaaa ttgttgaagc tccatcattg catggttgga 184320
aatggagctg ttcttagcca ctgtgtttgc tagtgcccat gttagcttat ctgaagatgt 184380
gaaacccttg ctgataaggg agcatttaaa gtactagatt ttgcactaga gggacagcag 184440
gcagaaatcc ttatttctgc ccactttgga tggcacaaaa agttatctgc agttgaaggc 184500
agaaagttga aatacattgt aaatgaatat ttgtatccat gtttcaaaat tgaaatatat 184560
atatatatat atatatatat atatatatat atatagtgtg tgtgtgtgtt ctgatagctt 184620
taactttctc tgcatcttta tatttggttc cagatcacac ctgatgccat gtacttgtga 184680
gagaggatgc agttttgttt tggaagctct ctcagaacaa acaagacacc tggattgatc 184740
agttaactaa aagttttctc ccctattggg tttgacccac aggtcctgtg aaggagcaga 184800
gggataaaaa gagtagagga catgatacat tgtactttac tagttcaaga cagatgaatg 184860
tggaaagcat aaaaactcaa tggaactgac tgagatttac cacagggaag gcccaaactt 184920
ggggccaaaa gcctacccaa gtgattgacc agtggccccc taatgggacc tgagctgttg 184980
gaagaagaga actgttcctt ggtcttcacc atccttgtga gagaagggca gtttcctgca 185040
ttggaacctg gagcaagcgc tctatctttc acacaaattc cctcacctga gattgaggtg 185100
ctcttgttac tgggtgtctg tgtgctgtaa ttctggtttt ggatatgttc tgtaaagatt 185160
ttgacaaatg aaaatgtgtt tttctctgtt aaaacttgtc agagtactag aagttgtatc 185220
tctgtaggtg caggtccatt tctgcccaca ggtagggtgt ttttctttga ttaagagatt 185280
gacacttctg ttgcctagga cctcccaact caaccatttc taggtgaagg cagaaaaatc 185340
cacattagtt actcctcttc agacatttca gctgagataa caaatctttt ggaatttttt 185400
cacccataga aagagtggta gatatttgaa tttagcaggt ggagtttcat agtaaaaaca 185460
gcttttgact cagctttgat ttatcctcat ttgatttggc cagaaagtag gtaatatgca 185520
ttgattggct tctgattcca attcagtata gcaaggtgct aggttttttc ctttccccac 185580
ctgtctctta gcctggggaa ttaaatgaga agccttagaa tgggtggccc ttgtgacctg 185640
aaacacttcc cacataagct acttaacaag attgtcatgg agctgcagat tccattgccc 185700
accaaagact agaacacaca catatccata caccaaagga aagacaattc tgaaatgctg 185760
tttctctggt ggttccctct ctggctgctg cctcacagta tgggaacctg tactctgcag 185820
aggtgacagg ccagatttgc attatctcac aaccttagcc cttggtgcta actgtcctac 185880
agtgaagtgc ctggggggtt gtcctatccc ataagccact tggatgctga cagcagccac 185940
catcagaatg acccacgcaa aaaaaagaaa aaaaaaatta aaaagtcccc tcacaaccca 186000
gtgacacctt tctgctttcc tctagactgg aacattgatt agggagtgcc tcagacatga 186060
cattcttgtg ctgtccttgg aattaatctg gcagcaggag ggagcagact atgtaaacag 186120
agataaaaat taattttcaa tattgaagga aaaaagaaat aagaagagag agagaaagaa 186180
agcatcacac aaagattttc ttaaaagaaa caattttgct tgaaatctct ttagatgggg 186240
ctcatttctc acggtggcac ttggcctcca ctgggcagca ggaccagctc caagcgctag 186300
tgttctgttc tctttttgta atcttggaat cttttgttgc tctaaataca attaaaaatg 186360
gcagaaactt gtttgttgga ctacatgtgt gactttgggt ctgtctctgc ctctgctttc 186420
agaaatgtca tccattgtgt aaaatattgg cttactggtc tgccagctaa aacttggcca 186480
catcccctgt tatggctgca ggatcgagtt attgttaaca aagagaccca agaaaagctg 186540
ctaatgtcct cttatcattg ttgttaattt gttaaaacat aaagaaatct aaaatttca 186599

<210> SEQ ID NO 4
<211> LENGTH: 210642
<212> TYPE: DNA
<213> ORGANISM: Homo sapiens

<400> SEQUENCE: 4 ggggggaag ggggagggag ggggaggagg tgactcgagc atttagacac aagcgagagg 60
atcatggcgg atggccccag gtgtaagcgc agaaagcagg cgaacccgcg gcgcaataac 120
ggtgagtggc ggaggggacc ggggagcggc ggagtcaggg ggagctgggc agccggggcg 180
cccccggggg tgagggggc gagccgggct gggggcagcc ggggcaggga cggcaaagtg 240
gagtgggaaa gtagaaagta gtgctctctg cccccctccg ctgccgccgc tgccggagcc 300
gcgccgcggc cgctcgctct ccctgaaccg ttatgtctct tacctggtct ctctccgcct 360
agcggctccc gccgcccctg ccgcctccct ggaccgttag ccggcgccga cgccgccgca 420
tccccggcgc agggcgggcg gccgggacgc actggccact tttctggtcc cgggtggagc 480
ggctgttgct tctttccgca cttttcccca ctcttgtgcc cttcggcgcc tccctctccc 540
cctcctcctg gccccctcag cgcgattctc cctcagcgcc caggcccccg ggagccgcgg 600
aacaaacttg tgcccggcgc tgaccgtgca aagtggcttc cgcgcgccgc ggccccggcc 660

```
ggcgccgtcg ctgtcgctcg ggccccgcga ctcgggccgg gctgtgggcg cgcggcaggc    720
gggctgcggc ggcggcggga cggggcggcc gcgggttgcg tggggtttgt gcgcgcgtgt    780
gcgcgggcgc cggctgtgcg cgccgcgggc ggacagggtt cggccggcgg cggtaaagtt    840
gggacccgcg ggccgggcgc gctcgcgtaa cggggattag aggcgcgggg gcgcgggtcc    900
ctaagcgccc ctcctccctg gcgcctcccg ctgcccggcc cagagccccg gcctggggac    960
tccgcggcga gccccgcgag tggggtccac gtttggcggg gcgcggcggg gcggcgcggg   1020
gaacaaggca ggaaaggtac ccacttaacg ccgccgggag ccgcgcggat gggggcgagc   1080
tgggcggcgg gtgtgtttgc ggagttgtta cctgggctta gagaccggga agcaccacag   1140
acagatcccc ctcccggggc agacgaggtc tctgcgccgg gatgggccgg tgtgcgtgcg   1200
cctcgcgctt ttctctttcg gtttttgggg aagttgttac ctgggccgga cgcacggagc   1260
gctgaagccg gataatgggg cttggatggc gctctgggtc tcgggtggaa ggagggtggg   1320
ggagggggcg gacggaccga cggacgcgcg gggctgctac ttgcaccgca gctgcagtgt   1380
ttattgattt gtgctgctgt gccaagggaa acacacaccc ctctgcctgg cgtgagagtt   1440
aaaaaaaaag agagacagcc cgagggatcg agacctgaac atgtggtggt ggttgcacag   1500
tcgccttttc cagtttggag agacgttgta agttgattgt atttctggtt atctcggggc   1560
gatgctatgc tttctctccc tctcgtgcag cagcgaaatg tctgctgatt gttattgtct   1620
ggacagttcc tgtggcgaga ggggcgagac ttgtccgccc gggggcggcg ggagcgcagg   1680
gagagcagcc cccgcctgcg ccgccccggt acctgtttgt ataataatgg gcggcaacgg   1740
ccctgccgcc ggccgcagcc caggctatat aaggaattac acgtacattt cggaccgagg   1800
ggctcgcttt ggttcctgcg ttatttttaa aacgactttt aagagagggg caataaatgc   1860
gtctataatg ggaccgctgc agcgtcgaga aaacgaggaa atacgtgttt aggagaaaac   1920
tctctcgtgc tcccccagcc ccaccccccg cgcctgggct ccctttctcc ctcccctctg   1980
ggatgcgaaa cgcgaggttt tgtaaccttt cctggcaatt ttagattttg tgtgggattt   2040
cctgtctaga agcagatacg aagattttta agctgtttca agatgtttcc ttccaatcca   2100
taattatatt tttaatatat tcgagccatc attaaaatca ctgctttcgt gattttaatt   2160
attcaaataa acacttgcat tttaaagacg tctgttgatt ataaacgaaa ggtattttgg   2220
tattctcatt gtggagagat gacttgttat agcaaggagt ggagcatagg ctattgcaat   2280
tttaatttcc tgttttagcg tcaaatagtg tgtgttccat attgagctgt tgccgctgtt   2340
gctgatgtgg ctttatgaaa ggtaagttgg ttcggaaaga gctgttcgct ttttacctta   2400
tttaaaatgt tgatcgccag agaaaggggc ttttcttgtt gctgacgaca tgtgtgtgac   2460
atgtgagtct gaaccaccca gcgtctgtgc agctgctgta aacatgttta cctgaacagg   2520
aaagaatgga tttttctcct tgagatcctg tgatatgaat attacactcg taaggcatat   2580
caacagatga cttaaggggg gaaaagcgat cctgaaagat acttgaaatc aacaggaaag   2640
agaggttctt gatcgctgca gcaaatggca acttgtgcag gtagaaaaaa agatggtgtt   2700
tagttttctc ctgcatgtat gtcagccccc tcctgtctgc tgctttcatt ctcaagggag   2760
ggatttattt accacgcttg ctgtcagtgt ttttcctttg tgtttaatat tagaaaaaca   2820
gatttgcgtc tgtttagcac aaaacgtctt gtctgcagta tgcattactc tcagaaaaca   2880
aaaggtgttt aagatagcac tgtactacta caggtatctt ccattttcat cacttttggc   2940
tctgtccttg tatttctttt tgttctcaaa tgcatttcat ccattgctgg tgattatagc   3000
catgctattt gatttagcct tatattttgc aaattaaaaa tgaagttata ttccattgtg   3060
```

```
ttgtgaaacc tcagtatatg tgctggttaa tatttcttag cagtgcagtc atatttaagt   3120
tgcagatgtt tattggagaa aattgcctgg caaaacgtta actctcaaat ctttttaatg   3180
aagaaatatg tgatatatac agtggaagat tgtcgtagag atagtttatg ttgttatata   3240
tgtaaataat gttttattca ttttgaaata agatacgtgg attttgctgc taagccttct   3300
gtaaaatatt ttaatttcct ttctggaata tgtctgaagg taggatatta aaaggagtat   3360
caggtaatgt aactgacagg ggtaaaccaa ttgagtaagg tttggccaaa gcatcaaacc   3420
ttgtgtggta acttaatgat gttagtcatc cgtaaaggag tgacattaga attgcttgaa   3480
ttagttttta ccatttataa tttcatgctt tgttgcattt taaaaaatct gtctttttct   3540
ttttctgctt tcttctatgt ggttttcttc ttgttctacc tttttttttt ttgagagaga   3600
gatgtactct actaatgacc acatgctgat taattctctt tagatggaat agaaggtaca   3660
tatccttctg tcatcagcac catttcccct tgctgtcatt ggaaaccacc agtagaggat   3720
gctaacaaaa atgattattg gtgtggtagc atcataagtc tctctatcga ctgtgctgat   3780
tgggaccttc agtataattc tgagtcttat tgttacttaa aactagcctt ggttaaatta   3840
ggcataagca ttttctagtt tgccgaaact agaaagaagc aggactgttt taacttgaat   3900
aattttataa atttgagtta tttaagtctc taattgagat tgctgttaat tcattcttgt   3960
tttagagcag ttgtattact ccttatttta aaaagatttt gttttatgtt cttaggtttg   4020
gagaagaata tgtaataatt gacccatatt tatgttgcat atttagaata ctttttaatc   4080
accccttttt aaaattcata gtaagatccc ttaaaatata tattttagat gttaaaatac   4140
atctaaaatg gtcaaagttt aagagtagca aggaaaatta caattgattg ataatactgt   4200
gtaattattt ttatataact tatgtagact tagactatgg atgggttggc agagagctac   4260
taacggaggt ggtaactagc agtcacttag atgttagtga tttttagatt ttatcttttc   4320
cttccccttc aggtcttttc ctactggtag ccctccccca cctttttagt taagaatcag   4380
tgagtgcata cgttttaaat ttgtcagttg taattaagga atataagttt gctttgagat   4440
cttatatgca gtaaaactct gtagttcgta cgttgctgta tgcttgtatt taaataattc   4500
ctttcaagaa actatataaa ttgcatataa ataattgcat gagactgtat ttagttatgt   4560
cttttcattt tgtgttctta taggtatatt aatataactg taaattttaa gcctctcatt   4620
aggtagaaca ttagaagtat ttatttcctt aattattttt agtggtgttt ttataaatgc   4680
atcaatatca gtaccgtaat ggaatagcca tactgtttat cttgaactaa gtaggtattg   4740
aattgccagg taagcctgtg ttaatttctt attttaggat gtcatggttc ttcgtgtgtg   4800
tgtgtgtgtg tgtgtgtgtg tgtgtaaata gtttttcatt tcctgacagg tatttcttga   4860
atttagtatt ctaattcctg agggctcagt agtgaatagg tgtgattcac ttaaatgttt   4920
atgaactcag aaactttgcc acaaagtcac gagatacatt gtagcatgga gcaaaactta   4980
aagtatctta taaattgaaa atattaatcg tttatgaaga tgaccctgat ataaaaagca   5040
tgtgaaatat ttgtttaata ctgttttctt cctttctcta gtctctagta tgtttgaaat   5100
ggcatacctc ctatgtagta gcttttgaag catgtgctga gaaacttctg ttaaattgag   5160
aatgatattt ttaaaataag agcataatga tttctcatag ttgtgttttt cttttgcttt   5220
atcctcttgt ggatttacct gtataaatca cttttaagca tgtggttaga gccagatgta   5280
aacacagatg cagtatcatg tggaattata ttgttagcta ctcttaacta cctgtattga   5340
attgcagcag aggaggagaa aaatcatgca gatgttggaa gaagatatgc attagtgtgc   5400
```

```
aagagtacag cgagaggtta gaaaacttga agctgtagaa ataggattga aaaaggtttc   5460
tttgcagtac agtcactaat ttatgtggaa atgcatgctc tttatttcta attgagatat   5520
aagctaaaat aaaagtccat tgttgaaaga aaactcaaaa aattttaaac tagaaaaagt   5580
gtcctgatta ggaaatatga taaaatgatt ttttaaacta ctttttaaag ggtagatgtt   5640
gtacatatta ctggctaaat aatcattcaa ctagatatga actaaaagta gtaagcaagt   5700
agaaatatat gtagtagaga aagttttgta gcaaccctag ttaaaattaa atttgatcta   5760
ttatgtaggc attgccatat aaactaatca ttcttttgca tggggcagtg ttttgagtat   5820
tatgtcacta aaggaaacat ctttaggaca ttagttttac taaataaaaa tttcaatatg   5880
ttatgagcat gtctggattt tagccttgat ggaggtgggt tacgctgtta acttaaaact   5940
gggttgctta aaaagatggc aatataatac agtacttaag tagcaaaatg ctctctaata   6000
agtaaaattt gctttatgat tgttttcaga gaaaacaact taatttttag aacttcatta   6060
attttgttaa agcatatttt tggattatat aatatggatg tagataaatg gaaagattat   6120
gaaaggaaaa gcaaaaaatt gaattcaagt gtctatttgt attatagctg tgaaacttta   6180
agcttttttc attctctaca aagttacttt tctctttctt caaacagctc cctgttgttt   6240
aatacacgtt ccctctatac atagggattg catttatctg tccatatgca catttctcct   6300
cctaatcaac attatgtatt tattgagact tggtacatgg aggttgaggt atgaactatg   6360
tttgtagaaa accttacagt atggcaacct gggaaaacct tcatctcttt tgcagtaaca   6420
actacatctg tgctgaaatt attcataaca gatgttttgt gatctcttaa ttccctccct   6480
ctcccttccc ctcccccatt cagatttaaa attaaatgtg aatggaagat aaatttataa   6540
attatgttaa tttcttttta ttgttttatt ctatattgaa agtcctctgt tttctctttt   6600
taaaatattc taattttaaa tgtttaagat attttaagta ctctgatttc aattatcttt   6660
taataaaata tgacaccatt atttatatat ctgttactat tcatgctcac ggcctaaaat   6720
atattctgat ttcccttact cttaaggtct ttgtattcat ttaatccaca attctagcag   6780
agtgtttggt tttgggtttt tttttttttt tttaagtaga tagtgctgag tgtaactagt   6840
ttgctgatga aaaaaactca ttttcttgga atcatatatt tttaatatgg aagattcatc   6900
ttttccaaaa taacttttta tctgaaaact gacacagata agctgaaatt tagggtcttt   6960
aagtagaaac tctagaagag actttaatgt gtgttttaag aaggggtaat gccaggcaga   7020
tacagtgaca tatggaataa catgtagtga aatccttcaa ggagtagatt ttctgaacct   7080
gggctcaggg taaccttgct ctgccttgaa tacttgaaaa ggctgtcaaa atcactgtat   7140
ctctttaacg ttttctcctt tctaccctaa agttaagttg ctatttgctc ctattgctac   7200
atcacttttc tgaatctctt ttgatacact tggcttttgc tttatttggg agggagaaag   7260
taaaggaagg aggaattgga gtagacaaaa aataacttta tatgaataaa tattcattaa   7320
gaaaatgaag tggaataatt ttggactgga gagatttggg agaatcatcc aaagccattt   7380
tgcagtaaag cagacagtca aagagataag atgactttgc caagtttatg ttactagtta   7440
gcttggacta ggtcacagct ttttgggttc ctagttcggt attcttttca ttaggtcatt   7500
tgagcatatt tatctaagac ggtaacaagc aagaactaga taccatgaat tttcaaattt   7560
attatactta aaaccaaaat gtgtagaatg cttcatcatc tcaaaggcaa gttctaatac   7620
atatgcatac atctgtcaaa tttagtagtt gatgtagtta tatcacttaa aatatttcag   7680
atgcagagca ttagtattat ttagaggcat cctctcattt ggattatact tttggtcact   7740
attcccaatt tcagctccca ttcactctat ccttcctacc ttggacccaa tctaatatgt   7800
```

-continued

```
tttttatatg ctgttggttt tgtagctagc cttgtaaaat tttgtacctc ttttgtgtgt   7860
tttgtattta cataagtgct ataagtgcta ctttgctcta tcatttactt tctttttctt   7920
ttctttttctt ttttttttt ttttttttt gagacagttt gacagtttga ctcttgtcac   7980
ccaggctgga gtgtaaaggc gcgatatcag ctcactgcaa cctctgtctc ccaggttcaa   8040
gtgattctcc cgcttcagcc tcccaagtag ctgggattac aggcacacac cgccatgcct   8100
ggctgatttt tgtattttta gtaaagatgg ggttttgcca tgttagccag gctggtctca   8160
aactcctgac ctcagctgat ccacctgcct cagcctccca aagtgctggg attacaggtg   8220
tgagccactg cacctgacat ataatttact ttctttactt agcattgttt gatagctaga   8280
tatgttgcta tatgtacagc tagttcattg cttttaacct tgcagtagtt catttatgta   8340
gtaagcacaa attacctatc aattccccta atggcagatt cccagattga ctccaattct   8400
tagataccaa taattctgta ataaacatcc tcctacgtgt tgctaatggc tgtggaagag   8460
tttctcagca ctaccatatc tagggacatg gtattgtcca gacatagtat tgctgagtat   8520
aggtcaatca catatttaat aattactaaa ttctgtcaga ttattttaaa aacagcaaca   8580
ccatttttta cgctcaccaa caatgtaaaa gaactatttt ctcacgtttt tgccagcctt   8640
cggtattgta caacattcta cattttgcta atttttcagt tgctaaatat aatctgatag   8700
ttgctttaat ttatgtttct ctgtttatta gggaggttga tcatttcttc atatccttgc   8760
tagctgtttg ggtttccctt tccatatctg gcctattcat accctttacc cctctttttg   8820
gatagatttc catttctctt gtgtatttaa gatgataatc cccaacgttt cagtcatttg   8880
actttggtac aggaatcctt aattttaatg tcaaaatttt gactttatgg gtagtaagaa   8940
gtccttccta atctatagat tataaagata ttttcctgga ttttcttcta ttagtttctt   9000
agttgtattt tttgtattta tatgtctaat gcatcaggag ttcacctttt gaatacaccc   9060
tttcttaaga ggaacaagta tagcagttaa gagtttgggt tgatcctgta acttactacc   9120
tatcaccctg gccgggttac ttagtctttt tatgcttgag tttctctgca tgtaaattgg   9180
acatgacagt ctaagaattg ggaaagttta aatgaagcat atgacgcatt gtgcctaata   9240
catgttttaa gttttcaaca catgttcatt taaaatttta cttatttatt ttaaatatat   9300
cttggatcag ctgacaattt tttatccttt tgaccagtat taactccagc taatgtaact   9360
accatctgaa agggggttgc tgtaaaattt gtacattgtt tgtgtaactt tgacatttaa   9420
cattgcttag ttcagacctt ggacaaagct gttaaatgat caatagacac tgaagcttca   9480
tcttaatgct acttttggta tgtctttcag ctttaggaag gattccttgg atctttttaa   9540
gggccattat atgagagaga ccttaccata tcacttttat gtataacatt gacatgaact   9600
tcaaggataa tgtcccattg ttattctgtt acataaatca aagaactcaa gtccaaggaa   9660
taaaagctgt gcattctata tttgaatagt ctaagcaaca tggagtctgc accttctcat   9720
atatccattt ggctgggaat gtatttaaga agatggctgt cttactgtgt tcctatggta   9780
tagatcagga ctattctaag ccaaaagtta aaaccatacc ctggtgtgtg tgtgtgtgtg   9840
tgcgtgtgaa cttaattgag gtataattta tatacaataa gatataccac tatgcatgta   9900
cattttgata gagttttgac atacttgcat acatgtgtaa ctgctaccac agtcaagatg   9960
taatagaaca ttatttccat catcctaaag agttcttgtg tacttaatct cagccaatct  10020
tccccaccta ttgcccccta gcaatgatct gcttttggtc actagaggtt agatttaatg  10080
tttctagagt ttcatataaa ccgaatcatg cagtatgtcc tttctgtgca ccttcttttg  10140
```

```
cacaggatat tatcaaaatt aataagtatc agtagctcat tccttttgta ttgctgagta  10200
gtattccatt gtatgaatgt tatatcacca aatacacaat ttgtgtcgcc attcacctgc  10260
agtggaacta ttaacttggg ttgtttctgg ttctttgctc taatgaataa agctactgtg  10320
aacatttaca taaaatttat atgcatatat atcttacatt tttcttgagt caatacttaa  10380
gagtacagtt atagtacagg taactgtact tctaagtaca tatagtaagt atatgtttaa  10440
cttggtaaga agctgcaaaa ttgcaaactg cttgtaacaa acatttttac atttccacca  10500
gccatgtatg agagttctgg ttgttccaca tccttgcaaa caattgtcca tgtttttaat  10560
tttaaccatt ctagtagatg agtggtagta tcattttggt tttgattgga tttcaccggt  10620
gactaatgat gtttgaagat cttttggtgt atgtattggc cacttgtata ttttcctttg  10680
tgaactgtct gttcaaataa tttgtccatt tttaattgga ttgtttgtct ttttattatt  10740
cagttgtaag agttctttgt atattctgga ccaaaatttt ttgttggata caagtattaa  10800
agatatttct ctctttctgt tggcttatca gttttcttaa tggtaccatt gaagtgccaa  10860
agctttaaat tttgatggag tttaattcat aattttattc atttaagctt tgtgtccttt  10920
ctgagaaatc tttgcctatt ccagatcttc aggatttctc ccatgtattt ttagaagctt  10980
atagctttac catttaggtc tgtaatccat ttcaggttaa tgtttggtct taactcacca  11040
gaatttggca taagaatttt tatttgaaat ttttaaaaat gtttctcagg gcccaactaa  11100
tacccaaagc tcaggattat agaggaacac aagtcctact tccctggttt tgaacatttt  11160
taactgagag tgagtacatt gtgcctagtt ggggttttca aggttcttca tgtccttgac  11220
acattttaat tcactgaaat atactttatt gaggatacag tttcagagaa agatgcctaa  11280
ggagagtggc cctagttagg ggaatgcgag tgttgtcttc aaggtttctt atttcctaca  11340
aggttttaag gaatttagca ctataccaat tcattttcat gttccgtagc ttttatcttt  11400
agatggggag tttgtttaaa cctaacattt atcttgagtt tttaagggat gtagtttttct  11460
ccttgagata aatgcttgat cttactgatt tttggctaca tattttacct cctcactttg  11520
ttatagctaa agaaaaagtt tttagttact tttaactttg ataagttgat tacagatggg  11580
tttattatat ttatttcttt catttcttag aaaatataga tgttacttat tcctatgtaa  11640
ttcttatttt aagatagttt tttaactttt ctgttttatt ttatcaccta ttcctattcc  11700
ttgaaaattc gttataagta acctgtgcct tatttttgtt tttacagatc tcgcttttta  11760
atactccttt tagctctgtg tctgtcttga acgttctgta tattaatgca taattccttc  11820
tgagctggta tccttaggtg catttataga aaaagcattg aactgggaag gagtcttaaa  11880
tttcattttc ttttcttttt tctttctttc tttttttttt tttttttttt tttttttgaga  11940
cggagtcttg ctgtgttgcc caggctggaa tgcagtggca tctcggttca ctgcaacctc  12000
cgcctcctgg gttcaagtga ttctcctgcc tcaacctcct gagtagctgg gattacaggc  12060
gcgtgccacc atgcccgact aattttttgt atttttagta gagatggggt ttcaccgtgt  12120
tagccaggat ggtctccatc tcctgacatc gtgatctgcc tgcctcagcc tcccaaagtg  12180
ctgggattac aggcgtgagc caccacgcct ggcccgaagt gttaaattct aatattgaat  12240
ctgccattat ttggcctctg aaattgagaa aataattcca tttatctggg cctatgtttg  12300
ttcatctgtg ggatgaatat gatggattat tgtatgcaag gtaatgagac cctgaagatg  12360
agagatgtag taccttgccc taaggagatt atagtgtggt agggaagaaa aatgaggaaa  12420
gaaaccttta gaatacagtt tggtaactga tgtgatattc tgtcttatat gcatagaggg  12480
gatggtgctt aaaccaagtc ttaaagtatg tgtgtgggtt atcctagtaa aatatcctag  12540
```

-continued

```
tggaaaataa tattccatac agggggaata ttatgtgcaa aggcataaca cacatgcaca  12600
cacatattgt gggactcaag tcacgtttgg taaaactgta gggtgagcgg aagaatggct  12660
agagatgagg ctggagaatt ggatagtaag caaatgaaga aaaaatgctt tatattgctt  12720
tcctgaattt agattttatc ttggacatga tgggaaatta ccacaggtct tgaagcaaag  12780
agtgacatga ttacatttat atacagtaat ttataatatt atgtttcttt atatactcag  12840
tgttaatatg attaaaaatt taagaatata tatgcttgct ttactaaaag tgaaaaaagt  12900
tgtaaaacct gatgtatcct gctttcctga gtttttgctt atctattctg ataatactaa  12960
tagatttgca tagtaattgc ttcgaaatgg tgctgccact accacttcta ccaccaccat  13020
aaattagtag aagacttacg ctactagaag cataagcagc cttacgttat agtggctggt  13080
atctgtgcac caagtttggc tgtgcatttc tagtccctgc actgttaggg ggaattgtat  13140
attttttttt ccttttctca aatcagtaaa tcagtgcaaa caaatgtgtt gtggatttac  13200
aaacctatgg aataaaatgt ttttacttct atcaattatg gctctccaaa gacataaaat  13260
actcttcatt cactattact agttaatttt ctagattatt tctggcattt attaatggtt  13320
ctgcatagag ctccaccttg tgaacatgtt attgtacttt gatatcagtt ctgtgtcata  13380
gatatttaat aaataaaata aaactttatt tacctgaatg tttctcattc agaatagctg  13440
taattcaggc ctggtatatg tttttatttg aatagaaaca gttcactgtt tttttggagg  13500
ttatgctgta tactacaaga tagattaaaa ccagtgcctt tttttagacc agctgctgag  13560
gaaatacctt tatcatgttt caacctctta agtttaataa ttctcatgta aaaattagtg  13620
cttgatttat gcatcaattt tctaaacatt tcacatgtga tctactttgt atattcaggg  13680
acttttgtgt tctatgttat tatatagcgt attttttaac caaaacttta aaaattaacc  13740
tcatttcatt agtatttgtt tatactttac tataccttgt ttacatgctt aacctgccta  13800
tgtattatct gtgacagtaa tgaaactgaa tggttataaa atgctatata attttatcaa  13860
gttaagctga ctttttttggt ggggaacatc atcttcctct tgctaataga taaaggagtt  13920
ttactgtact aatttcaaaa atggtataaa gcagtaaggc agatcttcac agcctattct  13980
ttgacagtat attaagcatg tggagaggaa agcaaggtgt tagctatttt aaggtttcac  14040
agcaacactc ccatcttgtt cattttcacc tgagttgtat agagcctggg aattgctata  14100
tatctttaat gtaaagtcag cagtgcaagt aacagtattg gatcatactt ccaccattac  14160
attctctgag tttctgatca ccacattctc acagataagg aaaatagttg tagatggatg  14220
gtctgaaatg taaaaaggat aaagaacaca agaagtggta aatatgttta gtttcagaca  14280
gacattatat aaaacttggg aggagggtaa aattattgat tagctacggg taggcttggt  14340
aagttttaac gcatgttaaa atttctaaga taaggaataa aaatctagaa ggtatgtgta  14400
ccttacaaac tagtagagaa gggaagtaga acaagaaaca atattcaatc tgaaaaaaag  14460
gtaaagaagc tgaagaaaga aaacatggaa aagagaagac aagtagcaca aaagtacata  14520
gcagcaataa gtgcaaatat attagtaatt acagtgcata tgagttgaaa aaatcctcca  14580
cttaacagaa actggttatt agatgggata aaataacaaa atatatttat atgctgttta  14640
caagcaatac cttaaaaagc atattctcgc ttgaaagtaa aaaggattta aaaagatatt  14700
cctgacacta ctaaccaata gaaatgttgt atggctatat atatcatgta aagttgactt  14760
tgaggcagaa aacctgtccg agagagtgag ggtcactcaa tagttataaa aggaaggtat  14820
aattttaaat aagtgactac ctgataatac actttcaaaa tacattaagc agaaactagg  14880
```

actgcagaag aaataggtaa atttatcatt attatagctt atttaaaata atctctgtta 14940
atgtgagaac aagcagaaaa aaattaagaa aaatatagat gattttaata acaggactta 15000
caagcctgct gtaatggaca cgtatggaac attgtattcc acaactaaag tagaggagga 15060
acacttagaa aaactgatca cattctggtc aaatacagcc agctttaaca aatttcagtg 15120
gattggcatc acattacact ttctgtttac aattccatta acttaaatag aaattttgtg 15180
tgtgtgtgtt ttggaaatta acatgtttat ttcaaaataa cttgtggatc aaagaaaaac 15240
ttgtaatgat agcagtaaat tattgtacac gacaacttat gtatagctaa aatgggaatt 15300
tatagatttt aatgcttata ttatgggact aaaggttgag gaataataaa catgcaattt 15360
taagaattag aaaaaaagca tactccccga ttgaaataac aggggaataa ttaatgaact 15420
agagaaagta aaagtaattc aaaaaggaaa caatgcaact aaaaatagat tatttgagaa 15480
gagtaacaaa attagcaaac cactggcaag attaataggt ggggaaagaa gtcataaagc 15540
agtatctgga atgaaaatgg gaatgttact acaggtgttt catgaatgat caactttatt 15600
ttaatgcagt tgaaagatta agtggaccaa ttcctaaaaa aaaatgtagc tcatgctggc 15660
ccaagaagta atagaaaatg gaataccctt aaaacaaaaa ggaaaaatat tcttacaaag 15720
aaaaaaatac caattctaga caggtttact ggcaaattct acaaaacatt caaggaacaa 15780
taattccagt tgtacagaga gtatttcatg gtttggaaaa agaaatgact gtccccaact 15840 ttttttttacg aagctctaag tataaaaaat gatgattgtc tttaactcag acctatgtac 15900
aaaaattcat agattagata tcatcacatg gtagtacccc cttatccatc tgtaggtggt 15960
tacctatgct caatcacagt ccgaaaatat taaatggaaa attcaagaaa taaaaattca 16020
tatgttttaa attgtacgcc caggatgtgg atcctccctt tgtccagcat atccacactg 16080
tatatgctac ctgcccatta gttaccattg gtagccgtct tggtcatcag ataataaaaa 16140
aaaacatagt atttataggg cttccatgct atccatggtt tcaggcatcc tcagggggtc 16200
ttgaaacgta tgccctgttg ataaagggga attactgtac ttgaccaata atgtgtaaga 16260
aagtaaccca tcataaccaa gttgggttta ctctagaatt tcaaagttgg ttttatatta 16320
gaaagtcact taatagaatt taccacatca tctgtttaaa ggaaaagaat catgtgagca 16380
tctcaataga tccatctgtg ataaaactct tagcaagtca gtaaatgaga aggccccttt 16440
cttaacctga taaaggcatt tttttccaaa gaaaatttcc agccctacct tctttccact 16500
tcatggtaaa gtattgaagg cattggttcc ctttgatatc aaaggacaag tgtgcctgct 16560
aatgccactt ttagtcaaca ttgtactaga agtatagcta gtacagtaaa caaacaaaga 16620
tacaatgatt agaaagaaaa agctattatt atttgcagat tatatgatta tctgtgtaac 16680
ccagaaaaat tcacagatga attactcaaa gtttaaattt ggatgcagaa ttattataca 16740
aattcaatta tttttcagac tttttgctgg catagaaatg caattaagag gtagcattat 16800
atcatcataa aagtataaaa cactgtgagt aaatctaaca acgtgctcaa tatctttatg 16860
gagaaattat gaaacattgg cagacataaa gatctaatta aatagcataa tgtaccatgt 16920
ttataaaagg agacttgaac attgtaatgg tgccatttct ccccaatttt atctgtaagt 16980
tctgtgccat ctgatcaaaa tattgacagg tttttgttga atttgacacg ctaatccaaa 17040
aacttacatg gaagaactaa gagataatag caagatactc attcatgaaa tggatctgtg 17100
atggcactgg gattgccaat gagtgaaata ggatgaccct ttcaataatt ggggttgttg 17160
gttaattaaa tggaaaaaat tggggttgga ctgctgcctc acactattta gagaaaccag 17220
tggaaggatt atagatctaa atctgtaggt aaggtaaagg tataggtaaa gtaaaatggt 17280
aacactttat aaagatgata ggctagaata tctctatgac tttgagtaaa gataaaaagg 17340
cataaaacac agagcaaaag attggcaaat atgactacat caaaattaag aattttgttt 17400
cactaataga tactgtagag tgcctaatcc cgtatttagc acatatcaaa atctaccacc 17460
cagggaaata aagatgaaca atctgataga aaactgggct tgaataggca cttcacaaaa 17520
gaataaactc gtttggccaa ggagtgtatt ataagatatt caacctcatt aggaatcagg 17580
gaaatgcaaa ttaaaaccac gttaagaagg catttcatgt ctcctagatt ctcaaaactt 17640
agaagccagc taatactgct gttggtatag acatggaaca actgaacact taggcgttgc 17700
agatgctaat gtaagtaggt acattcactt tgggaaataa tttcacatta ttaaagttga 17760
agatacacat aacactatga cccagtattc ctatgtctta gagaaatctc tatacagaca 17820
taccaggtaa tgtatgtagt tgtttataca gtactgatca caataacaaa acaaaaaaat 17880
aaataatagg ataagtaaat tgtagtatat ttatacaatg gaatgcaaca caatactgaa 17940
aaatgaatga attacacctg tgcttaacaa cttggatcat cctaggaaaa taatgttcga 18000
acaaaacaaa tcactgaaga atatagtgtg attccattta tatagaatca aagaacacgc 18060
aaaattaagt aatatattgt ttaaggatac caatacacat aatacaagtc tatgataaac 18120
ataaaattta ggaatgagtg aatttggaca cagagtagat atcacaggtc aggataatgt 18180
gtgtttaaaa aaaaacgatg gtggaactca gatatttatt gtattactta ttataccttta 18240
aatttatttt atagaattct ttaatgtttg atattaataa ttactgatag taatttatgg 18300
ctactgataa tcaacattta atctaaaata gtaactgaaa aaataaaagt gaatgatttt 18360
tgggggaact cagtatttgc catgtatttc ctatgtacgt atgtttaatt tttgtgagtt 18420
ctcaaatgta atcaatttct tttgagtatc tttagtattt tatactatct ttgtatttaa 18480
tatagcagat aaagcttaat aatttctttc tgttttttt ttttttttt ttttgatgga 18540
gtcttgctgt gtctcccagg ctggagtgca atggcgcaat ctcggctcac tgctgcctcc 18600
gtctccccgg tcaagcgatt ctcctgcctc agcctcccca gtagctggga ttacaggcac 18660
ccaccaccac gctggctaat ttgtgtattt ttagtagaga cagggtttca ccatcttggc 18720
caggcaggtc ttgaactcct gaccctcatg atccacctgc cttggcctcc catagtgttg 18780
ggattacagg catgagacac cgcgcccggc ctaagcataa taatttctaa ccctggttgt 18840
gtgatactcc aaaatgtatt catttatttt taggggtata ggcattttta attcttttat 18900
atttttgtag tcactaaatt tacttggctt ctacctttac atattttctg tttattgacc 18960
accttttagg aagtttgaga aaggtattac cttattatat ttttttctaa cttaaaatat 19020
gtgtgttact attgcacttg tggatataac atttcatttt agaatattta cattttattt 19080
tgtttatcaa acaatagcat ttttgtatca ggcactattc tcaatatcgt taaaatatta 19140
atttatttag tattcattgc aaccctatga gaaagatcct gctatctttg ataggtaaag 19200
ggaaactgag gcacggaaag tgttgggtaa ggtcacttag ctagtaagtg gagcctgtgt 19260
tcaaacctag gcagtctggt tccacagtct gtgcacttaa ccactaagct gtaagagacc 19320
atatgaagta gatctctaag aggagtatgt catctatttc aatgttcttt aataaacagg 19380
gtactatttt tgagcggtgc cagcatattg tcagattatg atgaaataat tatattattc 19440
cctttgtttg atctgagaat gtaaaaagca atactggtaa attacacact gctggacatt 19500
gcttagattt actcttcaat gaattttgtg tccgtacgtt catgagatga gaaaaataga 19560
taggcaaaag tacctgttag tctgattgca gatctacccg taatgcacaa atggtgatag 19620

```
tgtactttct tcttccaaag gtgggttaat ggagtcatga tttaaaataa gagtttaaca  19680
gtagcgtgta taaatttgat atttatacat cataaatgat gtataaatca tttatgggag  19740
agtgatattt gattcaggga tgttgacatg atacctttgg gaaattctca tagtaaaata  19800
gagttagact gtcaacaggg aaaattctaa gtaatttgtg aagaaactag tagtagtagt  19860
ctaaagtgag gcaccaggca aagagagaag aatcagacaa atcctttaga gtaatagttc  19920
tttacccatt cagacccaca ctccatttag agcatttact gtagaagttc ttgagagaag  19980
atctcatcct gtagccatat atgctcacta tatatataga tataaaacat ctctaagaat  20040
ttcagcttct ctttgtgctt tttgttagct actttaaata gcttaacttt cagtgacaca  20100
tggttttaac aggcaaaaca catgactgtt aatgattttt ctttagagca gaaatggttt  20160
atatggccta aattcacttt tagagaatct tctgagagag agtatttcct gtctctttgc  20220
acatgtgtgg catattgtaa ggacttattt acttttaaat aaaaaggaaa gctcttgcag  20280
tgaagtagac atttattttg ttaagaacct atataaggcc aggcgccgtg gctcacatct  20340
gtagtcccag cactttggga ggctgaggtg ggtggatcac aaggtcagga gttcgagacc  20400
agcctgacca atgtggtgaa accccttctc tactaaaaat acaaaaaact tagccaggtg  20460
tggtggtgca cacctgtaat ctcagctact caggaggctg agacaggaga atcgcttgaa  20520
ccggggaggc agaggttgca gtgaactgag attgcaccac tcactccagc gacagagaga  20580
gactctgtct caaattaaaa aaaaaaaaaa acctatataa aatagtttat agcagtttat  20640
agctgtgacc atcaagtcag ataatttggg atgttcacag agagctctgg gtgattatga  20700
cagtgtacca cccacatctc ttatttgttt tgcttcattt ctctactagg gagaggaggt  20760
catataatat atggtatttt tatgttattt tagataaatc catatcaaca cagcacagga  20820
gaacaaatta taccccctggt agattttggg gtataaacgt catgaaatgt ttctcagaaa  20880
gtgagaaata tttcttgatt gtatctttaa aattaatgca aaattgttat gttactccat  20940
aatttatttg tgtgcattac tgtaaggttc atgtgtattc atattaaatt ttttctttta  21000
aaaattgggt tcaatgaatt atctaggatg attgcattgt ttgtggcatc aagtgttgtt  21060
tctccctttc cataccaagc atatcctgct tttggtacag gatatatttt tttcagatgt  21120
caaaacacct agggatacat tttatgaatt actaacttac ttttttagga cagacttgaa  21180
atcatttaga gggtaaactc tagcaatata gaaatctgtt ttttgttgaa tggagtagca  21240
gctaatcttt aagacccatt gatagcattt tagtagtagc acttaacatt cagaaaagaa  21300
aaacaaatca tccagcttct gatcttcagt tttatgtaac tttacaattt ggtacttgat  21360
gacttggtat tggtatgaga ctgaatagtg tgatgttaca aacatgtgat gtttgcctac  21420
catgttctag gcactgtgcc aagtgctaga gatggaatgg taggtaaagc tgtggtctat  21480
acttagggag ttcacagtca aatgaaggat acagtcacaa aacagacact tgtataaagc  21540
atggtcacta taatacagag aaatggaaag aatggccaga gaaagcttac ttgaaaagat  21600
aatgcctgaa ctgaatacta aagggaggtc agtgggagag acaaggaagg gtagatattg  21660
attgtgagtg catgagcatt gaaatgagag ggcccagggg aataggaaga gaggaatagc  21720
ctaaaggaga acaggagcaa aggcacatgg gtgagaaaca acatggaatg ttctggacat  21780
acaagcagat ctctgttgga aggagtatga gataagggta agagagtgat tggagttgag  21840
tctggagaga tacgaaacca aatcatggaa gctttttaaa tgccatgttt aggagcttga  21900
acttcatctt tttgtgagtt ggacagtcat tgaagggttt taagtagggg cccaatttga  21960
ttgtattcag gttgagtaga gtactctgat agctgatgtg aaggataaat ttgaagggaa  22020
```

aaagattgga ggcagagagg ccatttggga agtagttagc ttgataagag gtgacgaggg 22080
cttaaactga cacttaatag aaatggagaa gagggagtag atttcagagt ctgtactttt 22140
tttgttgttg ataaatagta aatttagtag gactcgatgc ttggaaatga ccagtgggag 22200
agaaaaaatg gacgagatta actccaaagt ttctagctga ggtgattcca gggatagcga 22260
tgacaccaaa cagagtgaat atatgaataa tcagttgagg agacaaacgg aagtcagttt 22320
tggatatttt gagtttaaga tggttgtgac atcactaatg gaggaaggct aacaaggcag 22380
ttaacctttg aacttgatgc tgtgggatat agatgggggt cctgggctgg aaatacagct 22440
tgaagagttc atcagtttgc aggaggtgat tgaaagcata agaccatcaa gggaaggtgt 22500
gtgggctgaa gagaaaaaaa ggtcagaaga caggagcttg gagaacagaa gtgtttcaga 22560
gtcaagtaga gaaaaagaag ccccacaaag ataagaaaag gaactgaaaa aaatgaaata 22620
atcagtgggc caacctgaag atccaagcaa gactagaaac cacacatttt taatggaaca 22680
aatctatatc gttgtgattt ccttagaagc cttaaattgg tgggggagat cagaatgtaa 22740
cattagtcta ggattgaggt tttaccagat ggtacagtaa aagttgtgag tttagggaaa 22800
ccaagttgtt tgaagttaga gcagtttaga tgatcagctg tgccaaatat tgcaaattat 22860
gtgctgtaca ttattcttta cgtatattaa ctcttaaccc tcaccacaac catagttgtt 22920
acagaagatt ctagaatgta agttccataa gagcaaggtg ggtatgcttt gttgtctgtg 22980
ctattctcag tgcctgacat acagaatagg ctcaaatact tgttgaataa atgagagaat 23040
atgagataca tactattatt cccattttac agatatggaa accgggtaag aagagattaa 23100
gtaacttaca ttcacaattt ttagtggtag agccagtagg aaaggaattg agcccaggat 23160
tagggagctg atggaaaata gagaaatttt aggtctggag atctctctga ggatagtgga 23220
aataaaggca tgagagatgt agaaggggag aaagttatca tcagagagta aaatggtgga 23280
ggttatgatt ttttgagata gggttgttca gtgttatgac aaagggtcaa gtcttagcag 23340
tggagtaaag gatgtttatt attgaatctc tgtaggcgtc gatgtagatg ttgaaggctc 23400
ctaaggttat actagaagtt tgaatagaga ggaacattat gataccatcc tcataaatga 23460
agtggtataa ttggagatct atagataaga agcagcagag agtggaatag ataagctttc 23520
ttatttcaat tctagctttt taaacgtaga ttgaggttag atctggtttg ctgaaaagac 23580
aggaataaat tgggcttgct gcatataatt tatttccccc atatggataa gctcgttgga 23640
aagctccaga aatattcaga atataaatac aaaagtttca aattttacct gacatgccag 23700
ctctacttaa ggtatgaatt ctaaatcttg tatctctccc ctgcaagaaa agctacctcc 23760
tcctttttat atagtagtag aacaaaattt ttgtttgtgt ttgtggcagc acatctcacc 23820
tctttgtttc atagctgttg ggtacacatt ccaaggacgg taaaaacaaa atgcacttgc 23880
tcttctaaat ctttagccac tggctagtgg attgcattta ttctcagttt ccttgccgat 23940
ccttttaccc ttcccctccc ccatttttct ttttgaatgg ttttgtttca tgaagctctt 24000
gagagctttc tatgttatat tgtggcacag gaaaaagttt attcatttta gcactaaact 24060
gtagttaaca ttttaagtta atcattttta gaatgttttg atgagcaatc ctgtttcatt 24120
tttagagatg attcaatctg atatttcatt tgcttttaaa gtctctaatt tcttttcatc 24180
tatttccata gcattgtaat ttgtatcctg aacgtttctc ttcagagaaa tataaaaatc 24240
cagcaatcca ttatagtatt gtattaagcc taagatttca ttatttatca tacacattta 24300
tttatttatt tttatttttt atcatacaca tttaaagtac ggcctttgat ttatagaatt 24360

```
tttcattttg tggttgtgcc tgcttatctt tgtttttgtg tgtgtatgtc tttcacagaa  24420
attagtatca ttctgtcata gctcttagga aattcagagt taatcaaata tgttataaaa  24480
tgtgtttgta taatgaaaag gttggaggag atgattctga aggtgccatt tagagcaggt  24540
gtgctatggt ttggtggctc tctattctct gcccgcttta aatcttagta ggcagcagat  24600
gaaatactac taagtgacct ttgacacaga acccatgaat gctccaagta tgatttcatt  24660
ttaccgtgtt ctttgtaaac tcaaatgcct gtcaaatcag atgtgtgttt cgatgttttt  24720
actgaatgcg ccttgaggag gagactaaag cttggggtca atttggcata atccccacgt  24780
ttttcttttt ctattataga ggtttcttgg ggaaggggtg acatttcttt ctgaggaaaa  24840
ggtgcaggct aagtgtaggt ggactttctg tcttctccat actttttctg acagcctcac  24900
tggatcctgg tgatatcata cataaatgca gagcagacta gatgggttgc tggttggtat  24960
ttttggttac catttgatct ggtgtctttg gttatgtaat aggcacatta actgacaaat  25020
tatattaagt aaatatatag ccatgggctt tttaaaatct cactttttaa agtcaataat  25080
tagattagat tgtctcccag taattaagtt tttcatatgt tcatggatat atgtagtata  25140
tattaaaaga ttatttgtgt attttttaca ttaatttggt aattttgaca atttgtcaac  25200
tcaagtataa aatacttaca tataaatata cttaaataag tatttaagat ttaatgtcaa  25260
ctttacagta atgaaataga aaattcttga atgttactca tttaaatttt ctgatttgag  25320
ttctgataat ctgttagaaa attagtaata tgcttaggct cacttcaatt tccccagcag  25380
aaactattgt atccttactg gttagaagct gccaatagtc attaattgtt aaaatataag  25440
aaggttgtag gggaccatat gacaaaagaa ctagttacct ttacagtttg ttcgctgtac  25500
ctcatacact ttgtgttaga agaaaagctc tattcagtgc cttgagtgaa aagatcctta  25560
cctcctttta gactccgatt gtgggaattt tcttgctatc ctggacattt taacttgttc  25620
tgggttattt tgaacatatt aaggtggact cctggaatag ttgagaacta attcatgttt  25680
gtttgttttt ctgaatcagc agtttagtga ttaaagctta agattctttt aatagattta  25740
atgaaaaaga aatcttaact tgaaatttaa attaatgaaa aatattacca gaggagatgt  25800
ctgatatttt gatacgggaa aatacagaaa ataaaaacat ttaaaaattt atccagatgt  25860
taatgtttga ctggaagttt tctactggaa gaattagttt ggattttaca atttgggaga  25920
ggcagaaggg agttggggag gtggtcaagc ccaaattagc atgttgaata tccagattca  25980
cagacatttc actaaaccat ttatgtactt agcatttttg ttgactagtc ttttcattta  26040
tagtgctctt aaatcactcc atttgtcagt tactccattt acctgaagat taaagtatac  26100
actgtgatag aaaaaaatag attggcaggg gcgggggttg tattatataa tgtaataaat  26160
cctattaaac ctgttaaagt agaaacatta attttacgtt ttagaatttt cttaatgaca  26220
ggaaagtaaa ctggtaacta aaattcattt tgttctgtag gtttgtggca ttttatgtgg  26280
ggaatgtaga tgctaagtgt tatgagttgt ccacctgtat aaaactactt cccagaagcc  26340
ttgatgttcc cataaagagc taaagacaaa accaaatcaa ctgctaacac cttttatggg  26400
agatcaactt gtgtgggtta tgaggcccac cttgactaag caggatatgt aggtaaacct  26460
gcccagttgg aattagtagc tgatactcta aaaggagaat ggtgaacagg aggccattag  26520
cagaaacagc ctcattcatt tatagagatc atcttgttaa aagggaaatc agcttcccta  26580
gatcccaagg gggtattgaa aatgctagga gagagcctag aaaacttttc tgtgcagatt  26640
gtcagaaaaa ggtgaaaata ttttctttta ctgtaaaaag aaagaaattc ttttccttct  26700
tccaaagatg ccttaccacc tttgaaaaag atttttaaaa gtctcagaga aaatgaaata  26760
```

```
tagattctta aagtggaaag ggaccttaaa aatccatctg gtctggttca ttttatagat  26820
agaactgaga acctcaaaaa gttatgtaat ttggcttaca tcacaagagc tagtttgaag  26880
cagaagctac gatttttctta ctgtgtccag ttgtttggaa gtatgaatag tcatcattaa  26940
aatgtaggga gtttataggg aagcttatga caactattag ttaatttaca atttgttcac  27000
tgtagctcat ctgctttgtt tcagaagaaa aattctatgt cttgtgtgga aaaactctta  27060
cctccctatg aacagaacta taggaaattt cttgctaact tggatgtttc agctacttca  27120
gggttatttt aagtaactgg atagttggtt ttcagaattc tagttacaga aactagtaaa  27180
agaatatgag ttgttgatac gtggaaactt tagacccaaa ataaaggtag gatgatgtga  27240
gtttagtgct tacaaatttg aatgaaatag taccttttg aggtgtttta gtagttgccc  27300
ttaatgattt attttaaatt agatggcttt gggagtaaaa atactgcttt tagcaaaaaa  27360
taaatataaa attgaaactt ttgcacgtag agtttttttt ttctttttga gatagataaa  27420
gccatctaat gtccttttct atcatgtctt gataagtcaa gagcagacca cttgatgaag  27480
aaaaatgaaa tatcatctaa aatagaaaaa tatcctgtta ggaaaaatac caccgttttt  27540
tcgctgcctt tagtctggtt gttcttattg tgtgaaggga acttaaatct tgtcaaatta  27600
catacattgt aagtcccatt tctgtcttaa aagtataacc atgcatgctc aattaagtca  27660
gttatcgtct tcagactgta cttttgctaa ttaagtcttt tccttggggt taagataaga  27720
caagatttac agatttttaa gtttaaggcc tgtaactact gaggatggtt taaagctttg  27780
ataagtgaga tgtggtgctt taaaggagga ctttccttta gtctcttaaa aacacttgga  27840
agatatttat tacagttttc caaagtaaga taaagctcag ctttaataat gaggaccttg  27900
aagtttttt atgtggtggg gaggtgttag gaaactcatt ttttaactac cttcaagtga  27960
ttatcgaggc aggtttttct tccctatgag gaagaaaatg aattgtgcaa tgccagttta  28020
aagaaactaa agcaatgtat ttcttacata aagtagatca ttctctctcc ctgtgtaact  28080
gccacctgtt taaaataaga ttccagtctt gcctctgtca gtcttaatgt gatagactct  28140
cactcagtga agatctatgg atttatttta ttgaaaacat ttgtttagca tatatctgtg  28200
ttattttaat tttaatgttt ttagagatga ggtctagcta ttttgcccag gctggccttg  28260
aactcctggg ttcaagtgat cctcctgttt ggcctcctag gtagctggga ctacaggcat  28320
gagccaccat gcctgggtaa gatctaatga tttatttgat tgaaaacact tatttagcat  28380
acattcatgt atttttgtaa cttgttgcct cctgacaggt cactagacat aggaaagtgc  28440
ctcttttaac actttcataa acctttaaca taaacatttt aaatttcttc attatagtgg  28500
aaatagcgtc tccccttatt attggacatt ttgaaaaatt aaaaaaattt taaaacaatt  28560
tttatcataa atactagatg ggaataatta tatatgaagc ttgtctgaca agttggattt  28620
ttatgatagg atagaatccc aggagtagaa ttattgggca taccctttta agcctcacag  28680
taaattatta ctaaagtgtg ttgcaaagat tttatcagtt gtatagactc ccagatatga  28740
attccagggc ccttcagggg aattagtggg gacattttgc aaagagcaac agatggtgtc  28800
tggaaacatg ttctttaatc tttgctgtgc cacatactag ttgtagatat ctgggttagt  28860
aacataggtt gtgtgggcct tactttcctc accataactc aggtgaattt taactattct  28920
actggcctta attctcattc tgtaaaatat gagtataatc aaggagaatc agtgcctata  28980
tattaccaag tgatttgtct gggaaaaaag cagaagcagg gaatgtcaga tgtacctaga  29040
aaaaggagca agttagggga aatgcacaaa acatgatttg ctcttctggt tttttaaga  29100
```

-continued atagagtcta ggctgggtgc agtggctcac acctgtaatc ccagcacttt gggaggctga 29160
ggtgggtgga tcacttgagg tcaggagtct gagaccagcc ttgccaacat agcgaaaccc 29220
catctctact aaaaatacaa aaattagccg ggtgtggtgg cgggctcctg taatcccagc 29280
tactcaggag gctgagacag gagaatcact tgcacctggg tggtggaggt tgcagtgagc 29340
tgagattgca ccattgcatt ccagcctggg tgacagagtg agactcggtc tcaaaaaata 29400
aaaagaaaaa agaaaaaata gagtcccata aaattatgtc agatagacac tcctcctgag 29460
acttagggat tttcaaacca tttcaaatag aaaatgaaag tgtaaggaga caagtgtgta 29520
actttccaaa agaagttgtg ttctgtgtcc gttttaggtt acagaatgac tcaagccaaa 29580
aaaaaagtat gttattcatt catttacaca aaatacaaaa tattttcatt atcttctgtt 29640
atttgtttaa attgataaaa ttatatttat ggtgtacaac tttatttttt gatatatgta 29700
cacattgtgg aatggctaaa tcaagctaat taacatatgc attacctcac atactttttg 29760
ttgtgagaac acctaaaatc tactcttcac aattttcagg tgtacagtat attaactgta 29820
ggcctatgat ttaccatgga tctcttgaat ttattcctcc tgtttagatg aaattttgta 29880
tcctttgacc aacatttccc cacccttct acaccccagc ctctggttac caccattcta 29940
ctctctgctt ccatgattta gactgtttta gattccacgt ataagtgaga tcattggcat 30000
ttctctttct gtgccttagc ttatttcact tattataatg tcctccaggt tcatccgtgt 30060
cgttgcaact gacaggattt tcttctcttt gaaggaagaa tagtattctg ttgtgtgcgt 30120
atactacatt ctctctatca gttcatctgt tgatggatac ttaggttgat tccatatcct 30180
ggctcttacg aataatgctg aaatgaacag gggagtacag atacctcatc aacacactga 30240
tttcatttct tttgtattta taactattgg tgagactggt ggatcatatg atagctccaa 30300
tgttagtttt tgaggaccct ccatactgtt ttccatagtg gctgtaccaa tttacattcc 30360
cagcaacagc gtacaggggt ttccttctct ctgcatcctc atcagcactt gttctgtttc 30420
atctttttga taatcaccat tctaacaggt gtgaggtagt ctctcattgg gttttaattt 30480
gcatttccct gatgattagt catgctgagc actatttcat atacctgttg gcaatttgta 30540
tgtcatccct tatgaaatgt ctgcaccctt tgctgttttt ttattaggtt tatttatttt 30600
cttgctattt agttgcttta gctttttaca tgttttggat actaatgtct tatcagttgt 30660
atggtgtgtt ttcaaatatt ttctcccatt ctgcaggttg tctcttcact cttgattgtt 30720
ttatttgctg agcagaaatt tttagtttga tgtaatccta tttgtctatt tttgtttttg 30780
ttgcctatac ttttagggtc atatttagaa agtcattgcc cataccagtg tcagagagct 30840
ttttccctat gttttcttgt aggagtttta tagtgtcggg tttcatgttt aagtatttaa 30900
tcaattttga gttgatttc gtaaatgatg tgagatgagg gtctaatttc attcttctgc 30960
atggggacat tcagttttcc caacaccatt tattgaggag actgtttttt ccccattgtg 31020
tgttcttggc atctttattg aaaatcaatt gaccataaat gtgtggtctc tctattatat 31080
tcatattttt taagtaaatt attttatgat gagaaaggtg gcaaaaaattc tgcattatct 31140
ttgatatgta agaaaaggcc atttgggcac agattggacc tgattatttc tcttttcaag 31200
aagcaagtac cttatctcta ttcttattcc aaagtgattt aatctctatt aataatttag 31260
gcaactaaac atcattactg attgtaggag aaatctgagt ctagtctgtc tatactgatc 31320
aagaaccagg actacctcat ggagactttg gtaaaataaa tctcaacagc actcaccaga 31380
tgaataaagg ttttcttgaa ctagtttaag atacttggtt atcagttgaa cacaaatagt 31440
aataatttaa ggtttcatga attgacatgt ctataattag cttcctaaac taagaataac 31500

```
aaaaaatgag tagtttgtta attcctaata gcctgtgatg aaagttatta tctggggttt  31560
tttttgggtc tgttttaaaa attaacactt tggctctgat tataaaattt ataaattgga  31620
aattgaaatt actggataaa atacaattta tgttttaaaa acattttcaa gtggaaaaaa  31680
ttacagcttg gctgaatagt gataattttc aaactaagcc tttgagttca ctatttagag  31740
ttctctgata aattgttaga gttagaagta gtgagttcat tgcttgactg aataaataat  31800
tcatatggca caaaagcagc tttttctttc tcttcagttc ccttctcccc cattatgttc  31860
actttctctc ttgtaaaagg ctcctttgca gccaaatagc aaccttgtgt gaatatgcag  31920
ggacttgggc atagtttcaa cctcagtgtt agctgagtat ctggagtcat ggaagagaat  31980
taagaatctg tcttgaatgt atattttcta gtagcaactg aaaagaaata tagtagttgt  32040
aaattgctag accttactct tacggtacag ttgctctgga aatctctttt tagcaaaata  32100
ggattttatt tctggatata gaatctttcg tagtgtctgc gtcaaaacaa aattaagttt  32160
taaaattgag taaatcattt attttttcta gtttttttcag aaatgctttt ttactagact  32220
aaataacttt tcagcatcag tctgataagc atagaatttt caaaattctt tacttgctat  32280
tttagaattc tttattttct aagaattatg aagactgtat taggtattta tgtggacttc  32340
cttttttttcc taccttttat tatagcacca aaattggaat tacgctagat tattttctct  32400
ctgctgttta aatcataaga gactctttta ttgggtcagg gcaattgtct ttctagcaca  32460
ataatcttct ttgataatgt cactactgga aattatgttt atccttcata aattaactaa  32520
tccttatttt tgtaataaat tatctgatat ccttcagagg ttatctaaaa atattccttt  32580
aagtctgcat gtattcagca tatttcatgg tataacaaga cttttacagt tgtataacag  32640
aaatttaaaa taaggcaacg gactgtaatc cagacttctg tcaactggaa atttttatga  32700
agtagtattt tgctggtata ctgatacttc accaaataca atgtttatct ttaaagaagt  32760
ttctaaataa gacaaaacat tatgtttagt aaaattcaat gtagtatgtt ttactgtata  32820
ctaattcttt atatagccca taatcataat acataggcta tataatacat gtaaagcata  32880
taattcataa tacataggat acaaatcaaa tatatgagct ttattttgat ataatcagac  32940
tttattctgt tacctatttg cctttctttt tcaaactttt aagcgttgcc cttattttca  33000
taagacttag tgtttcactc agtattaaat ttatccaaag tcattgtgat tttatgaaac  33060
attgtgattt taagtgctga accatgttgt ttttcaatgt aaaatgagtg taacttttag  33120
taattattga aatttaagcg ttactgtgat tttccataat tctatttcgg tagtcacaaa  33180
aaaacaaaaa tttggcttct tattggccct tctagtgcca acactggcat tgttgaaata  33240
catttctaag gaagatggtg agtgtttcac ttcattagta gctgcatgac aagccacccc  33300
aaagtttaat ggcttaaaac aacagtaatt cattatttct cataattttg agagttgact  33360
gagtgagtct tctgctttgt gtggtcttgg ctggggtgct aggaaagagg gcagtccaca  33420
gtggcctcac ttacatagct ggcagtggat gcaggctgct ggcgtggagc acagttgggg  33480
gtggcctggg tgcctcagct ctccttaagt gtgcctctct gtgaagttag ttgggcttgc  33540
ttacaacatg gtagctggat tccaaaaaga aatgttccaa gggcaaagaa gctgcagcct  33600
tttaaagggc catatttaga agttacttag cattacttct gcccattctg ttgatcaaaa  33660
caagtcacaa ggccagccca gatcaacagg aagagaaata ggcttcattt gttaaagatg  33720
gagtagcaag attacactgt agaagagcaa atggtttggg atgtattgtt gcagccatct  33780
atggaaatgc aaactaccac aaggaagtgc agtttttgct gagcatgggt atttgccatt  33840
```

```
accacatttc agaaactggt atagtcaagc acacatggat ttgaccactg gatttacact  33900
agggtcactt aagagctatc agccactgtc ttctcatctg tatgacagta gtagtatcaa  33960
cctcacagga ttgacagtta agtgagataa tttggaagta cacagcgtag tgctggaaat  34020
tccattactc ccatcctgtt tcttttccca tgtccctcat gtttaatttt tatatttgtg  34080
attataatac ttaaaggtat gttttaaaga taaatcataa ttcatctaaa gtctttgtct  34140
taccaagata gttcaatagt tccaatctga ataaagttta taacattaac ataatttata  34200
gatcttctaa tacaagcatc tgtctaatgc tagaattctt tataaaccac tgtatatagg  34260
ctactcacaa tgtaatgagc tactaattgg tagaaacaag tggctatttg ccatagttct  34320
acattctgtt ctaccttcta ttttgcagaa aaatcttaca gctttcctaa gccatctttt  34380
taggtcaatt ccagaatttg tttatgatca aattgacaag tacctagcca aagagattaa  34440
gatactgaat cagagaaaga agtctaaaga gataattttc caatgatcat ttctaaagaa  34500
ggaatagaga taaaatattt taaaacaggt actgaatagt cacagtcaaa ggtttgatta  34560
tgagtcagct ttgttggttt tagtctcatt agtcaccagc accaccaacc tgtcatattg  34620
gcaatacata gttttggtca ccaggagaag gagtcacaga aaaccagtac tactacttac  34680
agaagattaa ctgaaagcac atgtcctgat ttgttcttga agataagact gaggtgaata  34740
ttgcttaaaa cagtatcagc aaaatacaaa atcaagtgaa atattacatt gaatataata  34800
attgaaagaa tgaggataga cacaaagaac ttttggatgc tagtgattag atattagaat  34860
tagtttctca gaatatttta aagaatttaa caaatgacag tgttatgaat tatgtgggca  34920
gtgcttaaag tgggaacaga gcaaaagaag tggatttagt tttgtcaagt ctgtctgttc  34980
agcgttaggg ggaacatttt atttcttctg aaacaatgat attggaatcc catttcatct  35040
tttcattttc aaacactgac tttataagtg actttgggag aagcttttaa gttttatata  35100
aagcactttt tttgtactta gcacaaagtg ggcaccttta aaattacctg tttgtatagc  35160
agttaattta aagaatatgt tcatgcatat tactatattt tctcgattct aaaagctcat  35220
caattgtaag gcacattctt tgatttcata acaacttttt aatgtctctt tttggaaaaa  35280
taaaacactt ttcttggggg aggaggagaa tttttctaag gattattctg aattcctttg  35340
ggccataggc actgtagcaa atgctgctct tcctgatctt taacactttt aggattgata  35400
gtgtcgttct gagccatgtc caggaattac tttggcgagg tttccatttc ctatttaatt  35460
aaaatttttt tactaattat attacatttc actagaagtt aaataacttc tcttgaaagt  35520
catccagaag actttaacag ccagatattt ggtatctgct cagaattatc acttgtgaaa  35580
ccttcattaa acataattca gccacatgtc acagaaagtt ctgcatgtat aataactttt  35640
tgtttcaatg ctgcattata gtgatcttta aaagacattt taagaggtaa tttagggatt  35700
tcaaattaag ttaaaattta gctgtgcata gttctgttga tgctgataag tgaacagaag  35760
gtaaattctt agtcatgtct aagttcacac agagatacaa taatacacgt gggtgtaata  35820
caaagcatta tagtattttg tatagtatct cctttgttat taaaagttct tttgatatct  35880
ttggtaagac tcctattgat ttgaaaaatg ttactgtgaa aaaaatgtgc tttaagagtt  35940
gagaaagtaa attattcctt tttttctctc agcagctgtt taaggaagac agagcaggca  36000
ttggataata ttcttattaa ggtaaagaat ctgggtgttt gagccctaaa gtcatacagc  36060
aagtagtcca cctggaatca tgaaccaggt cttcaggact tccagatatt tgtgctgtat  36120
actatgctgc attttcaaca ataattcatt tatctgtggg tttgatttaa tgagactcat  36180
ttattcaaca aatatttatt aaatgctatt cttgccagtc attgtgttaa atgatagtgt  36240
```

aacacagtaa acaagacaga tatctttcca tgtcctcacg aaaccagcag ctttggaact 36300
aaacaaataa ttataactaa gatgagcatt aagggagaaa ttgtaagatg ataggaaaga 36360
atataacagg cggacttaac ctgctctggg atggtggggg agtgttgaat gtgaactgag 36420
ggtaggacat gagaaataac ttttgggctg agattggaag aatcagcatg agttagctta 36480
agcctaggaa ttaggagaag ggttaggatg gaacattgca ggcaacagaa atagcatcta 36540
caaaagtaaa aggaagaact gaaaagattc cagtgtgagc gttgaaaaga aggataagta 36600
aatgtagaga agaatgtagg aaagagatta tgcattcttc aggatttttt gacctatatc 36660
ctaagggata ttgggaaacc atggaaaggt tttaagcatc ggggtatgcc atgattaaat 36720
ttttcatttg aaaatcatga gtctgactat agtatatata gaagcattgt tgttagatgc 36780
tatttcggta ggccaggttg gagatgatgg ttacagcagt ggagctggag agaagggaat 36840
agatttgaaa tttgggatgt gaacaaagcc ttgtatttga cagaaatgta aaactattaa 36900
tagtattgtt attgttccac ctatagaatc tgattataag attatctcta aaatactttc 36960
aggtaacttg tacttaatgt taggaggaag tgactatatt ataaatataa tttagaaaac 37020
atcgttcctt aaaaaataat ttttgaattg tgctaattct tgttattgtt tgacttcatt 37080
aactaatata gggagtatag ggagaactta gttttaaaag ataatttgac ttcctgattt 37140
atacataaaa cacataagta attttggaca tatatgatgt gtatatatat atatatatag 37200
tgcaggtcat cttgtttaca ccacttatta atgaatatca gatttggaag gtgactcttt 37260
aggattttcc tattggttga ttgattgaaa cttacatgaa gaatttaacc cttttgtttc 37320
aaatagcttt ctattaagaa acactttttt catgattatt cagagaattt attgctggat 37380
cattggctct agagatagac tgctggttaa attaaaagat gccggaggaa acattttgga 37440
aacagacttc acagaattcc ttatgaactt ctgtactttc ttaaccaatc ttatttcttt 37500
catgtaccta tggctgttac tagcctgttg tatcagggat accatagtca actacctata 37560
cgggccttaa ctataaagaa ttaggccatt tagggaaata ataatgagac tggggcttta 37620
gagaatttgt gctcatctaa ctgagtagag ggacagctaa tattctgctc catctgatgg 37680
tgatcatggg agtattcagg ctgattgtta cccaatattt cagtttttcc aaaggatcct 37740
aaaatacaga tttttatgta aattagttgg taattaattt aggtgttttt aagatactct 37800
gtgacaataa ctctacaggg caaaatcgac ctgttaaata tatttggccc ataggctgtt 37860
gttttatagc cttgaccata tagaaatctt caatatctat ttaaaagtaa gaggtcaaaa 37920
gtatttctag gaaaagtgaa tgccaaaaga agggaggaag ggaaggcata aatgagatac 37980
tttttaaaag aagtacaaaa ctagttatct aggttatatt tttaaactaa gttcaaaaag 38040
aaattcactg tcctgagaat aattttcata tgcttcagaa catacttcta gcaacttcag 38100
ccatctgcgt gtgtataact gggaactcag agtaggatga gaatgcacag ggcgtagaga 38160
accaatgaac tgtagatgag agtgtagtgg ttctctgaaa ctgttgtgag cagagtacag 38220
caggaacaag agacagttga tattggagca aaatcaggct ataagaacat agcgatctga 38280
gtacatcatg ggcccctgaa agcattacta gactaaaagc ataatttttt atactgatga 38340
tcaagaagag gtcatattgg tacactaaga ttgaataact ctgctcccaa tagcacatgt 38400
aatacacaat cactgtagga aatcaggaaa atatacaaaa agtagcatat ggtttttttt 38460
taaagctagg aatgggtaaa attctaaagt tttctaaaag taatgaaaat agaacttggc 38520
aattgttagt ttcctaatag ctaattagtt tccaaattag tctaatttgg cttaaataaa 38580

```
aagaatattg gttagctcac ataagaaaat acatatatta ggattagtta cgccagtggc  38640
tcagtgattt ttttcaagga ctcagtttgt cgtctactct actctttatc cataatattt  38700
cctttatccc aacactgtag ttgccaaatg gctgctggct gcaatcagga ttgtgtgttt  38760
cctccttcag atccaaagag agaaataaac ttctcttggc gttctcatgg gcaatatagg  38820
ttcttttctc tgagaagtcc ttatgcactc ctgcccccaa cttgctcctt attgtcctaa  38880
attagcttaa ttctaaatat gccttaacta atcgttggca aaagggatga gcttaccata  38940
atggattaga ttaattgtgg tctacccttg cagctcagga cagtcagctt accctgaggc  39000
gcattgacca ctgggagaga tgtggatata gaaatccaat catggatcat taggaagaag  39060
gaagcgttgg ataggctctc agcatggtcc accacagttg cattaaggat tgtgtattac  39120
gtttttttact tatgtgaaac accaccttcc cccatcaagc ctgtaagtat gaagtcgagt  39180
ccctagtgaa tctactctct gactcctgtg tttcaagcac cctcattagc agagcttata  39240
tagttcggag ttgaagaatt ttttttccc aaaaattctc ttctcattta atagacacct  39300
gtctgtagag taaactatgc aggccataaa tggaacaaag atagtttagg aaaatacagt  39360
ttcttaaata aattactttt aaaaagtata ttttctctca gctcttctct ccaaaggagt  39420
tttgtatcat aacctctgta gtaaatagtg tcatctttat tgtctgatta taaaggtgaa  39480
gtataattta tgggataatt tacaaagcaa aaaagaaata cttattttta aagtttaaaa  39540
attttctgtg tagaaaatac tataataatg catgatttta agaatctgtt attttggcta  39600
aaatatttaa ccagccaacc atatatctta tttctttcag ttgctagatt tctgaatgtt  39660
agccaaatat tttagtatct gggtcacata gtcattacaa acaaatgtag gccaaaatgg  39720
tttatgcttc tcagttgcca gctcagttct ctctttgact ttttattatt tgtttctctt  39780
tgaactaaac tttatttact tatattagca cagtactgtg ttaattcttt gtgtagaact  39840
ggtcttcttg tgtcgttttg ccccaaatca aggtaacaaa caaataaatg actgtgctct  39900
tggctgttat ttagaattgt tactatacaa aaggtcacac atgttaaatt acctactgca  39960
gtgctaatta ttgtgaaacc ttgttcaaaa tgctagagag actgtgtttt ggcacttctg  40020
ctgtaacagt ttttaaagat ccaacctgta tgcattttgg tattgaaatc ctcaaaactc  40080
ctaaagaccc tatgttaatt taaaatgcaa agttgtctca cctttttata ctagatgaga  40140
tagcattttt cttaaagtaa aatgagaact cttatgtgtt atgatataga ggtaagggca  40200
gggaaagaga gggaaagaag aaaggagtac attggagtaa caaaaattcc accttcattt  40260
ataaagtgct ataggctcta aaactccatt ctgaaatact cttttaactt tgaaaggggt  40320
atgtttactg ccagcttctg ttaacacagg aaccatggtt tttctgttct taaaattaag  40380
aaccttatac cttttggaat ttttaatatt tttctctatg tttgtaatgc ttttaattat  40440
gtttattact aactgatgtt attaactata tttataattt gtacactcta ttctgtttgg  40500
aaagtacaaa atgataccat agatacttcc tgaatttttt tagaaaaatc aaaattttat  40560
tcatctttat tcatagcatc attggacatt cagttagtaa attttccaga taacaaacac  40620
ctatcttctt tgattgctag aatagttaat ctcaacccct cttgttataa aatatagtga  40680
ctgtggattg ttgatgaaaa tttcttaaga cagtgtattc aggaagacac tgcctcaggg  40740
ctactgaggt atgtcatagg gccatttgtc ctttcaaaaa taattctcag tagctattgt  40800
tgctttgcat ttgtataaag tgtctgtttt ttcaaagctt gatattaatt ctgatagcta  40860
ctagtgtaca gagaagggtg tctgtgaata aagtaagaga aagaatgttc ataatagatt  40920
tgaagagcac ttcaatgagt aaagtacttg gactttacaa tgtttgcttt tacttcacta  40980
```

agtcctgccc tgtgcccctg ctcctgcccc tttatgccat agtctctttt ttaacatggt 41040
acttggcagt gttccaggta gttattgtaa gaaggatgag cttagacttg gagctagaca 41100
aacatgatgg gaattaaaac aggataattt aatagctgtg agaccttaag caagttcaca 41160
actgcaaaat gggtttgtat atactatctc tcacggttgt aaggattaaa tataatggat 41220
atagtttagg aggtatttta acaaatgcta gttcctttcc ttatacttta agataaatga 41280
cccacttact ttggaaatgg tatttgccta ttttagtatg atgctataag gtttaaaggg 41340
tcagtatccc taaaatatga cagctgttaa gatctcttta attattcaga aatgaatggt 41400
atgtgacaag atattattgg ttaattcagt ggatcagatg aataaaatgt gctgaaatat 41460
tttggagact gaaaatataa atttagatgc aagaaatata ttttaaataa acatggaaaa 41520
cagttttttt atccgagtct aatcacgttg aaatatttta tgaatatccc cagagagttc 41580
gtaaattagt gagtgatttt tttaaatgca aaggtaaata cctagaaatc atatatacac 41640
ttaaagtaaa atctcacaga gttctcaagg ccattttgca tttactagtg ccacagtagt 41700
ggcgttacag tgagctgcag taacctgaaa cagtactgca tggatgctct aataaattgc 41760
atgtctggag gaagcagcta actatggcga ccgccacgga gcagtgggtt ctggtggaga 41820
tggtacaggc gctttacaag gctcctgctt accatcttat tttggaaggg attctgatac 41880
tctggataat cagacttctt ttctctaaga cttacaaatt acaagaacga tctgatctta 41940
cagtcaagga aaaagaagaa ctgattgaag agtggcaacc agaacctctt gttcctcctg 42000
tcccaaaaga ccatcctgct ctcaactaca acatcgtttc aggacgcagt cttgctctgt 42060
caccaggctg gagtgcagtg gtgcgatctc ggctcactgc aacctccact tcccgggttc 42120
aagccattct cctgcctcag cctcctgagt agctgggact acaggcacaa gccaccatgc 42180
ccgcctaatt tttgtatttt cagtagagac ggagtttcac catgttggcc agaatgatct 42240
tgatctcctt tttttaaatt aaaaagtaaa ctttaatgtc gaaaatgcaa acctggggag 42300
ggcagaaaga tcacacacaa ggctgtcact tcacacttgg aaggttgcac agcagccagg 42360
cagagaccct cctcacttcc cagatggtga gggggccggg tgggggcact cctcacttcc 42420
cagacggtgc aggggctggg cagaggcact cctcccttac aaatggtgag ggggctgggc 42480
agaggtgctc ctcactttcc agacagggcg gcggctgggc aggggcgctc ctcacttccc 42540
agatgggacg gtggccgggc agaggcgctc ctcatttccc agacggtgag gaggccaggc 42600
agaggcactc ctcacttcac agacaggacg gcagcagggc agaggcgctc ctcatttccc 42660
agacggtgag gaggccgggc agaggcactc ctcgcttcgc agacgggacg gcggcaaggc 42720
aggggcactc ctcatttccc agacggtgag gaggccgggc agaggcactc ctcgcttcgc 42780
agacgggacg gcggcagggc agaggcgctc ctcatttccc agacggtgag gaggctgggc 42840
agaggcactc ctcgcttcgc agacggggcg gcggcggggc agaggcgctc ctcatttccc 42900
acacggtgag gaggccgggc aggggcactc cttacttcgc agacaggacg gcggcggggc 42960
agaggcgctc cttgtttccc agatggggcg gcggctgggc agaggcgctt ctcacttccc 43020
atactgtgag gcagctgggc agaggtgctc ctcacttccc agatggggtg gaggccaggc 43080
agaggcggcg ctcctcctca attcccagat agtgggcggc tgggcagagg cgcgcctcac 43140
ttcccggacg gggcggtggc cgagcagagg cgctcctcac ttcccagagt gtagggggc 43200
cgggcagagg cactcctcgc ttcccagagt gtagggggc cgggcagagg cactcctcgc 43260
ttcgcagacg ggacggtggc tgggcagagg cgctcctcac ttcccagaca gggcggcggc 43320

-continued

```
ctggcggagg cactcctcac tgcccagacg gggcagggcc tgggcagagg cgctcctcac  43380
ttcccagact gtgaggctgc tgggcagagg ctcttgtcgc ttcccagaca gggcgggggc  43440
cgggcagagg cgctcctcac tgcccagatg gtgcggtggc cgggcacagg cgctcctcac  43500
ttcccagatg gtggagcagc agggcagagg cgctcctcac ttcccagatg gtgcaggcag  43560
agatgctcct caggtctcaa tctcttgatc tcctgatccg cccgcctggg cctcccaaag  43620
tgctggatta caggcatgag ccaccacgcc tgccctgccg tgtcttcttt ctcctcctaa  43680
gcaactgtct tagtctcctg aattttgata ttctacttaa cactctcatg ttcttacgca  43740
tgttgccatg ctggaggcgt ccttctcttt gggaagcctg acccaccaac agtgcctcag  43800
gagatagaca tggaagcttt gccggtgggg gccgctcgtc tctatcacac ctcagttgca  43860
ggggaggggt cggttgcagc tgcagcggtg gccccgacag ttttcttttg tgggacctgt  43920
ggccggcagc tctgggtgga gaagacctac ttgatccaag agctgcagga tccttgggct  43980
gcatgtcctc ccccaccatc agcaagcctg gagagctggg caggtggtct tcacccagca  44040
ccttcaaggc cgccttctct ggccacaggg agcagcccgg aactggggca gggagcactg  44100
ttggaagtgg gtcaggcttc ccaaagggaa ggatgcctcc agcagggctg tgtgaactgg  44160
cgactccatg gcccttggag tagaaactca ctgcatgcac ctgggccttg tcagtctgat  44220
tcttttctgt caagctcttg aggtggacat ttccctccaa gggcctggga ttgtaccagg  44280
aagaagtgag gtttccctga gtctccaggg gcctagaggt ggaggctgct tccccattgc  44340
tacaggggcc ccttttattg tcctcctgcc cctgggtctc tacctggtct ttcacctctg  44400
ttgcttcttt gggctcttct gcgctcacct ccgtcttcgg gagcctggct gggatcacct  44460
gatcatctaa tgaaggaagt tgaaggttaa acttgcctct gagacaaggg atccttacgg  44520
ggctgaggtg tccaaacatt atggagttgt gaggagacag cacgggtttc ttccttgagg  44580
gggggctcca gaccacagga cgcaggaccc tctgtggggt gcccgtgttc cgagggataa  44640
gacacagcct catagggcg ccgtcccacc tgactggaaa agaaggccca agatgtcgct  44700
gacggttgaa gaggagtggg aaacggccca caattccccg ggcaggcaca ggtgcaggag  44760
ctgcagggtg agcccggcca gctgggaagg cctcacggac aagacgagca ggttgccgat  44820
ggcatggcca ggacctgcgg cagaaccagg aacaaaatac gcttagcgag ttgcccattt  44880
tgagtgagtt gtgcacagac gaaactaagg gtcagaagcg gagaggatac tcctaagtca  44940
cccacttctc tgtggctggg tgcacactgg gcatctggga gtttatgaca tcactatggg  45000
gctggtgaca gagccagtgt gtggaggagt gcttaggagc ccagcgaggg tgcctacaag  45060
aggagtcaaa gggcaaaggg tgagaccctt ccaccggtcc agctggactc tagcctcagg  45120
gatatcctgc tcctgggggc aagtgtgtgg ccctggatgg gcccccctgt ggggctgttg  45180
ggggtgcgag gctgatccgc cagagccctt ccacctggcg cctggcccag gtgctggcta  45240
gcacccagtg gccctgtttt ggccggccct gtcccccagg ttacagggcc agaacctgga  45300
agcagagcgc aggaccagcc agatcgcgcc aggcttcccc ggggcctctc cagtgcctct  45360
gtgccacctg gagccaggcc cgccttctcc atggctgccg tggcctcaag ggccaccagc  45420
cttgctccgc aggtttccaa agagaggacg cagtgccctg acctgactgg atgcacctct  45480
taccacatgc ctccctggca ggcagggtct ccacttttta caaatttgcc tgagaccatt  45540
cctcaggtca ttcaggtggt catggcccag ccaggctttg aacccaggct gtgcgattcc  45600
acagctggcg ctctggcctg tgtgcctcat gatcatggat acagcatcta ttcttatttt  45660
ttcatgtagt cctggggtac ttagcaccgt ggcatatctg taataagcac atgcacacct  45720
```

cgaaggaggt cttcacttca acatacgagt tgaccatggc atgctctggg ctccagtcct 45780
ctacaaagac gtagggcagg aactaccagt tgtcagcaca gcaccatccc acattgctct 45840
tctaatggag cctttcaccc cagatgttct ttctcgtctg atgggaagga tccaagtatg 45900
taaagattat gttatagatc agctttggtc tgtcctaaaa gaaatttgcc agtggattat 45960
tccatatgga taaaagtcag tttctctggt cttcctggaa tgtgtctaga aagcaaatag 46020
attatttaca agttcatagt agatcaatgt attggattaa aatatgacaa acataatttg 46080
gtcattgtga gcatgccagc ttggtcaact attcaccaca catgatgccc taaatataac 46140
tctaggtttt cttatgccca agagagggac atactcttgg gtgtctggac tagggaaaca 46200
tgtatgaaaa accatttggc cactctacat cttgttattg gagaattgaa accatctata 46260
ttcaaagata ttattaaaag gcaagaagtt aaaaaaataaa aaaataaatt gcatgtctgt 46320
tgttatggaa ttttataact gtacatacct tttatttaat ccattcacag gtcatattat 46380
aggatatctt tcatttaata agtatactaa atccatacct tatactgttg agttttgata 46440
gtaccagagg gaaaaaagaa gaaaagcatg gcctctatct ttaaggagct atttaacagt 46500
catatgaatc actcgattga gaagatccat atgtgtaata taatgaattc cacaaaaatt 46560
gcttattaaa attttttgaa aaagtagggg tgagattgaa tatagcaaag ctttattgtt 46620
gatttttgtt gttggccagg ccaaatttgt gaacatttta catgatcagc tatatcgaaa 46680
tacatttgta tgctctactg aatataggga acataattta atatttaatt taaactccag 46740
gttaccatca tttacaggca ttctgtgcat taaaccgttt tgcctcttct ttcttcctca 46800
gtaacacgtt tagggccttt tgatgcattg gaaagaaaag gcagttgcga gctgctggct 46860
ctagcaaatc agagctaatc aacctgagaa taatgtttgc actttcccgc tttcaagtct 46920
ttgctcaaac tgctctctac ctttgctccc acaggttagt cctttccccc aatctaaaat 46980
ctctctgact agccctgaac ttacttttta tagctctcac tgtctaccat ctccttcatc 47040
ttgaatatac caggacagac tgggaagttc cagaaaaaaa cagacataat acttaaatca 47100
tctttgatac ctaatttgtc ctcactgcca attaattaat tttgttttgt tttatttaat 47160
tttgtaaaga cagggtcttg ctgtgtcacg caggctcctc tcaaactcct ggactcaagt 47220
gatcctccca cctcagcctc tcaaagtgct aggattagaa gccgtgagcc actgcgcctg 47280
gccataattt aaataatcct ttagattcct gtctctgtcc attttcaaag ccagggttac 47340
actatcataa catacccat gatgtacacc attgctaaaa caatcttcct gaagtactaa 47400
ttagattttt gagcagagaa taaaaccatc ctttccagtg ttggcaaata ttcaacgtac 47460
tgtcctgaaa tacctgtagt acttccaagt ttctgctttg tgctcacact gttttctttg 47520
acctgaaatg caatttctat ctataaaaat cttagtcatt atgaggtcta gcaaagatct 47580
ttttcttcta tgaagccttc ctatcgaccc taactaaaat ctcttctctg agttcccagc 47640
gtatactgct tgagctggag caagactcca gtgatccttg gaagaaagtg ggaggttatt 47700
ttcccagtgc gattccagga aagtttaatg tcttatagtt cagtcccctt tagcattcca 47760
catacagtta gtgctcaaat atttgataat tgctctactc acaaatattt ttgtgtgaaa 47820
ttgctagcta ttctctatcc aagaagtaat gaagtatata agcttcttca actctttgtt 47880
gagcccggga cctcttactt atttctgtat cctatctact cttgagtagt agggtcattg 47940
gaaagcaacc actgggtttg gggataagtt gtgtgtattt tagaggagga agtaaaggtg 48000
ttactggact tttaaaactg aagctttttc tgttttaaag tattttgctt cccgttactg 48060

-continued

```
tatttataag atgatactgg tatacgtagt gtcttggcta tttatctatt cccctttctc  48120
tttaacacaa tattccccaa ctttggtgtg atactgaatt gaaatctctg ggagtgtggc  48180
ctaggactct acacttttac taacaatcag ttgagatgct tatgaaggtg gtggtagtag  48240
tgataatggt agtgatgatg atgatgattg tattagctct gctttcgaag gcttatgatg  48300
tacttactgc acttttctag gcagtttgca actattaacc taatgttcac agcaagccta  48360
tgtggtaata cgctattatc ttcattatac aaatggagaa actgtggcag atataaatta  48420
agtaacttgt cgccaaaatg actttcttat aaataggtca agaatccatg aaaaggatga  48480
ggcatatttt tttggttgat agtttttaaa ctcactttct aaaggattgc tttaagtgat  48540
gtgaatgata tgaatgtaaa ctggttctta tataaattga agtatcaata tgctgactct  48600
atataggaat acttcaacaa ctagacctaa atatagatac ttgctcttgc ttttaggaag  48660
cctgtcacaa ttcttggtga aaaagtaagc atgcacccaa aaacgtagaa cattgaggaa  48720
aatttttaaa taattacact ttctaaaata catgatttta ggaagagtgc tttattatat  48780
actatatata tatatataca cacacacata gacatacaca cgtagatgca tatatattta  48840
ctctatatgg atgtgtgtct atatgtatag tcattcttca gtatcctcag gtggttggtg  48900
ccaggacacc ctcagatacc aaaatccaaa tactgtccca cagtatttgc atgtaagcta  48960
tgcatatcct ctcatgtact ttatttattt atttatttat tgagacatgg tcttgctctg  49020
tcgcgcaggc ttgagtgcgc tggtacaatc atggcttact gcagcctcga cctcctgggc  49080
tcaatcgatc cccccacttc agcctcccaa gttagctggg accacaggca cgcaccacca  49140
tgcccagcta acttttgaac ttttttgtag agatagagtt tcattgtgtc gcccaggctg  49200
gtcttaaact cctgggctca agcgatcctc ccaccttgac ctctcaaagt gttgggatta  49260
caggcataag ccactgcacc cacccatcct cttgtatacg ttaaatcatc tctagcttac  49320
ttataatacc taatacaata caaatgctgt gtaaatagct attatattga tttttatttg  49380
tattattttt tattgttttg ttgtttttta aattttttttc ctgaatatta tgtgtgtgtg  49440
tattgagatg ttactttgtg atttaatgta attcaagtaa aactcgttaa gcatttattt  49500
tctgttttag tagcataaga taaatttggt tttatatgct aaaatatttt atctttttaa  49560
taataaatga taagaatatt ttgttccctt ttagttcata gactatggga agtggagtag  49620
ggagtgaaag tggtggctgt ggtggtggta tggtggaagt aatttgttta ccatcactgc  49680
ctgtccaaaa taattttgat gaatgatttt aggtgttgcc taataagtgc tctgactttt  49740
gaaaccagtt gaactaacaa gcatgttgtg ctttgctaga aacatcttgt aagttctgac  49800
tttgaacaga cagtggaatc taaattgagt tagtggagga catatcttta caactaaatc  49860
taaagtgttt caactatttc ttttttttaat ctcctgttta tttttcttgt agaattaata  49920
tttttgattg accaatcata attgcataca tttatggggt acaatgtgat gttttgatat  49980
atgtatacag tgtgatgtgc ttatgctaat taacatatct gtcacctcac ctataatatt  50040
tcatattgag acatttgaaa tttgctttta ttattttgaa atacttaaaa cgttattatt  50100
gactctcgtc aacttgctac ggaatagatc tcaaacttat tcttcctctc tacctgaaac  50160
ttcatacccc ttgatcaact ccccccacca ccctcctacc ctagcctctg gtaaccattg  50220
ttctattctc tacttctatg aatttaatct tattagattc cacatgcaag tgagatcata  50280
tggtatttgt ttttctctgc ctgacttatt tcacttagca taatatcctc cagattcatc  50340
catgttgttg caaatgacag aattttcccc tttttaaatg ctgaatagta ttccattgtc  50400
tgtatatacc acatttcctt gattcatcca ttgatagaca cttaggtgtt tccgtatcct  50460
```

```
ggctattgta aataatgcaa caatgaacat aggagtgcag atatcccttt gacatactga  50520
ctccagttcc tttggctata taaccagaag tgggatcact agatcataca gtagttctat  50580
ttttagtttt tttgggggaa acttccatac tatttaccat aatggctgaa ctaatttgca  50640
ttcccaccaa caatgtactg tataagagtt atcatttctc cacacactgt ccaacattta  50700
cctttcatct ttttgataaa agctactcta acaggtgtaa agtaataatg cattgtggtt  50760
ttaatttgta attctctagt aattagtgat gccgagcatt ttttcttgta ctagttggcc  50820
atttgtgtgt cttctgagaa atgcctgttt aggttctttg cccatttttta aaaattgggt  50880
tatttgttgt tttgttattg agatgttgga gttacttaaa tattttagat attaacccct  50940
tattaaatgt atgatttgca gatatttctt tttatatttc ctgtttacaa atttcctgaa  51000
cttctctggc tgctcattta tatagaattg ggatgagtta tgtcacctga agcagtcaag  51060
ataagactgt ttctactgat atccatatgg caggcttact ttgttaccca atccaatgaa  51120
aaagggtgcc aggatgtgaa agaaaaatag atgtgatggc cgggcgcagt ggttcacgcc  51180
tgtaatccca gcactttggg aggccaagtc aggtggatca cgaggtcagg agatcgaaaa  51240
atagatgtga tgccatggaa cattctaggg aattaccatt tttagagaga gttttgataa  51300
aaattttacg tatttttaaa actcatattc ttagtctgaa gagttggaaa taaggttgaa  51360
tgtatgtctt aaagctaata gtataaaaag agaagtgtaa aatttaagtt aatcatacaa  51420
ctttctttcc ctaactttat gaattgactt tttgcaattt ccggagctaa tgaggtgaat  51480
gtctgaaatt gagtatgtag gttaaaaagt tgaaattttc ctaataaaat tgtatctctt  51540
tctaaggtgt aactctttct ttctttgatt atagtaaaag gagcatctgt ggttcttaag  51600
aggtcttgat ttttctgcca gctagttgtg tgactttggg taaataatgt catatgactg  51660
gacctgtttc tttatttgta aaattgtgtg tggtgttaaa ttctaagact gtttttaaaa  51720
aaatttttgc ggagactggg tgttgctttg ttgccaaggc tggtctgaac tcctggtttc  51780
aagcagtctt ccccaccttg acctcacaaa ctgctgggat tacaggcgtg agcctccatg  51840
cctggccaaa ttgtaagact cttataatgg atgagtagaa tatatttaag attatataaa  51900
aacacaagtc acttcatgat catcgtctgc tggaacatga aaccagcttt cttgtgtaga  51960
tgtgttatca gtaatgttat tcacaccgag aggatcattc tgtggttttt aattcatgat  52020
tttgtaatct gatagtgact tttcattatg tctcctgatt tataattaca tcacagccat  52080
tatgattgga atcattggga agagttgaaa tgagcaattt agaattgttt ctgaaataca  52140
gaaagcctta ttttttggtg ggggttgttg gaggagatat ctctgtgttc tgtaatttca  52200
tttgactaag gaatttatct ttggtcttct cccagagtga ggacatgaat acttccatag  52260
ctatattccg tattaatcac agtttgcttt gtgggtttca ttaggctaaa taagaaaaac  52320
gtcgttatgt attttctgct ttaaaaaatg cttcttgata taaagtcttc tcagatcagt  52380
cccacatgtg ataaatctat tcaaactatt aaactgcctc aatgtgcttg tttctctctt  52440
ggaaatctat ccatttctgt gtctttatgt accactcact ctccccccatc atattttagg  52500
ttataagctc ctttccttta tatctcatag cacccaggaa agaactttgt tagtctctga  52560
atagtttata agtgttattg ctattgagaa ttttggattt aaattattgg aatgaataga  52620
ataatgctat ttctagtata tctaactgag ggtcagtgtt attaactcaa agacatagca  52680
gttttattaa gctctaggct ttgtttctga agtcagtttc tcttaatcat aagtggatta  52740
ttcactttat attctcttat ataatgcctt ggtatcaggt tattgatagg taaacatcag  52800
```

```
aaataggctg gatagatatg catgcatgtg tacacatgca catgtatgtg agagagagag  52860
agaaggattg cacatagaat atatgagaat ttgaggtgtg tgtaatgttt ataactcatc  52920
tgagtcttac atagctatct agttatgtac acttaatttt gcacctttta tagttgaaat  52980
tcagaaacat tttttaagga aaataaggac gtgtttttct ttccttcatg ttttcagttt  53040
agctttattt gattgtattt ttgctaaaga cttaaattgt caataactat tgaaatgggc  53100
caacttatag ctgagcacaa agtatgttag gacactgaga tatatcttaa catttgggaa  53160
taatttaatg tgtctaatac ttgagaagga tcaaaacaga ctgtacaacc caataatcat  53220
aaagcctatg gtcaaaaatc gtatataaat gacaggccct atgaagagta gccgtaagaa  53280
tcaagagaaa aagaacctaa attggtacag aaaaggagct gagtcatttt tatattataa  53340
ttagaagttg gtaacgataa attttgtctt cccagtacaa aaagtatcat gatcaggcag  53400
gattacgcta aagtgtaacc tctaacttct tgtggtatgt actattacaa gtagttgatg  53460
atttaataaa tataaatata gatgatactg tcagagtgtt tccagacatt acagttagct  53520
tttaggtgaa ggcagtgctt gacagaacct aagtttgtga ctcaataatt tattatataa  53580
tctaatacca tttttatctt gtattaattt gggttatagg ataattgggg taactttttg  53640
gtgagggatt gaaattttct taaaagcgtt ttcagaagat actagaattt tatgggattc  53700
ttttattata gcatgtcttc tcaaatataa tattaggact gcttgaacag gaggcaaatc  53760
atattcacgt tattttccag tttagagtta ttgctcttat cagttggtgg gtgtgggaac  53820
aacttaataa agtttgggta atttagtttt cagtttaaat tctcaactgg caattggccg  53880
aaaactccca tctgaagaca tgatcatcca aatgtcattt tgtgatttgg ctactgtctg  53940
cttgacatag gaaagcacta tcaagaaaga ctaatggagt gactatcaaa aggaagtcaa  54000
tggtaagagt tttcatttaa attgtgtgtg tgtgtgtgtg tgtgtgtaaa gcctaccaat  54060
gtattatatt tgaattaaaa ttttagaact tttaaaatct aggacataat gacaagtgtt  54120
tgaattttat atgtctgtca cttatatttt aataaaatat atgcaaagaa tggttttata  54180
gataagagat tttacatact taatgttgat aaatagtata aaagtatgga aaatcaatta  54240
tatagttcat gtctggttta aaaattcaat ttttgtagtt ttattgtagt tatttaaaat  54300
agtatattat aaaattgctt gactgaagtt taacttctaa aaaatttgta ctaaactgag  54360
tttttctgtt cagtttcata agtgcttctt aaaatagaca tgcattttgt ggtagtctgt  54420
tgaatgctgt ttggtttttt actttcatta taaaatagga aagaaaaaag tataatatca  54480
tatgacaaaa tccatttagt ttaacattag ttctttaaaa atgtataatt gctactatac  54540
tttggcggaa actattaaat ttgtaagata agacgtttat actctatacc caaaacaaag  54600
tgaagtagct gttcataata tggcgcagaa tcaaatttg gtgataaaat cagacatctc   54660
tctcctgcct tacacatact cccactgaga aaataatttc taaatttggt tacattttca  54720
tatacttcag atgaccttaa atttatattt ttctcctgaa tatatttgat tcctgcatat  54780
ccctttttt gggcatctgt gtccaatcag atccatgatt agtcatgtta gctttggaca   54840
agagtggagg taggatctta gcaagtttga aatctttaag attgatgttt atctgagatt  54900
attccagcat gtccacggac atagtagttt tgtgataaca aggtaatggc tgatgaagat  54960
tagcatatta ataatagatt ataattctgt taaccattct attgtcaaat acgtgatttt  55020
tgcgattcac atagtttaag taatttttca tgcccaatta gagatgtcaa aattatgtta  55080
attgaatctg gccatgttct tagctgtttt ctagagctta ataacaaaca tatcaggaag  55140
agctcttgtg acaagcaccc agcacagcat ctgtcattat gtaatcattc caatgtttac  55200
```

agtgaactaa gtacttgaga tggcaacatt catactttag tccctctgtc tagtaattca 55260
tacttgtata gtctgtctac tatgtgtcac ccatttaggt aggtgctgag aataaaatgg 55320
tggggttaaa aacagatatt ccctgttatt gaacttccag tgccaatggt aattacagtg 55380
tagataataa ttacacactg caactggaac caatactata aaatggcata agttcctata 55440
agggtaggaa caataaagtt agtgtataaa taaagcacag aacctacaca tttatttatt 55500
agattgaatt gataacttgc ttttgaactt ttaaagttaa ttctattaat atctgctaag 55560
ctaggcatca gaaagactaa attctaacca tagagaaata catttttat gctgctattc 55620
tattttctta gatttcttaa gaatttacaa caaaaccctg tcaaagcagc attcttacgt 55680
gagaatttca cttacgggag agttcttaca ggatttcaag aaggaaagcc ctgaagaggg 55740
acactgattt cctcaactga atttaaaatt gttacatgca gacattttta aaggtagtat 55800
gattttcctt aatcaagtca actttatatc tttttatctt tttaaagaag ggaatgtgac 55860
atttatgttt ttcatacaca cacacacaca cacacacaca cacacacaca cacacacaca 55920
gagaagcata catgttgatt acgttttgga aaataaaatc caaagagcat ttggatgtct 55980
gaatgtttat gcttcatctc cgcagtgact tctaaattta gttttttct ggatatactc 56040
aaagtcacca acctgagttc aagtattctg atttgaagat ctcaacttag agatccaggc 56100
agtccccctt gtcagtgcta ggagaaagat gtccttccca taccttccag aaagagtgtc 56160
ttgaagaaat atattccttc ctgggtaacg tgctttggaa tgtacatgat attcattttt 56220
ctttgacagc tctttttggt tctgtttagt tggctttgat gggttcatga tgcccagtgg 56280
agaatttggt atttagccac aaaaagatat ttaagacaca taattatgta aatattgcag 56340
atggaggatg atacatagca tttcttttat caaaatgaat ttgaattgac ttctttctaa 56400
aacaaaattc taccaatagt catcagtttt taattatata acttctcaat ataggaaata 56460
atcagtgtct gattggctgt gtatgttgga gtgtaatggc ttttgttttg aatttggcag 56520
tttctactct cagaagaaat gagttgcgaa ttacagtggt gttagaagaa atgaattgga 56580
agttcgaatg agaaaaattt aaataaaagt tattgtttat agatatggaa aggaaaataa 56640
tgtttttagt tcaatatgag aaagaacctt ttaaatgtag aaataaaatg gggtgccttt 56700
ctacatccat tcttaagaat ttggcagaag ttatgaagaa gttaaaaaga aggagttcct 56760
gctgatataa gtcacgagga ttatttgaag gaaatttatg tcacatctcg taaaatcatc 56820
atattgacaa ttataaatat gtaaaacttt atgtgcaata gttattacta aaaatactga 56880
gctactattt atagtgagat cattattaaa taaatttaac agatagaata gcaaatcaca 56940
tttattcatt cagtatattc ttaccaacaa cctgctgtat gtcagtcatt gcataagact 57000
gatgtgatgc cataggtctt gcagggaatg tagacattaa gcaagtaatt acaataaagt 57060
atagtggctt atgatattat aaaaacaaag cagtccttaa gtataccttg caattgatct 57120
gtagtatatt aattttaatc cgctcatact cctcatgaaa tgaggttgtt cattttgatg 57180
taaaaattag actgacgttc tttgcagtta gtagagactg aaaaagttct tattatttgt 57240
ataacttatt taaaatgaga aactgctgtg gaaagatctg caggtttctg agataccaag 57300
aaacgtgaat atgagcagaa taaacacatg catattatat acattataaa cgtcatttaa 57360
gacaattata tgaagcagtt ttacatttaa aactaccaag ttgtaatagt taagaagttg 57420
ggctccagag tcatactggt tgggtgtgag tattaactct gacacttacc agctttgcag 57480
tcttaggaaa cctgcataac tctactgtgc ttcagtttcc ttacctgtaa aatggggata 57540

-continued

```
ataagagtat atatcttgtg gaaaaatata ttatttgata tatgaaaatg ctagaagagt  57600
atctagcata tggaaagtgc atagaaaggg ctccatatgt tgttttagtt aataattaca  57660
ataataattt cctcatctta aaaatatcct gcttcattca taaagttgtg ccaacggaaa  57720
taattgcaga tgatgcttaa aatacataca atatatattt cagagtggta tgtaaagagc  57780
ttttattatt actgctaaac aaaaaaaaag tccgtgaaat tctcatctaa gctttggggc  57840
ctctttagct gaatttcagc agtcactcaa aggctttcta gagatgccat ctagagatac  57900
tttataacct agtgtctttt tttttttttt tttgcaatac agaatttttt tttcattgta  57960
agatgctgaa tgagagaaaa ttatttcagt actacaagta tggtttccca tgaccacaat  58020
tagttctaat gtaaccagtc aacagttgtc tattgaaaac cactagctat taatatagta  58080
tcatggtagc ctaaaagaat tatgctatcc ttctacttag gctctaggga gacaagagcc  58140
atgtaaagaa tacttaaagc acaaaatgtg agactgctct gccactagtt cctgctctgc  58200
cactaataaa cagaggtatc ttagatatat gaacctgtta caattatgag gccatcttag  58260
catctcagta cccttattat atatatcgtg tgtatacaca catggccatc caatatttct  58320
ttcccaaatt gaaatgagag gaattcatta aggtggtttt aatttccaaa tttactgagt  58380
aaaagaattc tattctaaaa attattttgt ataatgccct tcaaattgag ttttacatgt  58440
actatttcaa ggcttctcag atattcccac ataaattatc tagtgtttct gcatcacttt  58500
gcgatctttt cattaatgtc aagtgtaatg ttttttaact tcacaaggga aacatgaaat  58560
tcctttagtg tgcctcattt tcagacattt tcttgttgat taaaattcct ttttaaataa  58620
agtttcaaca tgtactaaat aatttgttta cctttgaatt aactttttat aaatgaattt  58680
taaataatga cagcagtcat tacaaactct gctgttggca acactagagg gcatttctag  58740
ttcttcagac agtgtcatga gttctcagaa taatttacca attcattaaa cagcagatta  58800
gcattttaag ggaaaggaac taaaacaagc acaatacata tatcatacat atatatagta  58860
tgtatatatt atgcatagac agataatata aatatccata tataatatat acattatata  58920
atatatggat aatacatata tattggatgt atgtatactc acgtctgctt taccaaatgt  58980
tctcactgaa tcactactcc taaaaaggcg ggagagtatt tgtgatctgc tcactgaagc  59040
accactatat tatccagttg tttattagtg tcgtggaggt ctatgctctg ataggtttag  59100
catcaagtga acattgagta aaaaagtata tgtatatact catacataca tactcatcag  59160
aagttagttg ctgtgcttat tgaactacta gatgctaaca tagtcataat tagaataatt  59220
tttcagataa aaaatgagag ttaaaataga tgccctttat aggcttagta gaagatttaa  59280
gactacctat attttgaatt actgtatttt agatgttaaa atattttcaa gggttttgaa  59340
tgcaaacatt tttagggaaa agatacaatt atgtaatatt aaatatataa tattaaatat  59400
taacatgcaa tgatatgaaa gaagacaagt ttataagaaa attcaattag cgtaaagaaa  59460
aacttttttt tcttgggagg atttgcttac tgcggtgtat tggggaaaaa atcttatata  59520
tcattaagta atcattaaca cggtaaaagt aaagtcaagg accagcaaaa aataacctaa  59580
ttgttgtgaa aataaggtga caaacagaca atcccatctt acactgtaac atactttgta  59640
taagagggga tacatgataa ccactagaac agtggtggat gtgcaggtgg tagatacaca  59700
agggatataa gaaagtcttt ctagttcaaa tgtatttctg ccatgtactt tacccagtag  59760
aaatgcattt acatttttaa gaggagcgta taaatctctc aaatatttct gttgatacat  59820
atacctatca ttcacttaaa tacctgagta cctactaagt ataaaatacc ccgttatttt  59880
atgtttggca cagtgaggct gtaacagttt atactcctat tatgtagctg agaccagttg  59940
```

```
gtctctttta gagaggggag tatcagttag ttacagaagg actcatttga atcatgagat  60000
aatttgtgag aatgcagacc caagtaatat gctctaataa aatcagaagg cagcatgctt  60060
ttgttgagaa atggaggtag gaaggtaaca acataaaata acctactttg tactggttca  60120
gtataccccca taaactgtca tctcttttgt ttgtttgttt tgagggtaca aattatttca  60180
ttttctgata ttctctttcc taaggtattg ttggactgaa acttaaccaa ttctcctctt  60240
tttctgtctc tgtctgtctg tctctctctc tgtgtgtgta tatatatata catatatata  60300
cacatatatt ctttctacac acacacagta acagtatgtg caagtcaaat ttaattttaa  60360
aataaatctt ttaaagcgtg ggtcaatctg tgccagtcac acacagggca gtctgccgta  60420
tcttttgcat ccttgttttg tactgctcgt gaatgttcgt tatatagtag agtaggtaat  60480
tccatattta cttgtactag aatatatctg gcttaataga tgatgttcca aaggcttgaa  60540
ttaaaaaaaa aaaaccttag tgtaaaaaat ttcaggcata cacttaagag agactagtgt  60600
aataaacccc atggcctaga tttaacaatc agcaaaattt tgccacattt gcttcatcta  60660
ctctcttctt tttcctcaac tatttttaaa gtagatccca gacttcaagt cttttcactc  60720
ctgcattctt tcatatgcat ttctttaaaa gaaggaattt ttcttatata accacaatac  60780
ctttattaca tccaacaaaa ttaacaataa ctactaacca cctcatattc tctctgtatt  60840
cagtttctct gcttttaact gaaaaatgtc ctttttacgt ttagattgtt ctttcagaat  60900
ccaaccaaga tctgtatagc atttggttgt ttggactgct gtataattaa aaggtctttt  60960
ctttcccacc acttgtttac ctcactcacc cccaaacccc cttcttcctc cttccctccc  61020
cttttccctt taatgtgtta atgaaaaaac tgggtaaact atcctgtaga atatcctcca  61080
ttctggattt ctctgttgcc ttctaacttg ttcctgtagc ctctgaattt cctgcgaact  61140
aaaagttggc ttgaaagact taattagttt caggttcagc tttggttttg gtgttgagga  61200
tggaaggcat gcaggaatac tttgcacatg gaactgtttc ttcatactgc atcacatcaa  61260
ggagcatata atgtctgctt gtcatactct tatcaatgct aaaattgggc agtggtgcca  61320
acccaatctc tctattgaga gttttctacc aatctttcct cccgtgggaa aagttgctga  61380
ctgttctcca aatcaattct gtcattaggg tttgcaagag aatgaatttt taaatctgcc  61440
acccccttaca catttattag tggaaattct tctgtaagaa gaagtttcct tcataaatta  61500
cacctttttg atttatctga aacaatgtat actggaaaga agcctggtgt cttaaatatc  61560
atctgttaat acctagtgta acattccaaa ggtaacttga gatactgcaa ggaccacata  61620
gcaccttgag tacctatttt acatgtgact ctgaggactt tcacagaata aagatatttc  61680
ttattttaat gaacgttgtc agtatcagga taattttatg tagtcaacat atatacagtg  61740
ttggtcctat aggagttgga gaccttttgc cagttttatt tggtcaaata cattattttg  61800
tgatgaaata actgtgagtg atgagttgag cctcaaagaa catgatactt cattaaatca  61860
acaagctgaa cagtatcatc taaccaaagc tgtagaataa atggtgataa acttaaattc  61920
aggaatgaaa caatcaccat ttttgttaca aatttgtcca cccgtcatca ctaaccccat  61980
ttttatttaa tactggtaat gaacaaaacc tgaagaagaa ataaaactaa aatatttcat  62040
ttgtagatga catgattaat tatctagaaa aatctacagc aatcagctct aaaatgattt  62100
attaaataat aaaaatttaa taaagtacca gatatactgt atctttatac catgtgaaaa  62160
tcattctggg aaaatatccc attcagaatt gcaacaaacg atgtaatatc tagcaataca  62220
tttgagagag atgttagatc tttggaaaat aaattaacat ccagtgtatt tgaaacaatt  62280
```

```
ttaagattca aataaaagca gagaaactgt ttctaaatca agaatattgg caaattattt  62340
gactaaaagt aagatttttg ggtttaacct ctaacttcca aaatttctag tgatttattt  62400
tatagtgatt ctgtaatgag aagtctcgtc ctactaaata tcaaaaggtt ttaaagcaag  62460
aatgtctaaa acagtgatga tgatgtaaga ataggtgtgt tacccagata ccagaagaga  62520
cttctctgtc tgttggagat ttaagtatac attttctggc caggcccagt ggctcacgct  62580
tgtaatccca gcactttggg aggccaagga ggtcagatca cttgagatca ggagttcaag  62640
accagcctgg ccaacatggt aaaaccccat ctctactaaa aatagagaaa ttagctgggt  62700
gtggtggtgc acgcctgtag tctcagctac tcgggaggct aaggcagaag agtcacttga  62760
ccccaggtgg caggggttgc agtgagatga gattgtgcca ctgcactcca gactgggcga  62820
cagtgagact gtctcaaaaa aaaaaaaaaa aaaaaaaaaa aaacaaagta aatttccctt  62880
gaagcccgac ttcatggccg gtgagagtca agagacatgg cctggatccc gtgacttaca  62940
caaatccctg tggctgactc agaccttagt ttctctgcct ctgcttgcat gccaccttgg  63000
tttctgccag tgtcaataca tatgtgaaac cagccccttt actagtttca aacatttaac  63060
attttgtgag ttaagaaatc ctgaataggt gatagaccag caaatgattt tcttaatttt  63120
tgagtggaac atgctatcta tgttcattct tttcttctac tcatacttta ctgaattaat  63180
acagttgttt tcttaagagg aatactgaac aaataagctt gttttcattt tgtaaaacat  63240
agattactgg agcactatga ggaatacaaa atttgtccca tctgttatca tatacagtaa  63300
ctaaatgtat gacaaaataa tctttcctaa gagaggggca cttaaaggat atttgttcag  63360
tggtgttgga tagtactatt cagtgatatg tcttaaaact aattagacaa aaatcatccg  63420
tatattacac aaccatagga ataaaaaaga aaaggtaaca gagagaatac ctttacatct  63480
catatttgaa gaattagtag aactcaccca gaagatactt gaatattaaa aatttttgtt  63540
ggaccaaaat attatgatta aaaggataat agaaaattgt ggaaactaca ttaaaaatta  63600
taaggaaagt gataataggt ataagttata tattgttgta aatatgcaag tttagatatc  63660
aagattataa tacataagtg agaaatgaat atgacagatt aagaatatga aagtaaagac  63720
acatgaataa taaagaaata tgaggttttt ttcattgtat taaaggacat aaatttttaa  63780
aaagagaaat ctaatatttg caagtaagca gtgctaacag accctttttgg gaaataatgc  63840
agtaatacat gctgagagtc acaataatgt ttagaaattt cataataaca tattaggaaa  63900
cactatgcta attattttac atatatatat atataaaatg cccagcttaa aaactaatta  63960
tagaacagca acataaaata ttacatttaa atgattattt ttggagacta tagaacaaca  64020
ctgttcagga gagctttgtg gtgatagaaa tattctgtga ttgcactatc caatatgtag  64080
ccatttggca catgtggctg ctgagccctt aaaatgtggc tagggcaact gagaaactga  64140
atttttaatt taatgttaat tatttaaatt taaatagata aatggggcta gtggccacaa  64200
ttttagatag tgtagttcca gaaataaaga gaaatgtttg gtataagtga aaataaaata  64260
gtaaatttat atgccatgat tacaagtatg tacataacta aatgtacgta tggaaagtga  64320
tagtcataat taaaatattt gtgttaggat tgaaggaaat aggtaatttt tttaaaatgc  64380
taaattttta aaaggttaca tgacaataat gtaacacttc agcattgtac tggtactgtt  64440
cagtatggta gccaccagcc tgatgtgcaa tttaaactta catctgttta agtaaaatta  64500
aaaattcagt accttaatca cactagccac attccaaatg agcagtagtc atatatggct  64560
aatgtttgcc ttttcgaaca atgaagctat agaacatttt tgccattgcc aaaagttcta  64620
ttgtacagtg ttgtagaaag aactggtaaa aggaatatac tggaatcagt cactgatagt  64680
```

ttatttgtca gtagtttcta agggcacatg agaattaaaa ctggaaattg gattcagtaa 64740
aaagtataaa ggaagagtaa cataagatcc tactcctgta acttagatta gtgctttttt 64800
tttttttttt tttttttttt gagatagagt ctcactctgt cgcccagact ggagtgcagt 64860
agtgtgattt cagctcactg cagcctcacc acctcctgta ttcaagtgat tgtcctgcct 64920
cagctaccca agtagctgga attacaggca tgttccacca ctcctgacta atttttgtac 64980
ttttagtaga gacggggttt ctccatgttt cccaggctgg tctggagttc ctgagctcaa 65040
ataattcact tgccttggcc tcccgaagtg ctaggattac aggcttgagc cactgcgcat 65100
gacctacacc agtgctcctt gaagaatggg ctatgaactg gtgctggttt gttaatcaat 65160
ccatgactaa atgcttactc tcaatttcta tattggttta gaaactctta cagccatgtg 65220
atatttgtgt cattcaggca catcacctgt ctccccggtt gaagttcagg ccagtagttt 65280
taacgcagtt gcctggagag ttttatgcaa agtgagctga gtatagtcat gacggtagtc 65340
catgaacctg ggtccccaaa agggagaaaa cagtctttca ctacagattg cgtgagaaac 65400
attggccagc attaaagaag gaaagtagat tgctcaggga agttttgtag ggaacttaaa 65460
atgagatgtt agtatggctt agtaatctgt atttgcaggt gaaatgaaaa attcagccct 65520
aaatctctga atatggtaaa cttagacttc atcttctgca ggtggaaatg aggcaaggga 65580
tccattatcc acagcatgag taagtttcta gtcagttcct ctgtctaggg agtttgtttt 65640
cccttttcgc ccttgttggc ctgggagact caaccagctt agtagtcttt tcctttcagt 65700
aagatttcca actttgggtt ggtctttacc cctttttagc tctttttgtc gtattatctg 65760
cacttagtac tttgtaactg ttttcacccc ttccccccaa agttagttca aaggcttaca 65820
gcatgttgaa aataggaaaa ttgtttttaa attaagtgag tttttgtgta cacttatttc 65880
tttagtctaa agttttgttt taaatctctt tttcacattt aaacctgatt ccctgagaca 65940
agatataaaa ttgaattatt tgtgaaatgt ggaaaggttt ttattgcctg taatcaaagc 66000
ataatctgtc cattaaagca ttattttagt gatgaagggt ggacatacat cccaagttta 66060
ctacctgttt tcttactgtg gttttgacca tacagcaaat ggtattttat actctgaaat 66120
gaaatgcacc atacacattg tccagtatgt tttgagtttt aattctacat tttcagattt 66180
tggggtcaaa tgaaatcaag tactttataa atagttgttt cttctgattc tactggcctt 66240
acatgttaga tttttttaaa gtatacacat tcagtccttt atcagtacca ttaatcaaat 66300
gttgatttca gcatttcttc attttgtttt cttttttctt ttcttttttt ctttttcttt 66360
tctttttttt tttgagacgg agtctagctc tgtcacccag gctggagtgc agtggcacag 66420
tctcagctca ctgcaacctc cacctcccag gttcaagcag ttctcctgcc ttagcccccc 66480
caagtaactg ggattacagg cgcttgccac cacatccaac taatttttgt atttttagta 66540
gagatggggt ttcaccatgt tggccaagct ggtctcgaac tcctgacctc gtaatccgcc 66600
agcctcagcc tctcaaagtg ctggaattac aggcatgagc caccacacct ggccagcgtt 66660
tcttcttttt ctctctaatt tatcaaattt ggaaacagtt ggaaaacatt taaaggaaat 66720
aagtctctgt gtttttaata atagtttaaa agttaaagga aaacaaatga ataatattct 66780
gtttattata gtcagacaaa atgtacatac gaaaatacat aaggaaatat agaatggcat 66840
cttctgattt taatttaata ttatggtaat gatttactta ggcagaatta tagctataga 66900
caaccatttt atcactttat ttatatcgat ctactctcta tggatgaaaa cagttaatac 66960
taaagcatta agaaggtata ttgcttttca tctgtattaa tattcttctt ctgatatttg 67020
atatttaata atatatttta aaatactctg catgatttcc tgatcttaaa gcattccatt 67080
cctttcaagg aatttggatt ataatgattt atttatagta tttttgtcat taatatttta 67140
ggatatggca tcttaaaata ttgtattcct aacagttatt taatatataa ttaaacatct 67200
atattagtat tattttatat aacatatttt caaactcctc agaacatttg taggtttttg 67260
tttaatttta tgtaagtttc accttaagaa tattgactaa tcggttaata ttcttcttaa 67320
tcatcgcaat tttttaaaat gctttctatg taccaggacc tatttaaggt actacagata 67380
atcagtgtgt caaaaaacaa aaccaaaatt cctttcctca tggagtttta cattctagta 67440
gattgattct actgttgatt catactaaat taatttatta attatagtag attattctgt 67500
ggcatttaac agaattcaaa gggctacttt tctgttgtta ggaaatagca tatgccatta 67560
tcttggaaat acaaagggag gacagaattt ccgctggctc taacccattg ctttttaatg 67620
agtttagcta tgtatatata ttttaaaatg gaatttataa ttatgatcat ttggcaacct 67680
acagtttttc tgtatttttt caacttctca acttcccagt gatgggggtg gatgttgaac 67740
tagtcactta aggttttggg tctaaggagt aatatttgaa acatgcagta tttagaggag 67800
atatttttgt gaatgaagag aatgtgattt taagaatact catgatttta tctaatttct 67860
gttctcaaaa cttcatttg taatatagaa gataagcttg atcaaaatag tttgatccca 67920
gtataatctt ttactcttct ctcctccctt aggacaacct taaacttcca ccacaagagg 67980
aatataaaga ggtccctcct gcaccaagaa agatctgcag atctttttca gtgttcttgg 68040
aggtgtgggg tgtgagaact tgatcagttt gtgtcagcca ccttgttctc taaaggtaag 68100
cactgtgtag tgagtgcaca ctcgtgggcc caggctccta acctaagact ggttttggaa 68160
tgctccattg agggtgtgag accttcagac gttcgcacag aagggaggcc ctacctgtgg 68220
gtaggacatc acacattcat caagaggtgc ttttcgttat ttagaagtga agcatgtcct 68280
ggggatgtat ggatattttt gttttgtttt actttaaaaa aaatcccagt catagtaaaa 68340
ccttccagtt tagtctgcat ttattcagtt aataactgct ggagttaatc aaaaattttt 68400
cttgtatgtc ttgagatatg gattaagaat tttgaaacaa tgacaccatt taggcaatct 68460
agtgacataa tagcttcagt tgatagagcc agctgtgaag aattactttt catgatcttt 68520
ttgaagctgt atcttatctt tacttcaggg aaagcccctc aaaccatttt gtattctgta 68580
ttacacttca gaaagtgtgg aagcaaaggt catctaatct ttaaaaggta tgtaatcata 68640
aaatttttta tgtcagatct taattgaaaa atattactta aaacttgaaa aaattactta 68700
aaattggcaa tttcttttc gtcttacaac ttcttcctgt cttcaggaaa tgaagaataa 68760
atatgttggt tctatcaggg aaaccttatg aaggataagc aaattaatgt ctgtgcttta 68820
cttccaaatt ctgacatcag aaaaccttat tgttaactaa tataatctat agatgtctct 68880
caaaatgacc agtcttaaat tcaaatgtca tttggatatc attaattgac tatggagaag 68940
agcagaagca tgctgatttc gaaaatgtca ttaatattag gattaggtca gtcttaggca 69000
agaatacttt gaataacaag agactaaatg tctagtaaaa cattttagat tgtaattccc 69060
agtattctgt agtattaaca atgagactta aagtactggt gaagacatta aatttgtccc 69120
tttcatttat cttttcttaa agctcttaaa gtgatcctga agactttagt tctacaaaat 69180
gtgaacttct tatggaccat taaagtgggg agtaatctgc tgatttttgt ctagcaaccc 69240
tacctctgat gcaggataat ttttcaaaac cgttgttctt cctatagctg tataatagaa 69300
gatattaaag aggaaaaata cttgtgtgtt tgctgttaga atgaggaaaa aatacaaatt 69360
ggaccttttt gaaaaacctt gagaaccaat ttactttttt tgtatgtaaa tggtcgagga 69420

-continued

```
gttagaacta gtcttggtta ttataactgc aggtaaactt aaaagattta aatcttcaaa  69480
acagatatca tgtaggtttt attagaaaag aaatatagat tattgggtgt atagagataa  69540
tctatatata cgtacagttt tttttaattt ttatttgcaa gagcatgcta aatatcttag  69600
cctttataat agcatagaat agaatggaca aatatgttat cccttttttgc cagttgagaa  69660
aacactttga attaaatctc caacctaatg aaaattataa ggtgggttat agaaataact  69720
aaacaggtta ttatttctta accaaactaa aggtttattc taactaaaat acttgtaatc  69780
taagaagtct ccctaaacat acaccttttt taaagtgagt tttgttttat gatagtacat  69840
attttagcaa catactttag aaaagaaaag tttatttcac tatcctagaa ctcgtgttct  69900
aatttcagat cagttttgta ggatgtataa ataaaatggg gacctatgag atctatgaga  69960
tcttgccgtc tgtatctaca gtatcaaaaa taagatcatt tccttaacaa ttcttattaa  70020
taacttatcc atctcaattc ataggaggtg acaaaatcaa ctgttgttct atgattttga  70080
tcataggtag gagggaaaac ccaaaataat ggtaccgagg gcttcttcca ttgaaactaa  70140
tatctgggag aagatttgat tttcatgtgt acatatacac atacctatat tagtgtttat  70200
ttcttttttc taatcatgta agaatttgtc aaagatcagg tttctgattt gtctttcatc  70260
ggtatctgta tgccacattt tgtttttgtt tttgaagtgt tcctagccag ttcatgctag  70320
tccctactat aaattttgtt tccctggcat gatcatgctc tttacctact ctggtagctg  70380
gagggaggtg agagaagcag tcttatgtgt ttaccgtact gatttttttt tagagatggg  70440
acaacaaaga aattctagcc tttggagaca tctagaccag cactatatgg tacaaagata  70500
attcgagcca taaatagaag ctacgtatgt aattttaagt tcttaatggc catattaaga  70560
aaataaaaag aggcaaaatt agttttcatt acattttatt taacccaata tatacaaaaa  70620
tattattcca acatataatt aatagaatgt tttatgagat ttttttcata ctcagcattc  70680
aaaatctgtg tattttatac tcacagcaca tcttatattg gactagccac agttcaagtg  70740
ctcaatagcc gcacgtggct agtaggtacc atattccaca gttcagatct agacaatgag  70800
tggaattctc attttagcct catacatgcc aaaatccact ggatgaccct gcgaactccc  70860
cttgtttaga gtttccaaat ttagcagaag gaaaaaacaa aacaaaacag gatgtccagt  70920
gtaatttgaa tttcaagtaa ataacaaata atggtttagt gtaattttgt cccatgctat  70980
atttgaggca aacttttacc aaagaagtta ctgcttattc gaaattcaaa tttgactggg  71040
tgtcctatat tttatctgac aacccttctc tggtttaact tgagaagagg acatcatcag  71100
gctgcctgga atcttggagg actagaaaat agagcatctc tttctctgcg caggatttta  71160
ataatcctcc aaaaatcagc ctgtaaacta gaagatatct ctagcccatt tcttcctaat  71220
gacctagtat gtttaagaca gaagaggggc tcaaatggca aggatttagt ccatacatat  71280
ttaaacattt tacatctaaa ttattacatt aagatataag gtttacgaaa ttttacaatt  71340
tttgaatgat tacttgaatt tataaaatgt agatcatcta acagcacaac gctgctatca  71400
tttctcttga aaactaattc tcctttgaca gtaaccacag cagttttcag ggtcttggcc  71460
atttcaaggt attttcctac cattggtttc cattgcatct gtcacataaa cctctggtag  71520
tcaagcatga acacaaaata caaggctact gaatgcaggg attaggctta cttcgttaca  71580
agtatttaag tacttgtaat tcttagctct ggtgttgacc attggatcct gaccagttca  71640
gcaatcagtc tcctaagagc ttcttttaca gaggaacatc tttccgtttt cattctttaa  71700
catttttaat gtattgattt tagtacattt ttgaagcata cagtcacctc cttagtagtg  71760
```

-continued

```
tggatctacc ctcaagtgct atagaagaga ctgtttgtct cgaaagacag tcattgcacc  71820
acctctctcc agagaatact tttccttcac aaggtgcatg actcaagatg acaggcttac  71880
attattattt atgtaggcag gtggatgcca actgccagtg cagggtggca taagttagcg  71940
ttccaaagtt aagctatggt gcattccaaa tccattcaca cttaggagaa tgtacccaag  72000
agtgtgggga tgttttcaat tactgcattt ccttcagaga acaagaacca caggtaagtt  72060
tgtgtgtgtg tgtgtgtgtg tgtgtgtgtg tgtgtgtgtg tgtgtgagat ccaataatta  72120
tttctaaata agaaatttca gaatttgaaa atattgcccc tcccccaaaa cagtcacctg  72180
aaaggtctca aatatagctt tcggtatata tttttcttcc tcactctaag aaggaaggta  72240
ttggagttgg tggtgatggt ggagttggga tgagggagac aatttactgt catttgaaag  72300
ctgtgaatgt cacacatttt catgtctaga aatatcctgg gtttatgtaa gaatctgatt  72360
ttgcctaacc tctaatgtct caggtatgaa ttattttgtc agattaacac atctatataa  72420
gtaagatgtt cagccttgct tagctaatgt cttcaacagc aatgagtaaa ctaatgagtt  72480
gtgtctgcat ttttcacttt tattctcaag actgacttcc ttttgtttaa aggcttttgc  72540
cttatttctg aaaccataat ttaaagctac aaaagacctg aaatataatc tagtaccctt  72600
tttacctggg gatccttgga tggatttcag agattctgtt gaatccccta aaattacagt  72660
catattttgt atatatgtgt ttttactggg gagaatgtcc atattttcat catattctca  72720
gaggatttca taacaaaaaa tttggtcgac aaccactgtg atctagtcta atgtgatcat  72780
tttactgata aactgaagtt gaaagaattt aacttatctt catttgaaat ttaatacttg  72840
tgaaaattaa agtttatttc tttaaaattc atactgattt ttaaaagaaa aatacattta  72900
acttcaacta attaaacttg aaaataccag cctaaatggg agcagttagt ttgctaatgc  72960
tttcttctgt tctgcccttt gagtggactc tactagttaa cattaaaatg gccttccaat  73020
aaagtatgag gctatgtgat aagttcttga agatagatta aaaagaaaag gaattatcca  73080
ttataattta aatccctttt tctctcttca aattctgtct ccaaaactaa aactcaagaa  73140
aataggtgaa taatgttatt tttatatttc cagaatatta aaaaagtagg taattgcctt  73200
aataaacatt acactgggca ttattgggac agttttaggt tctgaaccct agttaaagaa  73260
attcttcagt agcctatata cacttcctgt tggttttcag tgataagggc attttaaggt  73320
ctttttgatc ataagatgct tttaatgtta tagtaggact ttagaaatgg taagtaagca  73380
agttctgtat taattaggga aactaatacc tttttctcaa aatgaaggaa atattatttt  73440
ttctttttct tggtactaac cagtaaagtc tgcctagttt aagatctagt gcatttatac  73500
cataaactga atattagaat aaaaagaaat atagaggatg ttatataaaa gacaattatt  73560
ttctgaaagg agtagaaaac aaggcaactt ggaacactac atatatataa atgtaaaata  73620
tattaatata cttttatata gatgatatta tatatccata tatatatttt tttgtttgtt  73680
tgagacaagg tctcactctg tcacccagcc tagagtgcag tggcacaacc acagctcact  73740
ggagcctcga cctctgaggc tcaagccatc ctcctgtttc agcctcctga gtagctggaa  73800
ccacaggtgt gcaccaagat gctgagctaa tttttctgtg ttttttgttg agacgggggt  73860
ctcatcatgt tgcccaggct ggtctcaaac ccctgagctc aagcgatcct cccaccttgg  73920
tctcccaaag agctgggact atcaggcatg agccaccatg cccagctgta ctatttatat  73980
tttttattta aattaaattg tgcttaaaga ttctaaaatt tatagtataa agctcattat  74040
agaaaatggt attgacttct gaaacattat agttttggtt ttgtttttat tccttcggac  74100
attttcactt aaggtagtta tcactcatgc ttttctgcta ttataaaaag tgaccagatt  74160
```

ttgctttttt atccaggaag aacagtttgt gaatgccact tgataggcca cctgtgttat 74220
tttccatggg tatttctaac aaataaaaag ttatattttt actttgtatt catcaaatta 74280
ttttatgttt aatttagaaa agcttaaatt cttcttagga atatttgcaa atatttgtaa 74340
atagtttttt tcaaaaaagt tgaggtagat agatattaaa tatttttgtg acttctcatt 74400
aaaagaaact gaagcaatta gttgacctca ctcaattcat taaaacagtg ctaggttcct 74460
ggttttcgtg acattaaaaa caattcaaca tctgtgtgta gacaatgact aaaactttat 74520
gattttgttt cagagtttta ttaccataga tattgtttaa aatagaactt tcaaatacat 74580
ttaagaacca ttaaaagtga cttctccctg tgcctgaaag atacatgcat ggcttatatc 74640
tttttgtgta taaacaattt aatgtttaac ttttatttcc tttaagtttg catatcaaac 74700
actcttagca atctcatcat ttatactgga gtacttagac tttgaaactt tgccacagct 74760
acctgccacg tccttgtata ggatataagt aaatatattc agtcatcaaa tctatagaga 74820
actgtgagaa tagagtggta aacaaaacac attgcctgcc ctcacagcta aagaggagtg 74880
atggtgggaa agtggaagtg atcagaaccc aatctgaggt cagaaaacaa aactacaatc 74940
tatttcaggt tgcacaaatg aaattttaac tgaatctgag ggacattaga tttaatcaaa 75000
ccaaatgaga aggcaaggtg gtgttttgag ctaagggcac agcagatgta agagtcataa 75060
aggaagaaga acaaaacaca ttcaagataa aagacacgga gagagggaaa gatgacactg 75120
tacggtgaaa tatcttgcaa gtcaatatta gatactagcc tttgggcttt agcttgagaa 75180
cagtgggaag acattgacgc tcagattttt ttttctaaag ttttttatta atgcctaata 75240
catatagaag cattagcata ctgcttcgtg aattttcaca gacttagcac acctatgtga 75300
tgaacaccta gatgaagaaa aacaacaata tcagcatcct aaaagttccc cttcattttc 75360
cttccagtca gtcctgtctc ttgcccacca agggagacct cttgcctgac ttctcactgt 75420
atatggagga tattgcctac attgtactta atataaatag gggcatacaa tgtgtattca 75480
cttgggtgaa gcattacgat tatgagattt atccatattg ttgactgtgg ttgctaattg 75540
ttctcatagc tgtataatgt tccgtcatat gcatgtacta cagatttgca tttttctgag 75600
attgctgaat ctgcatcatg aaggatggga gggtgtgaat ttagtaagct tcacagtaaa 75660
tctaggaaag agatactggg gcttgagcta gtgtggtgac aatgaggatg aagagaggtg 75720
ggtatataga gagatattta caagttagaa cttaattgga tgaggggatg aagaatcata 75780
caccagagat aactcctggg tcctgacttg ggcaggggtt aatggcagtg cccttcatta 75840
agtccaaata ctggagagga agtgggttgt tgcttgtgct ttagtgatac aggggattaa 75900
cgaattcaat ttctgataca gttaaggcat ctgtgaaaca ttgcatagat ctgctttata 75960
caactgtttt attaactgaa ttaatgaata accttacctt cattaacaac agtgtgctaa 76020
caaatagttc tacatatgga aaactgcaaa tcttgtctag tctcactgtt cttcacctct 76080
gaatctcacg agatactctt ttcctaaatg tgttaggagt ggttttgttg catctcatgc 76140
tttttttctt ttttatttat agaatatact tcatctaaac tagtgctaac tttatgcaag 76200
aagagtagca cttcctaggt atatgatatg aaaggcattg gtgaaatgcc ttcatactta 76260
aaggcattgt ttttccaaca ttatggtctt tcctttagca caataaagac accttaaaat 76320
gagtttgttt ataggaaata acctacttat ttagtaagac tttaatggac tgaagtaaat 76380
attcatgaga tttgggcagg ggaaagaaaa gaaagatagg gatgaggtct gacctgagca 76440
caaacctagg cagggtgcca cagggggaac cctgaacatc agagagcagg ttgaatgcac 76500

```
ctgattttaa aggaagatta tgccaaaaga gtgacgtagg agctgtaaag gagggacttc  76560
acctcttttc gatgctgcct gggactagtt atacttgtgg aaaattttat gtgaagataa  76620
ctaataattc tagcactgaa tgaaacaaat gcctgagacc tactggaaca ttaaatagac  76680
ttttatgcca gccagttatg attcagtgct atatttagac cacaaaattt gaactaaaat  76740
caaggcagtt tattcttatc ccatcatgtc catggggtgg agaggaacaa ctaagtaatc  76800
atgatcatgc acttcagttt atagcgtttt ctctagcttt gggcattgtc acttaacaga  76860
caatacaatt ttaaaaatta aatgctcaat ttcatttcac tgaggttttt tgttgttgca  76920
caacattgta agtatacagt aagttgtttt ttcttttaaa tttttgcctc taattcaggt  76980
ttacattgag caaccaaatc agtattttca gaaaccattg aagttaattc atttatttaa  77040
taattactta tgaaatatgt catgtataat agtgctatag cctaagatga tgatggtgag  77100
aagtactcct accttttgtt actggcacga tggtggcgat actcagaaca aacaaaaaca  77160
gtgtgataac acaaattatt atatgactcg ctgttttaat agtgtttaca aaagcagtga  77220
atcccaggaa aataaactat tggctacaat atcaaaaaag aaatgatgga agtggtagaa  77280
tttaatttgg gtcctgacaa ataggcagga tttgaacatg tatggcaaga acactgcagg  77340
caagggtaac atctcatgag aactgatgca gaaaaaaata cagcatatat tggcagagtg  77400
agaaactggc cagactgtag cagaaatcac aagctggtgt gaggagagag agaaaagctt  77460
cattaaggaa gttttgaatt actgaaaaat tcaccagtca taaggcatgg attattgtct  77520
tgctgtttag attacctata aatgtaattt tactttactc accaccatgt gataattatg  77580
tagggtttta tctttttaga aacctgatgt gaaattacct gaaggaatga agttagtgtg  77640
cttttaagtt aagaatatct tcactcagta tccatggata ggcttcaggg aatctggatc  77700
tctttgaaat taaagcaaaa gtttggatgt atttcttttt ctggaggaag gatccattgc  77760
ctttatgagt atgtaacagt ccagaagaag ttaataaaat agctcgagct ctcctaactt  77820
aaaacttttt tattttttat tattattatt ttttttttg tagagatgga gtctcgctct  77880
gtcacccagg ctggagtgca gtggcatgat ctcggctcac tgcaacctcc acctcccggg  77940
ttcaagcaat tctgcctcag cctcccgaga agcttcatct tgggtttttt attattatta  78000
ttattattat tattattatt attattatta tactttaagt tctagggtac atgtgcacaa  78060
catcttgggg tttttttaat gcagtaaatt aaaatgggga aattaaaaca cgttaaatac  78120
tttcccttta tttcactatt tactgatacg gtatttaaga gataatcctg aaaagtatat  78180
cagttgggtt gattatataa ccagagatag tggctatttt atcaattccg tggctttcag  78240
taaaaggaca gctcaattgc ctttttagat acagaatgtt tctgaatatg ctatttcaag  78300
tagaaattcc ttcctatttt tggacaggca tatgtctgct ttctgcagaa tacaaagaat  78360
tttcaatgtg tccagcttca gtcctgaaat ttgacttacc tggatcatat ttaatctttt  78420
gcacaactgt ttaaagcagg agtcaacaaa ttatatatag cccatgggcc aaatccagcc  78480
ctcaaaccta tttttgtatg gcctatgacc taagaattgt ttttacattt taaaattgtt  78540
aaatttaaaa aaggattgta agggattagg attttaaaaa ggagaatatg caacagagat  78600
tttatgtggc cctcaaagtc tatggtattt actaactggc ccttttttta aatgccaatc  78660
cgtggtttaa agtacagttt ttaagttctc ctagatgcat gtgttattct acaagcagat  78720
acaatgcttg tggatagata ttatttttga agttgggagt atatttatat aattttagca  78780
aagttgactg aataagataa cctgttttct atactgaata ttcagctaat agtttcgctt  78840
tctaaagtct ggatttgaaa gtgtatgaac aaagtgtgga cttagtaatc tacttcaaag  78900
```

-continued

```
aactatgtga atatgaaagt agattttgtt tttcatggat atattacaca gcaaccacaa  78960
ttcagatcaa gaaaaatatt aaaatataat ctttgtttta gaagacacca cttaaggcaa  79020
agaaggcaaa agaaaacatt tgtacctgtt aatgagttgg gaagggcagc tcttaaaaat  79080
tatactattc attggtttat tcaacattta tacttatttt tagaaccatt atatatattg  79140
gcttctttgt attatatttt attaatatta ttgtatgaga tactatgatt ctaaattttg  79200
gataaatatt gaaattattt ttaatggggg atatgtcata attagtgagt ctcaaaaaat  79260
tggggcaatt ctgccttctc tctctgcatc attatttttc cttcactact ggatcttttc  79320
caccaacata caaataatgt tgagtttttt cccccatctt aaaaaaaatc ttactcccag  79380
ttctccttta gttactaccc catgtctttc atgtaaagcc tatatctctg aagtatgtag  79440
ttgcctgtgc tgtctgaatt cagttcctat aacccctgcc atttcaccag aattgtactt  79500
cttaatgact gccatgctgc caatcagatg gtcatctcag tcttcctctt atttgacctg  79560
gcaacggtgt ttaacactcc ttgtttggcc ttttagatac tatactacac tgtcctgttt  79620
tttttctcc tacccctctg gctgctgctt tttcaatctc ttgctgattt cttcttgcct  79680
ccccatctcc aaattgggaa tgctccaaca tttggaattt tgaggccttt aaaactgcat  79740
gttcactccc ttagtgactt catatagtac catggcttta tatgatcatc catttgctaa  79800
tgatcagaag tcctttagtc tttttttttt tttttttgat atggagtttt gctctgtctc  79860
ccaagctgga gtgagtgcaa tggcatgatc tcagctcact gtgacctcct cctccggggt  79920
tcaagcgatt ctcctgcctc agcctcccat gtagcgggga ttacaggcgt gtgccagcac  79980
acctggctaa tttttgtaat tttagtagaa atggggtttc accatgtcgg cccggctggt  80040
tttgaactcc tgacctcagg tgatctgcct gccacggcct cccaaagtgc tgggattaca  80100
gatgtgagcc tccgtgcctg gcccctgtag tcttcttaga atgtaatata gtaaactgaa  80160
ttcctcatct ttcccccacc aaaacctcct ccggcagttt ttcccatctg agtaacagca  80220
cctgctgtct tttaatcagc cttggtgtca ccaaggatgc ctgtcctcct ttcattccac  80280
atatgataat tcttcacatt tctgttacca aaatattatc ttgcttctgt cccaaaaata  80340
tttctgagat tcagttattg cttaccatct ctactcctac aaccctgatc caaatcacct  80400
tcatctctta cctgtattga tgcaaaaagc ctcctgtaat tggtcttcct gttttttcct  80460
gttgacttaa cttcagtcca ttcttaatat agcaggtaaa gtagttatat ttaaatataa  80520
gccatattat gtcactcttt tgatgaaaat cctccattga cttttcatct caaccagaat  80580
aaaaactaaa gttcttaaaa tagcctacca ggctctgtgc tctgggctgt cattcccaga  80640
cagccactgc caaccactcc tgcctgctca cacccacttt gctctagtca tccacactgg  80700
cttctttgct gttcttagaa catgccaggc aagttcttgc tttagagcct ttgcactggt  80760
tgttctctgt aatactcttt ccctgtatat ctacagggat caatctctca ttacttgaga  80820
tttgtactta aatgtcaatt taatgaagct ttctttagcc acttgatcta aaattgcaga  80880
tttcccctac ttcaccccaa ttctccttcc tgctttatgt ttcttttctt gaagacctgt  80940
taccatctac catcccatat attttaccta cttttttcat ttattttttg ccttcctcca  81000
ctagaatata aaggcttttt gtttcctttg ttcactggtc tgtcctcagc acatagaaat  81060
atagtgtttg gcccacgtta tacacttagt taatattgat gaattaataa ataagtggaa  81120
tttaaaaata gccaacacaa aattttaaca tagttcaggg atttttgaga gctcctggga  81180
tcattgaata agcattcaaa tattccagta aatgacatgc atggagctaa aggtattaga  81240
```

```
aatatgactg tatacattgg tatcattata tatgtagaac tttctttttt gcacagatcc  81300
ttagctttga ccatttattc tatttttaaa gtgtggaata ctaaaaaaaa atattatttg  81360
aacttaaata tgattactat ttgagtatgc tatgatgtga atacttttta aaagaatctt  81420
ttatcattaa aagtagtcat ttagtacagt aggaattttt ttacaaaaaa acttataaaa  81480
taatttaaat ttccagaaga gtttcaaagg cagtacagag actgaacttt tcaggatcct  81540
tgttctgtgt cttataagtt ttcatcttca aaaagcatgg aacaaatact aattcagcct  81600
accaacatag cttttgttaa agtaactgct ttttaaaata atttttaaat acataaagct  81660
accaaataat tagtttcaaa tttcataatt atttttttctt gactatatgc ataactgatt  81720
taaatagagt cataatccaa attttctcaa ttatgacata catttcttca tgtttcatta  81780
tagtcttttt aaatgactaa taatagacca tcttgctgat gtatcattat taataaattg  81840
ttttcttcct gttggacatc ttaaggctgt tttgttttac tgttattaat aatatggtag  81900
gtgatatatt tgtgcatata acttcttgca tttgcctaaa ttatttcctt tagctaatta  81960
cccagaatta gattgggcaa taaaaatcat agggcttatg aggaaaatgg ggttggagta  82020
cagcccacaa taattttgtc agtgacacat ttttaaaaag acagaaaact aataacaagt  82080
gcagcacagt tttacatatg ttaaatggtt aagaaataca taattactat tatacaagtg  82140
acacttttta ccttgaacaa accctgatgt ttgcttgtgg aagtaggtat ggaattgtga  82200
tctccaagtt aatgtgaagt ggtagaagga ggattatctg aaatcagaag gaaagttgta  82260
acattgcatg tgatgggtgt ggctcgtaac agaagcacgg tgaactgaag tggctggtaa  82320
cttgagatgt gtgcaggtgt gctttttgtt tattcttatg tgacttagtt aagctggcag  82380
caattttctg tgttcactta gtgtttctcg cagataaaat catgcataag caaaggtgac  82440
attctcttta tgctcatgta gttctctaat aaaccaactg cactgaaaca aatttgcatt  82500
ttcaaaataa gtgttatggc agaagagact ccactaattt gttatcccat caattttact  82560
gcaattttaa catcgtgcta ggtttttaag cttttatatg gtaatttttc tgatatattt  82620
ttaaccagat gcctttagaa tacagtttgg tgcagtctta cagatataac tccaaccata  82680
ataggcagtg gagatgttat tttaaaataa taataaagct tggttaattg cacagagaca  82740
agaaaaaatg gaggacaggt ttcttccaag aatgactgaa gccagaatag aggttagaga  82800
aaacagaaga agaaaaaaaa aaccctaaaa cctgcaaagg gagtttgtac ctaggtagag  82860
cagtaccttg aataccagat taaagtttca acttccagaa ggcaaccaaa agtcagtatt  82920
ttgttgttgt tgttgttgct gttgttgttg ttgttgttgt tgttgttaac aggaaagatg  82980
aaagaccaga taaggaagaa aggccaagga ggaggacata ggaaaagtgt aggttggaga  83040
tggtatggtt accatccaat aagaacagaa aagaaagtat aaatgtaagg gttttgttag  83100
cagtactatt tgccttctga ttaaatgata aagaagatgt aaaataaatg tttgtctaag  83160
attactccaa agtattatcc tgagtggcta aagaatagcg atcctagaaa aaaaaaattg  83220
atgatcagga agaagagctg tatgagtggg aggagaaggt attcctgaaa tgatgagttt  83280
agtttgaaag gaagcctgac tgagtggaca cagcccctga ttgagcatta agaaaatttt  83340
tgattaatta ctggtggggc cctggacaat agtatacttc tctggctttc agttttctca  83400
cctgtaaaat aagtattgaa ctactagtga ctgctgaagt ttcttccagc tttgaaacaa  83460
ttgctgtgtg ttttttttt atttgaactt tattactgtt tcttcatgat tgctgtctag  83520
tgacctttta tgaagacttt ggtttataat gaaacaagga taaagtgctc agtcttgagt  83580
ctgttggaga ttaaactttc ctgactcctg aaatgcttga cttgacaccg gaagtgccac  83640
```

aactgccatc tcactttatc ttttttctgc caaaggaagc ttcttgcaga tcaaaattgg 83700
gagcaaggag aattggatgt ataaagccaa acttggaaaa agcattctgc aatttttctt 83760
aatacaatct tttggggctc tatttgttat tagctgttag aaatcccaat aaattatttg 83820
gaaagaaatt cagtacaaat ataataatgt tatagaagta tatgtatata gtaaatataa 83880
tctaggagag gcttaccata gaaaaggtgc aggctttgga attagcttga attcaaatat 83940
tagttttatt actctactag ctgtgtaacc ttaggtaaac agaaatgaaa agctttattt 84000
tggaggatga ttttatttct ttctgtgtaa aatggaaata gtaatactaa gtttcagaat 84060
tgttgtgagg attagagaca atgtttgtaa agaactgagt atacaacctg atacttaata 84120
aagagtaacc tttatcagtt accaggtaat agttattgtt gcagtatgag gacttggtta 84180
aaactttttc aaattcttac ctgtattaaa cacttaacct acattctcct cttgtaatca 84240
gaatctcgtg tgcatgtatg taatgatggg ttctctaata ttcagttttc tggcagatta 84300
aaacatctga caaaactaaa gaattatttt aaaaatattt agagtgtcaa catattcaat 84360
tcttagatgg aataatgatc tttaaagaga tgagactagt atgtaaaaag ttcattttta 84420
aaagtaagaa tcttcatcct aattatctgc tagctaagac aaaataatag aatcaacatt 84480
cttacagatt ttcgtttaca ctgcctcctt taaaagatgc ccaatactgt ggatattaaa 84540
gagtgattac tagtatatta tgtatattat atattcagct ttccttttgt aaattgattt 84600
taaacatttc caagaaatag tttcaaacta ggtacttctt aacatctctt atacttttgc 84660
cttaaataaa aacacattga taatgctaat tatatggtaa aactgttagg tctgcagaag 84720
tcatatttta tttctgaaat aataaaaata cattttaaaa cagatgcaga aaatgtgaaa 84780
ggtagattgc tgctggaaat tcacatagtc tttaaggaat aaactatgta cgtgttgact 84840
atgaacagac tagtctatat ttactatatt aaattttcac caagttataa agattcagta 84900
tgttatcctt ttggaaattt aaaaaatagt aaaacacatt ctttttaaga gcaggaacaa 84960
tgtacttgaa gcaacaaatt tatgactgaa gattatatat cagtataatc cttgcttctc 85020
tgattgctgt gtaccctttt ctgcagccgt ttttttttta actcttaaag tctgtgctct 85080
attacagtga ttctttttct tgtttctaaa agaataaatg aatagttttt tgttaataat 85140
taatgtaggc ctctgcttac ctgctttata cattctttac ctgcctgtac gtagcacttg 85200
cctatgcaag tattcattta ctgaaaaagt taccaacttt gtagccttga aatcatttaa 85260
aaaatatgtt aactgacttg aatactctgg ttagaagcaa aatgcatacc ttctacttga 85320
aggaatttgt tttcaccttt actgaaaaaa atacatattt agttgtattt taaacactac 85380
ttattttgac atagtaatca ctttatagtt ttctaggaag ttcatctttg tatgcatttt 85440
atatctccta ttcttttctt gtaaagatta ggttacaatt aaaataattc aaagatcatt 85500
gggaggtact gcattaaact gtgggttgga tcttgccttt tgtcttgttc aaactgcacc 85560
tctcctttta tttttttcaa tctgaagata gtagcatgct tagagcatga atgtaagcca 85620
tgtggtggct aagatagaga aggcagagat ggatgacttc agaggaagta agtgtttgac 85680
aggagactgg actgggtgat ggtgtgaacc aaagtcaagg tcacagggag aaaaagagca 85740
ggctggcttc atgggtgtgc aacctgtaca gttacacaag gctcagcttt tttaatgttc 85800
tgctactgct atgttgaaat tcttaatcaa tttcacacaa gaggccctga atttttattt 85860
tgcactgagt ctcacaaatt atctagcctg ttctgcagat gagaaataac aggaagcaga 85920
aatttcttgt ctttttagtt attaattcct tttcccagat tagccaaaat gggaattatt 85980

```
ttttaaatga tgacttacgg acatttaaaa aaatgtggaa aattaaccta atttgaaagc  86040
agttgtgtgt gtatgtatgt tatttagtaa tttacccaag tattggagag gggaaaaagg  86100
agcttgttaa attttcttat ggaagtgtca aaggtggtca aacttccaat agactttacc  86160
aagtcagtat gtaatataca tagtttgaga agtaaaaaca attggtatta cagaattgta  86220
tgtctgaatt acctactacg tgctgggctt tacccagaaa agtgtttctt tacccataaa  86280
gcctgatgct ttatattcag tacagtactt tattatttag taattattct ttcctagtat  86340
tatttctaaa gtggtaattg tttcttgcct ttatagtgct tgtaaacttt atttttttaaa  86400
gattttggaa attaaaattt agaaatttat aagcccattg tggtttttac acagtcctgt  86460
cagtttacta gttttatttg atagctatct aatacgcacc tgtttaaagt ggaacgtgtt  86520
tctattacac ctaggctctt ttttttttta aaatttaagt tctgggatac atctgcagtt  86580
tgttacatag gtatacatgt gtcatggtgg tttgttgcac ccatcaaccc gtcatctaca  86640
ttaggtattt ctcctaatgc tatcccccac ctagcctccc acacctcaac aggccccagt  86700
gtgtgatgtt ccctccctgt gtccatgtgt tctcattgtt caactcccac ttatgagtga  86760
gaacatgcgg tgtttggttt tctgttcctg cgttagtttg ctgagaatga tggtttccaa  86820
cttcatccat gtccctgcaa aggacatgaa ctcatccttt ttatggctgc atagtattcc  86880
atggtgtata tgtgccacat tttctttatc cagtctatca ttgatggaca tttgaattgg  86940
ttccaagttt ttgctattgt gaacagtgct gcagtaaaca tacatatgcg tgtgtcttta  87000
taagtagaat gatttataat cctttgggta tatactcaat aatgggattg ctgggtcaaa  87060
tggtatttct agttgtagat ccttgaagaa ttgccacact gtcttccata atggttgaac  87120
taatttacac tcccaccaac agtgtaaaag cattcttagt tctgcacatc ctctccagca  87180
tctgttgttt cctgactttt taatgatcgc cattctaact agcatgatga tatctcattg  87240
tggctttgat ttgcatttct ctaatgacca gtgatgatga gttttttttt tttcatatat  87300
tttttggccg cataaatgtc ttcttttgag aagtgtctgt taatatcctt tgcccacttt  87360
ttgatggagt tgtttttttc ttgtaaattt gtttaagttc cttgtagatt ctggatatta  87420
gccttctgtc agatggatag gttgcaaaaa tcttctccca ttctctcagt tgcctgttca  87480
ctctgatgat agtttctttt gctgtgcaga agctctttag tttaattaca ttcatttgtc  87540
aattttggct tttgttgcca ttgcttttgg tgttttgttc atgaagtgtt tgctcatgtc  87600
tgtgtcctga atggtattgc ctagtttttc ttctagagtt ttttatggtt ttaggtctta  87660
tgtttaagtg tttaatctat cttgagttaa tttttgtatg aggtgtaagg aagggttcca  87720
gtttcagttt tctgcatatg gctagccagt tttcccaaca ccatttatta aatagggaat  87780
cctttcccca ttgcttgttt tttgtcaggt ttgtcaaaga tcagatggtt gtagatgtgt  87840
ggtgttattt ctgaggcctc tgttctgttc cattagtcta tatgttttgt ttttttgttt  87900
atttttaact tcttatttat ttatttattt attattatta taccttaagt tttagggtac  87960
atgtgcacaa tgtgcaggtt agttacatat gtatacatgt gccatgctgg tgcactgcac  88020
ccactaactc gtcatctagc attaggtata tctcccaatg ctatccctcc cccctccccc  88080
caccccacca cagtccccag agtgtgatgt tccccttcct gtgtccatgt gttctcattc  88140
ttcaattccc acctatgagt gagaacatgc ggtgtttggt tttttgttat tgcgatagtt  88200
tactgagaat gatgatttcc aatttcatcc atgtccctac aaaggacatg acctcatcat  88260
tttttatggc tgcatagtat tccatggtgt atatgtgcca cattttctta atccagtcta  88320
tcattgtagg acatttgggt tggttccaag tctttgctat tgtgaataat gccgcaataa  88380
```

acatacgtgt gcatgtgtct ttatagcagc atgatttata gtcctttggg tatatacaca 88440
gtaatgggat ggctgggtca aagacaaaaa ccacatgatt atctcaatag atgcagaaaa 88500
ggcctttgac aaaattcaac aacacttcat gctaaaaatt ctcaataaat taggtattga 88560
tgggacgtat ctcaaaataa taagagctat ctatgacaaa cccacagcca atatcatact 88620
gaatgggcaa aaactggaag cattcccttt gaaaactggc acaagacagg gatgccctct 88680
ctcaccactc ctattcaaca tagtgttgga agttctggcc agggcaatta ggcaggagaa 88740
ggaaataaag ggtattcaat taggaaaaga ggaagtcaaa ttgtccctgt ttgcagatga 88800
catgattgta tatctagaaa accccattgt ctcagcccaa aatctcctta agctgataag 88860
caacttcagc aaagtctcag gatacaaaat caatgtacaa aaatcacaag cattcttata 88920
tgccaacaac agacaaacag agagccaaat catgagtgaa ctcccattca caattgcttc 88980
aaagagaata aaatacctag gaatccaact tacaagggat gtgaaggacc tcttcaagga 89040
gaactacaaa ccactggtca aggaaataaa agaggataca aacaaatgga agaacattcc 89100
atgctcatgg ctaggaagaa tcaatatcgt gaaaatggcc atactgccca aggtaattta 89160
cagattcaat gccatcccca tcaagctacc aatgactttc ttcacagaat tggaaaaaac 89220
tactttaaag ttcatatgga accagaaaag agcctgcatc gccaagtcaa tcctgagcca 89280
aaagaacaaa gctggaggca tcacactacc tgacttcaaa ctatactaca aggctacagt 89340
aaccaaaaca gcatggtact ggtaccaaaa cagagatata gatcaatgga actgaacaga 89400
gccctcagaa ataacgccgc atatctacaa ctatctgatc tttgacaaac ctgagaaaaa 89460
caagcaatgg ggaaaggatt ccctatttaa taaatggtgc tgggaaaact ggctagccat 89520
atgtagaaag ctgaaactgg atcccttcct tacaccttat acaaaaatca attcaagatg 89580
gattaaagac ttaaacgtta gacctaaaac cataaaaacc ctagaagaaa acctagacat 89640
taccattcaa gacataggca tgggcaagga cttcatgtct aaaacaccaa aagcaatggc 89700
aacaaaagcc aaaattgaca aatgggatct aattaaacta aagagcttct gcacagcaaa 89760
agaaactacc atcagagtga acaggcaacc tacaaaatgg gagaaaattt ttgcaaccta 89820
ctcatctgac aaagggctaa tatccagaat ctacaatgaa ctcaaataaa tttacaagaa 89880
aaaaacatac aaccccatca aaaagtgggc aaaggacatg aacagacact tctcaaaaga 89940
agacatttat gcagccaaca aacacatgaa aaaatgctca tgatcactgg ccatcagaga 90000
aatgcaaatc aaaaccacaa tgagatacca tttcacacca gttagaatgg caatcattaa 90060
aaagtcagga aacaacaggt gctggagagg atgtggagaa ataggaacac ttttacactg 90120
ttggtgggac tgtaaactag ttcaaccatt gtggaagtca gtgtggcgat tcctcaggga 90180
tctagaacta gaaatggtct atatgttttg ataccagtac catgctgttt tggttactgt 90240
agccttgtag tatagtttga agtcaggtag catgatgcct tcagctttgt tcttttggct 90300
taggattgtc ttggctatac gggctctttt ttggttccgt atgaagttta aagtggtttt 90360
ttctaattct gtgaagagag tcaatggtag cttgatgggg ataacattca atttgtaaat 90420
taccttgggc agtatggcca ttttcacgat actgattctt cctatccatg agcatggaat 90480
gtttttccat ttgtttgtgt cctctcttat ttccttgaac agtggttttt agttctcctt 90540
gaagaggtcc ttcacatccc ttgtaagttg tattcctaag tactttattc tctttgtagc 90600
agttgtaaat gggagttcac tcatgatttg gctctgtttg tttattatta gtgtatagga 90660
atgcttgtga tttttgcaca ttgattttgt atcctgagac tttgctgaag ttgcttatca 90720
gcttaaggag atttggggct gagacaatga ggttttctaa atatgcaatc atgtcatctg 90780
caaacagaga caatttgact tcccctcttc ctatttgaat accttttatt tctttctctt 90840
gcgtgattgc ccaagccaga cttccaatac tatgttgaat aggagtggtg agagagggca 90900
tccttgtctt gtgccggttt tcaaagggaa tgcttctagc ttttgcccat tcagcatgat 90960
attggctgtg ggtttgtcat aaatggctgt tactgttttg agttacgttc catcaatacc 91020
tagttcctgg agagtttttg gcatgaacgg gtgttgaatt ttatcaaaag ccttttctgc 91080
atctattgag ataattatgt cgtttttgtc attggttctg tttatgtgat ggattatgtt 91140
gattgatttg catgtgttgc agcttcatcc caggtatgaa gctgacctaa tcgtggtgga 91200
taagcttttt gatacactgc cggattcagt ttgccaatat tttattgagg atttttgccc 91260
caatgttcat cagggatatt ggcctgaaat tctctttttt tgttgtgtat ctaccaggtt 91320
ttggtatcag gatgatgctg gcctcataaa atgagttagg gaggagtccc tctttttctg 91380
ttgttcgaga tagtttcaga aggaatggta gcagctcctt tttgtacctc tggtagaatt 91440
cagctgtgaa tccatctggt cctgggcttt ttttggttgg taggctatta attactgcct 91500
cagtttcaga acttgttatt ggtctattca gggatttgac atcttcctgg tttagtcttg 91560
ggagggtata tgtgtccagg aatttattca tttttcccta gattttctag tttatttgca 91620
tagaggtgtt tatagtattc tctgatggta gtttgtattt ctgtgggatc agtggtgata 91680
tccccttat catttttat tgtgtctgtt tgattcttct ctattagtct ggctagcagt 91740
ctatctattt tgttaatctt ttcaaaaaac cagcttctgg attcattgat tattttaaag 91800
ggtttttcgt gtctctatct ttttcagttg tgctctgatc ttagttattt cttgtcgtct 91860
gctagctttt gaatttgttt gctcttgctt ctctagttct tttaattgtg atgcacttat 91920
tctaaaatca accacatagt tggaagtaaa acactcctca gcaaatgcaa aagaacggaa 91980
atcataacag tatatcagac cacagtgcaa tcaaattaga actcaggatt aagaaactca 92040
ctcacaacct cacaactgca tggaaactga acaacctgct cctgaatgac tactgggtaa 92100
ataattaaat taaggcagaa aaaaataagt tctttgataa caatgagaac aaagacacac 92160
cataccagaa tctctgggac acagttaaag cagctcacgc ctgtaatccc agcactttgg 92220
gaggccgagg cgagtggatc atgaggtcag gagatcgaga ccatcctggc taacaaggtg 92280
aaaccccgtc tctactaaaa atacaaaaaa attagccggg cgcggtggcg ggcgcctgta 92340
gtcccagcta ctcgggaggc tgatgcagga gaatggcgtg aacctgggaa gcggagcttg 92400
cagtgagccg agattgcgcc actgcagtcc gcagtccggc ctgggcgaca gagcgagact 92460
ccgtctcaaa aaaaaaaaaa aaaaagcagc attaggagag aaatttatag cactaaatgc 92520
tataaatttc tctcccacaa gagaaagcag gaaagaacta aaatcgacac cctaacctag 92580
gctctttttc tgggtctctt tctttctaaa gttttgctta ttttgtttac tgcacaatcc 92640
aactaaaacc aaatttttta catcatttca tttgagagtt acctttttatt ctaataaact 92700
gtggaataac tggggttggg gagggaattg cttaagttca taaggattct tgcaaacttg 92760
aatgtgtcga tacaagattt tttttgaaaa tttgtaattc catttcacga tctcaaccag 92820
aattcattat gtttaaacca cctgatatag actaaaacat tttttcagga gcacaattgt 92880
aaaaaggatg cagagaaata tttacaacat tacttatttc tttgcagatt tagtgaaagt 92940
atgtcctact tttacaaaat atcttatttt cctctctttt ttacacatat aatagagaac 93000
taacttttat aaactaaatg agaagggaat actaattttt aaattatgat gtcacttgta 93060
gaatttgttt taaaattgat aaaatacacc tcttttttta ttattatact ttaagttcta 93120
ggctacgtgt gcacaacatg caggtttgtt acatatgtat aaatggccat gttggtgtgc 93180
tgcacccatt aactcatcat ttacattagg tatatctcct gatgctatcc ctccccactc 93240
cctctacccc atgacaggcc ctggtgtgtg atgttcccct tcctgtgtcc aagtgttctc 93300
attgttcaat tcctacctat gagtgagaac atgcggtgtt tggttttctg tccttgtgat 93360
agtttgctga gaatgatggt gtccagcttc atccatgtcc ctacagagga cgtcaattca 93420
tcctttttta tggctgcata gtattccatg gtgtatatgt gccacatttt cttaatccag 93480
cctatcattg atgggataaa gcacacctct ttaagactgc ttatagaatg ctatggactc 93540
attggcttgg tttttatttt ccttggtttc agtccaaagt gtaataagct tttcagaaag 93600
tttctcctgg atgtgtaaag aataccaaca gatatcagaa agcatctggc tgaaagttta 93660
agcagggagt attgttattc atccagcgaa ggtggtaaaa ctctcctgta tcctcgaagt 93720
ataactaact gagagagaga ggccctatat aaagccagct gacttaccct gcaattgctt 93780
gtctggcaaa cagacaattt ttaaagactc atatatttag gaatttttaa atgccataga 93840
atcgatggac aaaatgattt tcatttatct taatccaaaa tcacaagatt gattatatac 93900
ttaggttata tggaaaatca gcattagaag cattagttct acacctcatt tgcatgacat 93960
tattacaaga tattaactgt aaaaatgaag taaatataat atctgttcac cagatgccta 94020
aaacatacaa cattagtata gacatataga aggatctgca agcaactaaa caagtagcgt 94080
aaatcaaaga atatactgat aaagtggtaa gtgccttttg ggcttcttag gtaataagcc 94140
cttgtatctg ccagaatagt ctagcaaaaa atgcattttt ttctttagcc tagggaaact 94200
tttcacagga gatggagttt taggtattgt gtagatgatg ggagaaattg cttttgataa 94260
gcttcagtga aaaaggaagg gaatgtgtca ttgcagatag agagggagag aaacactggt 94320
agttggtcgt agactggtag tggtgtagaa atagaaagca aaacctattg gacaaaggaa 94380
ctgaacagat ttgttaaaaa ggaatgagac aaacagatat gaaagataag gagtaagctg 94440
atacaggctg gtgagctcac tgatagcaga gtccaccaag aggcatttag tggttttcct 94500
tcagggcaaa aagtttgaaa gagaaaaata tgatctctaa atagggctac tcataaaaaa 94560
tattgactat taagaatata gatacagtct gtatctttaa gactgcaatt tagtacaatt 94620
taattttgtt tataggctaa acatttttat aatttcatag cgattaactt gataaaaaag 94680
ggaaaatttc ttggtctttc tgccaatctg tgtttctaac tgaccctaaa cagctctgtt 94740
ggtttcctgc tcatgcatta gagcttgtcc atagccacaa gcccctcttt tcctgtcagc 94800
cctgcaaaga ccgccccttc caaattgcct tctcctcttg atggcacatc caagcactag 94860
caaattcgga atcattttg acttatcgtt tccttttacc ctttttaatc ataggtacaa 94920
tcttttgcaa gttgctttat ctctctgacc ttagtttttt catatataac atggagttaa 94980
taaaacaata ttgccatttt cagaattcaa taagttaatg tgtaaaagca cacaacatag 95040
tgcatggcac ataatagttg agctttaatt gtacatgtta cttgtttttt ctatcttctc 95100
aactggtaat aataactcta ctgaataggt agtaatttaa tgaaaaaaat taaatgcatt 95160
gtggtgtttg ccaaaatttt tggtttgtat gtatacactg gattacagtt ttataaattt 95220
gtcctcatga aattgattgt caggtgtttt ctctttagtt gttttgttaa aaggttaatt 95280
ggagcataac aaatgcatca ctatcttatg tagctcctat aaaaacataa atactttaaa 95340
ataaatttga aaattagagg ggctactaca tgcaactgat tatagttcta attttagtta 95400
tgaaatttac ttctcaacta aggcacaatc tctaattctg tatctgcatt gatgactcag 95460

-continued tgattttaga ggttgtgagt tgatattttc acatttctac ctatggtaac tcattacaga 95520
atgtctgatc atgatatcct gttctgtgta gcatcatagt ggacacttca tgatatttct 95580
gctaaaccct ttacctgtca taactgtctc ctttctgttt tgcaaattcc ctcagcaaag 95640
tcaaattcag tcctcacttg gttataaata gcattataaa ccatattttt gatttaaata 95700
aagcacacaa atctcaaaga atgataaaag cattgttcat actttgtaaa acttaatcat 95760
tgattataga ttaaaactga aacaacatga agggatcaga ctcactcaca gaaggttatt 95820
gagaaccagg aatcatagat ttcattcaat tcaaattatc agttgtacat tgttgcttgt 95880
tcaaaatcat tttacaatcc actttgccca cctccatctt cttacgttac aaagaacttt 95940
catctgctag gcactgctga tggtagaatg ccatgccttt aaggtttccc tttggaatat 96000
aaagtctatg ttttcaatag aattaactgt tcgacagaga gagaacagga tttctgtgca 96060
aagatggtac agtgctagta aaatatatag ccccttact gtctacatta agcaaggatg 96120
ataccctaag aattctagct gctgctgttg atgctgctgc aactattact actactactt 96180
ctactaatca cgagtataga aaaatatctc tttgatcctg tgtgtgtggt ggtaaggttt 96240
tgggagaagc cattatctat gggtggtgga atcacatata ttttaaagtc ttttcgacca 96300
tgttcgtttt ctaatttttc tcaagtaaaa gattcttcta tacttttaaa aaaattataa 96360
tttaaaaaaa aatcttattg gacttgttta aattatcaga tatttttcag ttatgtaatt 96420
ggtttctggc atacatagac ttttatcatt tgctctgctt taacatacct tcatcagttt 96480
tataaataca gttcgaaagg attgttctaa atatatataa agggaaaact tcatttgaaa 96540
gcaaaatctg tatttgggat atttgttgtc tttttttgcct tctaaagggc aatctagaaa 96600
cactaatatt gattggttat tttgtttcat aatactttat agctgattct tggcaaaaat 96660
ggttgatttc tctttcattg taatacaata ataaaaaagt tactcagaat ttctccagtg 96720
ttttaagagc tgtccaggtt gacatccaaa aatttaagag agcgttagaa catgggatat 96780
ctaattgtta attgagactg gaattatttc taataatctt agttgtaaat actaatatct 96840
tattagtctt cttatctttg ctggtataaa aatggttgaa acatttgaaa ttattttctc 96900
agttacagtt ttgccctgtg tagaagtgtg attatctaag aagtgatttt ttttcagatt 96960
tcaaatatga agtgttgttt aatactaaca tatagttaca aagactatcg tgactatttt 97020
tggtgttctt gattatgatt taatacttca tactttagga aagacgattt agttctaaat 97080
atatttataa gtgagttcct aattttttgt gtgctgtaga cttctaagct attgatataa 97140
ttgaatgtta agcattttca ttttttatgg cttactactt taatgcaaag cagaataaaa 97200
tactaattta tttcttaccc tcagatgatg ttgtgctgat gtatattttc cagtcttgtc 97260
ataagctcac aattacctac ataatggtct tgaaccaaac gattaaatgg aagacaacat 97320
ttctggtctt ccattttaat tagtgtggtg caagactatt atgtaggttt ttgtgtaaaa 97380
tgtggaatgt gaatcctcaa ctctttagtc attcttccta ttagatattg aagcaaaatt 97440
taaaatatgc catttgacta aagatatcaa agtgctttat aaagatatta caatgtacct 97500
aagtcctgtt ttagagcacc agagagaaaa atagaagcgc atagaaggaa taaattcagt 97560
tgcacatttt gtatttaatc caatgactca aaaacatggg cacatattta ccaaattaaa 97620
cgctttcatc aaacatcttc ttgatcatac cataaaagcc cccaaagttt ttattggtag 97680
cattgctctg attaatgaaa tgagcttcag tgcaaaaact tgggctgtta gaatacttac 97740
aaaaccatta ttgtccagtt ctatagctgc taccctagtc cctggctctc atctttttat 97800
acctggttta ccacatcagc atccatgctg agaaccatgc ctcagtcttg cactgctcaa 97860
atacatttag tcatgaactt atttattcag cagacctttg aggacctaca atgtgccaac 97920
aatttattta aacaatattt gtatattttc catccccagg ctaggactta tagtccccag 97980
ttggttatca aatctaaact aaactcagcc taaaaattta gagttctcca aatctcactt 98040
attcttgttc tttcatgcca gtctccttat ggtaacattc attcttagca caatgtgtgt 98100
ctgttcccac ttcttgtcct agtgcatcat ctttcctctt caaggatgta ctccttctcc 98160
tccttaaaat tttaaaaatc atagctaaaa ctaccctgtg aggtgtgagg tttaggttgg 98220
tgtagtcatc tgacttggat cattcttttt attctggatc ctgagagtat ctagaggaaa 98280
ttgcgtattc tggttaatga gtggcttatc acatactgtc ttaacaacac taagcactct 98340
ttattcagta aaagttcaca ccataagaaa atatattgta atgtatttag tgcttcttcg 98400
gtgatatata aggtgttcta cttagaaatt tagatttgta ggaatgctgg ttaatagaag 98460
tttctaatat ttactgtctt ccatatttcc tgatgttttg tttattttaa gctattttaa 98520
atattttgca tttcatattt ttaaccaggc agtatctctg ttcctcattc tgaacaccca 98580
atatggtact ttgaacataa tagggtttca taaagtgctt gattcagtaa aaaaaaaaat 98640
tgaacatcta ctatgttcca ggcattttgc tggatttctg gactacaatc atgaaaagac 98700
agtctattct ctcagcctgc ttatagtcta gtgggaaaga taggttgaca gacatcccta 98760
atatagtata agttcttgaa tacaggtaaa tacaagagta tagagtacct agtctcttct 98820
aggagtgtca agcaaacttt tttagtagaa gcagcctctg caccaaggag ggaattagga 98880
aattttagtg cctgataatc tccttcagtc tcctaaatta taccaaatga aacaaagtaa 98940
cagtgtgtgt ttgctatggg aatacacctg gaagtcaaat atccagcatg cactccctaa 99000
agagtgccac cctaaacctt cccatgtagg aatgccagcg ccacctctga gaggaaggga 99060
tggctaaaca gaggcaagca gcagacaaga gcaggaggat tcctgcaagg ggaatatgaa 99120
caaataccca gtggcaaaaa caaaacaaaa caccaagggg agttggaaga agtcattttc 99180
caaggccaga atgtagattt gtttggacgg agtggatggg gggatatagg cacagtcttt 99240
gagctgcaga agaatgccag gagccaggtc ttaaaggatt ttaaatcagt gattttttaa 99300
aacctttatt ttcttaacag tagaattctt aagaatttta aaattttaac tttagctcaa 99360
tatttaaaaa ataaaaacag aactagtttg gttttgatgt tgtttaaggt ttattttgct 99420
gtgcgttttg gtggggtggt agaagtgtta gtttccttgg ttgcttgctt ctctctgtac 99480
tctactgagg ttaggaattg tgttctagag tcacatcatg ttactaactg gggctttgtg 99540
ttctgactgg tagtagcaat aggtttcacc ctttgtgatt gagtaggctc ctaggaattt 99600
actttcatct attcaacaaa aatgtgtata caggttgagc gtcccaaatc tgaaatgctc 99660
caaaatctga aacttgttga gtgccaatat gatgctcaaa ggaaatgctc agtggaacat 99720
ttttagattt cagattttca gactagggat gctgaaccag taagtataat gtacatattc 99780
aaaaaaaaat ctgatatcca aacacttctt ttctcaagga ttttggataa ggtatgctca 99840
tcctgtattc ttagtactag taatgtttct ctgagcaaaa tagacacaat ccctgacctc 99900
atggagtttc cagtataatg ccagagatgg atattagaaa gtaatcctgt aactataagc 99960
tgtgagataa atgctgtaca gaagaggtca cttacattga gagatctgta aagaaatgac 100020
atttagatag aaacttaagt ggagatctga acaatgagct ggtggtagac agtggtgtag 100080
gcagaggctg taacatgcat gaatgccctg gggggataag gtttgtggca gcagtaaagc 100140
cggagaggga ggtagaaccc agattatgga cagccaagtt agggatttcg attttatcct 100200

-continued

```
cagtgtaatg aaaaaatcat caaaaggttt tgaatagtgg aataatataa gatgacttgt 100260
tttattaaaa tattaattat actatggcta atgtgtggag atttgctaag agaacaggta 100320
gaatgagtga gtatggggac atcagttaca ggagtcatat tctcatatcc gccacatagt 100380
gggcactcat tcaccatttt gtggttagct gaatgatgac tagatcactg cctctgttgt 100440
aacatctcaa attatttgca ctttaaccat gagttaagtt ggatattttt gaggaatcat 100500
gaagtgttgc tgatttgtac taatttttcc tcataaaact ttagatattt tgaactgctg 100560
cttcatcttg ccaagggtga aaacaaagca tttattcatt cattcgagaa gtgcttaagc 100620
tgtgccaggt actggctgag agctgaggat acagactgaa tgaataagtt aggcatgata 100680
tctgccatca agtggcttgt agtctgggta accagagctg agtagagcag gcggtatgtt 100740
ggcctcatac ctccgaagta gtatgtctgg aattagcctg tctgtagtcc cagcctcagt 100800
atctggaata tcctaggtga agatgagatc tcttaacaat ttaattacat tttctcctac 100860
ctcctctttg ttctaatgta tactactaaa tttctacttc gatgaccttt gctgaaaata 100920
cagccactct taagtcctat aacacatgtg cccaggaccg gacaacctaa aaattaaatc 100980
ctgattcttc tttactctta gaaaagctgg gaccttcctt aatggattaa ccttctattg 101040
ctgcgtaaca aatgacaaga aatttagtga tttaaacaac acgtatttat tgtctcgtgc 101100
ttccatgggt caggagtcca ggcactgctt agctggctcc tctgcttaag gcagcaatca 101160
aggtaccagc caggctacat tctcatatct agctcagggt cctcttccaa gatcattcag 101220
gttcttgaca gaatttgttc ccttgtgctt gtaggaaggt tgcttctctc cacaggcagt 101280
tcacaatatg gctcttcacc ttttcacaag tggcagaata gagagagttt actgctttgc 101340
ctctctgaat tcagggaagg cctaactcct cttttaaggg ttcacctgat tacatcaggc 101400
tctcccagga taatctcctt tgataaacac aaatagctgt ttgggtacct taattacata 101460
tgcagaatca cttcacattt gccagataac ataatcacaa cagtaatatt ccatcatatt 101520
ctcaggtcct acttatactc aagggaaggg gatgatagaa gaccatggat cattggaggt 101580
cagtcatctt agaattgtgg ccacctcact tgctttttag taaaaactct cacatctttt 101640
agtttccaac aagtgatgct tgtctcagtc tcattatatc tttgatgact tcttcaccat 101700
tctttctctt ccttcattcc gtagatatcg agatttctca aaacatctca tcaacagtcc 101760
agcctgtttc ttgaccctgt acctcttatt tttcattggc tgaggaccaa ttttcttgtt 101820
ctaaaaataa agctaagagc aggcactttt ttctccagtc atttgctgaa aaacataaac 101880
tcatcagata ataaaacaaa tgctgtttct tgcctgcctt gtaccaattt agggagaagc 101940
ctaggggaga gtgactgatt ttagctccag ccactccagg tagggaaaac tgtgcatgga 102000
tgattgggag aaccttactt agatggggga caggcagttg tgttagtgag ttctagcaga 102060
tgcaccctcc atggcatgga ggagtattgt ccttttatgc cagggtacct tagaagagta 102120
tcggtgtggg ttgtgactta tgagaggggc tacacatgca tgggttggga caaccatgtg 102180
gtattaatct accagtggtt tcaagttata ttgataaaac aaatacattc ttacaattta 102240
agtgtagcct ttacacctga attcaaccat ctgctatcta gcaaaattca gtatcttgca 102300
aacttaaggc tgtcaggcgt ctgctgctaa tttaaggata gcttggtgga atttgcatgg 102360
agggagcagt tctcttttct ctttctgaaa tgaccttcat ctctcttttt atctgattgg 102420
tttatctgtt aaaacccagc ttaggaaaaa aaaagcttag acattgcctc cctgctaaag 102480
cctttccatt tctagaaacc tatctccagt gtccatcctt gagaaagtca atccttcttt 102540
tctctttgtt ctctacctgg attgaagttg tttctgtcaa ttaaaactac catattttat 102600
```

tataatttat ttacatgcct gtctcctcta ctagtgagat ccttggggat agaaactgat 102660
ttattaattt tcttaactat aaagtgcctg acctgtgaca aaagctcaat acatgttttg 102720
agtaaatcaa tcactgcacc aactcaaatc acagtattcc ccccctcccc gctgatttca 102780
agtgaccacc tctgatcccc ttagacacaa acattgaccc tgattaaacc tgtgtttgct 102840
ttgatccata gatacacatt tgaactacag gccatccttt ctggacgggg ttttgttact 102900
ctggcctaca gttctttatt ctttttctcc ccactgacca gcatgtatta aagtcacaag 102960
accagtcttt caaatagatg ttttgaatgg ggcaaagcct tttcatcttg aagccctgta 103020
agtcactcca gagagtgtgg gaaaagcaaa gtgcttggca tagggtacgg tagtagcaga 103080
ggatcttaat tatagttctt cacatttgag tgaagttctg aagctatgaa gtagaaagta 103140
ggaattatca tctcagttac cttagttttg atgtgtggac caaagaaaat gttcaggaat 103200
cttcatattg tgaaatgtgc agtacatgtt taaggttgta gaatattggc tctaaggaga 103260
attttatatt cattcttaaa agagaactaa gttagagaca gtatcttcag attattgttt 103320
ccccaaagac ccttacctgg ttttactgtt gaattaaaca gtaaaattaa actgttgagt 103380
taaacagcat taaagatggt gcagtagcat cattagatgc atggccttgg aagaacatag 103440
ctttcatatc agaaatgtac ttttcaaaaa atctatattt ccttttaaat aatttatataa 103500
tctcagcttt cattttagag ttgggggtac atgtgtaggt ttgctatgtg gatatattgt 103560
gtgatgctaa ggttttgggt gcaaatgatc ctgtcactca aatactgagc atagtgccca 103620
ataggtacct ttccagccct tactcctttt cttttgttcc ccccttttggt tgtccccagt 103680
gtctgttcca atctttatgt ctatgtgtgc ccaatgctta gctcccactt agaagtaaaa 103740
acatgtagta tttggttttc tgtgccagtg ttaatttgct taggatgaca gactccagct 103800
gcatccatgc tgccgcaaag gacatgattt cattcttttt aatggctgcg tagcatttca 103860
tggtgtgtgt gtatatatat atacatgtat atatataaat gtatatataa atgtactttt 103920
tcatgtgaga attcttccaa taaaatattg atgactgtgg cataggagtg taaaattaga 103980
agtgcttcat atggatacaa tgcctacatt tcagaaatct tcatgcagct cttctggaat 104040
gtgggcaaat tagtctcccg gttttctcta tggtcaacca ttttctatta tactcacctt 104100
gtcagaagat atttaattta ccacaattaa ctaaaagctt ttgtttaaaa agtatgtctt 104160
atggaaaaca gaacagaggt gactaatttt ttgtgtgcag taaatgtttt taagtaagca 104220
tttctacaac caggtgaagg aaatgattaa gtagaaattg ggacttgcat gtaatttttt 104280
aaaagattgt gaaacttgtt aatattatgc atgtatccaa cttcttttct attttcaaat 104340
tattccagta acaaaggttt atgcaatagg tatactccca aaaggttgtg ttactatata 104400
atgcaaatgc atgaggatca gtgtttaagc aattagtcaa aacctctaat ttacctcttc 104460
ccaaacataa tgtattatct cttgagttat ctataagcgg ctagttgtag gaaaaaatga 104520
gaaaagctgg ctatatagca agtttgttca tccagaaaac ttcagggttt ttagtttgaa 104580
accttcatga gaaattttta aatagttaaa agcaactgta attgtagcta cttgttatca 104640
gttgttcttc aggcctagtt cttaaaagag aaattttagg agtatgctac tctaatttca 104700
gcagataatc atttaagatg ctgtcatgat agaaaacgac tccagaataa taaggatagt 104760
ttatatgttt cttagagatt ctgtaatgat caatttttag aaagtatact tcatacaaag 104820
ccaaatattt gcttttgttt ttttgttgtt gttgttttc ttttgtttgg ttgatttcag 104880
ccaaccccat ttaccccatt atactcaatt ttaatttaat tgttttggaa aatgttcttc 104940
catttcatta caacatttta cgttttctct aatatgtgtt tacgtaaatt cactttgaag 105000
aaatgcattt ataccatcag ctttatggag ttattgcaaa ccaatgccat catcagtgag 105060
actataaatt tttttttgca gactagtctt ttcatcatga ctttgcataa cattgttcca 105120
gctagatcaa caaattgatt attatatttt actatatcat gaataatgcc cagaggctta 105180
gtaatatgag tgaaacttac tggggatgat attttattta agctgctata tttaaatggt 105240
gctgcaattt aggtattcca ttgaatctac atatagtgca tacttgacat agttaagaaa 105300
aggttttgtt acttttctta tattgaatat ttgagtaata cacagttctg ttgtacgtta 105360
ggatttgagt cccttatgta caaaaatatt tactaccttc tttgtttcat ttcagaatga 105420
ccttatttaa aagtgtatga ggctatttat aatcaactct gtggaagtga ttaaagaggt 105480
gtgaataata ggttattgga acttgacagc tcatagtttg ctaaactagt gttagaacat 105540
ttatgctgct cagatgtacc ttattttcct taagtgagaa tttctgtttt gacatgtggt 105600
ttgttgatat aatatattgc ataggttttt ctcttttaag tggtttacca aatcttgata 105660
ttttattgcc ttattttaca ttttcagctt aatcaacatt ttatgcttaa taagaataac 105720
cttggtacag gctataaaca aaacagtcag tatagacaga gtacggtcct taagtggagc 105780
atcagccttc catttcaagc tatcctataa aataaataca atcaaatttt ttttaaatgg 105840
gaaaaaaact cttttcttac agaaaatttg aaaacatttg gtaggttaac attcagcagt 105900
tgttactctg ggaggaatgt tagaactcct gaagaaattt gggatagcca atatatccat 105960
aaaaagaaga ggtgtgtatt tggtatttca ttaaatcttt actaatttta aatacaaaga 106020
ccagaaaacc acgaatttga atcaattgaa tttgagttag acagcctttt tatttgagaa 106080
taaaaagaaa tctaggaaag catttttaaa attttgaaac cattacttaa tgagtttcca 106140
ctgttctcat ggattcagag cattgtcatt tggtagtact ctcaagtatt ctcaagattt 106200
actaaaatgc attttaataa tcgcaattca gttttcccta accagccagg aggtaatgtt 106260
tctaaaaaga acgtggttgg gaaaactgtg gcagagaaaa tcaggcctca tagacaacaa 106320
aggttagaga aataaaagta aaaattactg tgtatatatt ctacaataaa cctgagaaat 106380
tctttataaa aaaatccaaa attaaccaca tttctcaaca tgaaaaactt cctagactaa 106440
ttcatcactg gacccattta ctcagttgtg attttagcat tagtcaccca caaattttga 106500
attatgtaaa ttacacccat tttaaagttt ttgaactatc tggcttgaaa cctaattttt 106560
ctcttgattt cctcttgtct tatttttcaa gtctgagaaa ttattgtgca gcagtctata 106620
ttttggtgga acttaagggt atatttttct agacctgact tcatttatta aaaagttgga 106680
gtacaagtgt ttatgaaagg atggtataat tgtttgaaag tatcagttgt atatgcatac 106740
atataaatag cccaaatgtt ttataaaaat gaagtgtgat gatatattca aagaacgctg 106800
caataattta tttttggagt accatggtac tttggagaga actctagaga cctgttttta 106860
atccttttct tctaattact ctctgtgtga atttgaatag tttgcttagc tttactaagc 106920
ttcctatatc ttttccttaa aaagtgatga taataccaac tctaccaatg ttacagtatg 106980
ttgttctgag gatgttctgg ttaaagtgct ttgtaacttg tgaattgcaa gggaattgta 107040
agatttgcca atgttgcact tgttgccaat ctgaagattc aagctataag ttgaatacaa 107100
agtatgtgac ctagagaaaa cattactctg ccccctaccc tcatcccacc cccatgactc 107160
aggttgacag ctattcttag ttaagagata cttggggaaa agaggacagt ttagagaact 107220
tcctgtaggt attcattgac tcgtagttcc ttttggcctt ctcagacact tttcttaaaa 107280
gacagtttta tatcggtaac ctcactctaa agtctgtaga ataatagcac attctgatta 107340
tagagtcagt ctaactttat aacgctagag tagtacagag aactctcatg ttgtttaggt 107400
tttccaactg gggacatcct gtgatctgac tgttcctagt gcacaagcta atcccaccca 107460
tatcctgttt gtgagtaatt ggatggatgc ctggaaaatc tagtgccaga ttgtatagtg 107520
cctttacaac agaaatctct agtttgaatt gatttaccct ctacctaaac aaacacctct 107580
cataggtgag cctctactct aaaaaggcaa gattatataa catagatccc tagttcttgt 107640
ttccatagtc atgctttgga tggtactccc attgatctgg atcagagaca tatgtaaaat 107700
acaatttcag ggtgttgttt ttctgtataa ctgaagcagt agattttgaa ttgtatacct 107760
cttcccatga atatagaaga cagctttgta ggaaaaaatt tcttcttaaa tcatcttttt 107820
tatctaaatt attaagaata ggaaaatacc atttgcatca ttgtagtctc tcttacttct 107880
tgggttctct ttacaagata tcaaaatatg tttaaaaaaa aaacccggat gcatataggt 107940
gtgtgcaagc ttgtcgtaat tcaaaaaaaa aatccattgt taaatttcaa agacgtgtaa 108000
tagtgctagc atttactaca gcattgtgat aaagggcaca agctctagag tcagtatcct 108060
ggatataaat gctaaatcca ccacttactg aagaattcta ccaggcatgg caaaaataaa 108120
acctttcttc taattgccat attcttagcc ataatttgtg aattattcaa aattaataat 108180
ttgttttgga accccaactc agtaggtata agccgaaaaa gggaaggact gaaaagtatg 108240
aaaagtgata gcttcagtga gccctggttg ataccagggc tcaaattata ttatgactca 108300
ctctctttct ctccccccac ctcccttgta tttcttcctc cctttcctct gtctgagaca 108360
tagggcttga actgattgct ttaaaaggca atgaatcttg gccaggcgcg gtggctcaac 108420
gcctgtaatc ccagcacttt gggaggccaa ggcgggtgga tcacgaggtc aggagatcca 108480
gaccatcctg gctaacatgg tgaaacccca tctctactaa aaatacaaac aaaaaaaatt 108540
agccgggcgt ggtggcgggc gcctgtagtc ccagctactc gagaggctga ggcaggagaa 108600
tggcatgaac ccaggaggtg gagcttgcag tgagccgaga ttgcgccact gcactccagc 108660
ctgggcaact gagcaagact ccatctcaaa aaaaaaaaaa aggcaatgaa tctctaatgg 108720
ttgattgtat ttctgtgggg tcagtggtaa tatccccctt gttgttgttt ctgattgtgt 108780
ttatttgaat ttttggtctt tgtctagcta gcagtctgtt tcattaattt ttttcaaaaa 108840
aactagctcc tggattcgtt gatcttttga atgtttttc ttgtctctgt ctccttcagt 108900
tcagctctga ttttggttat ttcttgtctt ttgctagctt tgggatttgt gtgctcttga 108960
ttatctagtt attttagttg tgatgtcagg ttgttaactc gagatctatc ttttcgatgt 109020
gggcatttgg tgctataaat ctccctctta acactgcctt agctgtgtcc cagagattct 109080
ggtacattgt ctctttgttc ccattagttt taaagaactt ttttattatg tccttaattt 109140
cattatttac ccaaaagtca ttcaggagta ggttattcag tttccatgta attgtatgag 109200
tgagtgaatt tcttagtctt gattttgaat ttgattgcac tgtggtccaa gagactgtta 109260
agatttcagt tcttttacag ttgctgagga gggttttact tccaattatg tgagcagttt 109320
tagagagaaa gtgccatgtg gcaatgaaaa gaatgtacat tctgttgttt ttgggtggag 109380
agttctgtaa atatctatca ggtccatttg atccagtgct gagttcaggt cctgaatatc 109440
tttgttaatt ttctgtctca gtgatctcat attgtgagta gagtgttaag tttcccacta 109500
ttactgtatg agagtctcag tctctttgaa ggtctcttaa gaagttactt tatgaatctg 109560
ggtgctcctg tgttgggcac atacatattt aggatagttt gatcttgttg aatgtaaacc 109620
tttaccattg tataatgccc ttctttgcct tttttaaaat ctttgtttgg tttaaagtct 109680

-continued gttttgtcag aaactagaat tgcaacccct gctttttgtt ttgttttgtt ttccgttagc 109740
ttggtagatt ttcctcattc cctttatttt gagcctatgt gtgtcactgc atgtgagatg 109800
gatctcttga atacagcata ccattggatc ttggtttttt atccagtttg ccatcctgtg 109860
tcttttaatt ggggcattga gcccatttac atttaaggtt aatagtgata tgtgtggatt 109920
tgatgctgtc ataatgatgt tagctagtta ctttgcagac ttgtttatgt ggttgacttt 109980
atagtgccac tggtctgtgt acttcagtat ggttttgtag gatctggtaa cggtctttcc 110040
tttccctatt taatgtttcc tttaggagct cttgtaaggc agatgtggtg gtaacaaatt 110100
cagcatttgc ttgtctgaaa aggatcttgt ttttccttca cttatgaagc ttagtttggc 110160
taactatgaa attctgggtt agaatttatt taagaatgtt gaatattgac tcccaatctc 110220
ttctggcttg tagggtttcg gaggccatta tccttagcaa actaacacag gcatactgca 110280
tgttctcaca tgttaagtag gaactaaatg atgagaacac atgggcacac agaggggaac 110340
aacagacact ggggcttacc agtggtggag ggtggaagga gaggatcaga agaaataact 110400
aatgggtact gggcctaata cctgtgtgat gaaataatct gcacaacaaa ccctcatgac 110460
acaagtttaa ctatgtaaca aacctgcact tgtacccctg aatttaaaag ttaaaaaaaa 110520
aaaaaagcca gtgaatctgt tgtgaatact tacaggcaga actttttttt tttttttttt 110580
tttttttttg agacgaagtc tcactcttgt cccccaggct ggagtgcaat ggcataatct 110640
cggctcactg taacctccac ctcctgggtt caagcgattc tcctgcctca gcctcctgag 110700
tagctgggat tacagcctgc caccatgcct ggctaatttt tgtatttcta gcagagacag 110760
ggtttcacca tgttggacag gctggtctcg aactcctgac gtcaggtgat ccacccgcct 110820
tggcctccca aagtgctgag attacaggcg tgagccacca cgcccagcca taggcagaac 110880
ttttacttga gggaaggatt gatataagat tctgacattc tgttttttat gttctttgta 110940
tataattgca tatgattttg aaatataaat cttttgaatt tcttattaaa cttgtaaatg 111000
atgtttgtaa tcgtaggcaa tttaagattt cgtactagtt aaggtataga ctgttagaat 111060
gaattcaggg taaactgtgt gtgtttgtgt actggggaaa ctgtgtagtg gtagcttata 111120
gggtcatctg ttaattagtt actgagatag gcagtttata taaattgctc attcagtcct 111180
taaaaaatct tataagtagt tattattctc ccattatatg tgaggaaaat acaagaaact 111240
gcttcctttt gcaaaccaaa cactgccttt aaacttagca tcttagactg ccactacctg 111300
cagacatgac tagaacttat taaatattgt ctttttttcag tttaatagtt acttagtaat 111360
atggccttta tctaaatttc ctaattttgc catgttaaaa tgtaatccta tttgaactat 111420
gaactttgaa tttactttaa taaaaataat ttctaccact gctaatacaa tgtaaaattt 111480
ttaagcttag cttaagatta atgttacttt ggaaataaat tgctacacat ttacacacat 111540
aatttatata ggaaataaat cagtctatgg aaatatattt agattataag cctttttagc 111600
tacagaaaca aaattgttta gaatgaactt acatagcaag acaaaattga aaacagaggc 111660
tttagaagct agtgtaatat aaagtttaca atttacaaaa attacttcat ttaaatagca 111720
gttattttta cttactttca ttgaagaaat aaaatcctat gattcaactt acagtataca 111780
gtctttttgc atggagggat gattttgtaa ggcccaaatc agtactgctt aaatcagtac 111840
aaagagtgta tttgttttat ggatcatgtt tctggttttt tcacccagaa taaaacttta 111900
aaaggaaaaa ttttcttctg tttccaaaag gaactattgg ggtatgtgga ggggttgatc 111960
cacaacccta aactggcaga gagcttgggt gtatatataa gcagctaatc tctcacctag 112020
ttccaggtac atatctttgt tgttgaccag aaaagtgcct gaccagaagt ccacatacct 112080
ctcctgttat tttccttcct ataaatgtgg ccttgcctgc cagggagcat tgccttaaac 112140
taaactggaa ataagaagca gcattcatta tactatacac ttgatcttag ccaaaaggcc 112200
aagaagcaat cattcattat actataaatc tctattgtat gaggagtaat agagggcaga 112260
tatatcacta caggacatgc ctagtatttt tacatcccag agtatgttgc agggatccta 112320
gtatgtaaaa atctcagaag cataaacaaa atttatttta aattttagtt ttaataagct 112380
tttttaaact ccgcatccta cttttagtgg gatataaggg ttattaaatc acacttcaaa 112440
aagttagaaa ccctacaaag gccatacaga aaataaaatc ctctgaacct aggtgctact 112500
aattcactca agataaattt aatcatttta ttatttatgg atataatcta atggaataat 112560
tttaatactt taatgaaaac attactttca atcagatgta cagaactcac aggaaaactt 112620
gaaaattctt aattataact gtaagaccta cgtagtataa ctaacagata aaaggattgt 112680
ctttaaatct ttatgaaaac gtgaaatgaa gcaacataaa cattaattca ttgacaaaac 112740
agtttatttt aaacacgtaa gaacagaaaa ggtggagact tggtggttgt aaatttggac 112800
aggaatatat tgaaatatca tgtgtatgtg gatacagata tcagtattct ggttactgcc 112860
ctcaaaaagc atatgttctt tttaaggagt taacaaagat atgataaaat actgaaagaa 112920
taataccagt gatacttagt aagtgctaat aactaccttc agaatatagt atagaccaac 112980
actgtccggt agaactttct tggatgaaag aaatgttctc tattttatct aatagccact 113040
ggctacctgt ggttatttga gcacttgaaa tgtatgctgt atgaatgagg aatttaattt 113100
tatattttat ttagaaattt aattaactaa tttaaggata gacatggtgg ctcacacctg 113160
taatcctagc agtttgggag gccaaggcag gtggattgct taagcccagg agtttgagac 113220
tagccttggc aatatggcaa aaccctgtct ctacagaaaa tttaaaaatt agccaggtgt 113280
ggtactgtgt gcctgtggtc ccagctactc aggaggctga ggaaggagga tgtcttgagc 113340
ctggaaggtt gaggctgcaa tgagctgtga tcatgccact gcactccagc gtgagcaaca 113400
gagcgcaata ccctgtctca attttttttt aattcagtgt gaatagatac atttgattag 113460
tggctaacct tattaaattc tacaattctc aaaagatgct tgtctcagga acccttcatt 113520
taaaagtgat ttacggcccc agagtgcttt tgactatgtg ggttatattt actgatattt 113580
acagcattaa aaatagaaaa attttaaata tttattcatt cttaaagtta ctacatgtta 113640
acataaaata tctttgagga aaagctattt ttaaaaaaga gtggcattgt tttacatgtt 113700
tacaaatctc tttaatgtgt gggttaatag aaggcagttg aattctcata tctgcttcta 113760
tattctagct gttgcaatgt gttgaactgt attaaaacct aacctcacat agatagttag 113820
ttggaattag cctttttaga taattgtgga tattctttga ttaccaaaac tcaccaagta 113880
gcagtttctt aaagtttagt tgtgatgtaa aatataaaac catatcaatg aattttatag 113940
ttacattaaa aaatcactgc tctcttgaac tttgagtggg ccttttaccc acttactaat 114000
ttgcaacatc atgcattagt tatttggaag atattggttc actgaattgt ccagatcttc 114060
caaatgttga cacattccat tttacccaat caaaaaatca ctaatagcag caccaatctc 114120
ttcagaaggg tcttcaaaat taggaaattg caaaattcaa ctcagctgca gttaacatgt 114180
tttccaaaat tctcatttac atctgaaagc tcaaatttta ttggcaacaa atttggccaa 114240
tttgtcttcc tttaaatgac aggcttattt ggcttatttt tgagaaaata tctgccaaat 114300
actcaaacct gaataaccat tgtttgtcag ttggttattc tttcaagtta aatagatgta 114360
ccatgaaaaa agcagctact tcggtagcaa cttaattcca ggagtgattt tccataagac 114420
atctgttata ctttgatgtc cagcagaagt gttttgtgta tacatcccat tttgttgtac 114480
agaacactaa aaagacatac actacagggt caaaacttat taaagtaatt tttactactt 114540
catcaaggat gtacttaagt gaaactggca aatttttaa ctggaaatga gtggcagtga 114600
gggctacaag gatatagttt gctgctgctg ccttggtaag tgctaagatg ccaacagttt 114660
gacctaccat tgtctttgta tcatcagtgc aaatgccaaa gaagtgaaaa gggcaagtac 114720
tgccttagta ttattataaa aatggttttg accttgctga aaagacaata atggaggaaa 114780
gaaattgctt ttagttcaaa taagttaaag aagactccat gataaagatc aatgtaatat 114840
gcatgcccta ctttattttt ctttacctgc tttttctat aaaaataaaa gtaggaaagc 114900
aattagcatg ttaaaaatta tttaaccatg ttacttttaa aatcattctt tgattcagca 114960
attatttatt aactattttg cataagttat ttttgttgtt gataagtggg caatatgtaa 115020
tgtttagaat aatgatcatg ccaataaagc atctgtgccc ccactataaa gcactgctat 115080
gtgctgggca ctgtgtttat gtgcttttaa atgcattcac ggaatcttca tggtaacctt 115140
aggaggtagg ttttatagaa agttaactgg aattagtgcc agctcacaat ttttatataa 115200
ctagataaat tacttaactt atttggattt cagttttctc aagtataaaa tacgaagctg 115260
agacatatct tcagatgctt aaccaggctt aaaattcatt aaataaacat atatttcaca 115320
gcaggataac cctttattga cacattatca gaatactctg aattttatta ggaagccata 115380
aaaacaatta ccaaatcatt aacataaact ttttgaaact ttatgtccct ttcattttaa 115440
aattcgttga gtcaatacat ttttcataac acttaatcct ttactgacac atgatcagaa 115500
cactgaacac ttgaccaaag acctaatgat agatgtgaac ataatgtaaa catgaaggga 115560
tatagtcact attgtagcgg aataaaaaat aatacaaaag cgcaaagaac aagagtcagg 115620
aaaggtcaag aagagcatca ataaagcagc agtgttttag tttgttcatt agttcaacag 115680
atgtcttata tgcctttgtt atgccctgta aagcttggaa tttagactac tggagggaac 115740
aaaatgatgt ccttgccctc atggagctta cattttagtg ggggagtgtg gtaggtagga 115800
tagtggcctc ccaaatatgt ccatgtccta atccctaaaa cctgtgaata tgttacatta 115860
cttaaaaaaa gattattaag tagcaaagga atagggagat tacttcgggt tatgtggcta 115920
ggcaaaatgc aatgttaaaa gtggaagctg gagtttgaag aagggtcagt ggcagaatga 115980
tgcgacatga gaaagtttca actggccatt tctggctttg aagatggaag gggccatgtg 116040
ccaaggaatg cagcagcctc tacaagctgg aaaaggcagg aaagtggatt ctcccctaga 116100
gtctccagaa agaacacagt tctgccaaca tcttgatttt agtccagtga gacccatatt 116160
gggcatctaa ttgtgaaata ataaatgtat gctattttaa gcctcttagg gatatgtcag 116220
tttgttacat caacaataga aaactaatac agagtaaaag aaagtaaaca agtaactaaa 116280
caagataatt acaaactacg atggatgctt tgaaggaaat aggatgatgt gaaagagtaa 116340
aggataaagc atgttggttt aggtgatcat ggaagtcttc tttggaacta tgacactgga 116400
gtggaaaaga aagacccagc tgtgtggagt tggaaacaga atctcaggcc aagggaaagg 116460
caagtgtagg ggcatggagt agagaaggct tgccatttac aaagaacaaa aacaggtcat 116520
ttagcgagaa tgaatagaat agtggaaaag gtgcaggccc aaaaatgtgg agccttgcag 116580
gaatgatgga acaatggaaa gccattgaaa ggttttaaga aggagagtga tacattttgc 116640
tttacatttt tgaaagatca ccccggctgc tgtgtggtaa atggaaacaa gggaccaatg 116700
acatggtatt gtagtcctga ggaggaagtt tacaggcgga agcaaactag tggcattggt 116760
gcctggagag gattgttgat gatagacggg atatgagttc caaaagatga gtaggaattt 116820
gcccctagag aagaggaaga atacatagca gaagcatgaa agttcaggat gtctgggaaa 116880
ttgaatatac tttgcagaac agtagcaagt gaagatgaag agattgttta agcgataatg 116940
tatgcagtcg ggagaccctt attcgccatg tatgggagtt tggaatttat ggcatatgca 117000
atggagagcc atctgaaatt tcgaatcaag agaacaaaac aatctcttga cctgaagttt 117060
tgtgattatt atgtatgtcc ttcattttca ttctgaagta aaggagaata ataagggtgc 117120
tttaagtttt atcatcttag attctgagaa gttcagaaag atttgattaa gtacttgtca 117180
atgaagtctt taataattca ttgggaacca cacttttatt ctgttttgtt tttttgtaag 117240
gacttttttt tcatttatgg gctctactct tctgctgtct ttggagagac agcacagtaa 117300
cctgttcaga gcatgtccgg agccacatgg cctagggtac agtcctggtt accagtacta 117360
actggtcaac ctttggcaag ttatgtaatc taagtcttag tttcattgtc tataaaataa 117420
ggataataaa aattcttcaa gtggcttctg taaggattaa tggattcagt gcatataaag 117480
cactgaatat gtaataagca ctttgtggat cagggttgaa gcagggtgca gaagtatacg 117540
aggagcattg gttgtaagct tttctatata tcagtagtag aaatgtgaca ggtcataatt 117600
tctttaaagt acgtttaaaa tacctatttc ccacttcatt tttatatatg gtattaaatt 117660
ttctatttgt ttgtgttttc caagaatgtc cacttctttc atcacaaagc ccacttattc 117720
tccaaaaagt ttatataaga aaatgggtag ttagtttgca tgatcttctg ctttattgga 117780
tattatttat tttctggaat aagttatgtc cacagatgat tttaattcac actgctactc 117840
aggtaactta ggtaaaacaa aacatcagga ttttttggta ctacagttca aatttattta 117900
acttcccaac aatatatttt aaataacaaa gaaacaaaat actcaatttt acctctgttg 117960
cacattagca aggcataaaa gagagattaa tataattagg taaggattct tatagtattt 118020
attttctgca tcacttttaa tttagcattt aattatgtac tatgacattt ctctatataa 118080
tacttcatgt atattactca tatttgcaaa gattacgtat atctcagagg tggagactag 118140
atattaaatg tcttcattct cctatcttct gaagcactta agtcagagga actaaattat 118200
tcattctaat ttgacaactc aagcttgtaa catattataa tgcttagaaa agctcagtaa 118260
aactaaactc tagttaccta taaattgttt gtttttaata cttcatcagg aaataaattc 118320
caattaaaat ttcattaatt atccccottg ttctttcatg tctttccaat gaaggagtag 118380
aaagactttc tttacaaaac taggctcagg gaattagtgt cccatgttga aatttggctc 118440
tcaggaaagc tcccagaaag gaagtctcct agttggcaac caataagcct tacttagatt 118500
actatatgtt gtcattccca tggaagtaag ggaggatccg tcctcaaact acatccttgg 118560
ggttcatgat ctttttcttt tcacttttcc tatgatttct cttcccatgg tcaggagttt 118620
taaattacac atacagcatt actagtttga aggaatcttg gagaaccaaa taaaatgaat 118680
tagaatgtaa ttcttgtcct cttccttcat cttattttc acaaccagtt ctgctactaa 118740
tcgataagcc tcaaagccaa tcaaaggaga attaccttct gggattagta aatgtcaaaa 118800
tatttcttaa aatttttca taagatgaga aaagctgaaa atcatgccaa ctcctgtggt 118860
tgaaactatt taaataattg actgtgtgtt tgggtgtatg tgagatacta taacctgtac 118920
tttggggatg ctcattgccc ttgacaagtg aaagcgtgcg ctctccacga ggcctccctc 118980
ctggcgtctg tgcagtaaga gagcagcttc cctcagcact agctggaagg agaagtcact 119040
tgtgctggtg ttcagcaagt attaccttcc ttttcatttt atataatgtt atgtagccat 119100
gaataggaaa ggtaaatgtt tttcatactt taaatagact actatctttc aaaaataaga 119160
aaatagatct tattattgtc tcataaaacc ataaaataaa aattgtttta tttcaaaatc 119220
cacagatatt tatttacaac atagtattca tcaactaata aatgtccttt ttacctttca 119280
ttattcttta gattttattt cagtatcctg attagtgttt ttaattatac ctcctattca 119340
ccgtgataac aaattcaaat aacataaaaa tgttaaggaa gagagctggg tgcagtggca 119400
cataccagta atcctaacac tttggaaggc caagccggag gattgcttga ggccaggggc 119460
tcaagaccac cataggcaac atagtgagac cctgtctcta taaaaaaaaa atttctttta 119520
aattacctgg gtgtggtggc acaggccttt agtcccagct acttgacaga ctaaggcaca 119580
gaggatcgct tgagcctagc agtacacagg tgcagtgagc tacgatcatg ccactgcgct 119640
ccagcctggg tgacagagtg agacctcgtg tctaaaatat acatacatct atagaaatat 119700
acacatatac atacgtacat acatgcatac atagagagcc agcaaatatt ttgcccaatc 119760
ccagttcagt tttctaaagt ttgccactag caacattatg ctgaaaatta tttggctttt 119820
tctttgcaca tttaaaatat atctttaaaa ttttttttaaa gtaatataaa cattaaaata 119880
atatcaaagg aataagccag aaaaacaagt cactcctttg gtacctgatt tcctcatttg 119940
tatgtcctag acatcatgaa ttgatgttaa ggcacatgta tagtatggat actatactgc 120000
atctactgta ttttctggaa ggatggaatc aaactatttt ggaagacttt ctatatcagt 120060
accaaacaat atatcttaga tgactattaa ggtttttttg taattaaaaa caagttttca 120120
gataaacata tgtatgcata tttgcataca tgtgttaatt tgcacggtgc caagaaattg 120180
ttagatcaac aggtcggcat tttaaatttt gataaatatt gccaaagtaa cacagcatat 120240
aagagtgtac tcttttattt aaaccttgca tatgtcaggc gttactggga ctttttttgcc 120300
gatttactaa acatcattta tctagggatt agtatctaca gccagtgttc tagatgaggg 120360
gaacagtggt gatcgaaaca gaaaaaaattc ctgtctgaat ggaacttgca ttgtagtgta 120420
gtagataatc aatcaataag atattatagt gacaagtatt tttaaaagaa ataaattgag 120480
ggagaatagg gagtgcaatg ggggtggggg tggtatttaa atagagcagt cataggagac 120540
ctccctgagg aggtggaatt gggcagttca taaagaatat tacaggtaga gtgatatgaa 120600
gcaagaggcc agtatacctg gaatgcagtg agccggggta aagtagaaga caaagtctga 120660
gagagacagg tgaggagagt cagcccatgg agggccttgg attacagtga ataggatggg 120720
aagtcattag atggtttgac aagattccac tgatgcttta gaaggttttg tctgctgtgt 120780
tgagaactga ctacaggaag acaaaggtgg cagcacggag accagatagg aaccagtgac 120840
agtactcgaa gtgagagatg atggtaccat caggtagtta gtggcaggga attggtagtg 120900
ggtggtcaga tcttgaatat atttttatag gtatttcctt ccagagtaga tgcatgggat 120960
atgagagaaa aagaggagtc aaaactatca ctgagacttt tggcctgaac aactggagga 121020
atggaattgc cgtttactga aatagagaag actgagagac caggaattgt atttggctat 121080
ggtaaaaaat ttcccattag aaatccaagt ggtgatatca ccaaagacaa aagccacatg 121140
attatctcaa tagatgcaga aaaggccttt gacaaaattc aacagccctt catgctaaaa 121200
actctcaata aattaggtat tgatgggacg tatctcaaaa taataagagc tatttatgac 121260
aaatccacaa ccaatatcat actgaatggg caaaaattgg gagcattccc tttgaaaact 121320
ggcgcaagac aggggtgccc tttctcacca ctcctattca acatattgtt ggaaattctg 121380
gccaggacaa tcaggcagga gaaggaaata aagtgtattc agttaggaaa agagggagtc 121440
aaattgtccc tgtttgcaga tgacatgatt gtatatttag aaaaccccat tgtctcagcc 121500
caaaatctcc ttaagctgat aagcaacttc agcaaagtct caggatacaa aatctatggg 121560
caaaatcaca agcattctta tacaccaata acagacaaac agaaagccaa atcatgagtg 121620
aacccccatt cacaattgct tcaaagagaa taaaatacct agaaatccaa cttacaaggg 121680
acgtgaagga cctcttcaag gagaactaca aaccactggt caaggaaata aaagaggata 121740
caaacaaatg gaagaacatt ccatgctcat ggataggaag aatcaatatc gtgaaaatgg 121800
ccatactgcc caaggtaatt tatagattca atgccatccc catcaagcta ccaatgactt 121860
tcttcacaga attggaaaaa actactttaa agttcatatg gaaccaaaaa agagcccaca 121920
ttgccaagac aatcctaagc caaaagaaca aagctggagg catcacacta cctgacttca 121980
aactatacta caaggcaaca gtaaccaaaa cagcatggta ctggtaccaa aacagagata 122040
tagaccaatg gaacagaaca gaggcctcag aaataatgcc acacatctac aaccatctga 122100
tgtttgacaa acctgacaaa aagaagaaat ggggaaagaa tttcctgttt aataaatggt 122160
gctgggaaaa ctgactagcc atatgtggaa agctgaaact ggatcctttc cttacacctg 122220
atacaaaaat taattcaaga tggattaaag attgaaatgt tagacctgaa accataaaaa 122280
ccctagaaga aaacctaggc aataccattc aggacatagg cacgggcaag gacttcatgt 122340
ctaaaacagc aaaagcaatg gcaacaaaag ccaaaattga caaatgggat ctaattaaac 122400
taaagagctt ctgcacagca aaagaaacta ccatcagagt gaacaggcaa cctacagaat 122460
gggaaaaaat ttttgcaatc tacacatttg acaaagggct aatatccaga atctacaatg 122520
aactcaaaca aatttacaag aaaaaaacaa ccccatcaaa aagtaggtga aggatatgaa 122580
cagacacttc tcaaaagaag acatttattt atgcaaccaa aagacacatg aaaaaatgct 122640
cattatcact ggccatcaga gaaatgcaaa tcaaaaccac aatgagatac catttcacac 122700
cagttagaat ggcaatcatt aaaaagtcag gaaacaacag gtactggaga ggatgtggag 122760
aaataggaac acttttacac tgttggtggg actgtaaact agttcaacca ttgtggaaga 122820
cagtgtggcg attcctcaag gatctagaac tagaaatacc atttgaccca gccatcccat 122880
tactgggtat atacccaaag gattataaat catgctgcta taaagacaca tgcacatgta 122940
tgttgattgc ggcactattc acgatagcaa agacttggaa ccaacccaaa tgtccatcag 123000
tgatagactg gtttaagaaa aggtggcaca tatacaccat ggaatactat gcagccataa 123060
gaaatgatga gttcatgtcc tttgtaggga catggatgaa gctggaaacc atcattctca 123120
gcaaactatc gcaaggacaa aaaaccaaac actgtacgtt ctcactctta ggtgggaatt 123180
gaacaatgag aacacttgga cacagggtgg ggaacatcac acaccggggt ctgtcgtggc 123240
atgggggtag gggggaggga tagcgttagg agatacacct aatgtaaatg acaagttaat 123300
gggtgcagca taccaacatg gcacatgtat acatatgtaa caaagttgca cgttgtgcac 123360
atgtacccta gaacttaaaa gtataataat aataataaaa aaaaaagaaa tccaagtgga 123420
gctatcaagt agataatttg ggattcatag gagaagtcac ctgggatata aaactgggag 123480
tcaacaaatg gcatttagag ccatgaaaca gattgaggaa gtggaggaaa gaaacgaaaa 123540
agaagcagtt ggtgagttaa gaggaaactg atagagtcaa gagaagagat tgttttgaaa 123600
aggagagagt aatgaattat gtcaaatgct gctaaaagat caagtcaaat gaggactgat 123660
aattgtcatt gcatttagca gtgctcacag tcatgacaag aacagtgttg gtggagtgtt 123720
gtaattggag taatttaaga taaaatagga agaaacaaat tagagacaca tgtaggcaac 123780
ttttccaaaa agctttgaag tatagaggga ctgagatata gaattaggag tgctggagtt 123840
taatcaaggt aagagattag ccagcataga gattttgaag ccagagagag caagaaagtt 123900

```
gagagtgtac gtgagaagtg attataaaaa tataagatta aaatggatat ttcttctgtt 123960
actgaggttg agcatctttt tacatgttta ttgggcattc atttttgtgt gtgcgaattg 124020
cttgtgcata ttcttactgg gtggttcatc ttatgagtgt ttaagaattc tctgtaaaat 124080
aaagatgtca gcctttagtc atatgtgttg cacatatttt tcacaatttg tcgtttgtct 124140
tttgacttga tttttttctg tgtatagtta tgggtttcat ttcatgctta taatggcctt 124200
cttattccag gtttgtaaaa ggatttgcct atattttctt cttttttttt tttattatac 124260
tttaagtttt agggtacatg tgcacattgt gcaggttagt tacatacgta tacatgtgcc 124320
atgctggtgc gctgcaccca ctaactcgtc atctagcatt aggtatatct cccaatgcta 124380
tccctccccc ctccccccac cccacaacag tccccagagt gtgatattcc ccttcctgtg 124440
tccatgtgct ctcattgttc aattcccacc tatgagtgag aatatgcggt gtttggtttt 124500
ttgttcttgc gatagtttac tgagaatgat gatttccaat ttcatccatg tccttacaaa 124560
ggacatgaac tcatcatttt ttatcgctgc atagtattcc atggtgtata tgtgccacct 124620
tttcttaatc cagtctatca ttgttggaca tttgggttgg ctccaagtct ttgctatcgt 124680
gaatagtgcc gcaataaaca tacgtgtgca tgtgtcttta tagcagcatg atttatagtc 124740
ctttgggtat atacccagta atgggatggc tgggtcaaat ggtatttcta gttctagatc 124800
cctgaggaat cgccacactg tcttccacaa tggttgaact agtttacagt cccaccaaca 124860
gtgtaaaagt gttcctattt ctccacatcc tctccagcac ctgttgtttc ctgacttttt 124920
aatgactgcc attctaactg gtgtgagatg gtatctcata gtggttttga tttgcatttc 124980
tctgatggct agtgatgatg agcatttttt catgtgtttt ttggctgcat aaatgtcttc 125040
ttttgagaag tgtctgttca tgtccttcac ccacttttttg atggggttgt ttgttttttt 125100
cttgtaaatt tgtttgagtt cattgtagat tctggatatt agccctttgt cagatgagta 125160
ggttgcaaaa attttctccc attttgtagg ttgcctgttc actctgatgg tagtttcttt 125220
tgctgtgcag aagctcttta gtttaatgag atcccatttg tcaattttgt cttctgttgc 125280
cattgctttt ggtgttttag acatgaagtc cttgcccatg cctatgtcct gaatggtaat 125340
gcctaggttt tcttctaggg tttttatggt tttaggtcta aagtttaaat ctttaatcca 125400
tcttgaattg atttttgtat aaggtgtaag gaagggatcc agtttcagct ttctacatat 125460
ggctagccag ttttcccagc accatttgtt aaatagggaa tcctttcccc attgcttgtt 125520
tttctcaggt ttgtcaaaga tcagatagtc gtaggtatgc ggcgttattt ctgagggctc 125580
tgttctgttc cattgatcta tatctctgtt ttggtaccag taccatgctg ttttggttac 125640
tgtagccttg tagtatagtt tgaagtcagg tagtgtgatg cctccagctt tgttcttttg 125700
gcttaggatt gacttggcga tgcaggttct tttttggttc catatgaact ttaaagtagt 125760
ttttttccaa ttctgtgaag aaagtcattg gtagcttgat ggggatggca ttgaatctgt 125820
aaattacctt gggcagtatg gccattttcg cgatattgat tcttcctatc catgagcatg 125880
gaatgttctt ccatttgttt gtatcctctt ttatttcctt gaccagtggt ttgtagttct 125940
ccttgaagag gtccttcacg tcccttgtaa gttggattcc taggtatttt attctctttg 126000
aagcaattgt gaatgggagt tcactcatga tttggctttc tgtttgtctg ttgttggtgt 126060
ataagaatgc ttgtgatttt tgtacattga ttttgtatcc tgagactttg ctgaagttgc 126120
ttatcagctt aaggagattt tgggctgaga caatggggtt ttctagatat acaatcatgt 126180
tgtctgcaaa cagggacaat ttgacttcct cttttcctaa ttgaataccc tttatttcct 126240
tctcctgcct aattgccctg gccagaactt ccaacactat gttgaatagg agcggtgaga 126300
```

gagggcatcc ctgtcttgtg ccagttttca aagggaatgc ttccagtttt tgcccattca 126360
gtatgatatt ggctgtgggt ctgtcataga tagctcttat tattttgaag tacgtcccat 126420
taatacctaa tttattgaga gtttttagca tgaagtgttg ttgaattttg tcaaaggctt 126480
tttctgcatc tattgagata atcatgtggt ttttgtcttt ggctctgttt atatgctgga 126540
ttacatttat tgatttgcgt atattgaacc agccttgcat cccagggatg aagcccactt 126600
gatcatggtg gataagcttt ttgatgtgct gctggattcg gtttgccagt attttattga 126660
ggatttttgc atcaatgttc atcaaggata ttggtctaaa attctctttt ttggttgtgt 126720
ctctgccagg ctttggtatc agaatgatgc tggcctcata aaatgagtta gggaggattc 126780
cctctttttc tattgattgg aatagtttca gaaggaatgg taccagttcc tccttgtacc 126840
tctggtagaa ttcggctgtg aatccatctg gtcctggact ctttttggtt ggtaaactat 126900
tgattattgc cacaatttca gatcctgtta ttggtctatt cagagattca acttcttcct 126960
ggtttagtct tgggagagtg tatgtgtcga ggaatgtatc catctctcct agattttcta 127020
gtttatttgc atagagctgt ttgtagtatt ctctgatggt agtttgtatt tctgtgggat 127080
cggtggtgat atccccttta tcatttttta ttgcgtctat ttgattcttc tctctttttt 127140
tattagtctt gctagtggtc tatcaatttt gttgatcctt tcaaaaaacc agctcctgga 127200
ttcattgatt ttttgaaggg ttttttgtct ctctatttcc ttcagttctg ctctgatttt 127260
agttatttct tgccttctgc tagcttttga atgtgtttgc tcttgctttt ctagttcttt 127320
taattgtgat gttagggtgt caattttgga tctttcctgc tttctcttgt gggcatttag 127380
tgctataaat ttccctctac acactgcttt gaatgcgtcc cagagattct ggtatgttgt 127440
gtctttgttc tcgttggttt caaagaatat ctttatttct gccttcattt cgttaggtac 127500
ccagtagtca ttcaggagca ggttgttcag tttccatgta gttgagcagc tttgagtgag 127560
attcttaatc ctgagttcta gtttgattgc actgtggtct gagagatagt ttgttacaat 127620
ttctgttctt ttacatttgc tgaggagagc tttacttcca agtatgtggt caattttgga 127680
ataggtgtgg tgtggtgctg aaaaaaatgt atattctttt gatttggggt ggagagttct 127740
gtagatgtct attaggtctg cttggttcag agctgagttc aattccctgg gtatccttgt 127800
tgactttctg tctcgttgat ctgtctaatg ttgacagtgg ggtgttaaag tctcccatta 127860
ttaatgtgtg ggagtctaag tctctttgta ggtcactcag gacttgcttt atgaatctgg 127920
gtgctcctgt attgggtgca tatatattta ggatagttag ctcttcttgt tgaattgatc 127980
cctttaccat tatgtaatgg ccttctttgt ctcttttgat ctttattggt ttaaaggctg 128040
ttttatcaga gactaggatt gcaacccctg cctttttaa ttttccattt gcttggtaga 128100
tcttcctcca tccttttatt ttgagcctat gtgtgtctct gcacgtgaga tgggtttcct 128160
gaatacagca cactgatggg tcttgactct ttatccaatt tgccagtctg tgtcttttaa 128220
ttggagaatt tagtccattt acatttaaag ttaatattgt tatgtgtgaa tttgatcctg 128280
tcattatgat gttagcaggt gattttgctc gttagttcat gcagtttctt cctagtctcg 128340
atggtcttta cattttggca tgattttgca gcggctggta ccggttgttc ctttccatgt 128400
ttagtgcttc cttcaggagc tcttttaggg caggcctgct ggtgacaaaa tctctcagca 128460
tttgcttgtg tgtaaaggat tttatttctc cttcacttat gaagcttagt ttggctggat 128520
atgaaattct gggttgaaaa ttcttttctt taagaatgtt gaatattggc ccccactctt 128580
ctggcttgta gggtttctgc cgagagatca gctgttagtc tgatgggctt ccctttgagg 128640
gtaacccgac ctttctctct ggctgccctt aacatttctt ccttcatttc aactttggtg 128700
aatctgacaa ttatgtgtct tggagttgct cttcttgagg agtatctttt tggcgttctc 128760
tgtatttcct gaatctgaat gttggcctgc cttgctagat tggggaagtt ctcctggata 128820
atatcctgca gagtgttttc caacttggtt ccattctccc catcactttc aggtacacca 128880
atcagatgta gatttggtct tttcacatag tcccatattt cttggaggct ttgctcattt 128940
ctttttattc ttttttctct aaacttccct tctcgcttca tttcattcat ttcatcttcc 129000
atcgctgata ccctttcttc cagttgatcg cattggctcc tgaggcttct gcattcttca 129060
cgtagttctc gagccttggt tttcagctcc atcagctcct ttaagcactt ctctgtattg 129120
gttattctag ttatacattc ttctaaattt ttttcaaagt tttcaacttc tttgcctttg 129180
gtttgaatgt cctcccgtag ctcagagtaa tttgatcgtc tgaagccttc ttctctcagc 129240
tcgtcaaagt cattctccat ccagctttgt tccgttgctg gtgaggaact gcgttccttt 129300
ggaggaggag aggcactctg cgttttagag tttccacttt ttctgttctg tttttttcccc 129360 atctttgtgg ttttatctac ttttggtctt tgatgatggt gatgtacaga tgggttttcg 129420
gtgtggatgt cctttctgtt tgttagtttt ccttcttaca gacaggaccc tcagctgcag 129480
gtctgttgga ataccctgcc gtgtgaggtg tcagtgtgcc cctgctgggg ggtgcctccc 129540
agttaggctg ctaaggggtc aggggtcagg gacccacttg aggaggcagt ctgcccattc 129600
tcagatctcc agctgcgtac tgggagaacc actgctctct tcaaagctgt cagacaggga 129660
catttaagtc tgcagaggtt actgctgtct ttttgtttgt ctgtgccctg tccccagagg 129720
tggagcctac agaggcaggc aggcctcctt gagctgtggt gggctccacc cagttggagc 129780
ttcctggctg ctttgtttac ctaatcaagc ctgggcaatg gcgggcgccc ctccccccagc 129840 ctcgctgccg ccttgcagtt tgatctcaga ctgctgtgct agcaaccagc gagactccgt 129900
gggcgtagga ccctctgagc caggtgtggg atatagtctc atggtgcgcc attttttaag 129960
ccagtctgaa aagcgcaata ttcgggtggg agtgacccga ttttccaggt gcgtctgtca 130020
cccctttctt tgactcggaa agggaactcc ctgacccctt gcgcttccca ggtgaggcaa 130080
tgcctcgccc tgcttcggct tgcgcacagt gcgcgcaccc actggcctgc gcctactgtc 130140
tggcactccc tagtgagatg aacctggtac ctcagatgga aatgcagaaa tcacccgtct 130200
tctgcgtcgc tcacgctggg agctgtagac tggagctgtt cctattcggc catcttggct 130260
cctctctgcc tatattttct tctaatactt ttatggtttc agtttttttt ctaagttaaa 130320
gtctttgatt tcgtgtgggt ttcattttgg tgaaagtctt ggggtgggga tctgattttt 130380
ttccaaatga tttttattaa ataatgcatt ttccccccac taatttgcaa gactcctatt 130440
tgtttagggt ctattttgta ttatattcaa gtccattgat tgcccatccc tgtaatagta 130500
caaatctatt tccatttctg tagcttcaag ataaagttta ctctctggta tatctagttt 130560
atgttctcct accaccacca ttactattat ttttctgaat tttcctgagt attttaatgt 130620
gtttgttttc tcagataata ataccaacag tatgtatcaa gaatatatgt gcagtattac 130680
caagtgtttt gcatatatac ctattttcat cattgtgata accatgtcag gggtatacta 130740
ttaatatttc aatcttggca atgaggaaac tgagacatta gaagaatata taacatgctc 130800
aaggtgacaa ggctagtaag cagtgaagct gtgatttgag ccaggcagtt aggttccaga 130860
gaccatgctc ctacttctct atataaactg tagacgtgtt gatctaagtc atttagattt 130920
agaatccaag ataccatgtg tagcatttgg atcaaaattg cattgaattt atagaaaaat 130980
ttaggtagaa ttgacatatt tatgacacaa aatcattcta ttcaaaacca agatatagct 131040
tttcatttat tcaaatattt gatgactttt acatagaatg ctagttttct tcatgtaggt 131100
cctccatgtt ttattttaag ctttttcctt catgtgtttc atttgtgttg ctagtaatag 131160
aatttttttcc tctttcgtgt ttttagctgg ttattgttga ttattggaaa gctgttgatt 131220
tttttctgtt ggaaagatat tgattttttt cttttaaatt tgtaattaac catttaccaa 131280
atgtccttac tgctaatagt ttttttattg atttttcctg aattttctat aaatgttatt 131340
ctgcaaataa ttttgcttct cctttctaat atttatactt tctcttttat tctttttaaa 131400
aattggttta ttcttgtaaa tcattgttaa ctaatgatga aactaagcat ctttatctta 131460
caaatgcctg tcattcataa tcatttatta tgatactaac ttcagttttc ttttcatgca 131520
aaagtatcag caagggaatg gtgaattttt ttcaaatgcc tttctgtatc tatagatgtc 131580
gtttgtcctt tatgttaata tagtaaaagc acatatattt tctaatatta agtaatgttt 131640
gcttcattct tttaatttaa tattttattt aggaccattg catattttat ttaggactga 131700
gcgtgtgtgt gtgtgtgtgc gtgcgtgcgc atgtgtgcct gtgtgtgtgt gtgtgcacat 131760
gcatgtatat ccttcctcag attttaatta ttatgttgac ttcctagaat tcagactttt 131820
cattttcctc tctctttaaa aagttacaaa attatcagtc ctttacagat ctgaagaaat 131880
ttacctgtga aaacacctgg cagttttggg tggttaacta ctatcttcct aaatttattc 131940
tatgatgtgt ctgtctatgt ctcttaaata attttccaag ttctataata cagtgataat 132000
tatttacatt ttcctagaaa gggttttcat ctaggttttc aaatttattt gcttaggttt 132060
ggacaaaata tttaaaaagt aagtttccta aatttcttta tagttgtagt taactccatt 132120
tgcattttaa tattgaacat tcgtgctgct taattttttt ctctaggatt aagtaggctg 132180
gtaatttatc tttttcttg attctttaaa gtttgggctt ttggactgat atatcaatta 132240
catggcttct ctattttttg actaagtact ttccgcattt gtatttttga ttttgtcttc 132300
acacttagat ttcgtcatac tacctatctt ccataagtaa cagtttctat gaattaaaaa 132360
gcatcctttt ataaatgcag actttactta tgaaggaaat attagttata ggtaatttag 132420
tgtgaattat tttactccaa atactttcct caacacaaaa aggaatcatc tttttttggga 132480
ctgaatttaa tttaatctct tgaggacttt gctttttcac tgtttcatct atctgtgagt 132540
tgtacgaaca ctggctgaaa ttagctcatt gagtggatgg gagtttagat aaaaggggaa 132600
aaggggaagg taatttggga ggatggctct tgttgggggc agatagatac aggatctgtg 132660
gaggaagaga gaaaggccag aacaagaact gagagagtaa caaagaaatc ctacgaatcc 132720
ttagtaactt tcatgtaatg agagacagga gaaaataaga actagcattc tgtgagcaat 132780
gacaaccctt tccctgcgtt tgcctatcag ttttcattct attaatagca tgtatctgaa 132840
gatattaaaa accaccaccc cttttgcagg ggtaaaattt agaatgattg acttttattg 132900
gagttatgtt ttaaaatata ttttgaaaat ataaaaagag tttatgaaga ttttacctag 132960
agaaggattt aaaaatttca cccaaaattt actgaatcat tagaattact aaaatctaac 133020
atgttcatgg tacttggggt actctaaaac cattatgata cctattttta gattatttaa 133080
attaaaatta gataatatac acattgttca ttattatata acattacatt tgtatattac 133140
attatatcct tcattataca gtaaaatata tatagacagt aagctaacat tatcagttcg 133200
gtcaaaagtc agattaacaa aaatttacag taaatgctta gtatttatag acaagctcct 133260
ctttcctgga gtaatattat atgcagaagt tttctctgat cctatgaatt accacatgac 133320
ctctccattc cattttgtgt acctgtttgc ctggtctggt tatgactgca gttttgtttt 133380
cattttcctg aattgttgct aacacttaag tatattgact tgtttcttca ctgagaaaag 133440
aaaaaagtgt ggtcccatat tcagttcagc aaataattct atacctacta tgtagaaggc 133500
agtatgccag tgactgtatt taggataaaa tgtgtgtgtg tgtgtgtgtg tgtgtgtgtg 133560
tgtgtgtgtg tgagagagag agagagagag agagagagag agagatgtta ttgtagtccc 133620
aattgatgtt aaagaataat ggatggaaac acttggtcag tgtttccacc gatctttgca 133680
tcactcagca ttcatgccta aatttgtggt gttctcagaa ttgtgctaat gtgtaaaata 133740
ttcttatact taatatgagt acagtctgtt ggctctgtag aacacaactc aaagtgtatg 133800
tatttttcta gttatttctt aaattatgac aatatgctta tctgatatat gtggaaccag 133860
tttgttaaaa gtagtctgtt agtttttaag gattagtctt ctaagaaaga ttttctcttt 133920
cttttctaac atgcaaatga gtgcatgctt aggggcttga tggcaatgag tgggatatag 133980
ttaagcacat attaaaggca taacataata agggtgtcct ctggaaagaa aagcctttac 134040
acaacccaaa ataggtaaaa atgtggcctt cgcctgtggc tttaatcaat acatgccaca 134100
gttatcgtcg gacaagaatt gaagccctca aagttaatct tttccatctt tcttccccac 134160
ttccctaagt ttcttcctct acatggccct atcctgctat tccaagtcac aataaatgat 134220
gatagtgaga ttctttatga agcatttagg tgatcttgct ttcataccaa tgaataaaaa 134280
attgagaatg tattggtttt ggaaccatac tcatataagt tatctaatgc ttttttatga 134340
ttgtacatta cttaagaaac agatatttac atgagacttt aattactata gttgatacag 134400
tgctgcatgc aatcatgtgc taaaaataat atgtgaaagt tcttgtaaag atttattgac 134460
ctcgcaaata aactagaaaa tctggaagaa atggataaat tcctggacac atacaccctc 134520
ccaagtctaa acccagaaga agtcgaatcc ctgaatagac caataacaag ttctgaaatt 134580
gaggcagtaa ttaatagcct cccaataaaa aaaaatgtcc aggaccagac ggattcacag 134640
ccgaattcta ccagaggtac aaagaggagc tggtaccatt ccttctgaaa ctattccaaa 134700
taatagaaaa agagggaatc ctcccgaact cattttatga ggccagcatc atcctgatac 134760
caaaacctgg cagagacaca acaaaaaagg aaaatttcag gccagtatcc ctgatgaaca 134820
tcgatgtgaa aatcctcaat aaaatactgg caaactaaat ctagcaggac atcaaaaagc 134880
ttatccacca cgatcaaatc agcttcatac ctgggatgca aggctggctg aacatacaca 134940
aatcaacaaa cgtaatccat tgtataaatg gaacaaatca caaaaaccac attattatct 135000
caatagatgc agaaaaagcc tttgataaaa ttcaacaccc cttcatgcta gaaactctcc 135060
acgagctcta ggtattgatg gaatgtatct caaaataata aaagctattt atgacaaacc 135120
cacagccaat atcttactga atgggtgaaa actgcaagca ttccctttga aaactagcac 135180
aagacaaaga tgccctctct caccactcct attcaacata gtgttggaat ttctggccag 135240
ggcagagact tggcatgcaa gagaaagaaa taaagggtat tcaaatagga agagaggaag 135300
tcagattgtc tctgtttgca gatgacatga ttgtatattt agaaaacccc tttgtctcag 135360
ccccaaatct ccttaagctg ataaacaact tcagcaaagt ctcaggatac aaaatcaatg 135420
tgcaaaaatc acaagcattc ctatacacca ataacagaga accaaatcat gagtgaactc 135480
ccattcacaa ttactattaa aagaataaag tacctaggaa tacagcttac aagggatgtg 135540
aaggacctct tcaaggagaa ctacaaacca cttctcaagg aaataagaga ggacacaaca 135600
aatggaaaaa cattccatgc tcatggataa gaagaatcac aatatagtga aaatggccat 135660
actgccgaaa gtaatttata gattcaatac tgtccccatc aagctaccac tgactttctt 135720
cacagaattg gaaaaatcta ctttaaacat catgtggaac caaaaaagag cccacatagc 135780
caagacaatc ctgggcaaga agaacaaagc tggaggcatc acactacctg acttcaaact 135840
atactacctg gctacagtaa ccaaaacagc atggtactgg tatcaaaata gatatataga 135900
ccaatggaac agaacagagg cctcagaaat aacaccacac atctacaacc atctgatctt 135960
tgacaaacct gacacaaaca agaaatgggg aaaagattcc ctgtttaata aatggtgttg 136020
ggaaaactgg ctagccatat gcagaaaact gaaactggac cccttcctta cactttatac 136080
aaaaatcaac tcaagacgga tcaaagactg aaacgtaaga cctaaaacca tgaaaaccct 136140
agaagaaaac ctgagtaatc cattcaggtc ataggcatgg gcaaagactt catatctaaa 136200
acaccaaaag caatggcaac agaagccaaa attgacaaat gggatctaat taaactaaag 136260
agcttctgca cagcaaaaga aactatcatc agagtgaata ggcaacctac agaatgggag 136320
aaaatttttg caatctatcc atctgacaaa gggctaatat ccagaatcta caaagaactt 136380
caacaaattt acaagaaaaa aacaaccccca tcaaaaagtg ggcaaggata tgaacagaca 136440
cttctcaaaa gaagacattt atgcagccag cagacatatg aaaaaatgct catcatcact 136500
ggtcattaga gaaatgcaaa tcaaaaccac aatgagatac catctcacac cagttagaat 136560
ggtggtcatt aaaaagtcag gaaacaacag gtgctggaga ggatgtggag aaataggaac 136620
acttttacac tgttgtgggt gtgtaaatta gttcaaccat tgtggaagac aatgtggcga 136680
ttcctcaagg atctagaact acaaatacca tttgacccag ccatcccatt actcggtata 136740
tacccaaagg attataaatc atgctgctat aaagacacat gcacacgtat gtttattgca 136800
gcactattta caatagcaaa gacttggaac caacccaaat gtccatcaat aatagactgg 136860
ataaagaaaa tgtggcacat atgcaccatg aaatactatg cagccctaaa acaggatgag 136920
ttcctctcct ttgcagggac atggatgaag ccagaaacca tcattctcag caaactatca 136980
caagaacaga aaaccaaaca ccgcatgttc tcactcatgg gtgggagttg aacaataaga 137040
acacatggac ataggaaggg cagcatcaca caccagggcc tgttggcggg gtgggggtct 137100
aggggagaat agcattagaa gaaataccta atgtaggtga tgggttgatg gagcagcaca 137160
tcaccaaggc atgtgtatac ctatgtaacc tgcacgttct gcgatgtacc ccagaactta 137220
aagtataata ataaaaagat ttgactataa ggatgatatt atgctataat acactgttca 137280
aatattatga gattctaatg gttaaaattg tttagtcatt agaaaatatc tgcagtggta 137340
aattgttaag tatggaattt cagtacccca aaataagtat acacacaaaa gtttaagaat 137400
atttttcatc agtgtaacga ttttcagtca ggagcctttg cacataatga agtatgtagg 137460
ctgtggaatc tagccaacct ggctttcact cttcaactta gtagctacat aacctcagac 137520
aggctactta ggtactctgt ttttctttgt ctgtcagagg gatatataat aatacctact 137580
tcttaggagc tgctgtaaag atttaccaag ctaatagtag tagcagaaaa cacttctcta 137640
gtccttactg tgtaccagac actgatctaa gcacaataca tttaaaaatc attatatctt 137700
cacaaccact gtatgcagtg gttactgctg tgtctggcat taaatattag caaataatac 137760
caacaactac caccatcaag aagtcaacat gtctttacat tctgatgaca ataagtatgc 137820
attgaaaatg ttaccatctt ctattgaagt ttaaattcat attatctaaa gtcatgttta 137880
aagattttta aaactgttta ccatattttt taccettgct ttcttcatat tttaattaaa 137940
atcagaatca agatgtgatg atcacctatg attgttattt tcagataaac tatactatat 138000
tttcagccac aggttaaaca gttcaggggt atagagatca ttggacagaa catttagata 138060
actgaagccc tcattggcta ctagaattta tcaagggcct gcattactct gtatgctttt 138120

-continued ggtggtgggc catttttttaa ataagctgtg tagatccaca aacaaaatga tagattcaga 138180
aatacaagta agcttgacta ttaatttaag tttcagtcat taatatcagc agttttcact 138240
gtttttttc tctcagctaa gtgacagaag caaaagacag taaaaatctt ggaaaatagt 138300
tatcggtctt tttttccatc tcagcagata aaatacattg attttttgga tttttcccat 138360
tttatgacac atatcaaaca tgctctggga aaattcacaa gatagttata aaatatatac 138420
aatctctgtg ttttggattt atgacataat ctatcttaca atggcagctt atacagggga 138480
caggaaggag ttctgctaga gtcccagaaa gtgataggca gtctttaaga gtgctttgag 138540
ctatggttga cttgggcaga atagaacacc cagtatctct ggttaaaaag aactcagtaa 138600
aaaaatatga accatgcaag caagcatttg aaccagaatg catatatgtc ttaaagccta 138660
atttgggggga agttttcaag cccaaaatac tctagatata aatgtgttaa atgtgcaatc 138720
caaggtcaac cagagaacct acagctaaca aaattgataa tataatgcta ggctgcaata 138780
ttgcatcatt aaaaggtaag aatggcatca gcataaaacc atggccaact caagatacca 138840
aagatgtcca gaagcctccc ttcgcaaaac agcaggaatg tcagctatct aggcatgcag 138900
tttcactggt caagcatatt tgagagcctt gcagtgagcc agaccttaca tgatagccag 138960
atcttagtgg agtatagaat tgattaatcc tcagcaaata cttaccatgt tctaatttta 139020
gcttgtcata tataaatgcc aacttaaaat gactttatca agtaggttgc taataagtac 139080
tgaaagtaaa aatgaaagtt aatagcattg tgcatcattt gccagtaagc atctccattc 139140
cgtgtgtgtg tgtgtgtgtg tgtgttgtgt gtgtgtgtgt gtgtgtgtgt gtgtatttgc 139200
ctcttactat gagttaaagg cccatcagga aactcttaca gtcaggaaac ttaagcttat 139260
agtcagctgt gaaacagcct tttaaaaatc attcccctta cccacacacg gacttcactc 139320
tgcttgtagt gtggctgctc atagtgtggc tgtttttcca tcttgacacg tattttctca 139380
ttactatatt aaagtgactt ttttctttat tgtattgata tactgaatag acctcctcag 139440
ataatattta tggaaacata aaaccattct ggaaggcagt ttaacagtat ctacttcata 139500
agtcttccct tttactctaa agtttcaccc ctactaatct gataagtata tataaggaat 139560
ggccaaaatt atacatattt acaagaaaaa ttatggcatt gttgctagtg cttaacacag 139620
gcaaaaaaat tatcaataga tcataggttg aagtatatct gtatgataga atgctgtgta 139680
gctatccaga gggaaataag aaagctttat gtatatagat gccccttgac ttatgaatta 139740
tgatggtgtt atgtcctgat aaattcatcg taagttgaaa atactgtgaa atcgaaaatg 139800
catttaatat acttaaccta tcaaacatca tagctgagct tagcctgcct taaatatgcc 139860
tgcaacactt atagcttaca gttgggcaaa tcataacatg aagcctatgt tttaatatga 139920
tgttgaatat ctcttgtcat ttattgaata ctgtaccaag ggtgaaaaac agaatggtgt 139980
tgcaccatca taaagtcaaa acattgtaaa tcaagccata attagtcagg gactgtctgt 140040
actgacatag aaaggcttcc aagacatgtt ataaagtggc ataatataag tggcaaagca 140100
gtatgatgtg atcatgtgta ttttgaatta tatatacaca catttgtata taggtgatgc 140160
tggatttata ttaaatataa gataaggtga ggtttgtgtt acaactaagt aagaaaagta 140220
tataaaatga gttacatcat gcctacttag tgcattgaaa taattaataa aatttgccat 140280
tatttttatc tttatggagt ggattgagga aggaaaaata gggctgcctt tactaacttt 140340
acatgttttg cattgactga ttttacatgc attactttta taataaaata agagagaaaa 140400
ccatttactc ttgggaaaag atctggaaaa gcatattcat actaaaatat taatggcata 140460
acaaaacttg acgtttttct tctgacacaa gatattgaag aactcctaat atgtgagcac 140520
agtggtgacc tctggtactc ttttggacaa gagtcttcct aaagtctata aaagctgttt 140580
tggagttttg gttatttgtt ttcaccttta aatatctacc catattttca attgtatttc 140640
ttccttcgtg ttctcaggag tgtgtgtgtg tgtgtgtgtg tgtgtgtgtg tgtgtgtgtg 140700
tgtgtgtgtg tagagggata tgtatacata ttatttaagc atttaggtga ttatttttca 140760
agaattgttg gaaaatttaa ggaagcagtg gaaagaataa ctgatagtaa ttactgccta 140820
gttatctaaa taaagtgaag cttctttttc tcccttcttc cgaatctttt cttagcaaat 140880
aagaatcacc ctgaaagtag tttaaaagag atattctagt gaccataccc aatgaagtac 140940
taaatattca tcctgttaga gtgattattg caaggactct aaaggaaaac attgattata 141000
ctagattatt tattttatag aattttattc tcagcttata ctcctggttc tatgaactat 141060
agaaatcact cagaataata aaatgctgat gttatatttt attgaaattc attaaaaatt 141120
atagaaaaag gtgctcattt gaaaacttcc aaatgtcagt tattcagaat gacaaactta 141180
attatataga aattgactaa tttggttgat tctttctaaa gtcagtgttg gattaataat 141240
gtaatgcatg gatcattaac agcttaaaaa tacttgtggt aaacttgatg atgtaatgct 141300
attttgttag gaaagatggc ctcttttctt aagttgcaat cctttaagga ttcaaagccc 141360
taattgtaca taagcaatat cgtatgctgt aggctcgtta tcattggagg ggaggtttaa 141420
tatagagttt aagagcacaa aatatggaat cagactgttg ctgttaaaat cctggctctg 141480
ccacttccta gctgtgatct tagacaagtt actctctctc tgccttgatt ttcttacata 141540
taaaacaagg atataagtag taagtggtag aactcttatt tcataaggct gttataagat 141600
tgttgtaaga atttaatggg ttagtattta taaagcaggt ctatatatag taagtattca 141660
ataagggtag ctactatttg tcattttggt catgtaatat ctagtgttac atatgtgtgt 141720
tgtcaaataa attagttgtt aacattattt aaaagaaaac attgaattac aatctgtttt 141780
aagcatcttt tttattttc tgagatgtaa aaactgattg ttttactagt tggttttgat 141840
tatttgtttc ttgtttgtat tacagttaca aattataata ctgtggtaga aacaaattca 141900
gattcagatg atgaagacaa actgcatatt gtggaagaag aaagtgttac agatgcagct 141960
gactgtgaag gtgtaccaga ggatgacctg ccaacagacc agacagtgtt accagggagg 142020
agcagtgaaa gagaagggaa tgctaagaac tgctgggagg atgacagtaa gtctgatttt 142080
tttttgtaat attgtattct catgattcgt tttttaaaat atatattaac tgaaaagata 142140
aattggatga aaagtttgaa atcaatagta aatttggcta tcaataaata ttaggtgtcc 142200
tacttactaa aaagtggatt atgaagcaga ataagcaagt tattttgacc atatttacaa 142260
tgcatataat gtattgaaat ttagtagaat ttattaacca ggatcaagct ttccaaatat 142320
tgttgatata attgaaccta cctttaattt tttattgtaa ccccgaatga atactctact 142380
tagaaaccaa taaatatcat atagatatag tgaaattata attcaatatg caaaaatccc 142440
aaacacatat aaatcatgga ggtattttta gtgcttgtaa acctctctat acatacatca 142500
gaatccttta agtaaggtgg ttttttcact ttaaattttt acttttactc aaagtatggc 142560
tgagtggaag gagcggtgaa agtaaggaga ccctctactt gctgcacttt cagtgagtaa 142620
acactgaaag tttaatcttc ttcctcatct gtcaaatgga gaaattggac ctagtctttt 142680
attctagctc taaaatttct tctttctact tttcctaata aactaattaa attatttagc 142740
ctgtcttgcc aggttaagca ccaatgatat aaaaatggga tatggaagtg gcatagtatt 142800
aattagagag gttggggatc aggaacaagg gcatcagaaa aggtaaacaa gtacacgcaa 142860

-continued taaatcgaat ccaagaccag tcaaaggaga agcttcccag caagaattca agttcaaaga 142920
ggtcgtctag acaagatatc aaaactaaaa tctggaaaag tgggtcaggc atgcaggtca 142980
ggatattatc tggataatga aatatggaag tgtagataaa agctcagata ataggcacag 143040
attggcagaa gttaagattt ctacaatatg acaaatctaa tggttaacaa gggacttttg 143100
aaataatgta atcagccctc tcattttata gtgttgttca tttgtccatt cagcaacctc 143160
tgtagaaatt ggttgcaact gtggataaga ctctctgcat gaatgatgtt tatatggctt 143220
aatggagaag agagataaat aagtcacaaa tacattatag ttttatttag gtatacatta 143280
tatggcagca tcaaggagga gcatccgaat tagagaagga aggagaagtc gtagaagagt 143340
tctgagtgaa acagagtggt ctttagttct taaggaccga tggaggttaa ttagacaaag 143400
tacagtgaat ataaggtttt caggcaaaag aggcaacata catgaagcca cagaggcttg 143460
agcaaagtgt tcacagaaaa tgagatcaga gaagtaaaca agggaaaaaa tatgaagtga 143520
tttgtgtact atgtcaagga atttgaacct tatcatggaa gctatgagaa gaacatcatt 143580
aaaataattt ataaataagt ctggtgtaat atggaaaaag aattttagag ggagggaggc 143640
tgaggtagtg tcttcaacga gacggctgta ataatcaggc agtgttaagg gtttttgagt 143700
taaagtagtt gcccatggga tgggaataga agggagataa ttgaaagaca gaaaggagat 143760
agaatatata agaattggaa agggctgttt ttagatacag tcccaggttt ctagaaagtg 143820
agactcagag aagttgactt gctcacttat ggcagctggt taattgtaga gctatgaacc 143880
tgttaatgtt aatactaagc tcaaacattt ttggagcaag ggtttcttat gtatttctta 143940
tctgtggcct gaattacgta gttgatccag agtcttaata ggtaatcaag aaggaaatga 144000
tctgtctggg gaaaaaaggg ggcaataaga ataaggtaga tgaagggaga aaggaaggtg 144060
aaaaaatcag tgaacaggtt ctgcttctga gaatatgttg ggttcgatta tttgaactaa 144120 cccttttac tgaaaacaac taatggtgct agattaaaaa caaaaacaaa aaacttctta 144180
gcacttctaa agagctaagt aagacactac cttgtcaaaa tctaagtgaa aaaaggaacc 144240
catagaagta aacagagcag atcatagaag acactttggt cctgaataca tttgcctagc 144300
cagtgaaatg taaggtgatt ttcaggcttc tgagaggaaa caaagcccaa gaccaccaaa 144360
gatagtttaa tagcagtatg gattatgtct cgactgtgag gatgaactaa aagcaaacca 144420
ttttccatct ctaccatcct tgagagtgaa caagcaaagt ttccctggtt aggtattcag 144480
ggaatggagg attgtctttg agaagtagta accacaagct gtctcgcact gatttgaagt 144540
ccaagtttac attgctgtgt agcctgaaaa atctcaagcc atatttgagt ttaaagtgga 144600
actgctacaa atatctattg gcaccaggca gaagtaaaca caagtctttt ggagaaatat 144660
accttcatcc tagtactata gaagtctccc aaataattta gcaagaaggt agaaacatga 144720
gtgagaatta ccagaaacaa aaggaagcag aaactgaccc ataaaggcta attactagag 144780
ttacgtcata cagatttata aaatgactac tgtcttgttt aaagaaaaat cagatggtta 144840
tctgctatga tatgataaaa taaaaccagt gtgttttaag aataatctaa tagaactaaa 144900
aataaaaaat tgaatagtag gaatttgaaa ttcagaggat acatttaaca acaaattaaa 144960
cagggttaaa gaaaaattaa taatttggaa gatagagaaa aattacacta aatggaactc 145020
agagagacac atagaaaaaa tatgaaaaac aggtgcctgt agtcccagct actcgggagg 145080
ctgaggcagg agaatggcgt gaacccggga ggcagagctt gcagtgagcc gagatgatgc 145140
cactgcactc cagcctgggc gacagagtaa gactctatct cagaaaaaaa agaaaaaaga 145200
aaagatatga aaaacaggtt aagatacatg aagattcaat acatcttatg ccaggagaaa 145260

```
agatactagg gcagcagcca tacttgaaga aataatggct gaggttttta tttataatca 145320
gtgaaaaaca ccatactaca gattcaaaaa gcccaaatgg acattcagat ctgtaaagat 145380
caaagaagtc caatagattg aacataaaaa gatcttcact aaggcacatt acaatcaaat 145440
tatgaaaagt caacgacagt tttgaaagca gcaaaagaaa agttgcagac tccataagac 145500
tgtaggcaga tttctgtgca gaaacctgtc aagcaaggag aaagtgggat gatatattca 145560
aagtgccaaa agaaaaacac tgctgaccaa gcatactata cccagcaaag ttatacttca 145620
gaaatgaaga agaaatactt tcccaaaaac aaaagctgag ggattttgtc actgttaaac 145680
ctgcttcgta agaaaaactg aaggcagttt ttcaagttga aacaaaagaa cactaattag 145740
caacatgaaa acatgaaaga ataaaactca ctagtaaaga agttccaaac tataaatact 145800
attctatata gtgagaaaga atgaataaga cctactattt gatagcacaa tagggtgact 145860
gcagtcaata ataacttaat tttacatttt aaaataaaag agtataattg gattgtttgt 145920
aactcaaagg ataaatacct gaggggacag ttaaaaaaga aataaattca gaatgctgtg 145980
atactataat gatgttgtgt aaatgtcttg taactctaat ataaaaataa aaaacaaggt 146040
attaaaatat agctacaata atttttaata gatatacaat atacaagtat gtaaattgtg 146100
gtataaatta acacagaatg tgggagggga gaggtaaaag tgtagttttt atatgtgatg 146160
gaaattaagt tcttatcagt ttaaaataga ttgttatgac tataaaatgg tttttgtaag 146220
ccttttggat aattaaaaga aaaaaactgt gttagataca caaaagataa accatgcgat 146280
tgcaaaaaat atatatatat atataaaata tcaatggaag cagcaaagaa acaaaggcac 146340
ttaaaacttt tcagaaaaca ataaaatggc agtagttttt acttatcaat aattacttta 146400
aatgcaaatg gattaaactc agtaatcaaa atacattgtt actatgcatg tttttaatac 146460
agagataggg ccttgctgtg tcaccagggt agagtgcagt gatgcagtca cagcccactg 146520
taacttcaac ctcctggact caagcagtct tcttgcttta gtctcctaag tagctaggac 146580
tacaggcata tgccaccaca tgtggctaat ttaaaaaaaa aaaaaacttt catggaaaga 146640
tggggtcttg ctatgttgct caggctttaa atgcattttt taaaactgac ccaactacaa 146700
gctgcctaca ggagacttat tttaccttta aagatacaga taagatgaaa gaggaaggtt 146760
ggaaaaatat gttccatgta agtggaacca aaagagagca gtggtggcca tttttacacc 146820
aggcaaaata aattttaagt aaaaaattgt cacaagaggc aatgaaggtc attgtataat 146880
gataaagagg tcaatttatc aagatgatac aattctaaat atatttgcca ccaattttgg 146940
agcacataaa tatgtaaaga aaaaatataa ctgaagggag aaatagatag cagtacagta 147000
atcatagggg tcttcagtgc tttcaataat ggagaaatca tctagacaga aaatcaataa 147060
agaaacagtg gatttgaaca acactagaca aaatggacct gatatacaga acattccatt 147120
caacagtagc agaatatgca catttttctc actcaaacat gtaacattct ccaggacaga 147180
ttatttgtta ggccacaaga taagttttaa caaatttaaa attaaaatta tatcaagtat 147240
gttttctgtc aacagtggca tgaaaccata aatccgtaac aggaggaaaa ttggaaaatt 147300
cacaaatatg tggaaattaa gcaacacact cctgaacaac caaaggtcaa agaagaaatg 147360
aaaggggaag taaaaaatat cttgaaacaa acaaaaatgg aaacataaca taccaaaaca 147420
tggaatgcag caaaagcagt tctaaaagag aattttatag caataaatgc ctacattaag 147480
aataaggaat gatcttaaat aaacaactta atattggacc tcatggaact agaaaaataa 147540
gaacaaagta aaaccaaagt tagaagaagg aatgaaataa taaagattag agcacaaata 147600
```

-continued aatgaaataa agagtagaaa aacaatacaa aagatcaaca aaactgagtt agtttttga 147660 gaagataaaa tcaacaaaca tttagctaga atttaaaaaa ggagggaata tccaaataga 147720
ataataaatg aaaaatgagg agagggatta aagatggcca actagctgga tctgggatgc 147780
acctcttcta cagagaggaa ccaaaatatt gagtaaaccc tcacactttc aacagatctt 147840
ttgagagaaa acactgaaat ttaatatata ggccatgaca gacatgattg aagaagtagg 147900
aagcaacact gctggctcag tattgccaga caccttagga ccagaatgga cccaaggaag 147960
gtgtgagtga agaaacccgg gaacaccact ttcccactgt caacctctga aattctagag 148020
gagttcccac aacccctgaa tacgtttgga ttggtaggag gagctgcctg gagaccatac 148080
agaggcacta cttgaagcca caaggagccc aaaagccttc agtgtgctag gcagctgcag 148140
caaaacgtga ctctgggcac ccacccccga gtgccctgca tccgagcggc tacatctgct 148200
gtctgccaca ccaggataga gtggggccca tgcatgttca catgaccaat tcaggatcca 148260
ccaccattcc tgcaggactg aggtgaatct aaaccacaca cgaccatgcc tgccagtccc 148320
tcctaagatt gcctgcctgg ccattgctgt ggagtgggac ccacagcata gcctccattg 148380
ccccacctga gtggtttatt ggctacctgg gaacacttta ctcctcctat cactgccagt 148440
ggttgatcct aaggagccag aggacaaatc cactggcctg gtctcagttt gccaggactc 148500
aagcatacca cccaggaata tggggatgag atctgtggcc tgatctcaag caggggagga 148560
acccccactg tcagaacaca gggaagagtg tggtgtgggt ttttcaggtg gtacagaagc 148620
tgggcacccc tcccttcatg agaatagact aggaagggta tagcctcata gccttgcttt 148680
ctgctgcagg gagtcttgca ttctggaatg cctgggatgg catggcagtc tgggcacagg 148740
tggtttggga tttgcataac taattgggcc ggctgccagg gtggacactg gagggagacc 148800
caccagtcag gggtgtagaa gctgagtggg cctcatggcc atctgctgga atgaaatccc 148860
agggctagcc ctcttaccct gaaccagctc ttgtggcaca gaagaggtgc ctgcacccct 148920
ccctagagtg ttgttccagc tgcctgagaa ctgcccctac agccctacca aggtcacgtc 148980
tgcctcagag agcctgatca cgggctcacc agacccagtc ccacccagct ttgccccctc 149040
tagccagcct tgggagcaga gcatgggatg ggaccactga gagctccaca ccccccaccc 149100
atcaccaaga acactcttgt attccttatc aacaaaggcc aagtaaaaat cccactgtca 149160
tcactgcagc tgcctctcac ctgccagcat cacctactgg ccaggaggtc aaaactgcat 149220
gtcctgtcgc agcaactgtt gatatcattg cacagcactc agacagctct tacctgcagg 149280
catcacctgc tggcctgtag ggtgaactgc acaacccaat ataattcctg ctgacaagta 149340
cacagctcta aggaatgagg taagtttccc ccaaaagacc tccaactttg catctctata 149400
ggagacagtg agccttacca catatacagc ataccactac tacaaactac aaacaattaa 149460
catttgagaa aacaactaca ctaaggctat ctgtaaccaa ggaatttata cagagccttg 149520
gccccctaaa agcacgtaga agcaaagcca aaggacacaa cccaacatat gcaagagtca 149580
caccctcaag gggcaacgaa aaataatccc acccaaatga agataaatcc aaaaataata 149640
agtgccagct tctacacatg agaaggaacc agcacaagag ctccaacacc aggaagaaat 149700
agaatgttgt gacaccccta aaggaccaca ttagctctct agcaatgaat cttaatgaaa 149760
atgaaaactt tgaaatgaca gataaagaat ttaagatatg gactgttaag aagcctagtg 149820
agatacaaga gaaagttgaa aaccaaagca actagagaaa caatctaaga gatgaaagac 149880
aacatagata tattttttaa aaaacaaatg gaatatctga aaatgataaa tttgctgaag 149940
gaacttcaaa acactgttga aagccttaac aatagactag acaaaccaga agaaagattt 150000
cagagcttga cgactagtct ttcaaattaa cccaatcaga aaatggccga ataggaacag 150060
ctccggtcta cagctcccag cgtgagcgac gcagaagacg ggtgatttct gcatttccat 150120
ctgaggtacc gggttcatct cactagggag tgccagacag tgggcacagg tcagtgggtg 150180
cgcgcaccat gcgtgagccg aagcagggtg aggcattgcc tcactcggga agcgcaaggg 150240
gtcagggagt tccctttcct agtcaaagaa aggggtgaca gacggcacct ggaaaatcgg 150300
gtcactccca cccgaatatt gcgcttttct gacgggctta aaaaacggca caccacgaga 150360
ttatatcccg cacctggctc agagggtcct acgcccacgg agtctcgctg attgctagca 150420
cagcagtctg agatcaaact gcaaggcagc agcgaggctg ggggaggggc gcccgccatt 150480
gcccaggctt ccttaggtaa acaaagcagc ccagaagctg gaactgggtg aagcccacca 150540
cagctcaagg aggcctgcct gcctctgtag gctccacctc tgggggcagg gcacagacaa 150600
acaaaaagac agcagtaacc tctgcagact taaatgtccc tgtctgacag ctttgaagag 150660
agcagtggtt ctcccagtac gcagctggag atctgagaac gggtagactg cctcctcaag 150720
tgggtccctg acccctaacc cccgagcagc ctaactggga ggcacccccc agcaggggca 150780
cactgacacc tcacacggca gggtactcca acagacctac agctgagggt cctgtctgtt 150840
agaaggaaaa ctaacaaaca gaaaggacat ccacaccaaa aacccatctg tacatcacca 150900
tcatcaaaga ccaaaagtag ataaaaccac aaagatgggg aaaaaacaga acagaaaaag 150960
tggaaactct aaaaagcaga gcgcctctcc tcctccaaag gaacgcaatt cctcaccagc 151020
aatggaacaa agctggacgg agaacgactt tgacgagctg agagaagaag gcttcagacg 151080
atcaaattac tctgagctac gggaggacat tcaaaccaaa ggcaaagaag ttgaaaactt 151140
tgaaaaaaat ttagaagaat gtataactag aataaccaat acagagaagt gcttaaagga 151200
gctgatggag ctgaaaacca aggctcgaga actacgtgaa gaatgcagaa gcctcaggag 151260
ccaatgcgat caactggaag aaagggtatc agcgatggaa gatgaaatga atgaaatgaa 151320
gcgagaagga aagtttagag aaaaaagaat aaaaagaaat gagcaaagcc tccaagaaat 151380
atgggactat gtgaaaagac caaatctaca tctgattggt gtacctgaaa gtgatgggga 151440
gaatggaacc aagttggaaa acactctgca ggatattatc caggagaact tccccaatct 151500
agcaaggcag gccaacattc agattcagga aatacagaga atgccacaaa gatactcctc 151560
gagaagagca actccaagac acataattgt cagattcacc aaagttgaaa tgaaggaaaa 151620
aatgttaagg gcagccagag agaaacgtca ggttaccctc aaagggaagc ccatcagact 151680
aacagcggat ctctcggcag aaaccctaca agccagaaga gagtgggggc caatattcaa 151740
cattcttaaa gaaaagaatt ttcaacccag aatttcatat ccagccaaac taagcttcat 151800
aagtgaagga gaaataaaat cctttacaca caagcaaatg ctgagagatt ttgtcaccag 151860
caggcctgcc ctaaaagagc tcctgaagga agcactaaac atggaaagga acaaccggta 151920
ccagccgctg caaaatcatg ccaaaatgta aagaccatcg agactaggaa gaaactgcat 151980
gaactaacga gcaaaatcac ctgctaacat cataatgaca ggatcaaatt cacacataac 152040
aatattaact ttaaatgtaa atggactaaa ttctccaatt aaaagacaca gactggcaaa 152100
ttggataaag agtcaagacc catcagtgtg ctgtattcag gaaacccatc tcacgtgcag 152160
agacacacat aggctcaaaa taaaaggatg gaggaagatc taccaagcaa atggaaaatt 152220
aaaaaaggca ggggttgcaa tcctagtctc tgataaaaca gaccttaaac caataaagat 152280
caaaagagac gaaggccatt acataatggt aaagggatca attcaacaag aagagctaac 152340
tatcctaaat atatatgcac ccaatacagg agcacccaga ttcataaagc aagtcctgag 152400
tgacctacaa agagacttag actcccacac attaataatg ggagacttta acacccccact 152460 gtcaacatta gacagatcaa cgagacagaa ggtcaacaag gatacccagg aattgaactc 152520
agctctgcac caagcagacc taatagacat ctacagaact ctccaccccca aatcaacaga 152580 atatacattt ttttcagcac cacaccacac ctattccaaa attgaccaca tacttggaag 152640
taaagctctc ctcagcaaat gtaaaagaac agaaattgta acaaactatc tctcagacca 152700
cagtgcaatc aaactagaac tcaggattaa gaatctcact caaaaccact caactacatg 152760
gaaactgaac aacctgctcc tgaatgacta ctgggtacct aacgaaatga aggcagaaat 152820
aaagatgttc tttgaaacca acgagaacaa agacacaaca taccagaatc tctgggacac 152880
attcaaagca gtgtgtagag ggaaatttat agcactaaat gcccacaaga gaaagcagga 152940
aagacccaaa attgacaccc taacatcaca attaaaagaa ctagaaaagc aagagcaaac 153000
acattcaaaa gctagcagaa ggcaagaaat aactaaaatc agagcagaac tgaaggaaat 153060
agagacacaa aaaacccttc aaaaaattaa ttaatcccag agctggtttt ttgaaagggt 153120
caagaaaata gatagaccac tagcaagact aataaaaaaa gagagaagaa tcaaatagat 153180
gcaataaaaa atgataaagg ggatatcacc accgatccca cagaaataca aactaccatc 153240
agagaatact acaaatacct ctatgcaaat aaagtagaaa atctagaaga aatggataca 153300
ttcctcgaca catacactct cccaagacta aaccaggaag aagttgaatc tctgaataga 153360
ccaataacag gatctgaaat tgtggcaata atcaatagtt taccaaccaa aaagagtcca 153420
ggaccagatg gattcacagc cgaattctaa cagaggtaca aggaggaact ggtaccattc 153480
cttctgaaac tattccaatc aatagaaaaa gagggaatcc tccctaactc attttatgag 153540
gccagcatca ttctgatacc aaagcctggc agagacacaa ccaaaaaaga gaattttaga 153600
ccaatatcct tgatgaacat tgatgcaaaa atcctcagta aaatactggc aaaccgaatc 153660
cagcagcaca tcaaaaagct tatccaccat gatcaagtgg gcttcatccc tgggatgcaa 153720
ggctggttca atatacccaa atcaataaat gtaatccagc atataaacag agccaaagac 153780
aaaaaccaca tgattatctc aatagatgca gaaaaggcct ttgacaaaat tcaacaaccc 153840
ttcatgctaa aaactctcaa taaattaggt attgatggga cgtatttcaa aataataaga 153900
gctatctatg acagacccac agccaatatc atactgaatg ggcaaaaact ggaagcattc 153960
cctttgaaaa ctggcacaag acagggatgc cctctctcac cactcctatt caacatagtg 154020
ttggaatttc tggccagggc aattaggcag gagaaggaaa taaagggtat tcaattagga 154080
aaagaggaag tcaaattgtc cctgtttgca gacgacatga ttgtatatct agaaaacccc 154140
attgtctcag cccaaaatct ccttaagctg ataagcaact tcagcaaagt ctcaggatac 154200
aaaatcaatg tacaaaaatc acaagcattc ttatacacca gtaacagaca aacagagagc 154260
caaatcatga gtgaactccc attcacaatt gcttcaaaca gaataaaata cctaggaatc 154320
caacttacaa gggacgtgaa ggacctcttc aaggagaact acaaaccact ggtcaaggaa 154380
ataaaagagg atacaaacaa atggaagaac attccatgct catggctagg aagaatcaat 154440
atcgtgaaaa tggccatact gcccaaggta atttacagat tcaatgccat ccccatcaag 154500
ctaccaatga ctttcttcac agaattggaa aaaactactt taaagttcat atggaaccaa 154560
aaaagagcct gcatcgccaa gtcaatccta agccaaaaga acaaagctgg aggcatcaca 154620
ctacctgact tcaaactata ctacaaggct acagtaacca aaacagcatg gtactggtac 154680
caaaacagag atatagatca atggaactga acagagccct cagaaataac gccgcatatc 154740
tacaactatc tgatctttga caaacctgag aaaaacaagc aatggggaaa ggattcccta 154800
tttaataaat ggttctggga aaaccggcta gccatatgta caaagctgaa actggatccc 154860
ttccttacac cttatacaaa aatcaattca agatggatta aagatttaaa tgttaaacct 154920
aaaaccgtaa aaaccctaga agaaaaccta ggcaataaca ttcaggacat aggcacgggc 154980
aaggacttca tgtctaaaac accaaaagca atggcaacaa aagccaaaat tgacaaatgg 155040
gatctaatta aactaaagag cttctgtaca gcaaaggaaa ctaccatcag agtgaacagg 155100
caacctacaa aatgggagaa aatttttgca acctactcat ctgacaaagg gctaatatcc 155160
agaatctaca atgaactcca acaaatttac aagaaaaaaa caaacagccc catcaaaaag 155220
tgggcaaagg acatgaacag acacttctcg aaagaagaca tttatgcagc caaaaaacac 155280
atgaaaaaat gctcatcatc actggccatc agagaaaggc aaatcaaaac cacaatgaga 155340
taccatctca caccagttag aatggcaatc attaaaaagt caggaaacaa caggtactgg 155400
agaggatgtg gagaaatagg aacactttta cactgttggt gggactgtaa actagttcaa 155460
ccattgtgga agtcagtgcg gcgattcctc agggatctag aactagaaat accatttgac 155520
ccagctatcc cattactggg tatataccca aaggactata aatcatgctg ctataaagac 155580
acatgcacac gtatgtttat tgaggcacta ttcacaatag caaagacttg gaaccaaccc 155640
aaatgtccaa caatgataga ctggattaag aaaaggtggc acatatacac catggaatac 155700
tatgcagcca taaaaaagga tgagttcatg tcctttgtag ggacatggat gaaattggaa 155760
atcatcattc tcagtaaact atcgcaagaa caaaaaatca aacaccgcat attctcactc 155820
ataggtggga attgaacaat gagatcacat ggacacagga aggggaacat cacactctgg 155880
ggactgttgt ggggtggggc gggggggagg gatagcattg ggagatatac ctaatgctag 155940
atgacgagtt agtgggtgca gtgcaccagc gtggcacatg tatacatatg taactaacct 156000
gcacaatgtg cacatgtacc ctaaaactta aagtataata ataaaagaaa aaaaaaaaca 156060
aattaaccca atcagacaaa aaataagttt tgtaaatgaa caaagtcttc aagaaataca 156120
ggattatgta aagctaccaa aactgtgact tacaggcatt cttgatggag aagaggaaaa 156180
agtagaaagc ttggaaaaat atttgagggg ataatttagg aaaatcaccc aatcttctag 156240
agatgtagac atcaagatac aagaaattca gagagcacct gaaaaatact gtacaacatt 156300
aacatgacca aggcatatag tcattaggct attcaaagtc aatatgaaag aaaaatctta 156360
aaggcagcta gagacaagtg tcaaatcacc tatgaaggaa gctcatcaac ctaatggtag 156420
acatctcagc agcaaccttg taaaacataa gagattagag gcctattttt aaccaccttg 156480
aaaaaatgtc agacatgaat tttatatcct gccaaactaa gcttcataat tgaaggagaa 156540
atagtctttc ccagataagc acacatagag agaattcatc accactacac catcttacaa 156600
gaaatgctca aaggagttct gaacatggca atgaaaggat aatactcacc atcatataaa 156660
gcacaggtaa gtagaaacct caaagatcca ataaagcagt tacacaactg agactccaag 156720
gcacctagct aacaaaacta tgatgggaaa aaaacacaca tattaatatt aaccttgaac 156780
ataaaaggcc taaatattcc atttaaaaaa taaacactag caaattggat aaaagaagca 156840
ggacttaacc atctgctgcc taccagagac ccacctaatg gcaaaagaca actacagact 156900
caaagtaaag ggactagcag aagaagagaa ataacaaaga gcagaaccaa atgagattga 156960
gaccaaaaaa aaatgatgaa aaggatcaac ataatgaaga gtttgttctt tgaatggata 157020
aacaaaattg gtagaccact aactagttta atgaagaaaa aagagagaaa attcaagtaa 157080
gcacaatcag aaatgataaa ggtgacagta ttgctgatac aacagaaata caaaagctca 157140
tcaggggtta ctatgagcat ctctatgtgc acaaactaga taacctagaa gaaatatgtg 157200
aattcctgga acacacaact tcctgagatt gaatcaggaa gaaatagaaa tcctgaacag 157260
acaaattatg agtaaggaaa ttgaatcaat agtaaaaaaa aaccttccaa caacaaaaaa 157320
gcccaggacc agagagattt acaggacagt tttgccttat ctacaaagga gagcaggtac 157380
cagtcttaca gaaactattc caaaatacca aggcaggaag gatacctccc taactctttc 157440
tgtgatactt gttatctccc tgatgaatat aaatgtaaca atcctcaaca aaattctagc 157500
aaaccagatt tatcgcacat caaaaacaaa atgtatcaca atcaagtgtg ttttatttca 157560
gggatgcaaa gatggttcaa catttgcaag tcagtaaatg tgattcacca tatatgcaga 157620
attaaaaaga aaaacgatat gatcatgtca atcaatagat gcagaagagg ctgttggtaa 157680
aattcaatgt cacttcatgt taaaaaccct caaaaactag gcattgaagg aacgtaccta 157740
aaaatagtaa gaatcatata tgacaaagtc acagccaaca tcatattgaa tggggaaacg 157800
ttgaaagcat tcaccctaag aactggaaca agacaaggat gcctactcac accacttcta 157860
ttcaacatag tactggaagt cctagacaga acagttgggc aagagaaaga aacaaaaggc 157920
atccagattg gaaaagagga aatcaaatta tctctggtca ctgatgacat gcccccatac 157980
ctagaaaatc ctaaagactc ctagacttga taaacaactt cagtaaagtt ttaggatata 158040
gaatgaatgt acataaacca gtagcatttc tgtatactgt tactgaatct gagaaccaaa 158100
tcacgaactc tatcccattt acagtagtca cacacaaaaa taaaataact aggaatacat 158160
tgaaccaaag aggtgaaagt tctctacagg aagattacac aaatggaaaa atatctcgtg 158220
ctcatggatt ggaagactca atattgttaa aaatgaccac aatgcccaaa ggaatctgca 158280
gattcaaagc aatccctaat taccaatgtc attcttcaca gaattagaaa aaacaatcct 158340
gaagttcata tggaccaaaa aaagagcctg aatagccaaa gcaatcttaa gcaaaaagaa 158400
caaagccaga gacatcagat tacctaactt cagattatac tacaaggctg aacagcatgt 158460
tactgatatc gtgataccat gataaagatg gacacataga tcagaggaat agaacaaaga 158520
actcataaat aaagtgacat acctacaacc aactgacttt cagcagattc aacaaaaata 158580
aacaatgggg aaaggacatc ctattcagta agtggtgctg ggaaattggc caaccacatg 158640
cagaaaaatg aaactggacc tctgtgtctc atcatattaa aaaattaact caagatggat 158700
taaagaccca taaatgtaag atgtgaaact taaaatcctg aaagaaaacc taggaaaaac 158760
tattctggac attggcttag gcaaagaatt tatgactaag accccaaaag aaaataaaac 158820
aagaacaaaa gtacacaggt gggacttaat taaaccaaaa agcctgttca cagcaaaaga 158880
aataacagag taagcagaca acctacagaa tgagagaaaa catttgcaag tcatacctcc 158940
gacaaagaac taatatccag aatctacaat gaacccaaat aactcagcaa gagaaaaaca 159000
accccattaa atattggtca aaggacatgg acagacattt cttaaaagaa gacataaagt 159060
tgccaacaaa cattttaaaa atgcttaata tcactaatca tcagagaagt gcaaattgaa 159120
gccacaatga gatattatct tataccagtc agaatggcta tgattaaaag tcagaaaaca 159180
acagatgttg gcatggatgc agagagaagg gtattcttat acactgttgg tgggaatgca 159240
aattagtaca accgctatgg aaaacagttt ggagattcct gaaaaaacta aaaatggaat 159300
taccattcaa ttcagcaatg ccactactgg gcttctaccc aaaggaaaag aaatcattat 159360
ataagaaaga cacctttatg tatgtttatc gcagaactac tcacaatagc agagtcatgg 159420
aatcaaccta agtgtatatc agtggataat tggataaaga aaatgtggtc catatatacc 159480
atgaaatact atgcagtcat aaaaacaaat gaaattatgt cctttttaga agtttctaca 159540
tggatggagc tggaggccat tatactaagt gaaataactc agtaacagaa aagcgaatac 159600
tgcacattct cacttgtaag tgggagctaa acagtggtta catatagatg caaagatgta 159660
aatatcagac gttggagact ccaaaaaggg ggaaggtaaa aggggaattc ggatttttat 159720
aattcgaatt tacaatttta caattgggta cagcttgttc actgtttgga ttatgggtac 159780
attagaagcc caaacctcac tattatgtaa tatatctatg tgataaacct gcacatgtgc 159840
cccccaaatc taaaatctta aaaaaagaaa tttataagga aaagggtaca ctacaactga 159900
tactaaacaa agacagagga tgataggaga ctgttatgaa cagttataca ctaacagatt 159960
ggataatcct gaagaaatgg ataaatgaat agaaacgtac aacctaccaa gatataccat 160020
gaagaaacag aagatataac agaccaagga aggagattga agctgtaatc aaaaatctcc 160080
caacaaagac aagtcaagat gagatggctt cattggttaa ttgtactaat catttaagga 160140
agaattaatg acaagtggtc aacttgtaga atcagttctt ctcaaattct tctagaaatt 160200
tgaagataaa ggaatactgc caaagtcatt ctgtaagacc agcattgtta tgatatcaaa 160260
ttcaaataag aacacaagaa aattataggc cagcatctct ggtgaaggta aatgcaaaaa 160320
tcctcaacaa gataatagca aattgaattc agtaggaaat ttaaaatatc atacaccatg 160380
atcaactggg acttactcct gggatgcaag aatggtttaa cctatgcaga taaaaaatgt 160440
gacataagac attaatattc tgatattcac agatctgtaa cataatgtca aagatctaaa 160500
ttatattggg aaatataata tgctattgaa attgttaagt atgtagtaag taccttttaaa 160560
aagctattat ctgtgaatga aactccaaat taggattaag ttcttaaaag aatcatatgg 160620
aaaaaggagt attttattgt aaatattaaa ctaggacatg tttgttatta aaaataaaat 160680
ttatacagta agtgctattg acttaaaata ctatcaactt tattctctgt agagaagaaa 160740
gtataagttg gcaatgttcc aacatgtctg tattaatctt acaagatctt gtggttcagc 160800
caaaaactct catgcttgtg tcagttaaac tttttaagta taacttttga aacacctgtc 160860
ttaaaggcat ccttatgctt tcagttttta aaacatatat aaaactgatc tgataatgtg 160920
aaatattgtt caacatgtta gctatttctt aatgttttgc aattggtgag ttttaaaact 160980
gtcccaagtt aacagcgatt taaaaacatt tttctcacat gtagttttta aagctctcta 161040
gaaattgaca tgtttaaaaa ctgccaagac aattaaactt tttatgttaa aaatgtttaa 161100
aactctgatc atatagcaca tagtaataac gctttcttgg gcataaatta taataaaata 161160
ctataagtaa tacatgtaaa gaatgtatca gtcactatct aagccttgaa gcaaattgta 161220
ttcatccttc aagattcagt tgaacctact ctttggaatc attttcaacc agaggtggtg 161280
tatgatttag aaaagattga gcacatggct tctagtcttc gctgtaccat ctcttgagtt 161340
ccacttgtac atatgtaaaa tgaaagcaat gggccagatg acccctgagt gttgttttat 161400
tttttagctc tacttataag ggaacacttc catttgcact aaatatactg tatgaatgtt 161460
taagtatttc tgggtatctt gagtattcag aggtggcact aatgaaggag tgtaggcttt 161520
ccctgcaatg ttgaaccttg gtgtacattt tgtcctcttt aaaaaaccaa tcaaacaaat 161580
ttgctaccta gaatacagtg tgtataggtc ttttggtcat tagccttata ataggtagtc 161640
atttaaaata ttttccaaag ttacttaggt aatttcttgt tttccatacc tcattcataa 161700
tagttttatt actgttggta ttgtattttt cattctccct atctgctgga tgatttaaat 161760
tatttatttt ttgagggaat aggaaacatt gccatagtta tataaataag ctctacaaaa 161820

-continued

```
gggtgtactc agggaagtat caatcctccc cctatgccta ctaccctgtt tccattctcc 161880
ttccagttat taaatttgtc atagagattt gggttgttct gaaactactt aagtgtatac 161940
tgggatataa caagtaagta aatatgtttc agataataag acccagattt ctcaccgtaa 162000
gataaaaggc tagtgtgttc agggctatgg tgttcagttg gaattggaag tatcagtatg 162060
aacttatggt tctgaatata tataaaaaca gataaatatg aaaatataga tggggtatgt 162120
tagtgtacat acatatattt ccaagccctg cctactaaca agacatgaaa gcagtgacac 162180
ccagtagtag tgaacataga taatacccag atctaggatt taaataccat tctccagtag 162240
aaggtactat gccgccttgg agaaatggct gattctatat ctagggcagg gaaaatggaa 162300
gatgagccta gaatagtaag tacacataaa taagtaaaaa taaatttcag gtgcagcggc 162360
atgcacctgc aatccctgct actcaggagg ctttgtaatc ccaactactc gggaggctga 162420
ggcaggagga tcgcttgaga ccaagagttt gagaccaacc tgggcaactt agcaagactc 162480
catctcaaaa aatgaatgac taaatgaatg aatgatgaga gcatgtcaaa aaaacacagg 162540
agccaacttg aaggagttcc caatagccaa ttctggagca attttagcag caaaataaat 162600
aatgatagca ttattataat ccagaaaata aaagaaatat ccatccatct gtattgatat 162660
aaatacttaa acacctggga gggaaaggac aggtcttcct tacagtagaa atccaattat 162720
aaattaataa gtaaatatgg aaatggagac tcaccattag gcaaatatca tggtaataat 162780
tgtttaaaag aactatcaat ggatattaaa ataagtgggt gaaagtgtca tgagaaaaaa 162840
gattttttgc ataattttga agtattttcc cagaagataa ttaataattg ctaagagaaa 162900
catcacaact ggtgtggaaa aataaacctg gcaggcacca ccttaaccag atgatcaatt 162960
acagatgata atatcaccag taataagaca tagtgacata ccatgtgcca ctagtgtggt 163020
atattgacaa gggcacctat tgctttagtt ctgtttttgc tcaaaataca tcacctcaat 163080
ctaataatta gaaaacatca gagaaatcca agttgagggg catatgacaa aatcagtgcc 163140
cagtacgctt caaaagtgtc aatgtcaagg tcataaaata caaataaaga cagaagcaac 163200
ttgtcaaaga caaacagatt ggattatcaa attttggtag aggttacagg aggttatgga 163260
cacatgatac agtgtagcat actaaattgg ctcctgggcc agaaaaaaaa aaaaaggatt 163320
attagtgggg aaactggaaa agggcaaata aggtccctag ataagttaat agcattgtat 163380
aatgttaatt ttatatcttt cataacactg ctgtgattat gtcatgttct ctttagggga 163440
tactggttaa agggtataca agaatgttga ttttttacag cttttctgta agtctgaaat 163500
ttttcaaatt gagatacttt gaaaatttct gatcaaaatg aagcaaaatc ctttccttgg 163560
gctttgttag tatgtattac ctgaaaaaag ttggaatttt caaaaatatt ttaataagca 163620
gtaataaaac aaaaggaaaa atattggaat ataataataa ttcagtttac aaagtgcata 163680
gtaggtcaga ggatcattcc tagatctctg actcttgtcc cattctgtta gcctaaaaga 163740
atgtcagata tcttgcccca aaggaaagtt ttttgtactt ttcctgatct gcctccatgt 163800
tgcagagtgc cagcttactt ccgcacattt cagacctggt cgcgatacct tgaacttcag 163860
gggcaaggat aaatcaggct aattctgctt tcattaggct tttctgttca ggcctggttg 163920
gggtttgaga gaatatgcct cttctctaaa acactggagg actgggaagg ctggacacaa 163980
taaattaaca atcagtggca atcccacatt tcatatattg ggtaagaaaa ataatactga 164040
gtgtacctgt acagacctaa tgctaattgc tttcccaaat attatttatt ttcatactta 164100
gaatagctct gtgagataga tgttggctcc tttctaaaaa taaggaaaat gaggctcaga 164160
caggttaaat atcttgccaa gatggtacat taagtaatgg aaagccaaga ttcaaaccca 164220
```

ggtctatttg attccaaagc atgctattct ttttttctta taggtccaac agaaaaatac 164280
atatacatta aatatgatat ccatacatat aatagagcag tgcagaggta attctgtcag 164340
tatcaatgcc catccatata gaaacatctt aagagaagtt accatatcat atattctttt 164400
taatttccca tggcctccaa taaggtagaa tccggtaatt actacattac tggtgatttt 164460
cagattcata gtatctgatg aaagtaaaac agcaaaaaga aaaaaatatt gacctctgca 164520
gggcaatctt atctgtagct agctggcaga ttgctgttat cttcattctt ctctctgttc 164580
tataaatatt taaccacctg tattggtttt ctgttgctgc cataacaaat gacaacacac 164640
ttacgattta aacaacacaa atttactttc ttttggctct gtgggttgtg agtccatccc 164700
aggtctcact gggctaaaat ctaagtgttg tattcctttc tgtaagttca tggggaagat 164760
tcatttctt cctcagatgg tggcatagtc agatcctttt gatcatacaa ggaccccatt 164820
tccttgctgg ctgaaggcca ttcccagctt ctagagggta cctgcattcc ttggcttgtg 164880
acttcttttc tctaaagcca ggaaaacagg tcaagtttgt ttcatatcgt atctccactc 164940
ctgcctcact ctctttcact tttaagagct cgtgattaac tggcccaccc aaataatcca 165000
ggataatctc cccaccttga ggtccataat tttaatcaca tctgcaaagt ccatttcacc 165060
atttaaagta atatagtcac agggtcagag tactaggatg tggacatctt catggatgcc 165120
ttattctgca gaccacaatg taaaaaaaat cacacaagtt cataaaccac tggctaatat 165180
taataatcat aactatactg agcagtttgt gtcaagtaat gttctaaatt gtgttttata 165240
tattaatcta atccttgcaa tactgtaatg aagcaggtta cttagcccta ttttatggat 165300
gagaaaaaat aagtacaaaa gacattaggt aatttaccag agtcactgat agtaattatt 165360
atctgtaatt tcaaccaggc ggtctgagtc tgtaaactat gccattaact tccgtactat 165420
cataagtcac tcagatgatt caggacttcg gatattttac ttaactgatt agggtcaaaa 165480
tgtttagcaa gcctatactg tatgtgggct ggttattctt agtttttacg gtaaatgaat 165540
atttttttct tgctggctga cagaaaagga atgataatga gggtacacag atgactgaaa 165600
ttgaatgtta tttccttaga ttattttact cattatcact attgtataag aatatgtcac 165660
tgtttgttat ataagttcct tcagaacaac ttagagaaaa aatatggtaa ttaggttatc 165720
atgtaatcca atgacataca tctctgttgc agcacttttg caatgatgtt gtaattctct 165780
gtctctctct cccccaacct ttgttctttg atgttagtgg tctttccaat tttgtatttc 165840
aacatctata gagtttctgg ctgatggatc ctcaaatagt gaattggatg aatggattag 165900
ttaattaatt aaatcattcc tataattgtc aatccattta taccctgctc ttaaaattta 165960
atgaattaat ttgaggtgaa aatgtttcag acaagatgat cttcaaattc tacatgtaat 166020
aaagataatt ttaagagtct caaaacaatt tgtatattta tagaatccct aataatggcc 166080
atttgcagtg tgctaagcat tgggctaaac gagagctcag tattcacaac aatcctgtga 166140
tgtaatgctc tagtcgtata catgtggaaa ctaaggacta actgagttgt atcactcccc 166200
aaagtctact cacggaccca gtagagccaa tgtcttcacc taggaataat tgactctaaa 166260
gcgtttgccc ttatccactg cctcatttct ttttattcct aaagtaaaac tactcataag 166320
atttctggat ctgatttctg tactacttgt ggattgatta aatacaaaaa cattattgtg 166380
tattattatc agttggtctt tcaaataact gagaccaaaa cattaaaata gttttaaaaa 166440
tctgtaaaca ctcctattct tctggatttc tacttacaga attagcacct agaactagaa 166500
aagtaagttt cttttttttt tctgagtgtt aagacctcag gaaatatttt tttaattaac 166560

-continued atactataaa attgacttga tattcattta tttgagcttt aatacacaca cacacaaaca 166620
gacacacaca taagtgtatt catgtagcaa ccatgacgat cagggcacag aacagttcca 166680
tcatcagagc actatcgtgc tacccgtttt tagtcacatt ttcattctac cacaaatcct 166740
ggcaaccgtg atcttttgct atcattttct cttcttgaga atgttataaa aatgaaatca 166800
tacaacatga aacataatct gtgtcactca gcatacaata tgaaacattt ctatttcact 166860
cagatgtatt caagttgttg cgtgtatcaa tagtttgatc ctttttatta atgagtagta 166920
tttcattgta tgggtgtgcc acagtttatc cattcattag tggaaggaca tttgggttgt 166980
ttccaattta cggagattat gagtaaagtt gctgtaaaca ttagtataca ggttttgggg 167040
ggtgaagtta agttttcatt tctctagggt aaatatttag aagtgtgatt gctgcataat 167100
atgttgtata tatttaatgt ttcaagaaac tgccaaactt ttccagagtg gttgtaccat 167160
cccaccagta ataaataaga gatgatccac tttctctaca tggccacagg cattttgttt 167220
tatcagatat tttttacttt aaccattcta ataggtgtgt tttcataaca ggtttggttt 167280
tcatttgcat tcccctaatg gctaatgaag ttaaacattt tatcatgtgt ttattatgtc 167340
ctcttcagtg aagtgtctgc ttaacacctt ttgtgtattt tcttttcttt tttttctgta 167400
gtgttttttt tttctttttt taattatact ttaagttcta gggtacatgt tcacaatgtg 167460
caggtttgtt acatatgtat acatgtattt tctagttgag ttacttattt tattaaattt 167520
tgagagttct ttagagttgt agtaaagact actgtagctt gtcttttcat tctcttatcc 167580
tagtctttca cagaacaaaa gttttaattg agatttagtt tatcactttt tctttttatg 167640
gatcatgatt ttcatcatgc ttggtgtcat gtgcaggaac tctgcttaac tccagatcat 167700 caggttttte tctttgtttt cttcaccttt ttattagggc ttgttgtatt ttgacctaat 167760 tttttataa gatgttagat tgaggtgaag tttcatttct tcaatatgga tgtccaattg 167820
tgccaatact gcttgttgaa aagactattc tttctctatt gaatatattt gcatttttgt 167880
cagaaattaa ttgtctatat ttatgtgggt cagtttctgg actttgttcc attctgttga 167940
tctgtacatc catccttttg ccaataccac gtaatcctga ttactgtagc ttgatagtaa 168000
gtcttaaaat tggaggatgt tatttctcta attttatttt tcaaaatcat tttggctatt 168060
atagttcctt tgccttttca tataaatttt agataatcta tttatattaa aaataatcat 168120
gctgaaattt tgatttgatt tgtgttaaat atgcagatca atttggagag aactgacttc 168180
ttccttaaag tgttgaggag tcttccaatt aatgaacatg gtgtgtgttt acatttattt 168240
aggttttctt tttcttacat cagtgtttca taatttcaga atacagatca tgtacatagt 168300
ttgttaaatt tacacctata tatttcttct ttggagataa gaactgtgaa tggcttgaag 168360
tttttttctt ttaatttggt ttccagttca ttgcctatgt agacagtctt gttttctgca 168420
aatagggaca tttttatttc ttcctttcta atgtgtatgc ctgtaattct tttattgact 168480
tattgcaaga catcaagaga ggtgataacg gacattcttg gctttttctt aatcttgaga 168540
agaaagcata gtctttctcc tttaagtgta atgttaactg taggtttctt gtagatacgc 168600
tttatcaaat tgagtaactt cccttctatt cctggttcgc tgcaagtttt catcatgaat 168660
aaatgttgct ttttttcaaa tgctttttct gcatcaattg aaatgatcat atggttttac 168720
tttaatctgt gaatatggag gaatgcacta atcaatttca aatattgaat caggctttat 168780
tctctgaaaa gcctcacttt atcattttct ttttgtatat tgctaatatt ttgttgaaga 168840
tttttgtgtc gatgttcata aggtatgtta gtctataatt ttttttcttt ttctttttct 168900
tttattttct tcgtactatt gtcctatggt tttggtatta gaataatcct ggccttaaaa 168960

-continued aaaatattta aattggtgtt atttcttctt taaatatctg ataaaatttg caagtgaaag 169020
ttggtcctgg agttttgttt tgcttaggag gaagattttc taattcaatt taaaaatatt 169080
tacaggaata ttcaggtttt gtattcatct tggatgtgtt tagtgtctga ttttcaagga 169140
atttacttat ttcacttctt taggtttatg tttacacaat tgttcagagc attcctttat 169200
atccttctaa tatctgctgg ttctacagtg gtattctctt ttcattcctg atagtagcaa 169260
tttgtggctt ctttttttgc ttaccgatcc tactacagtt ttgtccattg cattgatctt 169320
tacaaagaac cagcttttg tctcactgtt ttttttttta attttattgc tttttgattt 169380
ttattacttc tttctgcttg ctttgggttt attttgctcc ttgtttactg ttgttttaat 169440
acacaattca gaattttgat ctgagacctt cttttctagc acaagcattt aatgctataa 169500
attcccctct atacagtgtt ttagggacac tccacagatt ttgatgtttt ttatttccct 169560
ttttgatcca tagattctct ctaaatcagt ttattaattt ccagtgtttt ggagattttc 169620
ttatcttttt cctattgaca tctggtcatt atgatcatag aacatacttt atagaattta 169680
aatcctttaa aatttgtttt gttttatgat cttggaagtg gtgtgtctac atgaatattt 169740
tgtgtacatt tgaaaagaat gtgaatttcg tcattggggt gtgttctata aatctataaa 169800
tgttatttgg atctagttgt taatgttgcc tggttcttct atatccttgc taattttttg 169860
tctacttgtt ctgtcagtta atgcaagagg agtattagaa gcctgcaaga atattgtaga 169920
tttgtctcta ctttttgttc tgttcatttt tgctttgctt attttaaagc tctgttgtta 169980
aaggcataca catttaagat ctctctgttt tcttggcaaa ttgaccctct tatcattatg 170040
caatgttttt cttgatctct gataattttc ttatcactga agtctacttt gtctgatatt 170100
actataatca cgctagcttt cttctggtta atgatataat ttttcatgat agaatttttt 170160
atccttttac ttttaaacta tgtaattata attgaagaaa tttttgtaga taggatatta 170220
atggggattt tttttattat ttttggtcta ttctgatcat ctctgccctt aattggtttg 170280
tttaggccat ttatatttca taaaatgttt tatgtttgga tttgggttta tcattttatt 170340
atttgttttt tgtttttctc tctgtatttt cactcttctg gtcctctttt tctgccttgt 170400
tttggatcat ttgaatattt tttagtattc cattttaatt tagttttgac tatgtatctt 170460
tgtatagatt tcttttagtg gttgctctat ggattagaat gtacatccta acttttcaca 170520
gtctatttag aatcaatctt ttaccctgcc aagtggattg tataaatctt tcatgtaagt 170580
cttgttattc tccctccttt attttatagt ttttatatgt actacatcat ttctcttctt 170640
cttttattcc cgacattcca agtgtccctc atttcacctt ctttatgaca gtcttccttt 170700
agtaattctt ttagaacaga tctgccagca atgaactata ctttttatct gagaatgtct 170760
ttattttacc ttcgtttttt aaaggatatt cttattgaat ttagaatttt gagctgacag 170820
atattttttg ttttaaacat gttccacttt cttatggaat ctatgatttc tgattataac 170880
tctgtagtcc attgatcccc tataattata tattatttcc tctggctctt tttagtattt 170940
ttttaaacta gtttgattga tggatttgag cctagtgttt gattgatggg ttcgagccta 171000
gatttggggg gttaggaggt tactatttga ggttcagttc ttaaatctgt tggtttatgt 171060
ctttcactaa atttgggaaa tttttaaaca ttattcagtt ttttttctgc actacagctc 171120
ttttccttct gggactccag tgacatgaaa gttagatatt ttattattgt cctgcattat 171180
cctgagactc tttatttttt aataaatatt tttactctgt cttattcaaa gtggatagtt 171240
tccattgatg tactgtcaag ttcaccagtc tttgctctct tatctccatt ttactattaa 171300
gcccatccag tgatttttaa actttggtta ctgtatgttt agttctaaaa ttttctttta 171360
gtttttattt aaatatcttc catttgctga gacattctat ctttccattc ttttcaacag 171420
tgtttaccct tacttcttgg agcattttta taatagttgt cttaatgtct tagtttaata 171480
attctaacat ctttttttcc caatgttgcc attttttgat catcttttcc tatgtgactt 171540
gagacttttt ctgattcttc acatgccaag taatttgaga ttatattctg gatatttcaa 171600
gtattatgtt gtgagattaa taagttaaat aagactaata cttcgtctta tttaaatcct 171660
atcgagaatt ttgatatttt ttgcttaaca ggcaatttat ccagttgtat tcgggatgca 171720
gtctccagcc agtatatagg ttttgattcc acaactggtt cacttttcaa agcctttgaa 171780
atgctgttca gatctgtcct tcatgtacca cccagggtcc aatctagaac atgggtaatt 171840
gtctgtctat acttagtttc tcacagtctg tgatcagatt cacacatgag aagtttgagc 171900
ataaacccaa gagttcataa acagccttat gaggtcactt tcctgagcct ctctctttca 171960
tgatctcagt actttgagtt cctggagact ctgcttttca gtcctctagc caaaactctg 172020
ggactttatt taccctactt tgccacatgc ttcctgcatc tatgcctgta gaagagctga 172080
aagaagacag ggagagaaag agctcagtgg agtttatatt gtactcttag ggccacagct 172140
cctcctactg gagaggaagt tttccctccc tcaaagtttt aaattcttgc agttatcatt 172200
atctctgcta ctaccttgaa ggctaggatg caagagaatg aaggagaaaa gggcaatttt 172260
tctcttcttt gagacttttc ctgctccttg agcctaaact ataaggattc tcctagagcc 172320
ttcactgcca tgccccaggg cccactttca ggttttaagc tcccttgaat ccaggccagg 172380
ggtacctttt aaaaaaagaa gaagaaagaa aaaggtaagg ggaatcaccc tgtgctactc 172440
tgaattcttg tcatgtcatc ttctccagtc cacctgctgt gacttaccct ttagagtctt 172500
taaataaccg tttccttcat tctcaagttt tattatctag attcagtagc agacataaac 172560
agtttgtgga ttctccatat taactggatc tgacctcagg tatatatttt taatcattat 172620
ctaagttaat gggtgttcat ggaggttgtg agttgcattt gttttaactt tgctatacag 172680
ttacacccca aatattcaca tacatattat aaattggaag atacaggagc aggaaaatga 172740
aactatctgg aaaagtatac agtgaaacat ttcatctcta aagtttgaac acattcaggt 172800
ctgaatttag gaatctgttg gcattcgctt ttttgatagt tttcccttag cagggaatag 172860
ggtaggaata gcagaaagct ggctcagcga tgacttacag aatgagagag atgtgaattg 172920
gccttttaaa aatctgtgga agttactcat ttggactggg taacggcttt ctaggcagag 172980
ggagcaactt caggaaaggt atagagaagg tccccaactt acaacattga cttaagactt 173040
ttcaacttta cagtggtgtg aaagaaatat gtattcaata gaaaccacac tccaaggacc 173100
catgtaatcg tttctcattt tcaatatagt gttcaataaa ttatatgaga ttttaatact 173160
ttattataaa atgggcttca tgttagatga ttttgcccaa ttgtaggata ctgtaattgt 173220
cctgagcatt aaggtagact aggctgaact gtgttgttca gtaggaccgg cgtattaaat 173280
gcattttgac atgatatttt ccatttataa cggggtttat caatatttaa cctcatcata 173340
agtcaaggag tatctataca ggtataaatg tgcatggcat gtgtgaatgt gtgtcaaaga 173400
ggagtagaca aaccaggaaa gggaaatatg attcagttag gcatttactg tgccttctta 173460
gaggttgcag taagatattc ccatgaacat atttgaaatg gttagaaaca catgggtgtg 173520
aatttcaaaa aatacaagtt tttgaattta acacatatgc taaataatca gtccttcagc 173580
ttaaactatg ttatcctgca aatgatagta agtcttctgg atttttatta gaatgaatca 173640
cattttccat ccttgttttt atttactagg aatttcatct tatgactaaa aagaacaagc 173700
cataagctct tttggtctaa atttgagata tttgcctttg acttattttt aaattaaact 173760
ttttattttg acataataat agattcacaa ataatacaga gaaatcctgt gtacccttta 173820
cccagtttcc tccaatggta acataatata atgtcacaac aagcatattg acattgatac 173880
agtcaagata cagagcagtt ctgtcactaa caggctctcg tttcccatta catgttcacc 173940
cctgtccctc taccttgccg cattccttac ccctggcaac cactaatctc catctttaca 174000
attgtgttat ttgaagaaag ttacataaat gaaatcatac agtatgtaac cttttagact 174060
gactttttca ttctctataa attcttggaa attcatctga gctgttgctt gtatcaatag 174120
tttgttcttt tttattgctg agtaatattt catgacttat tttttagccc accttttttcc 174180
attatgtttc attttgaaaa aacaaagtct tactactcag gcatttttct cacttacata 174240
tttgctttag aatttatact ataaacaaaa accttaggag cattctagtg ttctttttaa 174300
aattgcattt aggttaacca gttaatctgt tgacattatt acgtcttaca ggaaaaaaat 174360
atgtacaagt agattttatt actttactcc ccttttaatt cctaaatcca gaagtaagat 174420
cagaacacat gagagatact gctgcttgaa aaatacttag cacagcctgt ttgcagacac 174480
actcatgcta gtccacggct gatgcagaaa ggagcctatc ccaaggcagc atttttttgc 174540
agtgctaaag gccaacatta ggatgttgtc tgttttcatt aggcaccatg gtcttagttg 174600
ctcaaccaaa actccagcct caataatgag ggaaaaaaat atacttctag tttttaaatt 174660
gtgggaaata ggtctgggag tagattctga agtatgttaa atactcatct aaagagccta 174720
gaatttatcc caagggggga tgaagaaatg aagaaacaaa taaattaatc aaattgcagt 174780
tcctaaaata gttataagta gaaaaattag cagtgtccaa aaatgtcatt ttacctttaa 174840
tatcaatgtc atattccatc ttacgaggta gtaactctgg ctgttttgat tttcatttta 174900
gaagaataag gaacataggt ttacaataat cagtaactat attaccatca tataattacc 174960
cagttggcat actgtttatt attttagttt aaggagacac attgaagcga gaaaaagggg 175020
gtgctagagg tttgcagaca cttagcaaac actagtgttt atcctacagc tttgtaaaca 175080
ctttaccaag aatttttaaa ctgtcatttt gctgatggaa agtgtaaaat gagacttcag 175140
cagaagttaa tctcatcatc tacttaaaac agtgtttttt acattgatct aaagaggttt 175200
gtgcatattt taactgtttt tcctatatga tcatcttcat gtactagtat gaaagttaat 175260
gagtaaagaa aatctgctga ataaatccac gtgataatcc aaggcactta aaagaaatac 175320
atgctataat gggatgcaaa gattttactt gattagtgct ctatttctca atttaacaat 175380
caaacctaag agaaatctca atcaagactt ttgactaaca tagtgcaatt tgattagggt 175440
gcagataagt acactatttc ggtgtgactg tataagtatt ctgatcataa ttatgacata 175500
tactctgcta ctagttagaa aaagaacagt ttttaacttc ttcatgcctt tcatttatgc 175560
acatgttctt aatacactat tataataaat aaaatgtacc tgaaaatata aaacatactt 175620
tttgcttgtc caaaaagtat gcatttattt ataatacaaa atatttattc tgaacctatg 175680
ctgtatgata gcccactata aatgtagagg tagcaaggga agatgacaga tatctaaaaa 175740
tatttgttag tagcactata ttgttgatta ctacatatca gtaattagaa taacgaataa 175800
agtgaaagaa aaagcataat gccttaggtg tttactttgg gcacagtaac atttggtcca 175860
gtcatctttc tagttttctg gtacccaagt taaatgagca agagtgtgat ggaaagtggg 175920
ctttggagcc aatcagacct gcatttatat ttcatttcta ccacctaata acggcatgtc 175980
tttgggcaag ttatttaact tctccaagcc tcaagttttt taacttataa aatatgttgt 176040
tacaaagctt aaaagaagta agttactagc acagtgcctg gaacatagaa atttgtgctt 176100
tagagaagaa ataaaaatat ataattctac cgtctatagg tagagctctt ttcccaaaat 176160
agtactaaaa ttccagtttg cttataatcc taaaatattt ataattccag aatatctaaa 176220
tctgtactgc ttttacttct ctaagatatc ttcgtgagtt tggtaagact gtccacttaa 176280
tttctttaaa cagctttact tttcaaggac acattaccat attcataaaa ggaaaaaatc 176340
caaattaaat ataatctgta ctgaaagttt ccttttcaga tttcgggaag ttaaaatgtt 176400
tgtgacaact ggatttgttt ttttaatctt ttattgatat ataatagctg tatatatttg 176460
gggagtacat gtgatatttt gatacatgta tacaatgtgt aatgatcaga tcagagtaat 176520
tgggatatcc aaaactttaa acatttgtct ttcgtttgta ttaggaacac tatagatcta 176580
ttttaatttc ttctttgatt tcagcaggaa aggaagggca agaaatcctg gggcctgaag 176640
ctcaggcaga tgaagcagga tgtacaggta ctctgctgcg actttctttc ataccatagc 176700
ctttaaaaga aggtctttgt gtcactgatt tcgcatttgt gagtcctgaa tttagtccgt 176760
ttccttctct tttatcttac cttccttaaa tgtttaagta cttaggcata tggtgcacta 176820
cataaaaaga agtaaatatt ccttaaatac agagtaactt acagattcat attatgtagc 176880
agatttctcc attctataag aatgacaagt ataacctaca gataatccaa aaaataagtg 176940
tttgaatgat gatttgaact tctatcaagt ttttgaccaa agttagagaa atgcagatct 177000
aacttttgag tttcgttatt agttacctgg gtctgctttg aattgcccac aagacaaaaa 177060
gcagaagaaa atagaaaaag catggattta tctataaatc cgatgagaat catgaatatt 177120
aatgagttga gtgaacatgt cacagcaaac gagaatcaaa aatttttctt aaattttctg 177180
tgattgaaaa agagtaaaat gaagttgaat tataataaac aaggaaattt gcttttaggt 177240
gactaaaaag tacatattcc ctgaaactta aggctattcc tctgtaatgg attcagatca 177300
gatttaagaa gcaaaagagt aggtggaaaa attaaatcag atcttatgta tagtaatacc 177360
agtcactttt tattgtgttc cctaagagag ccagaactgt tagaatgtaa acttcaaaaa 177420
tgcattccag atttttaaaa catttcctca aaatattata cttaaacgta gtgtaattgt 177480
actttgtata ttcaaccata aattagatat ttctgtcata tagttttaat tacattttct 177540
ttttccttct cttctatgag ttatcattta tagatttgtt tttttacttt gctgtgcatt 177600
ttaggaatat tccataaagg cttacaaatt atctttcatt aggtaagatg aggtatggtt 177660
catggctaat aagtgtcaag attagatttt tatctgtaat ataaacaata gcactcctat 177720
actcgtcagt catttctgta aaacagagta aatctttgtg ctgttattaa aagtgaattc 177780
caaaataatt aaataataat ggagtatgtg ataatttgtg gtgcgtatag cctgcgattt 177840
tatgttttgc ccctaacttc gttctgtgta acttgcatga ataatgtatt cagatatgct 177900
tgttatcaaa tatttgccat gctaagctat agaatatgta aaatatttaa gctggacatt 177960
tgttagtagt aatacagtag tgttaataaa cataagagta cactatttac ttttacctag 178020
aatcgttaaa ctttgatgac ttatattacc agaattacag aagacaactt gcccttctag 178080
gtaaaatgct atccaaaaag atgctcacag gtttacagta ttttatctgt catgctgttc 178140
ttcactataa aaataaatga attctttcag tttgaagtac tgaatagtat gtaaatttcc 178200
tcaaaaaagt tgcatctgga aggcagggta accttctcaa atttgtgttt aacaaaagtt 178260
gctgctgaaa tgtaaaatct cccccacgta cacaatgatg atccctgctg cattattcgc 178320
ctggaacatg gggagttagg agtaagcaaa cttccattaa agctccagtg agtgtagctt 178380
taaaaggaaa tttagctttt gagacttttg agcagttaaa ctgtaaaatg atgtcctgcc 178440
tttgcttttg ttacttcctt gacttctagg gaataatatg ctgacaaaat gagcaaaagc 178500
attgtacagc agtcgccatc attagttcag aatgttgtca gatctttttt atagcagact 178560
tccttctgca gctcgtgaag ttaaggaact atagtctgaa ctcagtaatc agagtaaaaa 178620
attcattgaa aacatccttt gttccttctg agcgtccctt tttttgttta tatagttgat 178680
aattttagaa agtttcaaac atggaggata aagataagag gaagcctgag gatactttat 178740
tcaggatgga aaaatagata gatagataga tagatagata gatagataga tagatagata 178800
gatttaaaaa tattcagtgt ttatattaaa tatttgctct ctcaaataca tgtatatagt 178860
catttaattc tatactttgt caattttgag ttttatcata tttaaagaaa acccaattac 178920
cttttatgct gtgtatattt gctcatctcc ctaatattta aatatataag tttatcatct 178980
aaagaccagg acatttgctt tataattgac cttttcaaga tgtgcatttc ccaacacttt 179040
aaattttaaa aaactgcaga aattctggtc tcagtttgaa attgggcctg gtaaatgtgg 179100
gttcatggat atagagtgta gtttaatgga aagagctcag attttatacc tgacacctaa 179160
taccaatttg tctgctctaa tagtaataca ttttctctct gtgatctcag aagagctttt 179220
ctgaccctaa tttttctatt gaggaaaaat tttaattgta aaattatgat gttcaccttg 179280
caggacttct ttaaggtgta aatagctaac aattacatag tacttactac ataccaggta 179340
ccctactaat aagtacatta ctatattaat taatctaatt cttacaacaa ccctaagagg 179400
tactgttata taaattttat aggatgtaaa cattatatac tgtctcacaa atttcttaat 179460
ggacatataa aatttttcat tttaaatgtc agtagttaca atttaatttc tggcagagta 179520
aaacattgac attttaacat cactattaca tatgaaatcc atagtatatt aatacctatt 179580
atctttttta aaaatatgaa aatgctcttt aagaaatgtt gtgtcataat atttactttt 179640
tgagctcata tttccattct atatgcacta tagaatttta tgcaaacgta tattaattac 179700
ttcataaaca gtaattaatt gtaatagctt aatattactt ctagaaggaa aagtgttcat 179760
cattcagttt cttttttta gcattgaggt acctttattc tcaaataaaa agatgaaata 179820
aaattttatg ttataactga gttgctcagt ttttatgcat cttcagctat aatgtcaaaa 179880
gttatttgtc aatgaaaata ttttaatgtc ctgtcagtat ttcttcaatt ttgttgaaaa 179940
caaaatttaa agccatctaa tttgcaaaaa gatttgtttc ccagtcatta caatcatcta 180000
ttccctcatt ttctgggacg tataccagaa agactttacc aatagttatt tatcaaagga 180060
ctaatgatac ctgttttggg ctttaaaatg tttttctca cagtcacttt gtttaatgta 180120
ttcagaaatg attaaggaaa ctgaaatatg ttaatttcag tatcttttat cagtatattt 180180
ttcatgaaaa acacttttat tacatgaact gtattttgag caataccttta ttggttcacc 180240 caatttctgg aaaatttcca ataacctacc cagcaaagcc agttatcaac atcacaccag 180300
ccagccaagt cagacttact ttctgtcagg aaaaaaagca ttttttcgtt ttttgaactc 180360
agtgtgtcaa tacatatttt gaggaattct ataaaatctc atcaataagg aagtgtatga 180420
aggatatatt taaaatacaa aagttaacca ggcatggtga tgcacgcttg taatcccagc 180480
tactcgggag gctgaggcgg gagaatcgct tggacccagg aggtggaggt tgcagtgagc 180540
caagatcgcg ccattgcact ccaacctggg cgacaagagc gaaactcatt ctcaaaaaaa 180600
aaatagaaat tatcaataat gaagaaaaca taaagtataa gtaaatacat cttataataa 180660
tactaagtag taaagtcaag attaagatta tgtagatcga atctaatttg tatgttaaaa 180720
aaatctttat ctctaaatgt gtatatttag acctaatcaa tgtataggaa agctagaatt 180780

```
tattgaagta gcaaaattca tatataaaat acagatcatg cagttctgaa aagtgtatac 180840
tatttaaaaa ctcattattc caacagctag cacacttata atttttatta ggatgtagaa 180900
aatataagat ggagattgct taattgaaat aaatatttta taatataatt tgataaaaat 180960
aattttaact atcttagcaa ctctacatgg aatctgtaag aaatcacata aaatattaat 181020
ttcatttttt acttttatct agtttaaatt gaaaaattga agttgctttg aaaagaatgc 181080
cactgatttg ttctgcttta gctcttcaga aatgcttttt gttctaccta atgacaaatc 181140
ctaggaatga tgtttgagaa tgttatttgc tttgctctta tcagtctcct gaaaagcaat 181200
gaatttttaa ataataggga ggtcattaag ggaaaattac cctcacttcc tctggccata 181260
ttatatagtt aattgcagct tcccaaccag gaccagcata cccccatttc agttgtgctt 181320
tatgcctaat agaaattcat gtaaacagga aagaccagaa aacctatagt gattctctgt 181380
tgccttgatt tgtcagtaaa gaaggctttc cctaatcggt attttgaact ttactccttt 181440
ggcaccctgg aggactttac actccaagca gtgtaccata atcatgtcat ggatggatag 181500
aggaatacgc cttttctctt tttttctttt aagaaagtga gaacaaggta tactgtataa 181560
aggagagcag ggagaagaat tttcaaggat gctaggaaag agtttacatg gaagctgagg 181620
atccgggagt tgattccttt aaacccaaca gtccagctta cattttaaaa gtcttcgctt 181680
acctctggat ccaataatcc caatttggta actactgaca tgaactaaat aatgcagttc 181740
ttggtatata gcaaatgcta aataattgat agctattgaa aagtggggaa aaaaattagg 181800
atcaccattt gttactgtca ttggttctca ggttttaaac agcagtcacc ctgatgagtt 181860
tggttaccgc tacagtgcag gagatgtagc aagattgttt taataaccat cgaacaaaca 181920
gatgcccata catccccatt ttaatttggc caaacttcag cctgctgggg agtgctgttt 181980
tacaaattta gacctgacag ttcagtcaga gtctataaag aagtcatccc tgaggcattt 182040
gggagccata ctaaggcatt gcagttgcca gcatggagta gagaccctct tctggagcca 182100
gtggaggaaa tggaggaaaa ccatagtgca gcaataatgc tttagaaact tggcagcacg 182160
ctgggctacc ttctcaaagc ataagccttt ctaattcaag aaaagttgcc actgccttaa 182220
tcccacagtt aaacatttac tgaggcagaa atagagaaag aataggcttg ttttatatga 182280
atactagcgt agctaagaaa gagttttcat agatttgata ccctttgatg cttattagaa 182340
atccttctta ctatagataa ttattaaaaa ctattttcta agaaatcata taactgaact 182400
gaacgtcaga gtggtttata tgagaattat tcagatttaa agtagagctc cccccccat 182460
tatctgtggg agataaattc caagagtccc ccattgagtg tcttaaataa atacttatat 182520
atactatact gtttcctata catacataca tatgataaag tttaatttat aaattttata 182580
cagagttgca acaagaacta taataaaata cggttataac aatatgcttt aataaattta 182640
tgtgaatgtg gtctccctcg ctcgctctca aattattctt cttgtactgt attcacctga 182700
tttcatattg cagttgacca caggtaactg aaaccatgga aaatgaagcc acagataagg 182760
ggctgtctat tgtccaactt taaataagta ttatgatatg ataggttgct aagaaggtga 182820
cctttgagaa ctaaagtttt tttcttgctt tatcattaat tgagaaagaa ttcagtcaac 182880
tatattgcct tctctgtgtt ttattagtaa aatgcaatag aagtatgact ttaacatttg 182940
aaagggatac tgtgagaatt tcacacattc atagcatttt aaacttataa agcaaagata 183000
tatcttaata cattacaaca aaatgagtgg aattcatttt taattttcaa gaaatatttt 183060
ctgcagattc aagaacaatc atatgttctc tcaagataaa taatttctta tttagaaaac 183120
ctttgtaata acttagtggt gagattgctg tcttaaaagt atgcattttt tttagtaaaa 183180
```

-continued

```
gatgatgaat gcgagtcaga tgcagaaaat gagcaaaacc atgatcctaa tgttgaagag 183240
tttctacaac aacaagacac tgctgtcatt tttcctgagg cacctgaaga ggaccagagg 183300
cagggcacac cagaagccag tggtcatgat gaaaatggta aatggatctt aacagttgtg 183360
tttctttccc tctttaaagg attcttgttt ctaccattct actatgggaa cctgctctac 183420
tatagggaac attcttgaag accaaacttt attacaggtg cctatagaga gtaatctgtt 183480
ttattaatgg aacactatga tgaccatgca gtaataaatt attagctgct catgtattgt 183540
ggtagtaatg ccactgcacg tgaaatgctt agaacagtgt ctggacatca aattccattt 183600
acttacatgg tagcaggcag tagaagtgag aactatacct ttactgccct ttggattctt 183660
tcccaccatt cttttaacaa ataaaaatat ggttgtctgc tttataccag aacatactaa 183720
tttggaaaca gtggttttcc tgaatctgcc ttagtccact ctgatatgaa tagtcagcgt 183780
acagagtgtg gaaaatgcaa taaaaatgtg ttcagactct cctgagaaga aataggctgt 183840
gatacagttt gggaggaaaa gactatgtta ttgtttcacc agaagaaact aggttatcaa 183900
agaaatgaaa gggaaataca aaatttaaaa atatatgtat atttacgtaa aatttttatg 183960
tgacaaaagg ctttcaaaaa gcctcactga aaggaaacaa tgaaacctaa agaaatgatc 184020
cattatgtag ttctaataaa ggttaaacct tttaaagttt gtcaggtcca tacagtacga 184080
tctaaaaatt gaggaactac cattctgaat tagtttgaat tatagaataa gttgttgatt 184140
ttgttattca ttactttcag atatttaatg taatttaatt aaatgctaat aaagcatttt 184200
gaagtattct gtcatatcag cgacatttgt ttacatattt atcccttttt ataaccaaat 184260
agtattcatt cgtgtgtata tgccacattt gcttcatcca ttgatgtaca ctgaggttga 184320
ttccatatct ttgctattgt gaatagtact gtaataagca tgaagatcca ggcatctctt 184380
tgatatacca acttcctttg gataaatacc cagtagtgga attgctggat catataatag 184440
ttctattttt agttttttttt gagaaatctc cgtagtattt tcacagtggc tgtcctaatt 184500
ttcattccca ccaagaatgt atgagagttc ccttttctcc acatcttcac cagcattcat 184560
tagtttttgt ctttaatagc aatactaact gggatgaaat gatatattat tgtggttttg 184620
atttgcattt ctctaatgat tagtgatggt gagcattttt ttgtatatct gtggctattt 184680
gtatgtcttc ttttaagaaa tgtttattca tatcctttgc ccacttttca ataggattat 184740
ttgggttttt taaatctgtt gaatagtttg tgtattcttc atattagtcc cttgtcagat 184800
gagtaatttg cagatattca ctctgttgtt tcctttgctg agtcttagca ataaagtctt 184860
tgcctaccca aatgtcctga gtgttttctg tatgttttct tctagtttta tggtgttgtg 184920
tcttatgttt aagtctttca ttgatcttga gttgattttt gtatgtggtg agaaatagga 184980
gtccagtttc attcttcaca tgttaatatt cagttttccc agcaccattt attggagagt 185040
gtgtcctttt cctggtgtat gtttttggtg ccttgtcgaa atcaaatggc tgttaataat 185100
gtggatttta ttctgggttc tctgttctct tccactggtc tgtgtgtctg ttttttacta 185160
atgccatgct gttttcctta ctgtaccttg tattatattt tgaagtcagg tagtgcgatg 185220
tctccagctt tgttcttttt gctcaggatt gctttggcta tattggtctt ttgtggttcc 185280
gtaaaagttt taggattgtt ttttctgctt ctgtgaaaaa tgacatagat attttgatag 185340
ggattggatt gaatctgtag atcgctctgg gcaatatgat cattttaatg atgttaattc 185400
ttctgatcca tgagcatggg atgtctttcc atttacttgt gtcttcttca atttctttca 185460
tcaatatttt gtagttttcc ttggagaggt ctttcacctt cttgggtaaa tttatcccta 185520
```

-continued ggtattttac ttttttgtag ctactataaa tgagatggtc ttcttgattt atttctcgtc 185580
tagttcatta ttggtgtaca gaaacactgc tgatttttat gttgagtttt gtatcctgca 185640
actttcagtt tatttagcag attgcagttt tttggttgtg tctttaggtt tttctagata 185700
ttagatcata tagtctgcaa agagagacta tttgacttct tttccaaatt ggatggcttt 185760
tatttctttc tcttgcccaa ttgctctggc taggactttc caatactgtg ttgaatagga 185820
gtggtgaagg agtggaaatc cttttctgat tacacttctt agagggacgt ctgtcagctt 185880
gttccatgca gtatgctgtg gttctgtcat atatgtcctt tattatatgg aggtgaacca 185940
tctttgcatc cctgggataa atcccacttg atcatattgc attatctttt tgacgtgctg 186000
ttagatttag tttgtgaata ttttttgag gattttgtat ctgttgtcat cagggatatt 186060
gacctggata gttttccttt ttttgtttca tctttctctg gttttggtat caagatagtg 186120
atggacttat agaatgaagt agggagaatt ccctcctctt cagttttttg gaatagtttg 186180
aggagaacta gtgttagctc ttctttgaca gtttggtaga attcagcagt gaaccctttc 186240
agtcccggac ttgaaatatt cattatggat tcaatctcat tactcattat tggtctgttc 186300
aggttttcta tttctttcta atttaatctt ggtaggctgt gtccaggaat ttatccatat 186360
cctctaggtt tttcagtttt ttcatgtata gttgttcata attgtctctt ttgtatttct 186420
gtggtatcat ttgttagtct tctttttcat tttttatttg catcttctct gttcttttct 186480
tagtctagct agtggtttat cagttttgtt accttttcaa aaaaaccaac tttttgtttt 186540
gttatttgtg ttgtttttta gtcttcattt cattgatttt gttctgattg ttattatttc 186600
tttccttctt aaatcctaat ttagggtttg ctttgttctt gcttttctaa gttcttgagg 186660
cacattgtta gattatttga aatgtttcta ttttttgttt taggtattta ttgctatata 186720
cttcctctta gtgcttttgc tatatttcat aggttttgat atgttctgtt ttgattttca 186780
tttaaagaaa ttttaatttt aatttcattt aaagaaattt taaattttcc tccttatttc 186840
ttccttgacc ccgtggttat tcaaaagcat gttgtttaat tttcatgtgt gtgtagagtt 186900
tccaaagttc ctcttattat taaaatctat agttgtatta ctttgtggtc taaaagctac 186960
ttgatatgat tttgattttt aaaaatttgt ttgagacttg tcatgggtcc caacatacag 187020
tctatcctag agtatgttct gtgtgttgat gacaagaata tgtatccttt agtagttggt 187080
taaaatgttc tgtaagtgtc tcacatccat tcggtataaa atgcagttta aattcagtgt 187140
ttctttgtta agtgtctttc tacatgatct gtctaatgct gataggggtg ttgaagtccc 187200
taactattat tgtattagaa tctgtctctc cctttagatc taataatatt tcctttatat 187260
agccaggtac tccagtcttg ggtacatata tgttaagaat tgttatatcc tcttactgaa 187320
ttgattcctt tgtcattctt taatgacctt ctttgtcccc ttatactgtt ttgtttactg 187380
gatttaagag tttatctcat tatagctact cctgctcact atggtttcca tttgcatgga 187440
catctttttc tgtcccttta ctttcagtct atatggatct ttacaggtga gatgaatttc 187500
ttctaggcag cacatagctg ggtcacagtt tttatccatt cagccaatct gtacctttta 187560
agtggaaagt ttaatccgtt tatgttatta ttattgatat gttagagcct atttctgtca 187620
ttttgatttc tggttgtttt gtgtatcatt tgttcctttc tttcttactg attattattg 187680
tggtttgata gttttctata gtggtaacat ttgagttctt tctctttctt atttgtactt 187740
gttctaccag tggattttat attttcatgt gttttcatta tggtagatat cttcctgtca 187800
cttccatgga taagactccc ttaaacattt cttgtagggc cagtctagtg gtcatgaatt 187860
ctctcagctt ttacttgttt aggaaagact ttatttctct ttcatttatg aaggataatt 187920
ttgctgggta tgatattctt ggctggcagg gtttttttct ttcaatactt tgaataaata 187980
tatcatttct ttctctcctt gcctataaag tttctgctga taaactgcta ttagtcgtat 188040
ggaggttccc ttacaagtga ttggacactt ttctcgtgtt gtttttagaa tatctctttg 188100
tcttttactt ttgacagtga atataatgtg ccatggagaa gatctttttg aattgtatct 188160
atttgggggt gcgctgagct ttctgtatct ggatgtctaa atcctttgct agacttggga 188220
aatttttgga tattatttca ttaaataggt tttctatccc ttttgtttcc tctttgcctt 188280
ataacacatc aaaaattcga atatttggtt actttatagt ttcttatatg tcacacaggc 188340
tttgttcatt gttcttttat tcttttttct cttactaggt tattttaaaa gacctgtctt 188400
caagttctaa aattcttctt ctgcttgacc taatctattg ctgaagcttt cagttgtctt 188460
ttgtctttca ttcggtgaat tcttcaattc cagaatttgt ttagttcttt tttatgatac 188520
ttacctcttt ggtaaatttc tcattcatat cctgatttgt ttttctggtt cctttgtgtt 188580
gcttttctgt tttcttctat ctcacttagc ttttataaga tcattatttt taatcatttt 188640
ccaggatttc ataaatttat tttgattgga atctgttgct ggataattat tgtatttttt 188700
ggaggtgtca tatttccttc ctttttcatg tttcttgtat tcttaccttg ataccacaca 188760
tctggtataa tagtcaatta ttctggtttt ttggatttgc tttcattggt tgagtagggc 188820
actttggctt tgattctggg tacatgtggt agtgtaattt ctgtatgata tctttcgtta 188880
taaatagtgt gagtagggtc cgtgatttcc tcgttggctt aggtgcaatt gttagtggag 188940
gctgaggtga agtttggctg ggacagggat gccaggtgga ccattccttg ggccctagca 189000
gtggtagtaa cgggcttaca gtacctgtcc ttagaccaca gggtggcaca ttgacacctt 189060
gtgttagcag gtccagttgg gctgatcctt ggaactccag gtggcttgct tgggtgctgg 189120
tagtggcagt ggtaagctgg gcaggtgggc aggttctcag gctcctgggc agtggatgtc 189180
acttgggcaa tggcagtagc agtggcagga caccctctgg ttccctagtg attcacgctg 189240
gtgttggcag tgactgcaat gggctgggtg agtcagtccc caggcctacc ggtggtgcat 189300
gcaggagggt gccagctgta gtgatagtag caggttgggt ggacccaacc tcaggcctcc 189360
aggaggagtg ttcaggtgac aacagtgttg gactgggctg ggtcatcccc acgtccctga 189420
atagcatgct cggaaactgg ggaggaggta agctgggcca gatggacctg tcctcaggcc 189480
ccttggtggt gtgtgtaggc attggctatc atggcagggg caggatgatc ccaggccacc 189540
agcagagtgc tcaggtaagg acatcagtgg ttgcactgtg gccttcttac tggggagggc 189600
aaggttgctc ttggtggcag cagccatagg gagggagctg ggaaatgtgc gctttagccc 189660
cagacagcgg ctgtggatgg ggtagcctgt cctcaggtcc cttataaatg cttagcagct 189720
cagctgctga ggaaattagg gtcgctgcca gtggctagca ctttgtcccc agcggtggaa 189780
gcccacagtg gcagcagtct gttggggagt ctgtccttgg ggcatgtaaa aatgtgtgca 189840
gctcctctgc tgggaggagg tatggtcact gccaatggct tgcacttcag ccttagcagc 189900
cgcaaccagc attagtgatg actgggaagg gaggtatgtc agtggggctc aacaggatgt 189960
agtctgttgg gggttgggct ctcaaaatag tgctgtgctg tagctactta gaactcaggg 190020
ggtgtacaga ttcagcataa gctccctctc cggagcagca ttgtcatgtg gtctccacat 190080
acctccctgt gttagtctca gagcccacga tggtccaggg gttctcccat ggctaggatt 190140
gcaggagtcc atggtgggaa tgtggacccc tgggggtctc tcacttactc tttccctgca 190200
ttggagagcc tttgcaggtt gctttacttc cttcttcctt acttgaggtg tttcctgtca 190260
cttttctgtt gaattccagt gttctctctt agatgatcta tgtgaagtgt gattattacc 190320
tcattatttt ggtttttcct tgtagaggag gtgagtacca gatgcctcta ttcagccatc 190380
ttgaagcccc tctctcaaca tatttgacca actatttaac attcaggtgc tcagtctatt 190440
atttgcagtc tggtccttga gcaagacatt tgatttatat ggacttgaat aaaggaatat 190500
atgttcagaa agcacttgga gattttatga aattatctgt ggtggtttgt ttttctatag 190560
tgaattcaaa atgaaaatag agatgatgtt tacaaaaaga tatcacttaa tttatttcat 190620
tgaagaaatg tcaaatatgg aaaactactc ttagttaaat aatattaatt ggcaaaatat 190680
tacattttag gattgtcagg cttagacagc tccaagtgta aaaataaagt tcattcagta 190740
aactaattta ttcagaatgc ctttgttttc taaaagctat atatattcat acatatacag 190800
ttatatagca gatttgccag tgtatttcaa taggggaaat tacaagcagg gtcatgcatg 190860
ggatgtgttt atgtagcagg cctagatctg gcccccatca gtctttcctt ccccacctta 190920
cacactattt ttttggtctg aactcagtcc tatggccaca cctacctgca agggactctt 190980
ggaaacatag tgtgtgtgta ctgtttactc tttgatgatg atgacttggt agtttcattt 191040
tcaaaatcag aggaataaac attaaataaa taatgataca taccattgtt accaatagac 191100
tctgttgtag agcacaaaat tccccttta a tctgtataca cttacaaaga caacctacat 191160
tctaatttta cttttgtttt cttttctagc taatcacatg acaaaaggga agaattatgg 191220
tttagggaaa aagaatggga cttgaaggtc agacagcccg tatttgaacc ctgacttcat 191280
cattttctgg ctctgtgact tttcttttaa gttatttaac cttcctggaa accactgttc 191340
tctctcttat aaaatagaga tgagtatcat tgcattgttt tgaggatcaa atataaagtg 191400
ggtagcacaa tatctggaac atagcatagg gactcagtgg aaactttggt aatattttct 191460
gaatgtttta aatttaaaat atatgatctt tcttttacag gaacaccaga tgcattttca 191520
caattactca cctgtccata ttgtgataga ggctataaac gctttacctc tctgaaagaa 191580
cacattaaat atcgtcatga aaagaatgaa gataacttta gttgctccct gtgcagttac 191640
acctttgcat acagaaccca acttgaacgt cacatgacat cacataaatc aggaagagat 191700
caagtaagtg caatgactga gagttcacta actttccaga ttttgacaac tcagccctca 191760
atggaaggca aggattttaa tatatttgaa agttaaaaga atgtactaaa cagtgctata 191820
tctgcagcct tataaaagtg aaaatgatta tttatttgag ttatctggtc attcctgaga 191880
ttaaaaacca catatgaacg ttactttaga ggtaactcag tattttgttc aggtaagacc 191940
ctttccatct tgacttaatt attttgctta tgccataaca gttaattctt caagtttaga 192000
agatgttaaa ttgcattcta ttaaaatgtt cagtgtagga aaaataagta ctgactatat 192060
aaaccacatt atactaacca aattgacaag aaagtcaaat taaaaagttt aagtttcttt 192120
gaaccagtta ctatttattc tcagtataag ctacgtggtt tttttccccc gtagtaaagg 192180
gagttgcctc ctctaaaaat ctaaagttta gattttttta ttctgaagac tcaattttta 192240
tatggtttat tctacttctg tgtcactgtg ccccagtttt cagaagtata aaccaagact 192300
gttttgtaac tataagttac atttaaattg ctggttctat atttaggatt aaagtcaaaa 192360
aagcttttat cagttgttcc tcttttacaa ggtcctcata gttatcagcc atcaacaatg 192420
aaattaatat tgccttaatt ctaactttaa aaattaaata aattttcagc cacacagggt 192480
ttgtgagggt acatgttggg gttaggccac atttccagtt tcttacatca aagaatgatg 192540
tatatctaca tacctgaact ctgccctatg gatgtaccta atatgtgtca catatcccat 192600
agagaacaag ttagaccatt tgctaaggtg atggctaggc caaacaaaca acaaaaaaga 192660
attgtaacag aaaaagaatg actgagcaga gtcaacctat ttccttagta ctttggcaac 192720
agtactcatg aaataacaag ataataagaa gagggtggca atcagggaga atagaaccaa 192780
gattttatag gtttatggtc cataagccca tgaaggagca cttgaaacag gtgagagctc 192840
caagagaagg acgaaattaa tacagagaag ggacgactga aggcaaactc cgtctccttc 192900
ctagtgcccc tattaatgag tcttatcaga gagaccagca gaagagtatg ttttatacct 192960
tagcgctgtg atgtggccac agtgtagaca aggcttggga aagagcctac tcacgtgaca 193020
ttcaggaagc agacccatcc tgcagctgct gccaccatat tccctctact ccaagggcca 193080
tcgtgaaagg agaggacaga ttgaactggt ggcgaaagca gaagatgcca ttataaaaac 193140
aaactccaaa atctttgatg agcatgaaaa ccaattctat gatgattttt ccagtgggtg 193200
caaatgtagt aggatttaca tataaaccgt gggtcagact aaggtcagga aggagctgtg 193260
ataaatatgg ggaccagtaa tgtgaggaaa tataactggg aggtcttgga aacaatttag 193320
tttgcaaggc agcaaactaa aaggtagaat gtatattttg ctggcccttg agaatcatac 193380
tgtgactaac aagcattttc aagtcttatt aacttgttta ttcaacaaac atttgtgttt 193440
cttttatatg tgaggccctc ttctgggtgt taaaggcaca gtagtcaaaa aggaagtccc 193500
tgatattagg gaccatacat tagtagatta tataaaacag aaataaaata atacatactg 193560
tgaagaaaaa tacagcagga taagaggata gaaagtgatg aaagctgcta ggtttcacag 193620
agaagggaga cttctctgag aatgggatat ctgaatacag tgaaggagcc agtcatggaa 193680
tattggagaa gggcattcca gtcagaggaa acagtgaaac ataagaaagc cttgaggcca 193740
gaacctgctg ggcacacact gagaacagca gaggccagtg tgaaagggag aaaggtaagg 193800
ccagagaggt gttgggggct acatattata ggccaagata aagacgttgg attgtattct 193860
aaagtgcagt ggggatgcct gtcaaggatc caggaatttt taatttttat ttttagggga 193920
acactgactg ttggatgata gataagagag acaagaacgg aagcagggag atcatttaga 193980
ggcttttgct gtaatctagg ccagaggttt tggtggcaga cagataaata agattgttgg 194040
cttcagaata tgttcatatg cttgctgatg gattgggtga gggtacatga gtaagagggt 194100
aatcaagaat aactccaaag tttaaggcct aagctataac caaataaatg atagtgctat 194160
tcacagagat aggaaatact aaagacggag ctggcttgca ggagggaaat taagagtttg 194220
gtgttaatca tgttaagttt cagatctcta tcaccttcca actggcaata tcaaataagc 194280
agttggttgt aaaagtctgg agttaagggg agaggtttag agatacaaat gtgggagtcg 194340
ccaccatata tttggtattt taagtcatgg gttttagtga agtaggacct gattcagagt 194400
aagtactaat tctctttcct tcctgtataa aaggcaaagg aagggagatt ccagctggaa 194460
gagcatgaag cagtagttga gttaagccgt taaaggctgg gtagaatctt agtagtcaaa 194520
attatgggaa aacacagtga aggagtaaga aattatgtaa accaaagcca aaagataaag 194580
aggagcaata tgtgtgcaga aaaccatggc tcgctaaatg actgaggcat agacttgtca 194640
taaaaaactg gtgaagaatc atcttggaaa ctcagggact ataatcttgg aatctgtaga 194700
cttggaatct ttattgaggg gttaatgggg atccttcaga agtttatgag gaggagttga 194760
tagaatgcaa ttcaagcagt gcttttgtaa gattaatcta agtatgaaga atacatttga 194820
aatatgtgaa aatgggaatt tgataaacca gacagaaagc tattataata atccacattt 194880
ggctgaaaaa actggaagta ttttttaat catcagatta aagtacattt tggaaatatc 194940
aaatagaaga gacaggataa agtacaggaa aaatcctgtc ttctattcag gaccttgttc 195000

-continued

```
tgttgagtga gctttagaca ggttattcag tatttgtgga tgcggtttct atatctataa 195060
attggaaagc aaacaagtta acctctagtt cctagcaaag tatatattac tttattttta 195120
ctaattttga atattgttta ataaaggatg aactctgata ctttagaaag ttggtatttt 195180
tctgtatcaa attctgtccc cactatcact atcctttttg gtaataattt caggagttac 195240
atttttgtga ctgctacaac tgctaataat ttcaagagtt agatttttgt gactgctgca 195300
atttgaggtc tttaagaaac aaaacaaaac aaccatcagg ctcacaaaaa tgtcactctt 195360
agtagattgg atgttcttta gtctaaagat cttttgcttt tcaaataaaa taccagttct 195420
tttcttacag agacatgtga cgcagtctgg gtgtaatcgt aaattcaaat gcactgagtg 195480
tggaaaagct ttcaaataca aacatcacct aaaagagcac ttaagaattc acagtggtaa 195540
atattttttt tctttctata ccctgaatat catagcatat gtggtaataa ataaatatca 195600
taacatgtaa tctacgtaca tgatcagaaa ctccttgcat ttcttttggc atacactaat 195660
tgggagaaat tttatgttta ttttatgttt tattagagtc ttaacctttg actaaagtat 195720
atcaaattaa tatagtatga catactccag atttcctaat cagaagataa tatagcatgt 195780
tttagtaagt acaacctgaa aacatattag ctttctgatg aatgtaaatg tcattgcctc 195840
ctttgcacaa ttagcagggg aatggaaaag agtatagaga tacgatttgc acaagagaat 195900
agggaagtga agacatcctt tatttgagaa aagttgaaat ggaactcaag attagaaaat 195960
attggagagc tgatatagag gcaatgagag ggagtgaaag gattacagca ttaatgagaa 196020
tctgaaagaa aaatgtgctc acccaccatc ttcacctgtc tattccatgt cattctgtaa 196080
attattactt acaaggttaa tactattatg cgatgaaagt gttgtgtcta ttttaggaac 196140
tcagagtaaa cagagagcta tatttgcatt tctttggaga cactacttga acaaaagcgc 196200
aaaaggaaaa cttgctggta tcccacaatg ccctatgaaa tctgttcatc tcctgataaa 196260
ttttgatatg ttattttaga tttaaatcat tttaatgaaa aaattattaa ccatgaatgg 196320
gaaattatgg gttttcacac attgcttatt ttgtgaaaat tatgtattga catttacatt 196380
ttacaaacat cttcctacaa aaaaagtata gttggatagc tttgtgaagc atagttgatg 196440
atatttatgt tttattttgg aactgcattt ctaaaagttt tactgtattg ctcattaagg 196500
ctaaccctca atgttaaacg tgctgaagtt accacttgaa aatgctcaaa ccaagatcct 196560
taccaaaaca tttattttca cacattgatt attgtttcta aaaagtagag gttgtctttt 196620
gcagcctgcc acaatattct gtttcttagc ttctatgcta ttgaacaatt tttatcaata 196680
ataaatatatt ttaacaacct accttcttac cagagatgat ttaaagttgt taataaagat 196740
atagctaatt caagagggat ttttaaatgt tgaaatcagg gcagaggaag gaaaataaag 196800
ctaacagtaa gattcatgta tataatgagt catattcatt ttgtcatatt gcagtcatgg 196860
aagatttatc agatctataa ataatacaaa gttggaaagt ataaatcaga acaaggattg 196920
aaatactggt ctagaaataa gaagttgaaa gttaagcatt ggtatttaaa aatcagtctc 196980
aatcaagtag taaatttgaa tggcccagag cttaatatga gctgactgta tgctgatact 197040
gctcaaaagc taatgcaaat ttaggccaga tcatggaaca caaagctccc actgtactct 197100
gcactgtcca ctcattatgt atgtacttat ttctgtcttg tttttaaaac atctaatgtg 197160
aggcttgtat acctttaaca tagcaagtaa ttttaattta aaaatatgta ggaaaaaatta 197220
agaaacacta acatggagta aattgttggg gggacaaaat gaatgctgtg aaatgccata 197280
catatgctgg aagtggacca caaattaagc tctaaggttt aggaagaaaa tgacaatcag 197340
taaccaagac ccagggtgtc tgtaagtaaa aaaaaaaaaa aaaaaaaaaa aaaaaaaaaa 197400
```

aaaaaatcag ttgctagaaa aaggactatt cttccttcct gataccaagt ccatagaaaa 197460
cgttattcct tggaacaaca taaagagaaa agaacaaaac agaagttata taatcctcag 197520
aaatatcctt aaaataacac agcagagaat ttgatagggt ttcttttta aatcagatta 197580 ttcaatagaa gccagtcata gttcaccaaa gtgctattta ggaaaagcat tgctccaggg 197640
tggccacgta gatacagttt aagtacacag ctctctgatg gtctggttga ttccaagaga 197700
agatttttga gcaaaggcta cccaaagtga catctcagga ctggtaccag tctgcaaacc 197760
ctgtgttact cattcttgag ataagtacag aaattgagag taagcattta gcatttatta 197820
taccaagact ttgtgacatt ttactatatt ttataaaata ttggtccaca gtagattgga 197880
aacttaaaaa agaaccaaac aaagccaact ggtcattcac cacaaatagt ttgaaaagct 197940
ctgcctaggg tatctaataa tggaagagct gaatatcttt taggaaacct ccataacttt 198000
cttttcacat gacttttgaa aagatgttga gaatcaggat ccaaaattat actctctaaa 198060
attacctata ttgttgctaa atactggtac ccaaaaaatt ttgatcatga ccctatgcag 198120
aaccgtgtgt gttaataatt agttgattct acctgtagga attgagctat catgaggaaa 198180
aggctaccag acctccactc agattagaga caaaagaaca cctgcatatg gctgtggtcc 198240
acccccaaaa ataattttcc atggtcttag taatttttgc ctggaaaatt tttgtatcag 198300
atgcagccaa acacccacct tagccattaa aaaaaaaaaa aagtcagtat acatagtata 198360
ccgaactttg agtagtgaaa cttcctgatg taaccttcag gctaaaatac ttgtaaaccc 198420
taacctccat agataaatta gtgatatgcc taactaataa actgtaaagc tatgaagcta 198480
gaaacaagga gttttaaatt aacaaatata gtgactttgg ctttagaata attgttgtgt 198540
aaactttctt tctggcaatg ataaaatatc aagataattt ttaacaataa taatgataac 198600
tagcacttat tggatcctta gctatgtata gccacatgtt agttatttgt atgcattaat 198660
tcatatagtc ctcaggataa ccctatggag taggttttat tattttctac tttttactga 198720
tgagaaaatt gaggctcaga gggcttaatt aacttgtcca aggtcactca ggtagtacat 198780
ggcaaagcta gggctgtgat gtagtcatcc tgacccaaag tcattccctt acgtaccatt 198840
tctgtccccc tgttttaaaa aatagtctgt atttatagat gtttatcttt ctagcgtctc 198900
tagaaggaaa ataagcatgt agttcatgta aaaatgttat caagtaatta aaagtgttaa 198960
aatagagatg tactagagta tattccttgt tttacccccca ctggaaactt ttgtctgttg 199020
tattttgaga attgaatcct attccaggca tcgcattgga aaaatattga taaattggag 199080
aatccccaga ggtgggttaa caagcaggta agggttctaa aacccacatc ctgtgcagaa 199140
tgtttgaagg acctaggtat atttaaccta tataagagaa gtttaagaat acatatagca 199200
gctcttgatc catttgaagg tttgacttga gaagaaaagt tacacttgtt ctgtgtggca 199260
tcaggacaaa ctaggatagg gaaataggca tcatagctat ttttttggct caaactcagc 199320
ctgtctctta gtagaattgc ctttttaaaa agtgactagc atttgttgag agcatactaa 199380
gagttttgct atataatctc atatgacccc tataacagtc caatgagaat gtatctgcat 199440
ttgcacattg aaaaactaag gcttggacag gttaagaaaa tactatgtga tggagccagg 199500
atttgaaccc aaatccatgg acctcaacag aaccagacag gaccatcttg tgcagggctg 199560
tccagcaggt cctaactccc cttttattaa agaagctcaa gcagagatta gctggtgtca 199620
agaatgatat gaaatgaact cttcattgaa aaggaggctg tactacaagg gtttcttaaa 199680
tctcttccaa ttcttatata tgattcttca aataatcata tttattagaa aatataactc 199740

-continued acatgtttaa actatagcat tgaagttact attaagcaat ttttagtagg gcttaaattg 199800
attcctcact gctttcattt taattcttaa aaagagcagg agatggagag ttttattttg 199860
atactaagta gacaaatcag tgtcatcaca tctcatcatt caacaattag ccattcactc 199920
atccaaaaaa ggtttaatga gcatctttgc aacctgtact ttgatgggtg caagggataa 199980
atggcaaaca agcctcagag gctcctgcct tactgaagct tatagtctgt aacctttaaa 200040
ttataaatta gtgaactata acttaaaact caaaggaaac attaggtttg taggaaaata 200100
ttccatttag ctcggtgctt tcaaaatttt ctaccaaagt atccctaaca gccaaggaga 200160
ataaatgcct tttaccccac agagtctagg gaagcagctt gagggaagcc tctgcaagcc 200220
aaaggctact ttgacagtgc gtggcttttc ctagcaagtc acacaaatgt gtttttctct 200280
gttttaatat aaaaataatg ttttatcata tccactgtca ctaaaattga aactccaagg 200340
tgctttgata cccactacag tgtttatcct gggagtatat acatttcagt ttaataagcc 200400
aatgcttata gaatatctta tataagtttt cctcccatta gggaaaaact attttcaaga 200460
aagccctatg ggtacaggaa ttattattaa tcaaagatag atattcatac ttgttaagtc 200520
atatgggaca ttttacttat ttttcttttc tttaatattt ctcctacaga tggttgagta 200580
gagtaaaata tagaaaatta tataggtcgg tgaaatggga taagaaaaaa catacttgaa 200640
agagtagaat gtaattactt ttgatacttg agaattattt gaagttataa agattggtgg 200700
aaatattata cacatatgct gagaagattc catgattggt tagcagaaca tgtacctcag 200760
acttagttac tagcgttcat cacatctatg taggttttga agctaaaaag tttattctaa 200820
atacagttct gtcacaagca tgcatggcag tcttcttttt aaaattgata ccgcttgttt 200880
tagggaaatg aggatacata aaaatttata tgtaataatt cagtgaatat aatttgtttg 200940
tttgtttgtt taggagagaa gccatatgaa tgcccaaact gcaagaaacg cttttcccat 201000
tctggctcct atagctcaca cataagcagt aagaaatgta tcagcttgat acctgtgaat 201060
gggcgaccaa gaacaggact caagacatct cagtgttctt caccgtctct ttcagcatca 201120
ccaggcagtc ccacacgacc acagatacgg caaaagatag agaataaacc ccttcaagaa 201180
caactttctg ttaaccaaat taaaactgaa cctgtggatt atgaattcaa acccatagtg 201240
gttgcttcag gaatcaactg ttcaacccct ttacaaaatg gggttttcac tggtggtggc 201300
ccattacagg caaccagttc tcctcagggc atggtgcaag ctgttgttct gccaacagtt 201360
ggtttggtgt ctcccataag tatcaattta agtgatattc agaatgtact taaagtggcg 201420
gtagatggta atgtaataag gcaagtgttg gagaataatc aagccaatct tgcatccaaa 201480
gaacaagaaa caatcaatgc ttcacccata caacaaggtg gccattctgt tatttcagcc 201540
atcagtcttc ctttggttga tcaagatgga acaaccaaaa ttatcatcaa ctacagtctt 201600
gagcagccta gccaacttca agttgttcct caaaatttaa aaaaagaaaa tccagtcgct 201660
acaaacagtt gtaaaagtga aaagttacca gaagatctta ctgttaagtc tgagaaggac 201720
aaaagctttg aagggggggt gaatgatagc acttgtcttc tgtgtgatga ttgtccagga 201780
gatattaatg cacttccaga attaaagcac tatgacctaa agcagcctac tcagcctcct 201840
ccactccctg cagcagaagc tgagaagcct gagtcctctg tttcatcagc tactggagat 201900
ggcaatttgt ctcctagtca gccaccttta aagaacctct tgtctctcct aaaagcatat 201960
tatgctttga atgcacaacc aagtgcagaa gagctctcaa aaattgctga ttcagtaaac 202020
ctaccactgg atgtagtaaa aaagtggttt gaaaagatgc aagctggaca gatttcagtg 202080
cagtcttctg aaccatcttc tcctgaacca ggcaaagtaa atatccctgc caagaacaat 202140
gatcagcctc aatctgcaaa tgcaaatgaa ccccaggaca gcacagtaaa tctacaaagt 202200
cctttgaaga tgactaactc cccagtttta ccagtgggat caaccaccaa tggttccaga 202260
agtagtacac catccccatc acctctaaac ctttcctcat ccagaaatac acagggttac 202320
ttgtacacag ctgagggtgc acaagaagag ccacaagtag aacctcttga tctttcacta 202380
ccaaagcaac agggagaatt attagaaagg tcaactatca ctagtgttta ccagaacagt 202440
gtttattctg tccaggaaga acccttgaac ttgtcttgcg caaaaaagga gccacaaaag 202500
gacagttgtg ttacagactc agaaccagtt gtaaatgtaa tcccaccaag tgccaacccc 202560
ataaatatcg ctatacctac agtcactgcc cagttaccca caatcgtggc cattgctgac 202620
cagaacagtg ttccatgctt aagagcgcta gctgccaata agcaaacgat tctgattccc 202680
caggtggcat acacctactc aactacggtc agccctgcag tccaagaacc acccttgaaa 202740
gtgatccagc caaatggaaa tcaggtaaaa aataacctcc atcctgaacc tggctagtaa 202800
tatgctattt gactaatttc aattaacttt gtctaataaa tatcagtccc gtagagccaa 202860
ctagattatt acaaactgtc atttttaaaa ggatcaatgt ttgctttaac ttttctggca 202920
tgatgtcttc agttggttgt ttgctaatcc agggtattgt taccagctta aagtttgaaa 202980
tgctattcta ctgaaagatg atttttaagt cccagctaaa aacctgtttg aagttagaaa 203040
tcaaaaaaca aaattgaaat actcgctaat tgggtttctg tttttatagc taaattccta 203100
aaattagtaa tagtttctgc cttgattatg gtcattaatt aatgaaaata tgttcccatt 203160
cacaggttca taccaggcaa acttatctat cacttttata tactaataca tctgtttata 203220
aaaggtttta attaaataaa caggaatgaa gtatacaaag aacgcatctt gtgaatttac 203280
tgatcatttt atgaactgtg cataaacagt gttcagtcat aatgtatatg aggaagtgtg 203340
gctgtgaacc taaaaataca tatgcatttt cctccttaac tatcacagtg tttaccacaa 203400
cagtgtttat tctgtccagg aagaaccctt gaactggtct taccccaaaa tccacaatag 203460
ttttggatag agctattgta tgcctcattg tccagacttt ttccatgtca ctgatgttga 203520
tgttttccca ttttttccat caatttctga tggaatcaaa tgaatactag agacaaattt 203580
gatattttat gcaaatattt tctataagta taataatttc aatatcctgc tcaaacttgt 203640
atttgctgct tttgttttcc cttaaatatt gctattgatt gggtttcctg taattgtgat 203700
aactcttgaa aaaaagttct tacgtgatca ttgaattcct ctaaattttt agtgtacaga 203760
acactttgca tgcctttgaa tagaaaaaga gccatcctta gcatttcata gactcacgtg 203820
tcacgtgact agatcaagta gcagtgaaag tagaatcaag ttacttcagc accagggcca 203880
ctcacaaatg acagggacaa atggctgcac ctctcttgcc tcatagagcc ataagaaatg 203940
ttgtgaaaaa ccttcaactt ttagaaaatg tgtgggtttg aggcaatggc gtggaacact 204000
ctagataagg taggaagatc ttaggggacc cagttccaca acaggctccc tgcagggtta 204060
tttggcttac ataagaacgt gctgcccaaa attatctcca tgagactgcc tggagtttct 204120
aaaggttcat tttgattagc aattatttct gttaaaaaga tagaccctcc tgcattgttt 204180
ttccatcttg ctccttagac aagtggtaga gcacacctct ctcttttcaa ggagaccgtg 204240
gaggttaaag aaccctgaag ttctggagga tacaattgaa agaccaggtt ttaaaaatag 204300
aatgttagct tttgcttagt gaaacccaga atgagaaaaa tgaaggcaaa agatgcagtt 204360
agtaatgagc gattaattag caaactaata agttaaaacc ttctgcaaat ttctcgtaaa 204420
gtaatgattc acatgaaact aggtaaactc tgttactata tattttacat gctttctttt 204480
cggtgtcctt gctttctttc cagtaccagt tgagtatatg tctttgctat ggttttgact 204540
gtgttatccc caacctcact cttgtctttg tcatctccac ctgtgatctg gccccaccct 204600
tggggcacat gtgcagtgaa gatcagtgtg cttgctttgg tcaagtcctt gaaagtataa 204660
aagtataagt taaagtagtt ctttatctca tgcttttatg tatatctctt gtttatcttt 204720
taatgttaaa ttacattttc tcacaccttt ctccctctag gatgaaagac aagatactag 204780
ctcagaagga gtatcaaatg tagaggatca gaatgactct gattctacac cgcccaaaaa 204840
gaaaatgcgg aagacagaaa atggaatgta tgcttgtgat ttgtgtgaca agatattcca 204900
aaagagtagt tcattattga gacataaata tgaacacaca ggtatgtcag tgaacacaaa 204960
cataaagtgt ccatgatatg atatactgga agatgcaaaa ttaaaaacta aagttttaga 205020
atttgtttc ttttttttt tttttatttt gttttgagac aaggtctggc tctagtcacc 205080
caggctggag tgcagtggca cgcaatctca atctcggctc actgcaacct ccgcctcccg 205140
ggctcaagcc atcctttcat ctcagcctcc tgagtagctg ggactatagg cacataccac 205200
cacacctggc caattttgat atagacgggt tttgccatgt tgcccaggct ggtcttgaac 205260
taatgagctc gagccatcta cccacctcgg cctcccaaag tgctggtatt acaggcatga 205320
gccaccacgc ttgacccaga attaattttc ttattttttta cttatctgat ctggccattt 205380
tcacctgttt gcccacttct acctagtact taaggtctgt gcctttcttt tggtttttttg 205440
cttcatctgt tttttgttt ttttcatgac ttatttcctt taagctgaca cagcatttat 205500
tctgtccgca ttcatttaat gcaagcttat gctatattaa taaaaacata gtacatagta 205560
cccattaata aaaaatatga gaccagtggg ctaaagtcat agggagacag gatctggctt 205620
cataaaagaa aaagctgctt cataagcatg cggcaagctg tcctggcaag tcaagatctt 205680
ttgttttaag taagaagttc tgcctaagag gttggactag aagattctaa gatcctgtaa 205740
ttctgagatc ctgtaattct gccacaaaat atgcctcctt aggttgactc agggatggca 205800
aactatagct cacaggccaa atgtgagcat acgcatgttt ttctatgagg taagaatggt 205860
agtttttgat tttgttttta catttttaaa tgattggaaa agatgaaaag aatatttatg 205920
actgatgaaa attatgtgaa agtcaaatat cagcatccgt aaataaaatt agttggaaga 205980
cagcatcgcc tattcattta cattttgtct atgtcagctt tcatgctgtt ctacaatggc 206040
aggattgaga agctactaca gagaccattt ggcctgcaaa gcctttaata ctcactaccc 206100
tttacagaaa atagttgcca actcctggcc tatttcattc cttccatcag tgaagtactg 206160
ataaatttta acacctggtt ctctgaaggg tggggaagcc ctgatttgta gtgtttgcag 206220
ctttttgtgg cataaatact cccatcatgg tggatttcga gcttgaatgt gatgtcagct 206280
tgcagaattc ctgaaaattt agcagtagac tctctccagc cagtacaaac tggctccagc 206340
acactcctgt gtctctctct aacatgggtt gctgtagaag gggctgggtt tatcctgagc 206400
tctttaatcc cctacctgct cttccctgcc cccactacca gccattatga ctacagtatc 206460
catatttatc tttcatattc ttaactgttt cagtgtattt tttactcttg tgagaaaaga 206520
tagaattgtt tttccttctt caatctgtgg attcatacag tgacacttgg aaggttcttg 206580
gagctaaaaa ctggttacat aagagaaagt cacacctctc aaaatcagcc ccttgtaact 206640
cagtcctctg gttttcagag atctaagaag agttagaaaa tccccttcct cttcaggcaa 206700
agttaaatat tagcaaatat caaagtgaaa aatatatatg aaaaactaca ctatttctaa 206760
aattaaaaat catttctgca tttgttagtg ttaactgctt gatagctctg aaattggaca 206820
ttatcgatcc tgactatgat cagttgttgc cagtcctttt catgtctggg cagcaacact 206880
cctgtagccc atgcgttctc aggaggggca atattgccct cacgggccaa aacttgtttc 206940
ttagggggca aaaaagtctg agatactaca atggctgtgg ttttctaaag aagctcagta 207000
tatatactgt atatttatga gttttatcgt atataaaaag tgtatagtaa acattaaaat 207060
ttcactggga gcagagcttg tgactaggaa aacaaaatga ctaaaaaggg accttgtagt 207120
gataatgaac acaaggtgag cagcaagtct gtccctgtct gccctcactg tgctcgttca 207180
ctaccagaca tctcctccca gctgcacttg gcccattttc cacctcgctg tcatgatgct 207240
tgtatttttg gcatttcaat gtcatgtagc tcccattgac ctaatcatct gcacagcaga 207300
gtgtagagca ctacgttttt taatgtaaag aacaaaccaa attgcaatat tatattacaa 207360
agagtttggg acctggaaat gttttaaaaa tgaaactaat aaccctcccc tttctacaac 207420
atgaagtacc ccaaaaaccg tataaggatt ttatttgctg aataccacca ttttatttaa 207480
cagaattctt attttgcagg taaaagacct catgagtgtg gaatctgtaa aaaggcattt 207540
aaacacaaac atcatttgat tgaacacatg cgattacatt ctggagaaaa gccctatcaa 207600
tgtgacaaat gtggaaagcg cttctcacac tctgggtctt attctcaaca catgaatcat 207660
cgctactcct actgtaagag agaagcggaa gaacgtgaca gcacagagca ggaagaggca 207720
gggcctgaaa tcctctcgaa tgagcacgtg ggtgccaggg cgtctccctc acagggcgac 207780
tcggacgaga gagagagttt gacaagggaa gaggatgaag acagtgaaaa agaggaagag 207840
gaggaggata aagagatgga agaattgcag gaagaaaaag aatgtgaaaa accacaaggg 207900
gatgaggaag aggaggagga ggaggaagaa gtggaagaag aagaggtaga agaggcagag 207960
aatgagggag aagaagcaaa aactgaaggt ctgatgaagg atgacagggc tgaaagtcaa 208020
gcaagcagct taggacaaaa agtaggcgag agtagtgagc aagtgtctga agaaaagaca 208080
aatgaagcct aatcgttttt ctagaaggaa aataaattct aattgataat gaatttcgtt 208140
caatattatc cttgcttttc atggaaacac agtaacctgt atgctgtgat tcctgttcac 208200
tactgtgtaa agtaaaaact aaaaaaatac aaaatacaaa acacacacac acacacacac 208260
acacacacac acacacacac aaaataaatc cgggtgtgcc tgaacctcag acctagtaat 208320
ttttcatgca gttttcaaag ttaggaacaa gtttgtaaca tgcagcagat tagaaaacct 208380
taatgactca gagagcaaca atacaagagg ttaaaggaag ctgattaatt agatatgcat 208440
ctggcattgt tttatcttat cagtattatc actcttatgt tggtttattc ttaagctgta 208500
caattgggag aaattttata attttttatt ggtaaacata tgctaaatcc gcttcagtat 208560
tttattatgt tttttaaaat gtgagaactt ctgcactaca aaattccctt cacagagaag 208620
tataatgtag ttccaacccg tgctaactac cttttataaa ttcagtctag aaggtagtaa 208680
tttctaatat ttagatgtct tagtagagcg tattatcatt taaagtgtat tgttagcctt 208740
aagaaagcag ctgatagaag aactgaagtt tcttactcac gtggtttaaa atggagttca 208800
aaagattgcc attgagttct gattgcaggg actaacaatg ttaatctgat aaggacagca 208860
aaatcatcag aatcagtgtt tgtgattgtg tttgaatatg tggtaacata tgaaggatat 208920
gacatgaagc tttgtatctc ctttggcctt aagcaagacc tgtgtgctgt aagtgccatt 208980
tctcagtatt ttcaaggctc taacccgcct tcatccaatg tgtggcctac aataactagc 209040
atttgttgat ttgtctcttg tatcaaaatt cccaaataaa acttaaaacc actgactctg 209100
tcagagaaac tgaaacactg ggacatttca tccttcaatt cctcggtatt gattttatgt 209160
tgattgattt tcagaatttc tctacagaaa cgaaagggaa attttctaat ctgctttatc 209220

```
catgtacttg catttcagac atggacatgc tattgttatt tggctcataa ctgtttccaa 209280

atgttagtta ttatggaccc aatttattaa caacattagc tgatttttac ctatcagtat 209340

tattttattt cttttagttt atagatctgt gcaacatttt tgtactgtat gtcttcaaac 209400

ctggcagtat taataccctt cttactgaca tatgtacttt tagttttaga aaacttttat 209460

atttatgtgt cttattttta tatttcttta tttattacac agtgtagtgt ataatactgt 209520

agtttgtatt aatacaataa tatattttag tatgaaaatt tggaaagttg ataagattta 209580

aagtagagat gcaattggtt ctcctgcatt gagatttgat ttaacagtgt tatgttaaca 209640

tttatacttg ccttggactg tagaacagaa cttaaatggg aatgtattag ttttacaact 209700

acaatcaagt cattttacct ttacccagtt tttaatataa aacttaaatt ttgaaattca 209760

ctgtgtgact aatagcatga tgctctgcag ttttattaag aaatcagcct aaccatacaa 209820

ctctcatttc cttagtaagc caaattagga ttaacttcta taaacagtgt tgggaacaat 209880

gtttaacatt ttgtgccaat ttgttcctgt attcatgtat gtaagttaca gatctgactc 209940

ttcattttta agttccttgt tacatcatgg tcattttcta gtttttttacc agactcccat 210000

ctcacaataa aatgcatcaa caagcctgaa ctgctgtcat tcttttcatc attatcagta 210060

ttttctttgg aaaactgtga aatggggtac attgtcatcc tgcatttgat tcatcttgag 210120

ctgaatttgg gtaacactaa atgttttaga cattctccac taaattatgg attttcttgt 210180

ggctaaatgt ttctggagag gtcagagttg acaaaacctc ttcacaggtt gctccttctt 210240

cctgaaatcc ttaatcctcc gcatttcatg cttcaggtca tttcagggaa gcctgggttt 210300

agatgccttt ctgactctca gctcctgcac ttctgtcatc atacctctga tactattatt 210360

tatattcctt ccccactagg aacaggaacc acatttgtca tagtcactct cacattcctc 210420

actgcctaac agggtgcctg gcataagttg ggacaacaga tatttgttga ataaaaatat 210480

aatttgcatg tttatggagc tcagctatgt tctcactttt tttgcttcta attccagaat 210540

atatgttaaa tgatctaata atttgattat tttcttataa gtcttattaa acactagtca 210600

taatagacac aataaattat gccttctttt tctattgcct ta                    210642
```

```
<210> SEQ ID NO 5
<211> LENGTH: 508
<212> TYPE: PRT
<213> ORGANISM: Homo sapiens

<400> SEQUENCE: 5

Met Trp Glu Leu Val Ala Leu Leu Leu Leu Thr Leu Ala Tyr Leu Phe
1               5                   10                  15

Trp Pro Lys Arg Arg Cys Pro Gly Ala Lys Tyr Pro Lys Ser Leu Leu
            20                  25                  30

Ser Leu Pro Leu Val Gly Ser Leu Pro Phe Leu Pro Arg His Gly His
        35                  40                  45

Met His Asn Asn Phe Phe Lys Leu Gln Lys Lys Tyr Gly Pro Ile Tyr
    50                  55                  60

Ser Val Arg Met Gly Thr Lys Thr Thr Val Ile Val Gly His His Gln
65                  70                  75                  80

Leu Ala Lys Glu Val Leu Ile Lys Lys Gly Lys Asp Phe Ser Gly Arg
                85                  90                  95

Pro Gln Met Ala Thr Leu Asp Ile Ala Ser Asn Asn Arg Lys Gly Ile
            100                 105                 110

Ala Phe Ala Asp Ser Gly Ala His Trp Gln Leu His Arg Arg Leu Ala
        115                 120                 125
```

-continued

```
Met Ala Thr Phe Ala Leu Phe Lys Asp Gly Asp Gln Lys Leu Glu Lys
    130                 135                 140

Ile Ile Cys Gln Glu Ile Ser Thr Leu Cys Asp Met Leu Ala Thr His
145                 150                 155                 160

Asn Gly Gln Ser Ile Asp Ile Ser Phe Pro Val Phe Val Ala Val Thr
                165                 170                 175

Asn Val Ile Ser Leu Ile Cys Phe Asn Thr Ser Tyr Lys Asn Gly Asp
            180                 185                 190

Pro Glu Leu Asn Val Ile Gln Asn Tyr Asn Glu Gly Ile Ile Asp Asn
        195                 200                 205

Leu Ser Lys Asp Ser Leu Val Asp Leu Val Pro Trp Leu Lys Ile Phe
    210                 215                 220

Pro Asn Lys Thr Leu Glu Lys Leu Lys Ser His Val Lys Ile Arg Asn
225                 230                 235                 240

Asp Leu Leu Asn Lys Ile Leu Glu Asn Tyr Lys Glu Lys Phe Arg Ser
                245                 250                 255

Asp Ser Ile Thr Asn Met Leu Asp Thr Leu Met Gln Ala Lys Met Asn
            260                 265                 270

Ser Asp Asn Gly Asn Ala Gly Pro Asp Gln Asp Ser Glu Leu Leu Ser
        275                 280                 285

Asp Asn His Ile Leu Thr Thr Ile Gly Asp Ile Phe Gly Ala Gly Val
    290                 295                 300

Glu Thr Thr Thr Ser Val Val Lys Trp Thr Leu Ala Phe Leu Leu His
305                 310                 315                 320

Asn Pro Gln Val Lys Lys Lys Leu Tyr Glu Glu Ile Asp Gln Asn Val
                325                 330                 335

Gly Phe Ser Arg Thr Pro Thr Ile Ser Asp Arg Asn Arg Leu Leu Leu
            340                 345                 350

Leu Glu Ala Thr Ile Arg Glu Val Leu Arg Leu Arg Pro Val Ala Pro
        355                 360                 365

Met Leu Ile Pro His Lys Ala Asn Val Asp Ser Ser Ile Gly Glu Phe
    370                 375                 380

Ala Val Asp Lys Gly Thr Glu Val Ile Ile Asn Leu Trp Ala Leu His
385                 390                 395                 400

His Asn Glu Lys Glu Trp His Gln Pro Asp Gln Phe Met Pro Glu Arg
                405                 410                 415

Phe Leu Asn Pro Ala Gly Thr Gln Leu Ile Ser Pro Ser Val Ser Tyr
            420                 425                 430

Leu Pro Phe Gly Ala Gly Pro Arg Ser Cys Ile Gly Glu Ile Leu Ala
        435                 440                 445

Arg Gln Glu Leu Phe Leu Ile Met Ala Trp Leu Leu Gln Arg Phe Asp
    450                 455                 460

Leu Glu Val Pro Asp Asp Gly Gln Leu Pro Ser Leu Glu Gly Ile Pro
465                 470                 475                 480

Lys Val Val Phe Leu Ile Asp Ser Phe Lys Val Lys Ile Lys Val Arg
                485                 490                 495

Gln Ala Trp Arg Glu Ala Gln Ala Glu Gly Ser Thr
            500                 505
```

<210> SEQ ID NO 6
<211> LENGTH: 21
<212> TYPE: RNA
<213> ORGANISM: Artificial Sequence
<220> FEATURE:

-continued

```
<223> OTHER INFORMATION: AR exon 2 siRNA

<400> SEQUENCE: 6

gcuucugggu gucacuaugu u                                                21


<210> SEQ ID NO 7
<211> LENGTH: 21
<212> TYPE: RNA
<213> ORGANISM: Artificial Sequence
<220> FEATURE:
<223> OTHER INFORMATION: AR exon 7 siRNA

<400> SEQUENCE: 7

ggaacucgau cguaucauuu u                                                21
```